US012637449B2

(12) United States Patent
(10) Patent No.: US 12,637,449 B2
Yoo et al.
(45) Date of Patent: May 26, 2026

(54) ORGANIC COMPOUND AND ORGANIC LIGHT EMITTING DEVICE INCLUDING THE SAME

(71) Applicant: LG DISPLAY CO., LTD., Seoul (KR)

(72) Inventors: Seon-Keun Yoo, Paju-si (KR); Young-Jun Yu, Paju-si (KR); Sang-Beom Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 872 days.

(21) Appl. No.: 17/967,947

(22) Filed: Oct. 18, 2022

(65) Prior Publication Data

US 2023/0212161 A1 Jul. 6, 2023

(30) Foreign Application Priority Data

Dec. 30, 2021 (KR) ........................ 10-2021-0193029

(51) Int. Cl.

*C07D 413/14* (2006.01)
*C07D 417/14* (2006.01)

(Continued)

(52) U.S. Cl.

CPC ......... *C07D 413/14* (2013.01); *C07D 417/14* (2013.01); *H10K 50/125* (2023.02); *H10K 50/16* (2023.02); *H10K 85/342* (2023.02); *H10K 85/615* (2023.02); *H10K 85/654* (2023.02); *H10K 85/657* (2023.02);

(Continued)

(58) Field of Classification Search

CPC ................ C07D 413/14; C07D 417/14; C07B 2200/05; H10K 85/654; H10K 85/657

See application file for complete search history.

(56) References Cited

U.S. PATENT DOCUMENTS

2018/0323397 A1 11/2018 Ahn et al.

FOREIGN PATENT DOCUMENTS

CN 107266385 A * 10/2017 ........... C07D 417/10
CN 112279844 A * 1/2021 ........... C07D 413/10
KR 10-2017-0051198 A 5/2017

OTHER PUBLICATIONS

Machine-generated English-language translation of CN-112279844-A.*

(Continued)

*Primary Examiner* — Vu A Nguyen

(74) *Attorney, Agent, or Firm* — Morgan, Lewis & Bockius LLP

(57) ABSTRACT

An organic compound and an organic light emitting device including the same are disclosed. For example, an organic compound is represented by the following chemical formula in which one of X1 and X2 is N, and the other one of X1 and X2 is O or S. The organic light emitting diode and the organic light emitting device each includes the organic compound.

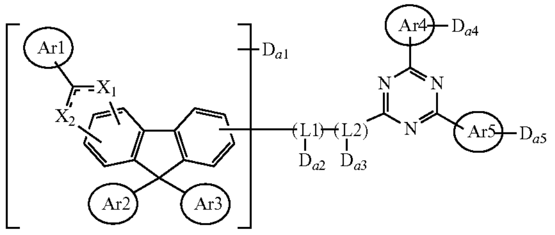

20 Claims, 5 Drawing Sheets

(51) Int. Cl.
*H10K 50/125* (2023.01)
*H10K 50/16* (2023.01)
*H10K 85/30* (2023.01)
*H10K 85/60* (2023.01)

(52) U.S. Cl.
CPC ..... *H10K 85/6572* (2023.02); *H10K 85/6574* (2023.02); *H10K 85/6576* (2023.02); *C07B 2200/05* (2013.01)

(56) References Cited

OTHER PUBLICATIONS

Machine-generated English-language translation of CN-107266385-A.*

* cited by examiner

ORGANIC COMPOUND AND ORGANIC LIGHT EMITTING DEVICE INCLUDING THE SAME

CROSS-REFERENCE TO RELATED APPLICATION

The present application claims the benefit of and the priority to Korean Patent Application No. 10-2021-0193029 filed in the Republic of Korea on Dec. 30, 2021, which is hereby incorporated by reference in its entirety.

TECHNICAL FIELD

The present disclosure relates to an organic compound, and more specifically, to an organic compound having improved emitting efficiency and lifespan and an organic light emitting device including the same.

BACKGROUND

Recently, as requests for a flat panel display device having a small occupied area have been increased, an organic light emitting display device including an organic light emitting diode (OLED) has been the subject of recent research and development.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage to operate other display devices. Moreover, the organic light emitting display device has advantages in the power consumption and the color sense.

The OLED includes a first substrate as an anode on a substrate, a second electrode as a cathode being spaced apart from and facing the first electrode and an organic light emitting layer between the first and second electrodes.

Although there have been many studies and developments on the materials of the organic light emitting layer, the OLED still has a limitation in the lifespan.

SUMMARY

The present disclosure is directed to an organic compound and an organic light emitting device including the emitting compound that substantially obviate one or more of the problems associated with the limitations and disadvantages of the related art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure is an organic compound represented by Formula 1: [Formula 1]

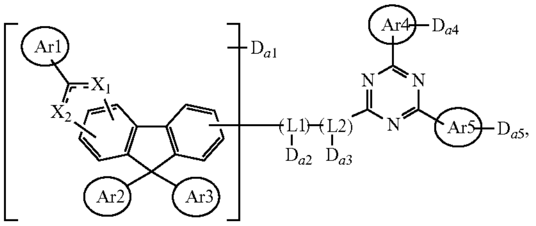

wherein L1 is a substituted or unsubstituted C5 to C30 heteroarylene group, and L2 is selected from the group consisting of a single bond, and a substituted or unsubstituted C6 to C30 arylene group, wherein one of X1 and X2 is a nitrogen atom, and the other one of X1 and X2 is O or S, wherein each of Ar1, Ar2, and Ar3 is independently selected from the group consisting of hydrogen, deuterium, a substituted or unsubstituted C1 to C10 alkyl group, a substituted or unsubstituted C6 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, wherein each of Ar4 and Ar5 is independently selected from the group consisting of a substituted or unsubstituted C6 to C30 aryl group, and a substituted or unsubstituted C3 to C30 heteroaryl group, and wherein, a1 is an integer of 0 to 95, each of a2, a3, a4, and a5 is independently an integer of 0 to 30, and at least one of a1 to a5 is a positive integer.

Another aspect of the present disclosure is an organic light emitting device comprising a substrate; and an organic light emitting diode positioned on the substrate and including a first electrode; a second electrode facing the first electrode; and a first emitting part between the first and second electrodes, the first emitting part including a first green emitting material layer, wherein the first green emitting material layer includes a first compound that is an organic compound represented by Formula 1: [Formula 1]

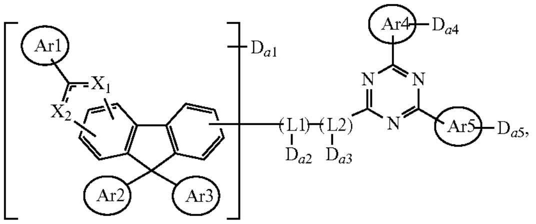

wherein L1 is a substituted or unsubstituted C5 to C30 heteroarylene group, and L2 is selected from the group consisting of a single bond, and a substituted or unsubstituted C6 to C30 arylene group, wherein one of X1 and X2 is a nitrogen atom, and the other one of X1 and X2 is O or S, wherein each of Ar1, Ar2, and Ar3 is independently selected from the group consisting of hydrogen, deuterium, a substituted or unsubstituted C1 to C10 alkyl group, a substituted or unsubstituted C6 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, wherein each of Ar4 and Ar5 is independently selected from the group consisting of a substituted or unsubstituted C6 to C30 aryl group, and a substituted or unsubstituted C3 to C30 heteroaryl group, and wherein, a1 is an integer of 0 to 95, each of a2, a3, a4, and a5 is independently an integer of 0 to 30, and at least one of a1 to a5 is a positive integer.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION

Figure 1:
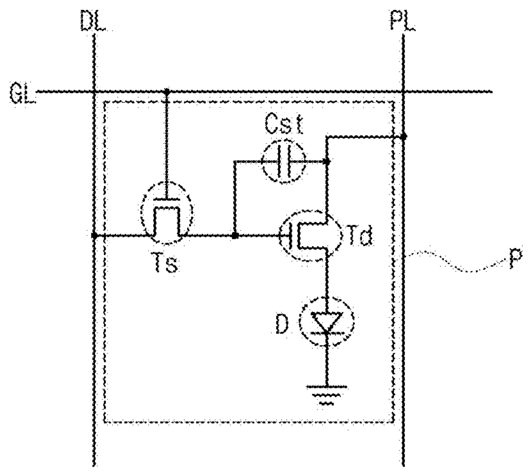
FIG. 1 illustrates a schematic circuit diagram for an organic light emitting display device according to an example embodiment of the present disclosure.

Reference will now be made in detail to some of the examples and embodiments of the disclosure illustrated in the accompanying drawings. Wherever possible, the same reference numbers will be used throughout the drawings to refer to the same or like parts.

Advantages and features of the present disclosure, and implementation methods thereof will be clarified through following example embodiments described with reference to the accompanying drawings. The present disclosure may, however, be embodied in different forms and should not be construed as limited to the example embodiments set forth herein. Rather, these example embodiments are provided so that this disclosure may be sufficiently thorough and complete to assist those skilled in the art to fully understand the scope of the present disclosure. Further, the protected scope of the present disclosure is defined by claims and their equivalents.

The shapes, sizes, ratios, angles, numbers, and the like, which are illustrated in the drawings to describe various example embodiments of the present disclosure, are merely given by way of example. Therefore, the present disclosure is not limited to the illustrations in the drawings. The same or similar elements are designated by the same reference numerals throughout the specification unless otherwise specified.

In the following description, where the detailed description of the relevant known function or configuration may unnecessarily obscure an important point of the present disclosure, a detailed description of such known function of configuration may be omitted.

In the present specification, where the terms “comprise,” “have,” “include,” and the like are used, one or more other elements may be added unless the term, such as “only,” is used. An element described in the singular form is intended to include a plurality of elements, and vice versa, unless the context clearly indicates otherwise.

In construing an element, the element is to be construed as including an error or tolerance range even where no explicit description of such an error or tolerance range is provided.

In the description of the various embodiments of the present disclosure, where positional relationships are described, for example, where the positional relationship between two parts is described using “on,” “over,” “under,” “above,” “below,” “beside,” “next,” or the like, one or more other parts may be located between the two parts unless a more limiting term, such as “immediate(ly),” “direct(ly),” or “close(ly)” is used. For example, where an element or layer is disposed “on” another element or layer, a third layer or element may be interposed therebetween.

In describing a temporal relationship, when the temporal order is described as, for example, “after,” “subsequent,” “next,” or “before,” a case which is not continuous may be included unless a more limiting term, such as “just,” “immediate(ly),” or “direct(ly),” is used.

Although the terms “first,” “second,” and the like may be used herein to describe various elements, the elements should not be limited by these terms. These terms are used only to identify one element from another. For example, a first element could be termed a second element, and similarly, a second element could be termed a first element, without departing from the scope of the present disclosure.

Although the terms “first,” “second,” A, B, (a), (b), and the like may be used herein to describe various elements, the elements should not be interpreted to be limited by these terms as they are not used to define a particular order, precedence, or number of the corresponding elements. These terms are used only to identify one element from another.

The expression that an element or layer is “connected” to another element or layer means the element or layer can not only be directly connected to another element or layer, but also be indirectly connected or adhered to another element or layer with one or more intervening elements or layers “disposed,” or “interposed” between the elements or layers, unless otherwise specified.

The term “at least one” should be understood as including any and all combinations of one or more of the associated listed items. For example, the meaning of “at least one of a first element, a second element, and a third element” encompasses the combination of all three listed elements, combinations of any two of the three elements, as well as each individual element, the first element, the second element, and the third element.

Features of various embodiments of the present disclosure may be partially or overall coupled to or combined with each other, and may be variously inter-operated with each other and driven technically as those skilled in the art can sufficiently understand. Embodiments of the present disclosure may be carried out independently from each other, or may be carried out together in a co-dependent relationship.

Hereinafter, example embodiments of the present disclosure will be described in detail with reference to the accompanying drawings. In adding reference numerals to elements of each of the drawings, although the same elements are illustrated in other drawings, like reference numerals may refer to like elements. Also, for convenience of description, a scale in which each of elements is illustrated in the accompanying drawings may differ from an actual scale. Thus, the illustrated elements are not limited to the specific scale in which they are illustrated in the drawings.

The OLED of the present disclosure may include an example of an organic compound of the present disclosure. The OLED may be included in an organic light emitting display device or an organic light emitting lighting device. The explanation below is focused on an example of an organic light emitting display device including the OLED of the present disclosure.

FIG. 1 illustrates a schematic circuit diagram for an organic light emitting display device according to an example embodiment of the present disclosure.

As illustrated in FIG. 1, a gate line GL and a data line DL, which may cross each other to define a pixel (pixel region) P, and a power line PL may be formed in an organic light display device. A switching thin film transistor (TFT) Ts, a driving thin film transistor (TFT) Td, a storage capacitor Cst, and an OLED D may be formed in the pixel P. The pixel P may include a red pixel, a green pixel, and a blue pixel. In addition, the pixel P may further include a white pixel.

The switching thin film transistor Ts may be connected to the gate line GL and the data line DL, and the driving thin film transistor Td and the storage capacitor Cst may be connected between the switching thin film transistor Ts and the power line PL. The OLED D may be connected to the driving thin film transistor Td. When the switching thin film transistor Ts is turned on by the gate signal applied through the gate line GL, the data signal applied through the data line DL may be applied to a gate electrode of the driving thin film transistor Td and one electrode of the storage capacitor Cst through the switching thin film transistor Ts.

The driving thin film transistor Td may be turned on by the data signal applied to the gate electrode so that a current proportional to the data signal may be supplied from the power line PL to the OLED D through the driving thin film transistor Td. The OLED D may emit light having a luminance proportional to the current flowing through the driving thin film transistor Td. In this case, the storage capacitor Cst may be charged with a voltage proportional to the data signal so that the voltage of the gate electrode in the driving thin film transistor Td may be kept constant or similar during one frame. Therefore, the organic light emitting display device can display a desired image.

Figure 2:
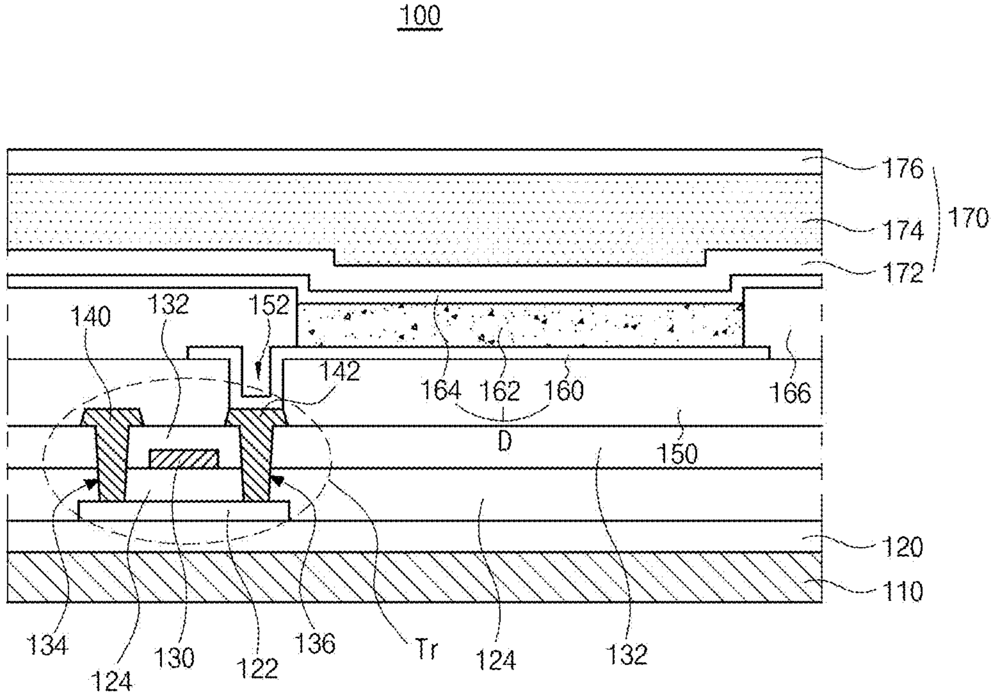
FIG. 2 illustrates a schematic cross-sectional view of an organic light emitting display device according to a first embodiment of the present disclosure.

FIG. 2 illustrates a schematic cross-sectional view of an organic light emitting display device according to a first embodiment of the present disclosure.

As illustrated in FIG. 2, the organic light emitting display device 100 may include a substrate 110, a TFT Tr, and an OLED D connected to the TFT Tr. For example, the organic light emitting display device 100 may include a red pixel, a green pixel, and a blue pixel, and the OLED D may be formed in each of the red, green and blue pixels. For example, the OLEDs D emitting red light, green light, and blue light may be provided in the red, green and blue pixels, respectively.

The substrate 110 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 120 may be formed on the substrate, and the TFT Tr may be formed on the buffer layer 120. The buffer layer 120 may be omitted.

A semiconductor layer 122 may be formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 may be shielded or blocked by the light-shielding pattern such that thermal degradation of the semiconductor layer 122 can be prevented or reduced. On the other hand, when the semiconductor layer 122 includes polycrystalline silicon, impurities may be doped into both sides of the semiconductor layer 122.

A gate insulating layer 124 may be formed on the semiconductor layer 122. The gate insulating layer 124 may be formed of an inorganic insulating material such as silicon oxide or silicon nitride.

A gate electrode 130, which may be formed of a conductive material, e.g., metal, may be formed on the gate insulating layer 124 to correspond to a center of the semiconductor layer 122.

In FIG. 2, the gate insulating layer 124 may be formed on an entire surface of the substrate 110. Alternatively, the gate insulating layer 124 may be patterned to have the same shape as the gate electrode 130. However, embodiments of the present disclosure are not limited to such examples.

An interlayer insulating layer 132, which may be formed of an insulating material, may be formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 may include first and second contact holes 134 and 136 exposing both sides of the semiconductor layer 122. The first and second contact holes 134 and 136 may not cover a portion of the surface of the semiconductor layer 122 that is nearer to the opposing ends than to a center of the semiconductor layer 122. The first and second contact holes 134 and 136 may be positioned at both sides of the gate electrode 130 to be spaced apart from the gate electrode 130.

The first and second contact holes 134 and 136 may be formed through the gate insulating layer 124. Alternatively, when the gate insulating layer 124 is patterned to have the same shape as the gate electrode 130, the first and second contact holes 134 and 136 may be formed only through the interlayer insulating layer 132. However, embodiments of the present disclosure are not limited to such examples.

A source electrode 140 and a drain electrode 142, which may be formed of a conductive material, e.g., metal, may be formed on the interlayer insulating layer 132.

The source electrode 140 and the drain electrode 142 may be spaced apart from each other with respect to the gate electrode 130 and may contact both sides of the semiconductor layer 122 through the first and second contact holes 134 and 136, respectively.

The semiconductor layer 122, the gate electrode 130, the source electrode 140, and the drain electrode 142 may constitute the TFT Tr. The TFT Tr may serve as a driving element. For example, the TFT Tr may correspond to the driving TFT Td (of FIG. 1).

In the TFT Tr, the gate electrode 130, the source electrode 140, and the drain electrode 142 may be positioned on the semiconductor layer 122. For example, the TFT Tr may have a coplanar structure.

Alternatively, in the TFT Tr, the gate electrode may be positioned under the semiconductor layer, and the source and drain electrodes may be positioned on the semiconductor layer such that the TFT Tr may have an inverted staggered structure. In this instance, the semiconductor layer may include amorphous silicon. However, embodiments of the present disclosure are not limited to such examples.

Although not shown, the gate line and the data line may cross each other to define the pixel, and the switching TFT may be formed to be connected to the gate and data lines. The switching TFT may be connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer (or a passivation layer) 150, which may include a drain contact hole 152 exposing the drain electrode 142 of the TFT Tr, may be formed to cover the TFT Tr. The drain contact hole 152 may not cover the drain electrode 142.

A first electrode 160, which may be connected to the drain electrode 142 of the TFT Tr through the drain contact hole 152, may be separately formed in each pixel and on the planarization layer 150. The first electrode 160 may be an anode and may be formed of a conductive material having a relatively high work function. For example, the first electrode 160 may be formed of a transparent conductive material, e.g., indium-tin-oxide (ITO) or indium-zinc-oxide (IZO).

When the organic light emitting display device 100 is operated as a bottom-emission type, the first electrode 160 may have a single-layered structure of the transparent conductive material layer. Alternatively, when the organic light emitting display device 100 is operated as a top-emission type, the first electrode 160 may further include a reflection layer. For example, the reflection layer may be formed of silver (Ag) or aluminum-palladium-copper (APC) alloy. In the top-emission type organic light emitting display device 100, the first electrode 160 may have a triple-layered structure of ITO/Ag/ITO or ITO/APC/ITO. However, embodiments of the present disclosure are not limited to such examples.

A bank layer 166 may be formed on the planarization layer 150 to cover an edge of the first electrode 160. For example, the bank layer 166 may be positioned at a boundary of the pixel and exposes a center of the first electrode 160 in the pixel. The bank layer 166 may not cover a center of the first electrode 160 in the pixel.

An organic light emitting layer 162 may be formed on the first electrode 160. The organic light emitting layer 162 may include one emitting part including an emitting material layer (EML). Alternatively, the organic light emitting layer 162 may include a plurality of emitting parts and each emitting part may include the EML. In addition, the organic light emitting layer 162 may further include a charge generation layer between adjacent emitting parts. Embodiments of the present disclosure are not limited to such examples.

The emitting part or each of the emitting parts may have a multi-layered structure including at least one of a hole injection layer (HIL), a hole transporting layer (HTL), an electron blocking layer (EBL), a hole blocking layer (HBL), an electron transporting layer (ETL), and an electron injection layer (EIL).

The organic light emitting layer 162 may be separated in each of the red, green, and blue pixels. As described herein, in the OLED D in the green pixel according to an example embodiment in the present disclosure, the EML may include an example of an organic compound of the present disclosure so that the lifespan of the OLED D and the organic light emitting display device 100 including the organic compound may be increased.

A second electrode 164 may be formed over the substrate 110 where the organic light emitting layer 162 is formed. The second electrode 164 may cover an entire surface of the display area and may be formed of a conductive material having a relatively low work function to serve as a cathode. For example, the second electrode 164 may be formed of aluminum (Al), magnesium (Mg), calcium (Ca), silver (Ag) or their alloy or a combination thereof. In the top-emission type organic light emitting display device 100, the second electrode 164 may have a thin profile (small thickness) to provide a light transmittance property (or a semi-transmittance property).

The first electrode 160, the organic light emitting layer 162, and the second electrode 164 may constitute the OLED D.

An encapsulation film (e.g., an encapsulation layer) 170 may be formed on the second electrode 164 to prevent penetration of moisture into the OLED D. The encapsulation film 170 may include a first inorganic insulating layer 172, an organic insulating layer 174, and a second inorganic insulating layer 176 sequentially stacked. However, embodiments of the present disclosure are not limited to such examples. The encapsulation film 170 may be omitted.

The organic light emitting display device 100 may further include a polarization plate (not shown) for reducing an ambient light reflection. For example, the polarization plate may be a circular polarization plate. In the bottom-emission type organic light emitting display device 100, the polarization plate may be disposed under the substrate 110. In the top-emission type organic light emitting display device 100, the polarization plate may be disposed on or over the encapsulation film 170.

In addition, in the top-emission type organic light emitting display device 100, a cover window (not shown) may be attached to the encapsulation film 170 or the polarization plate. In this instance, the substrate 110 and the cover window may have a flexible property such that a flexible organic light emitting display device may be provided.

Figure 3:
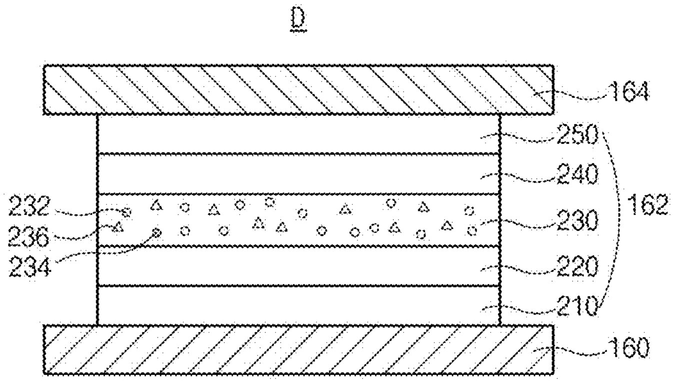
FIG. 3 illustrates a schematic cross-sectional view of an OLED according to a second embodiment of the present disclosure.

FIG. 3 illustrates a schematic cross-sectional view of an OLED according to a second embodiment of the present disclosure.

As illustrated in FIG. 3, an OLED D may include first and second electrodes 160 and 164, which may face each other, and an organic light emitting layer 162 therebetween. The organic light emitting layer 162 may include a green EML 230 between the first and second electrodes 160 and 164.

The organic light emitting display device 100 (of FIG. 2) may include a red pixel, a green pixel, and a blue pixel. The OLED D may be positioned in the green pixel. The OLED D in the red pixel may include a red EML, and the OLED D in the blue pixel may include a blue EML.

The first electrode 160 may be an anode injecting a hole, and the second electrode 164 may be a cathode injecting an electron. In addition, one of the first and second electrodes 160 and 164 may be a reflective electrode, and the other one of the first and second electrodes 160 and 164 may be a transparent (or a semi-transparent) electrode.

For example, the first electrode 160 may include a transparent conductive material layer formed of ITO or IZO. The second electrode 164 may be formed of one of Al, Mg, Ag, AlMg, and MgAg.

The green EML 230 may include an example of an organic compound of the present disclosure as a first compound 232. The first compound 232 may be represented by Formula 1.

[Formula 1]

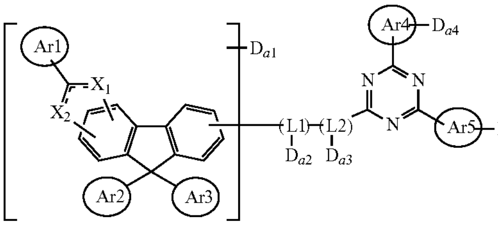

In Formula 1, L1 may be a substituted or unsubstituted C5 to C30 heteroarylene group, and L2 may be selected from the group consisting of a single bond (a direct bond) and a substituted or unsubstituted C6 to C30 arylene group. One of X1 and X2 may be a nitrogen atom (N), and the other one of X1 and X2 may be O or S. Each of Ar1, Ar2, and Ar3 may be independently selected from the group consisting of hydrogen (H), deuterium (D), a substituted or unsubstituted C1 to C10 alkyl group, a substituted or unsubstituted C6 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group. Each of Ar4 and Ar5 may be independently selected from the group consisting of a substituted or unsubstituted C6 to C30 aryl group, and a substituted or unsubstituted C3 to C30 heteroaryl group. In addition, a1 may be an integer of 0 to 95, each of a2, a3, a4, and a5 may be independently an integer of 0 to 30, and at least one of a1 to a5 may be a positive integer. In Formula 1, D denotes a deuterium atom, and each of a1 to a5 denotes a number of a deuterium atom.

In the present disclosure, without specific definition, a substituent of an alkyl group, a cycloalkyl group, an alkoxy group, an aryloxy group, an alkyl thioxy group, an aryl thioxy group, an alkyl sulfoxy group, an aryl sulfoxy group, an aryl group, a heteroaryl group, an arylene group, and a heteroarylene group may be selected from the group consisting of deuterium, a C1 to C10 alkyl group, and a C6 to C30 aryl group.

In the present disclosure, without specific definition, the C6 to C30 aryl group may be selected from the group consisting of phenyl, biphenyl, terphenyl, naphthyl, anthracenyl, pentanenyl, indenyl, indenoindenyl, heptalenyl, biphenylenyl, indacenyl, phenanthrenyl, benzophenanthrenyl, dibenzophenanthrenyl, azulenyl, pyrenyl, fluoranthenyl, triphenylenyl, chrysenyl, tetraphenyl, tetrasenyl, picenyl, pentaphenyl, pentacenyl, fluorenyl, indenofluorenyl, and spiro-fluorenyl. Likewise, the C6 to C30 arylene group may be a bivalent group that results from a removal of a hydrogen atom from a carbon atom in a group selected from the group consisting of phenyl, biphenyl, terphenyl, naphthyl, anthracenyl, pentanenyl, indenyl, indenoindenyl, heptalenyl, biphenylenyl, indacenyl, phenanthrenyl, benzophenanthrenyl, dibenzophenanthrenyl, azulenyl, pyrenyl, fluoranthenyl, triphenylenyl, chrysenyl, tetraphenyl, tetrasenyl, picenyl, pentaphenyl, pentacenyl, fluorenyl, indenofluorenyl, and spiro-fluorenyl.

In the present disclosure, without specific definition, the C3 to C30 heteroaryl group may be selected from the group consisting of pyrrolyl, pyridinyl, pyrimidinyl, pyrazinyl, pyridazinyl, triazinyl, tetrazinyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, quinolinyl, isoquinolinyl, phthalazinyl, quinoxalinyl, cinnolinyl, quinazolinyl, quinozolinyl, quinolinyl, purinyl, phthalazinyl, quinoxalinyl, benzoquinolinyl, benzoisoquinolinyl, benzoquinazolinyl, benzoquinoxalinyl, acridinyl, phenanthrolinyl, perimidinyl, phenanthridinyl, pteridinyl, cinnolinyl, naphtharidinyl, furanyl, oxazinyl, oxazolyl, oxadiazolyl, triazolyl, dioxynyl, benzofuranyl, dibenzofuranyl, thiopyranyl, xanthenyl, chromanyl, isochromanyl, thioazinyl, thiophenyl, benzothiophenyl, dibenzothiophenyl, difuropyrazinyl, benzofurodibenzofuranyl, benzothienobenzothiophenyl, benzothienodibenzothiophenyl, benzothienobenzofuranyl, and benzothienodibenzofuranyl. Likewise, the C3 to C30 heteroarylene group may be a bivalent group that results from a removal of a hydrogen atom from a carbon atom in a group selected from the group consisting of pyrrolyl, pyridinyl, pyrimidinyl, pyrazinyl, pyridazinyl, triazinyl, tetrazinyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, quinolinyl, isoquinolinyl, phthalazinyl, quinoxalinyl, cinnolinyl, quinazolinyl, quinozolinyl, quinolinyl, purinyl, phthalazinyl, quinoxalinyl, benzoquinolinyl, benzoisoquinolinyl, benzoquinazolinyl, benzoquinoxalinyl, acridinyl, phenanthrolinyl, perimidinyl, phenanthridinyl, pteridinyl, cinnolinyl, naphtharidinyl, furanyl, oxazinyl, oxazolyl, oxadiazolyl, triazolyl, dioxynyl, benzofuranyl, dibenzofuranyl, thiopyranyl, xanthenyl, chromanyl, isochromanyl, thioazinyl, thiophenyl, benzothiophenyl, dibenzothiophenyl, difuropyrazinyl, benzofurodibenzofuranyl, benzothienobenzothiophenyl, benzothienodibenzothiophenyl, benzothienobenzofuranyl, and benzothienodibenzofuranyl.

In examples of the organic compound of the Formula 1, at least one of the hydrogen atoms is substituted with a deuterium atom so that the emitting lifespan of the organic compound may be increased. In other words, the organic compound may have a deuteration ratio being greater than 0 and 100 or less.

For example, in Formula 1, all of a1 to a5 may be a positive integer so that the organic compound may be wholly deuterated. In an example embodiment, a1 may be a positive integer, and a2 to a5 may be 0. In an example embodiment, a1 and a2 may be a positive integer, and a3, a4, and a5 may be 0. For example, the organic compound may be partially deuterated. When a1 is a positive integer with or without at least one of a2 to a5 being a positive integer, there may be an advantage of increasing the emitting lifespan with minimum deuterium atoms.

For example, Formula 1 may be represented by one of Formulas 1-1, 1-2, and 1-3.
[Formula 1-1]
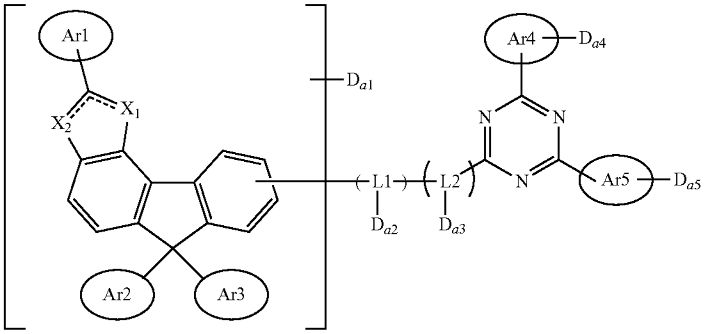
[Formula 1-2]
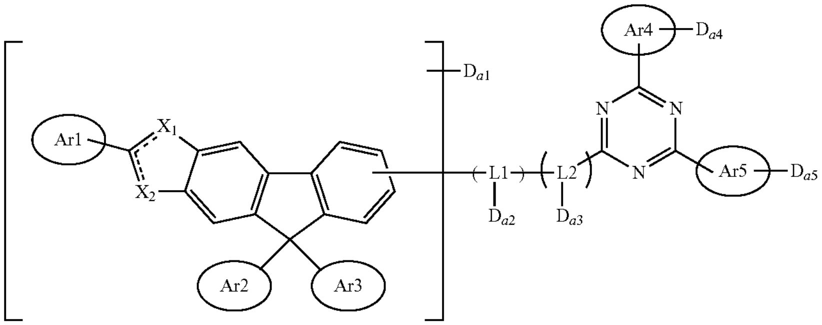
[Formula 1-3]
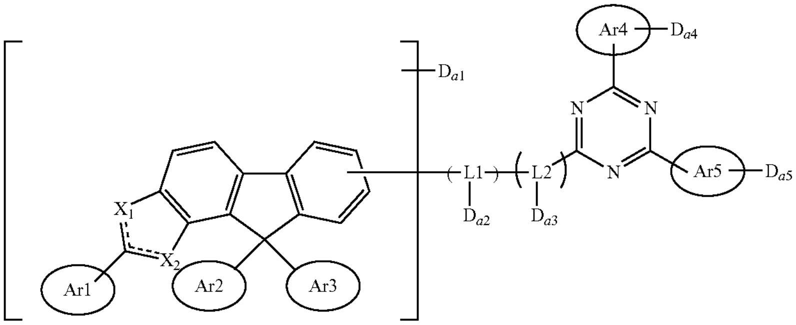
In Formulas 1-1 to 1-3, the definitions of L1, L2, Ar1 to Ar5 and a1 to a5 may be the same as those in Formula 1.
For example, L1 may be one of carbazolylene, dibenzofuranylene, and dibenzothiophenylene. For example, L1 may be one of structures of Formulas 1a, 1b, 1c, and 1d.
[Formula 1a]
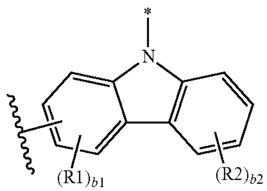
-continued
[Formula 1b]
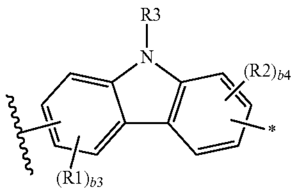
[Formula 1c]
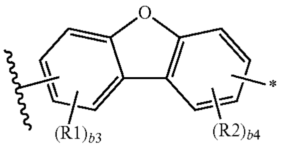

-continued

[Formula 1d]

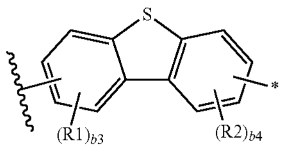

In Formulas 1a, 1b, 1c, and 1d, each of R1, R2, and R3 may be independently selected from the group consisting of deuterium, cyano, halogen, a substituted or unsubstituted C1 to C10 alkyl group, a substituted or unsubstituted C6 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted silyl group, a substituted or unsubstituted C6 to C30 arylsilyl group, a substituted or unsubstituted C6 to C30 arylphosphine group, a substituted or unsubstituted phosphine oxide group, a substituted or unsubstituted C6 to C30 aryl group, and a substituted or unsubstituted C3 to C30 heteroaryl group, b1 may be an integer of 0 to 3, and each of b2, b3, and b4 may be independently an integer of 0 to 4. In Formulas 1a, 1b, 1c, and 1d, one of a wavy mark and a "*" mark is a bonding site to a fused-fluorene moiety, and the other one of the wavy mark and the "*" mark is a bonding site to L2.

For example, a nitrogen atom of the carbazolylene moiety in Formula 1a may be bonded to the fused-fluorene moiety or L2 as a linker.

For example, Formulas 1a, 1b, 1c, and 1d may be represented by Formulas 1a-1, 1b-1, 1c-1, and 1d-1, respectively.

[Formula 1a-1]

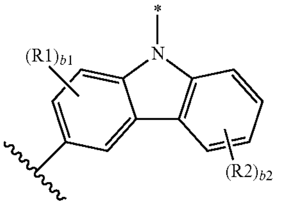

[Formula 1b-1]

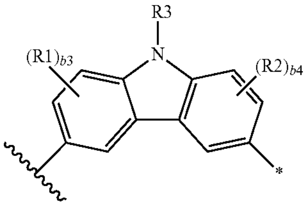

[Formula 1c-1]

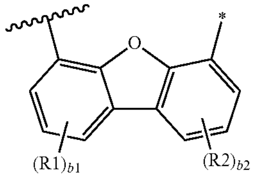

-continued

[Formula 1d-1]

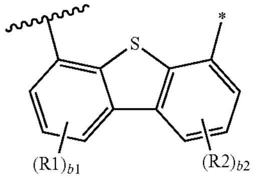

In Formulas 1a-1, 1b-1, 1c-1, and 1d-1, the definitions of R1 to R3 and b1 to b4 may be the same as those in Formulas 1a, 1b, 1c, and 1d, respectively. In Formulas 1a-1, 1b-1, 1c-1, and 1d-1, one of a wavy mark and a "*" mark may be a bonding site to a fused-fluorene moiety, and the other one of the wavy mark and the "*" mark may be a bonding site to L2.

In Formula 1, L2 may be a single bond or phenylene. Ar1 may be selected from hydrogen, deuterium, and a substituted or unsubstituted C6 to C30 aryl group, e.g., phenyl. Each of Ar2 and Ar3 may be independently hydrogen or deuterium, Ar4 and Ar5 may be a substituted or unsubstituted C6 to C30 aryl group, e.g., phenyl.

The first compound 232, which is an example of the organic compound of the present disclosure, may be one of the compounds in Formula 2.

[Formula 2]

H1-D1

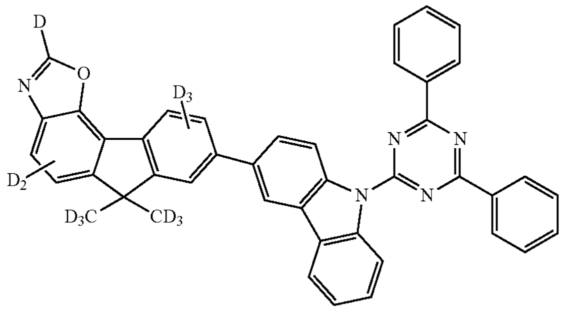

H1-D2

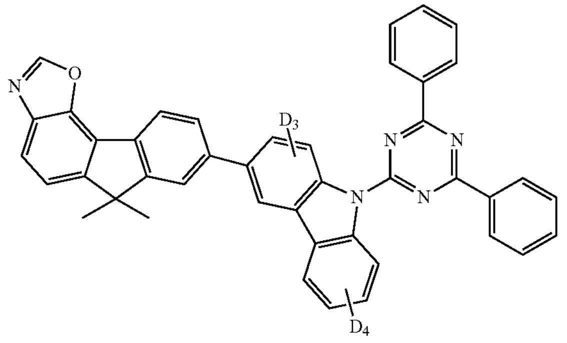

-continued
H1-D3
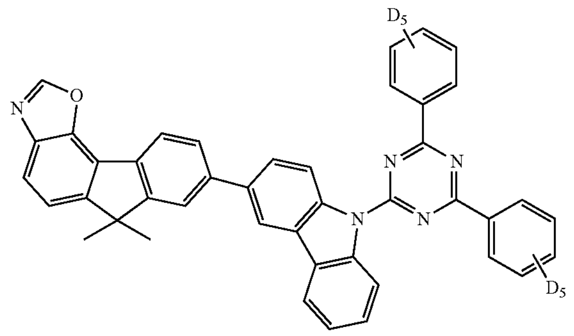
H1-D4
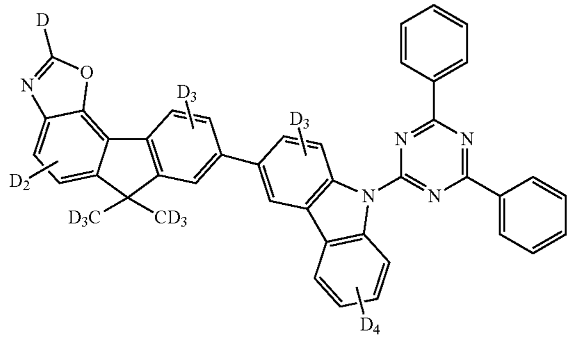
H1-D5
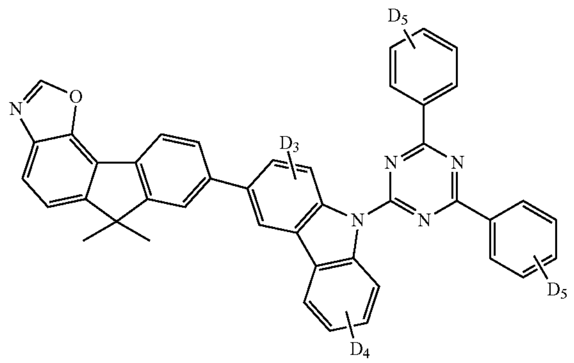
H1-D6
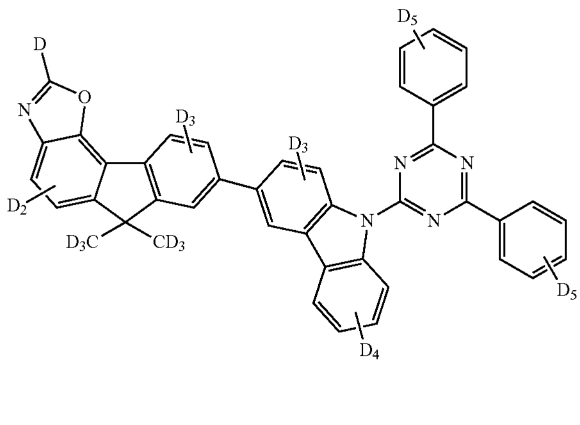
-continued
H2-D1
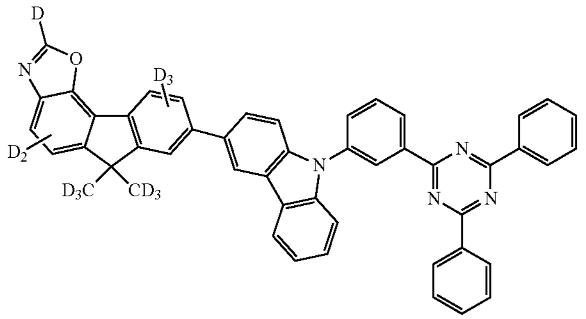
H2-D2
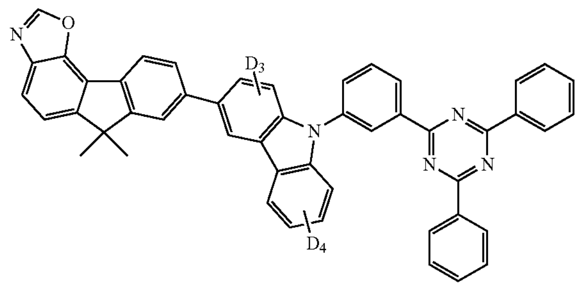
H2-D3
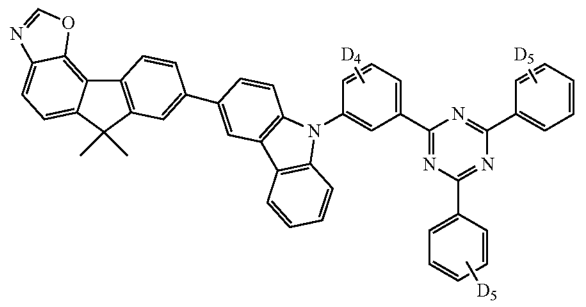
H2-D4
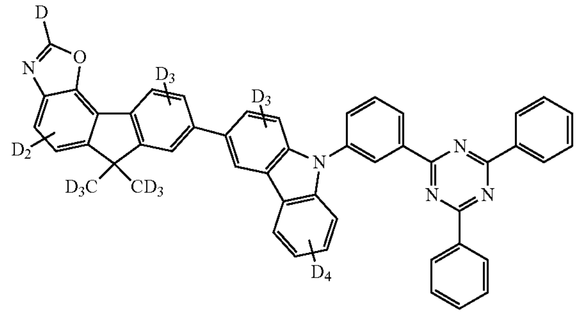
H2-D5
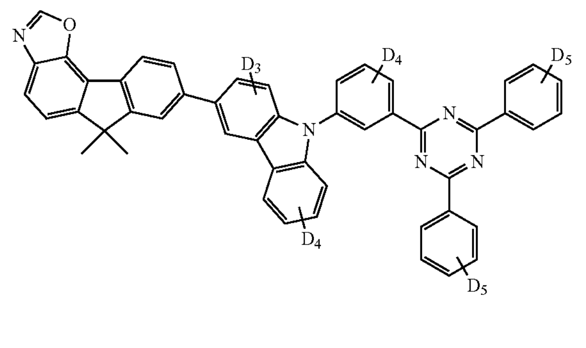

-continued
H2-D6
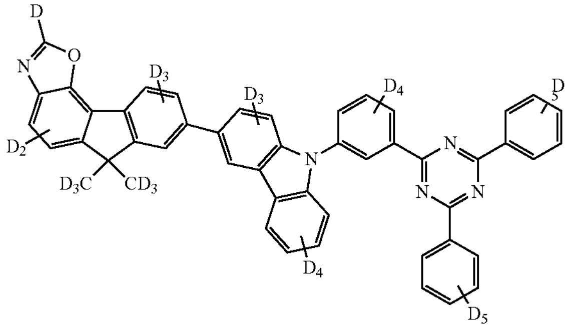
H3-D1
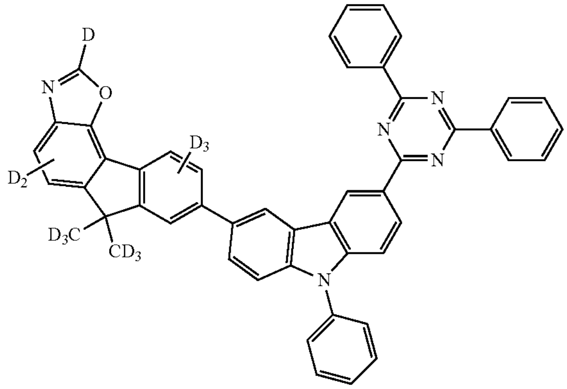
H3-D2
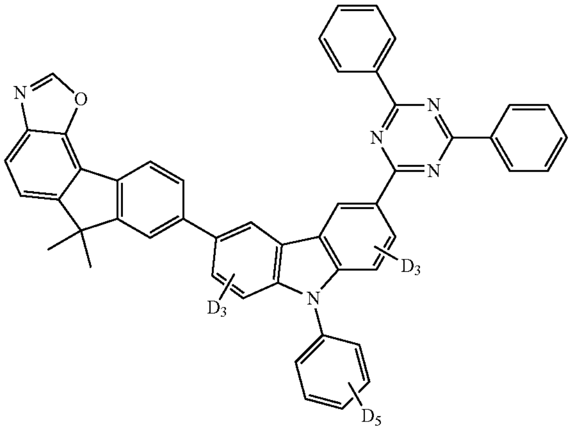
-continued
H3-D3
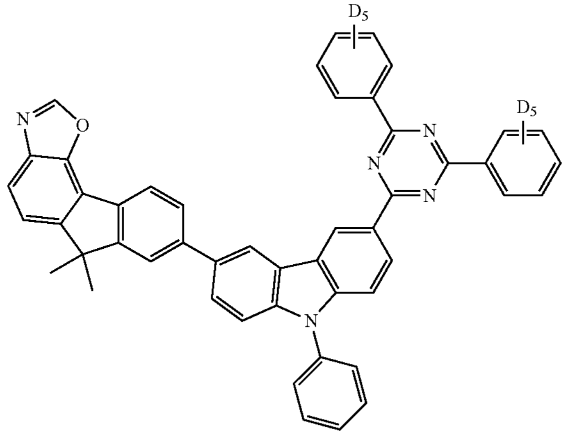
H3-D4
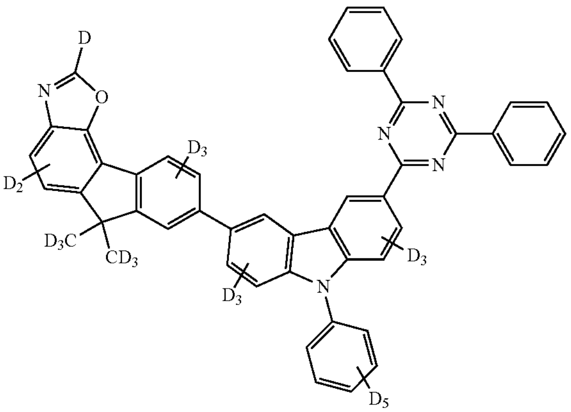
H3-D5
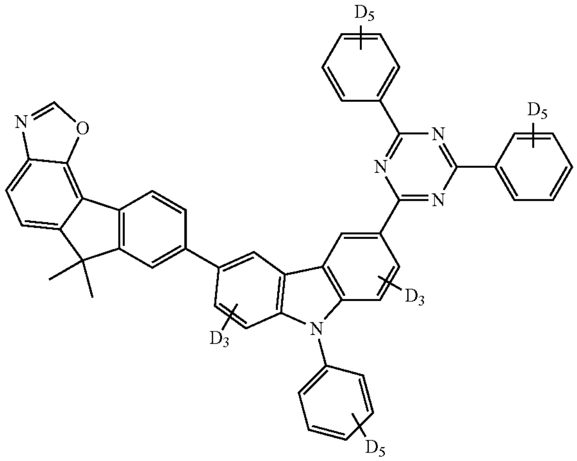

-continued
H3-D6
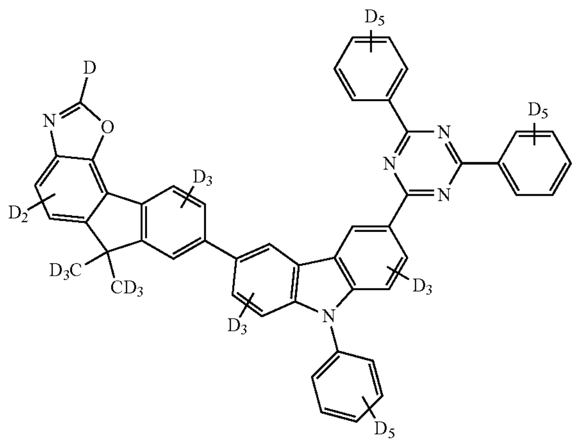
H4-D1
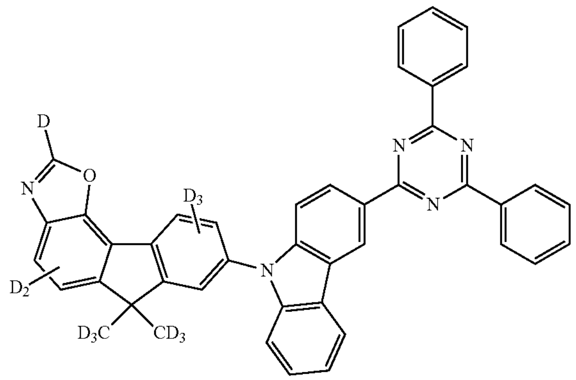
H4-D2
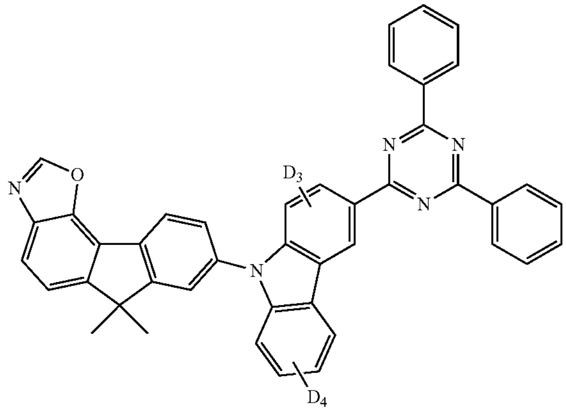
-continued
H4-D3
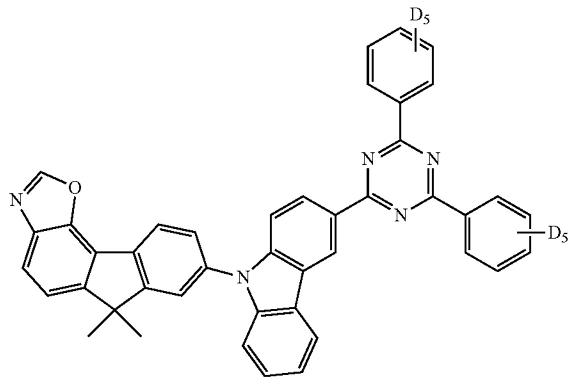
H4-D4
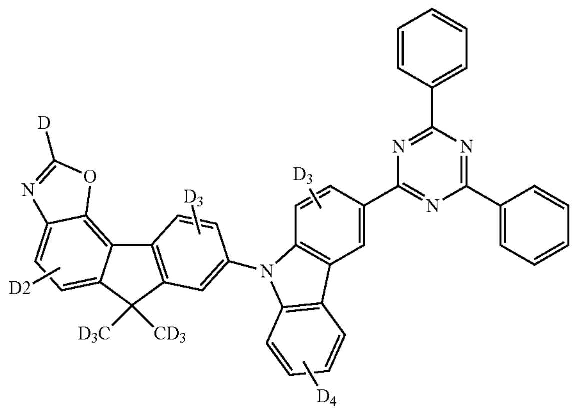
H4-D5
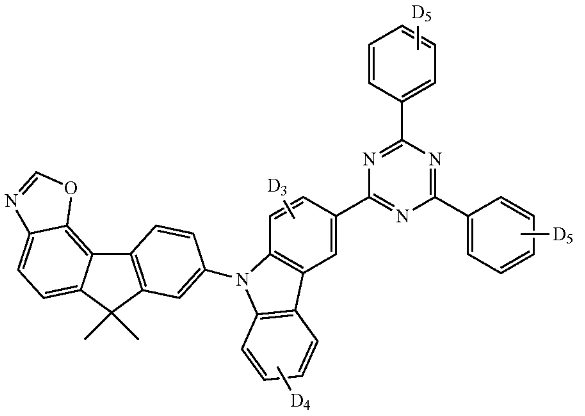

-continued
H4-D6
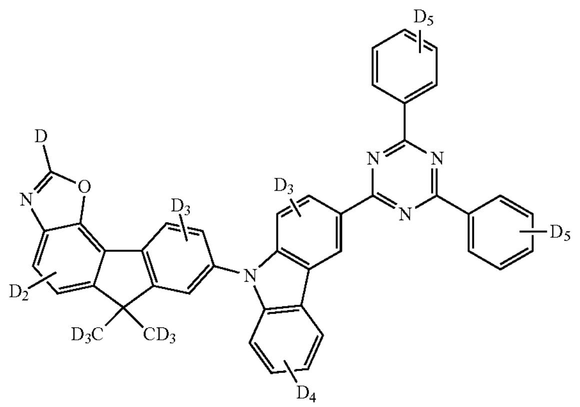
H5-D1
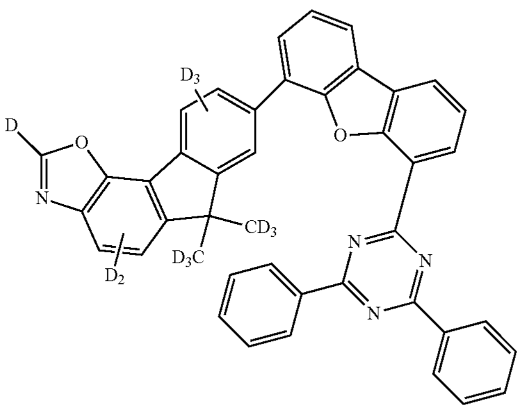
H5-D2
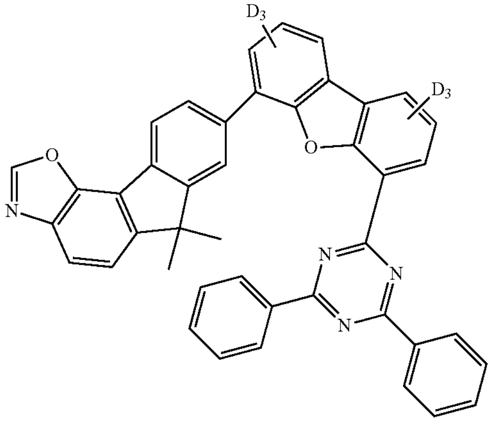
-continued
H5-D3
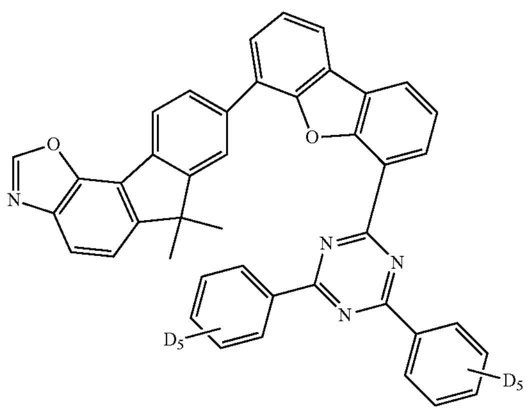
H5-D4
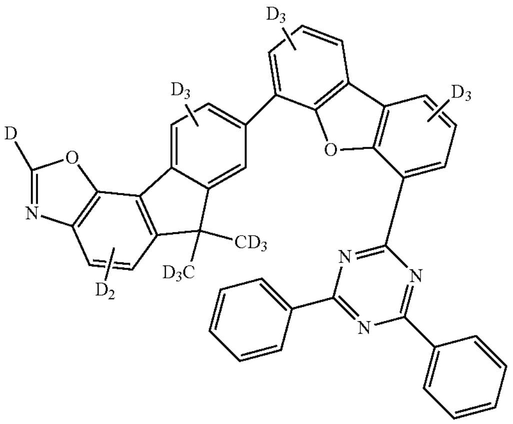
H5-D5
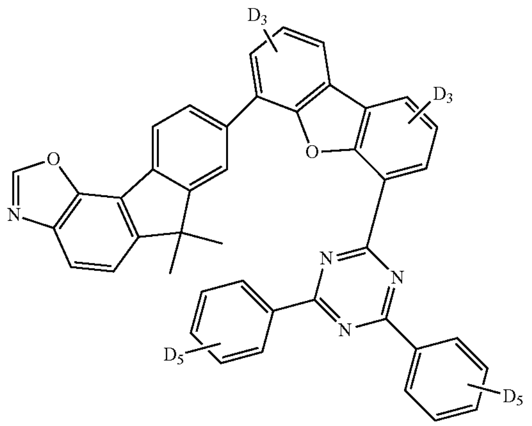

-continued
H5-D6
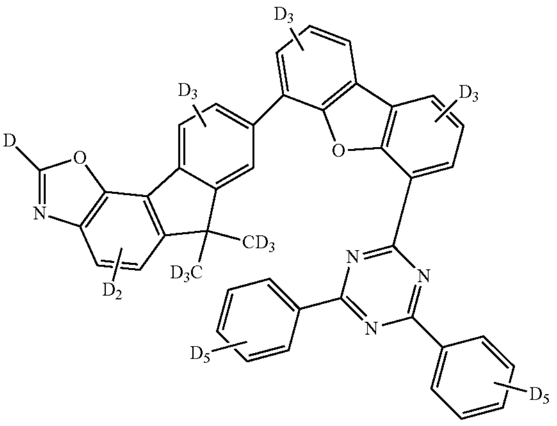
H6-D1
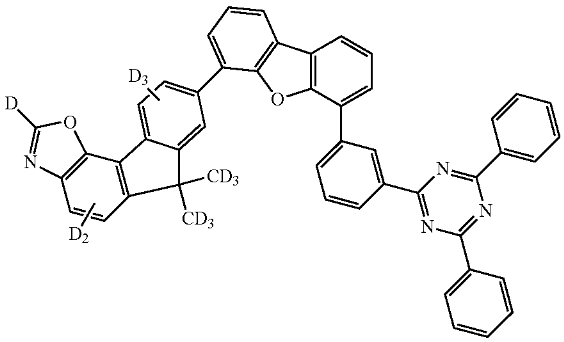
H6-D2
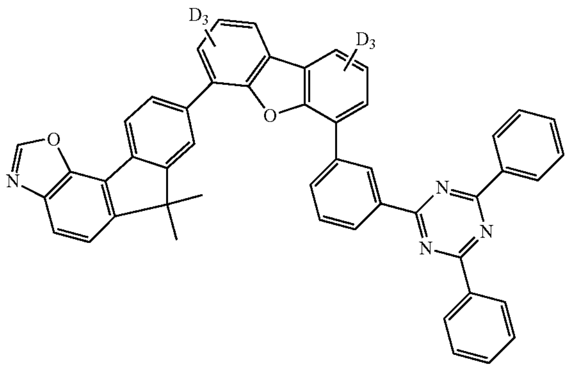
H6-D3
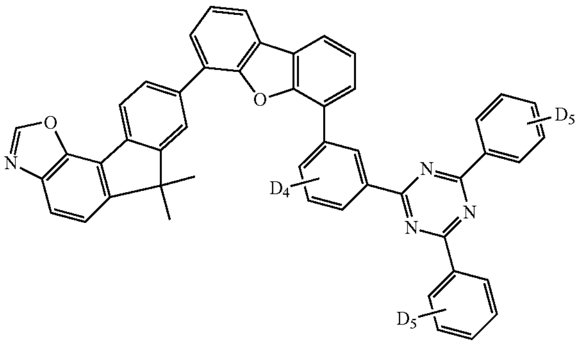
-continued
H6-D4
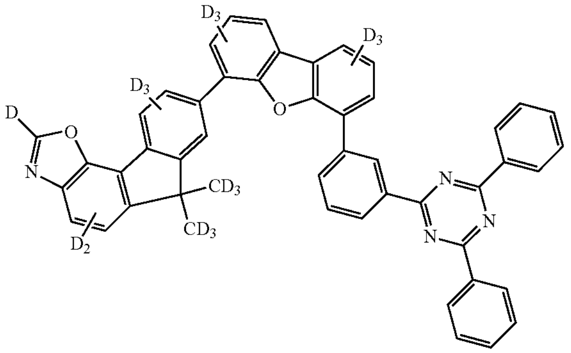
H6-D5
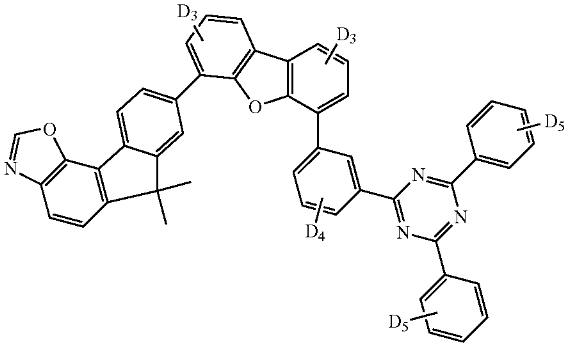
H6-D6
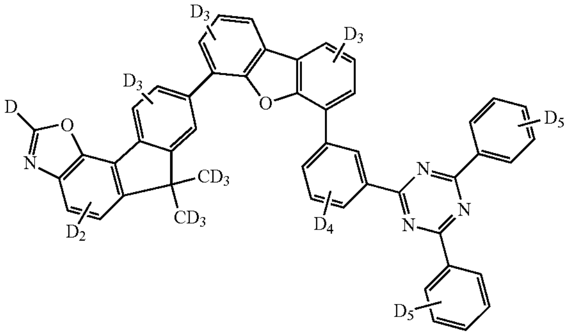
H7-D1
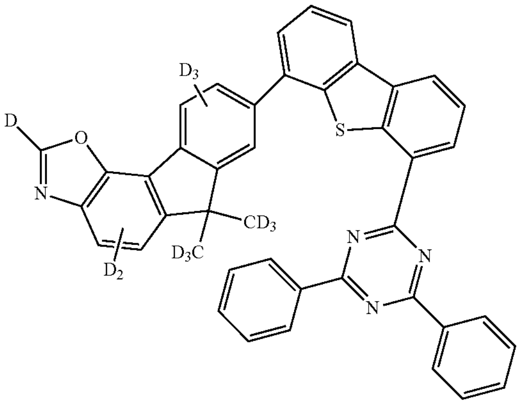

-continued
H7-D2
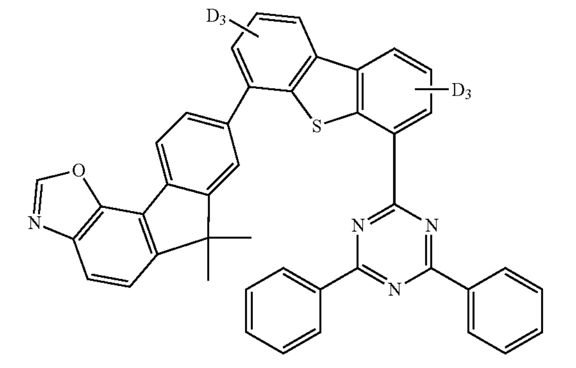
H7-D3
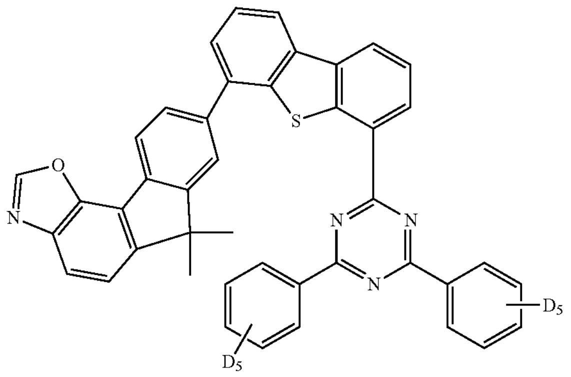
H7-D4
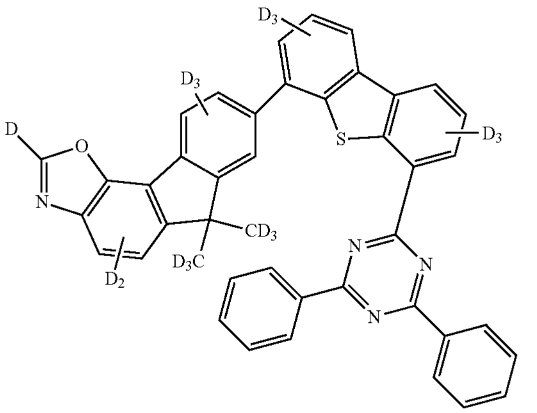
H7-D5
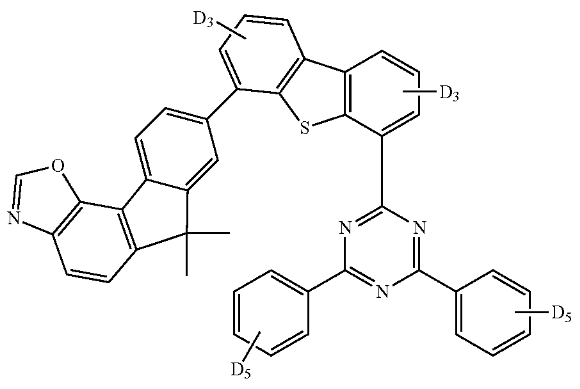
-continued
H7-D6
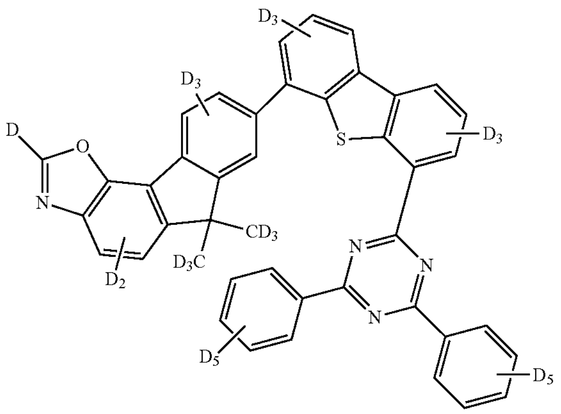
H8-D1
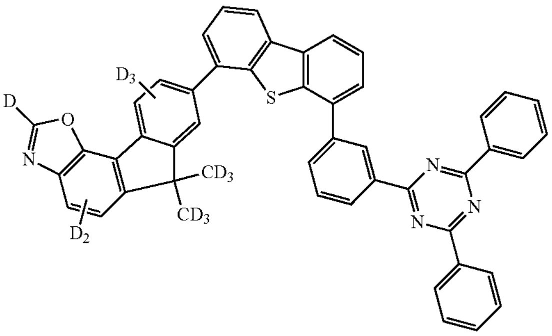
H8-D2
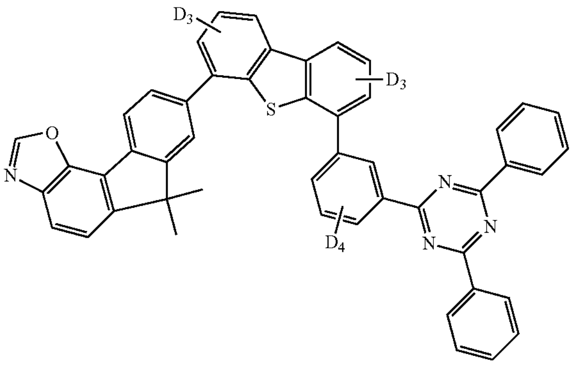
H8-D3
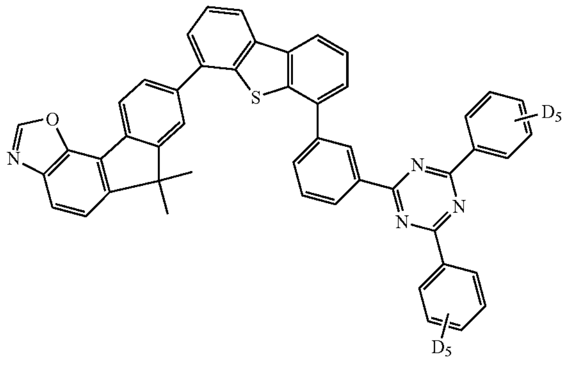

-continued
H8-D4
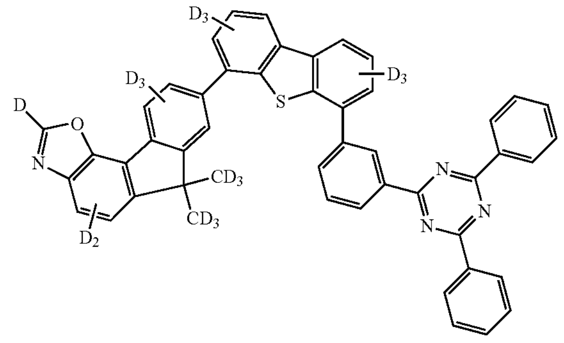
H8-D5
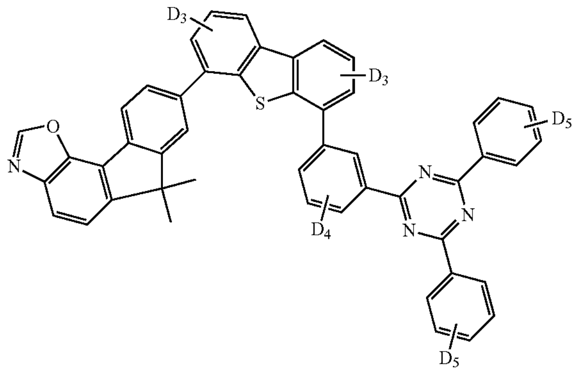
H8-D6
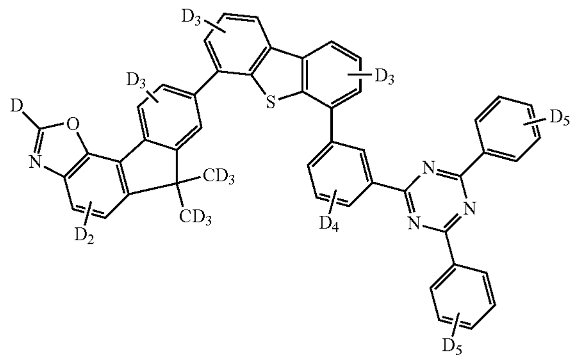
H9-D1
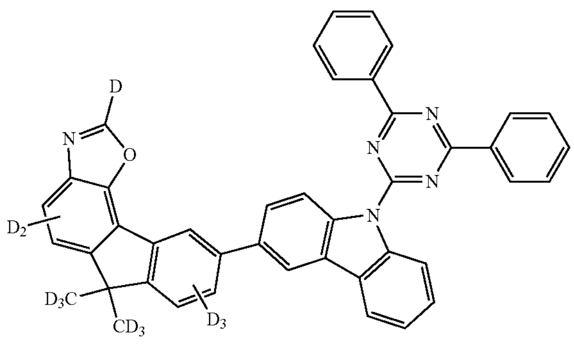
-continued
H9-D2
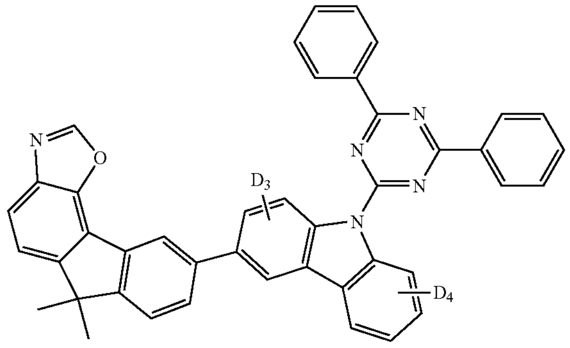
H9-D3
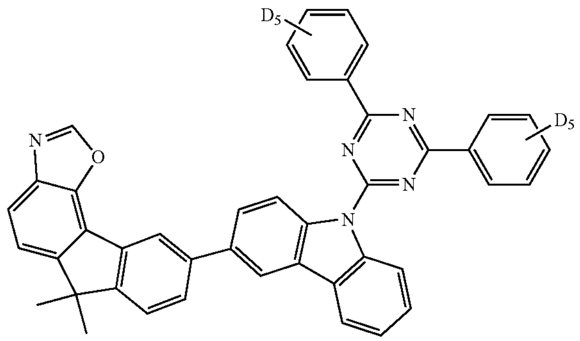
H9-D4
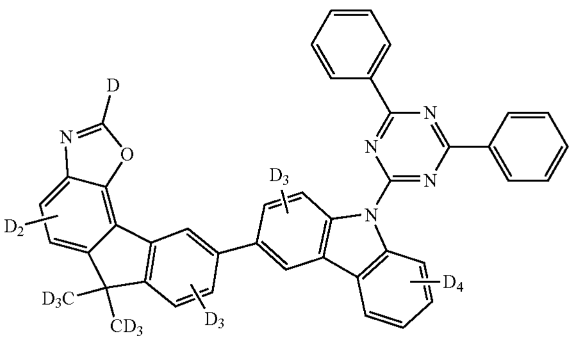
H9-D5
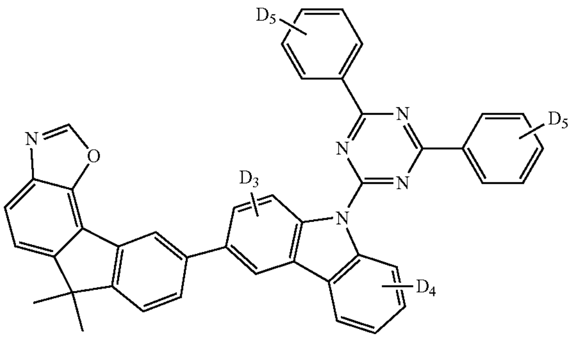

-continued
H9-D6
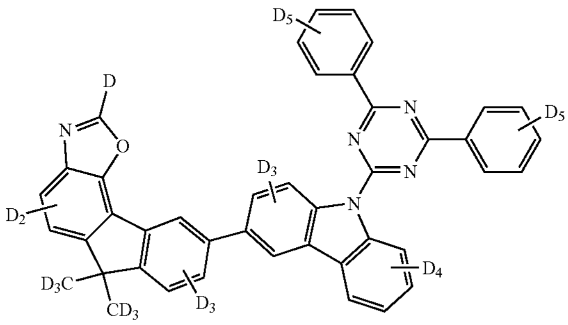
H10-D1
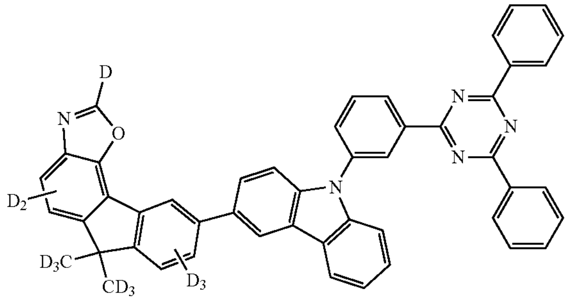
H10-D2
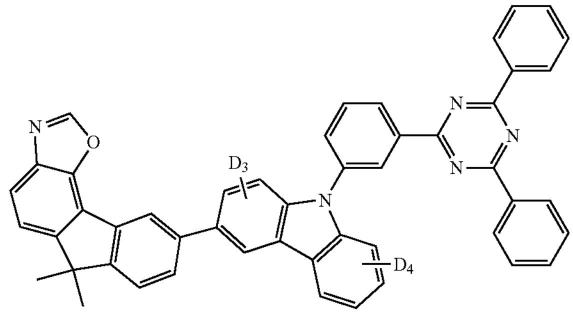
H10-D3
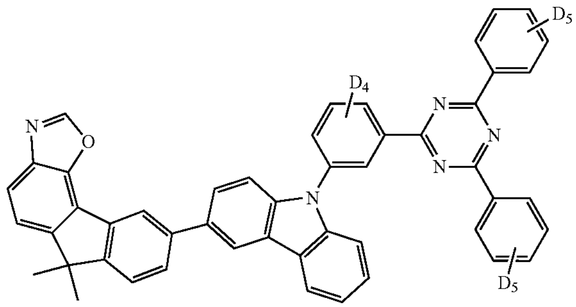
-continued
H10-D4
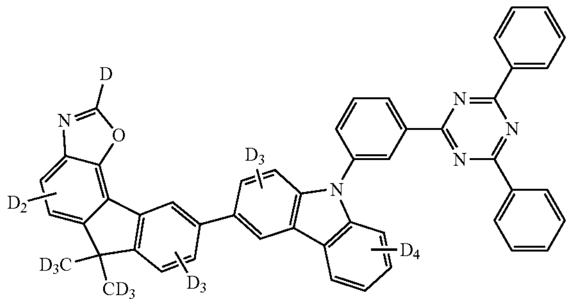
H10-D5
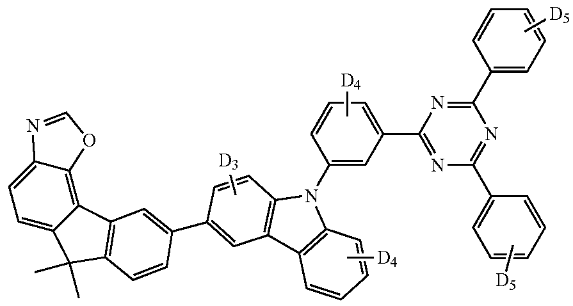
H10-D6
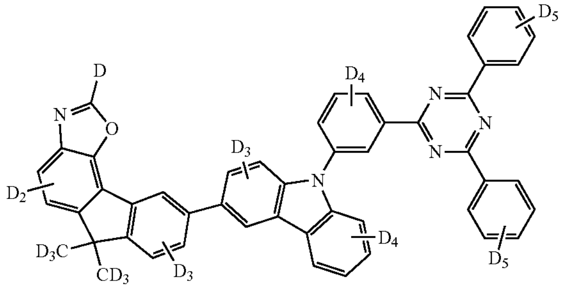
H11-D1
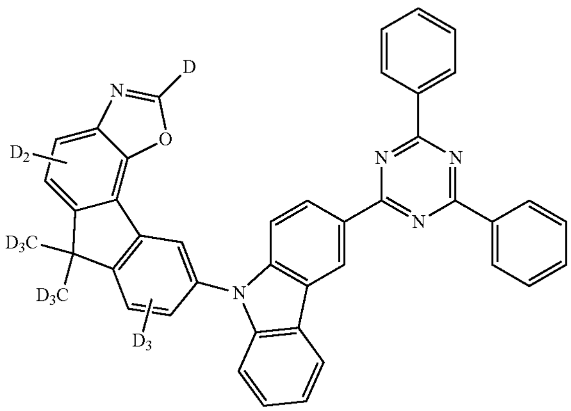

-continued
H11-D2
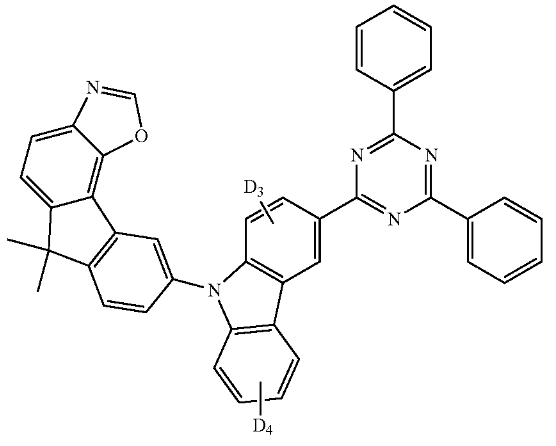
H11-D3
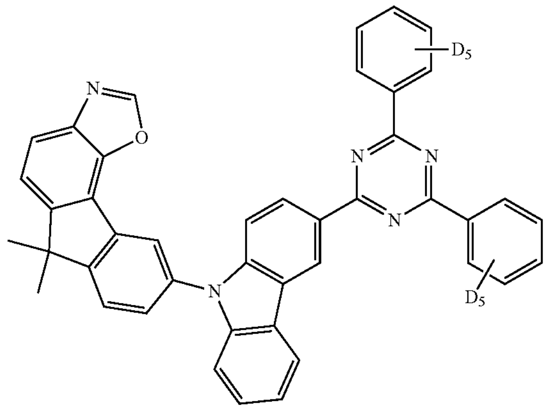
H11-D4
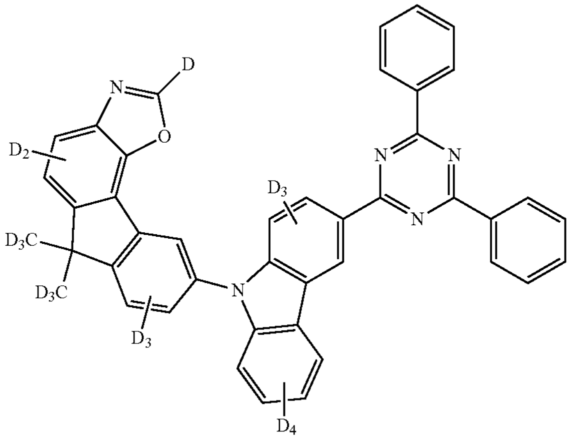
-continued
H11-D5
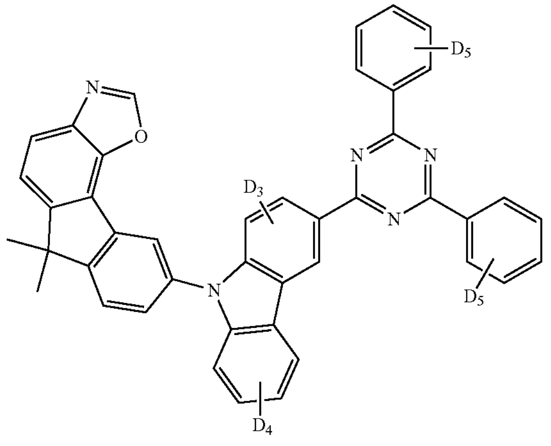
H11-D6
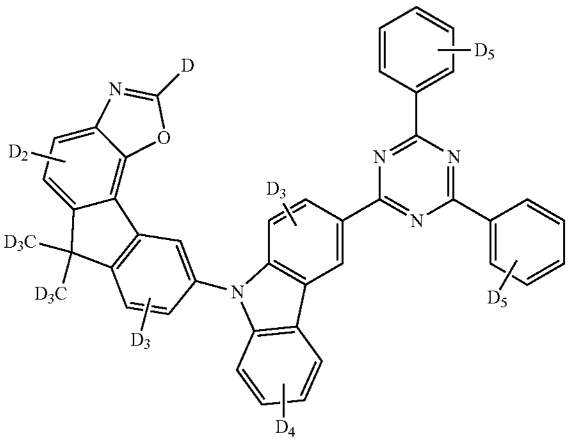
H12-D1
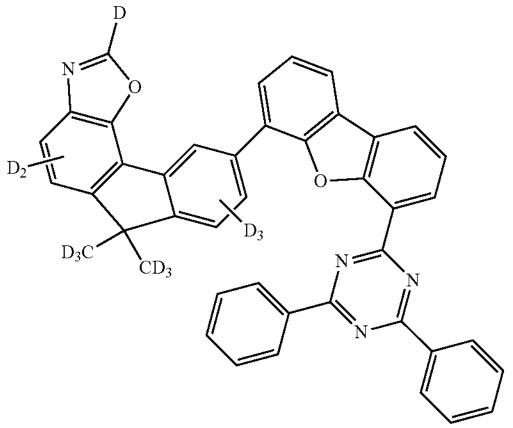

-continued
H12-D2
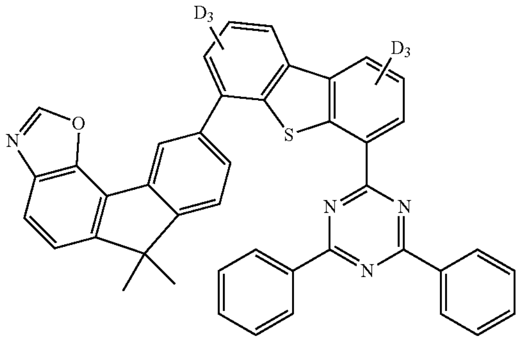
H12-D3
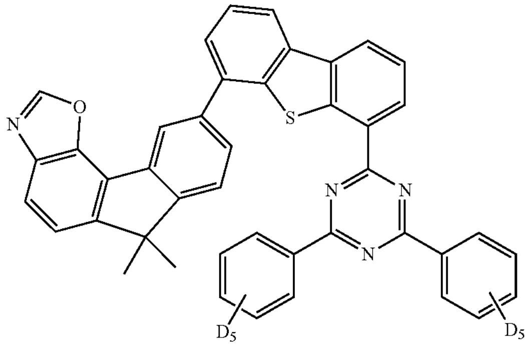
H12-D4
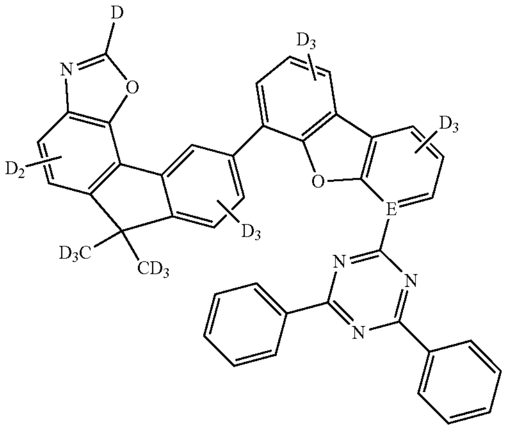
H12-D5
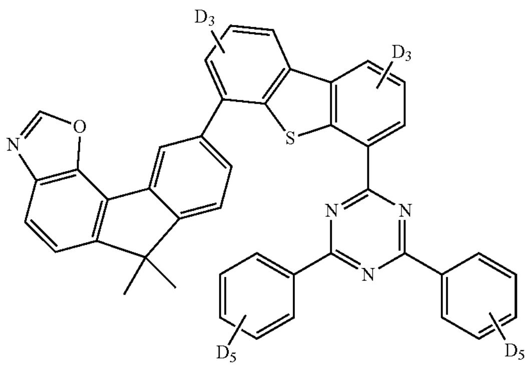
-continued
H12-D6
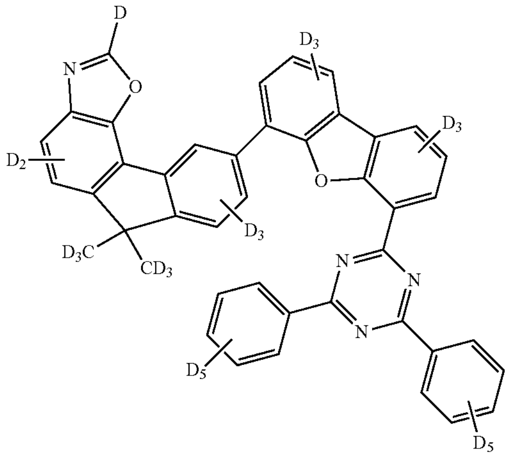
H13-D1
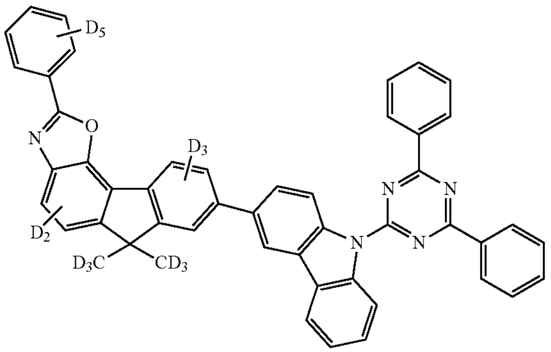
H13-D2
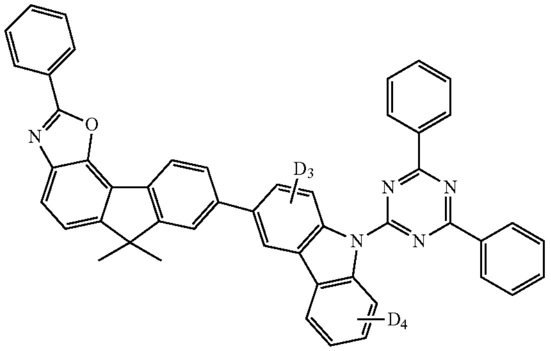
H13-D3
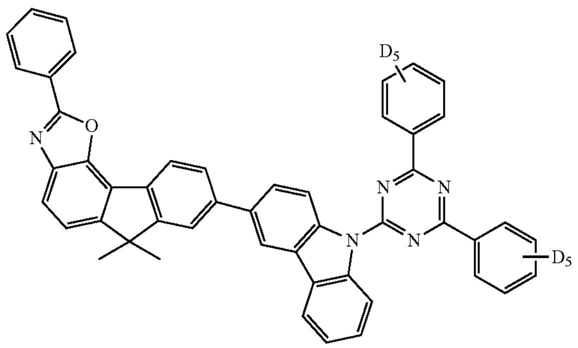

-continued
H13-D4
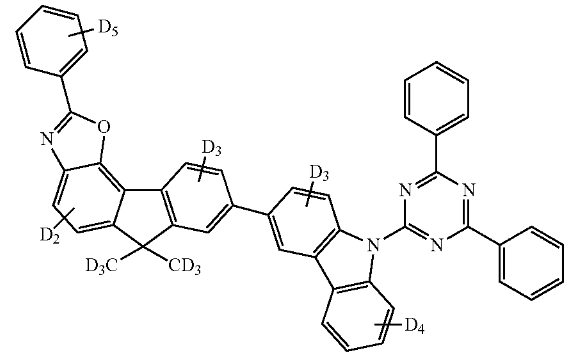
H13-D5
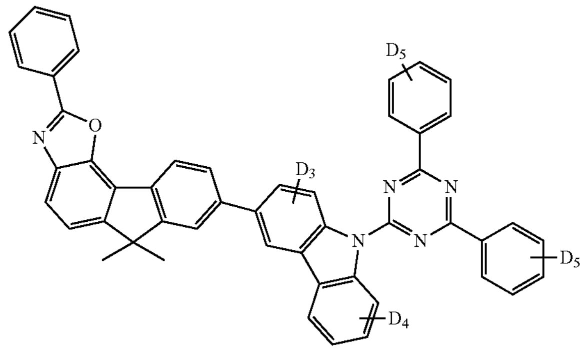
H13-D6
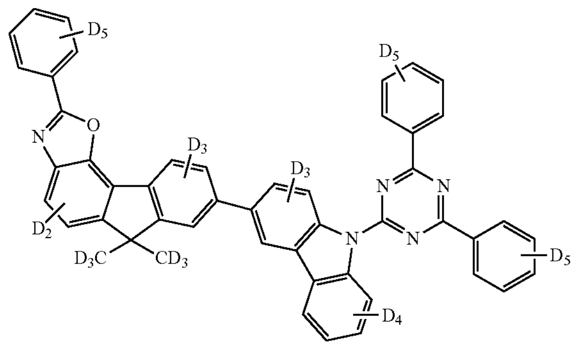
H14-D1
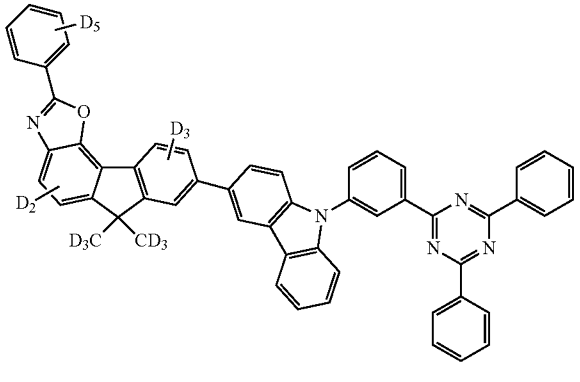
-continued
H14-D2
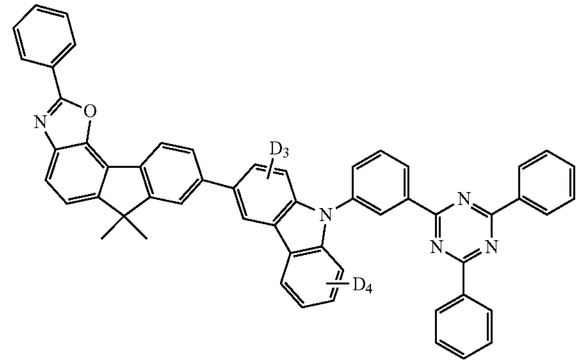
H14-D3
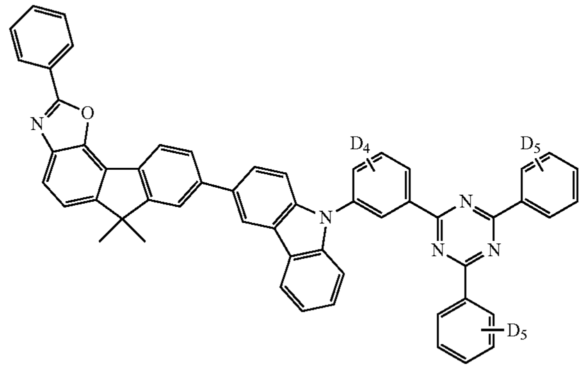
H14-D4
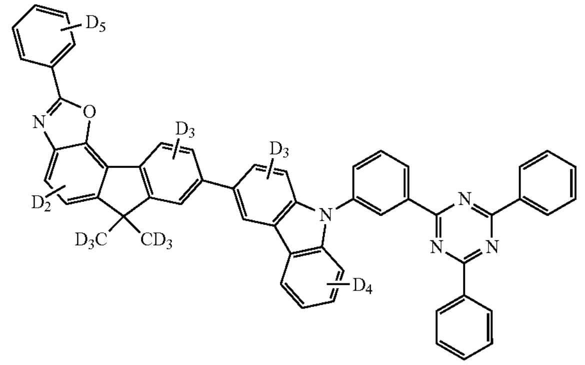
H14-D5
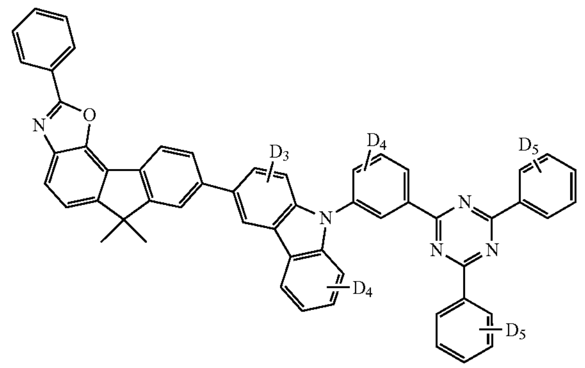

-continued
H14-D6
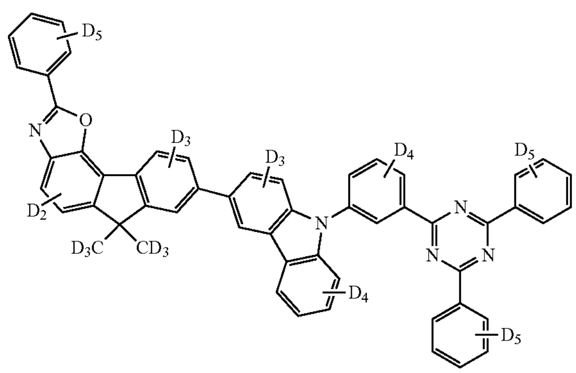
H15-D1
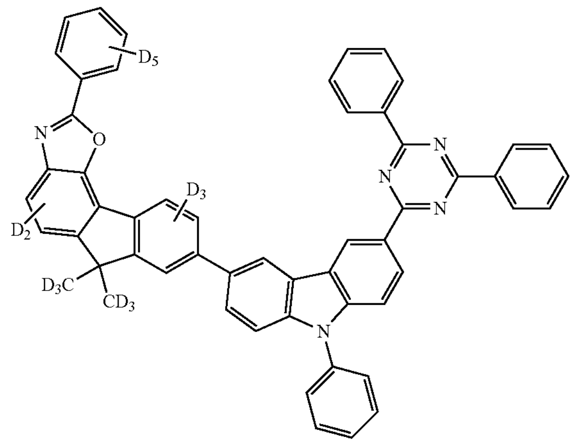
H15-D2
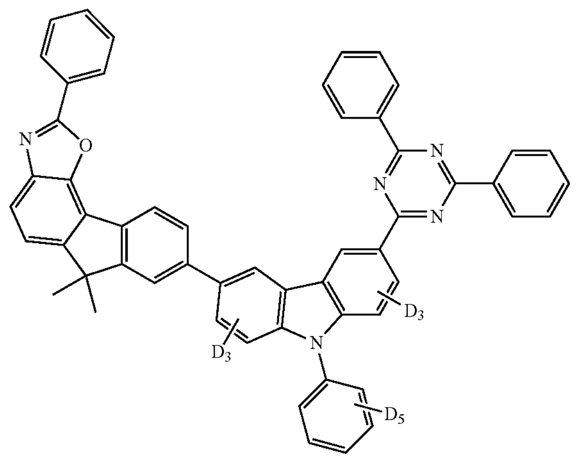
-continued
H15-D3
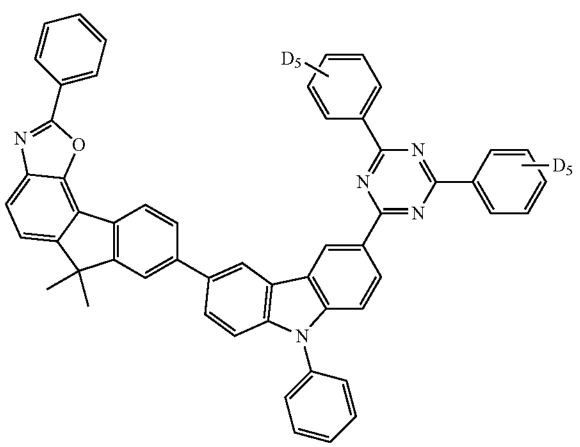
H15-D4
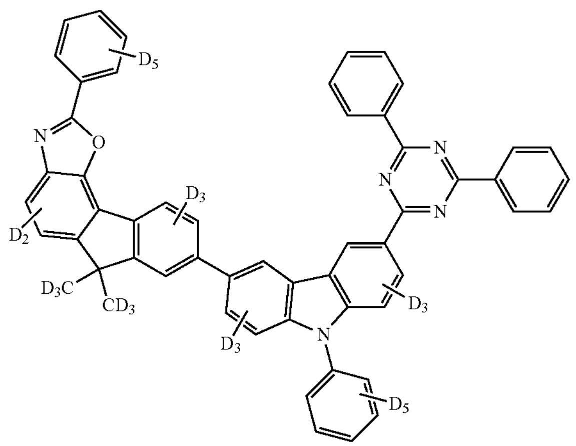
H15-D5
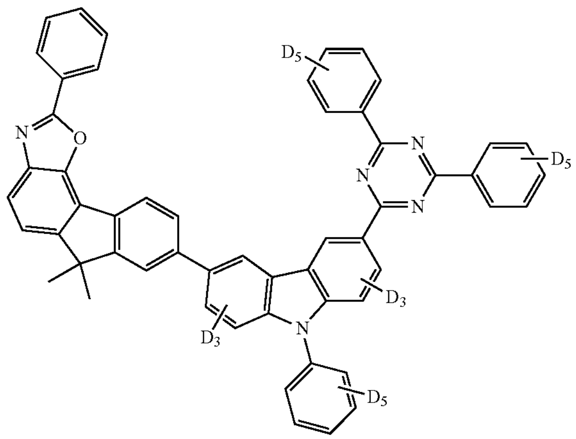

-continued
H15-D6
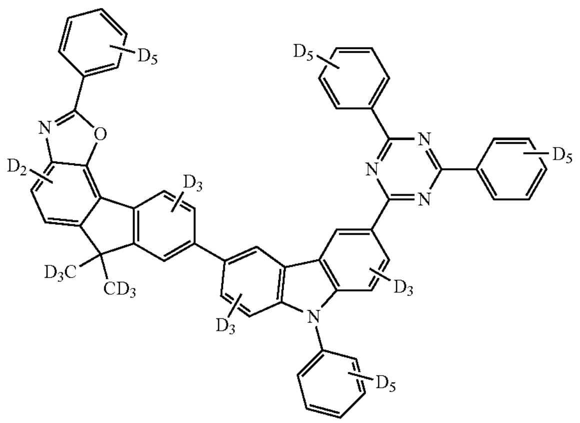
H16-D1
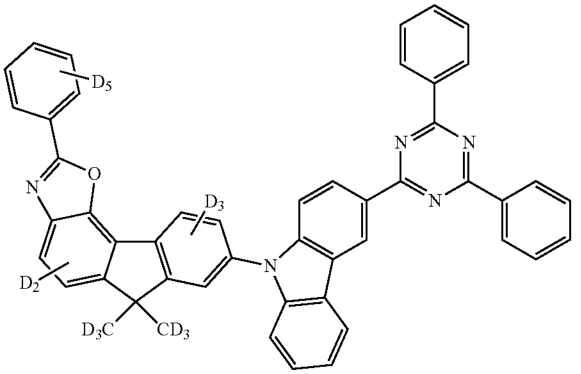
H16-D2
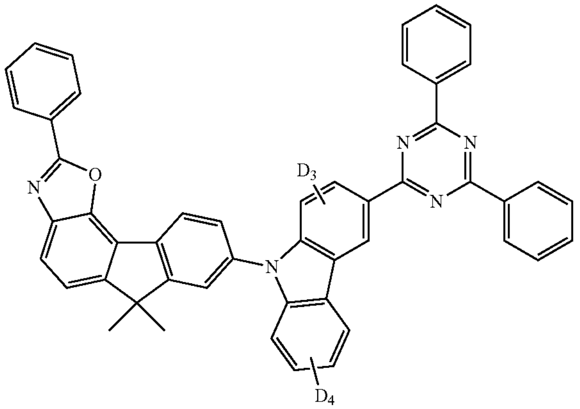
H16-D3
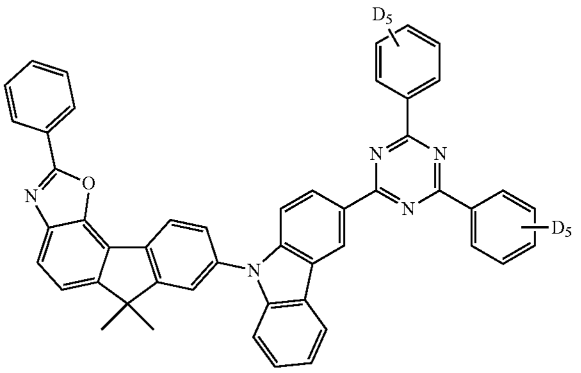
H16-D4
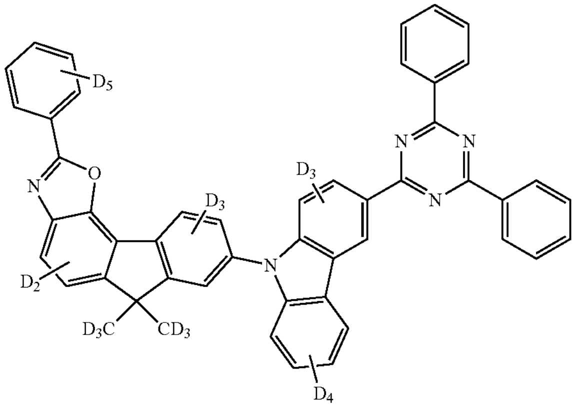

-continued
H16-D5
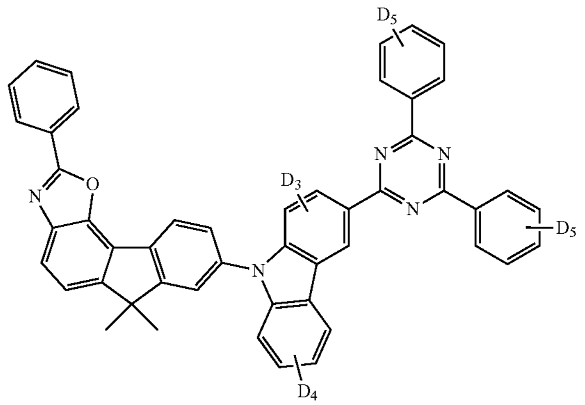
H16-D6
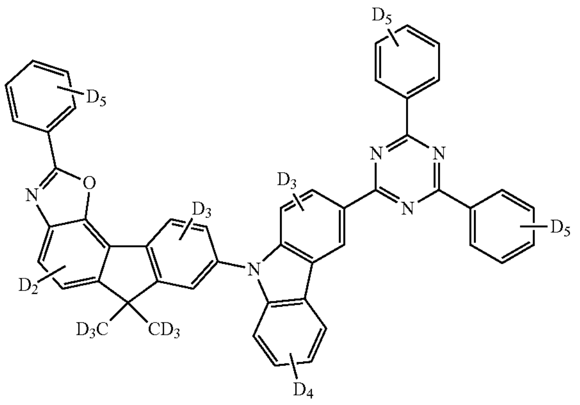
H17-D1
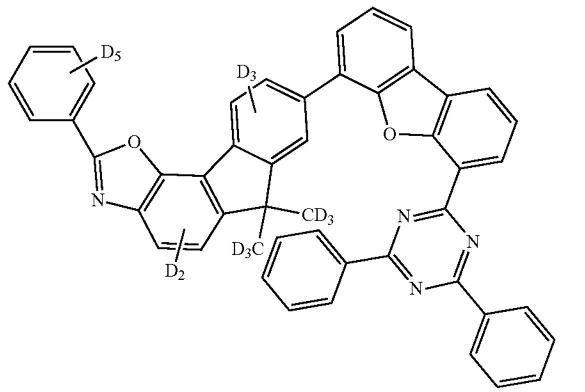
H17-D2
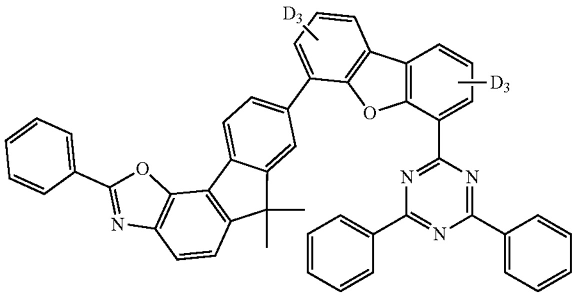
H17-D3
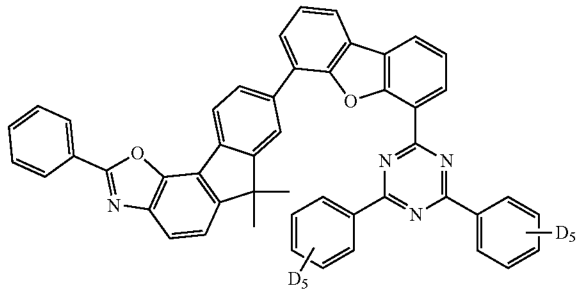
H17-D4
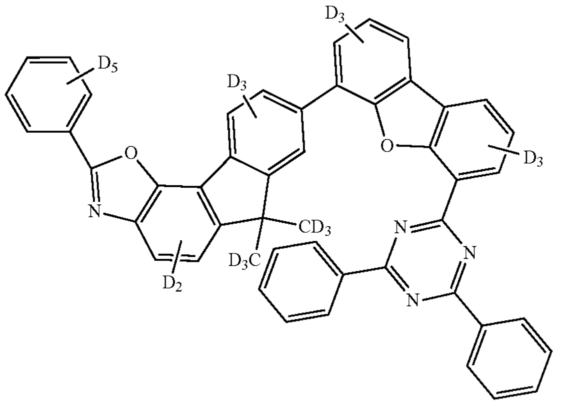
H17-D5
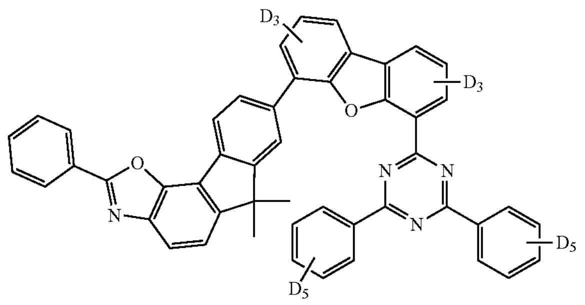
H17-D6
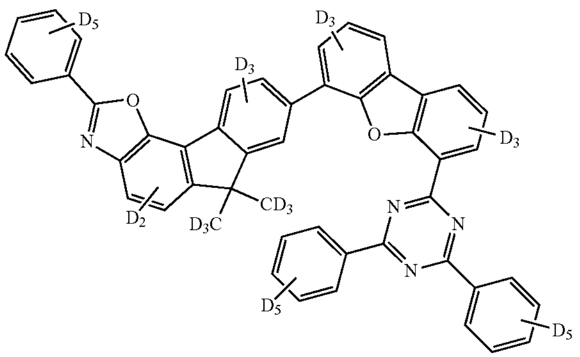

-continued
H18-D1
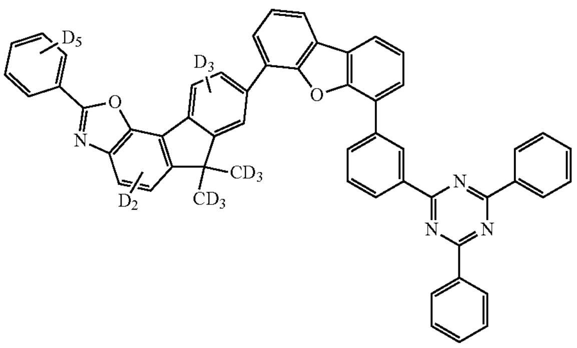
H18-D2
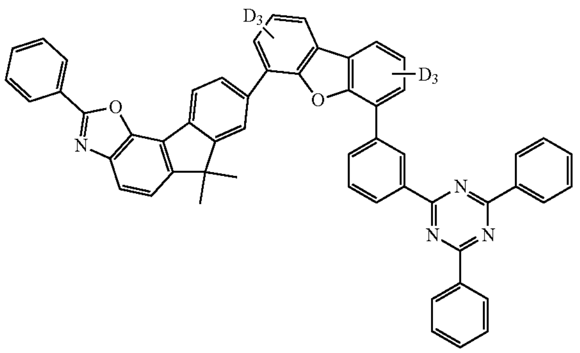
H18-D3
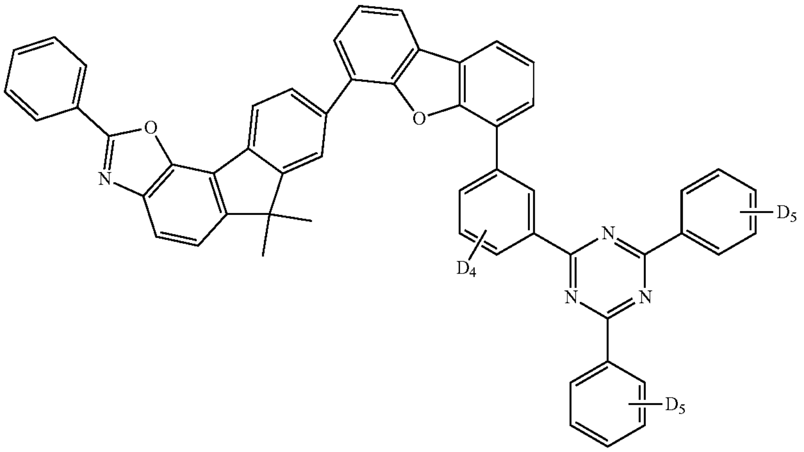
H18-D4
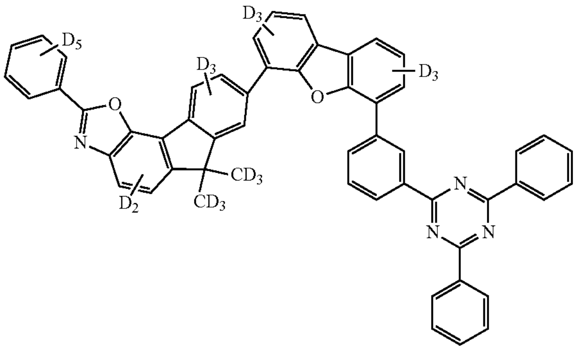
H18-D5
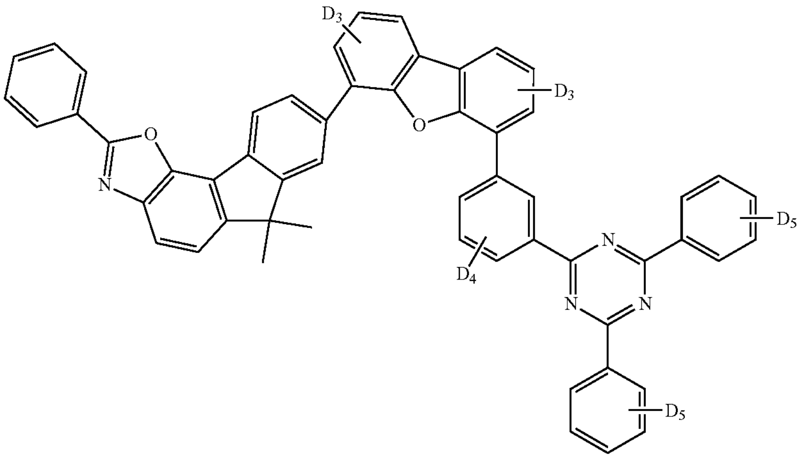

-continued
H18-D6
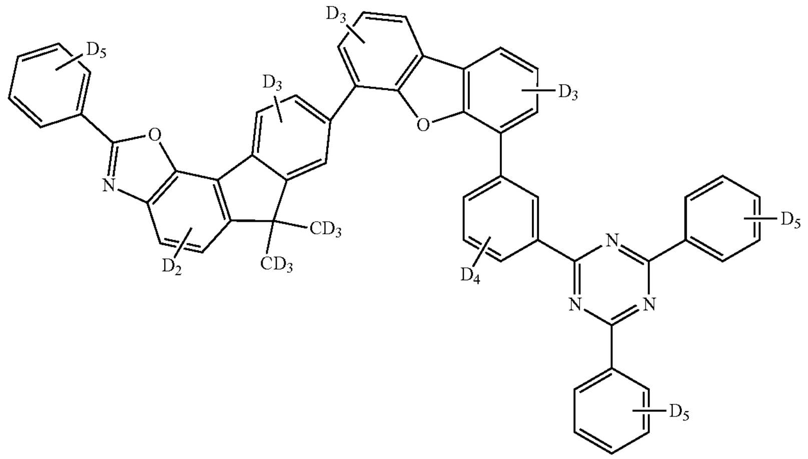
H19-D1
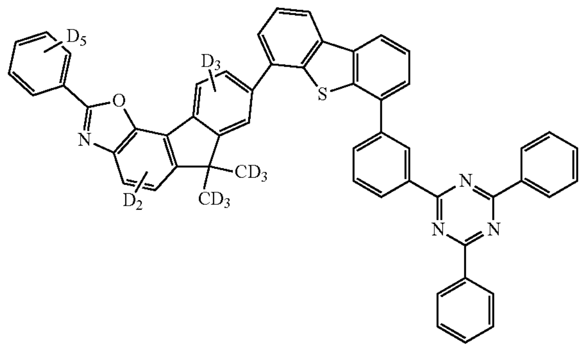
H19-D2
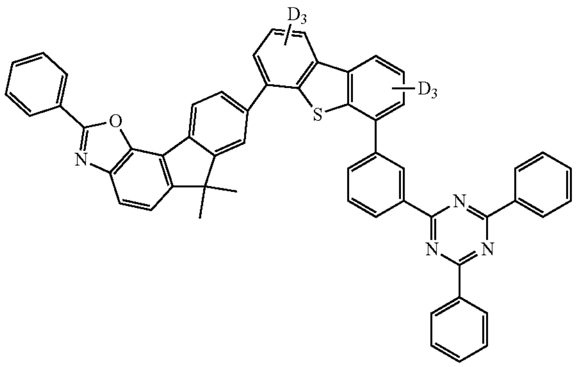
H19-D3
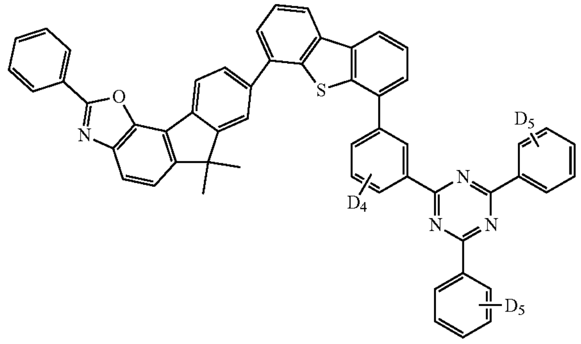
H19-D4
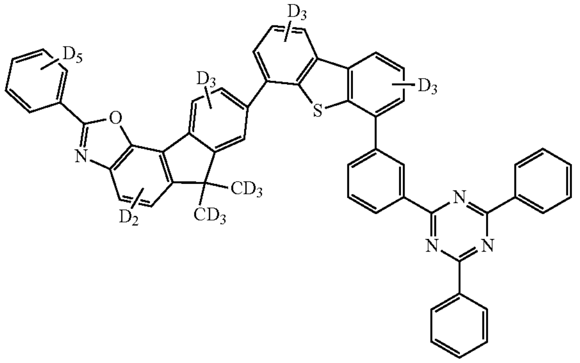
H19-D5
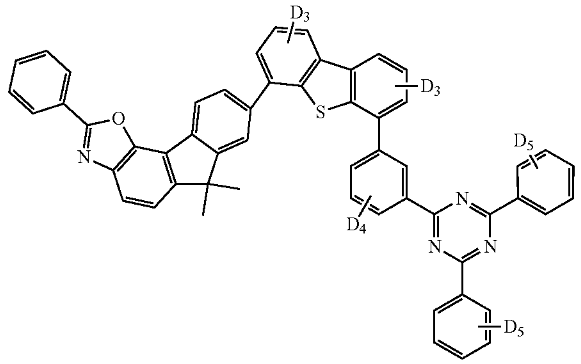
H19-D6
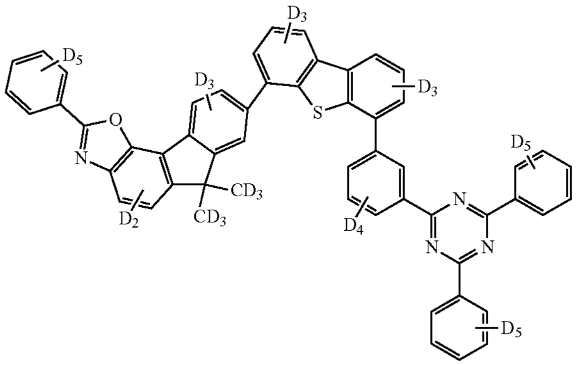

-continued
H20-D1
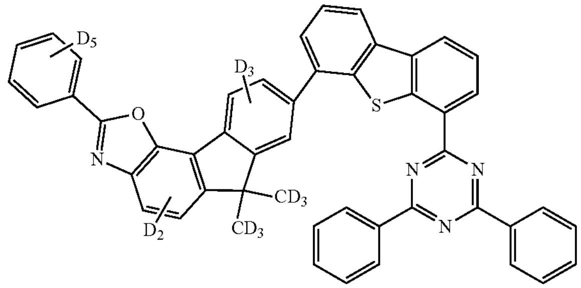
H20-D2
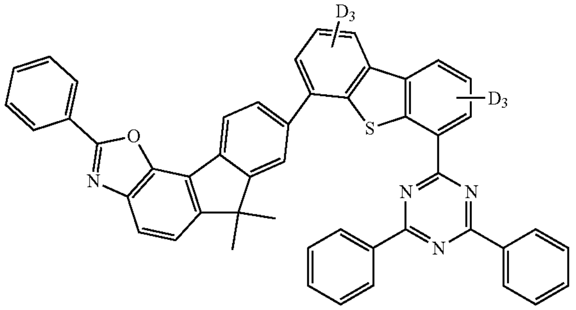
H20-D3
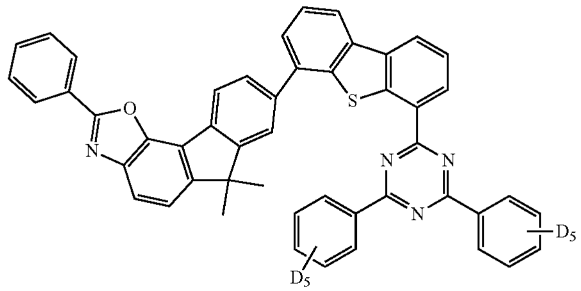
H20-D4
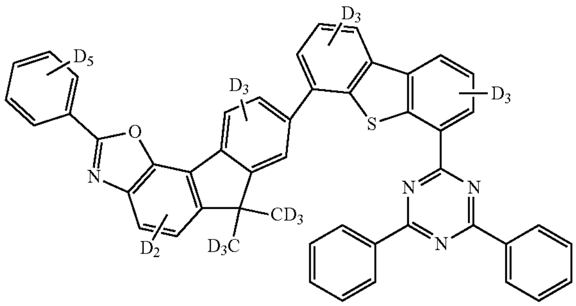
H20-D5
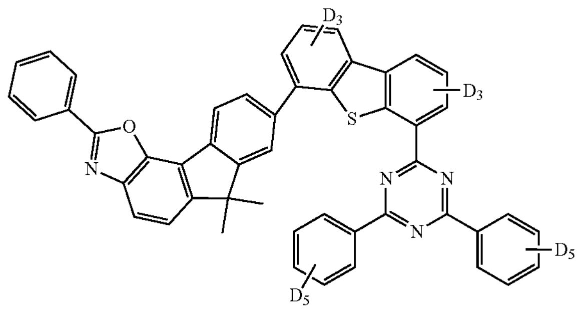
H20-D6
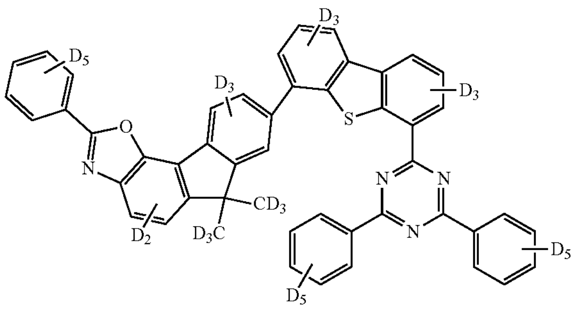
H21-D1
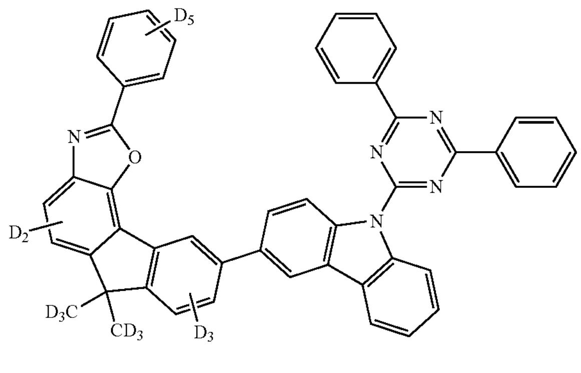
H21-D2
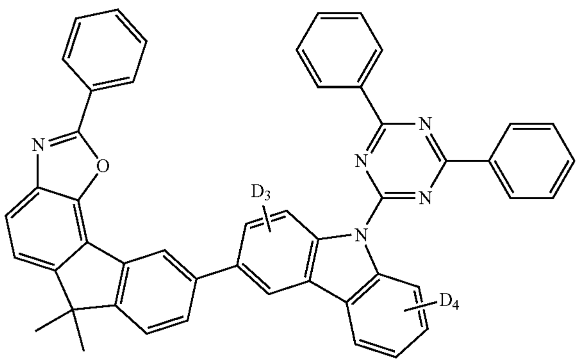

-continued
H21-D3
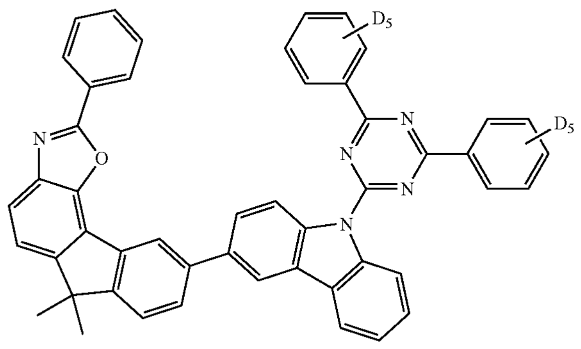
H21-D4
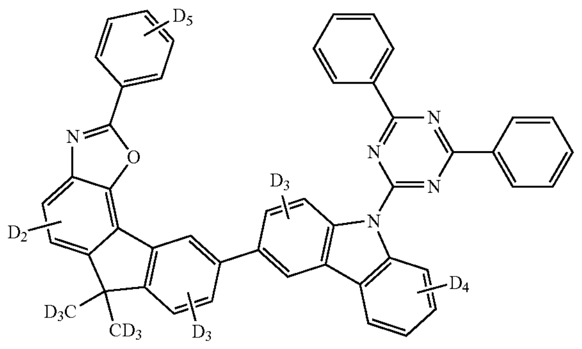
H21-D5
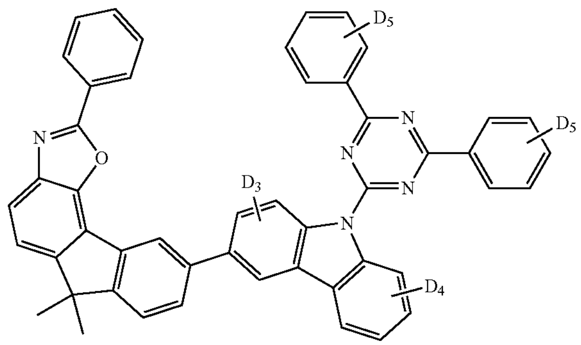
H21-D6
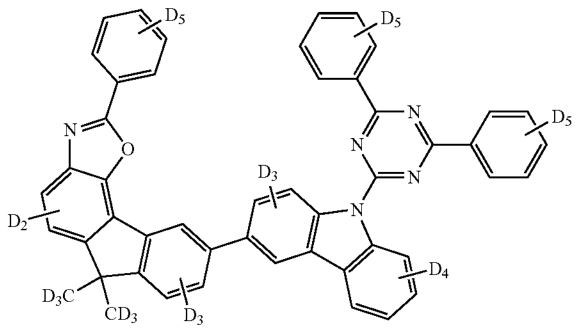
H22-D1
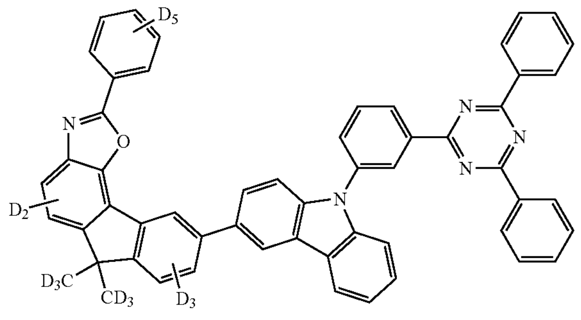
H22-D2
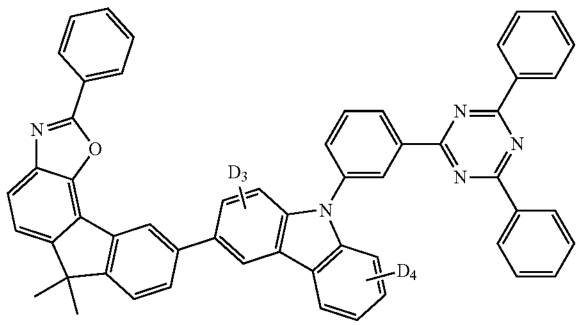
H22-D3
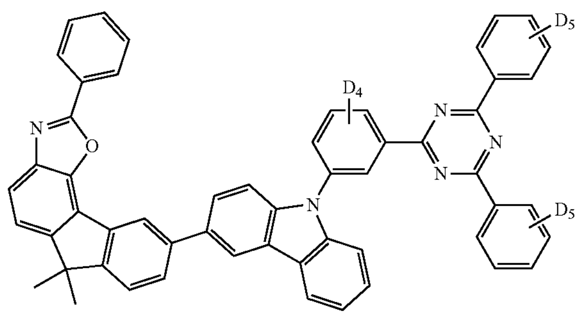
H22-D4
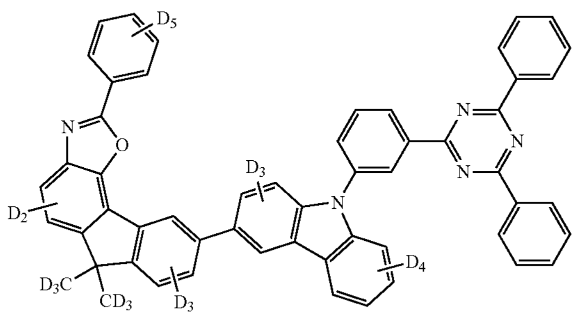

-continued
H22-D5
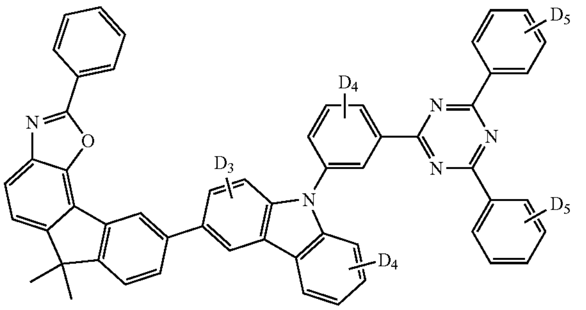
H22-D6
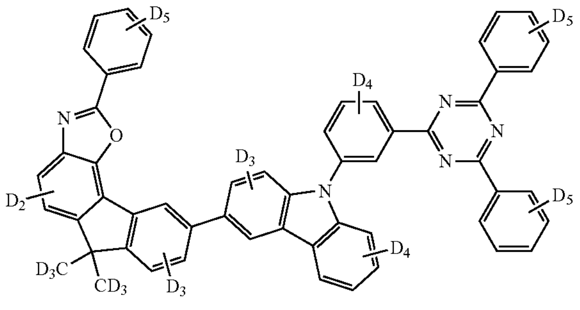
H23-D1
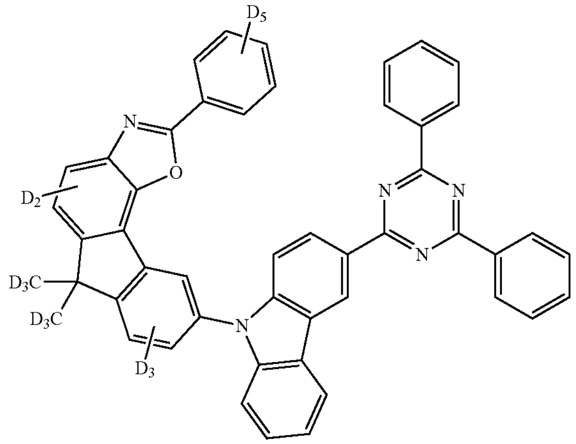
H23-D2
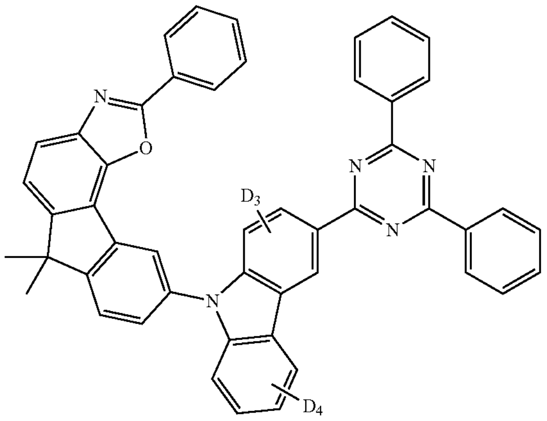
H23-D3
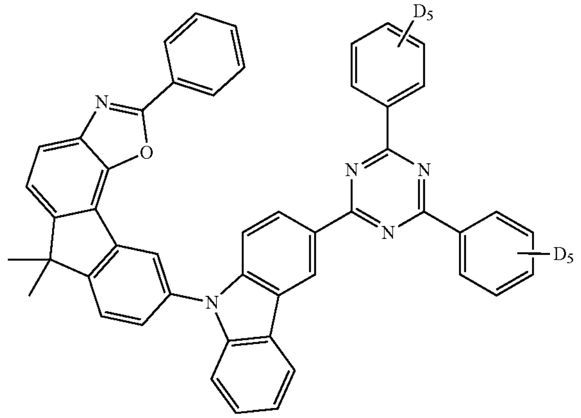

H23-D4
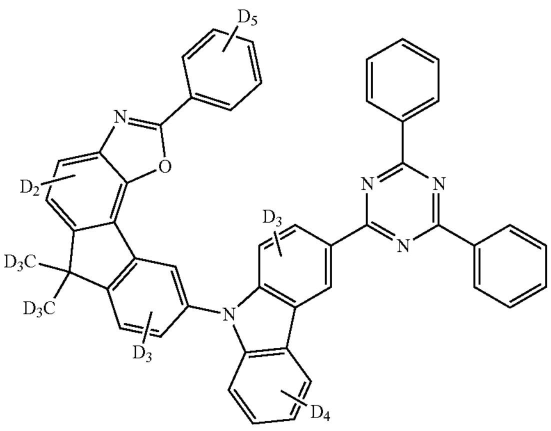
H23-D5
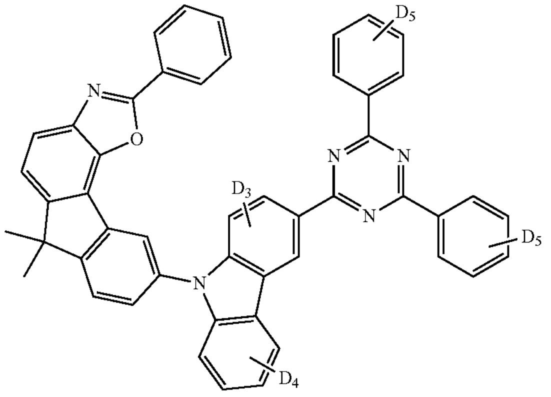
H23-D6
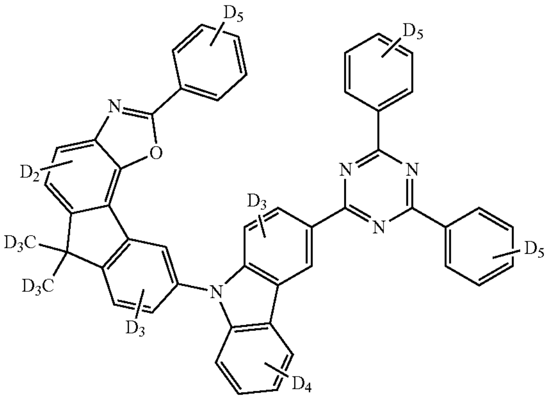
H24-D1
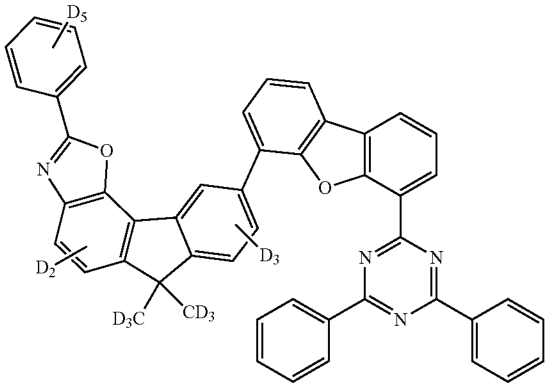
H24-D2
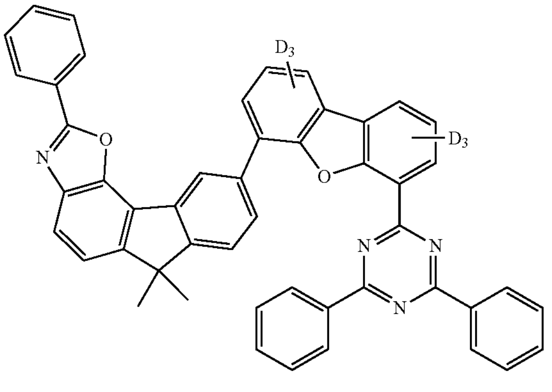
H24-D3
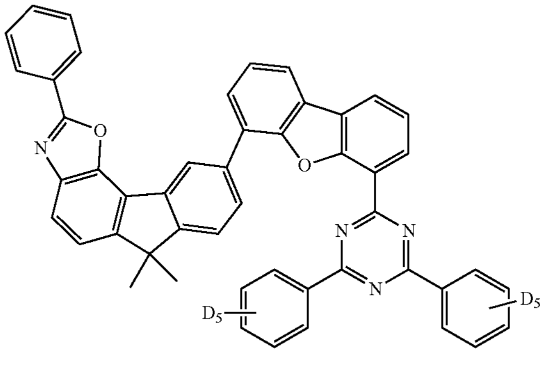

-continued
H24-D4
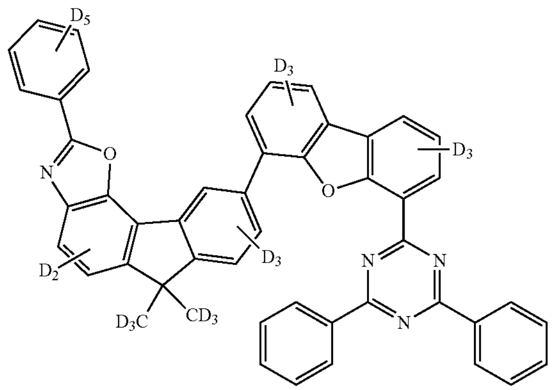
H24-D5
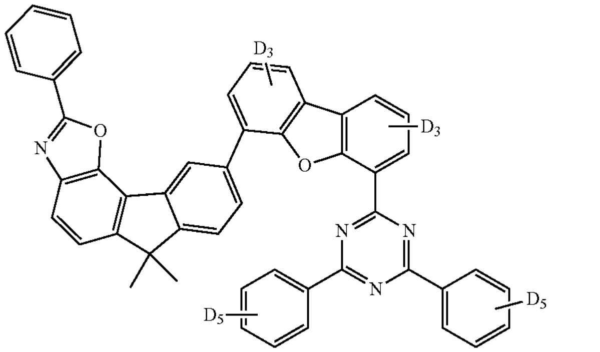
H24-D6
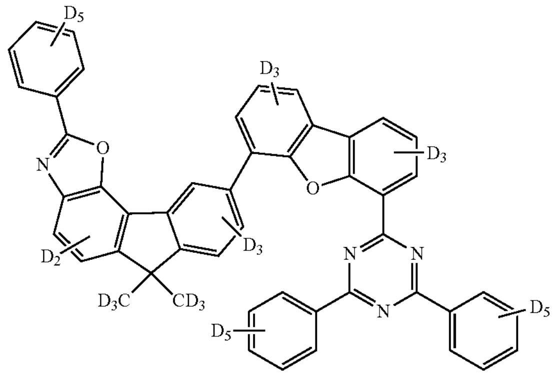
H25-D1
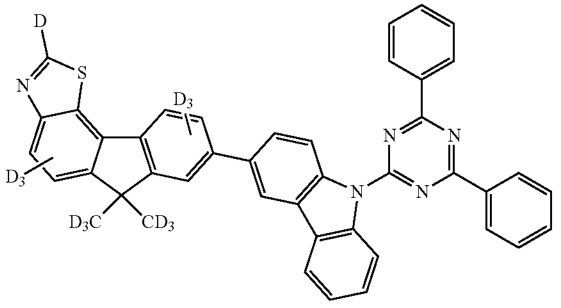
H25-D2
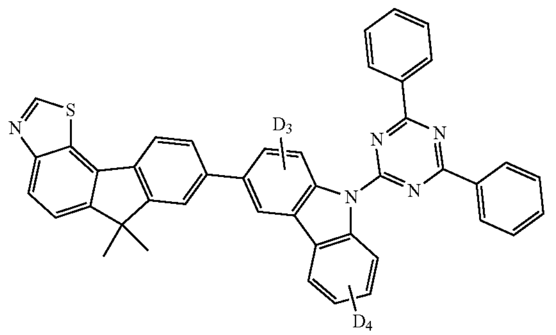
H25-D-3
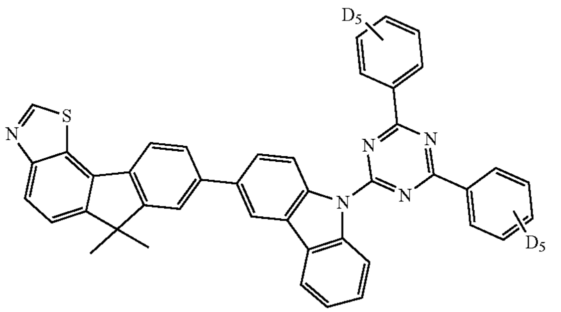
H25-D4
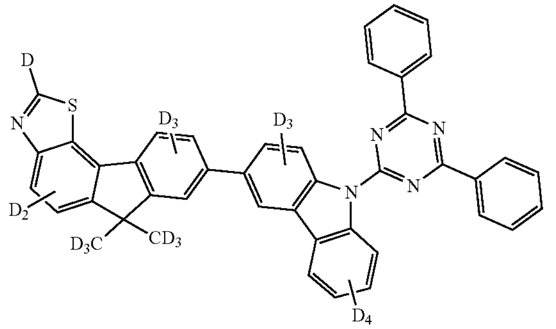
H25-D5
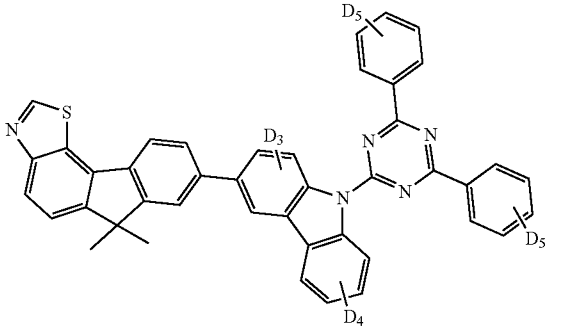

-continued
H25-D6
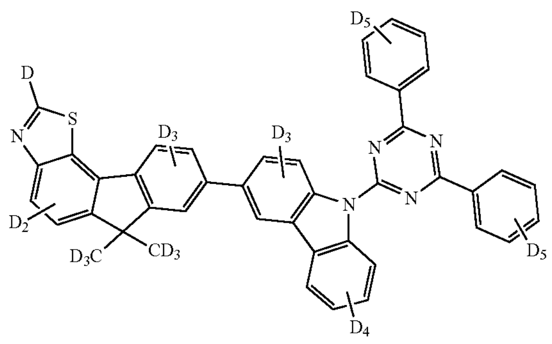
H26-D1
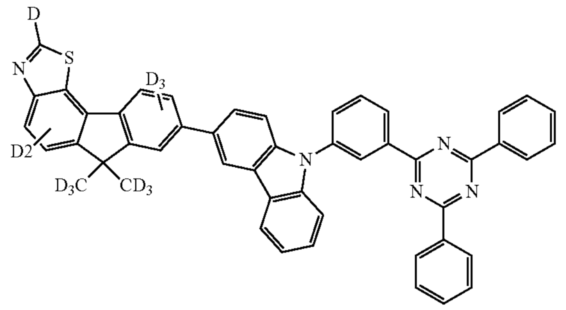
H26-D2
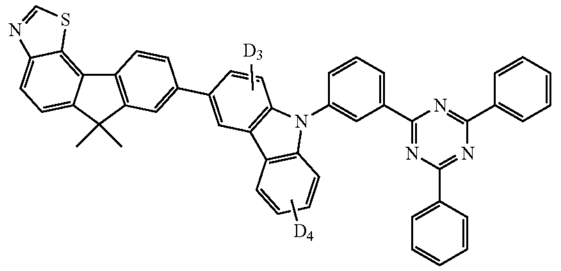
H26-D3
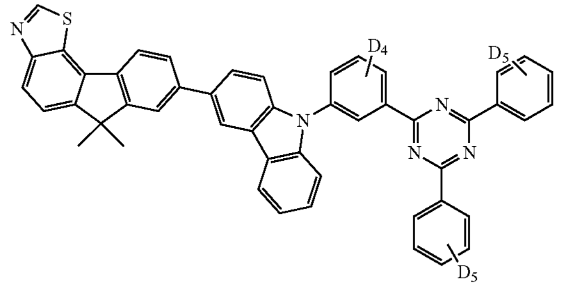
H26-D4
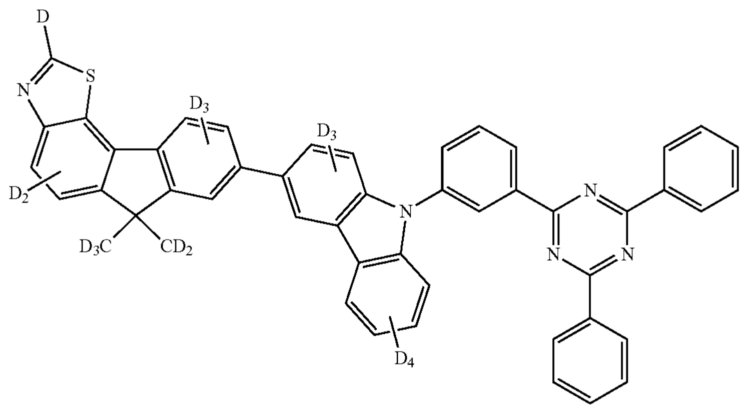
H26-D5
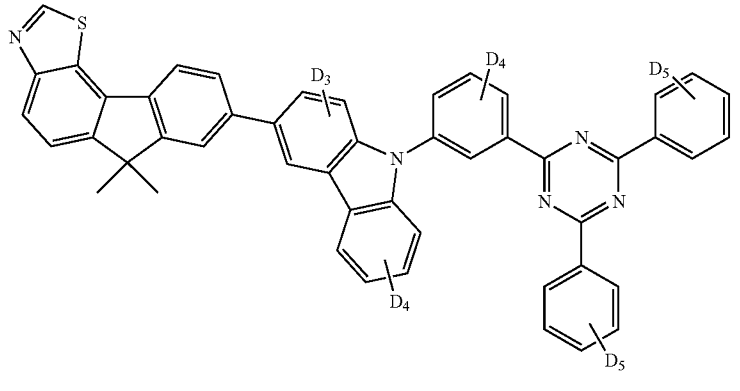

-continued
H26-D6
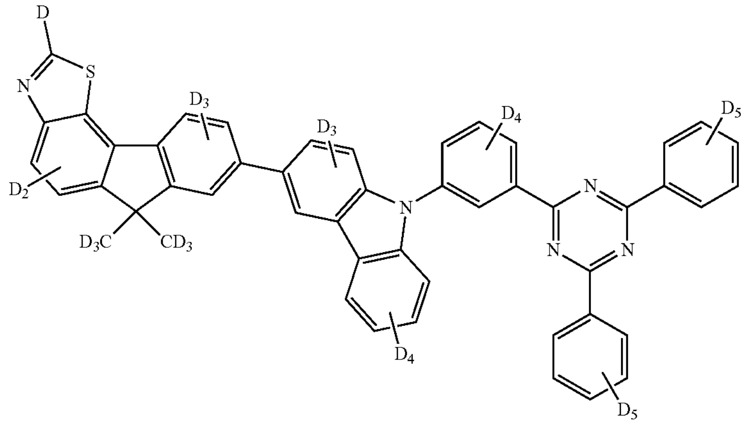
H27-D1
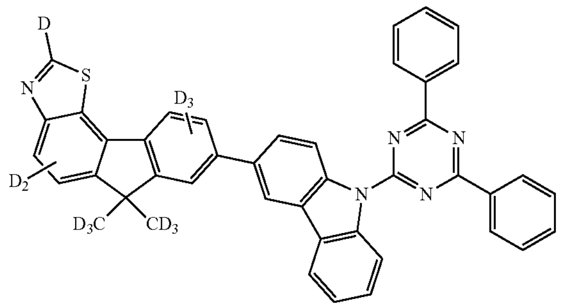
H27-D2
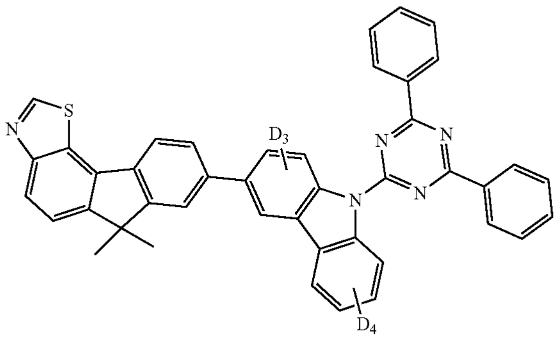
H27-D3
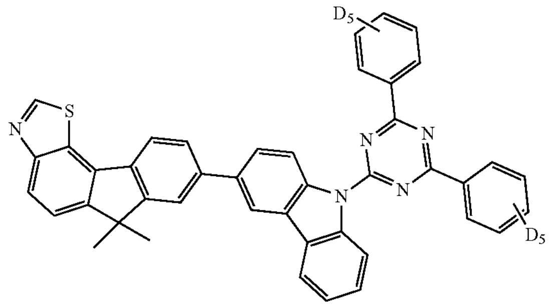
H27-D4
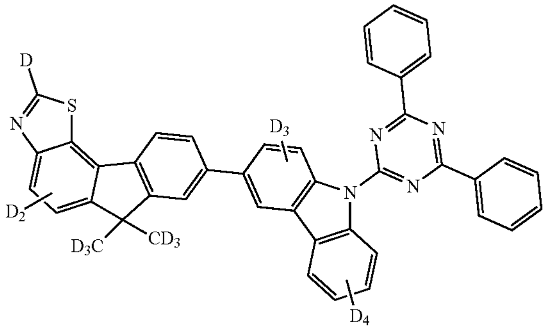
H27-D5
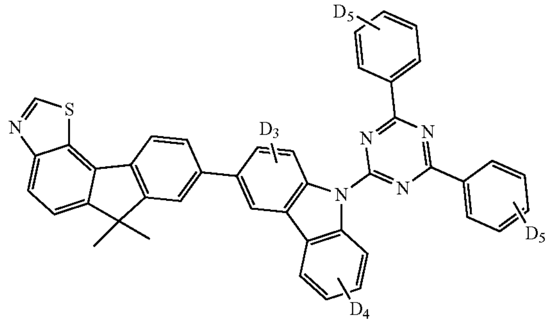
H27-D6
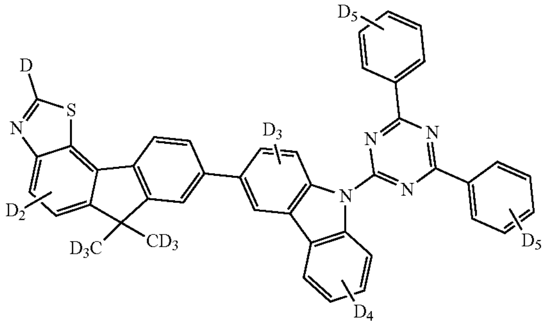

-continued
H28-D1
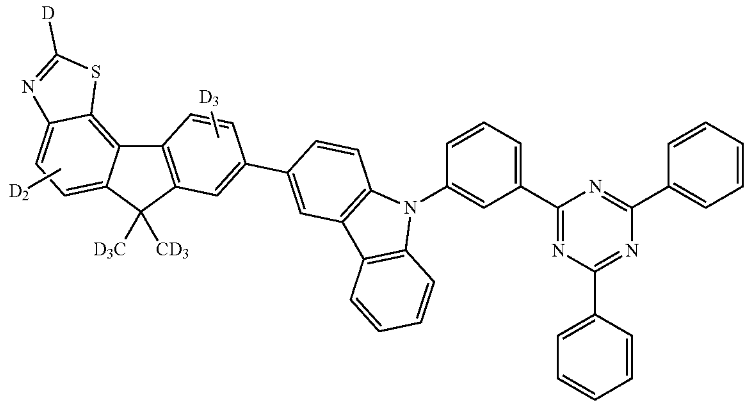
H28-D2
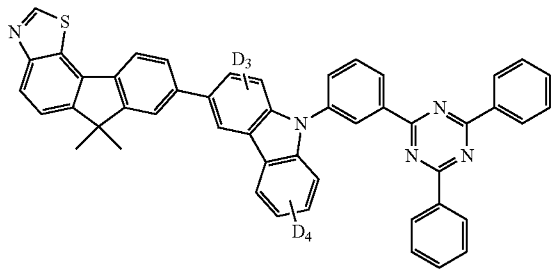
H28-D3
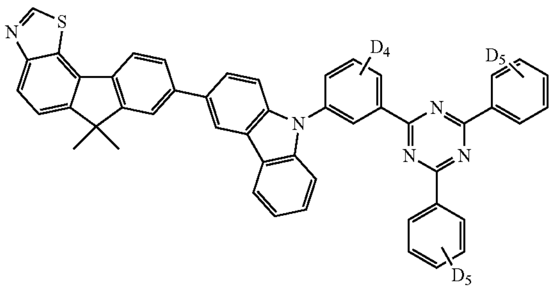
H28-D4
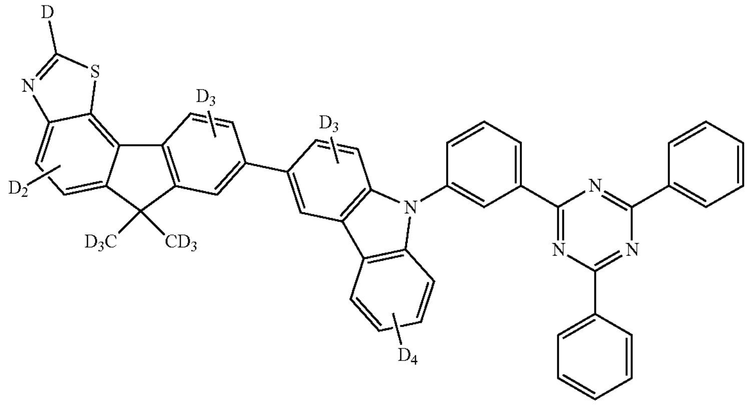
H28-D5
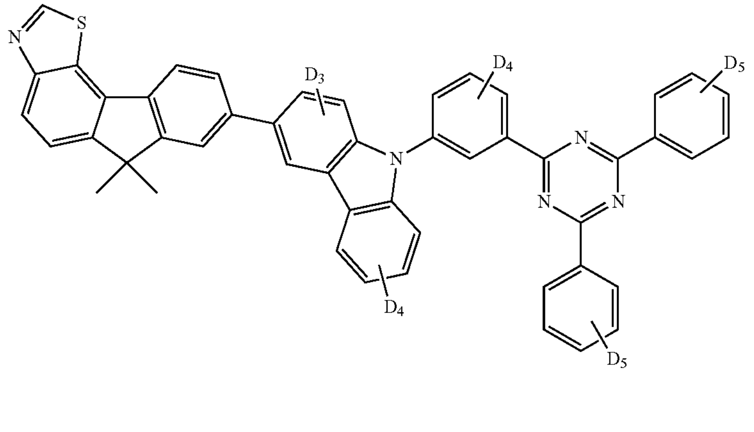

-continued
H28-D6
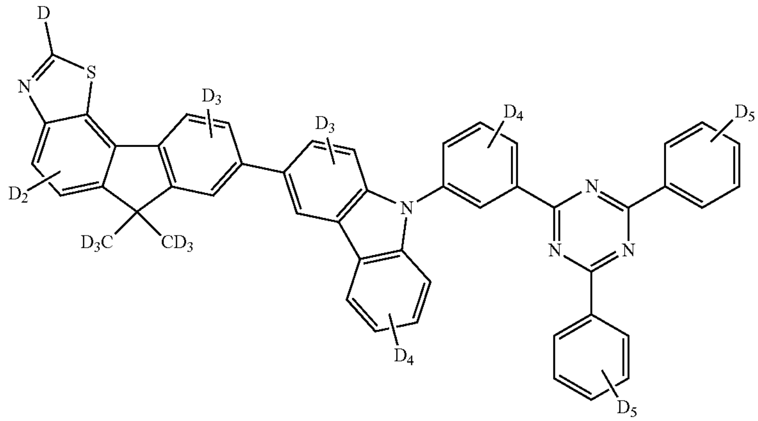
H29-D1
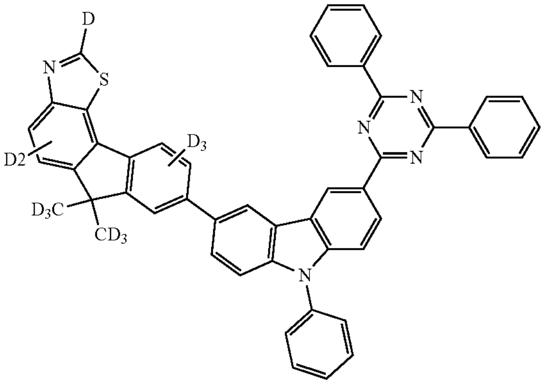
H29-D2
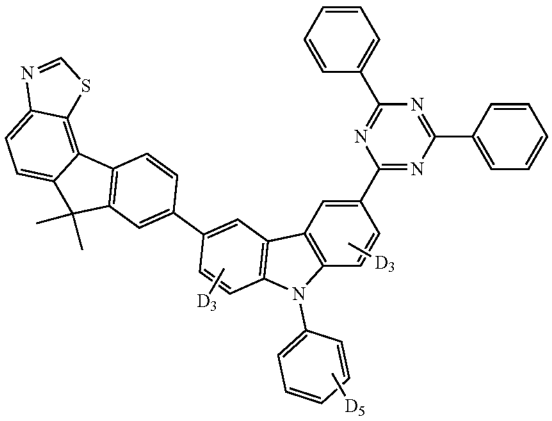
H29-D3
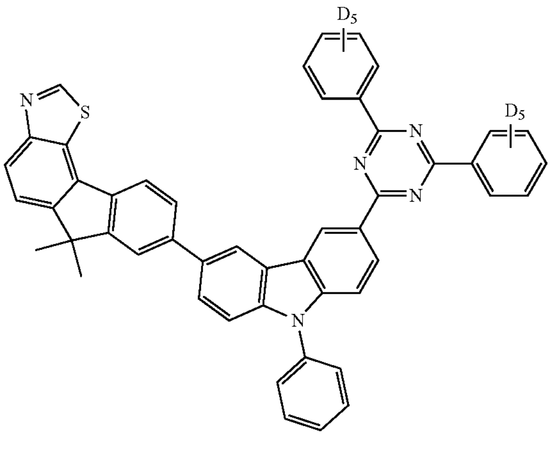
H29-D4
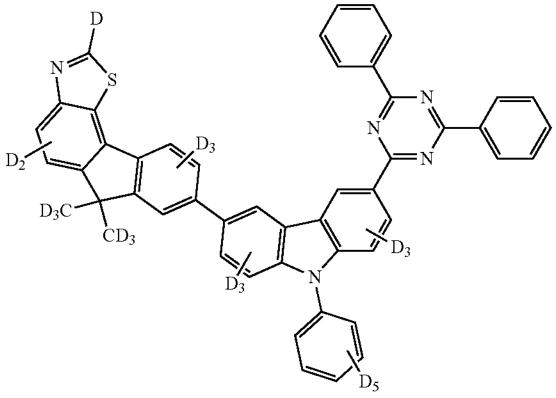

-continued
H29-D5
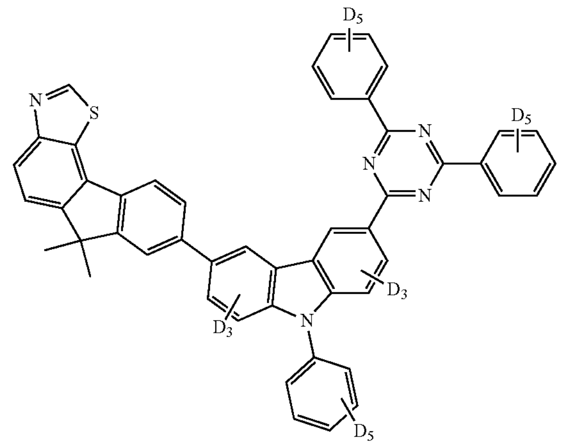
H29-D6
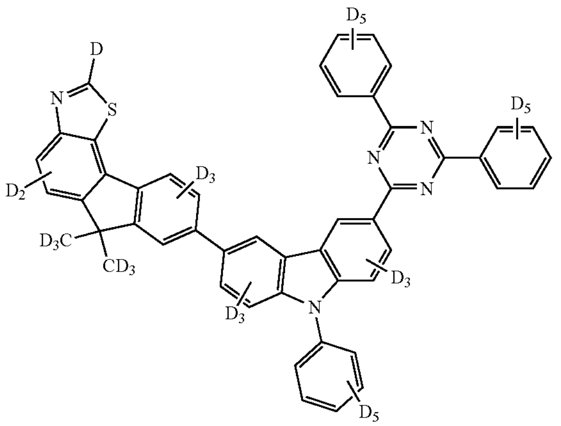
H30-D1
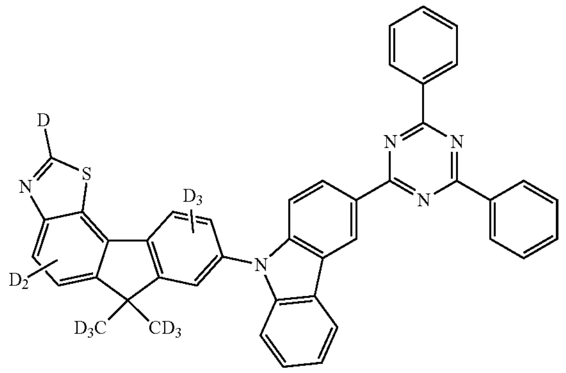
H30-D2
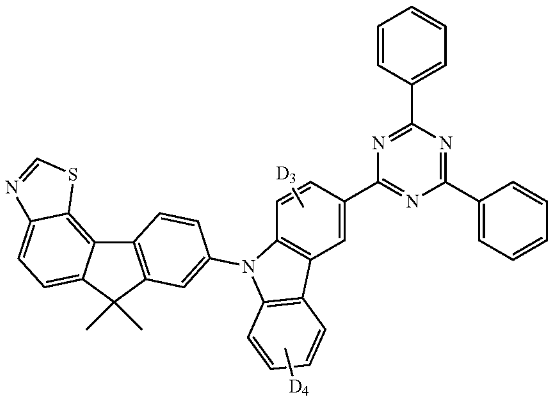
H30-D3
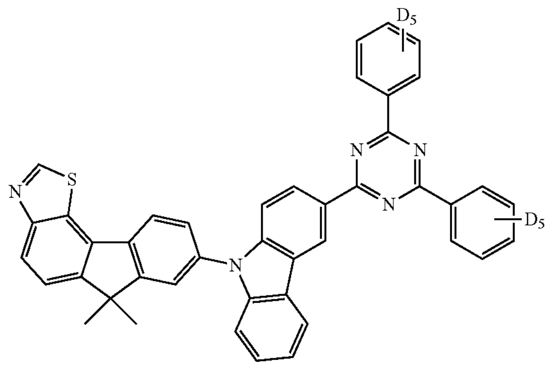
H30-D4
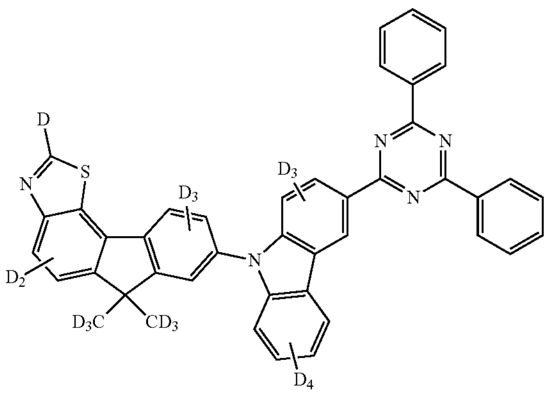

-continued
H30-D5
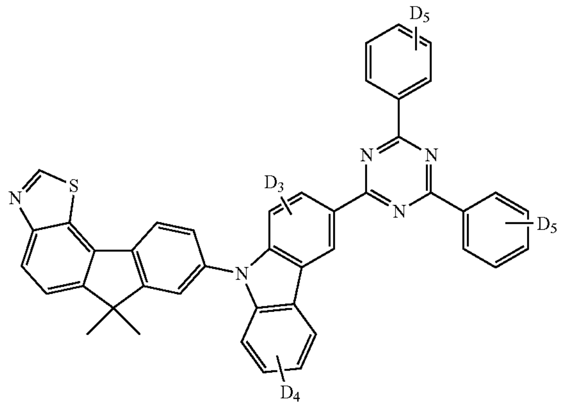
H30-D6
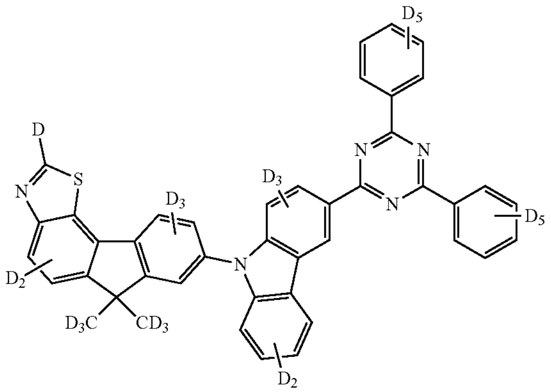
-continued
H31-D1
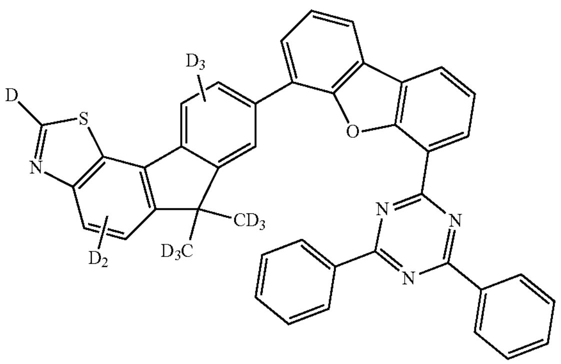
H31-D3
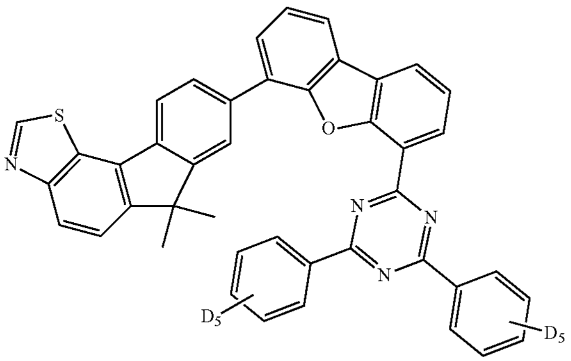
H31-D2
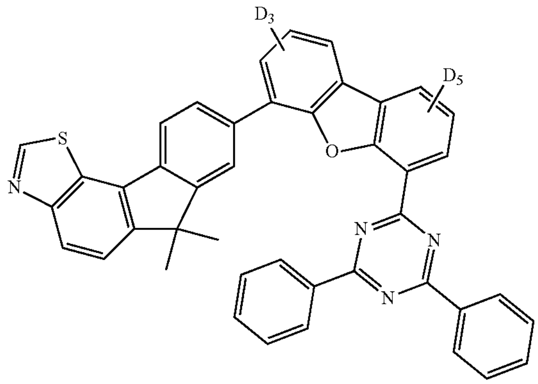
H31-D4
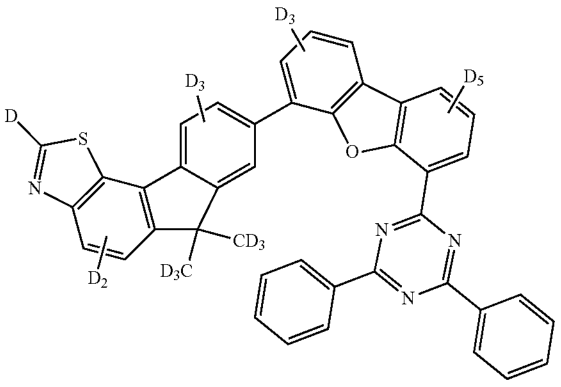

-continued
H31-D5
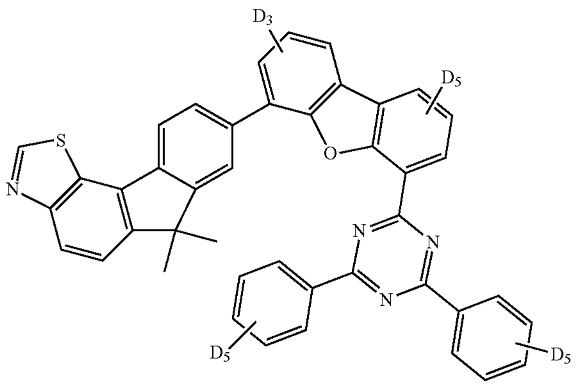
H31-D6
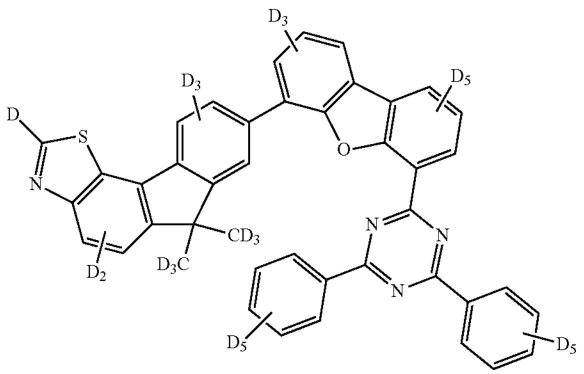
H32-D1
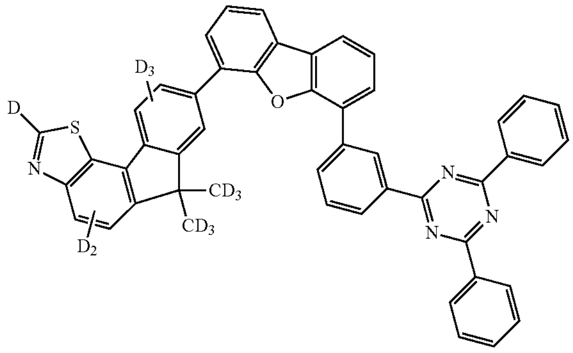
H32-D2
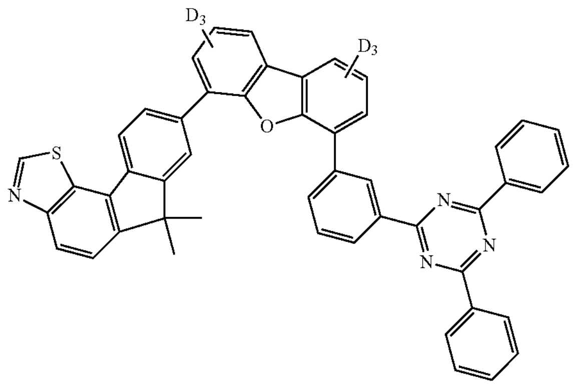
-continued
H32-D3
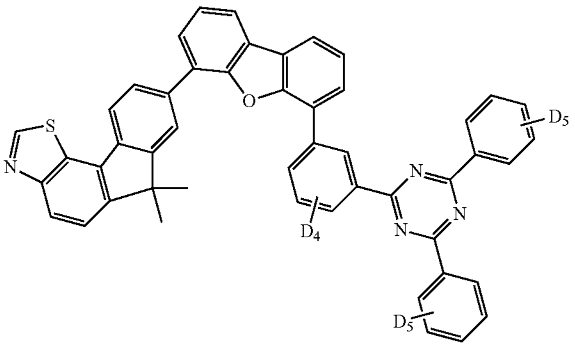
H32-D4
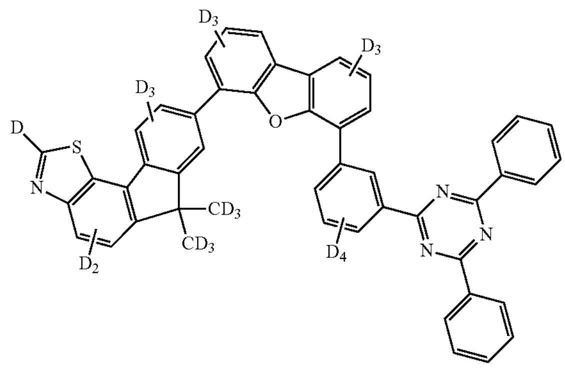
H32-D5
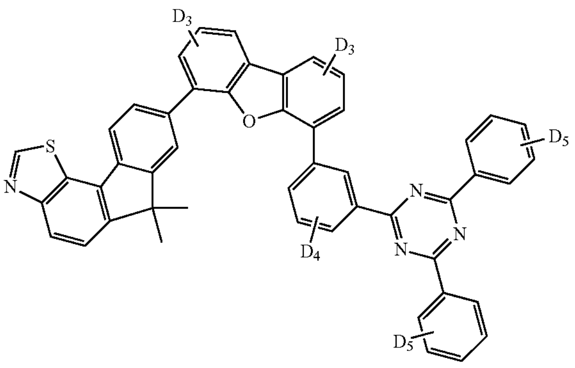
H32-D6
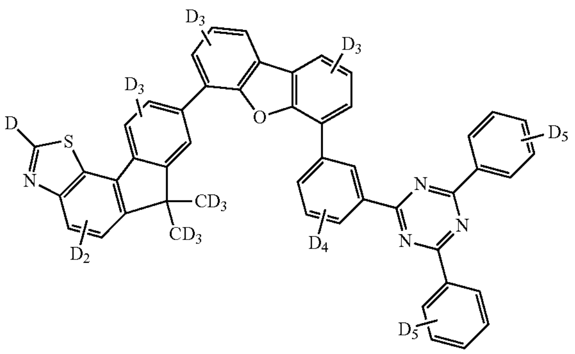

-continued
H33-D1
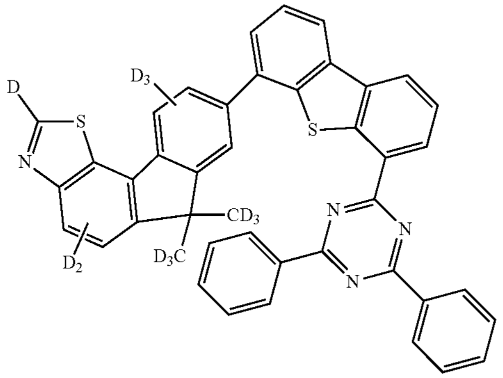
H33-D2
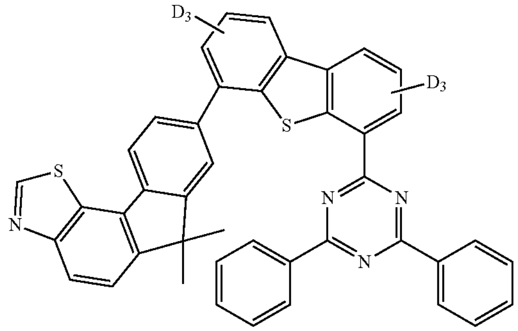
H33-D3
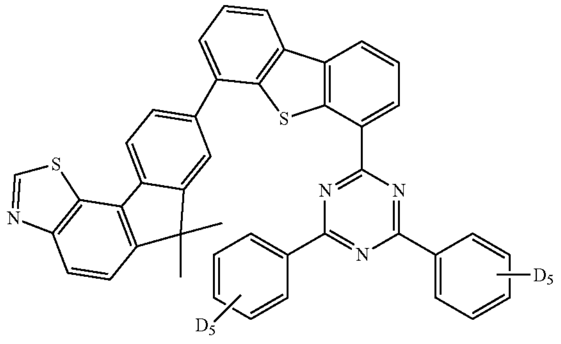
H33-D4
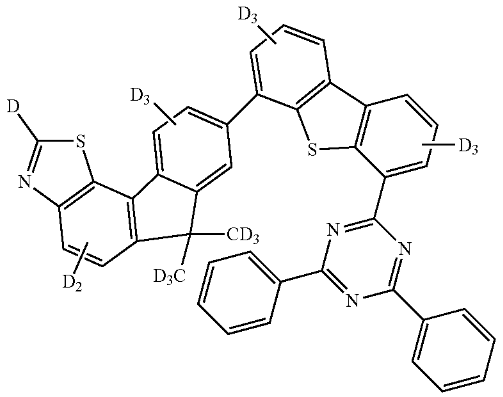
-continued
H33-D5
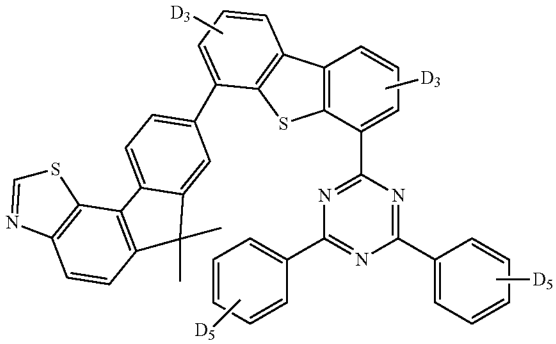
H33-D6
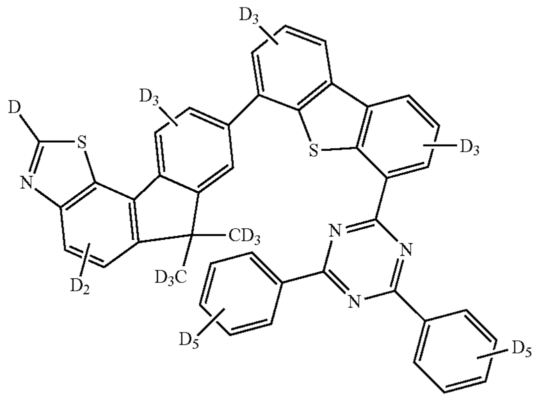
H34-D1
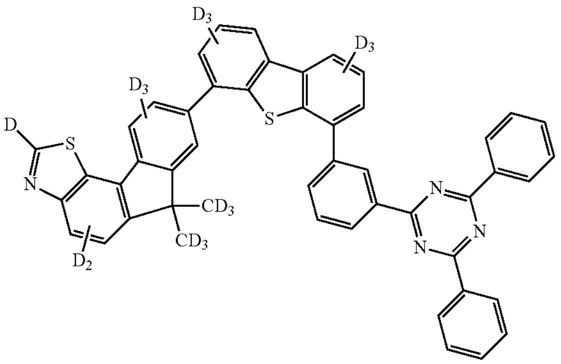
H34-D2
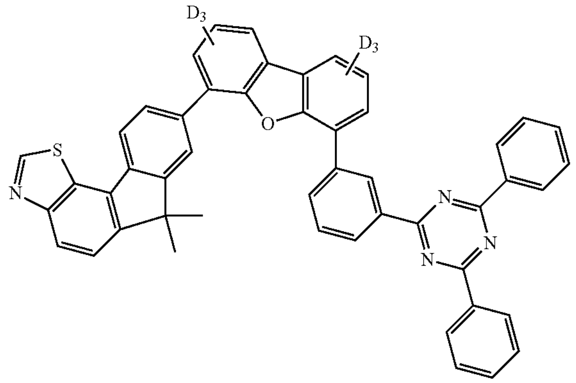

-continued
H34-D3
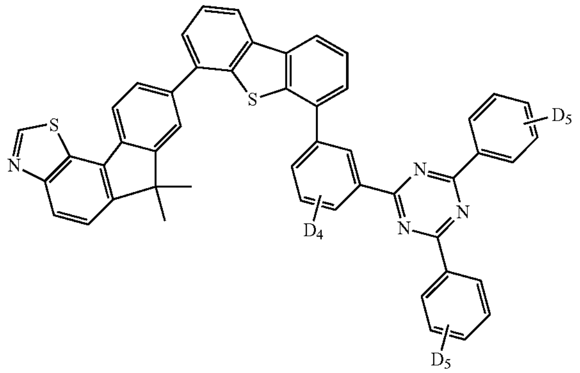
H34-D4
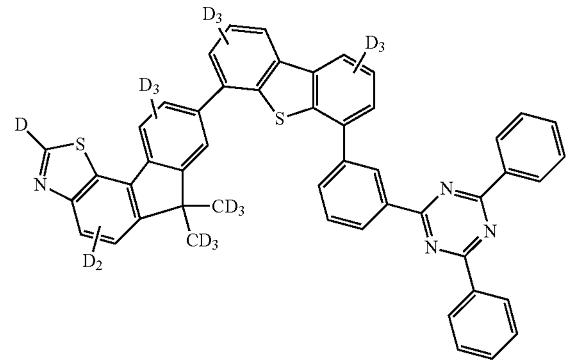
H34-D5
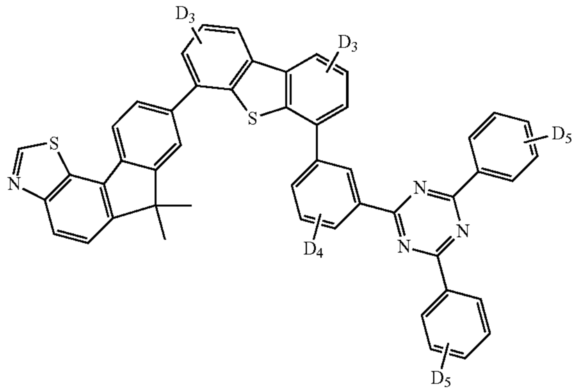
H34-D6
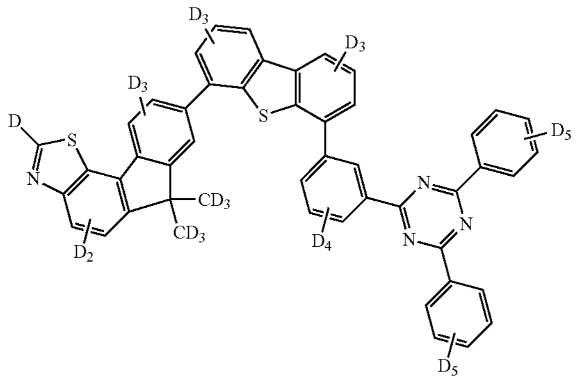
-continued
H35-D1
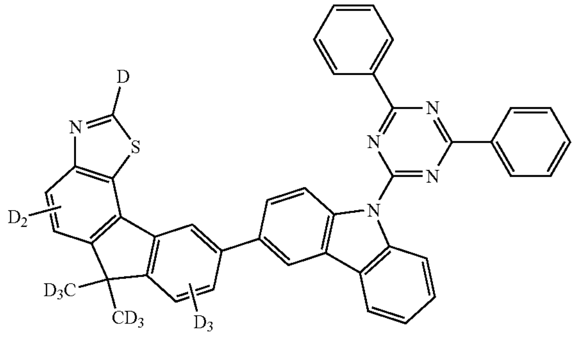
H35-D2
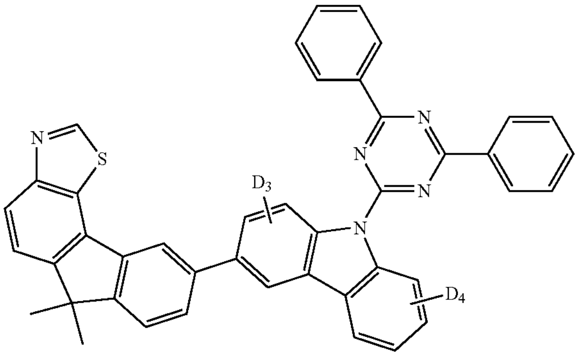
H35-D3
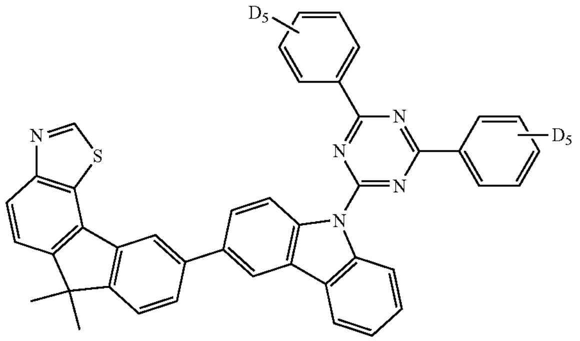
H35-D4
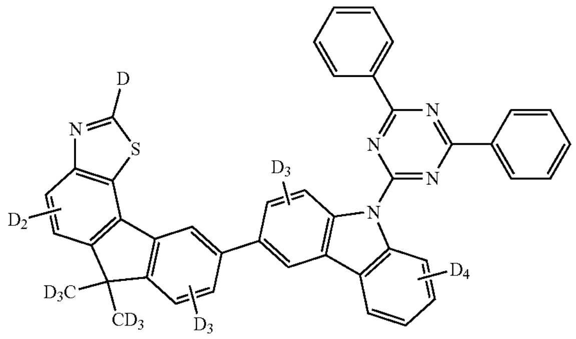

-continued
H35-D5
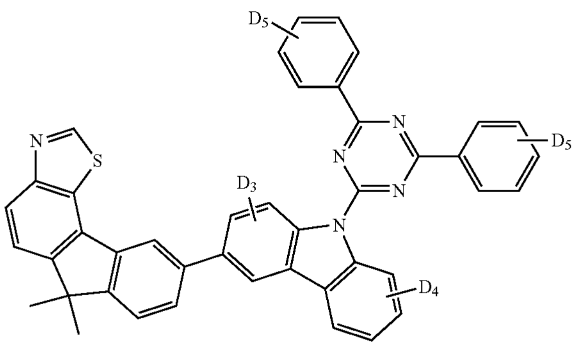
H35-D6
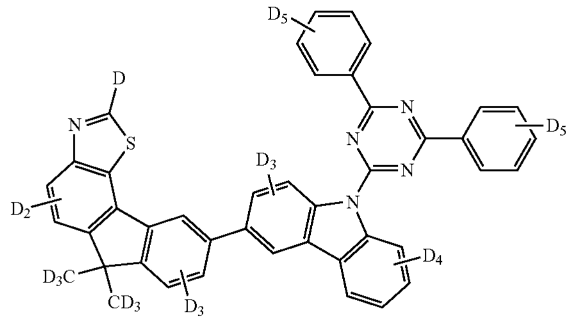
H36-D1
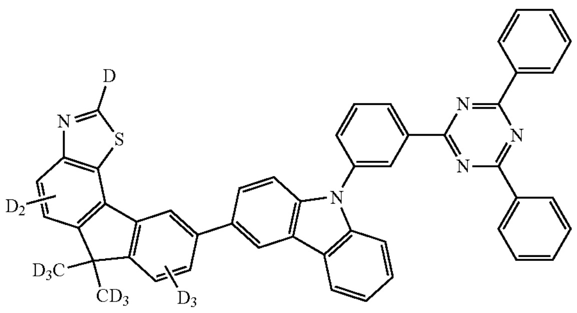
H36-D2
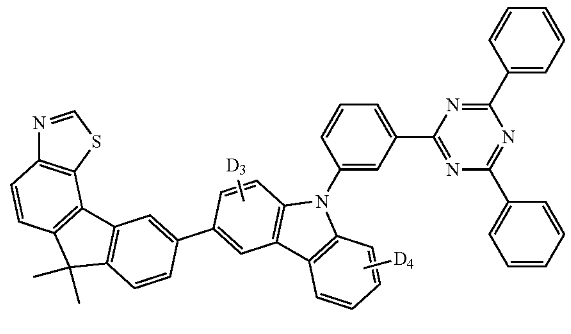
-continued
H36-D3
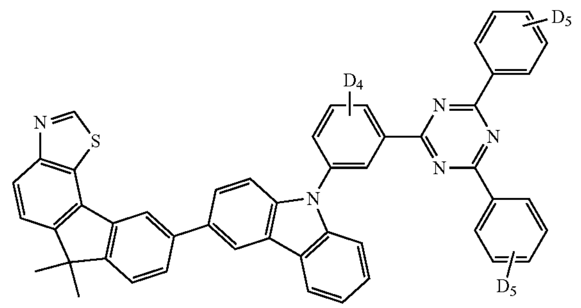
H36-D4
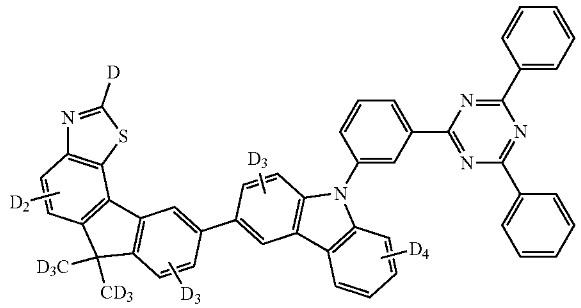
H36-D5
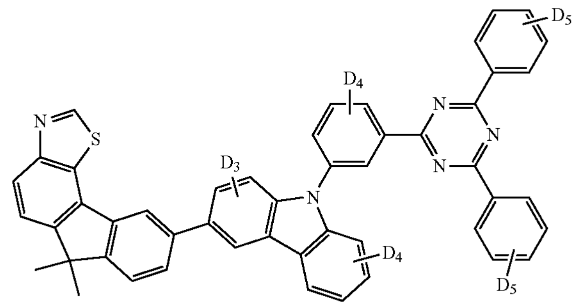
H36-D6
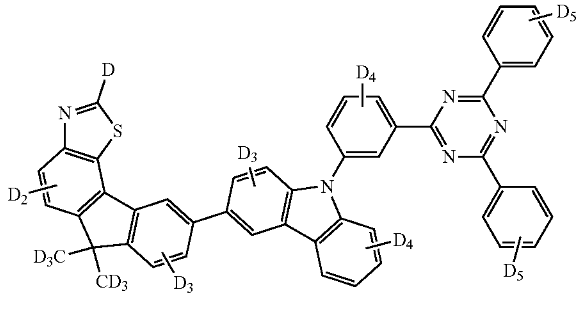

-continued
H37-D1
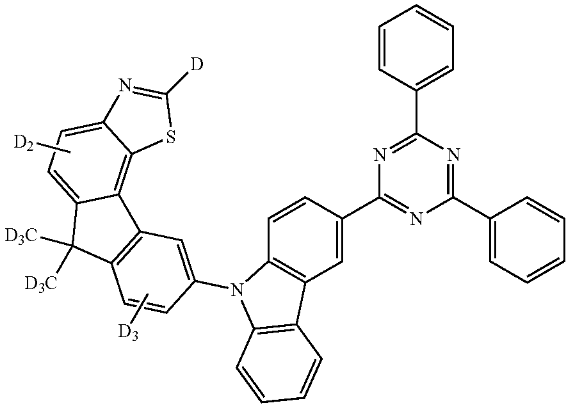
H37-D2
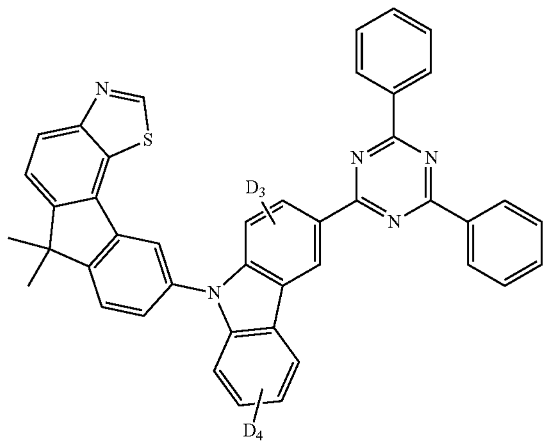
H37-D3
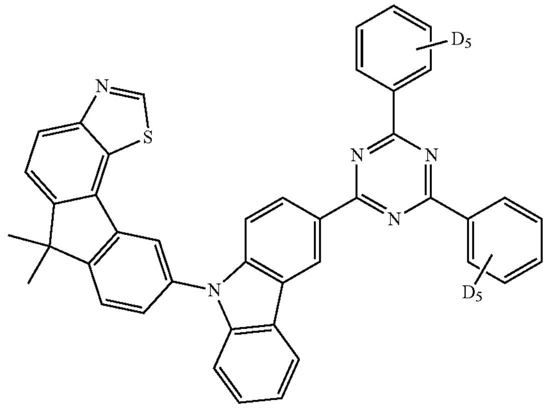
-continued
H37-D4
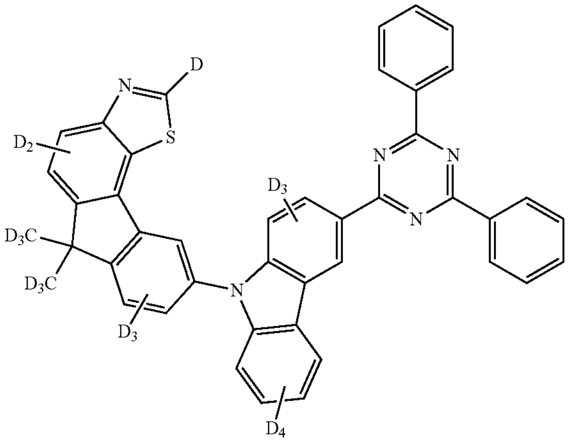
H37-D5
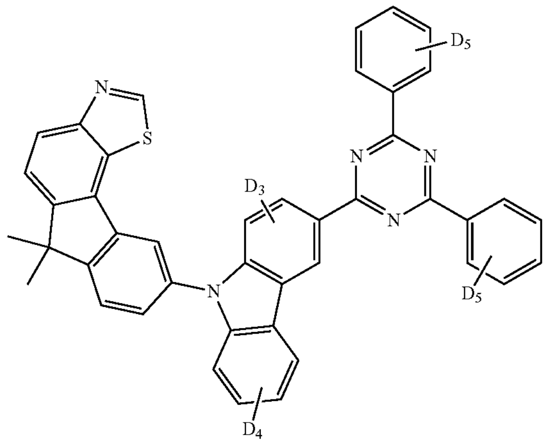
H37-D6
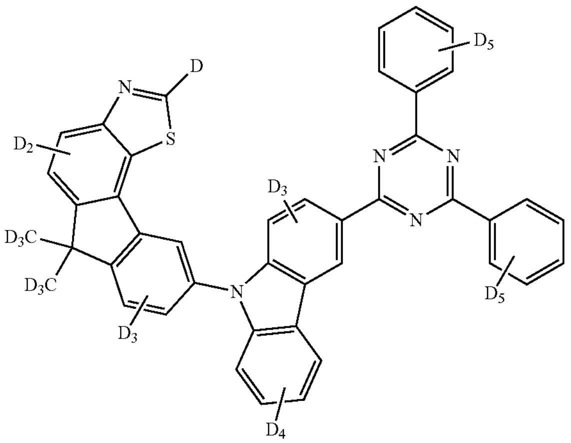

-continued
H38-D1
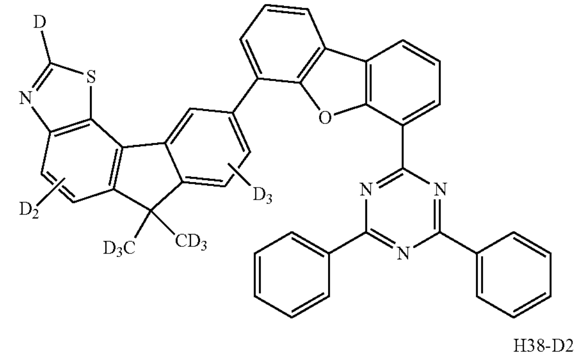
H38-D2
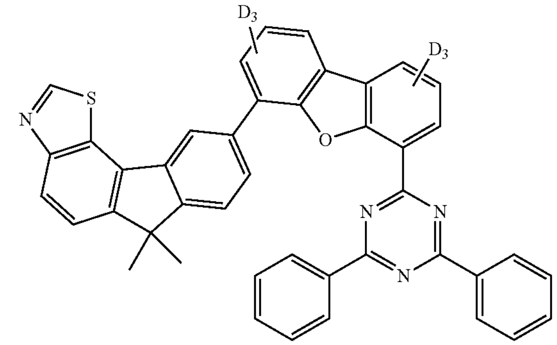
H38-D3
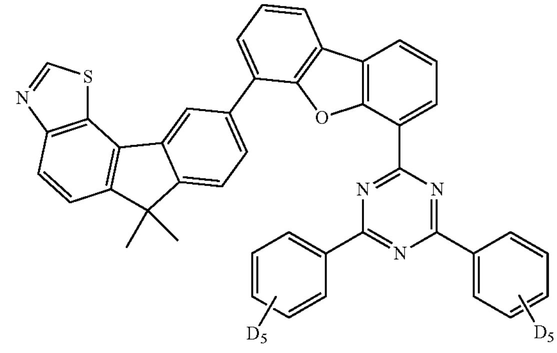
H38-D4
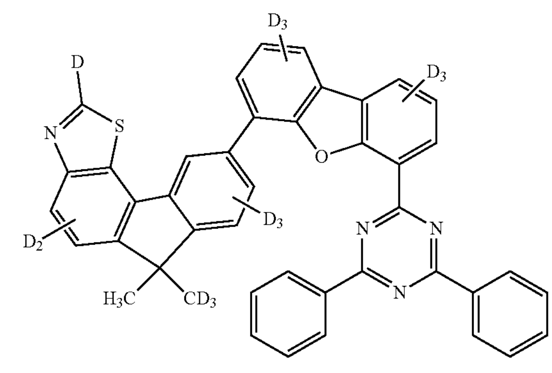
-continued
H38-D5
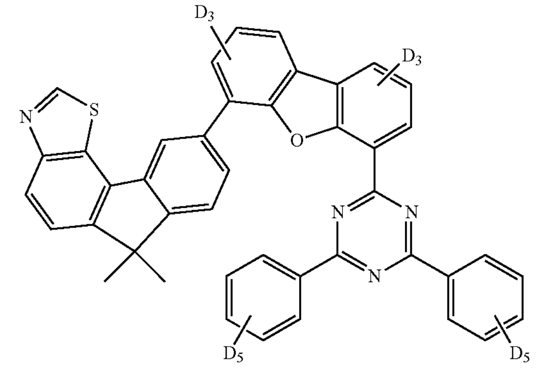
H38-D6
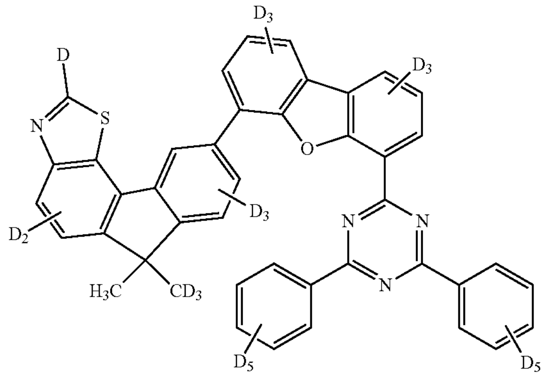
H39-D1
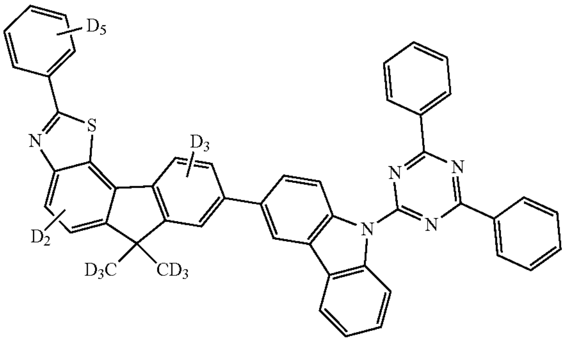
H39-D2
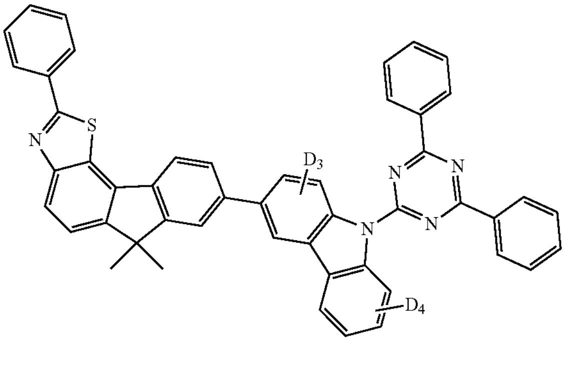

-continued
H39-D3
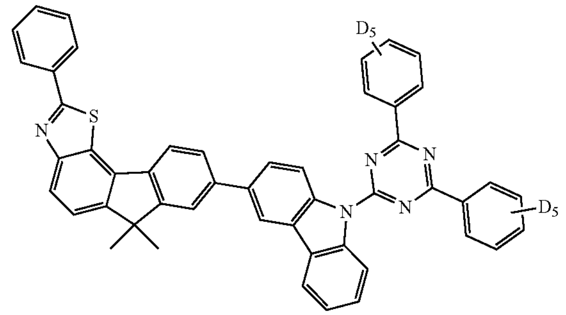
H39-D4
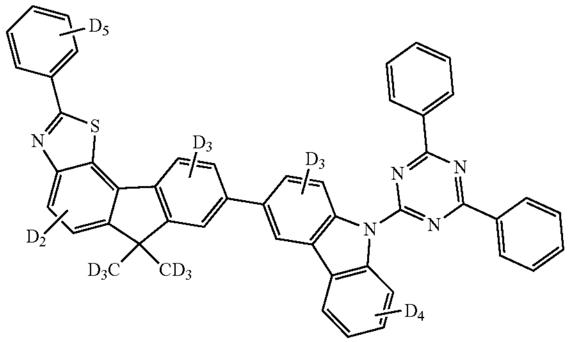
H39-D5
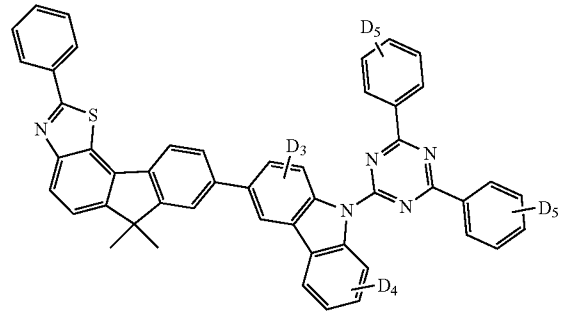
H39-D6
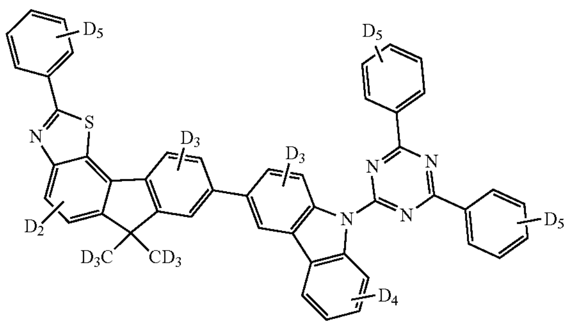
-continued
H40-D1
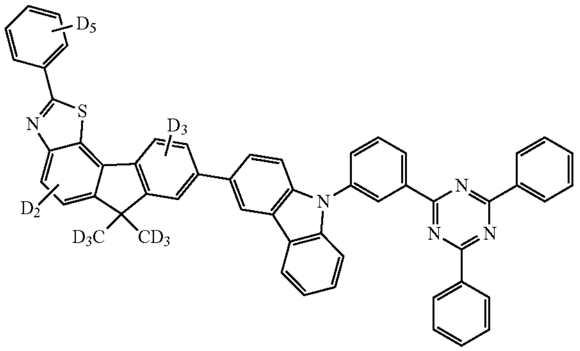
H40-D2
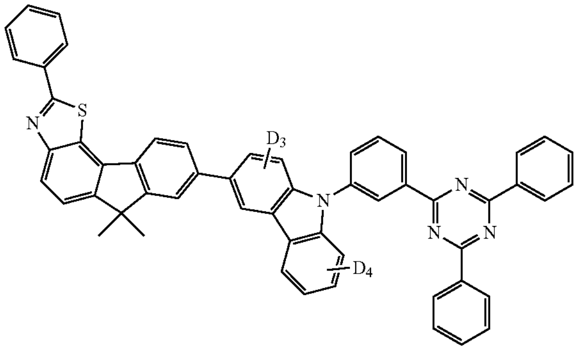
H40-D3
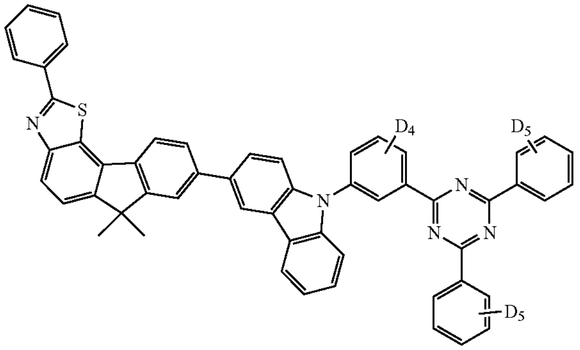
H40-D4
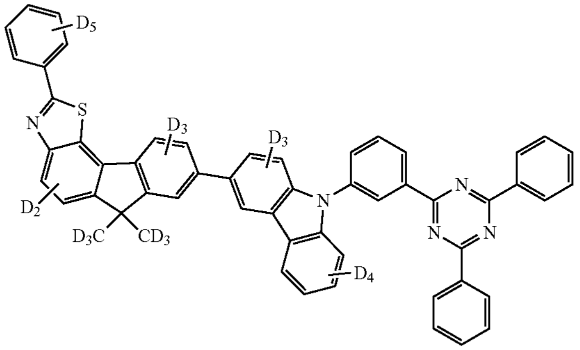

-continued
H40-D5
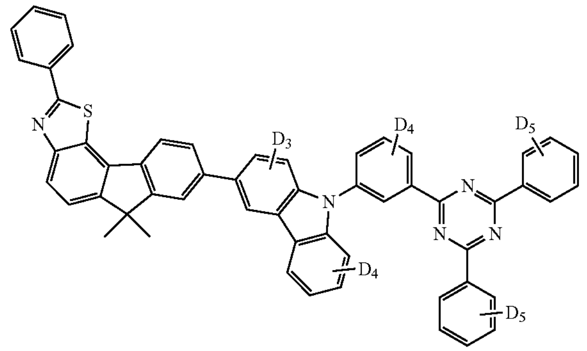
H40-D6
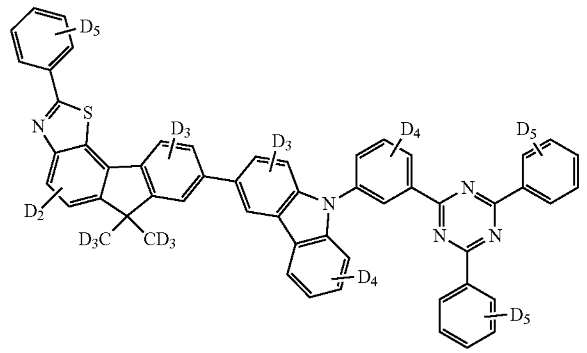
H41-D1
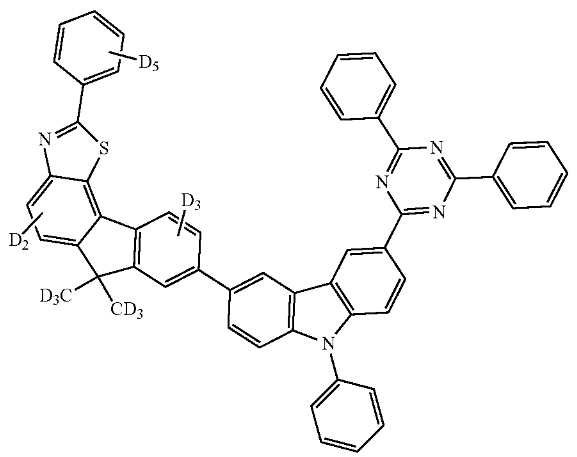
-continued
H41-D2
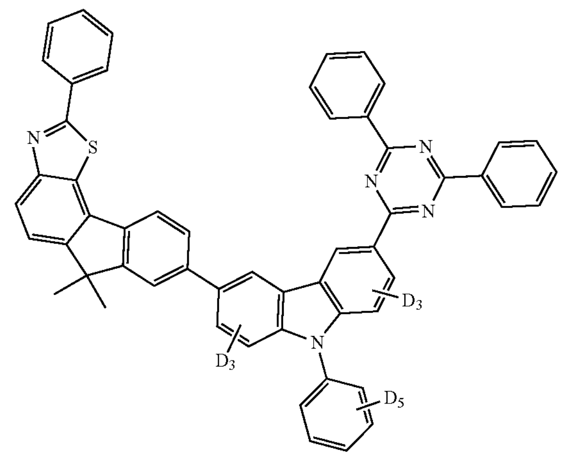
H41-D3
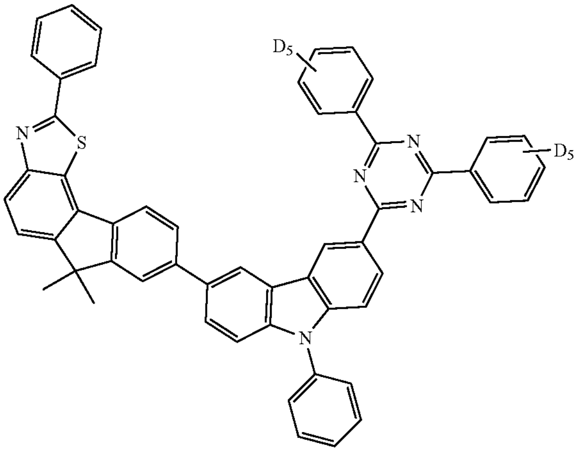
H41-D4
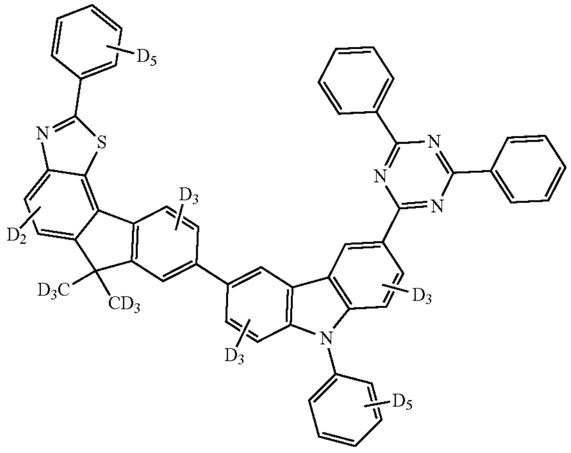

-continued
H41-D5
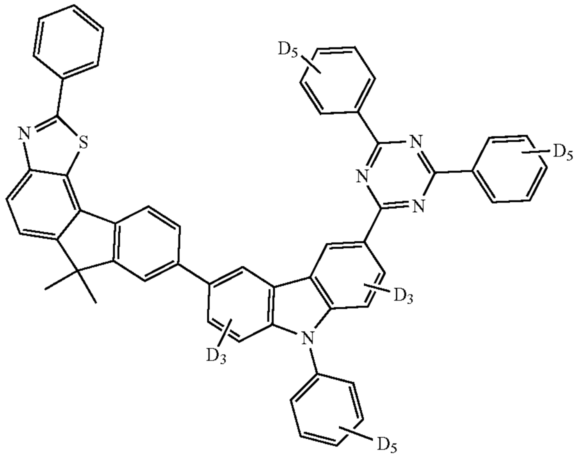
H41-D6
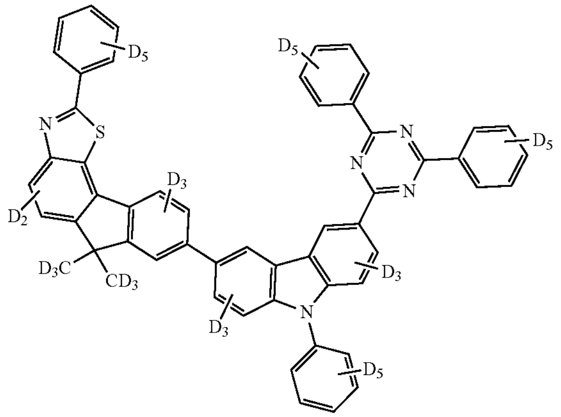
H42-D1
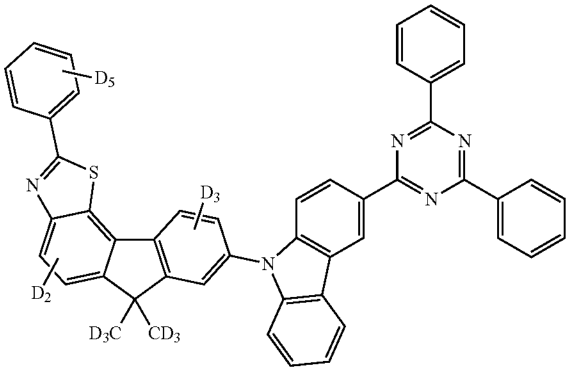
-continued
H42-D2
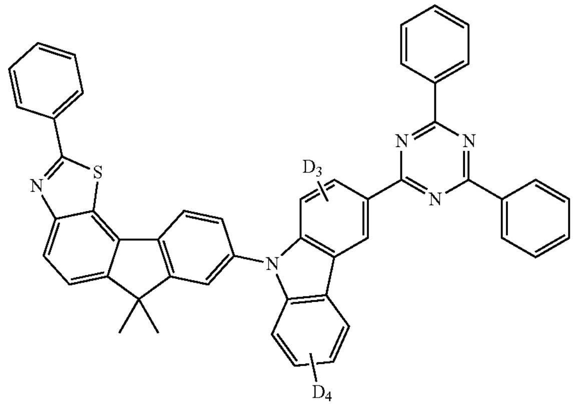
H42-D3
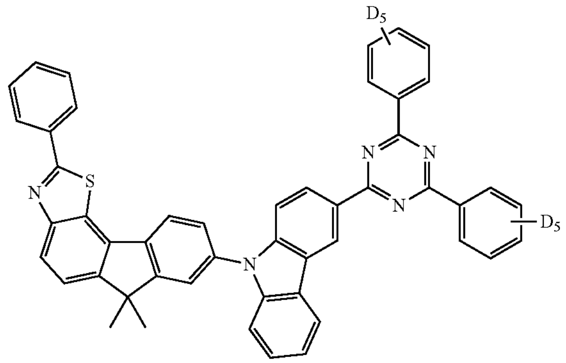
H42-D4
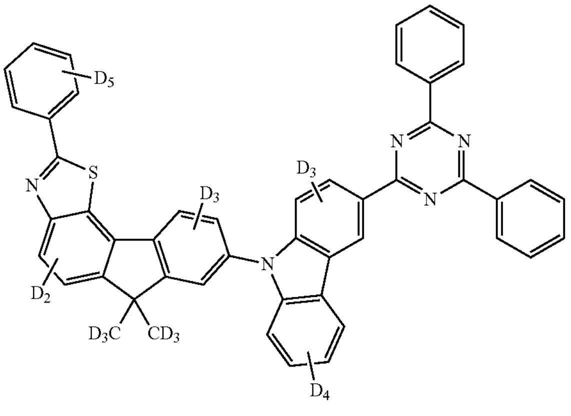

-continued
H42-D5
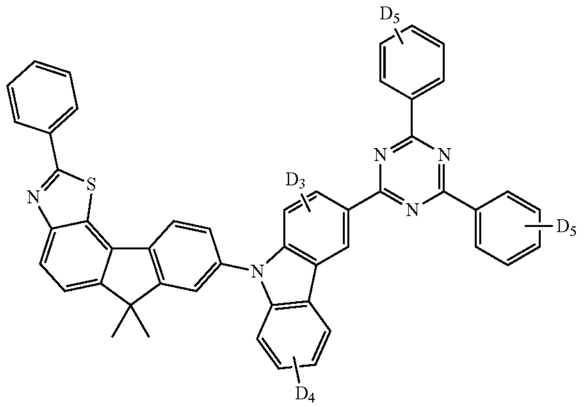
H42-D6
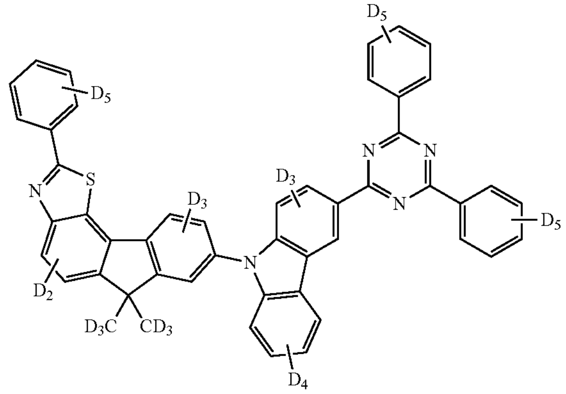
H45-D1
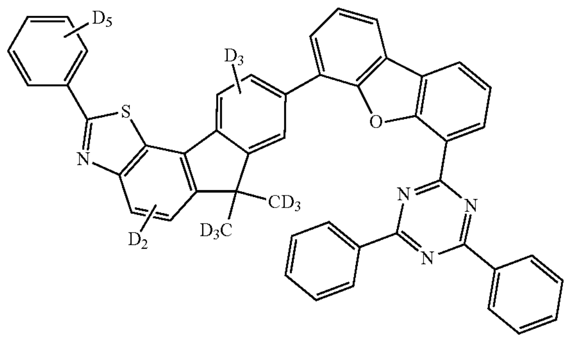
H45-D2
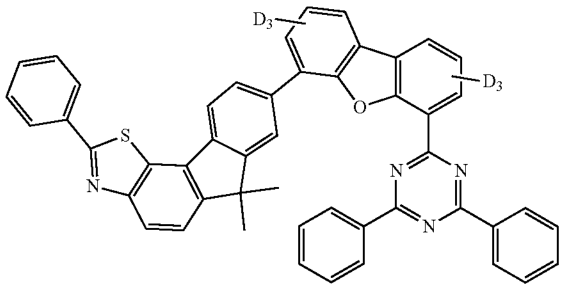
-continued
H45-D3
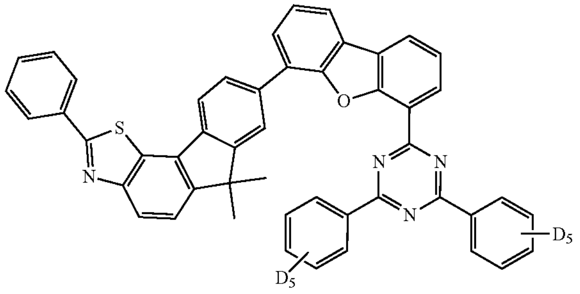
H45-D4
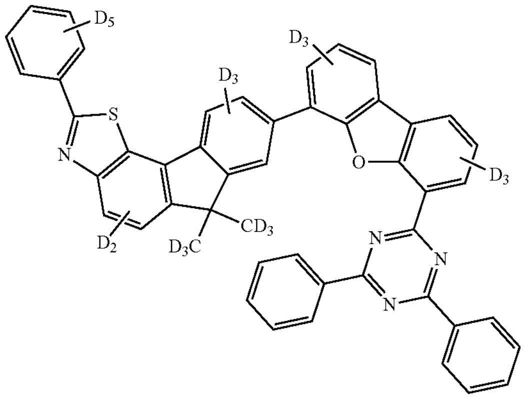
H45-D5
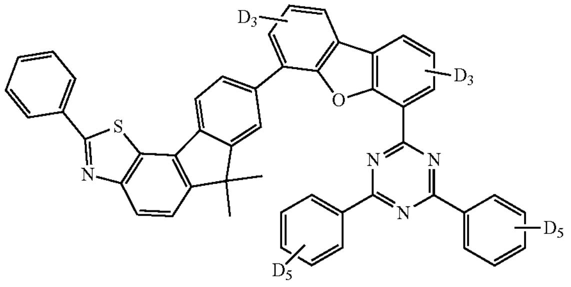
H45-D6
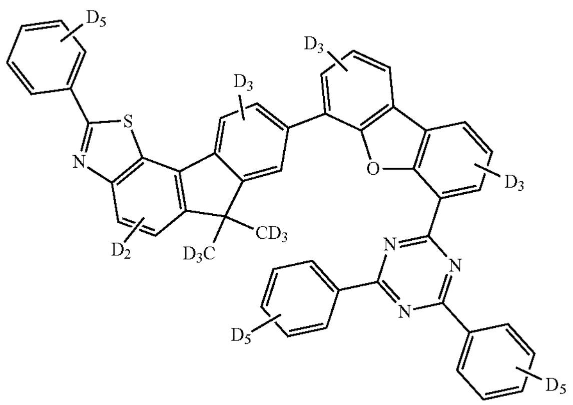

-continued
H46-D1
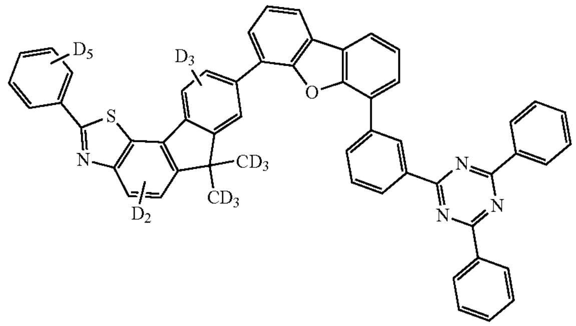
H46-D2
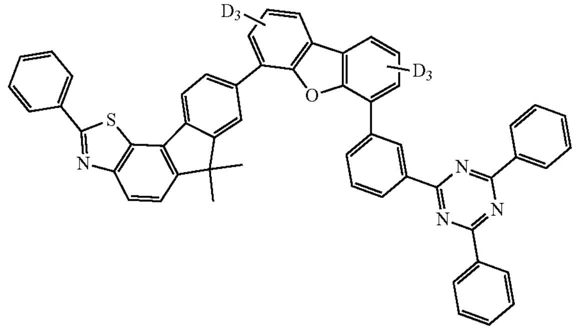
H46-D3
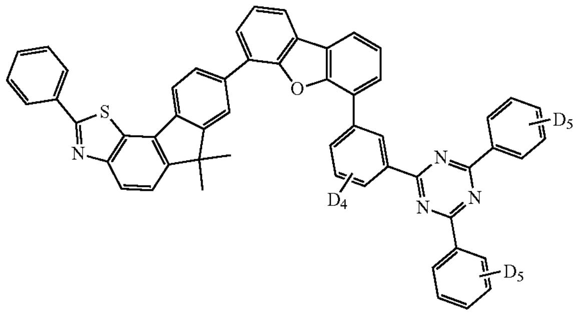
H46-D4
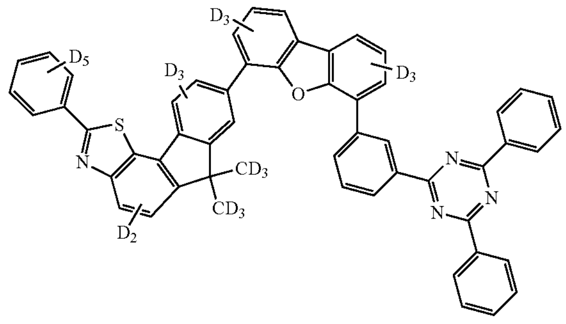
-continued
H46-D5
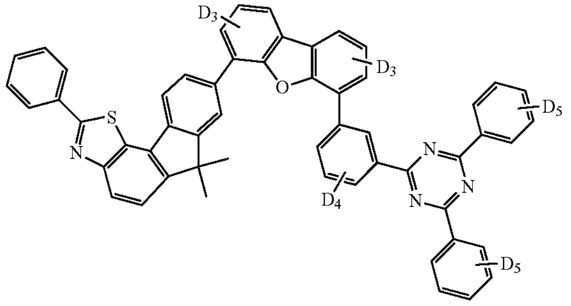
H46-D6
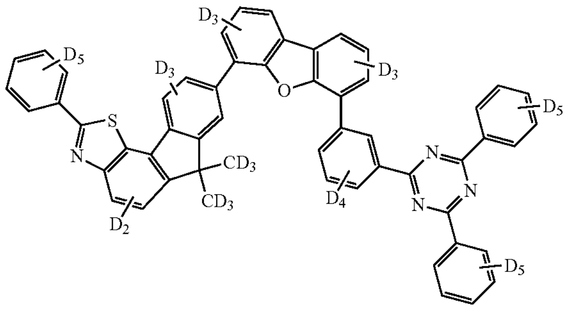
H47-D1
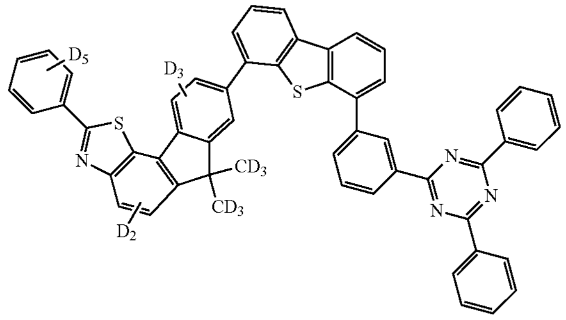
H47-D2
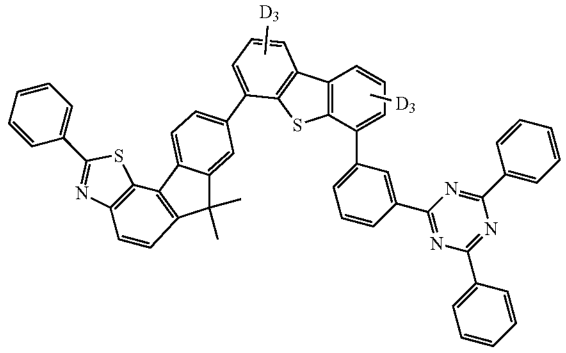

-continued
H47-D3
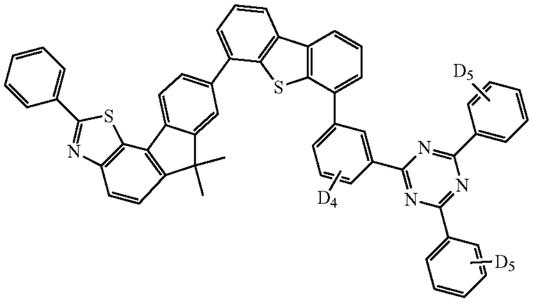
H47-D4
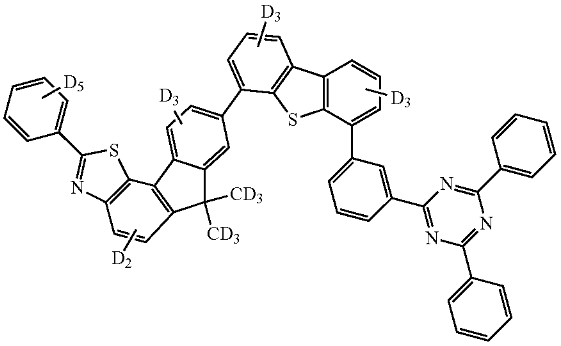
H47-D5
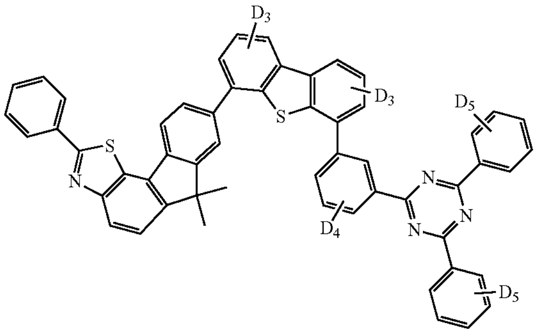
H47-D6
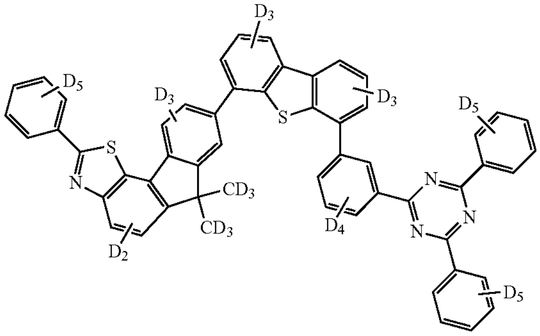
-continued
H48-D1
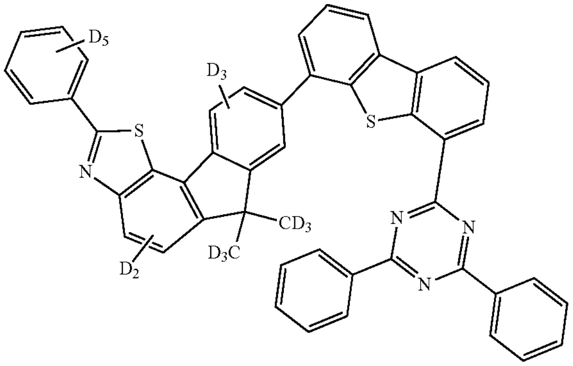
H48-D2
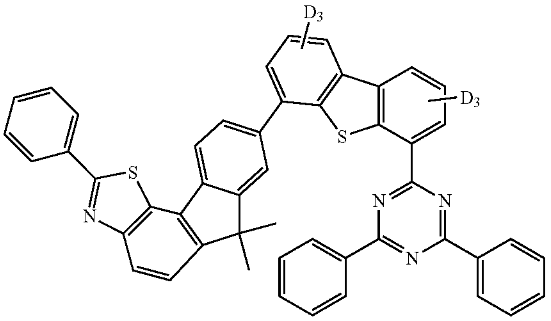
H48-D3
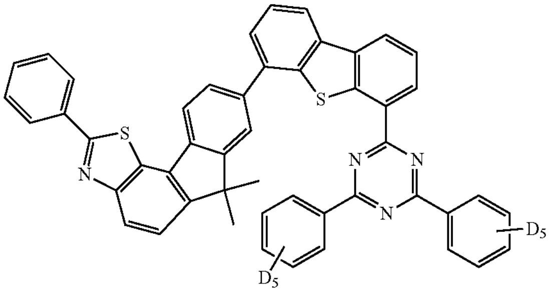
H48-D4
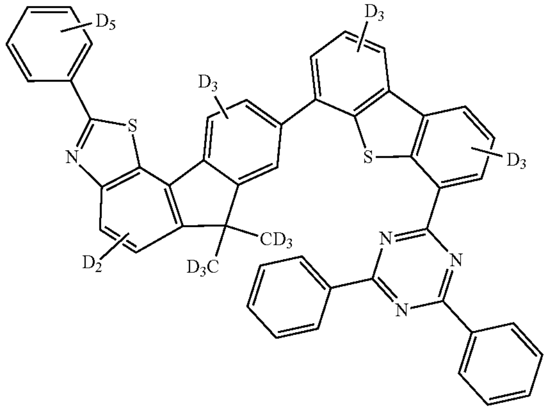

-continued
H48-D5
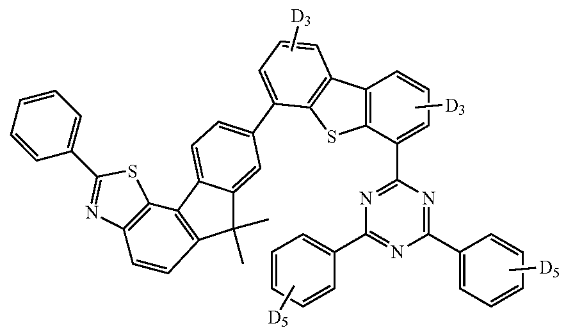
H48-D6
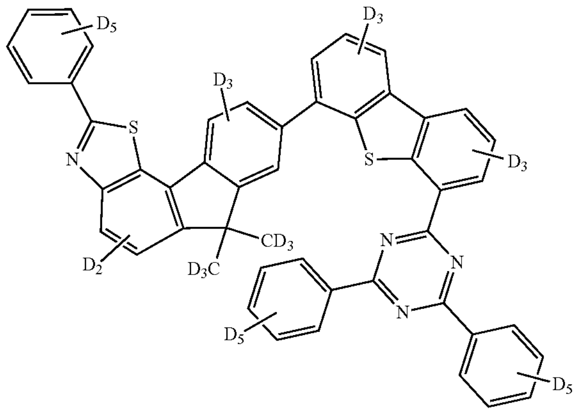
H49-D1
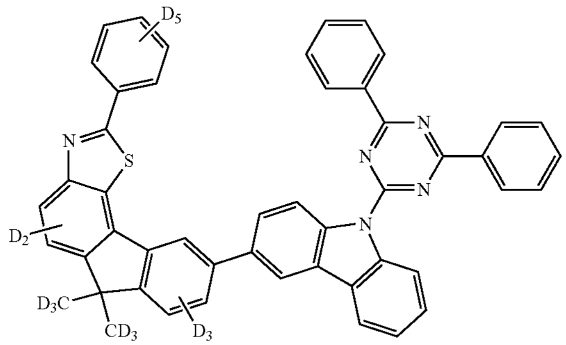
H49-D2
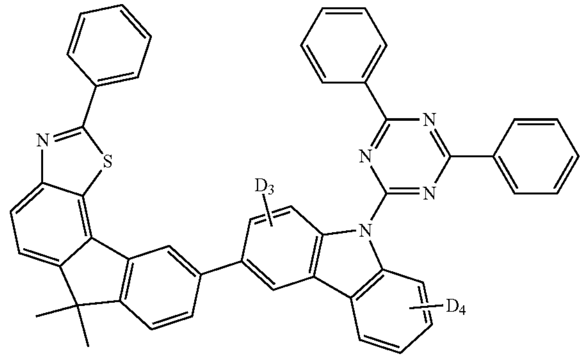
-continued
H49-D3
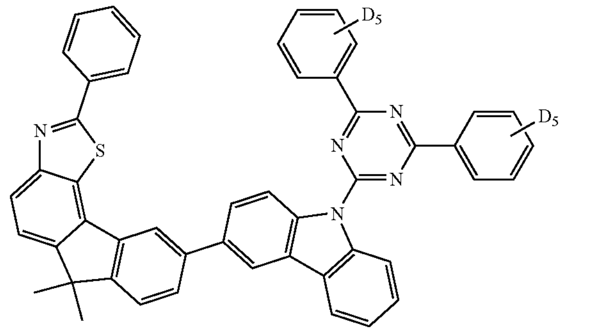
H49-D4
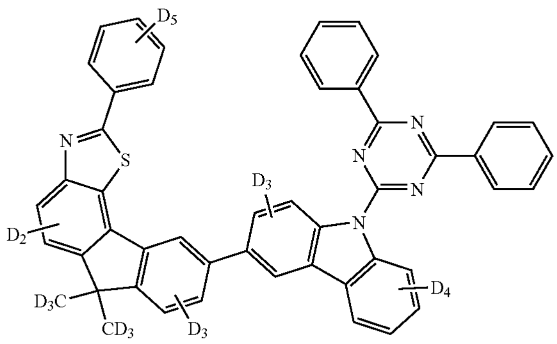
H49-D5
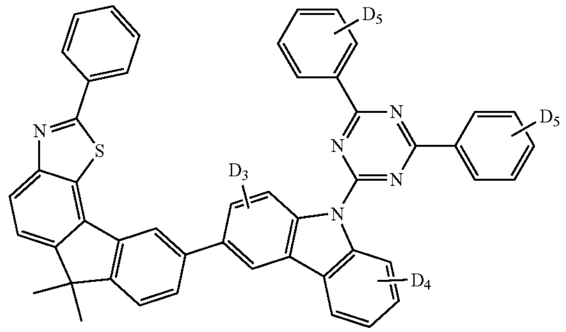
H49-D6
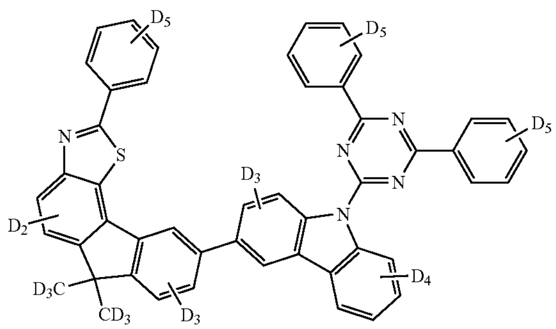

H50-D1
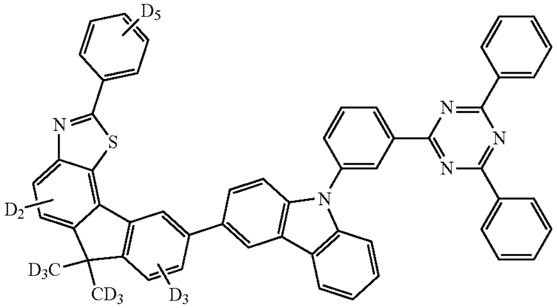
H50-D2
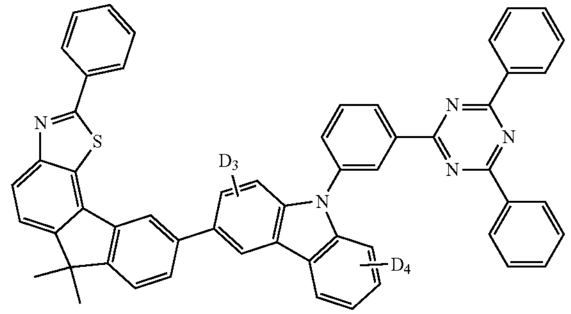
H50-D3
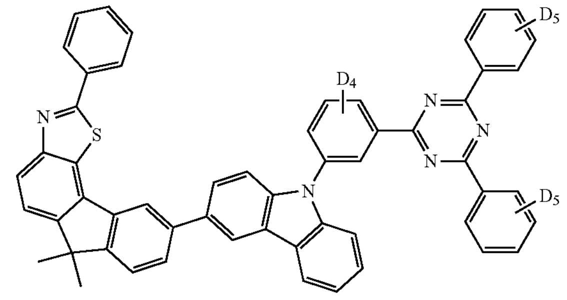
H50-D4
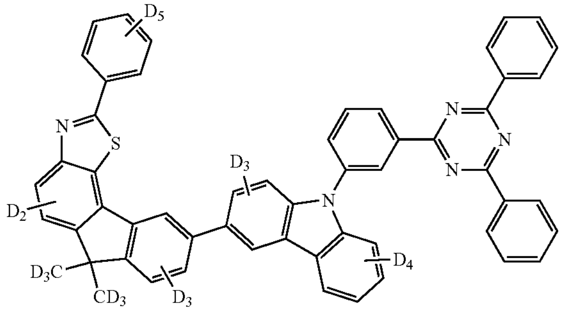
H50-D5
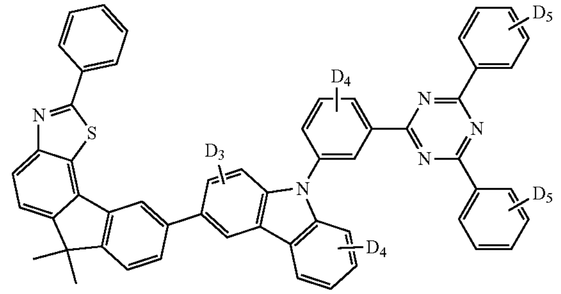
H50-D6
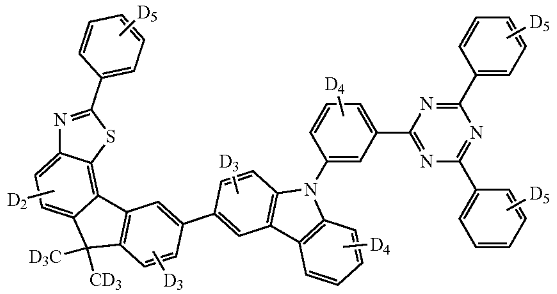
H51-D1
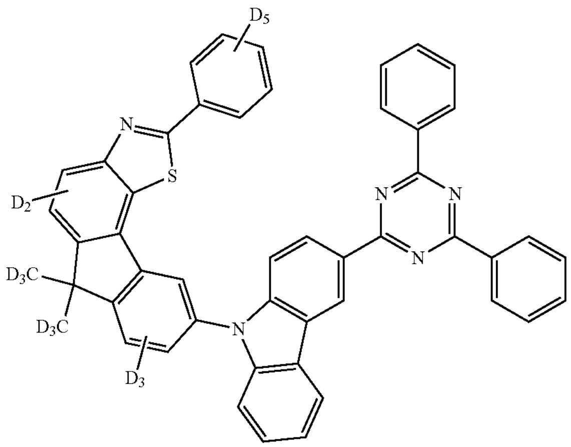
H51-D2
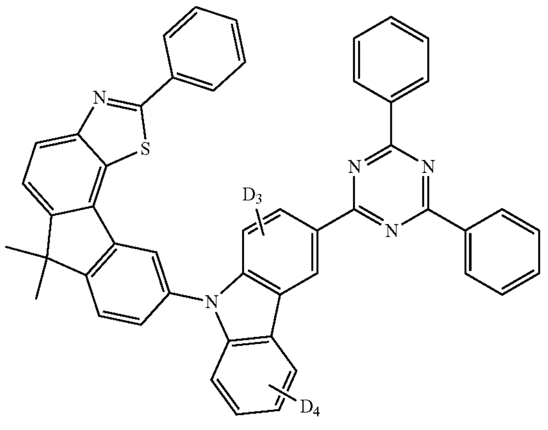

-continued
H51-D3
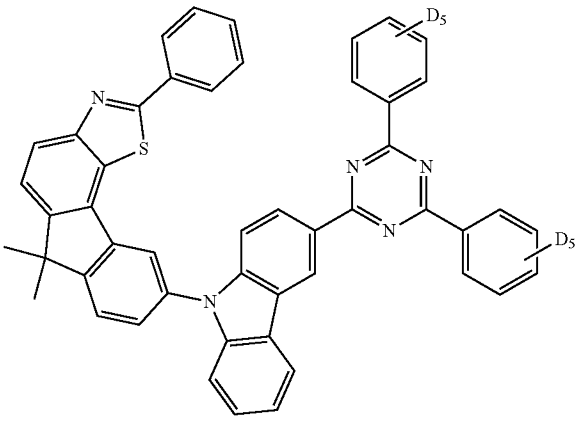
H51-D4
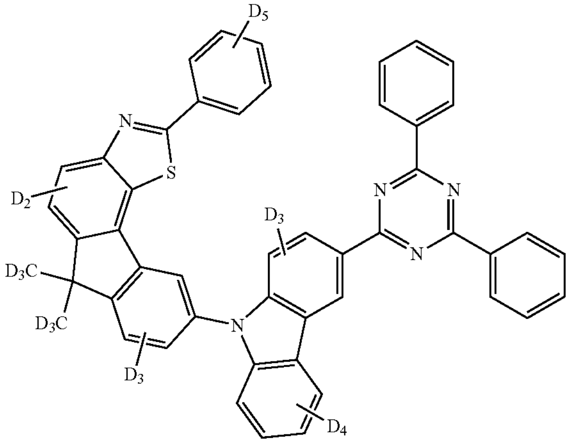
H51-D5
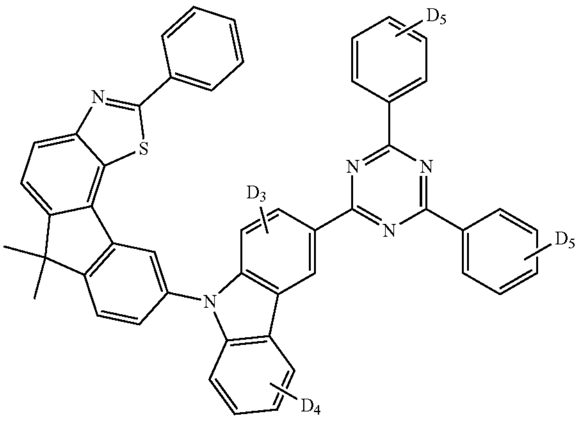
H51-D6
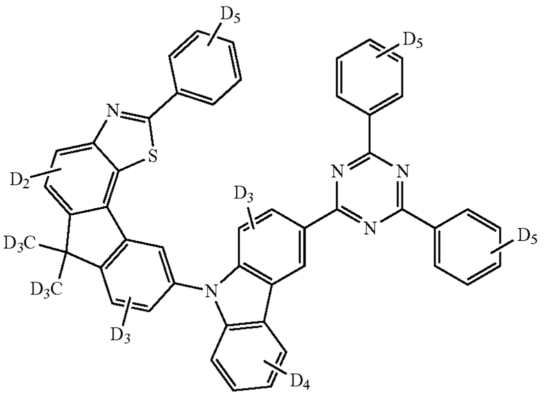
H52-D1
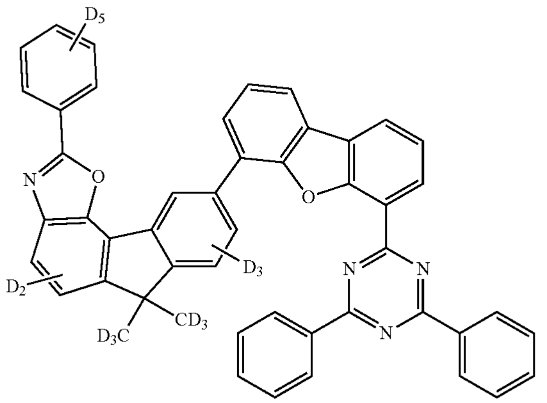
H52-D2
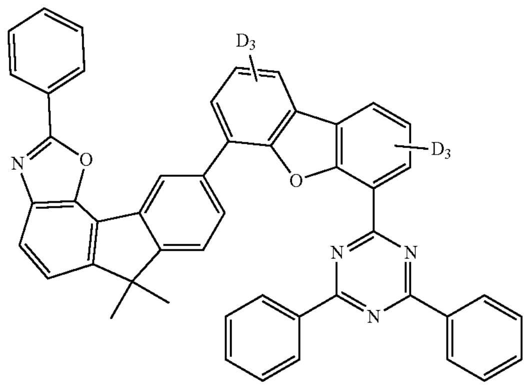
H52-D3
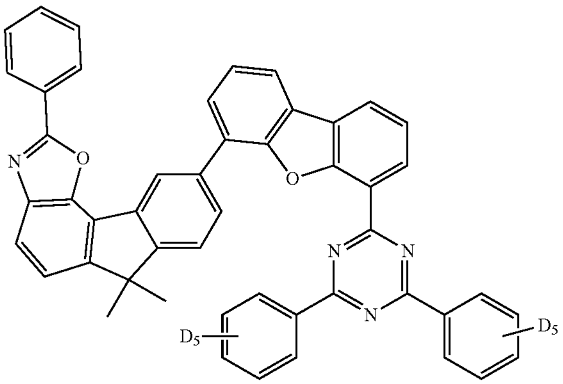

-continued

H52-D4

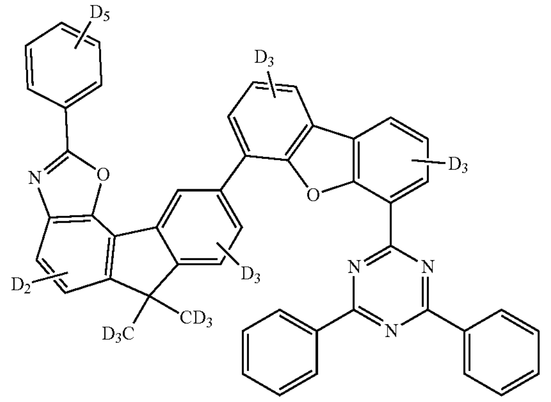

H52-D5

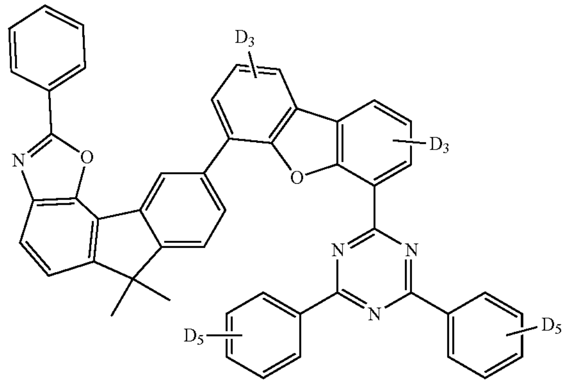

H52-D6

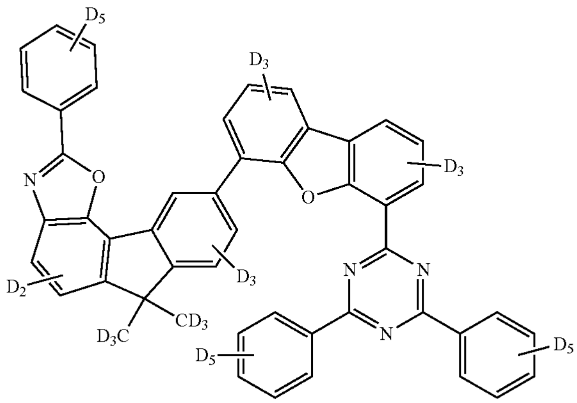

[Synthesis]

1. Synthesis of Intermediates (1) Intermediate 1A

[Reaction Formula 1-1]

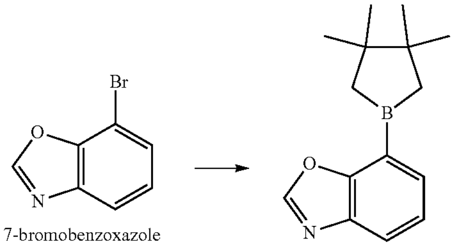

7-bromobenzoxazole

1A

In a round-bottom flask, 7-bromobenzoxazole (15 g, 0.061 mol), bis(pinacolato)diboron (23.3 g, 0.092 mol), [1,1'-bis(diphenylphosphino)ferrocene dichloropalladium (II) (0.90 g, 1.22 mmol), KOAc (potassium acetate, 12.01 g, 0.122 mol) and 1,4-dioxane 225 ml were added. After raising the temperature of the mixture, the mixture was refluxed and was stirred for 12 hours. After completion of the reaction, the reaction solution was cooled to room temperature and filtered using celite. The residual solution was concentrated under reduced pressure and recrystallized using dichloromethane to obtain 12.5 g of the Intermediate 1A.

(2) Intermediate 1B

[Reaction Formula 1-2]

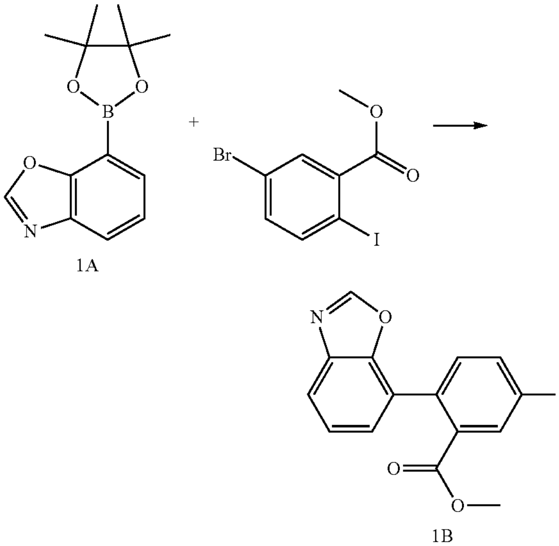

1A

1B

In a round-bottom flask, methyl-5-bromo-iodobenzoate (15 g, 0.044 mol), the Intermediate 1A (11.9 g, 0.048 mol), tetrakis(triphenylphosphine)palladium(0) (1.02 g, 0.880 mmol), toluene 225 ml, EtOH (ethanol) 30 ml, and 4M $K_2CO_3$ (potassium carbonate) 45 ml was added, and the mixture was refluxed and stirred for 12 hours. After completion of the reaction, the reaction solution was filtered to obtain a crude product. The filtered crude product was separated by column chromatography with methylene chloride and hexane to obtain 12.4 g of the Intermediate 1B.

(3) Intermediate 1C

[Reaction Formula 1-3]

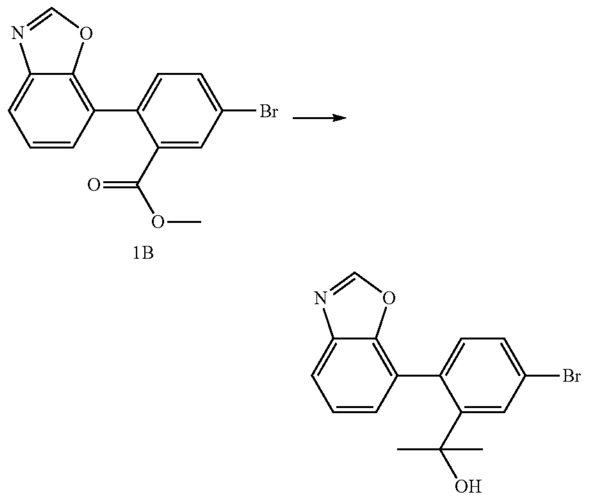

1B

1C

In a round-bottom flask, the Intermediate 1B (12.0 g, 0.030 mol) was added, and 150 ml of anhydrous THF (tetrahydrofuran) was added. The mixture was stirred in a nitrogen atmosphere. 61.9 ml of methylmagnesium bromide diluted in 60 ml of anhydrous THF was slowly added dropwise into the solution. The solution was stirred for 6 hours. After completion of the reaction, 180 ml of 10% $NH_4Cl$ aqueous solution was added to the reaction solution and stirred for 1 hour. The mixture was extracted with EA (ethylacetate), and the organic layer was collected and concentrated under reduced pressure to obtain 20.2 g of the Intermediate 1C.

(4) Intermediate 1D

[Reaction Formula 1-4]

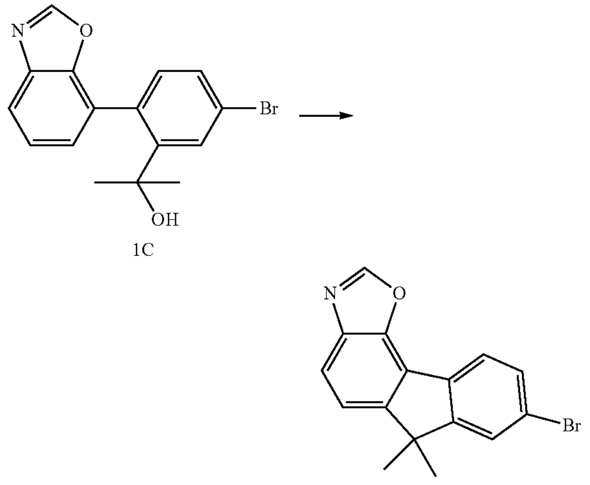

1C

1D

In a round-bottom flask, the Intermediate 1C (20.0 g, 0.045 mol), 300 ml of acetic acid and 30 ml of hydrochloric acid were added, and the mixture was reflux and stirred for 2 hours with heating. After completion of the reaction, the reaction solution was poured into distilled water to precipitate crystals, and the precipitate was filtered. The filtered precipitate was dissolved in MC (methylene chloride) 100 ml and dried with $MgSO_4$. Then, the mixture was reprecipitated using MC and ethanol to obtain 15.1 g of the Intermediate 1D.

(5) Intermediate 1D-D

[Reaction Formula 1-5]

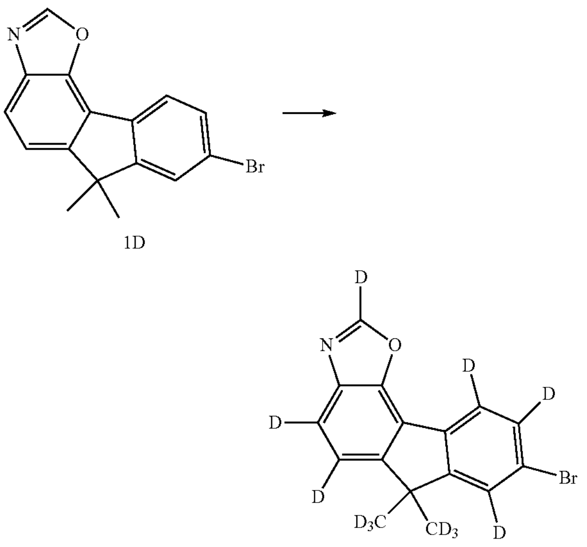

1D

1D-D

In a round-bottom flask, the Intermediate 1D and benzene-$D_6$ (50 times of the Intermediate 1D) was added, and the mixture was refluxed and stirred. Triflic acid (50 equivalents) was added at 70° C. After 5 hours, the mixture was cooled to room temperature. 40 ml of $D_2O$ was mixed and stirred for 10 minutes. The mixture was neutralized with $K_3PO_4$ aqueous solution, and the organic layer was extracted with ethyl acetate. After removing residual moisture using magnesium sulfate, the organic layer was distilled under reduced pressure and separated by column chromatography to obtain the Intermediate 1D-D in a yield of 72.

(6) Intermediate 1D-DB

[Reaction Formula 1-6]

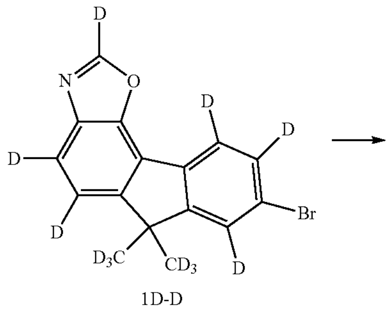

1D-D

-continued

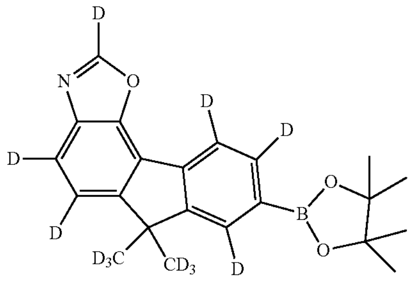

1D-DB

In the synthesis of the Intermediate 1A, 7-bromobenzoxazole was replaced by the Intermediate 1D-D to obtain the Intermediate 1D-DB in a yield of 83%.

(7) Intermediate 1D-Bc

[Reaction Formula 1-7]

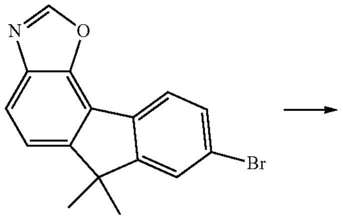

1D

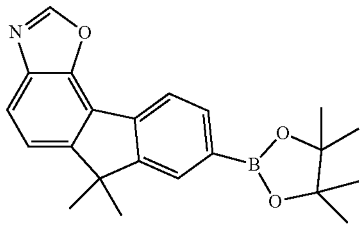

1D-Bc

In the synthesis of the Intermediate 1D-BD, the Intermediate 1D-D was replaced by the Intermediate 1D to obtain the Intermediate 1D-Dc in a yield of 85%.

(8) Intermediate 1AB

[Reaction Formula 1-8]

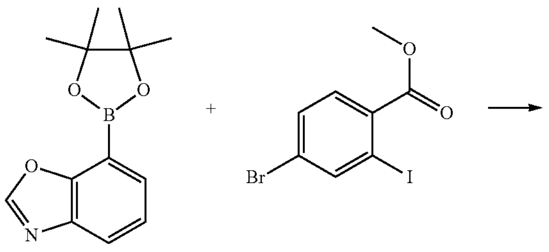

1A

-continued

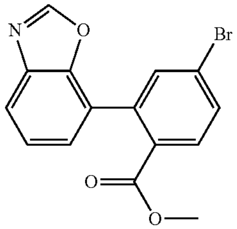

1AB

In the synthesis of the Intermediate 1B, methyl-5-bromo-iodobenzoate was replaced by methyl 4-bromo-2-iodobenzoate to obtain 13.8 g of the Intermediate TAB.

(9) Intermediate 1AC

[Reaction Formula 1-9]

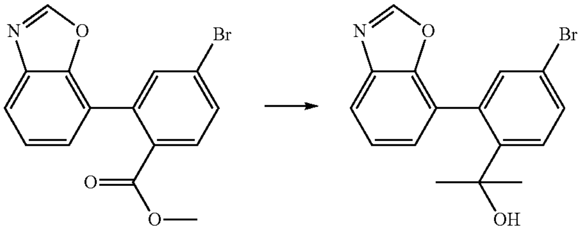

1AB 1AC

In the synthesis of the Intermediate 1C, the Intermediate 1B was replaced by the Intermediate 1AB to obtain 20.4 g of the Intermediate 1AC.

(10) Intermediate 1AD

[Reaction Formula 1-10]

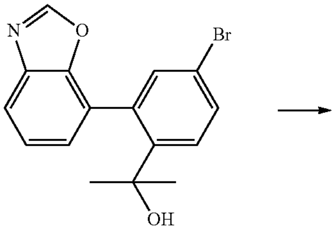

1AC

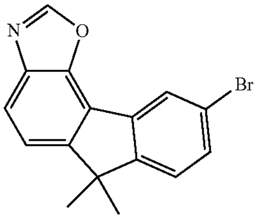

1AD

In the synthesis of the Intermediate 1D, the Intermediate 1C was replaced by the Intermediate 1AC to obtain 15 g of the Intermediate 1AD.

(11) Intermediate 1AD-D

[Reaction Formula 1-11]

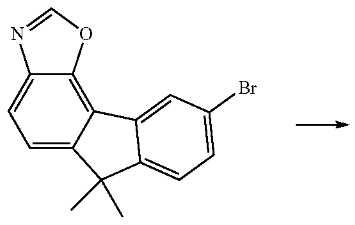

1AD

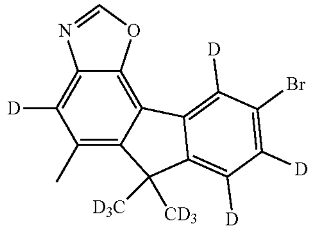

1AD-D

In the synthesis of the Intermediate 1D-D, the Intermediate 1D was replaced by the Intermediate TAD to obtain the Intermediate 1AD-D in a yield of 73%.

(12) Intermediate 1AD-DB

[Reaction Formula 1-12]

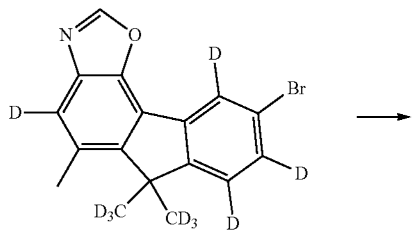

1AD-D

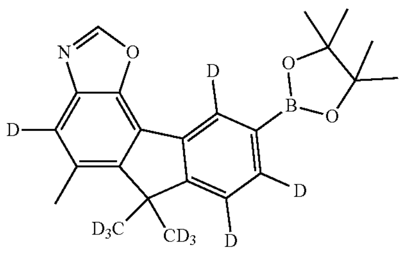

1AD-DB

In the synthesis of the Intermediate 1D-DB, the Intermediate 1D-D was replaced by the Intermediate 1AD-D to obtain the Intermediate 1AD-DB in a yield of 80%.

(13) Intermediate 1AD-B

[Reaction Formula 1-13]

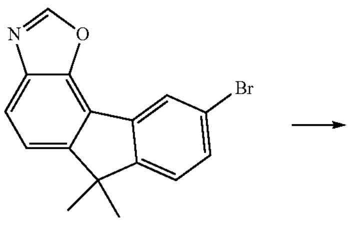

1AD

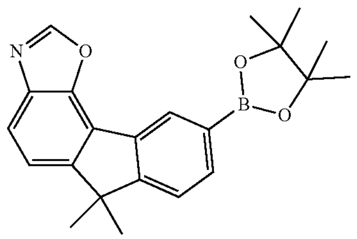

1AD-B

In the synthesis of the Intermediate 1AD-DB, the Intermediate 1AD-D was replaced by the Intermediate 1AD to obtain the Intermediate 1AD-B in a yield of 83%.

2. Synthesis of Intermediates (1) Intermediate 2A

[Reaction Formula 2-1]

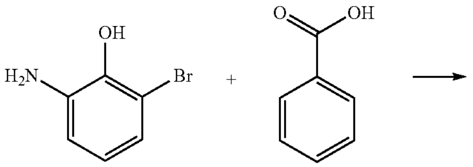

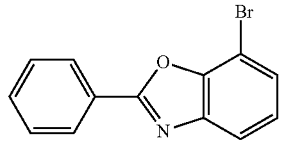

2A

In a round-bottom flask, benzoic acid (10 g, 0.082 mol), 2-amino-6-bromophenol (33.9 g, 0.180 mol), diisopropylethylamine (37.1 ml, 0.213 mol), 4M $K_2CO_3$ aqueous solution 82 ml and methylene chloride (MC) 300 ml were added, and the temperature of the mixture was lowered to 0° C. with stirring. Deoxo-fluor reagent (50% in THF, 66 ml, 0.180 mol) diluted in MC 45 ml was slowly added dropwise into the solution. After completion of the dropwise addition, the mixture was stirred at 0° C. for 2 hours. After the reaction was terminated by adding 100 ml of saturated sodium bicarbonate aqueous solution to the reaction solution, the temperature was raised to room temperature. The reaction solution was separated into layers, and the organic layer was collected and dried with $MgSO_4$ and concentrated under reduced pressure. The concentrated crude was separated by column chromatography to obtain 18.4 g of the Intermediate 2A.

(2) Intermediate 2B

[Reaction Formula 2-2]

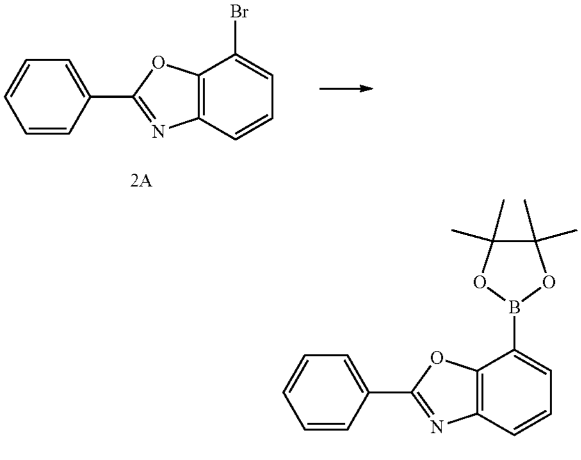

2A

2B

In the synthesis of the Intermediate TA, 7-bromobenzoxazole was replaced by the Intermediate 2A to obtain 13.5 g of the Intermediate 2B.

(3) Intermediate 2C

[Reaction Formula 2-3]

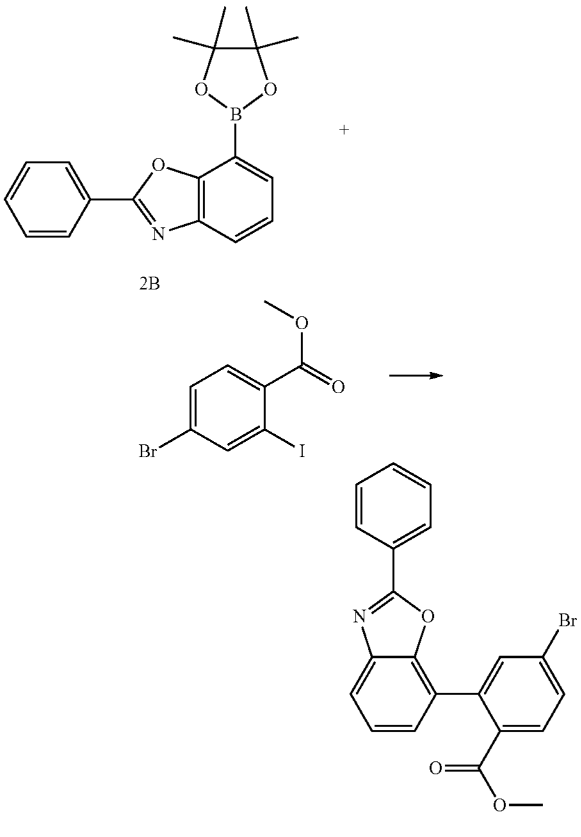

2B

2C

In the synthesis of the Intermediate 1AB, the Intermediate 1A was replaced by the Intermediate 2B to obtain 14.2 g of the Intermediate 2C.

(4) Intermediate 2D

[Reaction Formula 2-4]

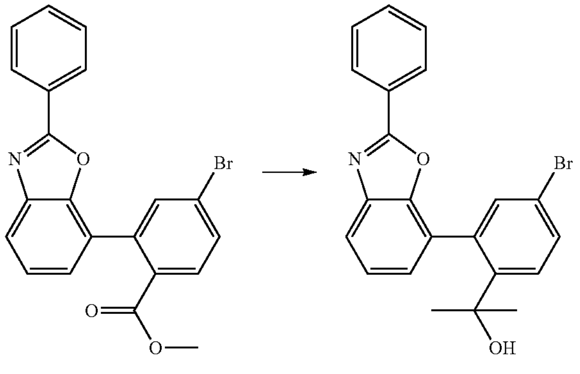

2C

2D

In the synthesis of the Intermediate 1C, the Intermediate 1B was replaced by the Intermediate 2C to obtain 17.3 g of the Intermediate 2D.

(5) Intermediate 2E

[Reaction Formula 2-5]

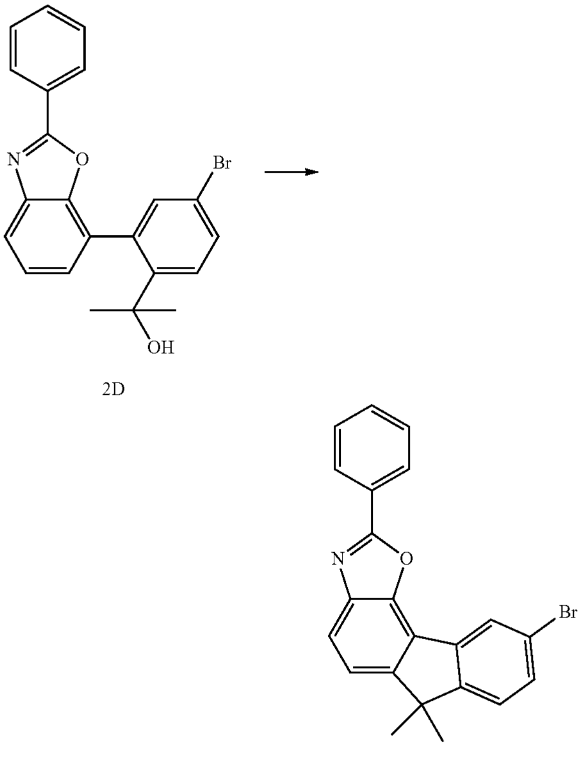

2D

2E

In the synthesis of the Intermediate 1D, the Intermediate 1C was replaced by the Intermediate 2D to obtain 11.5 g of the Intermediate 2E.

(6) Intermediate 2E-D

[Reaction Formula 2-6]

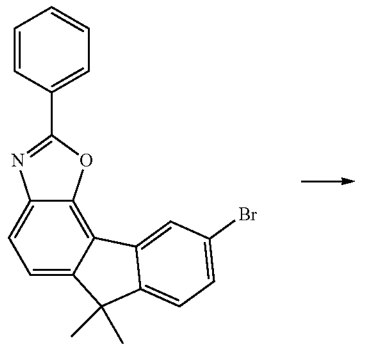

2E

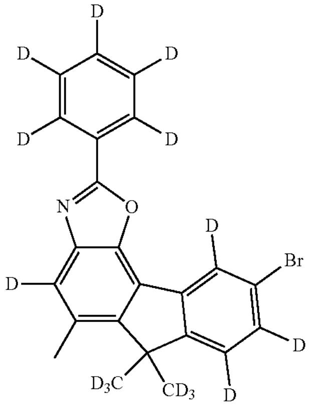

2E-D

In the synthesis of the Intermediate 1D-D, the Intermediate 1D was replaced by the Intermediate 2E to obtain the Intermediate 2E-D in a yield of 73%.

(7) Intermediate 2E-DB

[Reaction Formula 2-7]

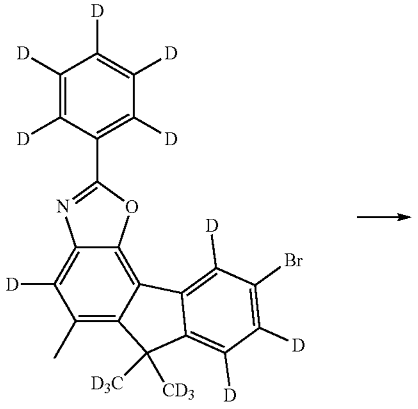

2E-D

-continued

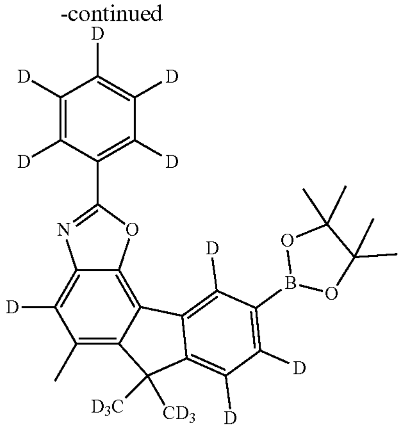

2E-DB

In the synthesis of the Intermediate 1A, 7-bromobenzoxazole was replaced by the Intermediate 2E-D to obtain the Intermediate 2E-DB in a yield of 85%.

(8) Intermediate 2E-B

[Reaction Formula 2-8]

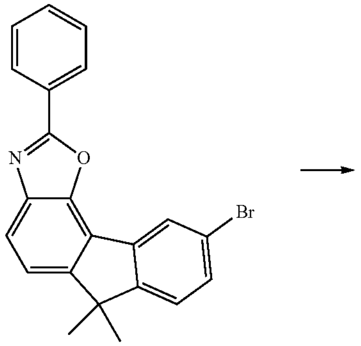

2E

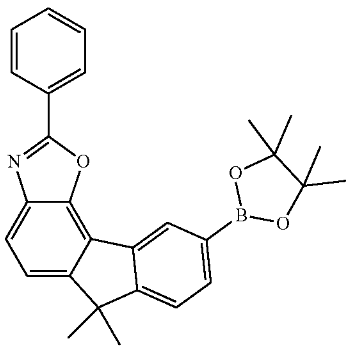

2E-B

In the synthesis of the Intermediate 2E-DB, the Intermediate 2E-D was replaced by the Intermediate 2E to obtain the Intermediate 2E-B in a yield of 810%.

3. Synthesis of Intermediates (1) Intermediate 3A

[Reaction Formula 3-1]

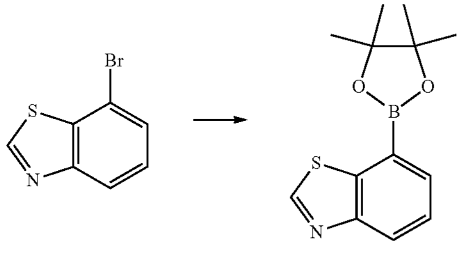

3A

In the synthesis of the Intermediate 1A, 7-bromobenzoxazole was replaced by the 7-bromobenzothiazole to obtain 14.1 g of the Intermediate 3A.

(2) Intermediate 3B

[Reaction Formula 3-2]

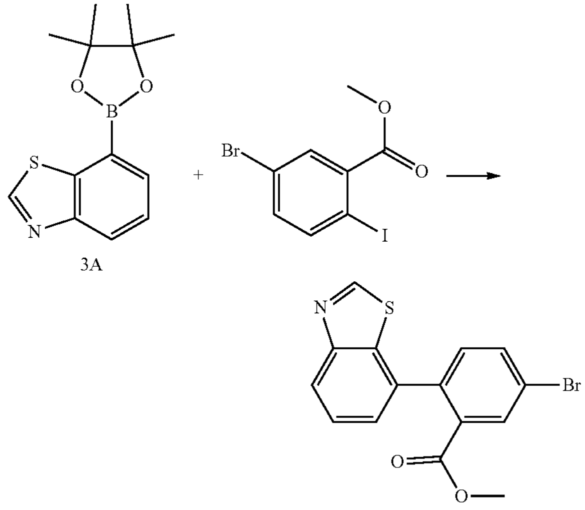

3A

3B

In the synthesis of the Intermediate 1B, the Intermediate TA was replaced by the Intermediate 3A to obtain 13.0 g of the Intermediate 3B.

(3) Intermediate 3C

[Reaction Formula 3-3]

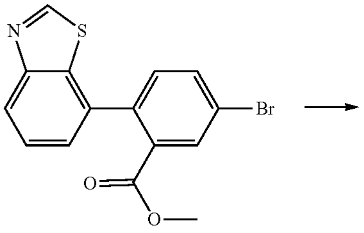

3B

-continued

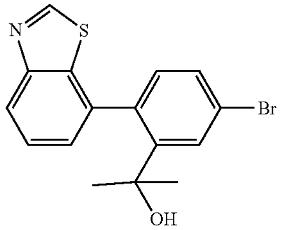

3C

In the synthesis of the Intermediate 1C, the Intermediate 1B was replaced by the Intermediate 3B to obtain 13.0 g of the Intermediate 3C.

(4) Intermediate 3D

[Reaction Formula 3-4]

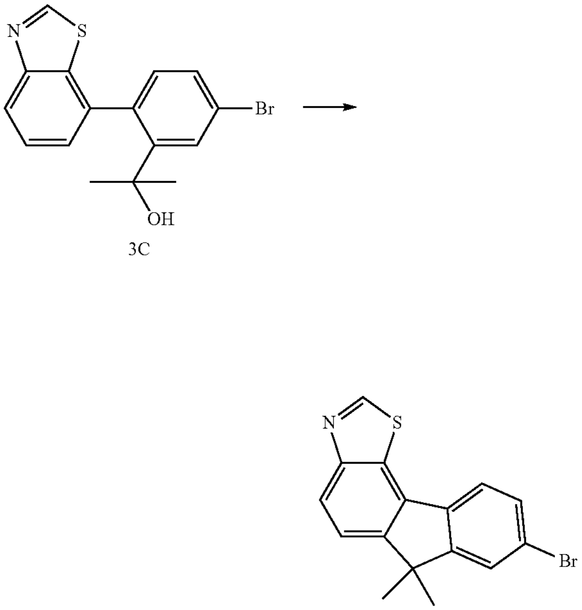

3C

3D

In the synthesis of the Intermediate 1D, the Intermediate 1C was replaced by the Intermediate 3C to obtain 11 g of the Intermediate 3C.

(5) Intermediate 3D-D

[Reaction Formula 3-5]

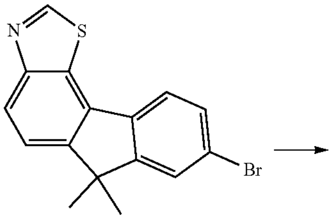

3D

-continued

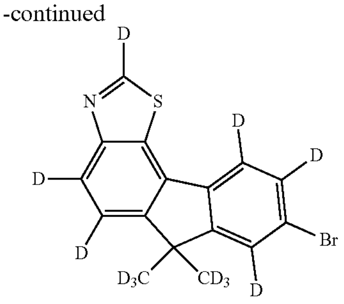

3D-D

In the synthesis of the Intermediate 1D-D, the Intermediate 1D was replaced by the Intermediate 3D to obtain the Intermediate 3D-D in a yield of 75%.

(6) Intermediate 3D-DB

[Reaction Formula 3-6]

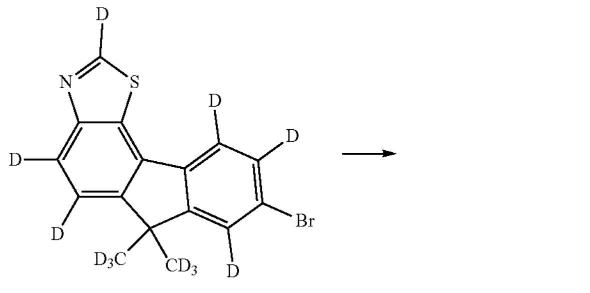

3D-D

3D-DB

In the synthesis of the Intermediate 1A, 7-bromobenzoxazole was replaced by the Intermediate 3D-D to obtain the Intermediate 3D-DB in a yield of 82%.

(7) Intermediate 3D-B

[Reaction Formula 3-7]

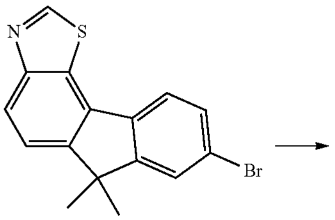

3D

-continued

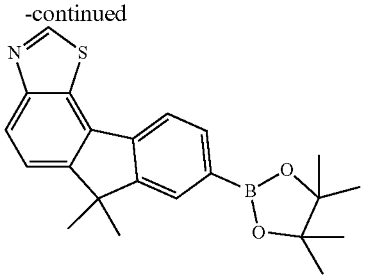

3D-B

In the synthesis of the Intermediate 3D-DB, the Intermediate 3D-D was replaced by the Intermediate 3D to obtain the Intermediate 3D-B in a yield of 81%.

4. Synthesis of Intermediates (1) Intermediate TD

[Reaction Formula 4-1

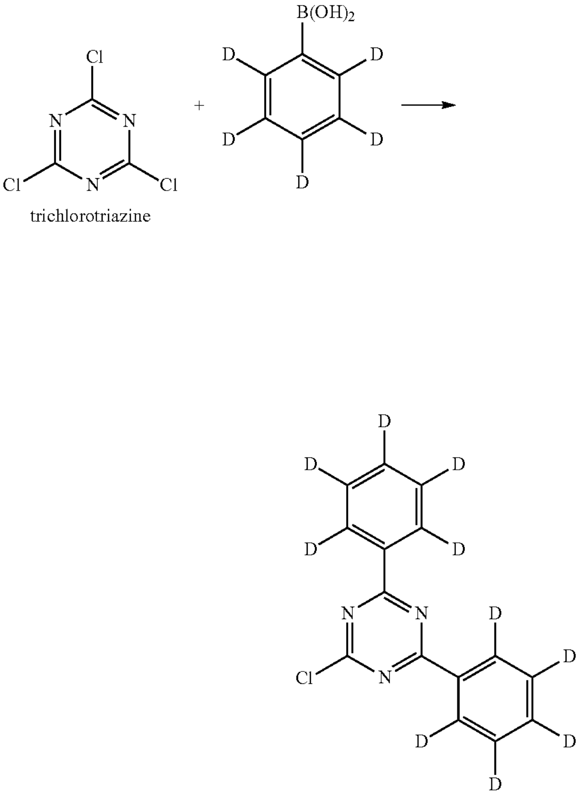

trichlorotriazine

TD

In a round-bottom flask, trichlorotriazine (30 g, 0.16 mol), phenylboronic-$D_5$ (41.3 g, 0.33 mol), tetrakis(triphenylphosphine)palladium(0) (7.5 g, 6.5 mmol), toluene 600 ml, EtOH (Ethanol) 60 ml and 4M $K_2CO_3$ (potassium carbonate) 160 ml was added, and the mixture was refluxed and stirred for 12 hours. After completion of the reaction, the reaction solution was separated into layers to remove water and the organic layer was dried using $MgSO_4$. The dried solution was concentrated under reduced pressure to remove all solvents, and separated by column chromatography to obtain 31.6 g of the Intermediate TD in a yield of 70%.

(2) Intermediate CZD

[Reaction Formula 4-2]

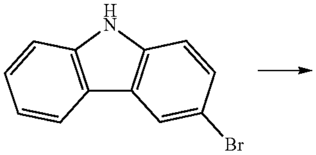

3-bromo-9H-carbazole

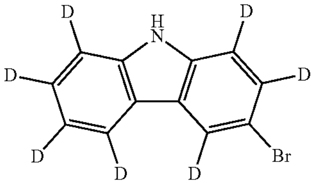

CZD

In the synthesis of the Intermediate 1D-D, the Intermediate 1D was replaced by 3-bromo-9H-carbazole to obtain the Intermediate CZD in a yield of 68%.

(3) Intermediate CZDB

[Reaction Formula 4-3]

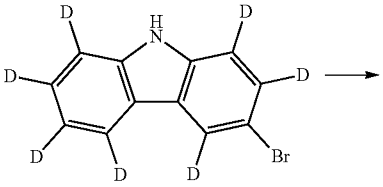

CZD

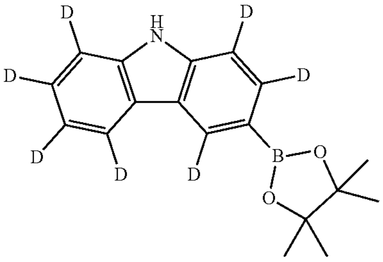

CZDB

In the synthesis of the Intermediate 1A, 7-bromobenzoxazole was replaced by the Intermediate CZD to obtain the Intermediate CZDB in a yield of 85%.

(4) Intermediate DBFD

[Reaction Formula 4-4]

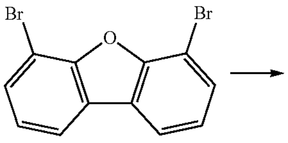

4,6-dibromodibenzofuran

-continued

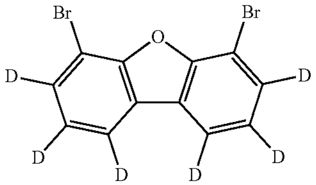

DBFD

In the synthesis of the Intermediate 1D-D, the Intermediate 1D was replaced by the 4,6-dibromodibenzofuran to obtain the Intermediate DBFD in a yield of 66%.

(5) Intermediate TBD

[Reaction Formula 4-5]

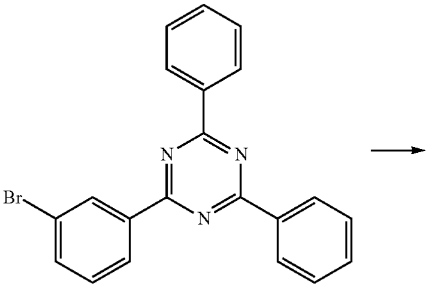

2-(3-bromophenyl)-4,6-diphenyl-1,3,5-triazine

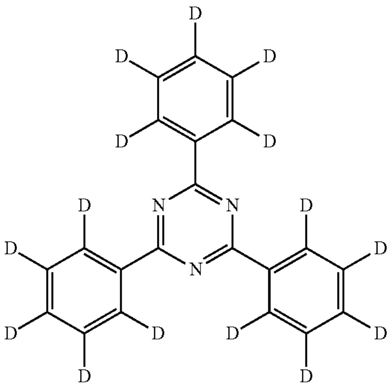

TBD

In the synthesis of the Intermediate 1D-D, the Intermediate 1D was replaced by 2-(3-bromophenyl)-4,6-diphenyl-1,3,5-triazine to obtain the Intermediate TBD in a yield of 78%.

(6) Intermediate TBDB

[Reaction Formula 4-6]

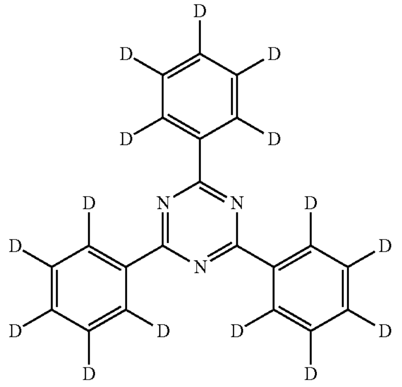

TBD

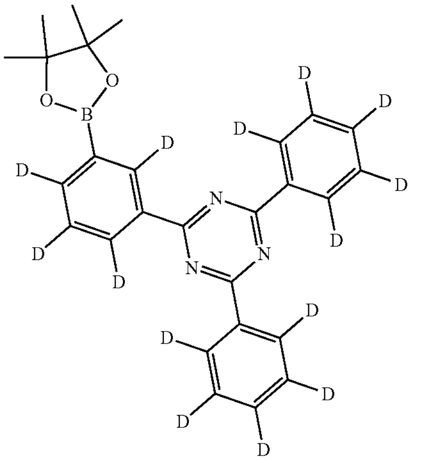

TBDB

In the synthesis of the Intermediate 1A, 7-bromobenzoxazole was replaced by the Intermediate TBD to obtain the Intermediate TBDB in a yield of 87%.

(7) Intermediate TBB

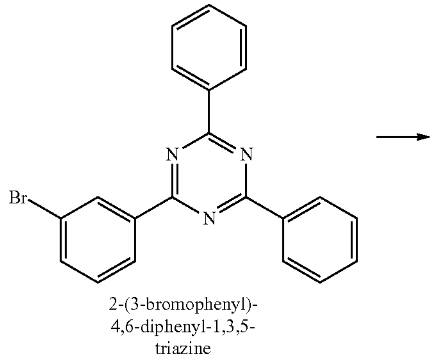

2-(3-bromophenyl)-4,6-diphenyl-1,3,5-triazine

-continued

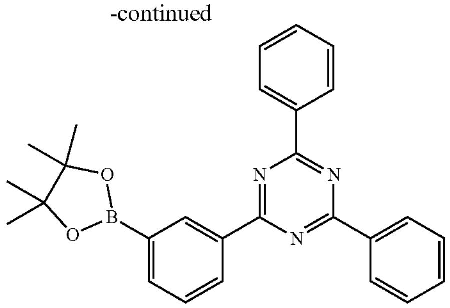

TBB

In the synthesis of the Intermediate 1A, 7-bromobenzoxazole was replaced by 2-(3-bromophenyl)-4,6-diphenyl-1,3,5-triazine to obtain the Intermediate TBB in a yield of 85%.

5. Synthesis of the Compound H1-D1

(1) Intermediate BB

[Reaction Formula 5-1

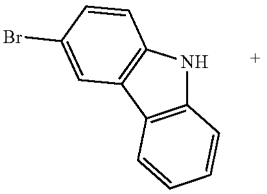

3-bromocarbazole

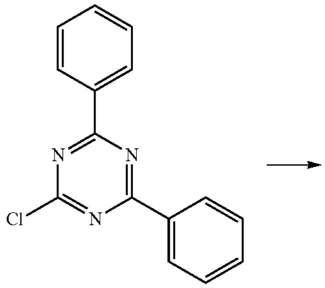

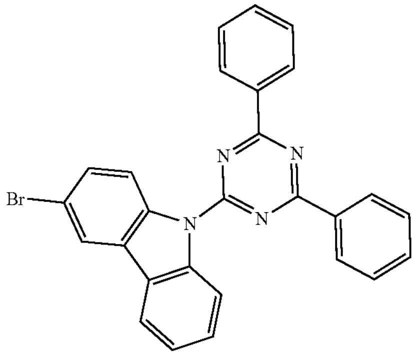

BB

In a round bottom flask, 3-bromocarbazole (5 g, 0.020 mol), 2-chloro-4,6-diphenyl-1,3,5-triazine (6.5 g, 0.024 mol), palladium acetate ($Pd(OAc)_2$, 0.09 g, 0.406 mmol), sodium t-butoxide ($Na^+t\text{-}BuO^-$, 3.91 g, 0.041 mol), tri-tert-butylphosphine (0.41 g, 2.03 mmol), and 75 ml of toluene were added, and the mixture was refluxed and stirred for 10 hours. After cooling the mixture to room temperature, the mixture was extracted with EA and water. The mixture was dried with $MgSO_4$ and concentrated under reduced pressure. The obtained crude product was separated by column chromatography to obtain 9.1 g of the Intermediate BB.

(2) Compound H1-D1

[Reaction Formula 5-2]

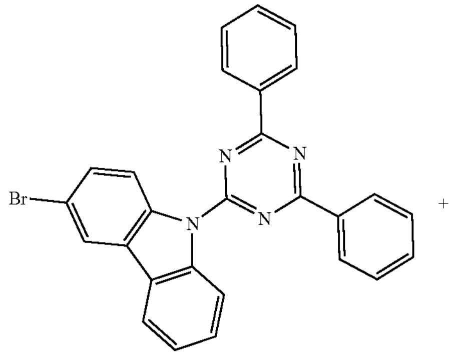

BB

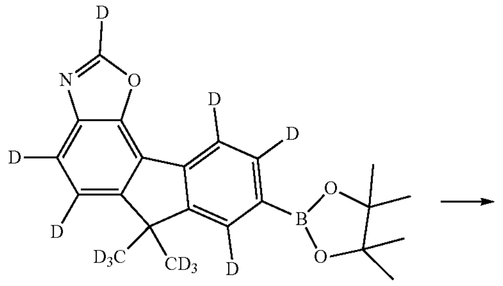

1D-DB

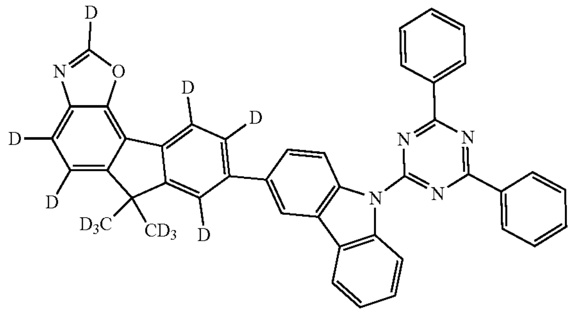

H1-D1

In a round bottom flask, the Intermediate BB (5.0 g, 0.010 mol), the Intermediate 1D-DB (4.3 g, 0.012 mol), tetrakis (triphenylphosphine)palladium (0) (0.24 g, 0.209 mmol), toluene 75 ml, EtOH (ethanol) 10 ml and 4M $K_2CO_3$ (11 ml, potassium carbonate) was added, and the mixture was refluxed and stirred for 12 hours. After completion of the reaction, the reaction solution was filtered to obtain a crude product. The filtered crude product was separated by column chromatography with $CHCl_3$ (chloroform) as an eluent to obtain 5.2 g of the compound H1-D1.

6. Synthesis of the Compound H1-D2

(1) Intermediate BC

[Reaction Formula 6-1]

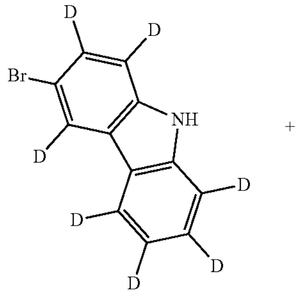

CZD

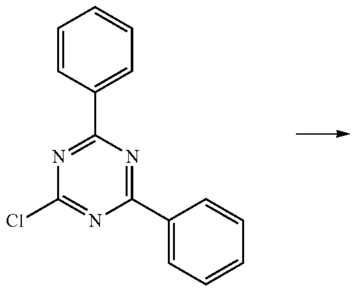

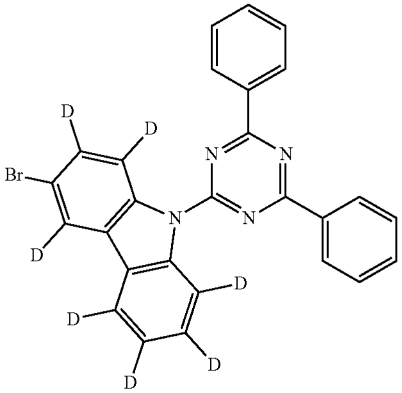

BC

In the synthesis of the Intermediate BB, 3-bromocarbazole was replaced by the Intermediate CZD to obtain 9.3 g of the Intermediate BC.

(2) Compound H1-D2

[Reaction Formula 6-2]

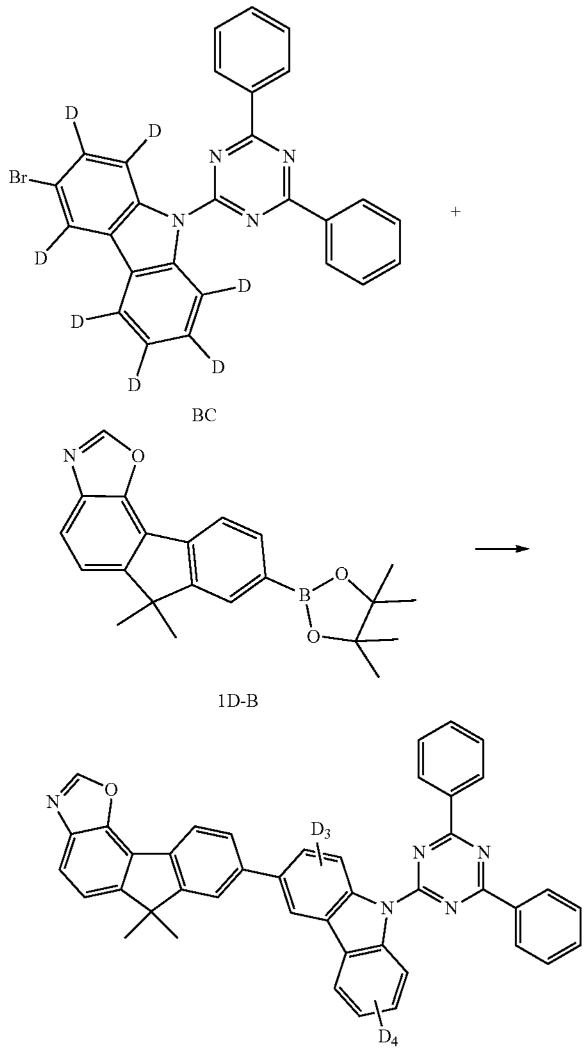

BC

1D-B

H1-D2

In the synthesis of the compound H1-D1, the Intermediates BB and 1D-DB were replaced by the Intermediates BC and 1D-B, respectively, to obtain 5.1 g of the compound H1-D2.

7. Synthesis of the Compound H1-D3

(1) Intermediate BD

[Reaction Formula 7-1]

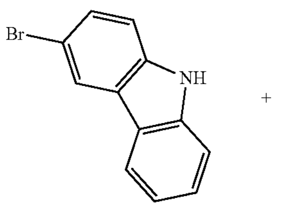

3-bromocarbazole

-continued

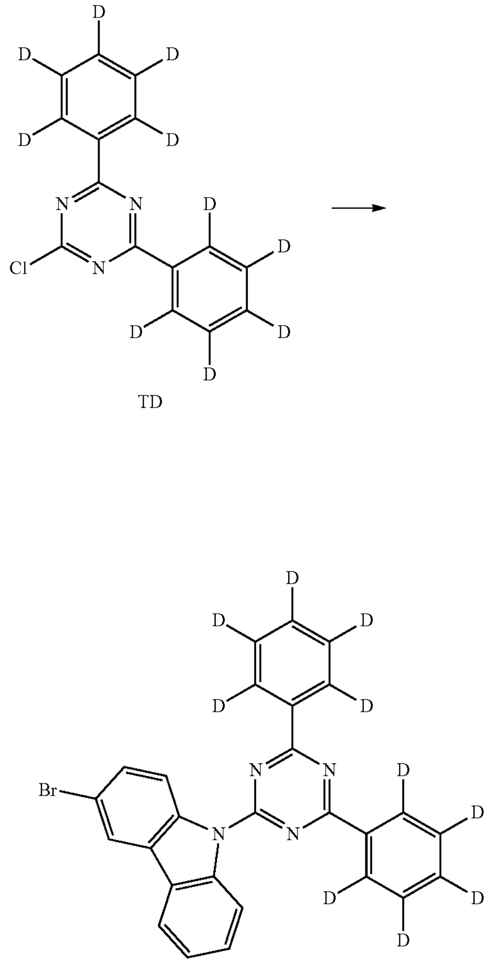

TD

BD

In the synthesis of the Intermediate BB, 2-chloro-4,6-diphenyl-1,3,5-triazine was replaced by the Intermediate TD to obtain 9.5 g of the Intermediate BD.

(2) Compound H1-D3

[Reaction Formula 7-2]

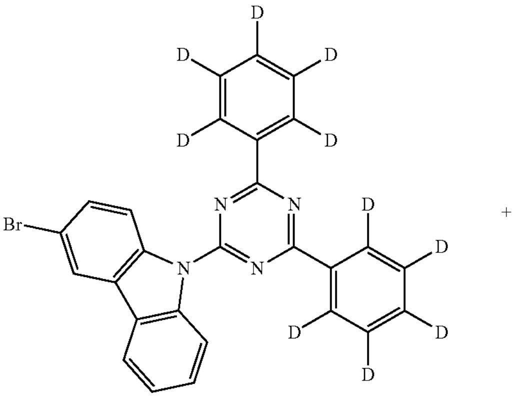

BD

-continued

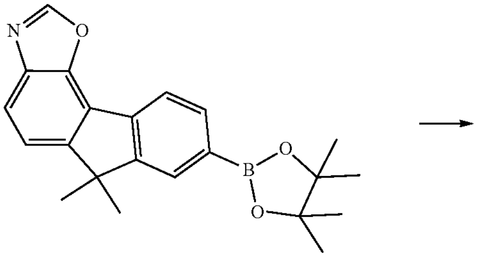

1D-B

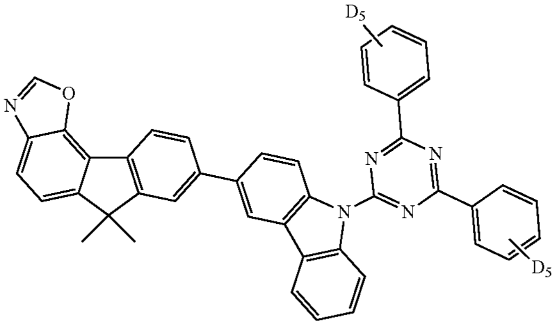

H1-D3

In the synthesis of the compound H1-D2, the Intermediate BC was replaced by the Intermediate BD to obtain 5.2 g of the compound H1-D3.

8. Synthesis of the Compound H1-D4

[Reaction Formula 8]

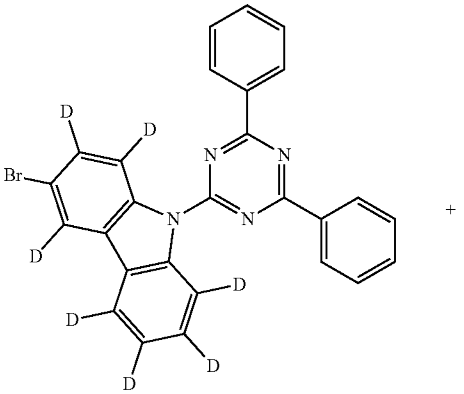

BC

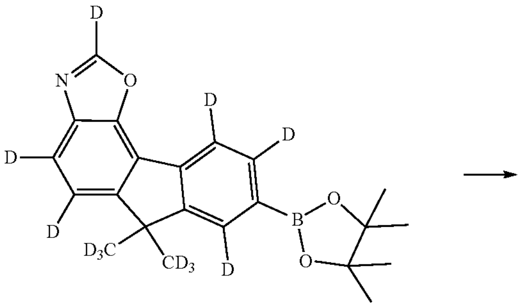

1D-DB

-continued

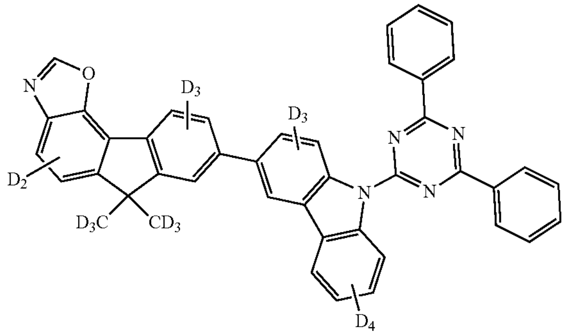

H1-D4

In the synthesis of the compound H1-D2, the Intermediate 1D-B was replaced by the Intermediate 1D-DB to obtain 5.0 g of the compound H1-D4.

9. Synthesis of the Compound H1-D5

(1) Intermediate BE

[Reaction Formula 9-1]

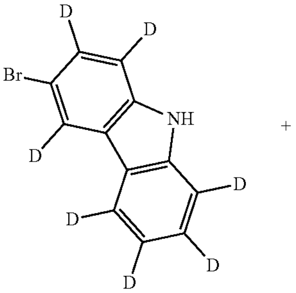

CZD

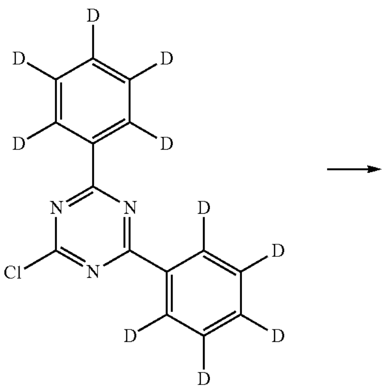

TD

-continued

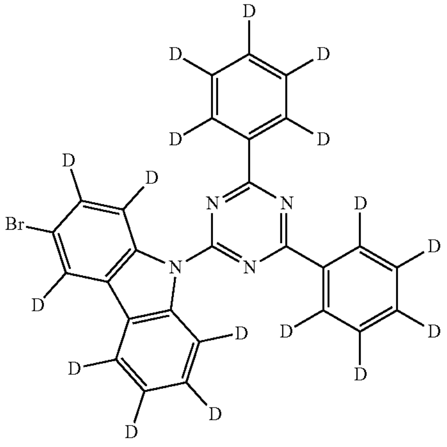

BE

In the synthesis of the Intermediate BD, 3-bromocarbazole was replaced by the Intermediate CZD to obtain 9.3 g of the Intermediate BE.

(2) Compound H1-D5

[Reaction Formula 9-2]

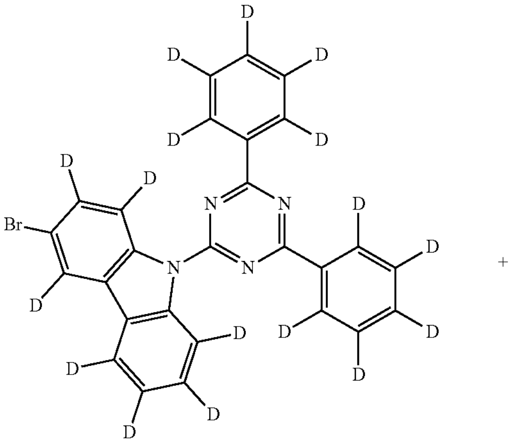

BE

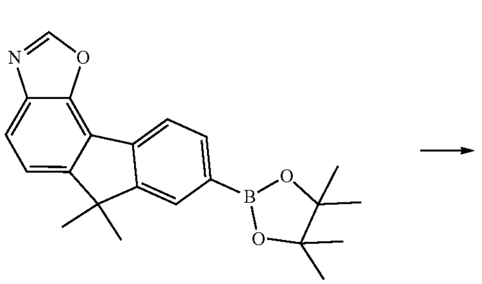

1D-B

-continued

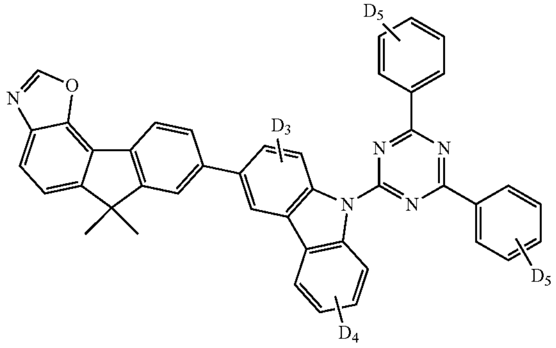

H1-D5

In the synthesis of the compound H1-D3, the Intermediate BD was replaced by the Intermediate BE to obtain 5.2 g of the compound H1-D5.

10. Synthesis of the Compound H1-D6

[Reaction Formula 10]

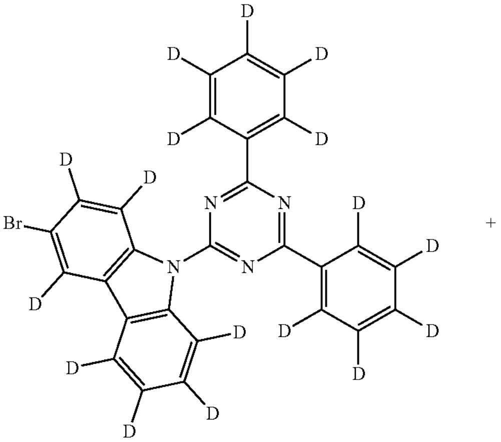

BE

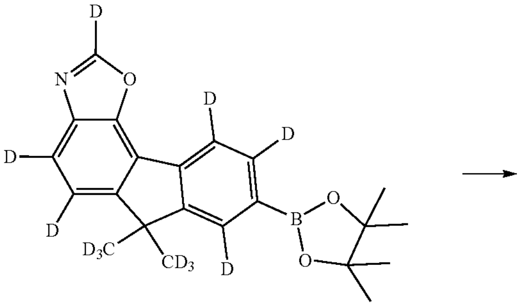

1D-DB

-continued

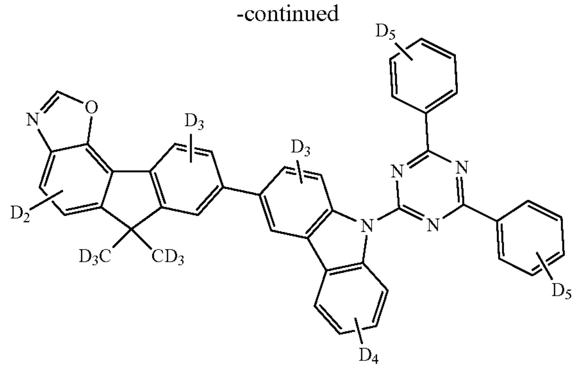

H1-D6

In the synthesis of the compound H1-D5, the Intermediate 1D-B was replaced by the Intermediate 1D-DB to obtain 6.5 g of the compound H1-D6.

11. Synthesis of the Compound H6-D1

(1) Intermediate TDBFBr

[Reaction Formula 11-1]

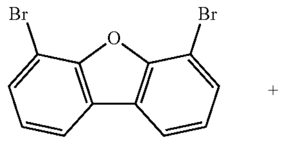

4,6-dibromodibenzofuran

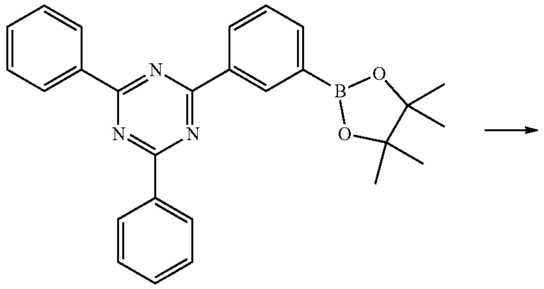

TBB

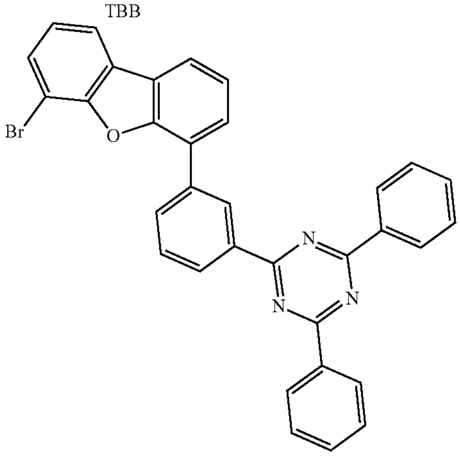

TDBFBr

In a round bottom flask, 4,6-dibromodibenzofuran (5 g, 0.015 mol), the Intermediate TBB (7.3 g, 0.017 mol), tetrakis(triphenylphosphine)palladium (0) (0.33 g, 0.307 mmol), toluene 100 ml, EtOH (ethanol) 10 ml and 4M $K_2CO_3$ (potassium carbonate) 15 ml were added, and the mixture was refluxed and stirred for 12 hours. After completion of the reaction, the reaction solution was filtered to obtain a crude product. The filtered crude product was recrystallized to obtain 7.2 g of the Intermediate TDBFBr.

(2) Compound H6-D1

[Reaction Formula 11-2]

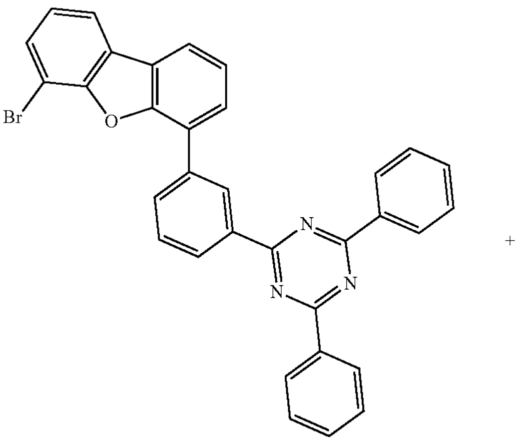

TDBFBr

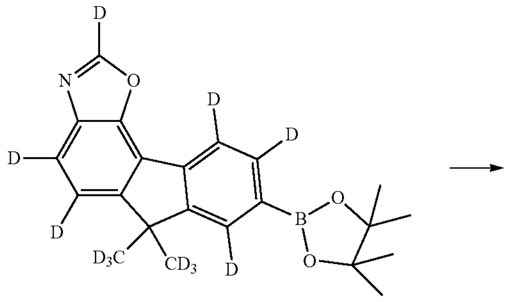

1D-DB

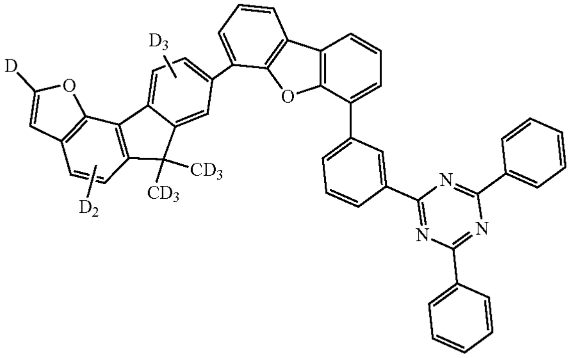

H6-D1

In a round bottom flask, the Intermediate TDBFBr (7.2 g, 0.013 mol), the Intermediate 1D-DB (5.3 g, 0.014 mol), tetrakis(triphenylphosphine)palladium(O) (0.3 g, 0.260 mmol), toluene 100 ml, EtOH (ethanol) 10 ml and 4M $K_2CO_3$ (potassium carbonate) 13 ml were added, and the mixture was refluxed and stirred for 12 hours. After completion of the reaction, the reaction solution was filtered to obtain a crude product. The filtered crude product was separated by column chromatography with $CHCl_3$ (chloroform) as an eluent to obtain 7.8 g of the compound H6-$D_1$.

12. Synthesis of the Compound H6-D2

(1) Intermediate TDBFDBr

[Reaction Formula 12-1]

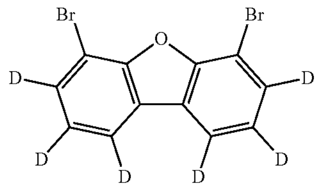

DBFD

+

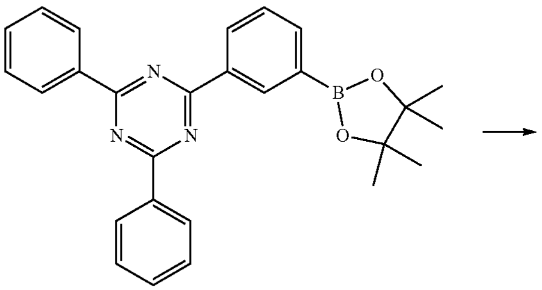

TBB

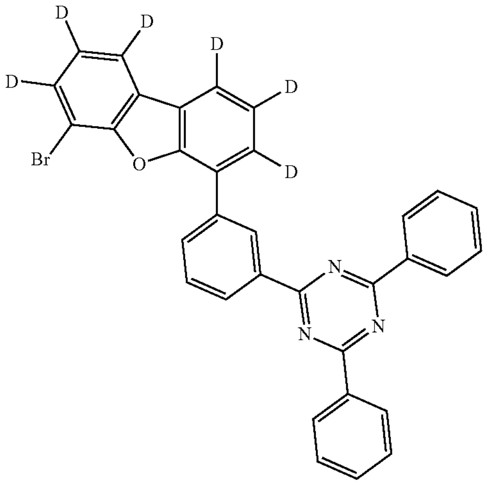

TDBFDBr

In the synthesis of the Intermediate TDBFBr, the Intermediate 4,6-dibromodibenzofuran was replaced by the Intermediate DBFD to obtain 7.0 g of the Intermediate TDBFDBr.

(2) Compound H6-D2

[Reaction Formula 12-2]

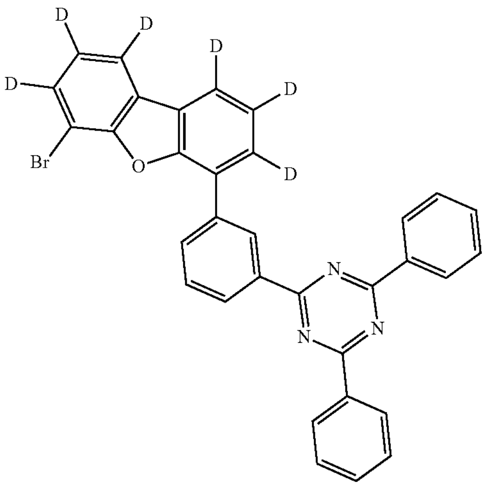

TDBFDBr

+

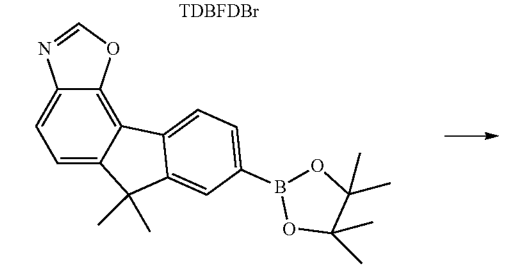

1D-B

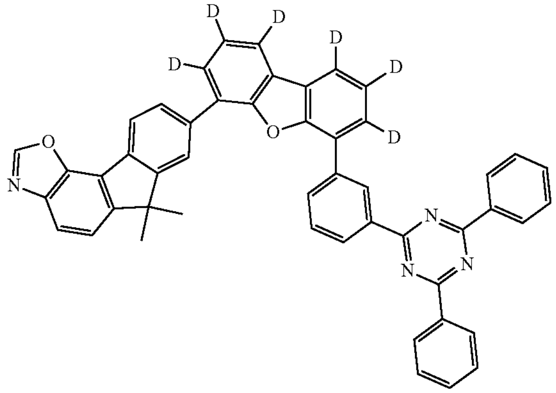

H6-D2

In the synthesis of the compound H6-D1, the Intermediate TDBFBr was replaced by the Intermediate TDBFDBr to obtain 7.2 g of the compound H6-D2.

13. Synthesis of the Compound H6-D3

(1) Intermediate DTDBFBr

[Reaction Formula 13-1]

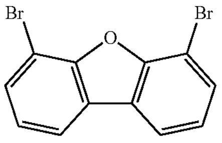

4,6-dibromodibenzofuran

+

-continued

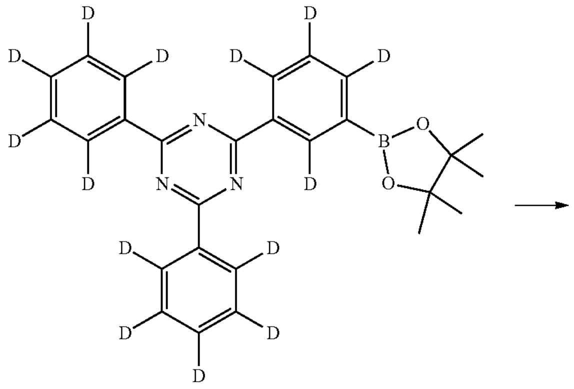

TBDB

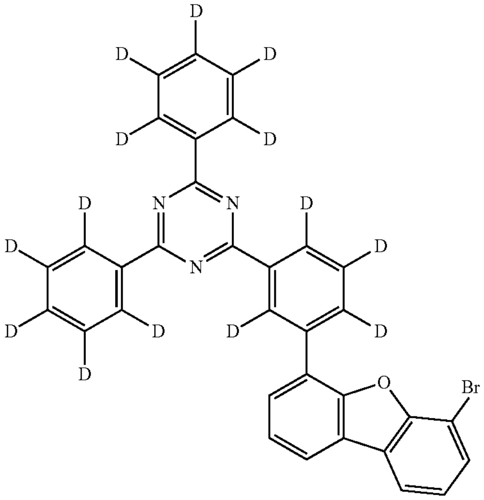

DTDBFBr

In the synthesis of the Intermediate TDBFBr, the Intermediate TBB was replaced by the Intermediate TBDB to obtain 7.3 g of the Intermediate DTDBFBr.

(2) Compound H6-D3

[Reaction Formula 13-2]

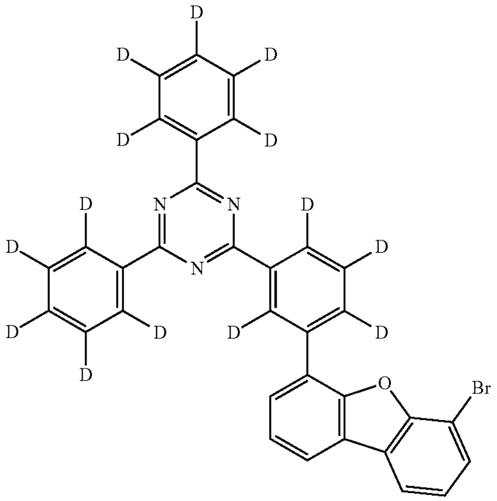

+

DTDBFBr

-continued

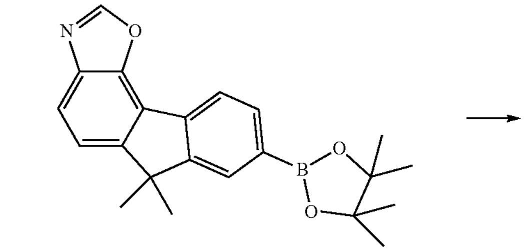

1D-B

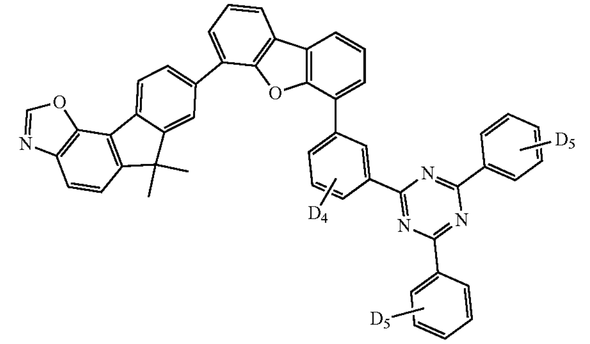

H6-D3

In the synthesis of the compound H6-D2, the Intermediate TDBFDBr was replaced by the Intermediate DTDBFBr to obtain 7.2 g of the compound H6-D3.

14. Synthesis of the Compound H6-D4

[Reaction Formula 14]

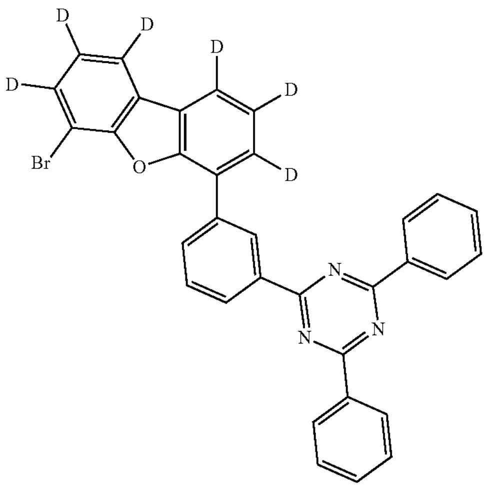

+

TDBFDBr

-continued

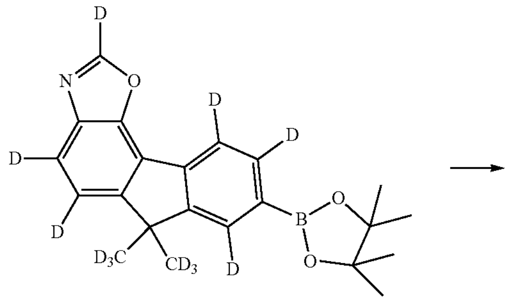

1D-DB

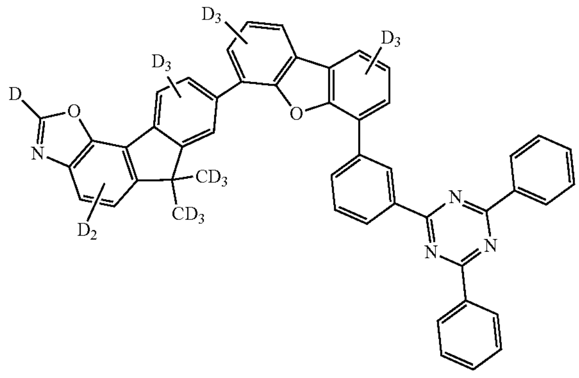

H6-D4

In the synthesis of the compound H6-D2, the Intermediate 1D-B was replaced by the Intermediate 1D-DB to obtain 6.9 g of the compound H6-D4.

15. Synthesis of the Compound H6-D5

(1) Intermediate DTDBFDBr

[Reaction Formula 15-1]

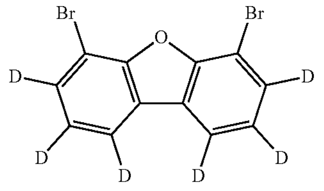

+

DBFD

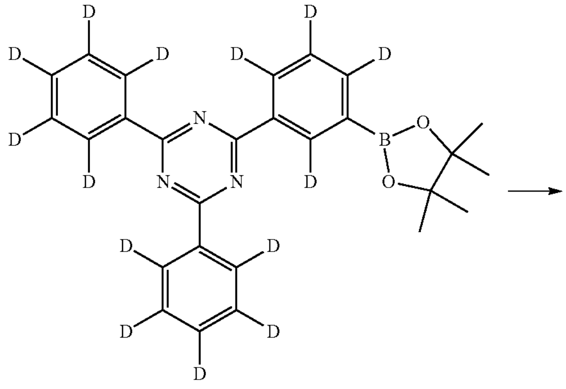

TBDB

-continued

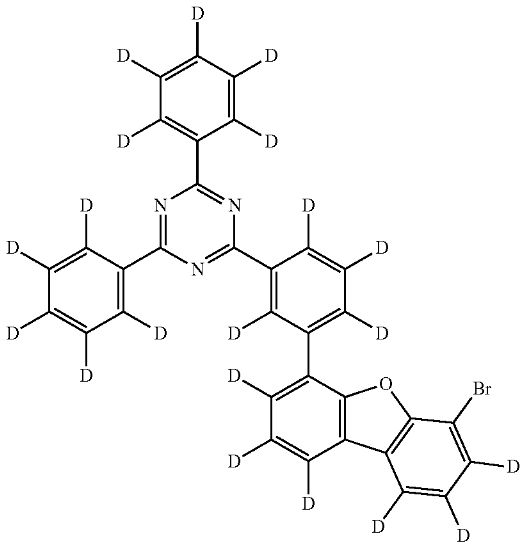

DTDBFDBr

In the synthesis of the Intermediate TDBFDBr, the Intermediate TBB was replaced by the Intermediate TBDB to obtain 7.0 g of the Intermediate DTDBFDBr.

(2) Compound H6-D5

[Reaction Formula 15-2]

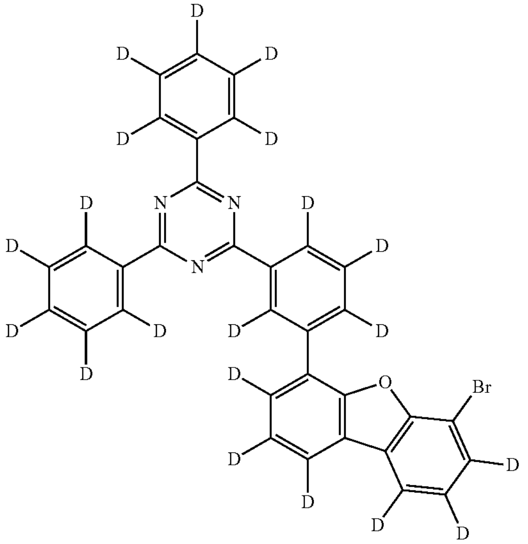

+

DTDBFDBr

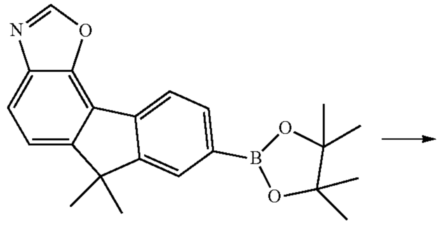

1D-B

-continued

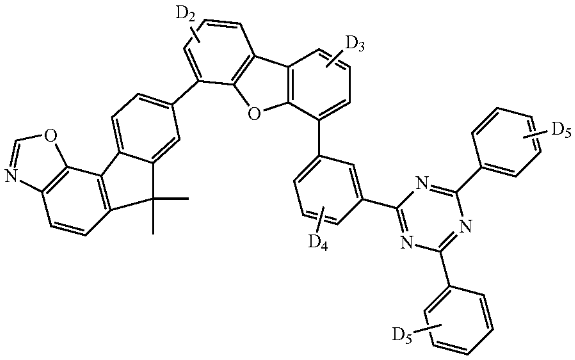

H6-D5

In the synthesis of the compound H6-D2, the Intermediate TDBFDBr was replaced by the Intermediate DTDBFDBr to obtain 7.1 g of the compound H6-D5.

16. Synthesis of the Compound H6-D6

[Reaction Formula 16]

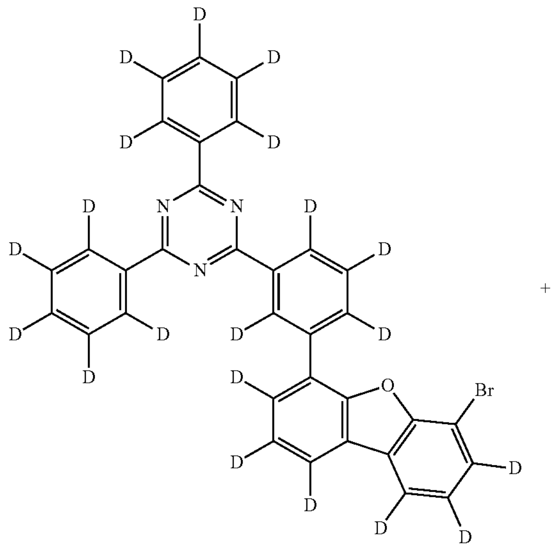

DTDBFDBr

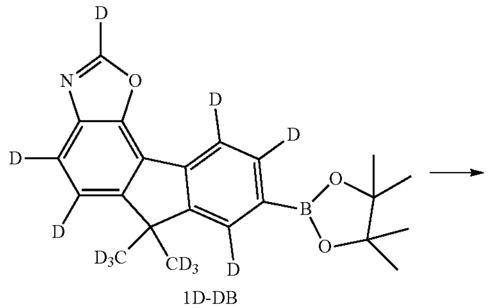

1D-DB

-continued

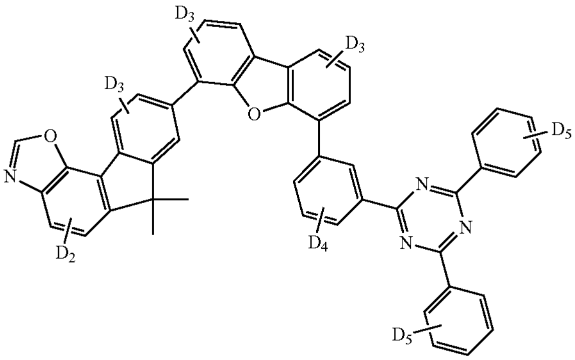

H6-D6

In the synthesis of the compound H6-D5, the Intermediate 1D-B was replaced by the Intermediate 1D-DB to obtain 7.5 g of the compound H6-D6.

17. Synthesis of the Compound H9-D1

[Reaction Formula 17]

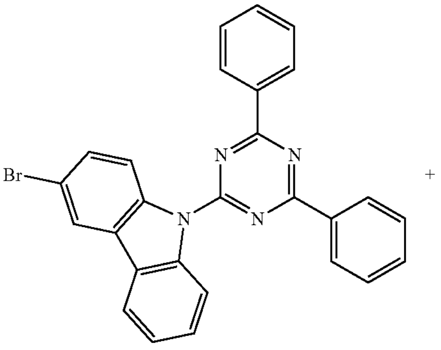

BB

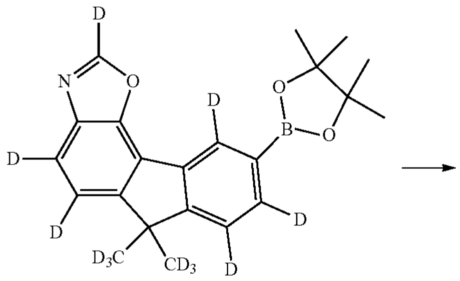

1AD-DB

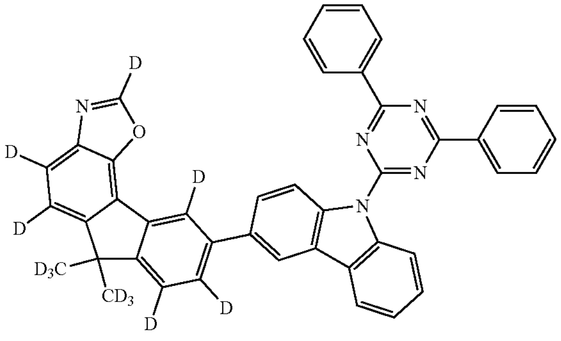

H9-D1

In the synthesis of the compound H1-D1, the Intermediate 1D-DB was replaced by the Intermediate 1AD-DB to obtain 5.3 g of the compound H9-D1.

18. Synthesis of the Compound H9-D2

[Reaction Formula 18]

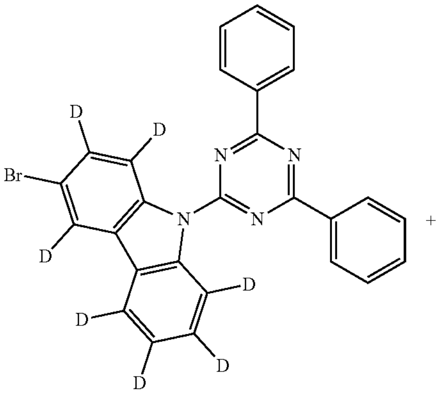

BC

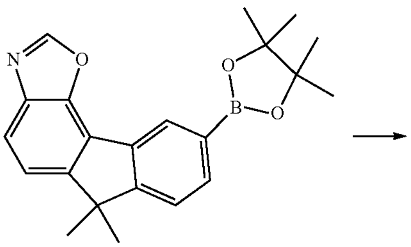

1AD-B

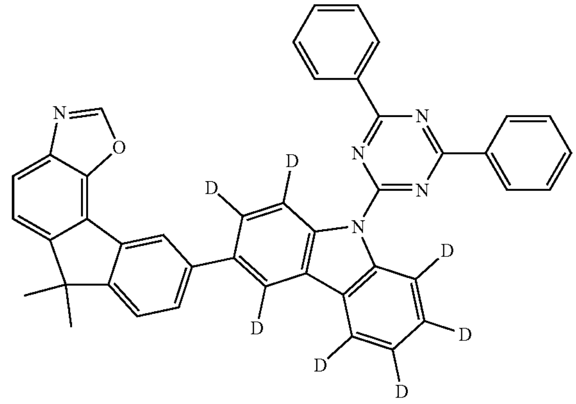

H9-D2

In the synthesis of the compound H1-D2, the Intermediate 1D-B was replaced by the Intermediate 1AD-B to obtain 5.3 g of the compound H-9-D2.

19. Synthesis of the Compound H9-D3

[Reaction Formula 19]

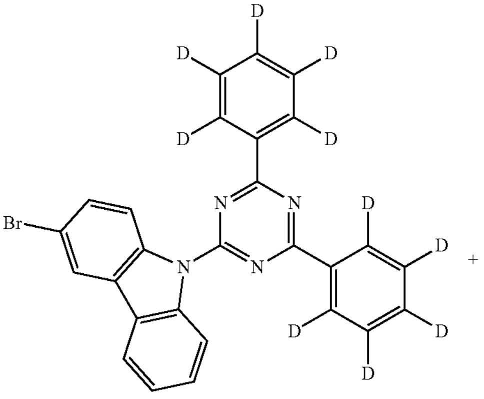

BD

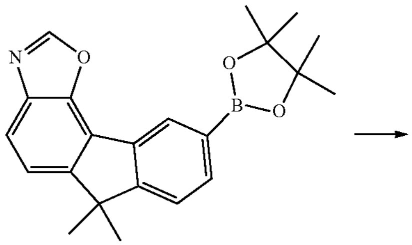

1AD-B

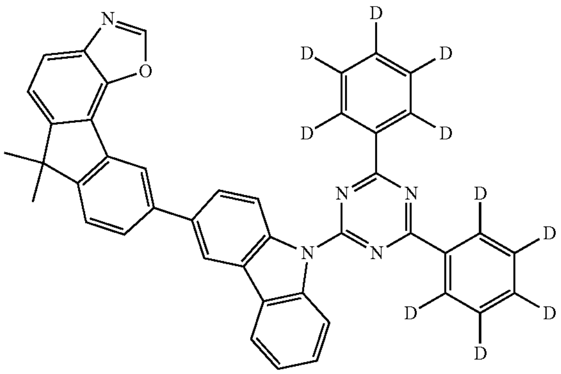

H9-D3

In the synthesis of the compound H1-D3, the Intermediate 1D-B was replaced by the Intermediate 1AD-B to obtain 5.2 g of the compound H9-D3.

20. Synthesis of the Compound H9-D4
[Reaction Formula 20]
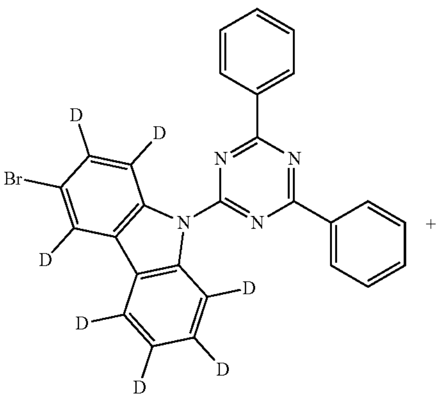
BC
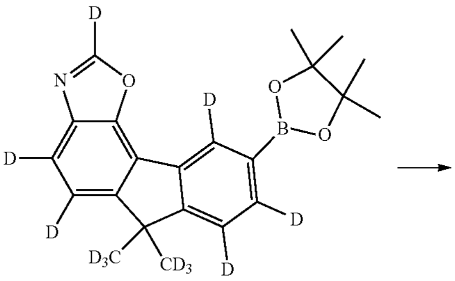
1AD-DB
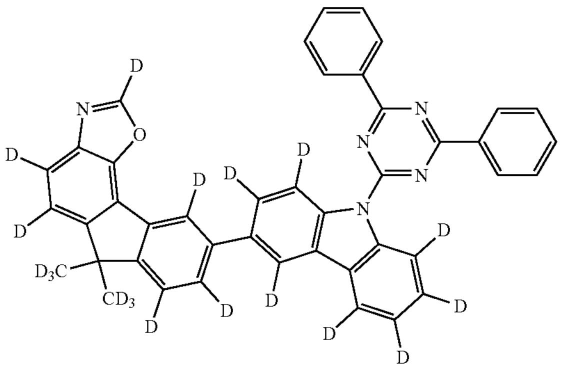
H9-D4
In the synthesis of the compound H1-D4, the Intermediate 1D-DB was replaced by the Intermediate TAD-DB to obtain 5.1 g of the compound H9-D4.
21. Synthesis of the Compound H9-D5
[Reaction Formula 21]
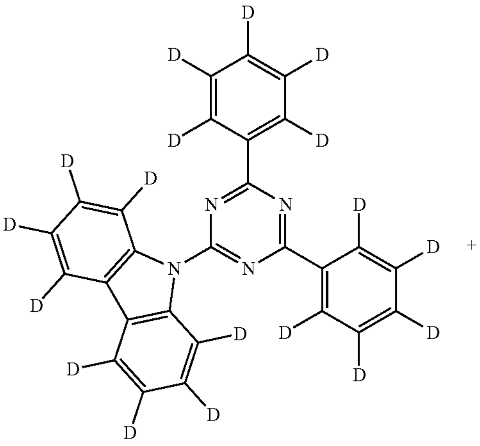
BE
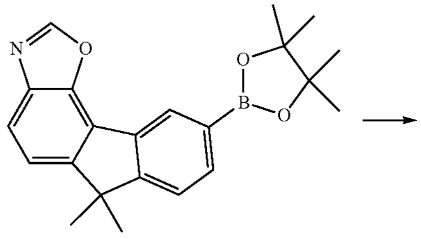
1AD-B
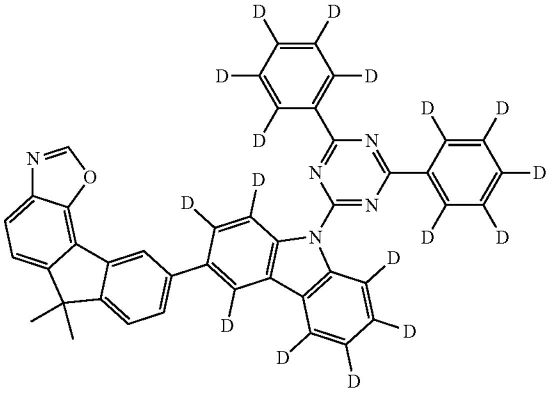
H9-D5
In the synthesis of the compound H1-D5, the Intermediate 1D-B was replaced by the Intermediate 1AD-B to obtain 5.2 g of the compound H-9-D5.

22. Synthesis of the Compound H9-D6
[Reaction Formula 22]
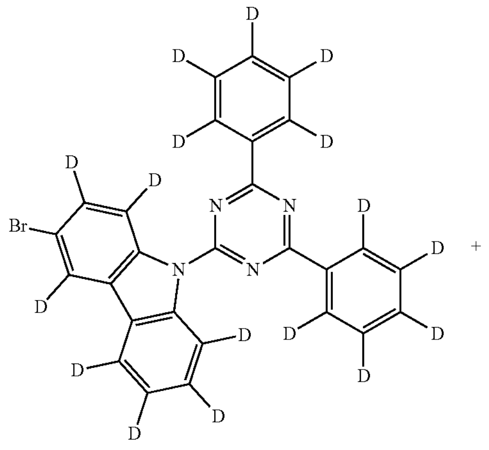
BE
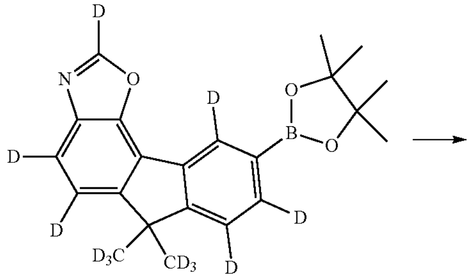
IAD-DB
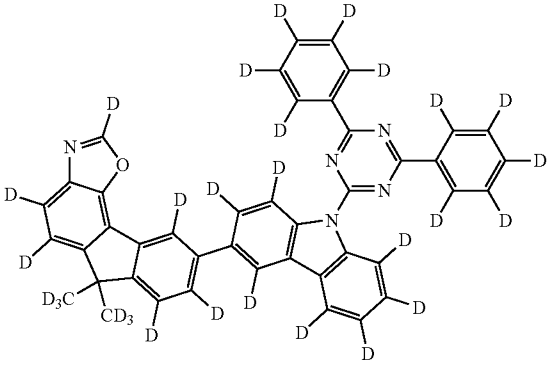
H9-D6
In the synthesis of the compound H1-D6, the Intermediate 1D-DB was replaced by the Intermediate 1AD-DB to obtain 5.3 g of the compound H9-D6.
23. Synthesis of the Compound H21-D1
[Reaction Formula 23]
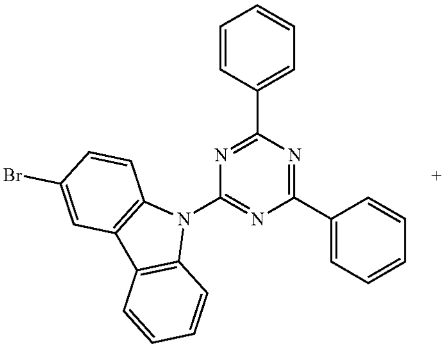
BB
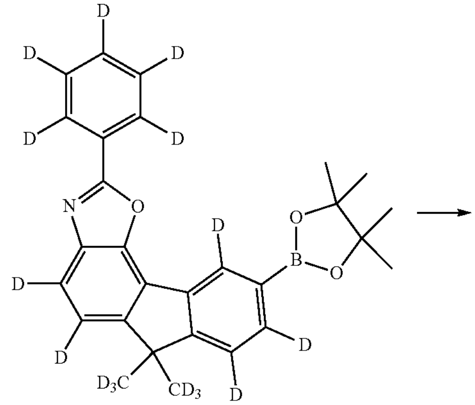
2E-DB
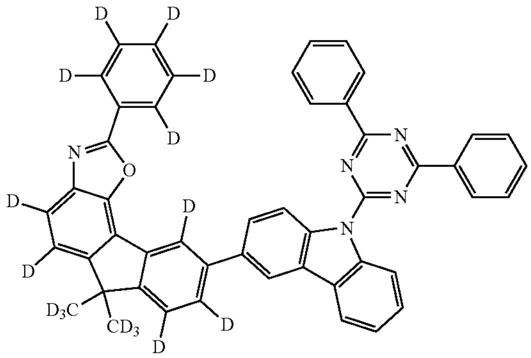
H21-D1
In the synthesis of the compound H1-D1, the Intermediate 1D-DB was replaced by the Intermediate 2E-DB to obtain 5.5 g of the compound H21-D1.

24. Synthesis of the Compound H21-D2
Reaction Formula 24
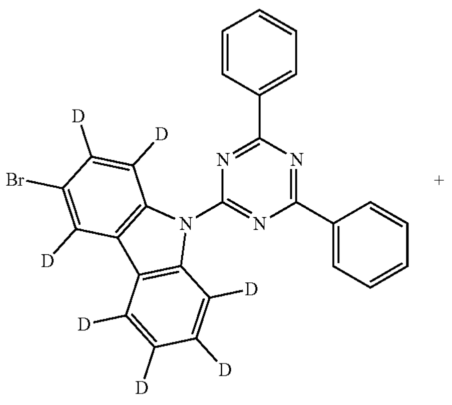
BC
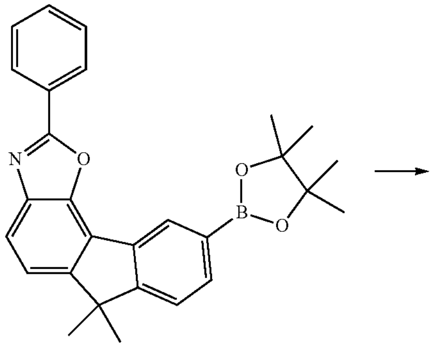
2E-B
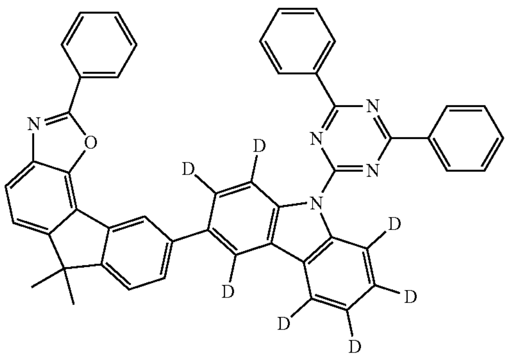
H21-D2
In the synthesis of the compound H1-D2, the Intermediate 1D-B was replaced by the Intermediate 2E-B to obtain 5.4 g of the compound H21-D2.
25. Synthesis of the Compound H21-D3
Reaction Formula 25
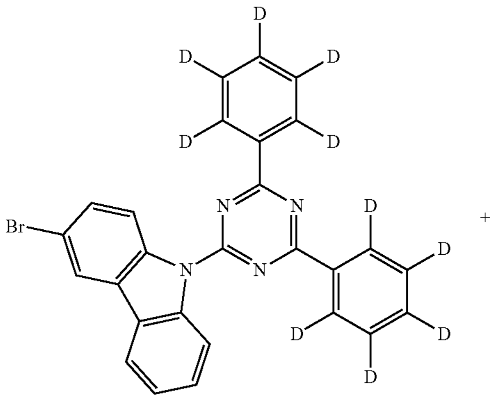
BD
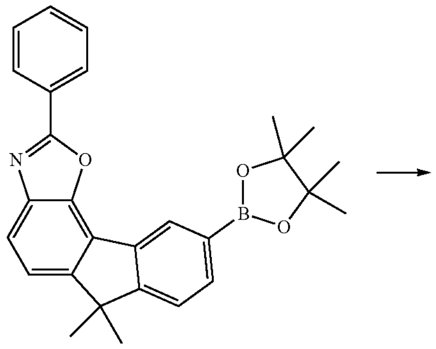
2E-B
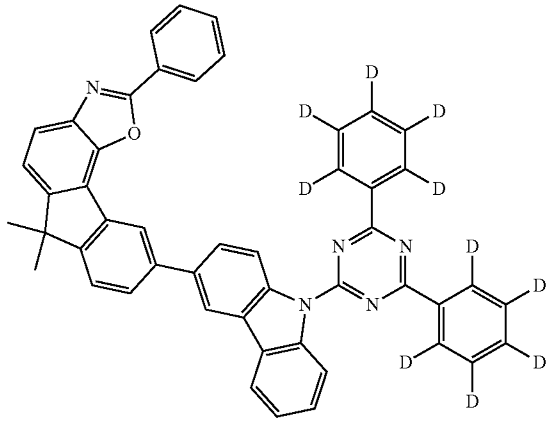
H21-D3
In the synthesis of the compound H1-D3, the Intermediate 1D-B was replaced by the Intermediate 2E-B to obtain 5.2 g of the compound H21-D3.

26. Synthesis of the Compound H21-D4
[Reaction Formula 26]
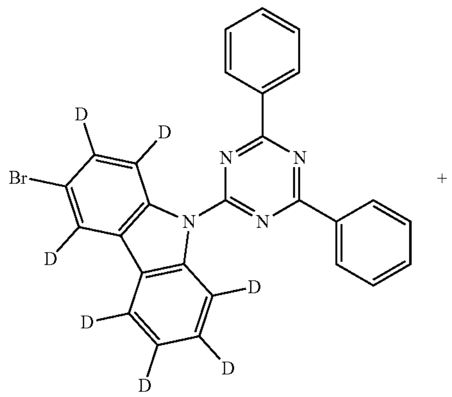
BC
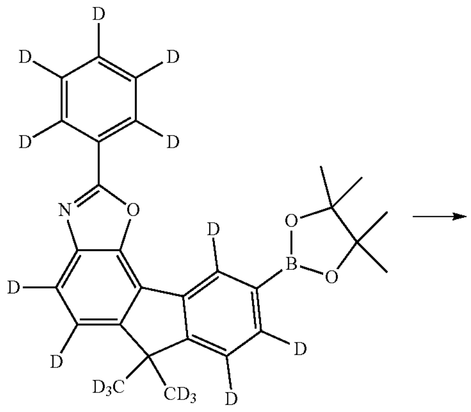
2E-DB
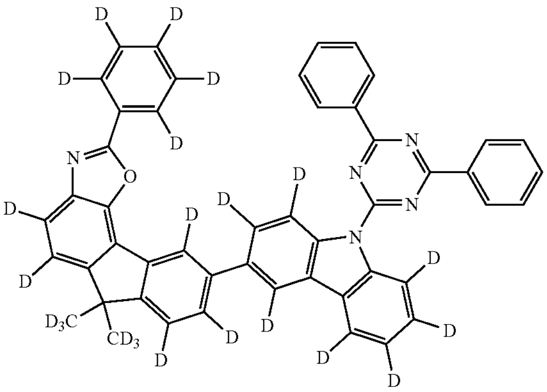
H21-D4
In the synthesis of the compound H1-D4, the Intermediate 1D-DB was replaced by the Intermediate 2E-DB to obtain 5.2 g of the compound H21-D4.
27. Synthesis of the Compound H21-D5
[Reaction Formula 27]
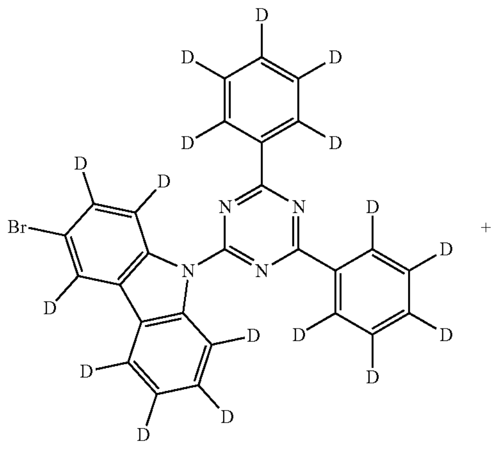
BE
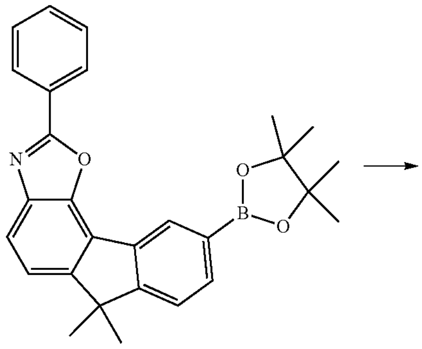
2E-B
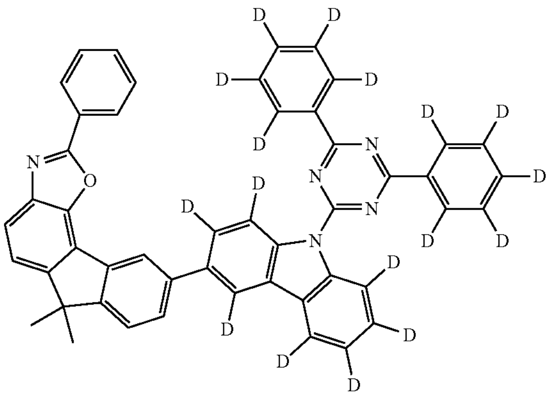
H21-D5
In the synthesis of the compound H1-D5, the Intermediate 1D-B was replaced by the Intermediate 2E-B to obtain 5.3 g of the compound H21-D5.

28. Synthesis of the Compound H21-D6

[Reaction Formula 28]

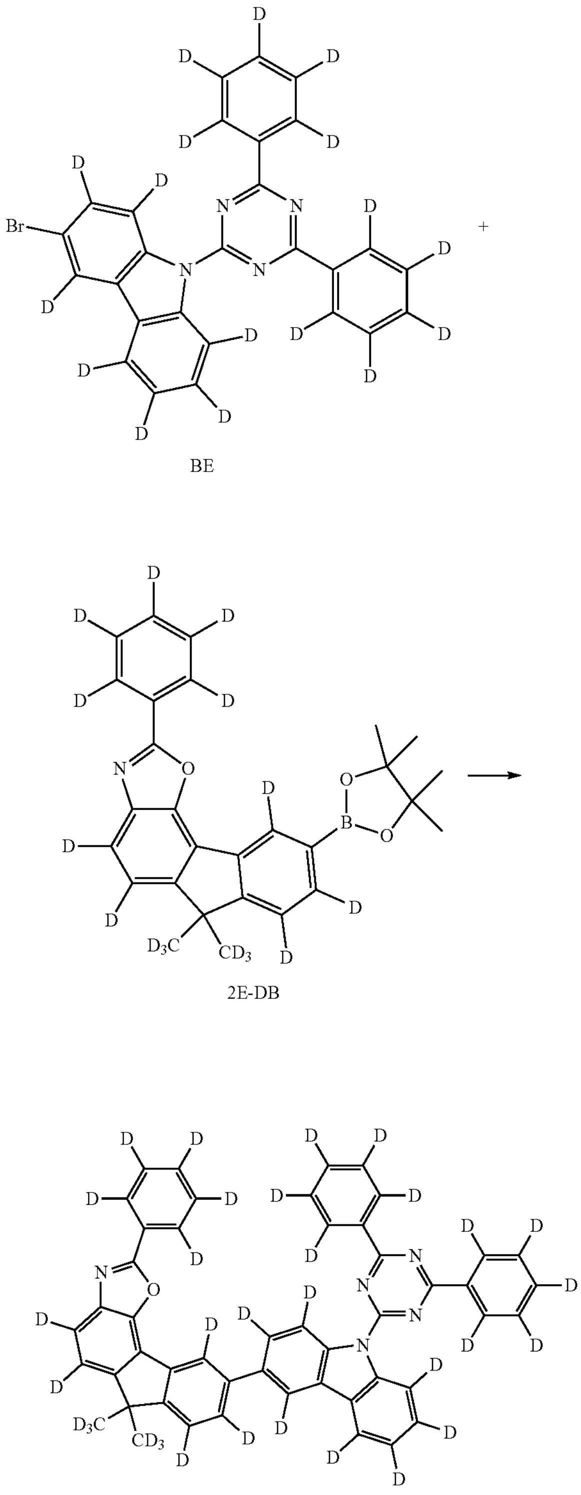

BE

2E-DB

H21-D6

In the synthesis of the compound H1-D6, the Intermediate 1D-DB was replaced by the Intermediate 2E-DB to obtain 5.2 g of the compound H21-D6.

29. Synthesis of the Compound H31-D1

[Reaction Formula 29]

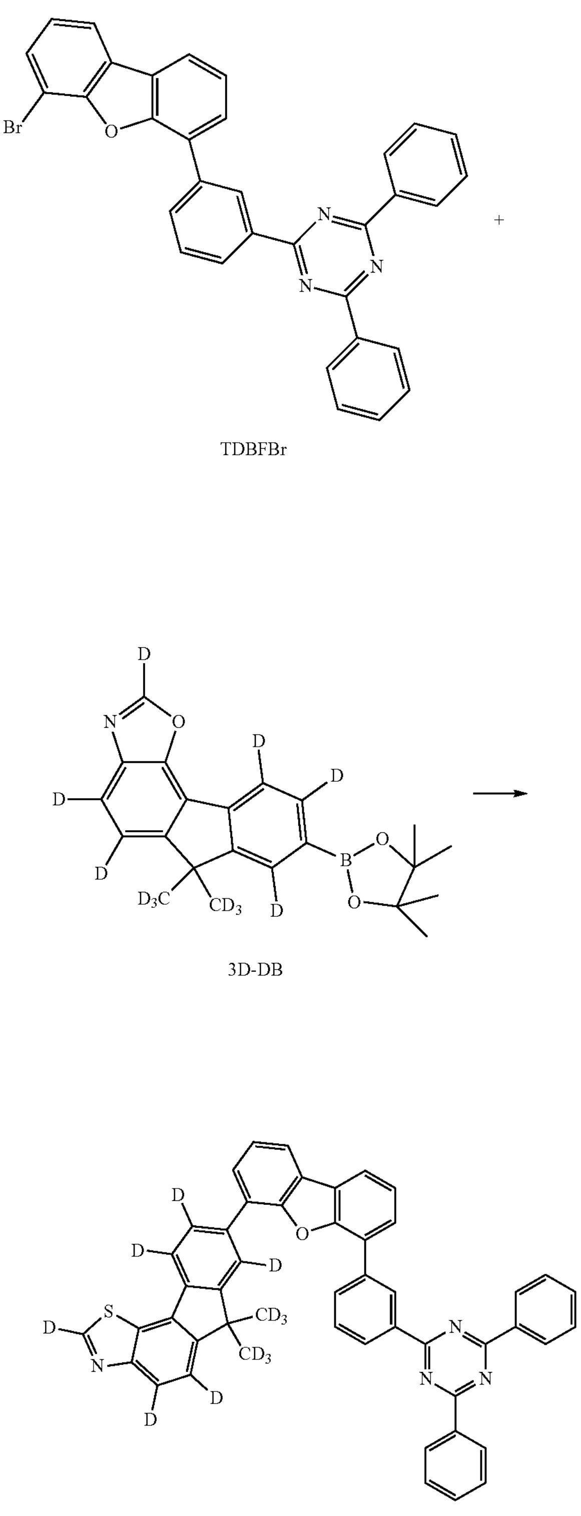

TDBFBr

3D-DB

H31-D1

In the synthesis of the compound H6-D1, the Intermediate 1D-DB was replaced by the Intermediate 3D-DB to obtain 7.5 g of the compound H31-D1.

30. Synthesis of the Compound H31-D2

[Reaction Formula 30]

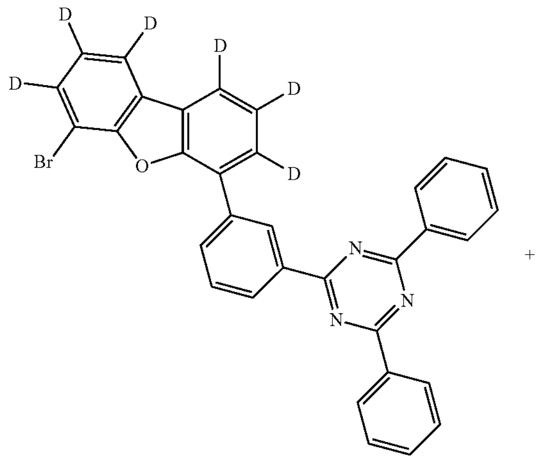

TDBFDBr

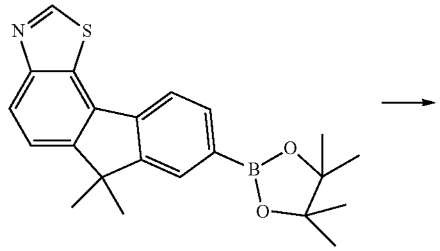

3D-B

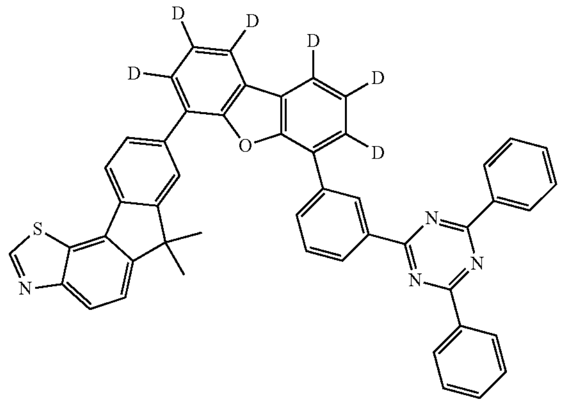

H31-D2

In the synthesis of the compound H6-D2, the Intermediate 1D-B was replaced by the Intermediate 3D-DB to obtain 7.2 g of the compound H31-D2.

31. Synthesis of the Compound H31-D3

[Reaction Formula 31]

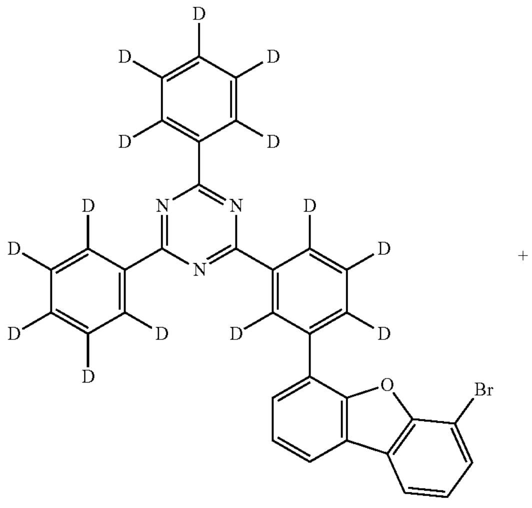

DTDBFBr

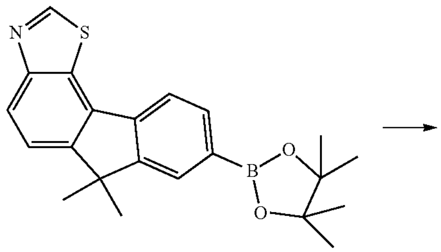

3D-B

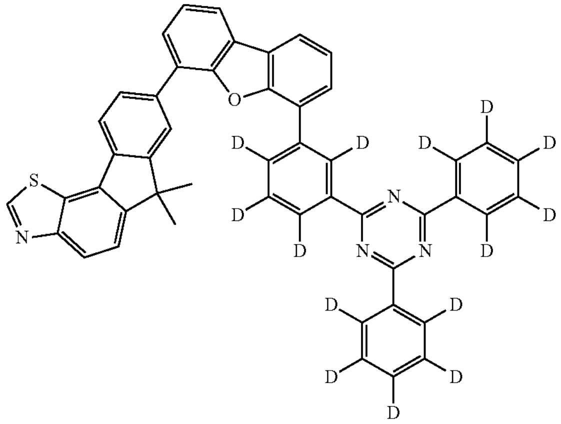

H31-D3

In the synthesis of the compound H6-D3, the Intermediate 1D-B was replaced by the Intermediate 3D-B to obtain 7.3 g of the compound H31-D3.

32. Synthesis of the Compound H31-D4

[Reaction Formula 32]

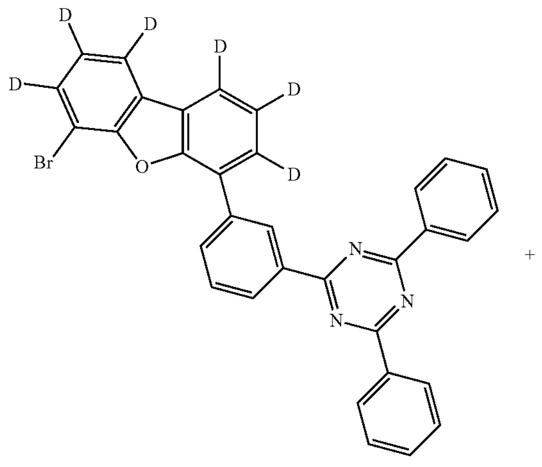

TDBFDBr

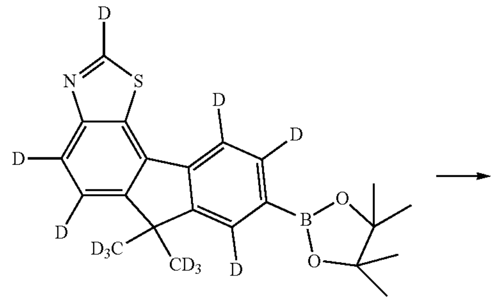

3D-DB

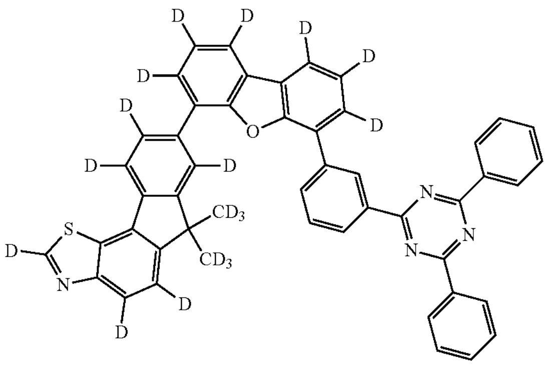

H31-D4

In the synthesis of the compound H6-D4, the Intermediate 1D-DB was replaced by the Intermediate 3D-DB to obtain 7.1 g of the compound H31-D4.

33. Synthesis of the Compound H31-D5

[Reaction Formula 33]

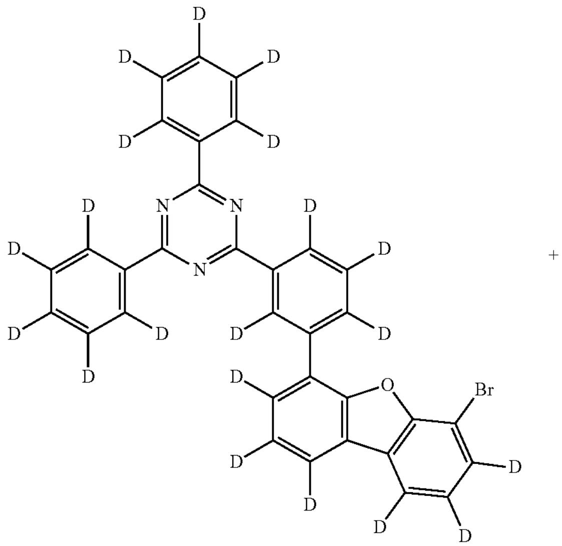

DTDBFDBr

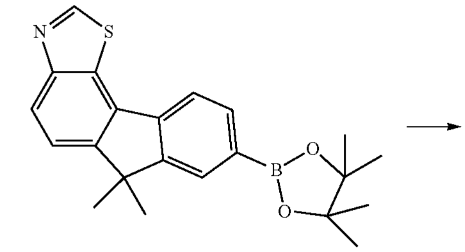

3D-B

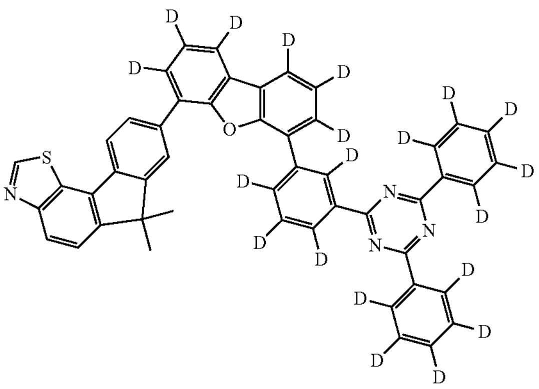

H31-D5

In the synthesis of the compound H-6-D5, the Intermediate 1D-B was replaced by the Intermediate 3D3-B to obtain 7.1 g of the compound H31-D5.

34. Synthesis of the Compound H31-D6

[Reaction Formula 34]

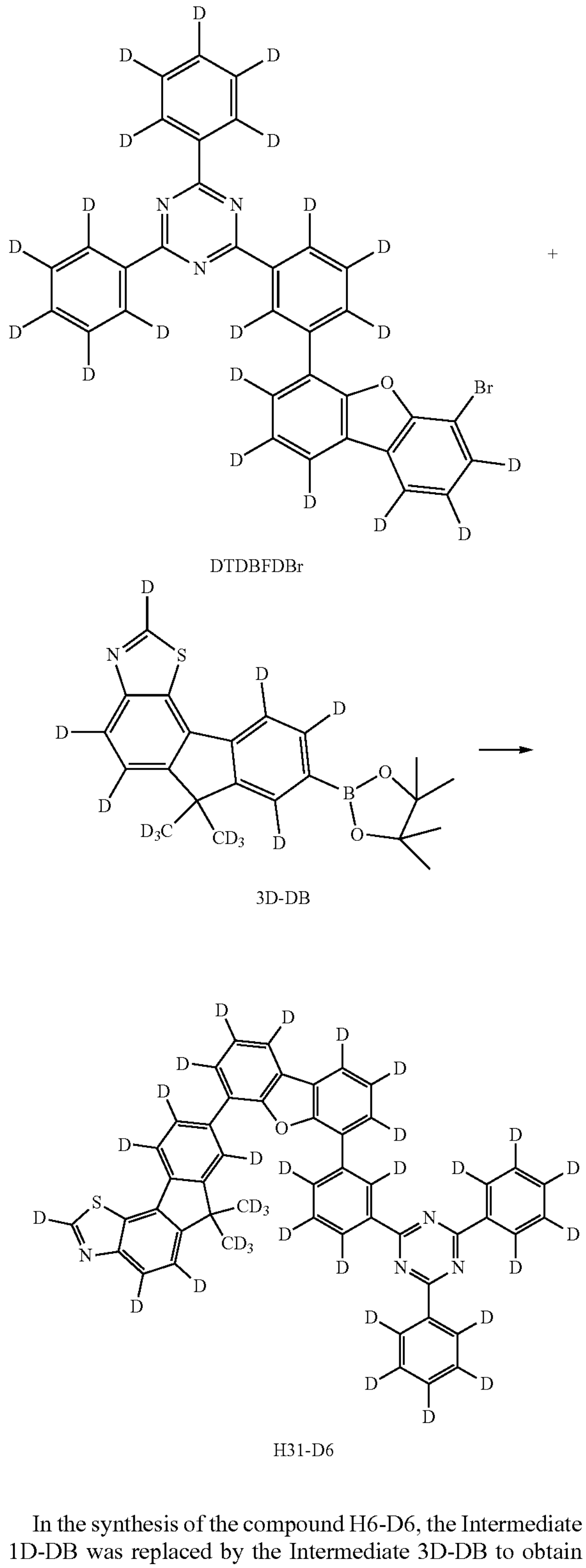

DTDBFDBr

3D-DB

H31-D6

In the synthesis of the compound H6-D6, the Intermediate 1D-DB was replaced by the Intermediate 3D-DB to obtain 7.4 g of the compound H31-D6.

The green EML 230 may further include a second compound 234 represented by Formula 3.

[Formula 3]

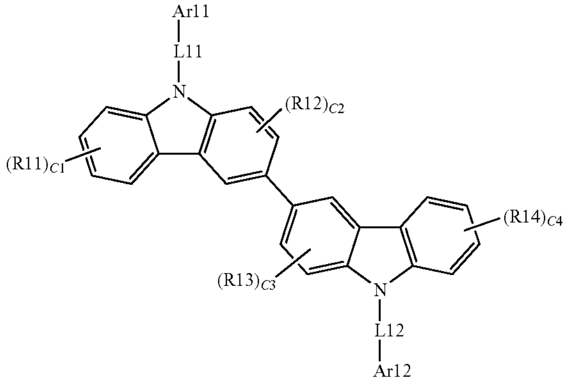

In Formula 3, each of R11, R12, R13, and R14 is independently selected from the group consisting of deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, each of c1 and c4 is independently an integer of 0 to 4, and each of c2 and c3 is independently an integer of 0 to 3. Each of L11 and L12 is independently selected from the group consisting of a single bond (or direct bond), a substituted or unsubstituted C6 to C30 arylene group, and a substituted or unsubstituted C3 to C30 heteroarylene group, and each of Ar11 and Ar12 is independently selected from the group consisting of a single bond, a substituted or unsubstituted C6 to C30 aryl group, and a substituted or unsubstituted C3 to C30 heteroaryl group.

For example, a substituent may include a deuterium atom.

In Formula 3, L11 and L12 may be a single bond. Each of Ar11 and Ar12 may be independently selected from a substituted or unsubstituted phenyl. For example, Formula 3 may be represented by Formula 3a.

[Formula 3a]

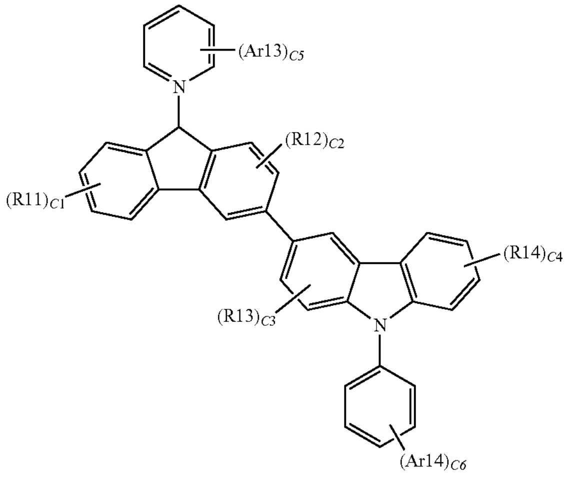

In Formula 3a, definitions of R11, R12, R13, R14, c1, c2, c3, and c4 may be same as those in Formula 3. Each of R13 and R14 may be independently selected from a substituted or unsubstituted C6 to C30 aryl group. Each of c5 and c6 may be independently an integer of 0 to 5.

For example, in Formula 3a, each of R13 and R14 may be independently selected from phenyl and biphenyl. Each of C5 and C6 may be independently 0 or 1.

The second compound 234 may be one of the compounds in Formula 4.

[Formula 4]

BCz-1

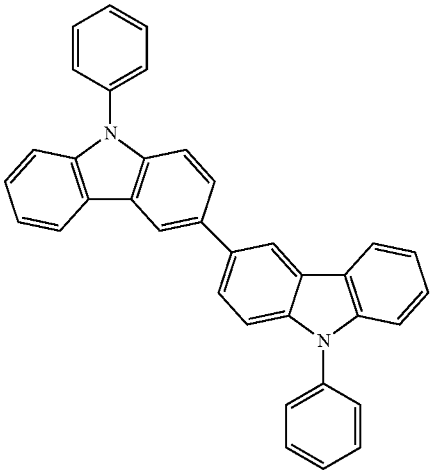

BCz-2

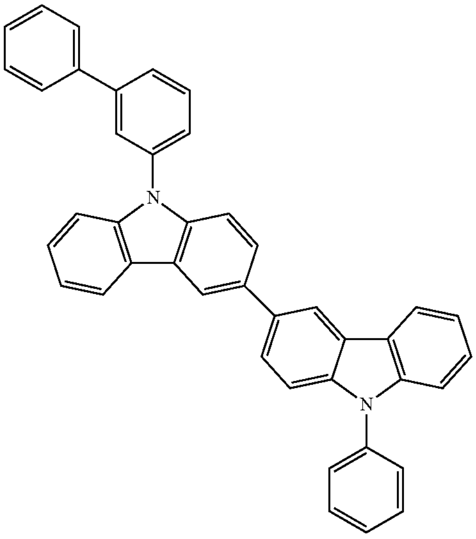

-continued

BCz-3

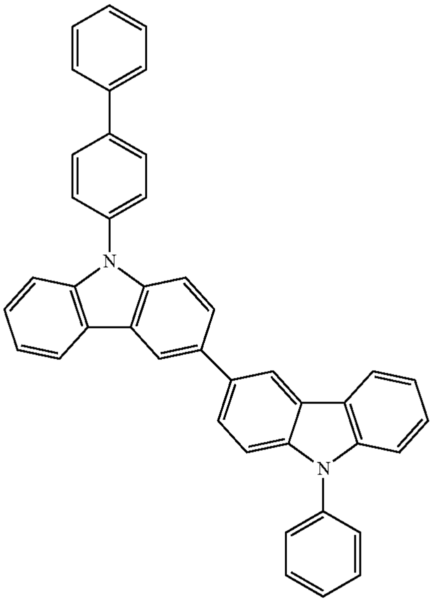

BCz-4

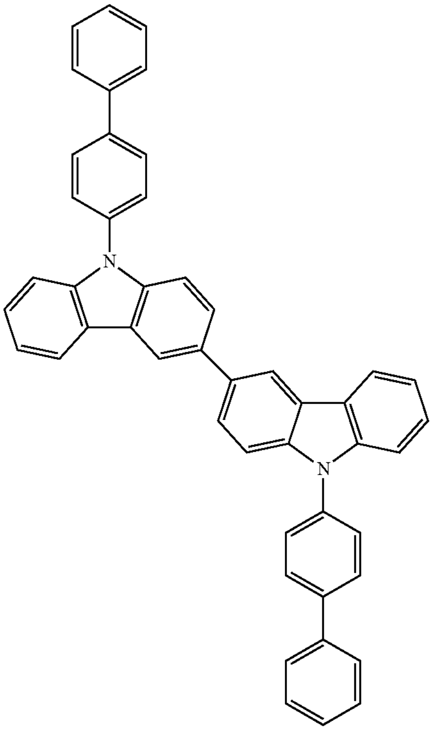

-continued
BCz-5
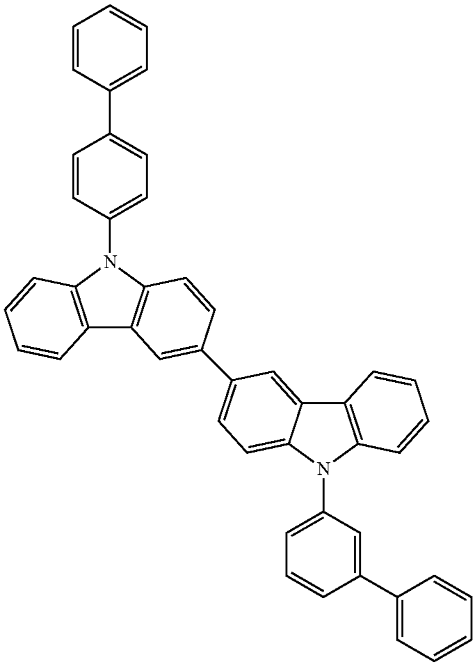
BCz-6
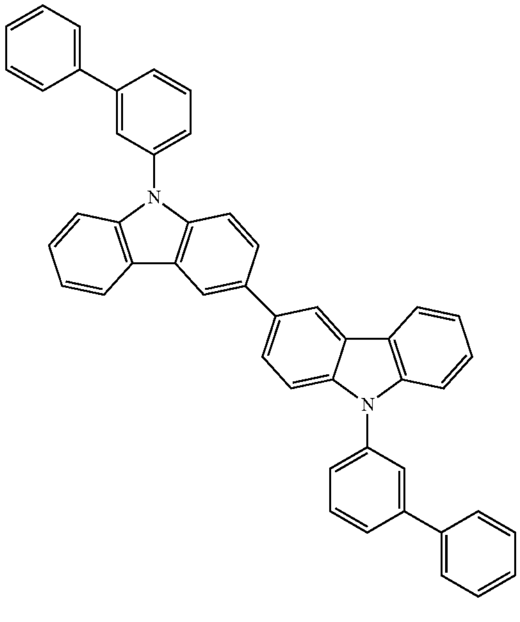
-continued
BCz-7
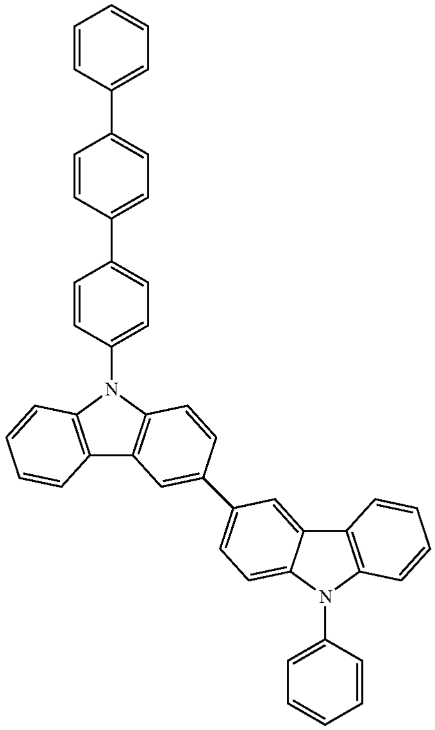
BCz-8
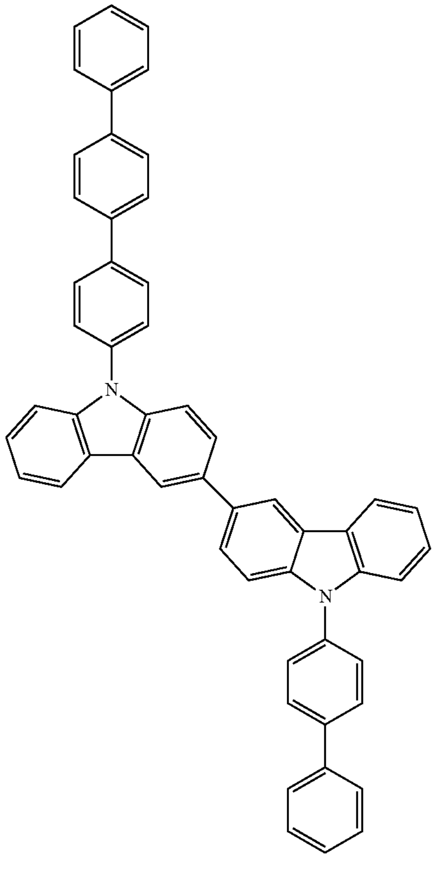

-continued
BCz-9
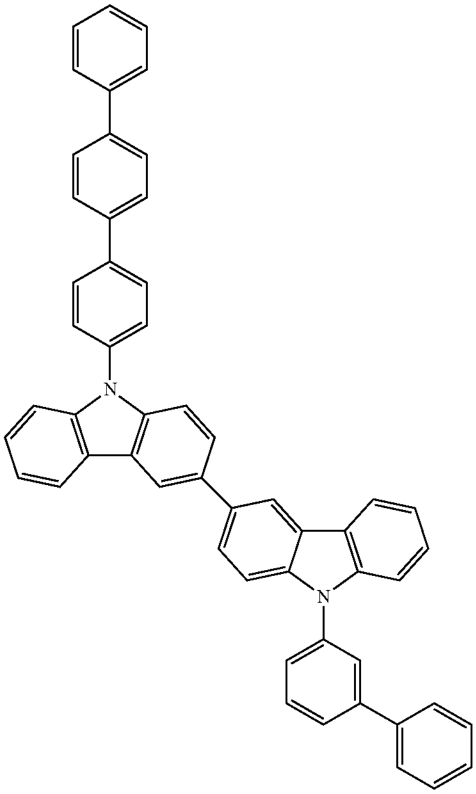
BCz-10
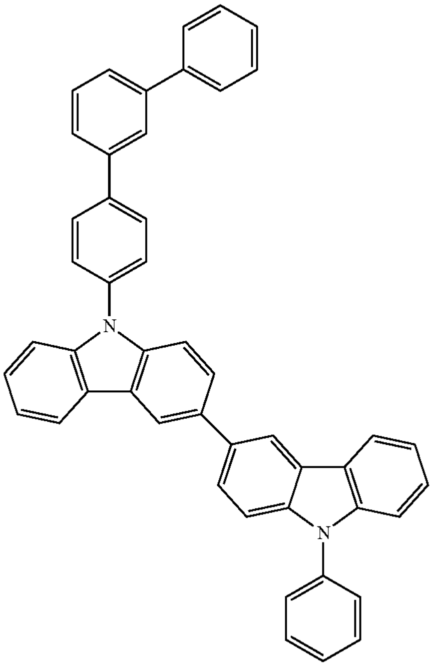
-continued
BCz-11
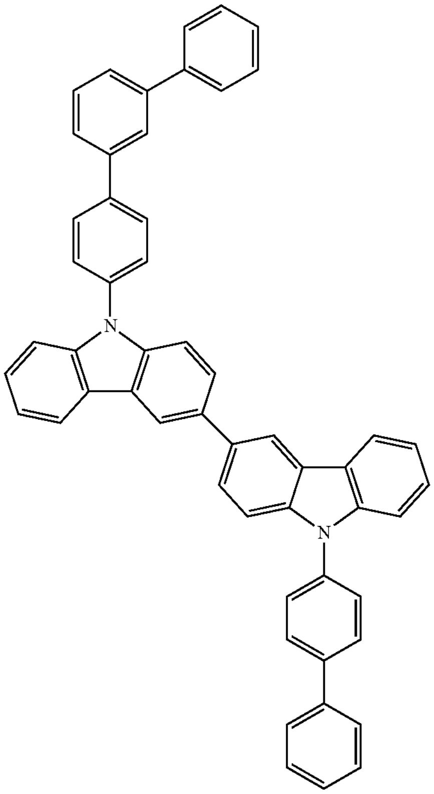
BCz-12
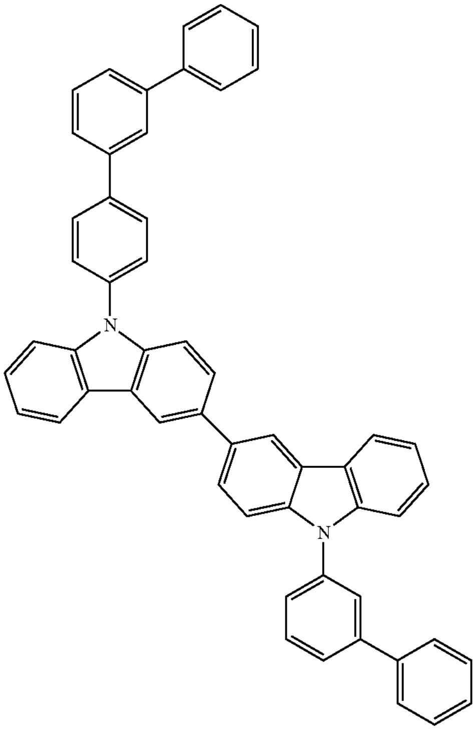

-continued
BCz-13
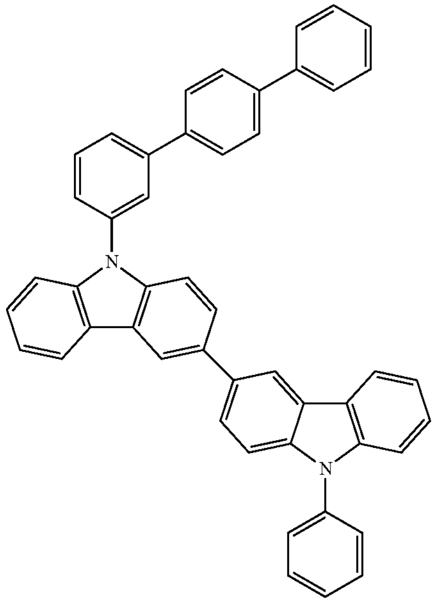
BCz-14
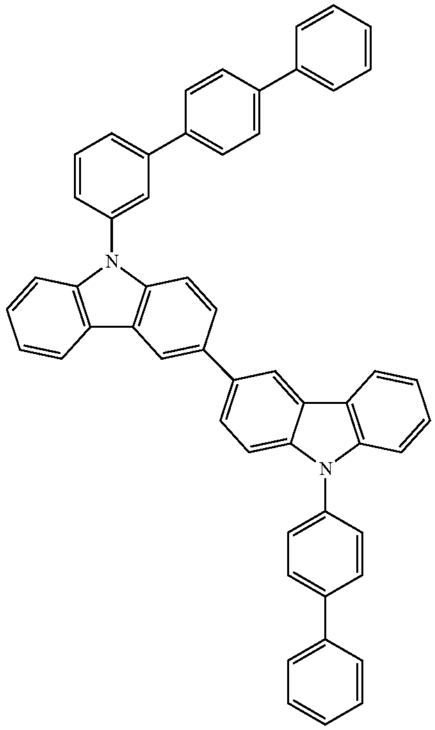
-continued
BCz-15
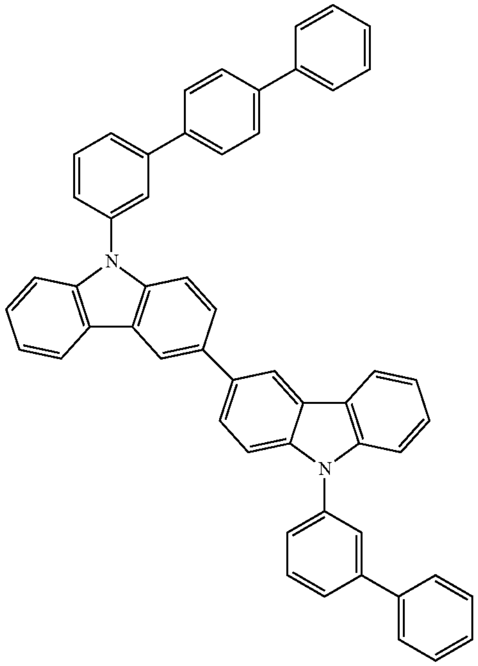
BCz-16
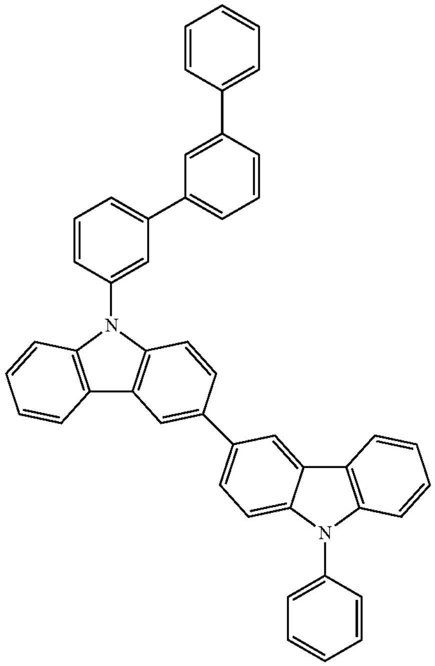

-continued
BCz-17
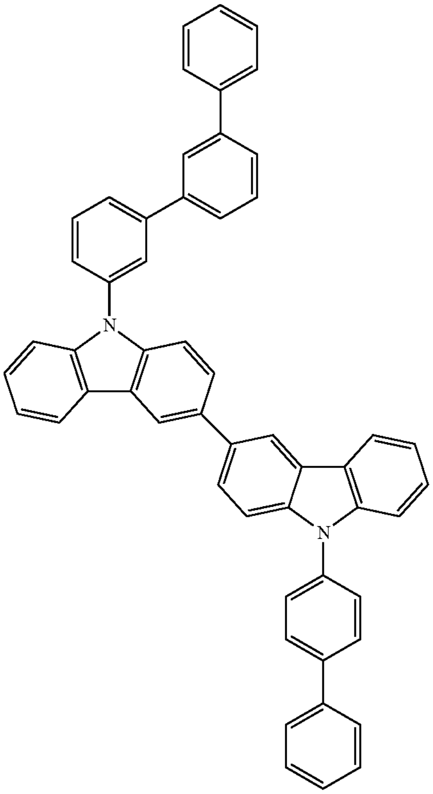
BCz-18
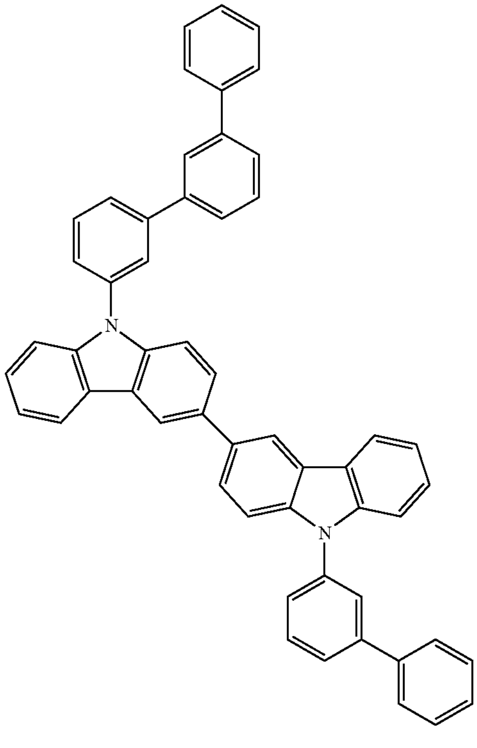
-continued
BCz-19
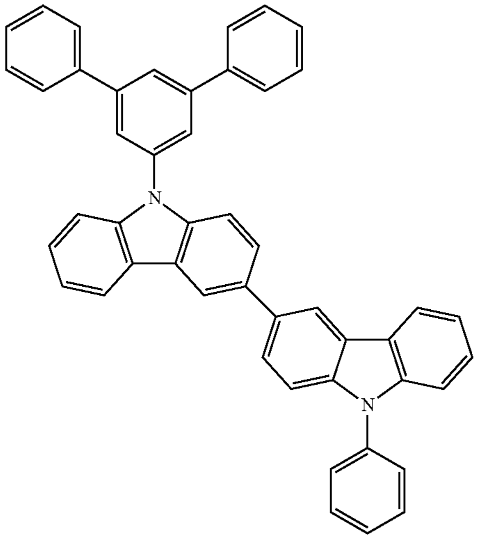
BCz-20
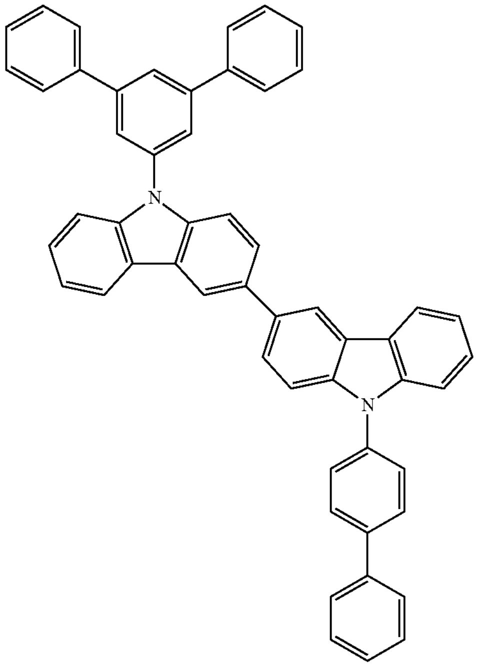

-continued
BCz-21
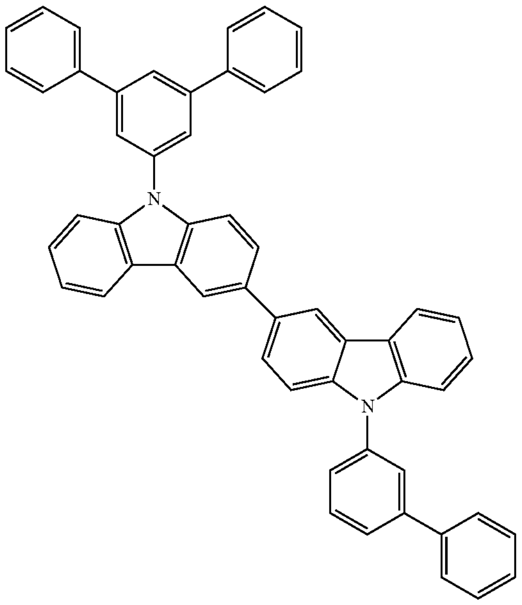
BCz-22
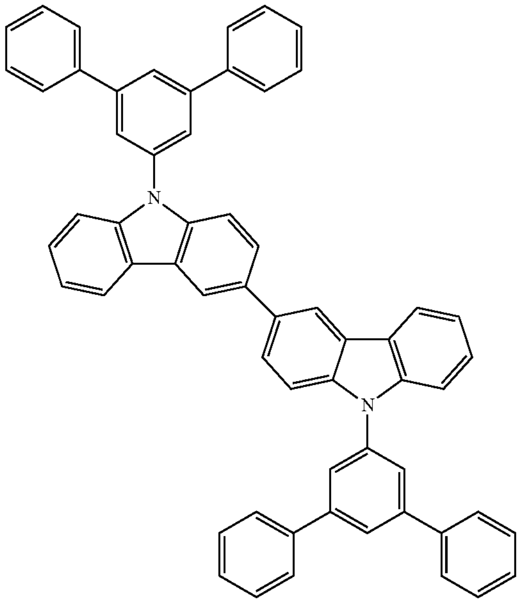
-continued
BCz-23
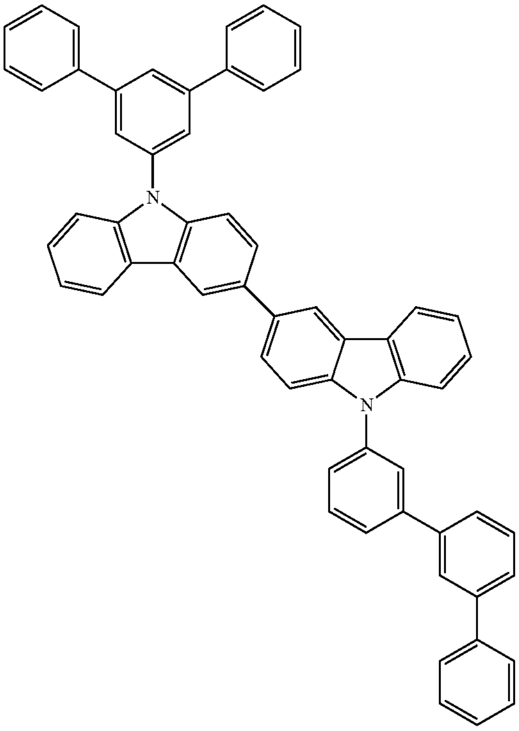
BCz-24
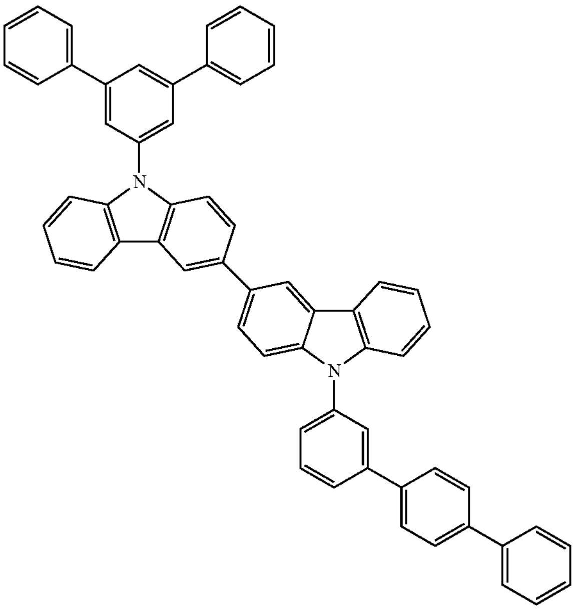

-continued

BCz-25

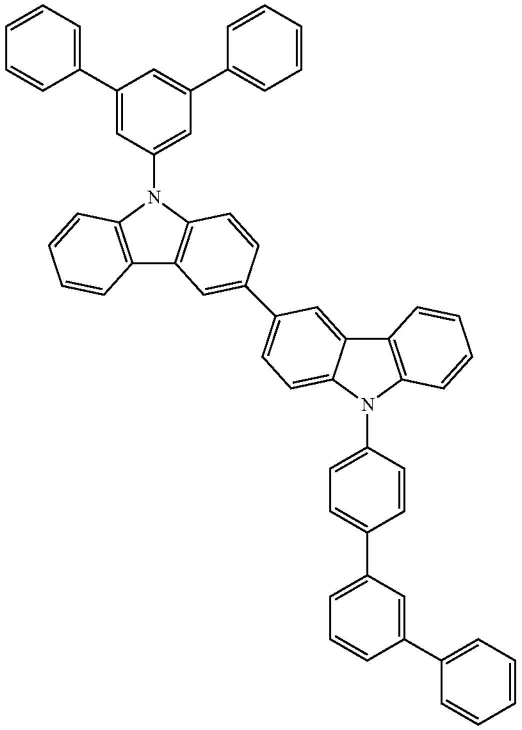

The green EML 230 may further include a third compound 236 represented by Formula 5.

[Formula 5]

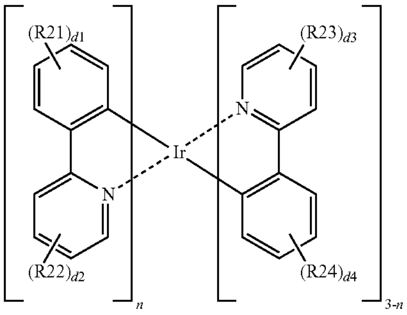

In Formula 5, each of R21, R22, R23, and R24 may be independently selected from the group consisting of a substituted or unsubstituted C1 to C10 alkyl group, a substituted or unsubstituted C6 to C30 aryl group, and a substituted or unsubstituted C3 to C30 heteroaryl group. Each of d1, d2, d3, and d4 may be independently an integer of 0 to 4, and n may be an integer of 1 to 3.

The third compound 236 may be one of the compounds in Formula 6.

[Formula 6]

GD1

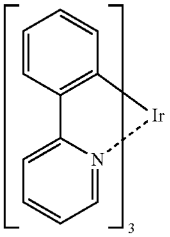

GD2

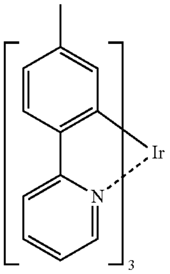

GD3

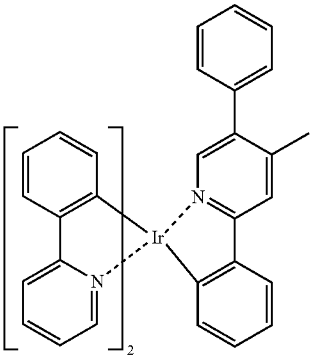

GD4

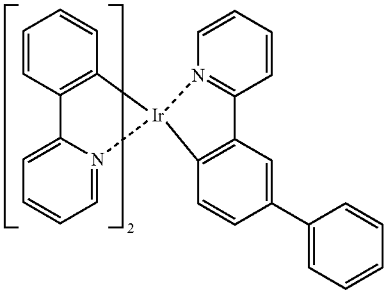

GD5

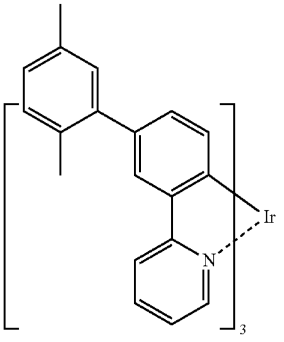

-continued

GD6

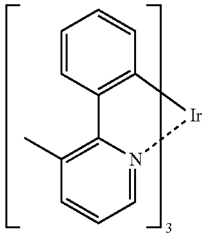

In the green EML 230, the first compound 232 may be an n-type host (e.g., a first host). The second compound 234 may be a p-type host (e.g., a second host). The third compound 236 may be an emitter (e.g., a dopant). The green EML 230 may have a thickness of 50 to 600 Å, for example, 200 to 400 Å.

In the green EML 230, a weight % of each of the first and second compounds 232 and 234 may be greater than that of the third compound 236. The weight % of the first compound 232 and the weight % of the second compound 234 may be same or different. In the green EML 230, a weight % ratio of the first compound 232 to the second compound 234 may be 1:9 to 9:1, 2:8 to 8:2 or 7:3 to 3:7. In some embodiments, the weight % of the first compound 232 and the weight % of the second compound 234 may be same. For example, the first compound 232 and the second compound 234 may be present at the same weight %. The third compound 236 may be present in an amount of 5 to 25 weight % in the green EML 230, based on a total weight of the components in the green EML 230.

The organic light emitting layer 162 may further include an ETL 240 between the green EML 230 and the second electrode 164. For example, the ETL 240 may contact the green EML 230. The ETL 240 may have a thickness that may be substantially the same as the green EML 230. For example, the ETL 240 may have a thickness of 50 to 600 Å, for example, 200 to 400 Å.

The ETL 240 may include a compound (e.g., an electron transporting material) represented by Formula 7.

[Formula 7]

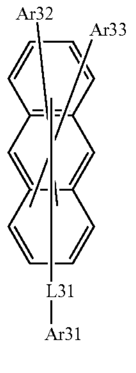

In Formula 7, L31 may be selected from the group consisting of a single bond, a substituted or unsubstituted C6 to C30 arylene group, and a substituted or unsubstituted C3 to C30 heteroarylene group. Ar31 may be represented by Formula 7a or Formula 7b. Each of Ar32 and Ar33 may be independently selected from the group consisting of hydrogen, deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group.

[Formula 7a]

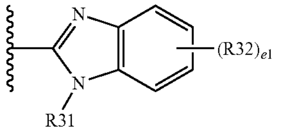

[Formula 7b]

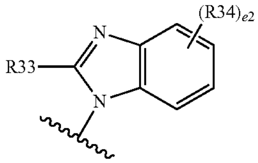

In Formula 7a, R31 may be selected from the group consisting of hydrogen, deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group. R32 may be selected from the group consisting of deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, and e1 may be an integer of 0 to 4. In Formulas 7a and 7b, the wavy mark is a bonding (linking) site to L31 in Formula 7.

In Formula 7b, R33 may be selected from the group consisting of hydrogen, deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group. R34 may be selected from the group consisting of deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, and e2 may be an integer of 0 to 4.

For example, Formula 7 may be represented by Formula 7c.

[Formula 7c]

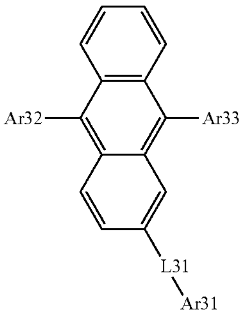

In Formula 7c, the definitions of L31, Ar31, Ar32 and Ar33 are same as those in Formula 7.

Alternatively, Formula 7 may be represented by Formula 7d. However, embodiments of the present disclosure are not limited to such examples.

[Formula 7d]

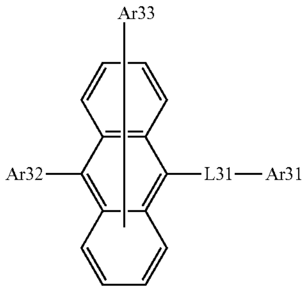

In Formula 7d, the definitions of L31, Ar31, Ar32, and Ar33 are same as those in Formula 7.

For example, the electron transporting material in the ETL 240 may be one of the compounds in Formula 8.

[Formula 8]

ET1

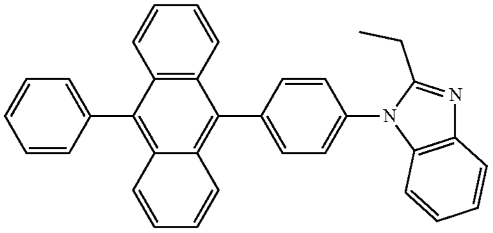

-continued

ET2

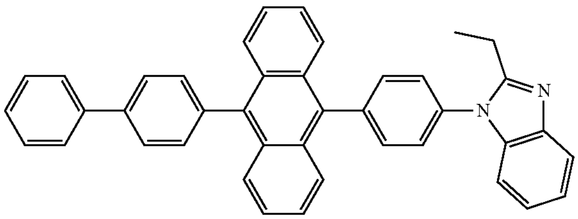

ET3

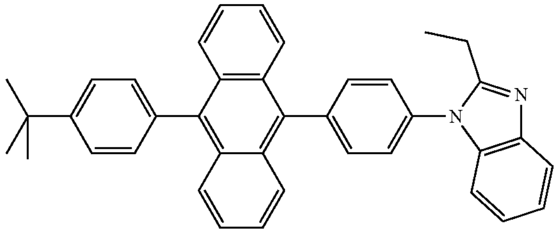

ET4

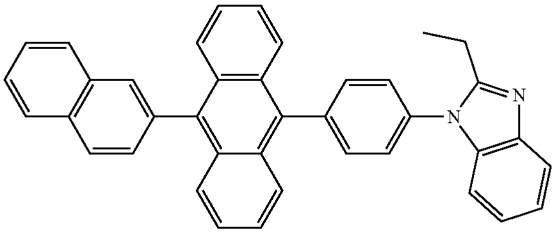

ET5

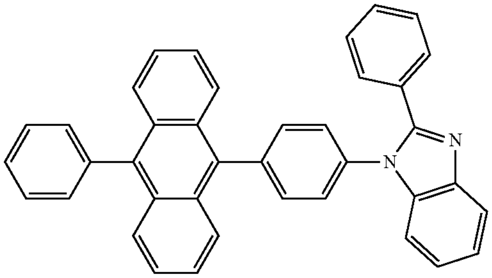

ET6

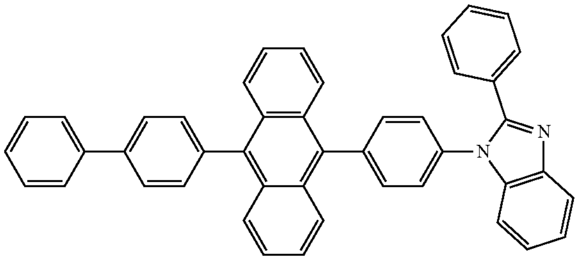

ET7

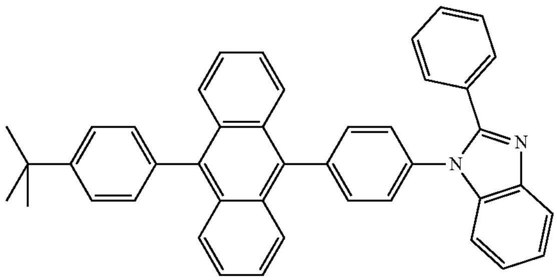

-continued
ET8
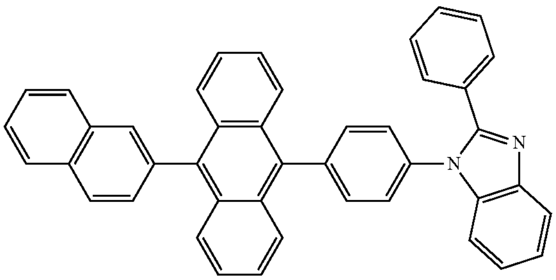
ET9
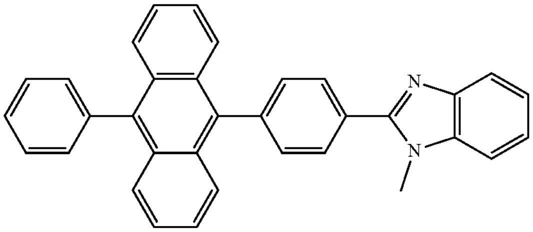
ET10
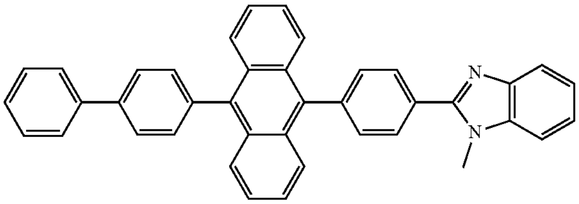
ET11
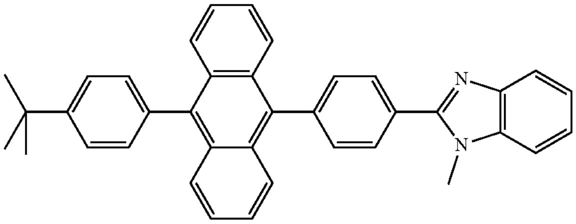
ET12
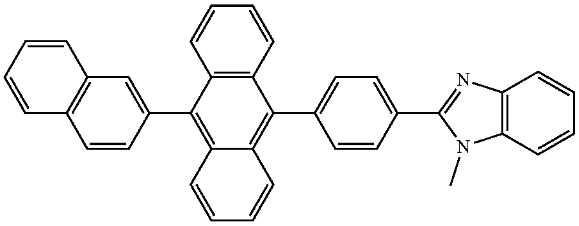
ET13
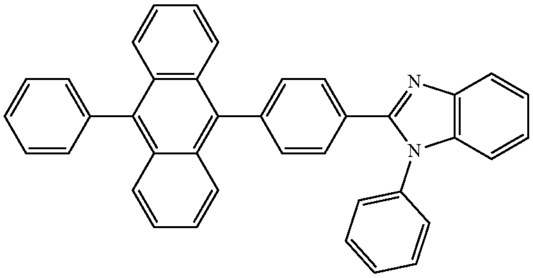
-continued
ET14
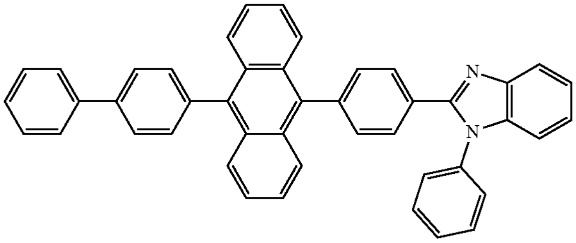
ET15
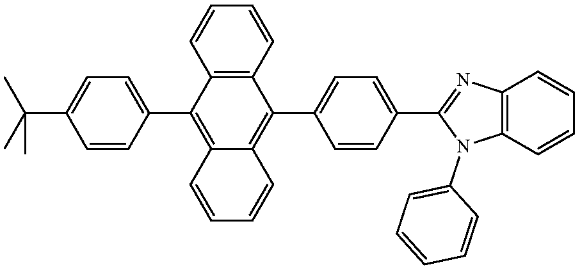
ET16
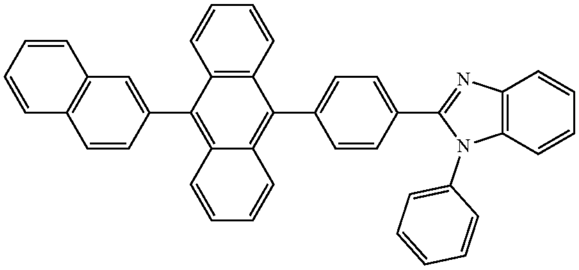
ZADN1
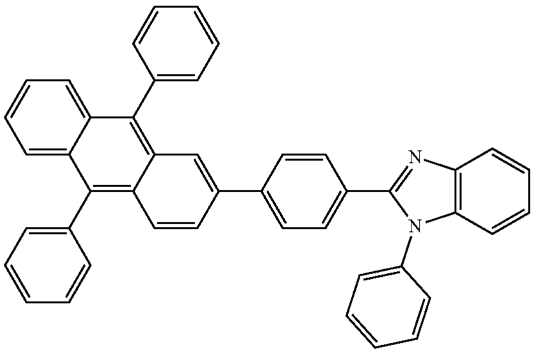
ZADN2
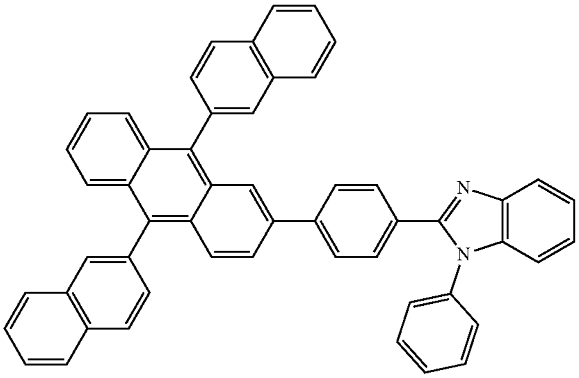

-continued
ZADN3
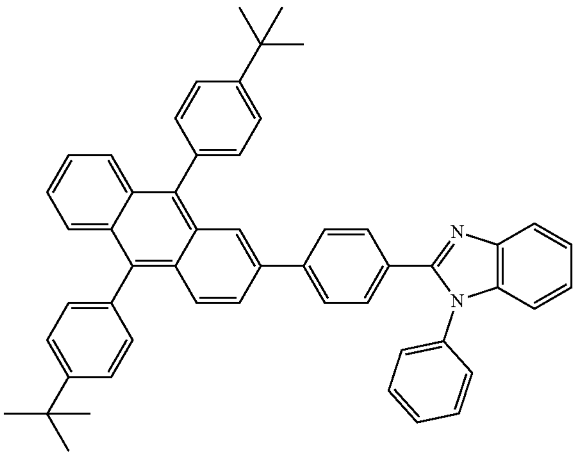
ZADN4
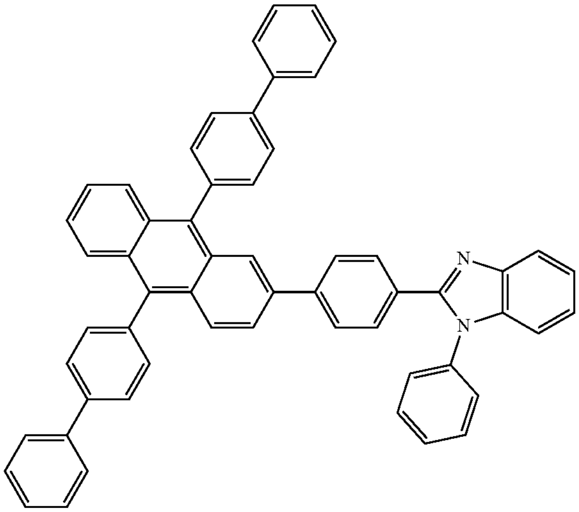
ZADN5
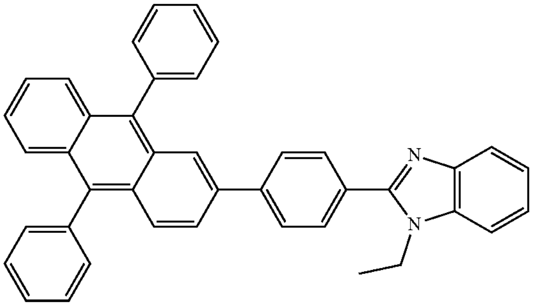
-continued
ZADN6
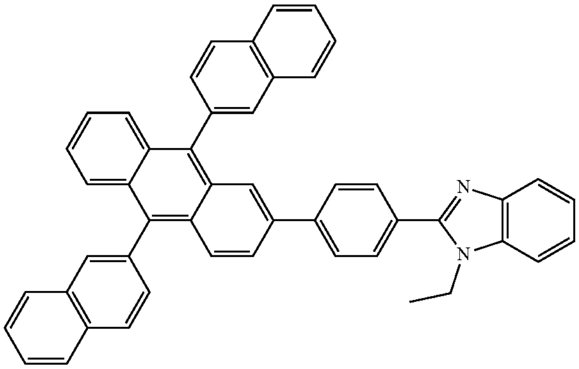
ZADN7
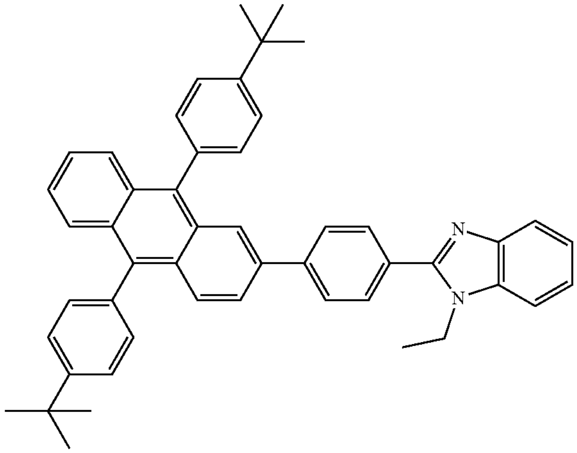
ZADN8
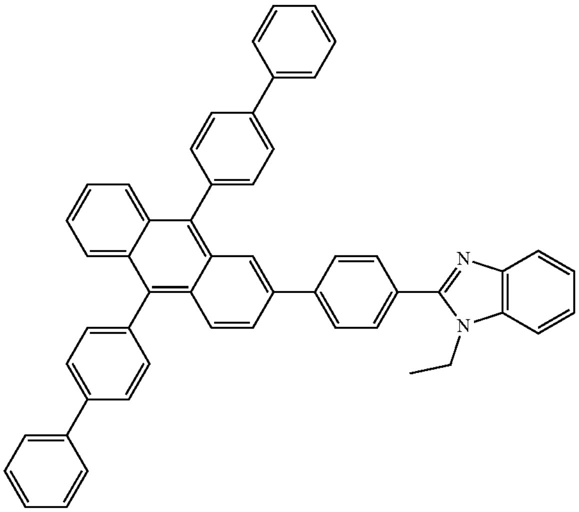

-continued
ZADN9
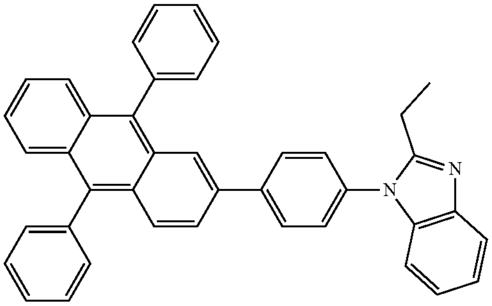
ZADN10
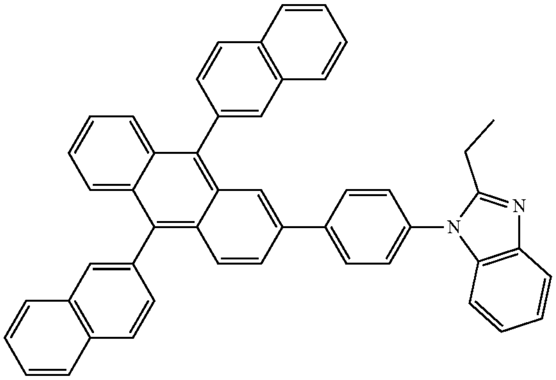
ZADN11
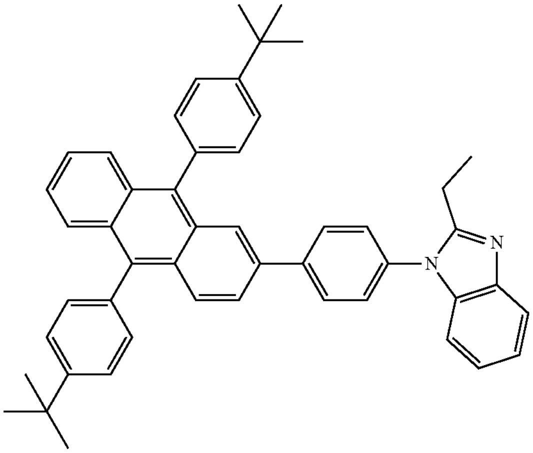
-continued
ZADN12
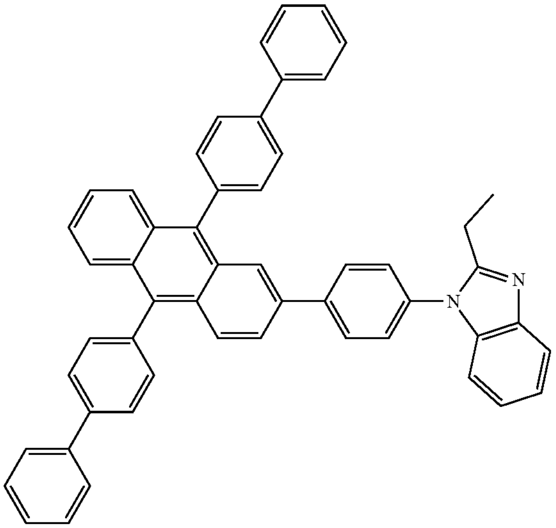
ZADN13
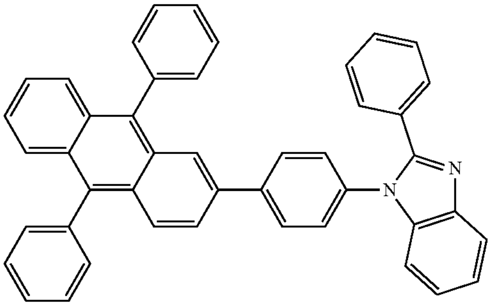
ZADN14
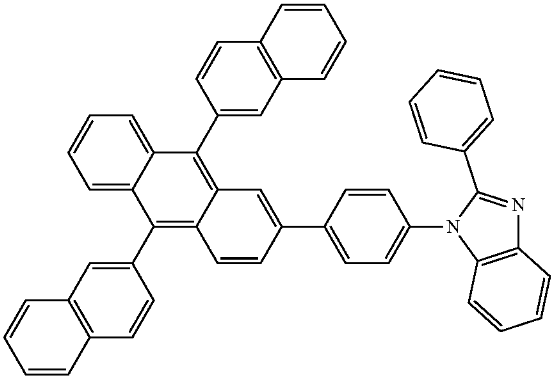

-continued

ZADN15

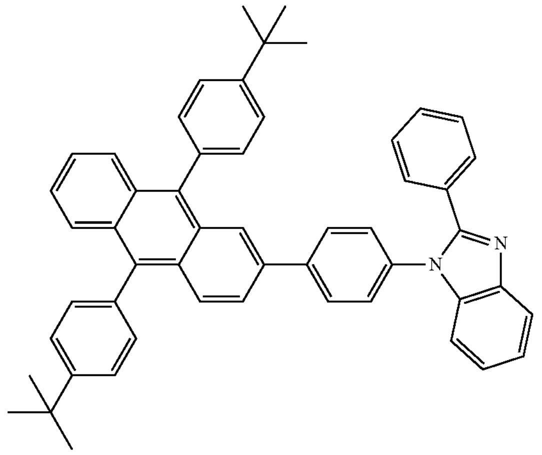

ZADN16

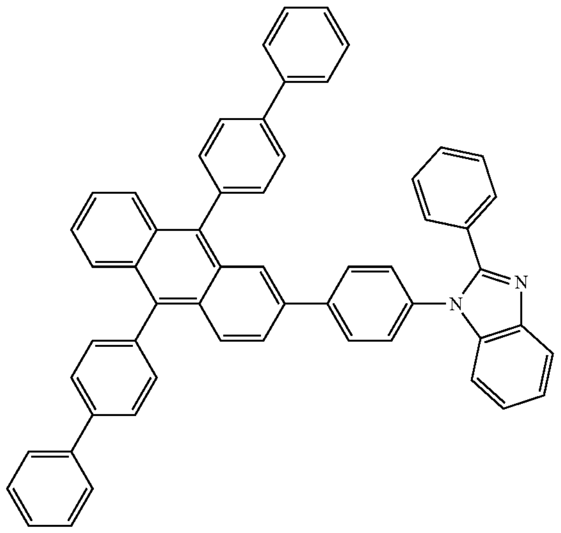

The organic light emitting layer 162 may further include an HTL 220 between the first electrode 160 and the green EML 230. A thickness of the HTL 220 may be greater than that of each of the green EML 230 and the ETL 240. For example, the HTL may have a thickness of 800 to 1200 Å, for example, 900 to 1100 Å.

In addition, the organic light emitting layer 162 may further include at least one of an HIL 210 between the first electrode 160 and the HTL 220 and an EIL 250 between the second electrode 164 and the ETL 240.

Although not shown, the organic light emitting layer 162 may further include at least one of an EBL between the HTL 220 and the green EML 230 and an HBL between the green EML 230 and the ETL 240.

The HIL 210 may include at least one compound selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino) triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB or NPD), 1,4,5,8,9,11-hexaazatriphenylenehexacarbonitrile (dipyrazino[2,3-f:2'3'-h]quinoxaline-2,3,6,7,10,11-hexacarbonitrile (HAT-CN), 1,3,5-tris[4-(diphenylamino)phenyl] benzene (TDAPB), poly(3,4-ethylenedioxythiphene) polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine. The HIL 210 may have a thickness of 10 to 100 Å, for example, 30 to 70 Å.

The HTL 220 may include at least one compound selected from the group consisting of N,N'-diphenyl-N,N'-bis(3-methylphenyl)-1,1'-biphenyl-4,4'-diamine (TPD), NPB (or NPD), 4,4'-bis(N-carbazolyl)-1,1'-biphenyl (CBP), poly[N,N'-bis(4-butylphenyl)-N,N'-bis(phenyl)-benzidine] (poly-TPD), (poly[(9,9-dioctylfluorenyl-2,7-diyl)-co-(4,4'-(N-(4-sec-butylphenyl)diphenylamine))] (TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl)biphenyl-4-amine. Alternatively, the HTL 220 may include a compound of Formula 10 below. However, embodiments of the present disclosure are not limited to such examples.

The EIL 250 may include at least one of an alkali metal, such as Li, an alkali halide compound, such as LiF, CsF, NaF, or $BaF_2$, and an organo-metallic compound, such as Liq, lithium benzoate, or sodium stearate. The EIL 250 may have a thickness of 10 to 100 Å, for example, 30 to 70 Å.

The EBL may include at least one compound selected from the group consisting of tris(4-carbazoyl-9-yl-phenyl) amine (TCTA), tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, di-[4-(N,N-di-p-tolyl-amino)-phenyl]cyclohexane (TAPC), 4,4',4"-tris(3-methylphenylamino)triphenylamine (MTDATA), 1,3-bis (carbazol-9-yl)benzene (mCP), 3,3'-bis(N-carbazolyl)-1,1'-biphenyl (mCBP), copper phthalocyanine (CuPc), N,N'-bis [4-[bis(3-methylphenyl)amino]phenyl]-N,N'-diphenyl-[1,1'-biphenyl]-4,4'-diamine (DNTPD), 1,3,5-tris[4-(diphenylamino)phenyl]benzene (TDAPB), 3,5-di(9H-carbazol-9-yl)-N,N-diphenylaniline (DCDPA) and 2,8-bis (9-phenyl-9H-carbazol-3-yl)dibenzo[b,d]thiophene).

The HBL may include at least one compound selected from the group consisting of 2,9-dimethyl-4,7-diphenyl-1,10-phenathroline (BCP), bis(2-methyl-8-quinolinolato-N1,O8)-(1,1'-biphenyl-4-olato)aluminum (BAlq), tris-(8-hydroxyquinoline aluminum ($Alq_3$), 2-biphenyl-4-yl-5-(4-t-butylphenyl)-1,3,4-oxadiazole (PBD), spiro-PBD, Liq, bis-4,6-(3,5-di-3-pyridylphenyl)-2-methylpyrimidine (B3PYMPM), bis[2-(diphenylphosphino)phenyl]ether oxide (DPEPO), 9-(6-9H-carbazol-9-yl)pyridine-3-yl)-9H-3,9'-bicarbazole, and diphenyl-4-triphenylsilyl-phenylphosphine oxide (TSPO1).

As illustrated above, in the OLED D in the green pixel, the green EML 230 may include the first compound 232 that may be an example of the organic compound of the present disclosure and represented by Formula 1. As a result, in the OLED D, the driving voltage may be reduced, and the emitting efficiency and the emitting lifespan may be improved.

When the first compound 232, in which the fused fluorene moiety in Formula 1 is deuterated, is included in the green EML 230, the OLED D may provide sufficient increase of the emitting lifespan while minimizing the increase of production cost.

In addition, the green EML 230 may further include the second compound 234, which is represented by Formula 3, as a second host with the first compound 232 as a first host so that the OLED D may have further advantages in aspects such as the driving voltage, the emitting efficiency, and the emitting lifespan.

The green EML 230 may further include the third compound 236, which is represented by Formula 5, as an emitter with the first compound 232 as the first host and the second compound 234 as the second host so that the OLED D may have more desirable advantages in aspects such as the driving voltage, the emitting efficiency, and the emitting lifespan.

Furthermore, the OLED D in the green pixel may further include the ETL 240, which may include the electron transporting material represented by Formula 7, between the green EML 230 and the second electrode 164 as a cathode so that the OLED D may have further advantages in aspects such as the driving voltage, the emitting efficiency, and the emitting lifespan.

[OLED]

An anode (ITO), an HIL (e.g., the compound in Formula 9, 50 Å), an HTL (e.g., the compound in Formula 10, 1000 Å), a green EML (e.g., a first host, a second host, and a dopant (the compound GD1 in Formula 6, 15 wt %), 300 Å), an ETL (300 Å), an EIL (e.g., LiF, 50 Å) and a cathode (e.g., A1, 1000 Å) was sequentially deposited to form the OLED.

[Formula 9]

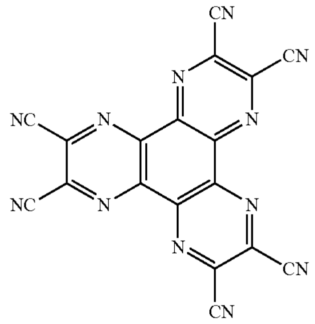

[Formula 10]

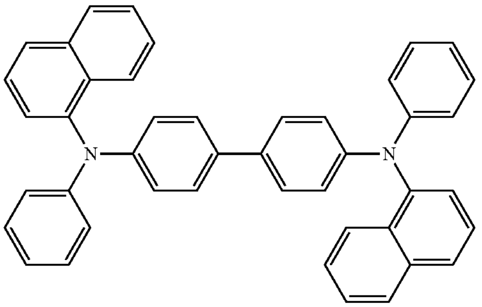

1. Comparative Example (1) Comparative Example 1 (Ref1)

The compound TPBi in Formula 11 was used as the first host and the compound BCz-1 in Formula 4 was used as the second host to form the green EML. (a weight ratio of (the first host):(the second host)=1:1) The compound ZADN2 in Formula 8 was used to form the ETL.

(2) Comparative Example 2 (Ref2)

The compound TPBi in Formula 11 was used as the first host and the compound BCz-1 in Formula 4 was used as the second host to form the green EML. (a weight ratio of (the first host):(the second host)=1:1) The compound ET2 in Formula 8 was used to form the ETL.

(3) Comparative Example 3 (Ref3)

The compound H1 in Formula 12 was used as the first host and the compound BCz-1 in Formula 4 was used as the second host to form the green EML. (a weight ratio of (the first host):(the second host)=1:1) The compound ZADN2 in Formula 8 was used to form the ETL.

(4) Comparative Example 4 (Ref4)

The compound H6 in Formula 12 was used as the first host and the compound BCz-1 in Formula 4 was used as the second host to form the green EML. (a weight ratio of (the first host):(the second host)=1:1) The compound ZADN2 in Formula 8 was used to form the ETL.

(5) Comparative Example 5 (Ref5)

The compound H9 in Formula 12 was used as the first host and the compound BCz-1 in Formula 4 was used as the second host to form the green EML. (a weight ratio of (the first host):(the second host)=1:1) The compound ZADN2 in Formula 8 was used to form the ETL.

(6) Comparative Example 6 (Ref6)

The compound H21 in Formula 12 was used as the first host and the compound BCz-1 in Formula 4 was used as the second host to form the green EML. (a weight ratio of (the first host):(the second host)=1:1) The compound ZADN2 in Formula 8 was used to form the ETL.

(7) Comparative Example 7 (Ref7)

The compound H31 in Formula 12 was used as the first host and the compound BCz-1 in Formula 4 was used as the second host to form the green EML. (a weight ratio of (the first host):(the second host)=1:1) The compound ZADN2 in Formula 8 was used to form the ETL.

(8) Comparative Examples 8 to 12 (Ref8 to Ref12)

Ref8 to Ref12 were similar to Ref3 to Ref7, respectively, with the difference being ET2 in Formula 8 was used in Ref8 to Ref12 instead of the compound ZADN2 in Formula 8, which was used in Ref3 to Ref7.

[Formula 11]

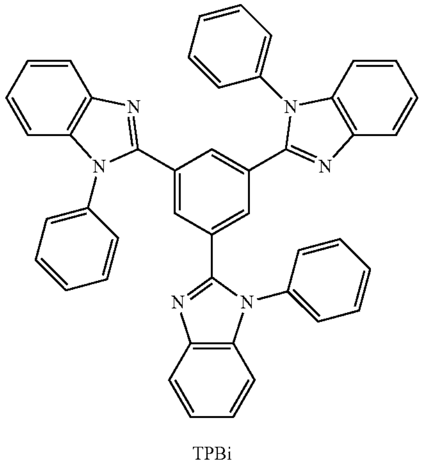

TPBi

-continued

[Formula 12]

H1

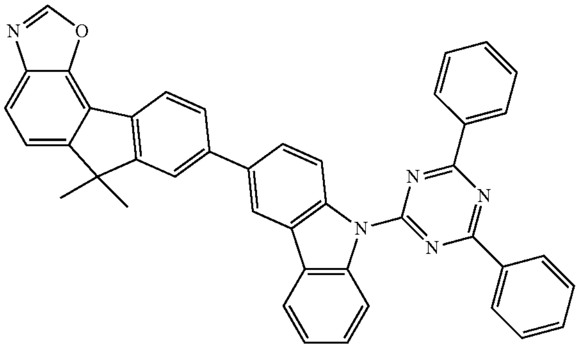

H6

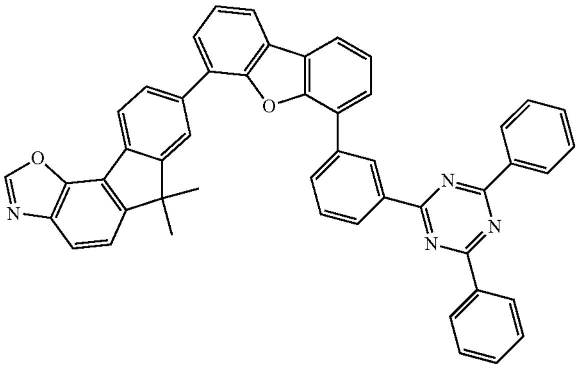

H9

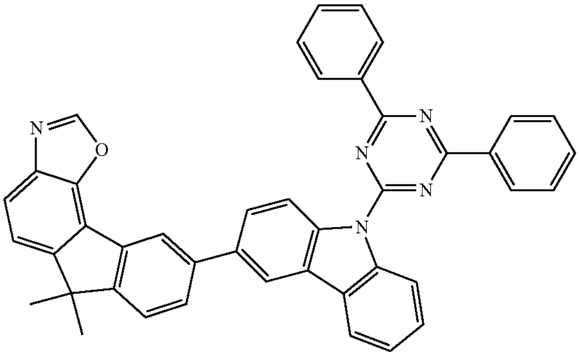

H21

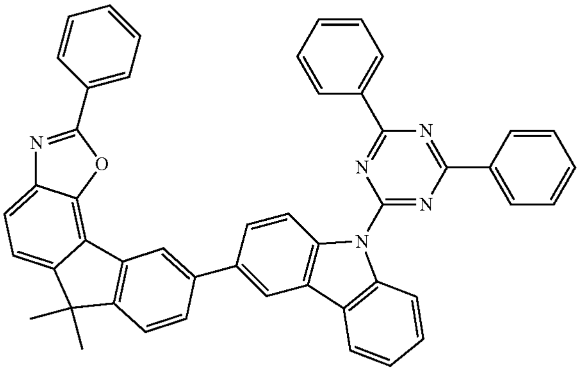

-continued

H31

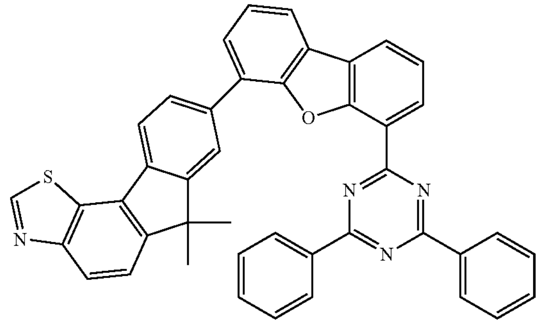

2. Example (1) Example 1 (Ex1)

The compound H1-D1 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(2) Example 2 (Ex2)

The compound H1-D2 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(3) Example 3 (Ex3)

The compound H1-D3 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(4) Example 4 (Ex4)

The compound H1-D4 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(5) Example 5 (Ex5)

The compound H1-D5 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(6) Example 6 (Ex6)

The compound H1-D6 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(7) Examples 7 to 12 (Ex7 to Ex12)

Ex7 to Ex12 were similar to Ex1 to Ex6, respectively, with the difference being the compound ET2 in Formula 8 was used instead of the compound ZADN2 in Formula 8, which was used in Ex1 to Ex6.

(8) Example 13 (Ex13)

The compound H6-D1 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(9) Example 14 (Ex14)

The compound H6-D2 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(10) Example 15 (Ex15)

The compound H6-D3 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(11) Example 16 (Ex16)

The compound H6-D4 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(12) Example 17 (Ex17)

The compound H6-D5 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(13) Example 18 (Ex18)

The compound H6-D6 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(14) Examples 19 to 24 (Ex19 to Ex24)

Ex19 to Ex24 were similar to Ex13 to Ex18, respectively, with the difference being the compound ET2 in Formula 8 was used in Ex19 to Ex24 instead of the compound ZADN2 in Formula 8, which was used in Ex13 to Ex18.

(15) Example 25 (Ex25)

The compound H9-D1 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(16) Example 26 (Ex26)

The compound H9-D2 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(17) Example 27 (Ex27)

The compound H9-D3 in Formula 2 was used as the first host and the compound BCz-1 in Formula 4 was used as the second host to form the green EML. (a weight ratio of (the first host):(the second host)=1:1) The compound ZADN2 in Formula 8 is used to form the ETL.

(18) Example 28 (Ex28)

The compound H9-D4 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(19) Example 29 (Ex29)

The compound H9-D5 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(20) Example 30 (Ex30)

The compound H9-D6 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(21) Examples 31 to 36 (Ex31 to Ex36)

Ex31 to Ex36 were similar to Ex25 to Ex30, respectively, with the difference being the compound ET2 in Formula 8 was used in Ex31 to Ex36 instead of the compound ZADN2 in Formula 8, which was used in Ex25 to Ex30.

(22) Example 37 (Ex37)

The compound H21-D1 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(23) Example 38 (Ex38)

The compound H21-D2 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(24) Example 39 (Ex39)

The compound H21-D3 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(25) Example 40 (Ex40)

The compound H21-D4 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(26) Example 41 (Ex41)

The compound H21-D5 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(27) Example 42 (Ex42)

The compound H21-D6 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(28) Examples 43 to 48 (Ex43 to Ex48)

Ex43 to Ex48 were similar to Ex37 to Ex42, respectively, with the difference being the compound ET2 in Formula 8 was used in Ex43 to Ex48 instead of the compound ZADN2 in Formula 8, which was used in Ex37 to Ex42.

(29) Example 49 (Ex49)

The compound H31-D1 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(30) Example 50 (Ex50)

The compound H31-D2 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(31) Example 51 (Ex51)

The compound H31-D3 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(32) Example 52 (Ex52)

The compound H31-D4 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(33) Example 53 (Ex53)

The compound H31-D5 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(34) Example 54 (Ex54)

The compound H31-D6 in Formula 2 was used as the first host and the compound BCz-1 in Formula 4 was used as the second host to form the green EML. (a weight ratio of (the first host):(the second host)=1:1) The compound ZADN2 in Formula 8 was used to form the ETL.

(35) Examples 55 to 60 (Ex55 to Ex60)

Ex55 to Ex60 were similar to Ex49 to Ex54, respectively, with the difference being the compound ET2 in Formula 8 was used in Ex55 to Ex60 instead of the compound ZADN2 in Formula 8, which was used in Ex49 to Ex54.

The properties, e.g., the driving voltage (ΔV), the emitting efficiency and the lifespan (T95), of the OLED in Comparative Examples 1 to 12 and Examples 1 to 60 were measured and listed in Tables 1 to 6.

TABLE 1

| | First Host | ETL | ΔV | Efficiency (%) | T95 (%) |
|---|---|---|---|---|---|
| Ref1 | TPBi | ZADN2 | 0.00 | 100% | 100% |
| Ref2 | TPBi | ET2 | −0.32 | 113% | 106% |
| Ref3 | H1 | ZADN2 | −0.13 | 102% | 112% |
| Ref4 | H6 | ZADN2 | −0.22 | 107% | 119% |
| Ref5 | H9 | ZADN2 | −0.18 | 113% | 103% |
| Ref6 | H21 | ZADN2 | −0.27 | 114% | 112% |
| Ref7 | H31 | ZADN2 | −0.16 | 105% | 114% |
| Ref8 | H1 | ET2 | −0.43 | 117% | 110% |
| Ref9 | H6 | ET2 | −0.47 | 124% | 118% |
| Ref10 | H9 | ET2 | −0.44 | 129% | 107% |
| Ref11 | H21 | ET2 | −0.52 | 131% | 110% |
| Ref12 | H48 | ET2 | −0.46 | 119% | 113% |

TABLE 2

| | First Host | ETL | ΔV | Efficiency (%) | T95 (%) |
|---|---|---|---|---|---|
| Ex1 | H1-D1 | ZADN2 | −0.13 | 102% | 134% |
| Ex2 | H1-D2 | ZADN2 | −0.12 | 102% | 118% |
| Ex3 | H1-D3 | ZADN2 | −0.12 | 101% | 123% |
| Ex4 | H1-D4 | ZADN2 | −0.12 | 102% | 140% |
| Ex5 | H1-D5 | ZADN2 | −0.11 | 101% | 132% |
| Ex6 | H1-D6 | ZADN2 | −0.10 | 100% | 144% |
| Ex7 | H1-D1 | ET2 | −0.43 | 117% | 132% |
| Ex8 | H1-D2 | ET2 | −0.43 | 117% | 115% |
| Ex9 | H1-D3 | ET2 | −0.42 | 116% | 121% |
| Ex10 | H1-D4 | ET2 | −0.42 | 117% | 138% |
| Ex11 | H1-D5 | ET2 | −0.41 | 116% | 131% |
| Ex12 | H1-D6 | ET2 | −0.41 | 116% | 142% |

TABLE 3

| | First Host | ETL | ΔV | Efficiency (%) | T95 (%) |
|---|---|---|---|---|---|
| Ex13 | H6-D1 | ZADN2 | −1.27 | 107% | 143% |
| Ex14 | H6-D2 | ZADN2 | −0.22 | 107% | 126% |
| Ex15 | H6-D3 | ZADN2 | −0.21 | 107% | 131% |

TABLE 3-continued

| | First Host | ETL | ΔV | Efficiency (%) | T95 (%) |
|---|---|---|---|---|---|
| Ex16 | H6-D4 | ZADN2 | −0.21 | 107% | 149% |
| Ex17 | H6-D5 | ZADN2 | −0.20 | 106% | 141% |
| Ex18 | H6-D6 | ZADN2 | −0.20 | 106% | 154% |
| Ex19 | H6-D1 | ET2 | −0.47 | 124% | 141% |
| Ex20 | H6-D2 | ET2 | −0.47 | 124% | 123% |
| Ex21 | H6-D3 | ET2 | −0.46 | 123% | 130% |
| Ex22 | H6-D4 | ET2 | −0.46 | 124% | 148% |
| Ex23 | H6-D5 | ET2 | −0.46 | 123% | 140% |
| Ex24 | H6-D6 | ET2 | −0.45 | 123% | 152% |

TABLE 4

| | First Host | ETL | ΔV | Efficiency (%) | T95 (%) |
|---|---|---|---|---|---|
| Ex25 | H9-D1 | ZADN2 | −0.18 | 129% | 128% |
| Ex26 | H9-D2 | ZADN2 | −0.17 | 129% | 112% |
| Ex27 | H9-D3 | ZADN2 | −0.18 | 128% | 117% |
| Ex28 | H9-D4 | ZADN2 | −0.17 | 129% | 133% |
| Ex29 | H9-D5 | ZADN2 | −0.17 | 128% | 126% |
| Ex30 | H9-D6 | ZADN2 | −0.15 | 127% | 138% |
| Ex31 | H9-D1 | ET2 | −0.44 | 129% | 128% |
| Ex32 | H9-D2 | ET2 | −0.44 | 129% | 112% |
| Ex33 | H9-D3 | ET2 | −0.44 | 128% | 117% |
| Ex34 | H9-D4 | ET2 | −0.43 | 129% | 134% |
| Ex35 | H9-D5 | ET2 | −0.42 | 128% | 126% |
| Ex36 | H9-D6 | ET2 | −0.42 | 128% | 138% |

TABLE 5

| | First Host | ETL | ΔV | Efficiency (%) | T95 (%) |
|---|---|---|---|---|---|
| Ex37 | H21-D1 | ZADN2 | −0.27 | 114% | 134% |
| Ex38 | H21-D2 | ZADN2 | −0.27 | 114% | 118% |
| Ex39 | H21-D3 | ZADN2 | −0.27 | 113% | 123% |
| Ex40 | H21-D4 | ZADN2 | −0.25 | 114% | 140% |
| Ex41 | H21-D5 | ZADN2 | −0.26 | 113% | 132% |
| Ex42 | H21-D6 | ZADN2 | −0.24 | 112% | 144% |
| Ex43 | H21-D1 | ET2 | −0.52 | 131% | 132% |
| Ex44 | H21-D2 | ET2 | −0.52 | 131% | 115% |
| Ex45 | H21-D3 | ET2 | −0.51 | 130% | 121% |
| Ex46 | H21-D4 | ET2 | −0.51 | 131% | 138% |
| Ex47 | H21-D5 | ET2 | −0.50 | 130% | 131% |
| Ex48 | H21-D6 | ET2 | −0.49 | 130% | 142% |

TABLE 6

| | First Host | ETL | ΔV | Efficiency (%) | T95 (%) |
|---|---|---|---|---|---|
| Ex49 | H31-D1 | ZADN2 | −0.16 | 105% | 137% |
| Ex50 | H31-D2 | ZADN2 | −0.16 | 105% | 119% |
| Ex51 | H31-D3 | ZADN2 | −0.15 | 104% | 126% |
| Ex52 | H31-D4 | ZADN2 | −0.15 | 105% | 143% |
| Ex53 | H31-D5 | ZADN2 | −0.14 | 103% | 135% |
| Ex54 | H31-D6 | ZADN2 | −0.14 | 103% | 148% |
| Ex55 | H31-D1 | ET2 | −0.46 | 119% | 136% |
| Ex56 | H31-D2 | ET2 | −0.46 | 119% | 119% |
| Ex57 | H31-D3 | ET2 | −0.45 | 118% | 124% |
| Ex58 | H31-D4 | ET2 | −0.45 | 119% | 142% |
| Ex59 | H31-D5 | ET2 | −0.45 | 117% | 134% |
| Ex60 | H31-D6 | ET2 | −0.44 | 117% | 145% |

As shown in Tables 1 to 6, in comparison to the OLED in Ref1 to Ref12, the OLED in Ex1 to Ex60, in which the green EML included an example of the organic compound of the present disclosure, exhibited superior driving voltage, emitting efficiency, and lifespan.

As shown by Examples 1, 4, 6, 7, 10, 12, 13, 16, 18, 19, 22, 24, 25, 28, 30, 31, 34, 36, 37, 40, 42, 43, 46, 48, 49, 52, 54, 55, 58 and 60, when the organic compound, in which the fused-fluorene moiety in Formula 1 was deuterated, was included in the green EML, the lifespan of the OLED was significantly increased.

On the other hand, in comparison to the OLED in Examples 6, 12, 18, 24, 30, 36, 42, 48, 54, and 60, in which the first host, e.g., an example of the organic compound of the present disclosure, being wholly deuterated was included in the green EML, the lifespan of the OLED in Examples 1, 4, 7, 10, 13, 16, 19, 22, 25, 28, 31, 34, 37, 40, 43, 46, 49, 52, 55 and 58, in which the first host, e.g., an example of the organic compound of the present disclosure, being partially deuterated was included in the green EML was slightly shorter. However, in the OLED in Examples 1, 4, 7, 10, 13, 16, 19, 22, 25, 28, 31, 34, 37, 40, 43, 46, 49, 52, 55, and 58 provided sufficient lifespan with less expensive deuterium atoms.

Figure 4:
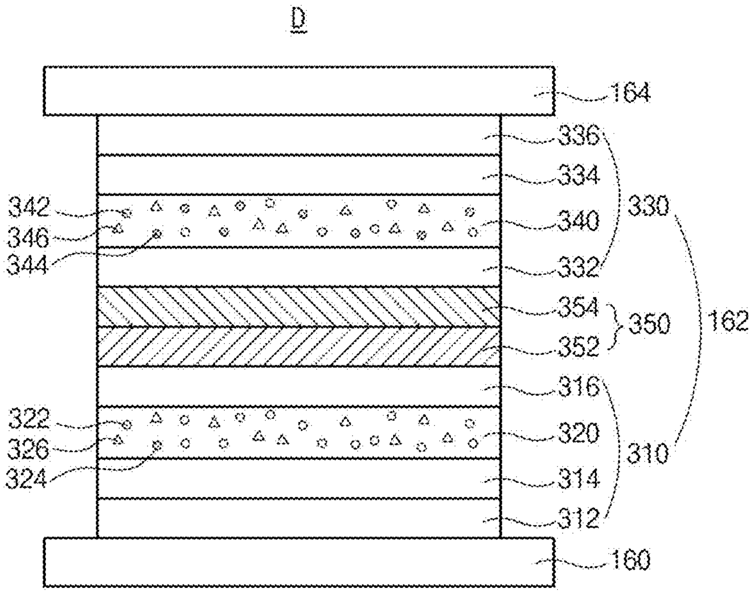
FIG. 4 illustrates a schematic cross-sectional view of an OLED according to a third embodiment of the present disclosure.

FIG. 4 illustrates a schematic cross-sectional view of an OLED according to a third embodiment of the present disclosure.

As illustrated in FIG. 4, an OLED D may include first and second electrodes 160 and 164, which may face each other, and an organic light emitting layer 162 therebetween. The organic light emitting layer 162 may include a first emitting part 310 including a first green EML 320 and a second emitting part 330 including a second green EML 340. The organic light emitting layer 162 may further include a CGL 350 between the first and second emitting parts 310 and 330.

The first electrode 160 may act as an anode for injecting a hole and may be formed of a conductive material, e.g., ITO or IZO, having a relatively high work function. The second electrode 164 may act a cathode for injecting an electron and may be formed of a conductive material, e.g., Al, Mg or AlMg, having a relatively low work function.

In the top-emission type OLED D, the first electrode 160 may further include a reflection layer to act as a reflective electrode. The second electrode 164 may have a thin profile to act as a transparent (semitransparent) electrode. Alternatively, in the bottom-emission type OLED D, the first electrode 160 may act as a transparent electrode. The second electrode 164 may act as a reflective electrode. However, embodiments of the present disclosure are not limited to such examples.

The CGL 350 may be positioned between the first and second emitting parts 310 and 330. The first emitting part 310, the CGL 350, and the second emitting part 330 may be sequentially stacked on the first electrode 160. For example, the first emitting part 310 may be positioned between the first electrode 160 and the CGL 350. The second emitting part 330 may be positioned between the second electrode 164 and the CGL 350.

The first emitting part 310 may further include a first ETL 316 between the first green EML 320 and the CGL 350. For example, the first ETL 316 may be positioned between the first green EML 320 and the CGL 350.

In addition, the first emitting part 310 may further include at least one of an HIL 312 between the first green EML 320 and the first electrode 160 and an HTL 314 between the first green EML 320 and the HIL 312.

Moreover, the first emitting part 310 may further include at least one of a first EBL (not shown) between the first green EML 320 and the first HTL 314 and a first HBL (not shown) between the first green EML 320 and the first ETL 316.

The second emitting part 330 may further include a second ETL 334 between the second green EML 340 and the second electrode 164.

In addition, the second emitting part 330 may further include at least one of a second HTL 332 under the second green EML 340 and an EIL 336 between the second ETL 334 and the second electrode 164.

Moreover, the second emitting part 330 may further include at least one of a second EBL (not shown) between the second green EML 340 and the second HTL 332 and a second HBL (not shown) between the second green EML 340 and the second ETL 334.

The CGL 350 may be positioned between the first and second emitting parts 310 and 330. For example, the first and second emitting parts 310 and 330 may be connected through the CGL 350. The CGL 350 may be a P-N junction CGL including an N-type CGL 352 and a P-type CGL 354.

The N-type CGL 352 may be positioned between the first ETL 316 and the second HTL 332. The P-type CGL 354 may be positioned between the N-type CGL 352 and the second HTL 332.

The first green EML 320 may include a first compound 322, a second compound 324, and a third compound 326. The second green EML 340 may include a fourth compound 342, a fifth compound 344, and a sixth compound 346.

At least one of the first and fourth compounds 322 and 342 is an example of the organic compound of the present disclosure represented by Formula 1, and at least one of the second and fifth compounds 324 and 344 is the compound represented by Formula 3. In addition, at least one of the third and sixth compounds 326 and 346 is the compound represented by Formula 5.

For example, at least one of the first green EML 320 and the second green EML 340 may include an example of the compound represented by Formula 1, the compound represented by Formula 3, and the compound represented by Formula 5.

In the first green EML 320, the first compound 322 may act as an n-type host, e.g., a first host, the second compound 324 may act as a p-type host, e.g., a second host, and the third compound 326 may act as an emitter, e.g., a dopant. In the second green EML 340, the fourth compound 342 may act as an n-type host, e.g., a first host, the fifth compound 344 may act as a p-type host, e.g., a second host, and the sixth compound 346 may act as an emitter, e.g., a dopant. Each of the first and second green EMLs 320 and 340 may have a thickness of 50 to 600 Å.

When the first compound 322 and the fourth compound 342 are examples of the organic compound represented by Formula 1, the first compound 322 and the fourth compound 342 may be same or different. When the second compound 324 and the fifth compound 344 are examples of the organic compound represented by Formula 3, the second compound 324 and the fifth compound 344 may be same or different. When the third compound 326 and the sixth compound 346 are examples of the organic compound represented by Formula 5, the third compound 326 and the sixth compound 346 may be same or different.

In the first green EML 320, a weight % of each of the first and second compounds 322 and 324 may be greater than that of the third compound 326. The weight % of the first compound 322 and the weight % of the second compound 324 may be same or different. In the first green EML 320, a weight % ratio of the first compound 322 to the second compound 324 may be 1:9 to 9:1, 2:8 to 8:2 or 7:3 to 3:7. In some embodiments, the weight % of the first compound 322 and the weight % of the second compound 324 may be same. For example, the first compound 322 and the second compound 324 may be present at the same weight %. The third compound 326 may be present in an amount of 5 to 25 weight % in the first green EML 320, based on a total weight of the components in the first green EML 320.

In the second green EML 340, a weight % of each of the fourth and fifth compounds 342 and 344 may be greater than that of the sixth compound 346. The weight % of the fourth compound 342 and the weight % of the fifth compound 344 may be same or different. In the second green EML 340, a weight % ratio of the fourth compound 342 to the fifth compound 344 may be 1:9 to 9:1, 2:8 to 8:2 or 7:3 to 3:7. In some embodiments, the weight % of the fourth compound 342 and the weight % of the fifth compound 344 may be same. For example, the fourth compound 342 and the fifth compound 344 may be present at the same weight %. The sixth compound 346 may be present in an amount of 5 to 25 weight % in the second green EML 340, based on a total weight of the components in the second green EML 340.

Each of the first and second ETLs 316 and 334 may include an example of the compound (e.g., an electron transporting material) represented by Formula 7.

In the OLED D in the green pixel, at least one of the first and second green EMLs 320 and 340 may include an example of the organic compound of the present disclosure represented by Formula 1. As a result, in the OLED D, the driving voltage may be reduced, and the emitting efficiency and the lifespan may be improved.

When the organic compound, in which the fused-fluorene moiety in Formula 1 is deuterated, is included in at least one of the first and second green EMLs 320 and 340, the OLED D may provide sufficient increase of the emitting lifespan with minimal increase in production cost.

In addition, at least one of the first and second green EMLs 320 and 340 may further include an example of the compound, which is represented by Formula 3, as a second host with a first host being an example of the organic compound of the present disclosure so that the OLED D may have advantages in aspects such as the driving voltage, the emitting efficiency, and the emitting lifespan.

Moreover, at least one of the first and second green EMLs 320 and 340 may further include an example of the compound, which is represented by Formula 5, as an emitter with the first host represented by Formula 1 and the second host represented by Formula 3 so that the OLED D may have further advantages in aspects such as the driving voltage, the emitting efficiency, and the emitting lifespan.

Furthermore, in the OLED D in the green pixel, at least one of the first and second ETLs 316 and 334 may include an example of the electron transporting material represented by Formula 7 so that the OLED D may have further advantages in aspects such as the driving voltage, the emitting efficiency, and the emitting lifespan.

Figure 5:
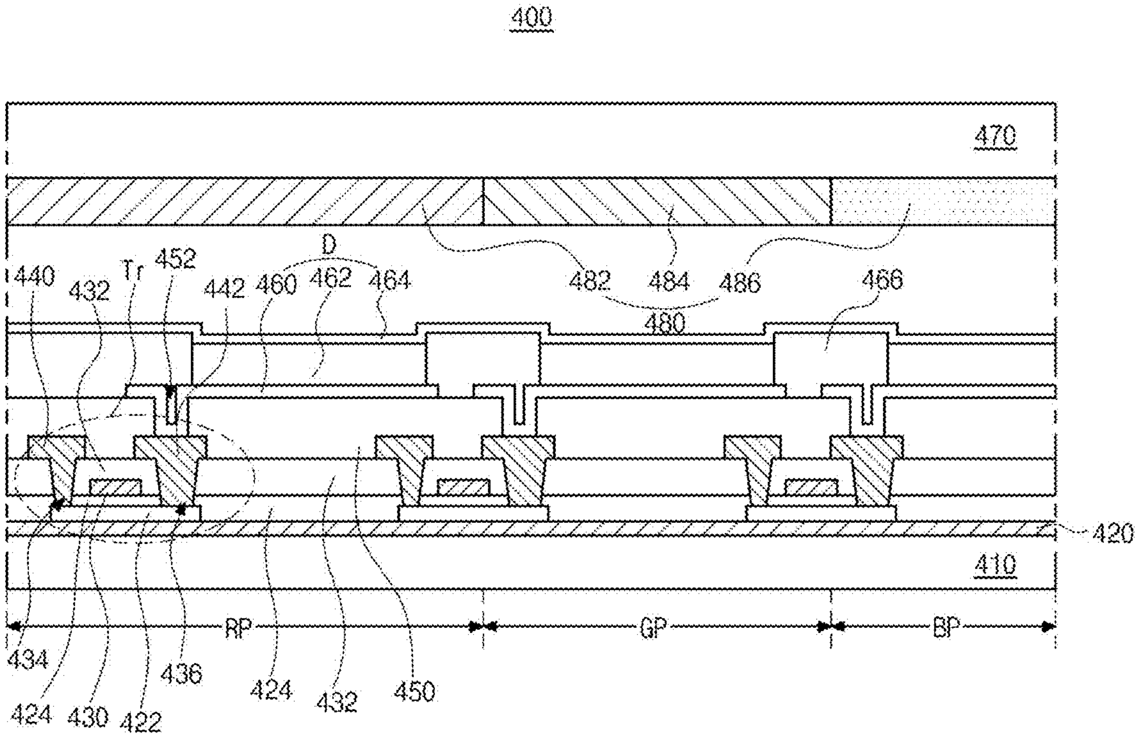
FIG. 5 illustrates a schematic cross-sectional view of an organic light emitting display device according to a fourth embodiment of the present disclosure.
Figure 6:
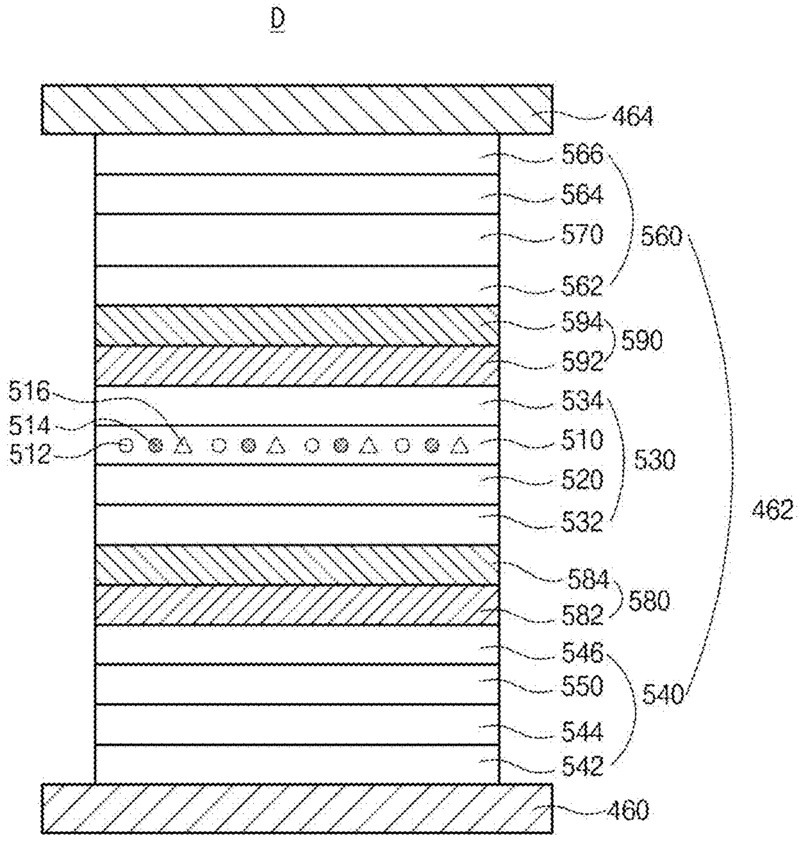
FIG. 6 illustrates a schematic cross-sectional view of an OLED according to a fifth embodiment of the present disclosure.
Figure 7:
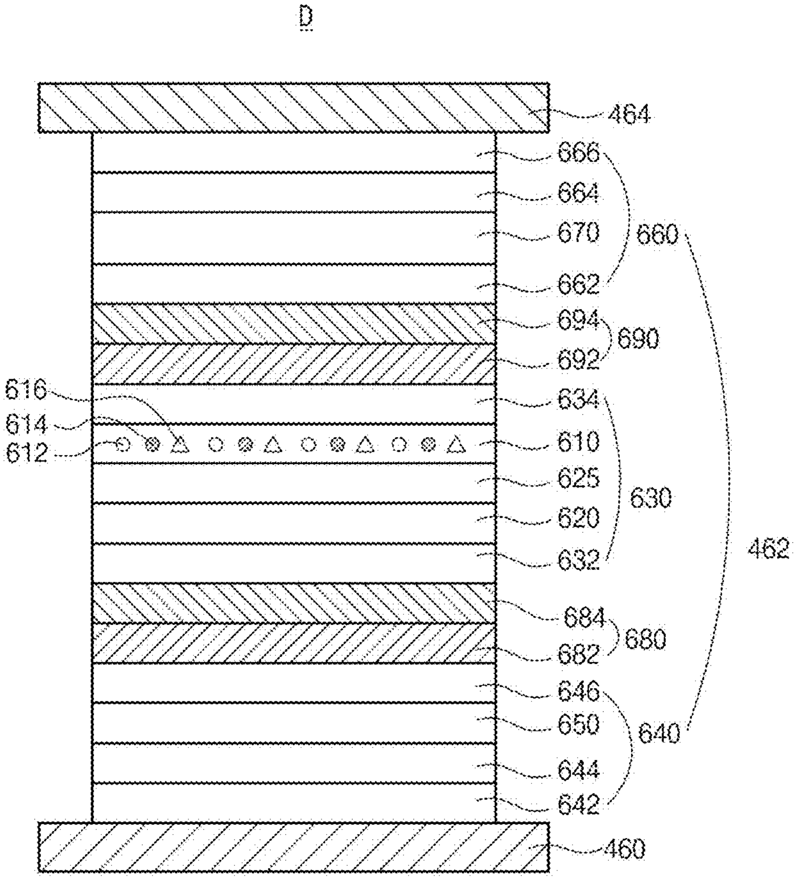
FIG. 7 illustrates a schematic cross-sectional view of an OLED according to a sixth embodiment of the present disclosure.

FIG. 5 illustrates a schematic cross-sectional view of an organic light emitting display device according to a fourth embodiment of the present disclosure. FIG. 6 illustrates a schematic cross-sectional view of an OLED according to a fifth embodiment of the present disclosure. FIG. 7 illustrates a schematic cross-sectional view of an OLED according to a sixth embodiment of the present disclosure.

As shown in FIG. 5, an organic light emitting display device 400 may include a first substrate 410, where a red pixel RP, a green pixel GP and a blue pixel BP may be defined, a second substrate 470 facing the first substrate 410, an OLED D, which may be positioned between the first and second substrates 410 and 470 and providing white emission, and a color filter layer 480 between the OLED D and the second substrate 470.

Each of the first and second substrates 410 and 470 may be a glass substrate or a flexible substrate. For example, each of the first and second substrates 410 and 470 may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 420 may be formed on the substrate. The TFT Tr corresponding to each of the red, green and blue pixels RP, GP and BP may be formed on the buffer layer 420. The buffer layer 420 may be omitted.

A semiconductor layer 422 may be formed on the buffer layer 420. The semiconductor layer 422 may include an oxide semiconductor material or polycrystalline silicon.

A gate insulating layer 424 may be formed on the semiconductor layer 422. The gate insulating layer 424 may be formed of an inorganic insulating material such as silicon oxide or silicon nitride.

A gate electrode 430, which may be formed of a conductive material, e.g., metal, may be formed on the gate insulating layer 424 to correspond to a center of the semiconductor layer 422.

An interlayer insulating layer 432, which may be formed of an insulating material, may be formed on the gate electrode 430. The interlayer insulating layer 432 may be formed of an inorganic insulating material, e.g., silicon oxide or silicon nitride, or an organic insulating material, e.g., benzocyclobutene or photo-acryl.

The interlayer insulating layer 432 may include first and second contact holes 434 and 436 exposing both sides of the semiconductor layer 422. The first and second contact holes 434 and 436 may not cover a portion of the surface of the semiconductor layer 422 that is nearer to the opposing ends than to a center of the semiconductor layer 422. The first and second contact holes 434 and 436 may be positioned at both sides of the gate electrode 430 to be spaced apart from the gate electrode 430.

A source electrode 440 and a drain electrode 442, which may be formed of a conductive material, e.g., metal, may be formed on the interlayer insulating layer 432.

The source electrode 440 and the drain electrode 442 may be spaced apart from each other with respect to the gate electrode 430 and contact both sides of the semiconductor layer 422 through the first and second contact holes 434 and 436, respectively.

The semiconductor layer 422, the gate electrode 430, the source electrode 440, and the drain electrode 442 may constitute the TFT Tr. The TFT Tr may serve as a driving element. For example, the TFT Tr may correspond to the driving TFT Td (of FIG. 1).

Although not shown, the gate line and the data line may cross each other to define the pixel. The switching TFT may be formed to be connected to the gate and data lines. The switching TFT may be connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer 450, which may include a drain contact hole 452 exposing the drain electrode 442 of the TFT Tr, may be formed to cover the TFT Tr. The drain contact hole 452 may not cover the drain electrode 442.

A first electrode 460, which may be connected to the drain electrode 442 of the TFT Tr through the drain contact hole 452, may be separately formed in each pixel and on the planarization layer 450. The first electrode 460 may be an anode and may be formed of a conductive material, e.g., a transparent conductive oxide (TCO), having a relatively high work function. The first electrode 460 may further include a reflection electrode or a reflection layer. For example, the reflection electrode or the reflection layer may be formed of silver (Ag) or aluminum-palladium-copper (APC) alloy. In a top-emission type organic light emitting display device 400, the first electrode 460 may have a triple-layered structure of ITO/Ag/ITO or ITO/APC/ITO.

A bank layer 466 may be formed on the planarization layer 450 to cover an edge of the first electrode 460. For example, the bank layer 466 may be positioned at a boundary of the pixel and may expose a center of the first electrode 460 in the pixel. The bank layer 466 may not cover a center of the first electrode 460 in the pixel. Since the OLED D may emit the white light in the red, green and blue pixels RP, GP and BP, the organic light emitting layer 462 may be formed as a common layer in the red, green and blue pixels RP, GP and BP without separation. The bank layer 466 may be formed to prevent a current leakage at an edge of the first electrode 460 and may be omitted.

An organic light emitting layer 462 may be formed on the first electrode 460.

As illustrated in FIG. 5, a second electrode 464 may be formed over the substrate 410 where the organic light emitting layer 462 may be formed.

In the organic light emitting display device 400, since the light emitted from the organic light emitting layer 462 may be incident to the color filter layer 480 through the second electrode 464, the second electrode 464 may have a thin profile for transmitting the light.

The first electrode 460, the organic light emitting layer 462, and the second electrode 464 may constitute the OLED D.

The color filter layer 480 may be positioned over the OLED D and may include a red color filter 482, a green color filter 484, and a blue color filter 486 corresponding to the red, green, and blue pixels RP, GP, and BP, respectively. The red color filter 482 may include at least one of red dye and red pigment. The green color filter 484 may include at least one of green dye and green pigment. The blue color filter 486 may include at least one of blue dye and blue pigment.

Although not shown, the color filter layer 480 may be attached to the OLED D by an adhesive layer. Alternatively, the color filter layer 480 may be formed directly on the OLED D. However, embodiments of the present disclosure are not limited to such examples.

An encapsulation film (not shown) may be formed to prevent penetration of moisture into the OLED D. For example, the encapsulation film may include a first inorganic insulating layer, an organic insulating layer, and a second inorganic insulating layer sequentially stacked, but it is not limited thereto. The encapsulation film may be omitted.

A polarization plate (not shown) for reducing an ambient light reflection may be disposed over the top-emission type OLED D. For example, the polarization plate may be a circular polarization plate.

In the OLED of FIG. 5, the first and second electrodes 460 and 464 may be a reflective electrode and a transparent (or semi-transparent) electrode, respectively. The color filter layer 480 may be disposed over the OLED D. Alternatively, when the first and second electrodes 460 and 464 are a transparent (or semi-transparent) electrode and a reflective electrode, respectively, the color filter layer 480 may be disposed between the OLED D and the first substrate 410. However, embodiments of the present disclosure are not limited to such examples.

A color conversion layer (not shown) may be formed between the OLED D and the color filter layer 480. The color conversion layer may include a red color conversion layer, a green color conversion layer, and a blue color conversion layer corresponding to the red, green, and blue pixels RP, GP, and BP, respectively. The white light from the OLED D may be converted into the red light, the green light, and the blue light by the red, green, and blue color conversion layers, respectively. For example, the color conversion layer may include a quantum dot. Accordingly, the color purity of the organic light emitting display device 400 may be further improved.

The color conversion layer may be included instead of the color filter layer 480.

As described above, in the organic light emitting display device 400, the OLED D in the red, green, and blue pixels RP, GP, and BP may emit the white light. The white light from the organic light emitting diode D may pass through the red color filter 482, the green color filter 484, and the blue color filter 486. As a result, the red light, the green light and the blue light may be provided from the red pixel RP, the green pixel GP, and the blue pixel BP, respectively.

In FIG. 5, the OLED D emitting the white light may be used for a display device. Alternatively, the OLED D may be formed on an entire surface of a substrate without at least one of the driving element and the color filter layer to be used for a lighting device. The display device and the lighting device each including an example of the OLED D of the present disclosure may be referred to as an organic light emitting device. However, embodiments of the present disclosure are not limited to such examples.

As illustrated in FIG. 6, the organic light emitting layer 462 may include a first emitting part 530 including a green EML 510, a second emitting part 540 including a first blue EML 550, and a third emitting part 560 including a second blue EML 570. In addition, the organic light emitting layer 462 may further include a first CGL 580 between the first and second emitting parts 530 and 540 and a second CGL 590 between the first and third emitting parts 530 and 560. In addition, the first emitting part 530 may further include a red EML 520.

The second emitting part 540 may be positioned between the first electrode 460 and the first emitting part 530. The third emitting part 560 may be positioned between the first emitting part 530 and the second electrode 464. The second emitting part 540 may be positioned between the first electrode 460 and the first CGL 580. The third emitting part 560 may be positioned between the second CGL 590 and the second electrode 464. For example, the second emitting part 540, the first CGL 580, the first emitting part 530, the second CGL 590, and the third emitting part 560 may be sequentially stacked on the first electrode 460.

In the first emitting part 530, the red EML 520 may be disposed under the green EML 510.

The first emitting part 530 may further include a first ETL 534 disposed on the green EML 510. In addition, the first emitting part 530 may further include a first HTL 532 disposed under the red EML 520.

For example, in the first emitting part 530, the red EML 520 may be positioned between the first HTL 532 and the green EML 510. The green EML 510 may be positioned between the red EML 520 and the first ETL 534.

The second emitting part 540 may further include at least one of a second HTL 544 disposed under the first blue EML 550 and a second ETL 546 disposed on the first blue EML 550. In addition, the second emitting part 540 may further include an HIL 542 between the first electrode 460 and the second HTL 544.

Moreover, the second emitting part 540 may further include a first EBL (not shown) between the second HTL 544 and the first blue EML 550 and a first HBL (not shown) between the second ETL 546 and the first blue EML 550.

The third emitting part 560 may further include at least one of a third HTL 562 disposed under the second blue EML 570 and a third ETL 564 disposed on the second blue EML 570. In addition, the third emitting part 560 may further include an EIL 566 between the second electrode 464 and the third ETL 564.

Moreover, the third emitting part 560 may further include a second EBL (not shown) between the third HTL 562 and the second blue EML 570 and a second HBL (not shown) between the third ETL 564 and the second blue EML 570.

The green EML 510 may include an example of the organic compound of the present disclosure represented by Formula 1 as a first compound 512. In addition, the green EML 510 may further include a second compound 514 as an example of the compound represented by Formula 3. Moreover, the green EML 510 may further include a third compound 516 as an example of the compound represented by Formula 5.

In the green EML 510, the first compound 512 may be an n-type host (e.g., a first host), the second compound 514 may be a p-type host (e.g., a second host), and the third compound 516 may be an emitter (e.g., a dopant). The green EML 510 may have a thickness of 50 to 600 Å.

In the green EML 510, a weight % of each of the first and second compounds 512 and 514 may be greater than that of the third compound 516. The weight % of the first compound 512 and the weight % of the second compound 514 may be same or different. In the green EML 510, a weight % ratio of the first compound 512 to the second compound 514 may be 1:9 to 9:1, 2:8 to 8:2 or 7:3 to 3:7. In some embodiments, the weight % of the first compound 512 and the weight % of the second compound 514 may be same. For example, the first compound 512 and the second compound 514 may be present at the same weight %. The third compound 516 may be present in an amount of 5 to 25 weight % in the green EML 510, based on a total weight of the components in the green EML 510.

Each of the first to third ETLs 534, 546 and 564 may include an example of the compound represented by Formula 7 as an electron transporting material.

The red EML 520 may include a red host and a red dopant. The red dopant may include at least one of a red phosphorescent compound, a red fluorescent compound, and a red delayed fluorescent compound. In the red EML 520, the red host may be present at a weight % greater than the red dopant. In the red EML 520, the red dopant may be present at a weight % of 1 to 10, or 1 to 5, based on a total weight of the components in the red EML 520.

For example, the red host may be at least one selected from the group consisting of 9,9'-diphenyl-9H,9'H-3,3'-bicarbazole (BCzPh), CBP, 1,3,5-tris(carbazole-9-yl)benzene (TCP), TCTA, 4,4'-bis(carbazole-9-yl)-2,2'-dimethylbiphenyl (CDBP), 2,7-bis(carbazole-9-yl)-9,9-dimethylfluorene (DMFL-CBP), 2,2',7,7'-tetrakis(carbazole-9-yl)-9,9-spiorofluorene (Spiro-CBP), DPEPO, 4'-(9H-carbazol-9-yl)biphenyl-3,5-dicarbonitrile (PCzB-2CN), 3'-(9H-carbazol-9-yl)biphenyl-3,5-dicarbonitrile (mCzB-2CN), 3,6-bis (carbazole-9-yl)-9-(2-ethyl-hexyl)-9H-carbazole (TCz1), bis(2-hydroxylphenyl)-pyridine)beryllium ($Bepp_2$), bis(10-hydroxylbenzo[h] quinolinato)beryllium ($Bebg_2$), and 1,3,5-tris(1-pyrenyl)benzene ($TPB_3$), but it is not limited thereto.

The red dopant may be at least one selected from the group consisting of [bis(2-(4,6-dimethyl)phenylquinoline)](2,2,6,6-tetramethylheptane-3,5-dionate)iridium(III), bis[2-(4-n-hexylphenyl)quinoline](acetylacetonate)iridium(III) (Hex-Ir(phq)$_2$(acac)), tris[2-(4-n-hexylphenyl)quinoline]iridium(III), (Hex-Ir(phq)$_3$), tris[2-phenyl-4-methylquinoline]iridium(III) (Ir(Mphq)$_3$), bis(2-phenylquinoline)(2,2,6,6-tetramethylheptene-3,5-dionate)iridium(III) (Ir(dpm)$PQ_2$), bis(phenylisoquinoline)(2,2,6,6-tetramethylheptene-3,5-dionate)iridium(ITT), (Ir(dpm)(piq)$_2$), bis[(4-n-hexylphenyl)isoquinoline](acetylacetonate)iridium(III) (Hex-Ir(piq)$_2$(acac)), tris[2-(4-n-hexylphenyl)quinoline]iridium(III) (Hex-Ir(piq)$_3$), tris(2-(3-methylphenyl)-7-methyl-quinolato)iridium (Ir(dmpq)$_3$), bis[2-(2-methylphenyl)-7-methyl-quinoline](acetylacetonate)iridium(III) (Ir(dmpq)$_2$(acac)), and bis[2-(3,5-dimethylphenyl)-4-methyl-quinoline](acetylacetonate)iridium(III) (Ir(mphmq)$_2$(acac)), but it is not limited thereto.

The first blue EML 550 in the second emitting part 540 may include a first blue host and a first blue dopant. The second blue EML 570 in the third emitting part 560 may include a second blue host and a second blue dopant.

Each of the first and second blue dopants may include at least one of a blue phosphorescent compound, a blue fluorescent compound, and a blue delayed fluorescent compound. In the first blue EML 550, the first blue host may be present at a weight % greater than the first blue dopant. In the second blue EML 570, the second blue host may be present at a weight % greater than the second blue dopant. In each of the first and second blue EMLs 550 and 570, each of the first and second blue dopants may be present at a weight % of 1 to 10, or 1 to 5, based on a total weight of the components in each of the first and second blue EMLs 550 and 570.

For example, each of the first and second blue hosts may be independently at least one selected from the group consisting of mCP, 9-(3-(9H-carbazol-9-yl)phenyl)-9H-carbazole-3-carbonitrile (mCP-CN), mCBP, CBP—CN, 9-(3-(9H-Carbazol-9-yl)phenyl)-3-(diphenylphosphoryl)-9H-carbazole (mCPPO1) 3,5-Di(9H-carbazol-9-yl)biphenyl (Ph-mCP), TSPO1, 9-(3'-(9H-carbazol-9-yl)-[1,1'-biphenyl]-3-yl)-9H-pyrido[2,3-b]indole (CzBPCb), bis(2-methylphenyl)diphenylsilane (UGH-1), 1,4-bis(triphenylsilyl)benzene (UGH-2), 1,3-bis(triphenylsilyl)benzene (UGH-3), 9,9-spiorobifluoren-2-yl-diphenyl-phosphine oxide (SPPO1), and 9,9'-(5-(triphenylsilyl)-1,3-phenylene)bis(9H-carbazole) (SimCP), but it is not limited thereto.

Each of the first and second blue dopants may be independently at least one selected from the group consisting of 4,4'-bis[4-(di-p-tolylamino)styryl]biphenyl (DPAVBi), 4-(di-p-tolylamino)-4-4'-[(di-p-tolylamino)styryl]stilbene (DPAVB), 4,4'-bis[4-(diphenylamino)styryl]biphenyl (BDAVBi), 2,7-bis(4-diphenylamino)styryl)-9,9-spiorfluorene (spiro-DPVBi), [1,4-bis[2-[4-[N,N-di(p-tolyl)amino]phenyl]vinyl] benzene (DSB), 1-4-di-[4-(N,N-diphenyl)amino]styryl-benzene (DSA), 2,5,8,11-tetra-tert-butylperylene (TBPe), bis(2-hydroxylphenyl)-pyridine)beryllium (Bepp2), 9-(9-Phenylcarbazole-3-yl)-10-(naphthalene-1-yl)anthracene (PCAN), mer-tris(1-phenyl-3-methylimidazolin-2-ylidene-C,C(2)'iridium(III) (mer-Ir(pmi)$_3$), fac-Tris(1,3-diphenyl-benzimidazolin-2-ylidene-C,C(2)'iridium(III) (fac-Ir(dpbic)$_3$), bis(3,4,5-trifluoro-2-(2-pyridyl)phenyl-(2-carboxypyridyl)iridium(III) (Ir(tfpd)$_2$pic), tris(2-(4,6-difluorophenyl)pyridine))iridium(III) (Ir(Fppy)$_3$), and bis[2-(4,6-difluorophenyl)pyridinato-C2,N](picolinato)iridium(III) (FIrpic), but it is not limited thereto.

For example, each of the first and second blue EMLs 550 and 570 may include an anthracene derivative as a blue host and a boron derivative as a blue dopant.

The first CGL 580 may be positioned between the first and second emitting parts 530 and 540, and the second CGL 590 is positioned between the first and third emitting parts 530 and 560. For example, the first and second emitting parts 530 and 540 may be connected through the first CGL 580. The first and third emitting parts 530 and 560 may be connected through the second CGL 590. The first CGL 580 may be a P-N junction CGL including a first N-type CGL 582 and a first P-type CGL 584. The second CGL 590 may be a P-N junction CGL including a second N-type CGL 592 and a second P-type CGL 594.

In the first CGL 580, the first N-type CGL 582 may be positioned between the first HTL 532 and the second ETL 546. The first P-type CGL 584 may be positioned between the first N-type CGL 582 and the first HTL 532.

In the second CGL 590, the second N-type CGL 592 may be positioned between the first ETL 534 and the third HTL 562. The second P-type CGL 594 may be positioned between the second N-type CGL 592 and the third HTL 562.

As illustrated above, the OLED D of the present disclosure may include the first emitting part 530 including the green EML 510 and the red EML 520, the second emitting part 540 including the first blue EML 550, and the third emitting part 560 including the second blue EML 570 so that the white light may be provided from the OLED D.

The green EML 510 includes an example of the organic compound of the present disclosure represented by Formula 1. As result, in the OLED D, the driving voltage may be reduced, and the emitting efficiency and the lifespan may be improved.

When the organic compound, in which the fused-fluorene moiety in Formula 1 is deuterated, is included in the green EML 510, the OLED D may provide sufficient increase of the emitting lifespan with minimal increase in production cost.

In addition, the green EML 510 may further include an example of the compound, which is represented by Formula 3, as a second host with a first host being an example of the organic compound of the present disclosure so that the OLED D may be superior in aspects such as driving voltage, the emitting efficiency, and the emitting lifespan.

Moreover, the green EML 510 may further include an example of the compound, which is represented by Formula 5, as an emitter with the first host represented by Formula 1 and the second host represented by Formula 3 so that the OLED D may have further advantages in aspects such as the driving voltage, the emitting efficiency, and the emitting lifespan.

Furthermore, in the OLED D in the green pixel, at least one of the first, second and third ETLs 534, 546, and 564 may include an example of the electron transporting material represented by Formula 7 so that the OLED D may have advantages in aspects such as the driving voltage, the emitting efficiency, and the emitting lifespan.

As illustrated in FIG. 7, the organic light emitting layer 462 may include a first emitting part 630 including a green EML 610, a red EML 620, and a yellow-green EML 625, a second emitting part 640 including a first blue EML 650, and a third emitting part 660 including a second blue EML 670. In addition, the organic light emitting layer 462 may further include a first CGL 680 between the first and second emitting parts 630 and 640 and a second CGL 690 between the first and third emitting parts 630 and 660.

The second emitting part 640 may be positioned between the first electrode 460 and the first emitting part 630. The third emitting part 660 may be positioned between the first emitting part 630 and the second electrode 464. The second emitting part 640 may be positioned between the first electrode 460 and the first CGL 680. The third emitting part 660 may be positioned between the second CGL 690 and the second electrode 464. For example, the second emitting part 640, the first CGL 680, the first emitting part 630, the second CGL 690, and the third emitting part 660 may be sequentially stacked on the first electrode 460.

In the first emitting part 630, the red EML 620 may be disposed under the yellow-green EML 625. The green EML 610 may be disposed on the yellow-green EML 625. For example, the first emitting part 530 of the OLED D in FIG. 6 may include an EML having a double-layered structure, which may include EMLs 510 and 520, while the first emitting part 630 of the OLED D in FIG. 7 may include an EML having a triple-layered structure, which may include EMLs 610, 620, and 625.

The first emitting part 630 may further include a first ETL 634 disposed on the green EML 610. In addition, the first emitting part 630 may further include a first HTL 632 disposed under the red EML 620.

For example, in the first emitting part 630, the red EML 620 may be positioned between the first HTL 632 and the yellow-green EML 625. The green EML 610 may be positioned between the yellow-green EML 625 and the first ETL 634.

The second emitting part 640 may further include at least one of a second HTL 644 disposed under the first blue EML 650 and a second ETL 646 disposed on the first blue EML 650. In addition, the second emitting part 640 may further include an HIL 642 between the first electrode 460 and the second HTL 644.

Moreover, the second emitting part 640 may further include a first EBL (not shown) between the second HTL 644 and the first blue EML 650 and a first HBL (not shown) between the second ETL 646 and the first blue EML 650.

The third emitting part 660 may further include at least one of a third HTL 662 disposed under the second blue EML 670 and a third ETL 664 disposed on the second blue EML 670. In addition, the third emitting part 660 may further include an EIL 666 between the second electrode 464 and the third ETL 664.

Moreover, the third emitting part 660 may further include a second EBL (not shown) between the third HTL 662 and the second blue EML 670 and a second HBL (not shown) between the third ETL 664 and the second blue EML 670.

The green EML 610 may include an example of the organic compound of the present disclosure represented by Formula 1 as a first compound 612. In addition, the green EML 610 may further include a second compound 614 as an example of the compound represented by Formula 3. Moreover, the green EML 610 may further include a third compound 616 as an example of the compound represented by Formula 5.

In the green EML 610, the first compound 612 may be an n-type host (e.g., a first host). The second compound 614 may be a p-type host (e.g., a second host). The third compound 616 may be an emitter (e.g., a dopant). The green EML 610 may have a thickness of 50 to 600 Å.

In the green EML 610, a weight % of each of the first and second compounds 612 and 614 may be greater than that of the third compound 616, and the weight % of the first compound 612 and the weight % of the second compound 614 may be same or different. In the green EML 610, a weight % ratio of the first compound 612 to the second compound 614 may be 1:9 to 9:1, 2:8 to 8:2 or 7:3 to 3:7. In some embodiments, the weight % of the first compound 612 and the weight % of the second compound 614 may be same. For example, the first compound 612 and the second compound 614 may be present at the same weight %, and the third compound 616 may have a weight % of 5 to 25 in the green EML 610.

Each of the first to third ETLs 634, 646, and 664 may include an example of the compound represented by Formula 7 as an electron transporting material.

The red EML 620 may include a red host and a red dopant. The red dopant may include at least one of a red phosphorescent compound, a red fluorescent compound, and a red delayed fluorescent compound. In the red EML 620, the red host may be present at a weight % greater than the red dopant. In the red EML 620, the red dopant may be present at a weight % of 1 to 10, or 1 to 5, based on a total weight of the components in the red EML 620.

The yellow-green EML 625 may include a yellow-green host and a yellow-green dopant. The yellow-green dopant may include at least one of a yellow-green phosphorescent compound, a yellow-green fluorescent compound, and a yellow-green delayed fluorescent compound. In the yellow-green EML 625, the yellow-green host may be present at a weight % greater than the yellow-green dopant. In the yellow-green EML 625, the yellow-green dopant may be present at a weight % of 1 to 10, or 1 to 5, based on a total weight of the components in the yellow-green EML 625.

The first blue EML 650 in the second emitting part 640 may include a first blue host and a first blue dopant. The second blue EML 670 in the third emitting part 660 may include a second blue host and a second blue dopant.

Each of the first and second blue dopants may include at least one of a blue phosphorescent compound, a blue fluorescent compound, and a blue delayed fluorescent compound. In the first blue EML 650, the first blue host may be present at a weight % greater than the first blue dopant. In the second blue EML 670, the second blue host may be present at a weight % greater than the second blue dopant. In each of the first and second blue EMLs 650 and 670, each of the first and second blue dopants may be present at a weight % of 1 to 10, or 1 to 5, based on a total weight of the components in each of the first and second blue EMLs 650 and 670.

The first CGL 680 may be positioned between the first and second emitting parts 630 and 640. The second CGL 690 may be positioned between the first and third emitting parts 630 and 660. For example, the first and second emitting parts 630 and 640 may be connected through the first CGL 680. The first and third emitting parts 630 and 660 may be connected through the second CGL 690. The first CGL 680 may be a P-N junction CGL including a first N-type CGL 682 and a first P-type CGL 684. The second CGL 690 may be a P-N junction CGL including a second N-type CGL 692 and a second P-type CGL 694.

In the first CGL 680, the first N-type CGL 682 may be positioned between the first HTL 632 and the second ETL 646. The first P-type CGL 684 may be positioned between the first N-type CGL 682 and the first HTL 632.

In the second CGL 690, the second N-type CGL 692 may be positioned between the first ETL 634 and the third HTL 662. The second P-type CGL 694 may be positioned between the second N-type CGL 692 and the third HTL 662.

As illustrated above, the OLED D according to an example embodiment of the present disclosure may include the first emitting part 630 including the green EML 610, the red EML 620, and the yellow-green EML 625, the second emitting part 640 including the first blue EML 650, and the third emitting part 660 including the second blue EML 670 so that the white light may be provided from the OLED D.

The green EML 610 may include an example of the organic compound of the present disclosure represented by Formula 1. As result, in the OLED D, the driving voltage may be reduced, and the emitting efficiency and the lifespan may be improved.

When an example of the organic compound, in which the fused-fluorene moiety in Formula 1 is deuterated, is included in the green EML 610, the OLED D may provide sufficient increase of the emitting lifespan with minimal increase in production cost.

In addition, the green EML 610 may further include an example of the compound, which is represented by Formula 3, as a second host with a first host being an example of the organic compound of the present disclosure so that the OLED D may have advantages in aspects such as the driving voltage, the emitting efficiency, and the emitting lifespan.

Moreover, the green EML 610 may further include an example of the compound, which is represented by Formula 5, as an emitter with the first host represented by Formula 1 and the second host represented by Formula 3 so that the OLED D may have further advantages in aspects such as the driving voltage, the emitting efficiency, and the emitting lifespan.

Furthermore, in the OLED D in the green pixel according to an example embodiment of the present disclosure, at least one of the first, second and third ETLs 634, 646 and 664 may include an example of the electron transporting material represented by Formula 7 so that the OLED D may have advantages in aspects such as the driving voltage, the emitting efficiency, and the emitting lifespan.

It will be apparent to those skilled in the art that various modifications and variations can be made in the embodiments of the present disclosure without departing from the spirit or scope of the present disclosure. Thus, it is intended that the modifications and variations cover this disclosure provided they come within the scope of the appended claims and their equivalents.

What is claimed is:

1. An organic compound represented by Formula 1:

[Formula 1]

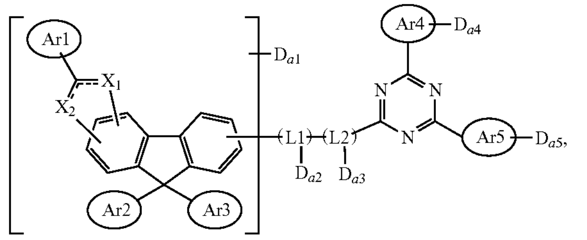

wherein L1 is a substituted or unsubstituted C5 to C30 heteroarylene group, and L2 is selected from the group consisting of a single bond, and a substituted or unsubstituted C6 to C30 arylene group, wherein one of X1 and X2 is a nitrogen atom, and the other one of X1 and X2 is O or S, wherein each of Ar1, Ar2, and Ar3 is independently selected from the group consisting of hydrogen, deuterium, a substituted or unsubstituted C1 to C10 alkyl group, a substituted or unsubstituted C6 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, wherein each of Ar4 and Ar5 is independently selected from the group consisting of a substituted or unsubstituted C6 to C30 aryl group, and a substituted or unsubstituted C3 to C30 heteroaryl group, and wherein, a1 is an integer of 0 to 95, each of a2, a3, a4, and a5 is independently an integer of 0 to 30, and at least one of a1 to a5 is a positive integer.

2. The organic compound according to claim 1, wherein L1 in the Formula 1 is represented by one of Formulas 1a, 1b, 1c, and 1d:

[Formula 1a]

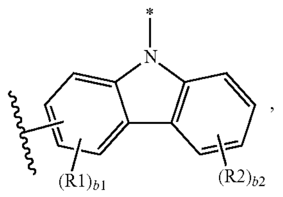

[Formula 1b]

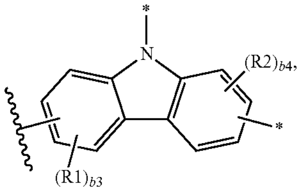

[Formula 1c]

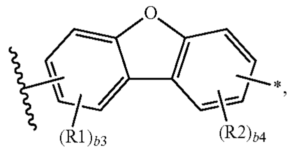

and

[Formula 1d]

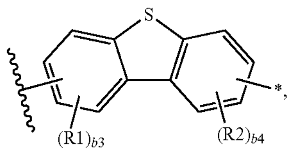

wherein each of R1, R2, and R3 is independently selected from the group consisting of deuterium, cyano, halogen, a substituted or unsubstituted C1 to C10 alkyl group, a substituted or unsubstituted C6 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted silyl group, a substituted or unsubstituted C6 to C30 arylsilyl group, a substituted or unsubstituted C6 to C30 arylphosphine group, a substituted or unsubstituted phosphine oxide group, a substituted or unsubstituted C6 to C30 aryl group, and a substituted or unsubstituted C3 to C30 heteroaryl group, and wherein b1 is an integer of 0 to 3, and each of b2, b3, and b4 is independently an integer of 0 to 4.

3. The organic compound according to claim 1, wherein each of a1, a2, a3, a4, and a5 is a positive integer.

4. The organic compound according to claim 1, wherein in the Formula 1, a1 is a positive integer, and each of a2, a3, a4, and a5 is 0.

5. The organic compound according to claim 1, wherein in the Formula 1, each of a1 and a2 is a positive integer, and each of a3, a4, and a5 is 0.

6. The organic compound according to claim 1, wherein the organic compound is one of the compounds in Formula 2:

[Formula 2]

H1-D1

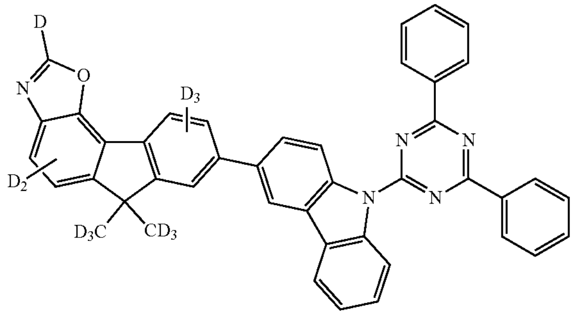

H1-D2

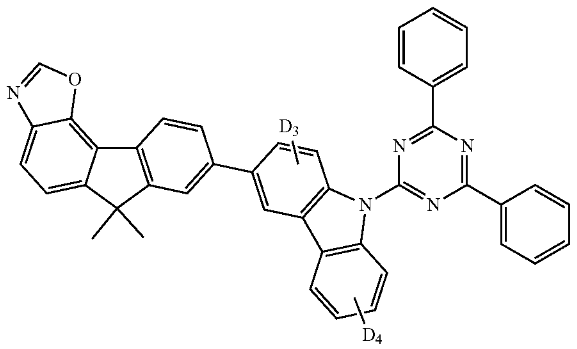

H1-D3

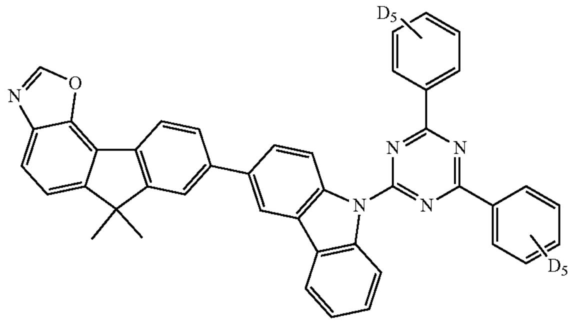

-continued

H1-D4

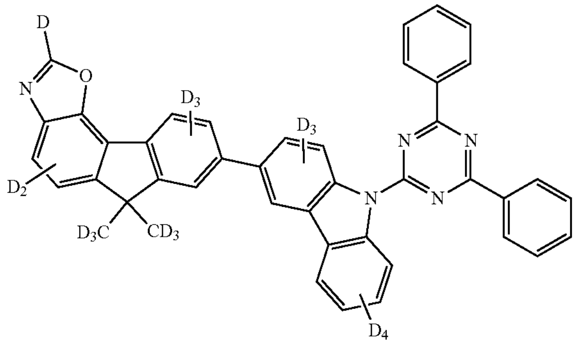

H1-D5

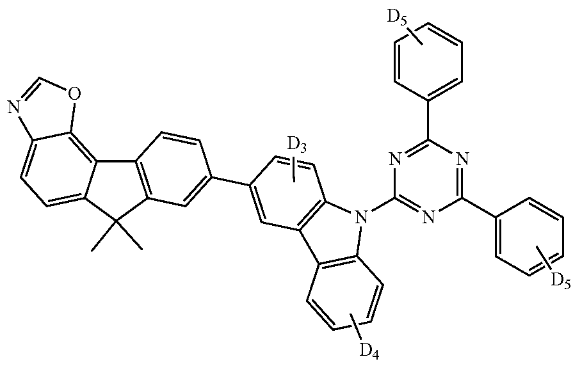

H1-D6

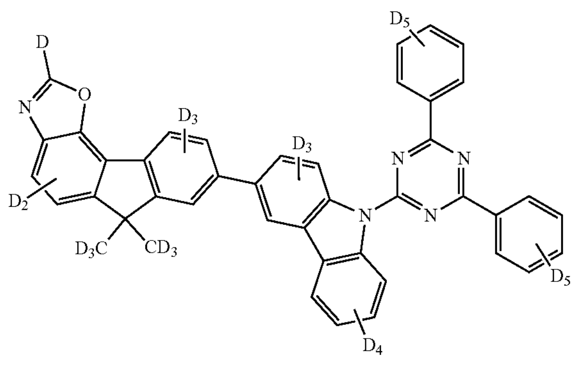

H2-D1

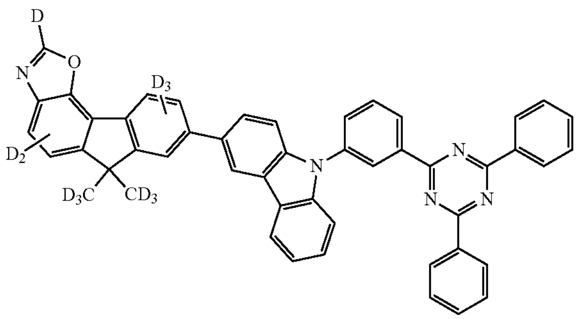

-continued
H2-D2
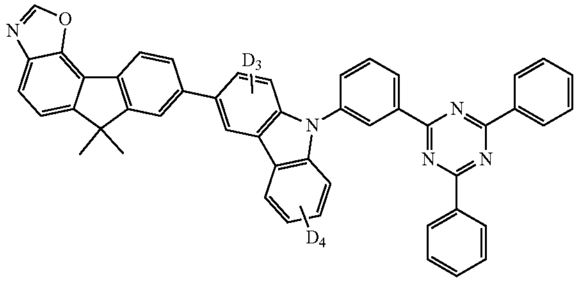
H2-D3
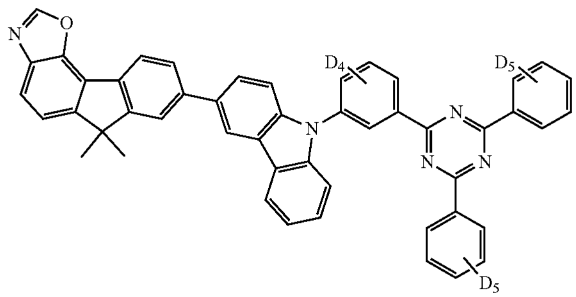
H2-D4
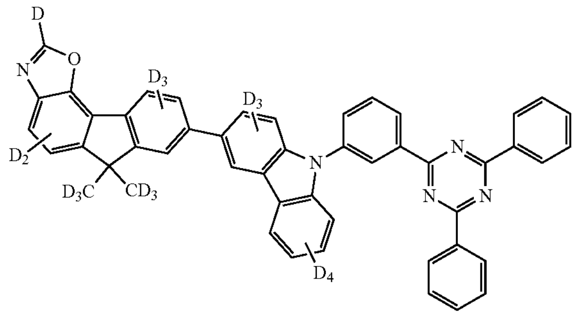
H2-D5
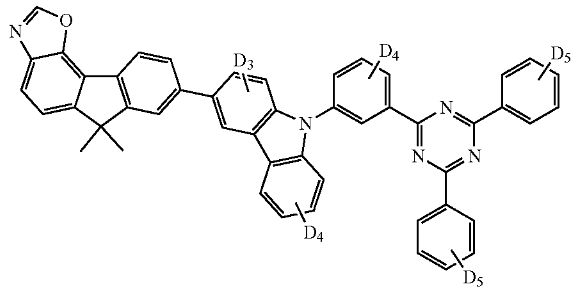
H2-D6
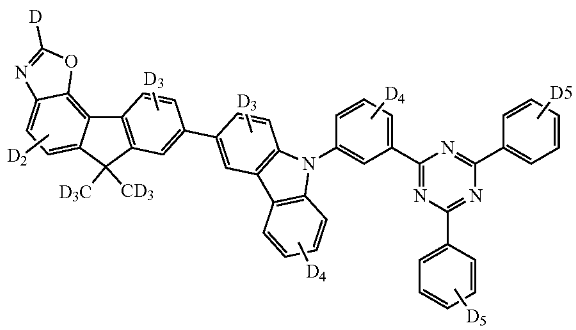
-continued
H3-D1
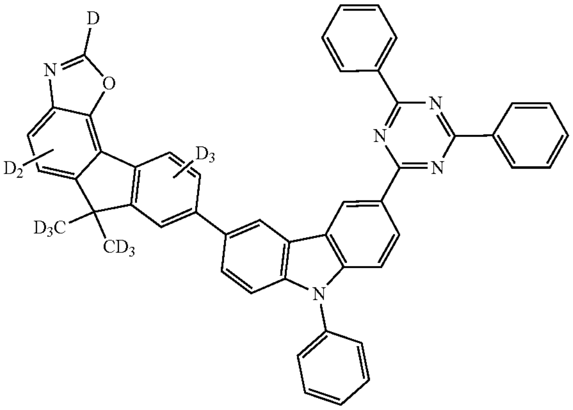
H3-D2
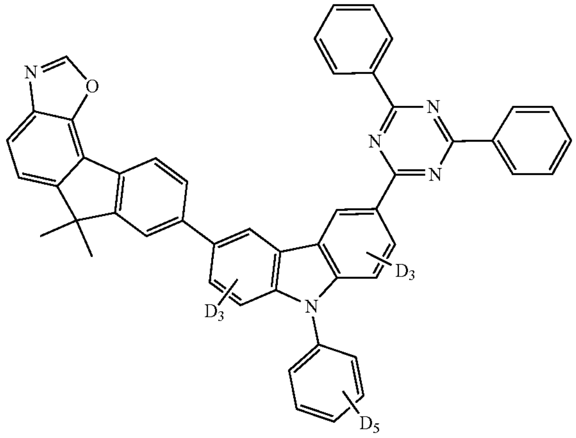
H3-D3
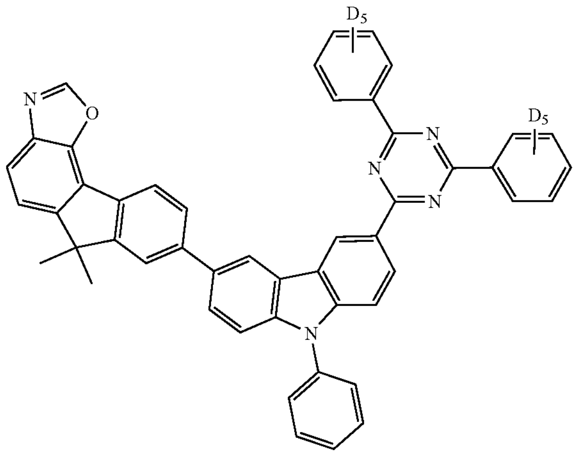

-continued
H3-D4
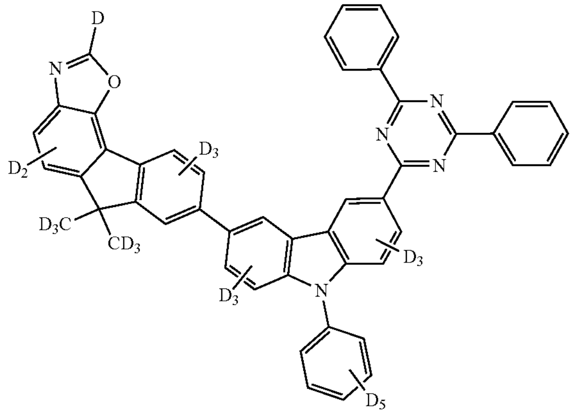
H3-D5
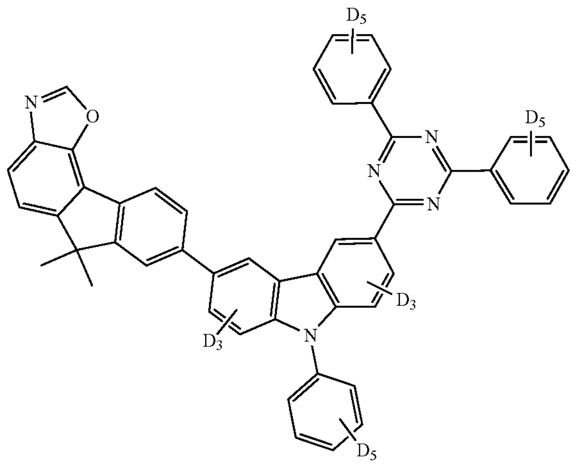
H3-D6
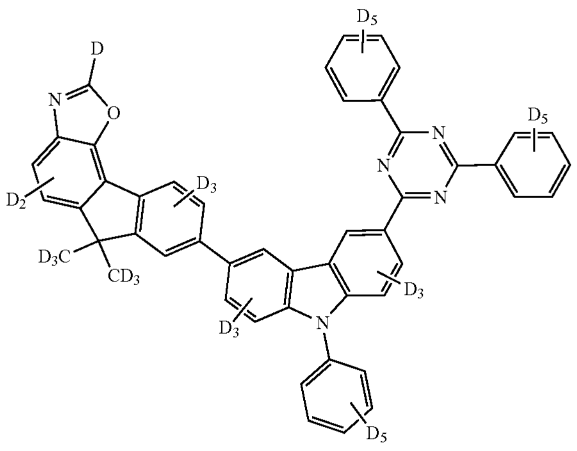
-continued
H4-D1
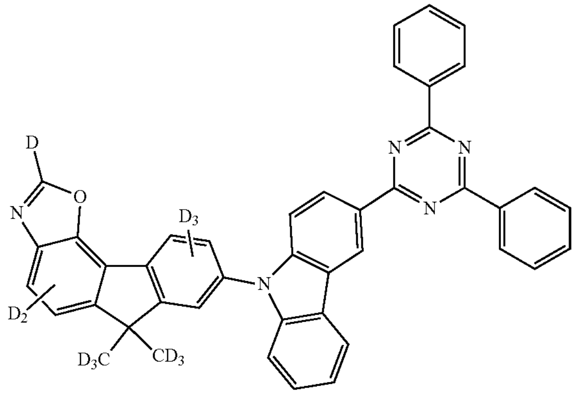
H4-D2
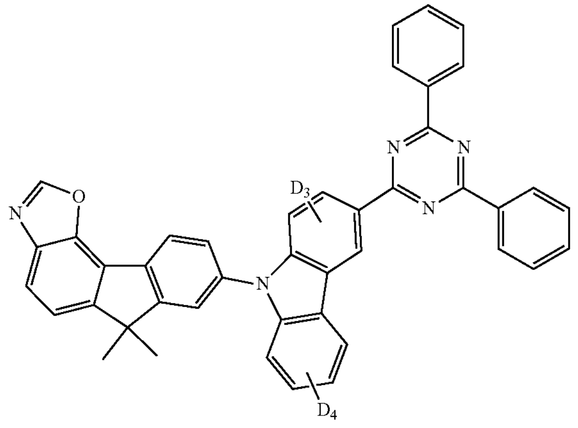
H4-D3
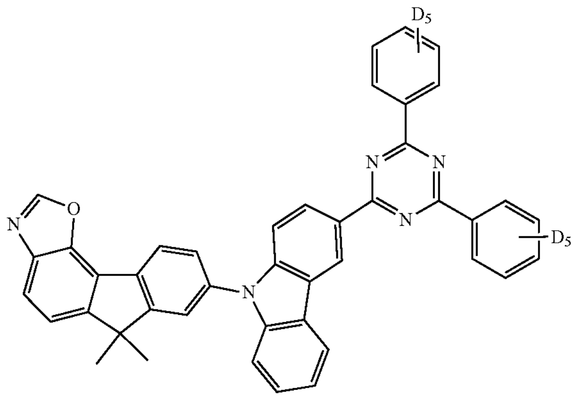

-continued
H4-D4
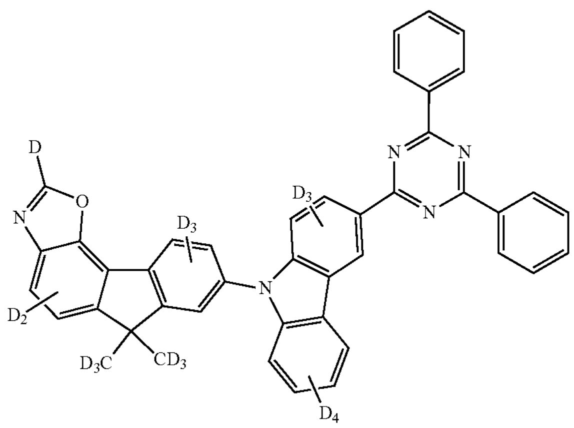
H4-D5
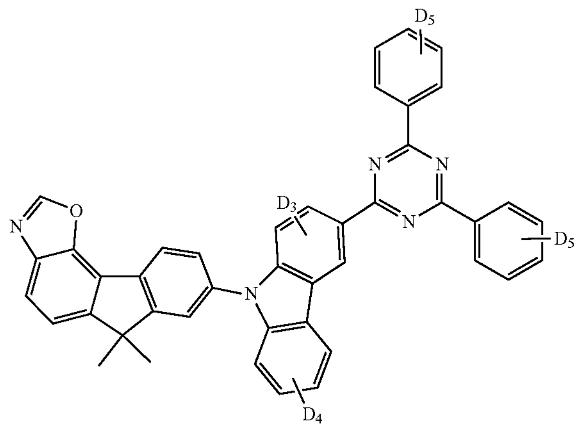
H4-D6
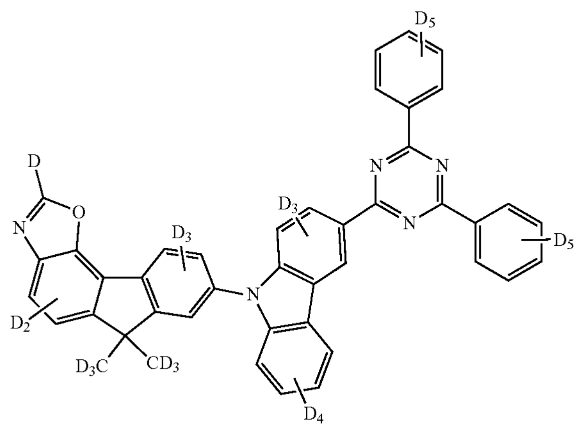
-continued
H5-D1
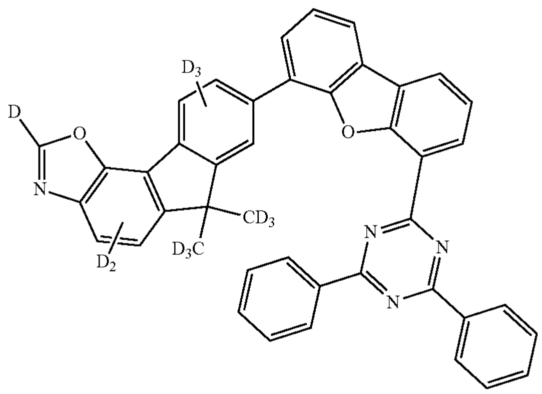
H5-D2
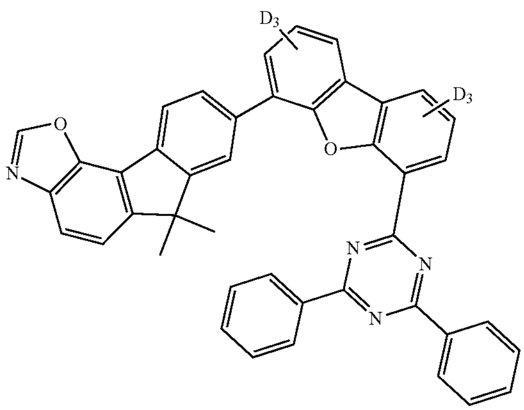
H5-D3
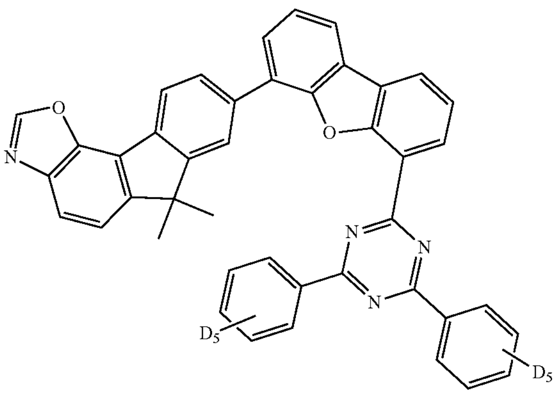

-continued
H5-D4
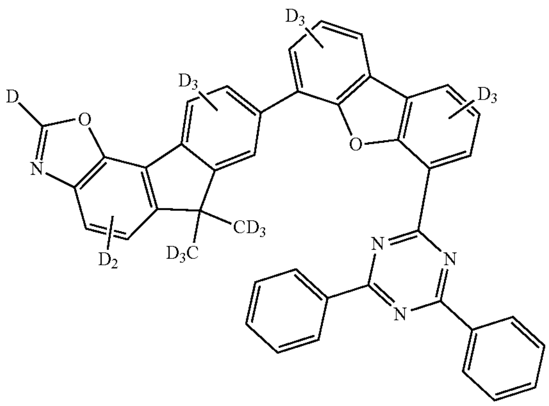
H5-D5
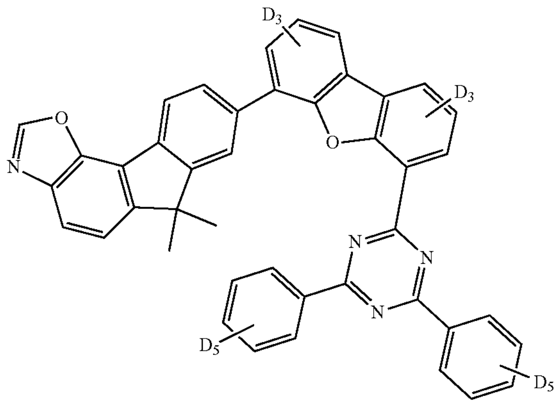
H5-D6
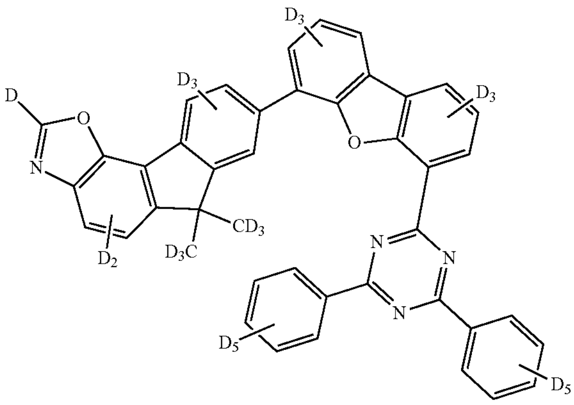
-continued
H6-D1
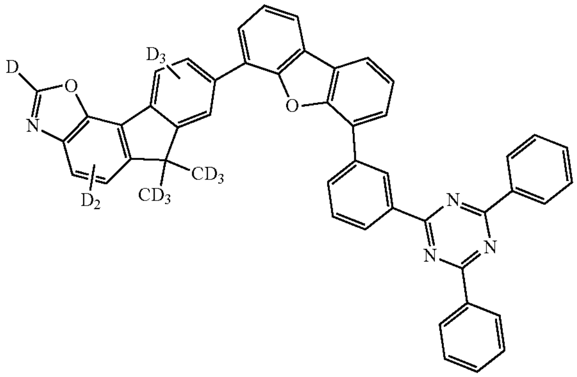
H6-D2
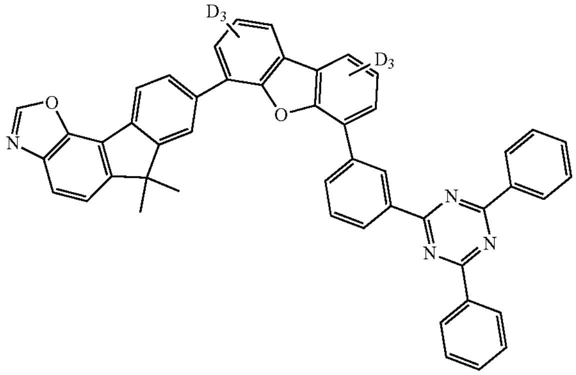
H6-D3
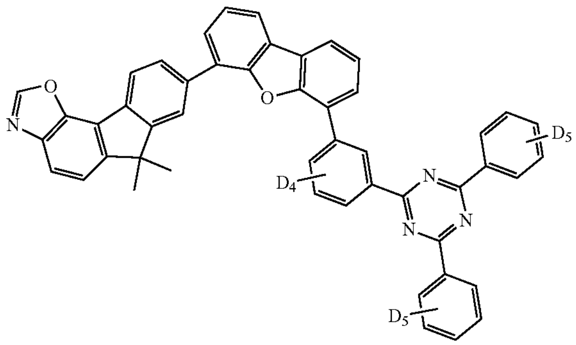
H6-D4
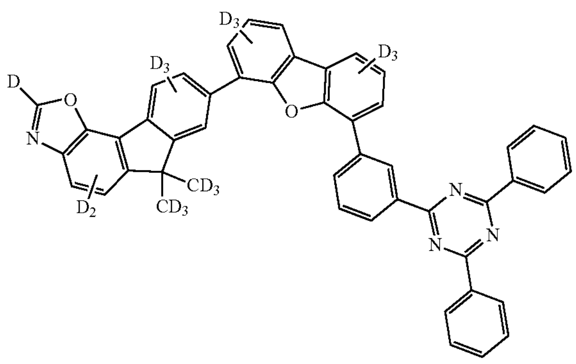

-continued
H6-D5
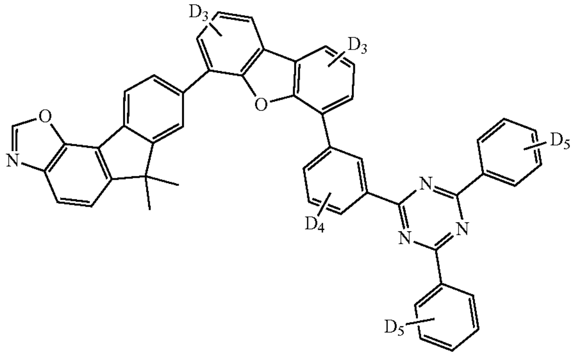
H6-D6
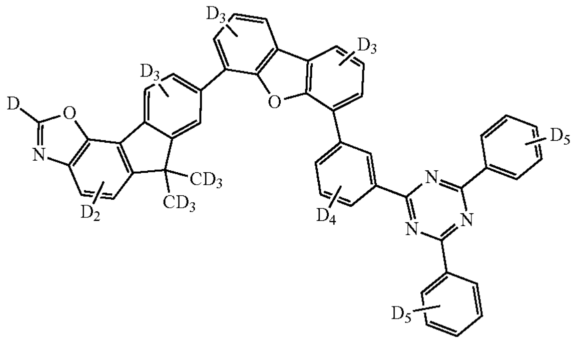
H7-D1
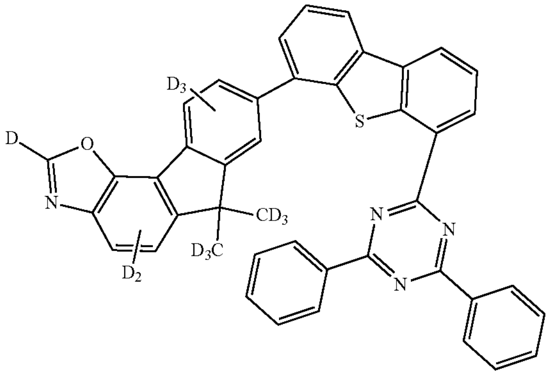
H7-D2
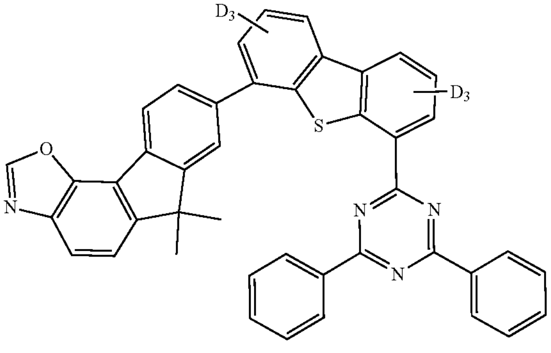
-continued
H7-D3
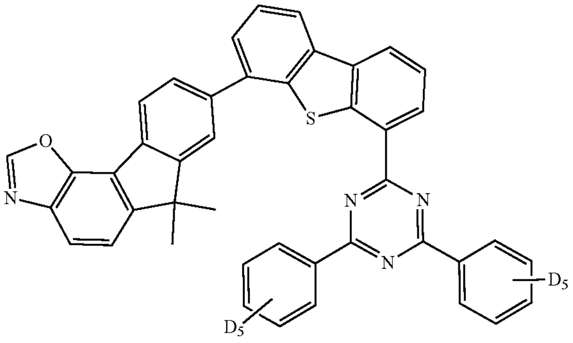
H7-D4
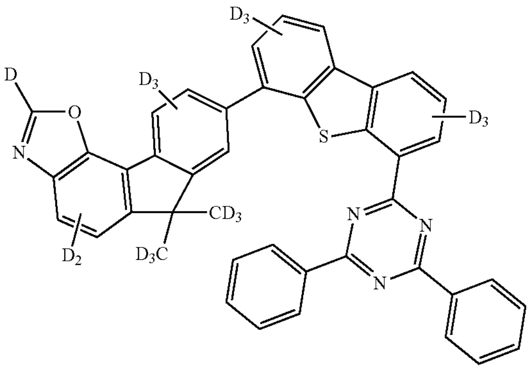
H7-D5
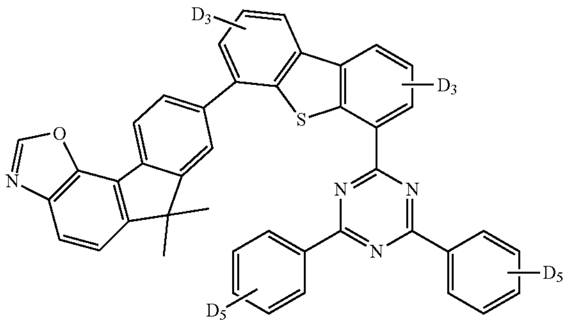
H7-D6
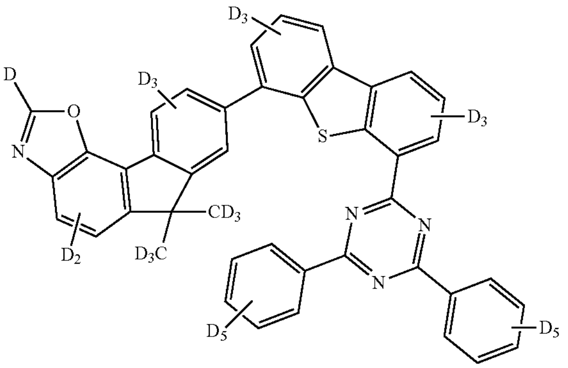

-continued
H8-D1
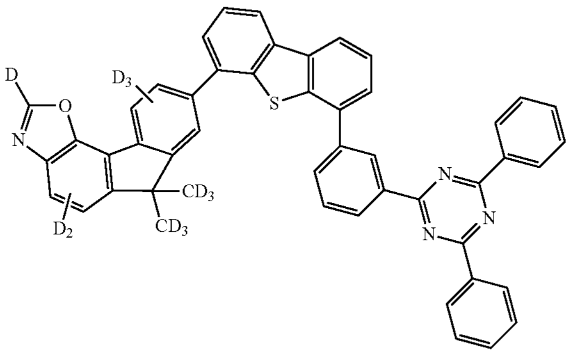
H8-D2
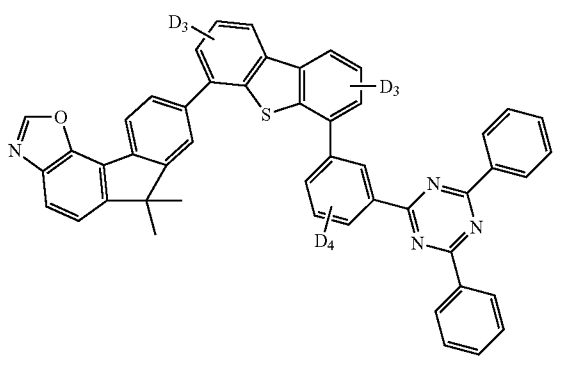
H8-D3
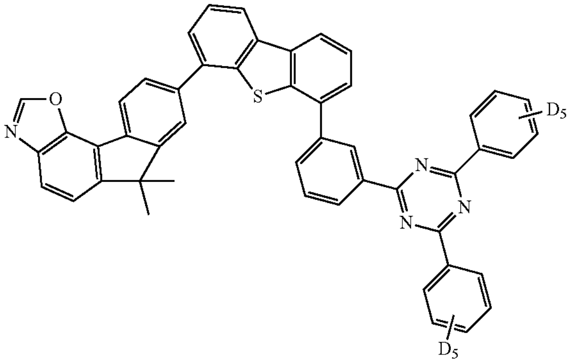
H8-D4
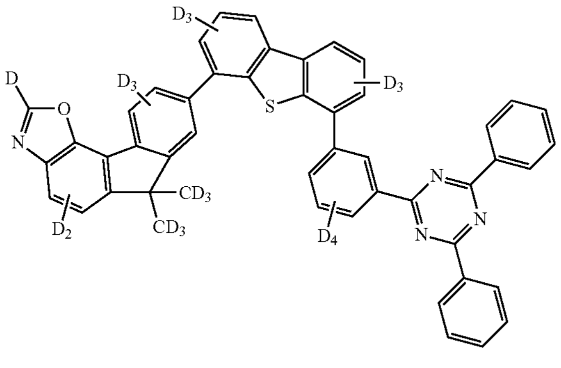
-continued
H8-D5
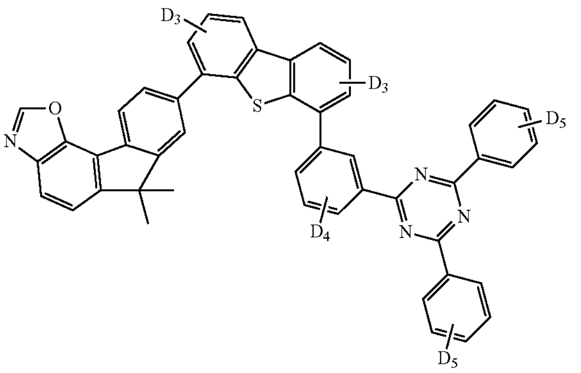
H8-D6
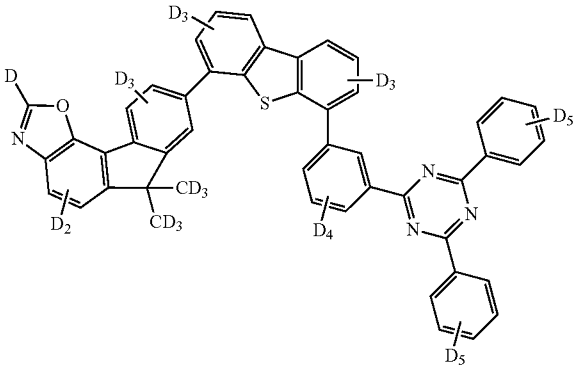
H9-D1
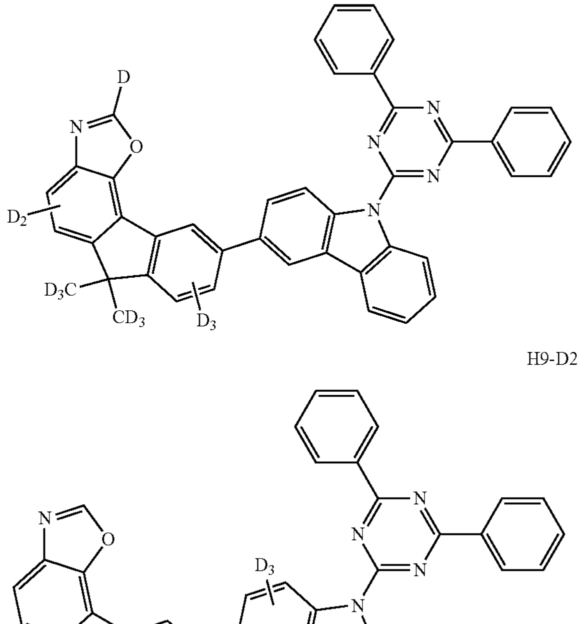
H9-D2
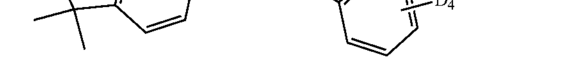

-continued
H9-D3
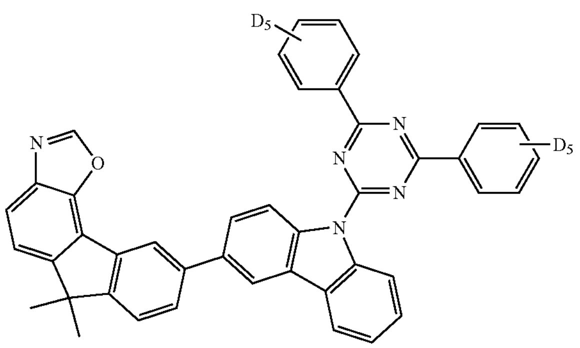
H9-D4
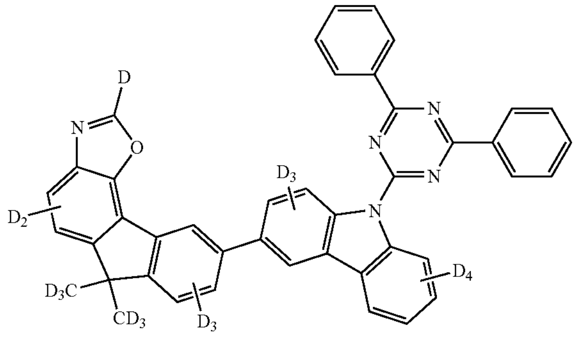
H9-D5
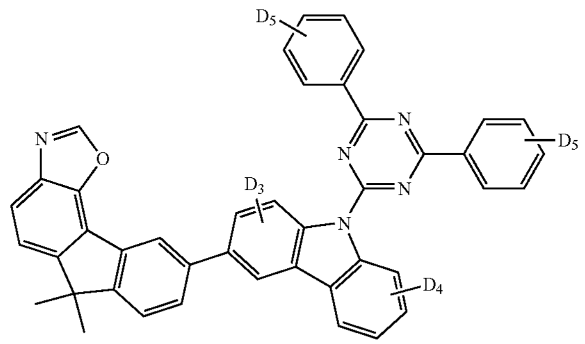
H9-D6
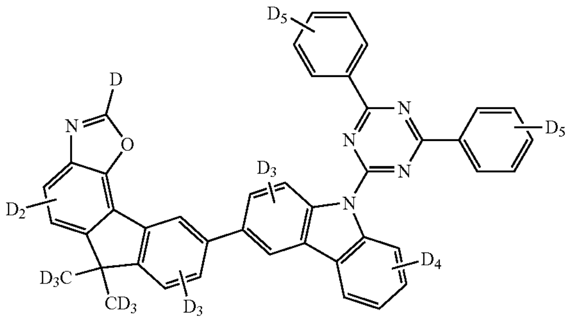
-continued
H10-D1
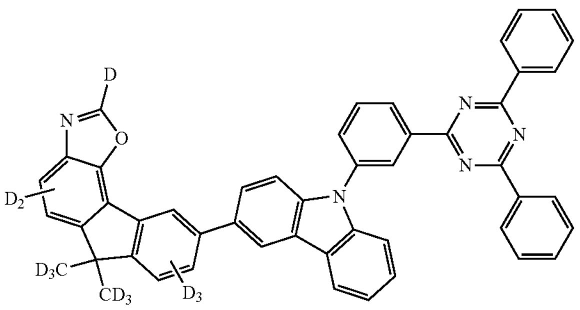
H10-D2
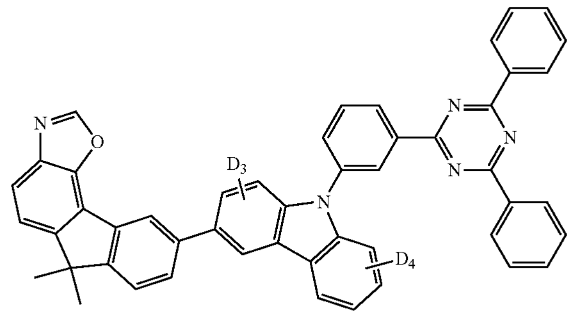
H10-D3
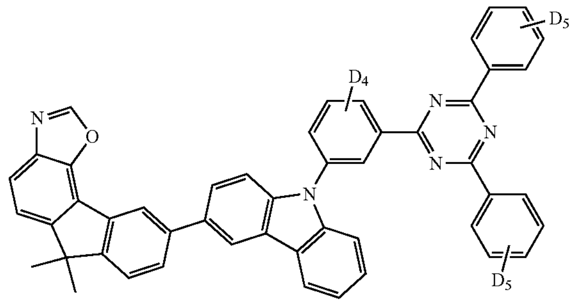
H10-D4
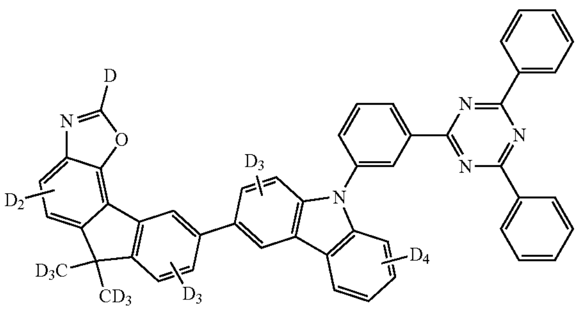

-continued
H10-D5
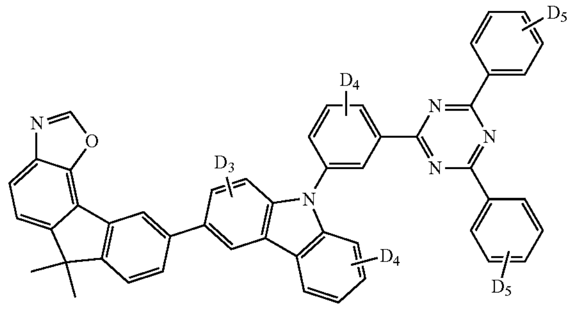
H10-D6
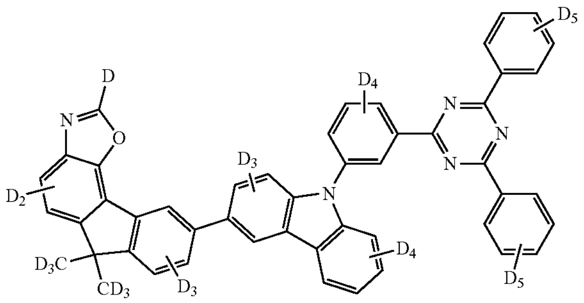
H11-D1
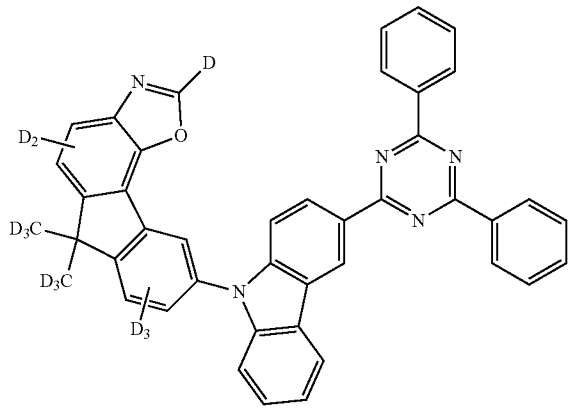
H11-D2
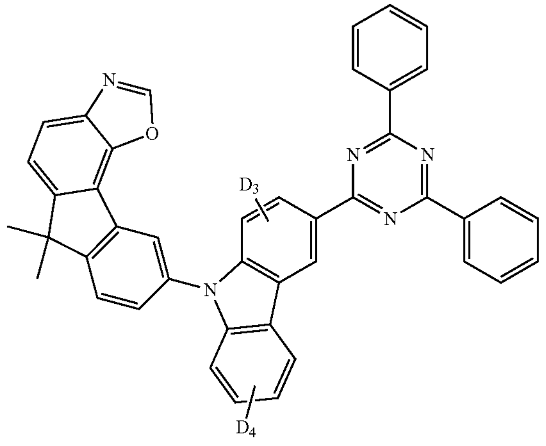
-continued
H11-D3
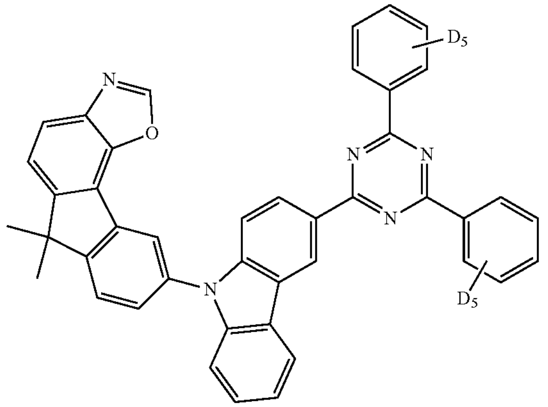
H11-D4
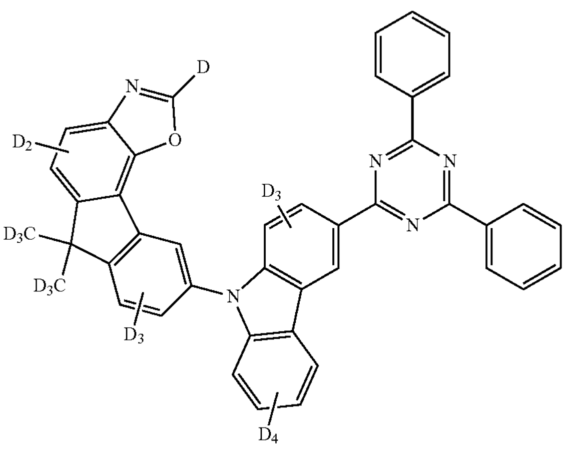
H11-D5
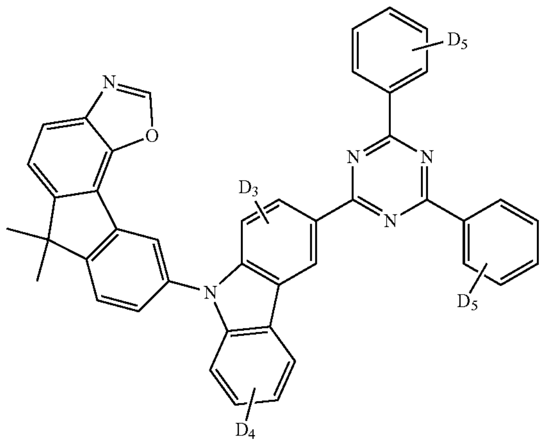

-continued
H11-D6
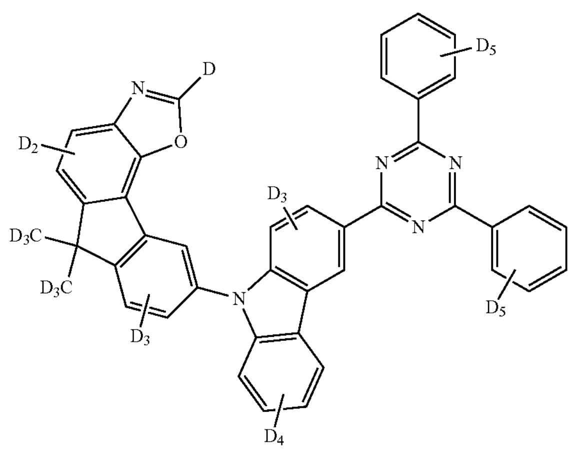
H12-D1
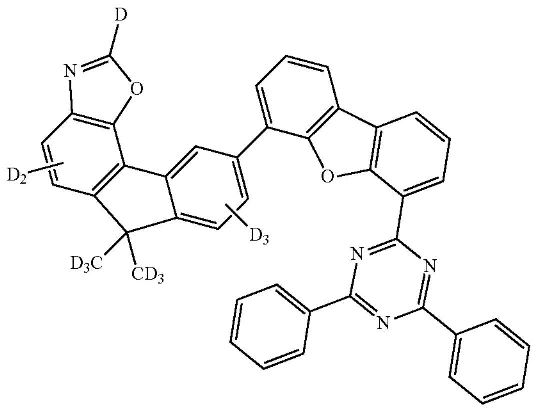
H12-D2
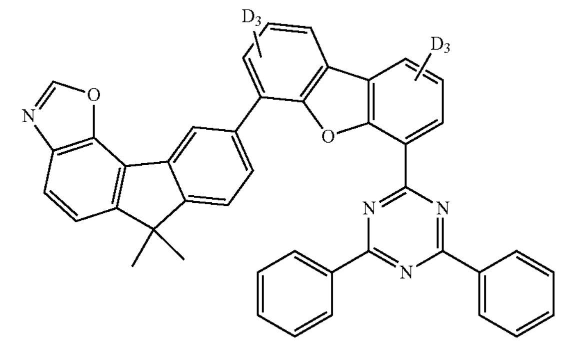
H12-D3
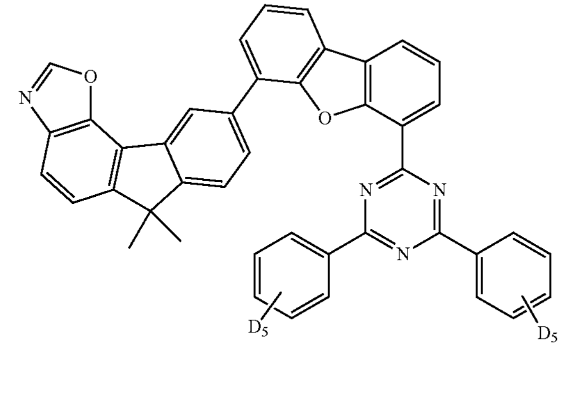
-continued
H12-D4
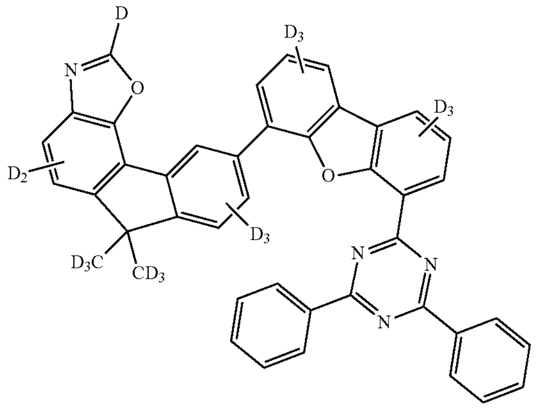
H12-D5
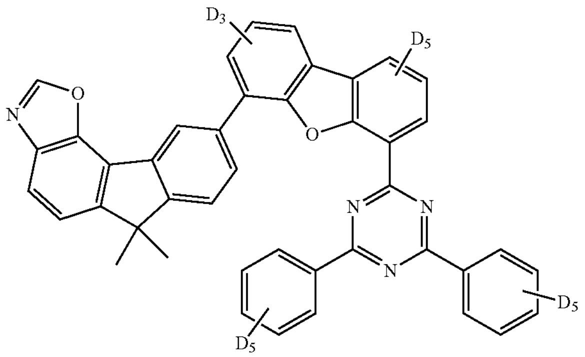
H12-D6
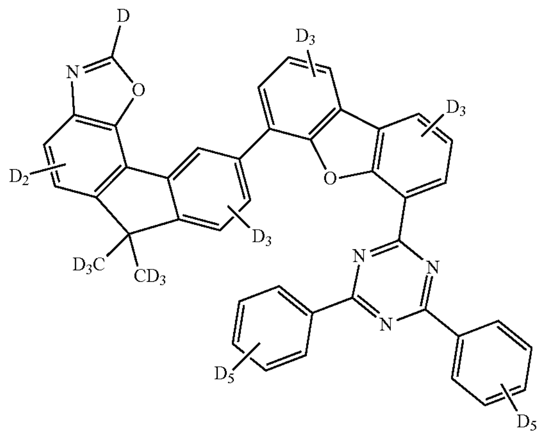
H13-D1
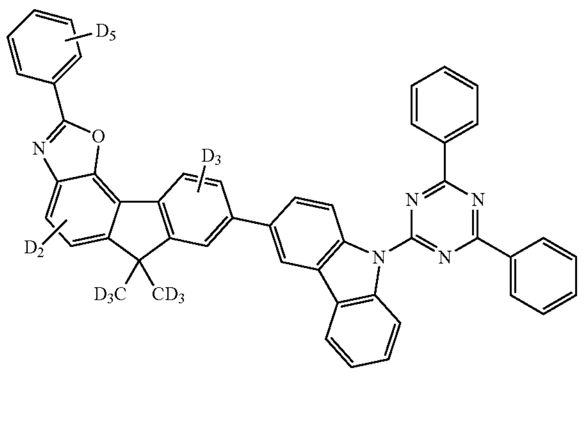

-continued
H13-D2
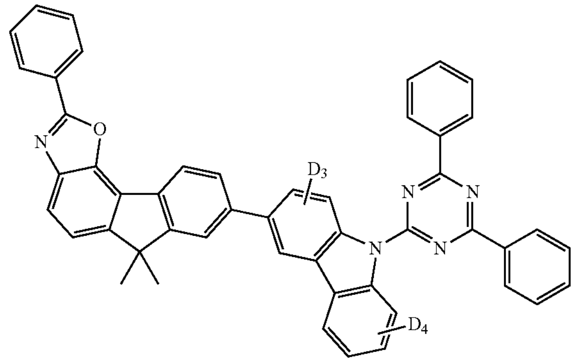
H13-D3
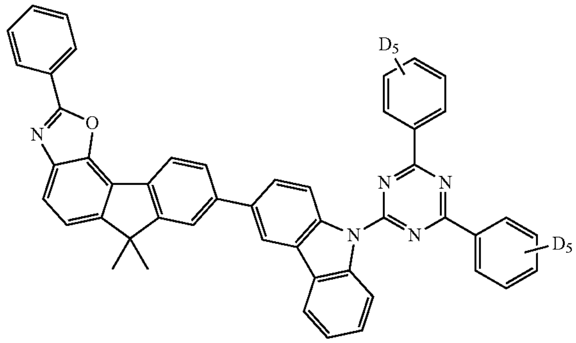
H13-D4
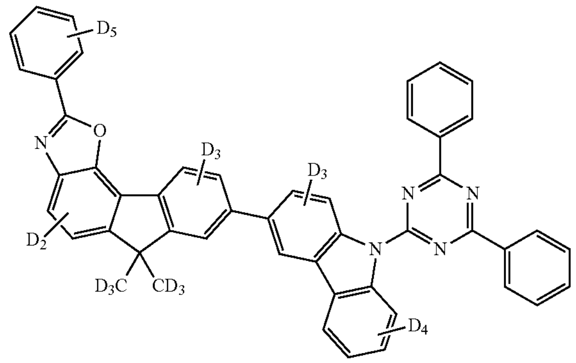
H13-D5
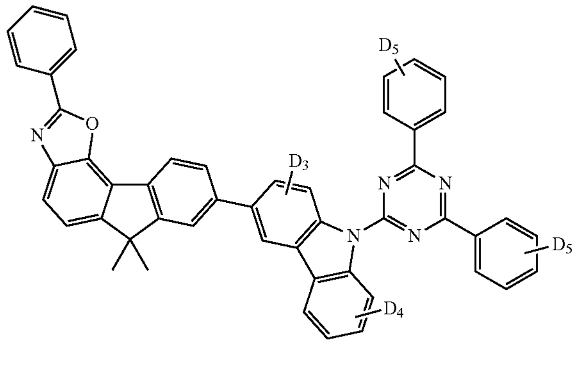
-continued
H13-D6
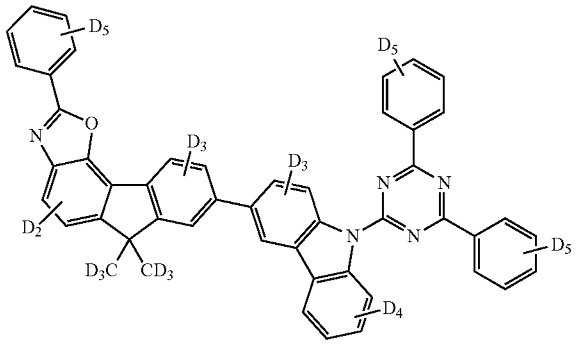
H14-D1
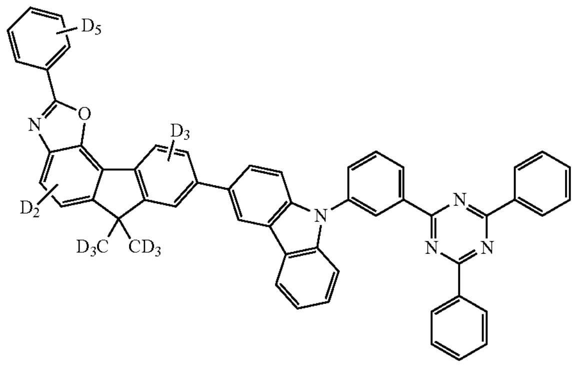
H14-D2
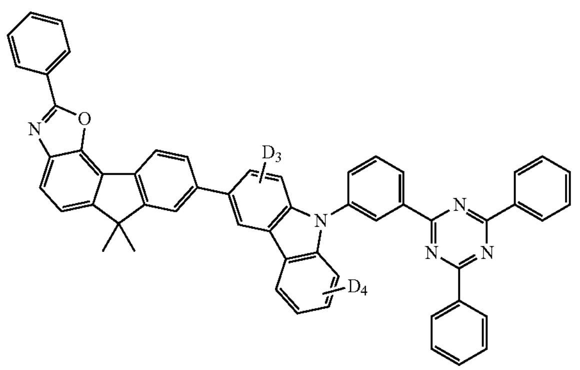

-continued
H14-D3
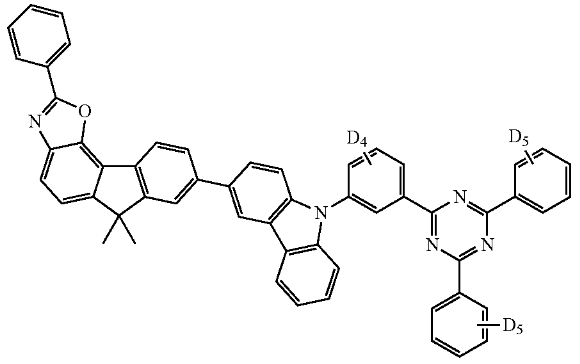
H14-D5
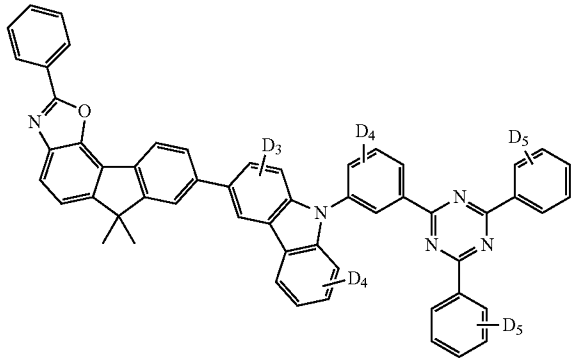
H14-D4
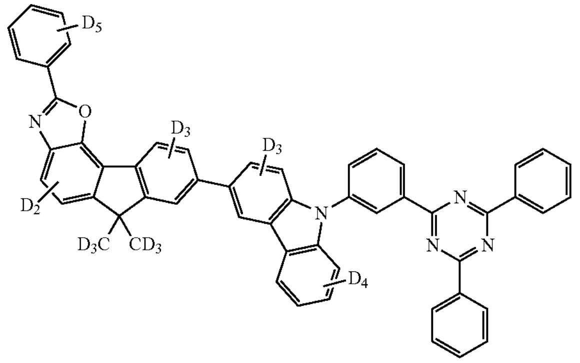
H14-D6
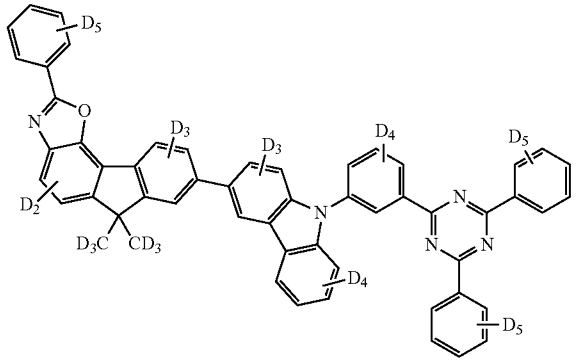
H15-D1
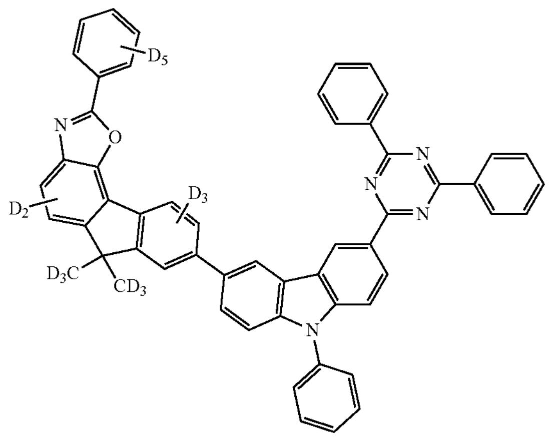
H15-D2
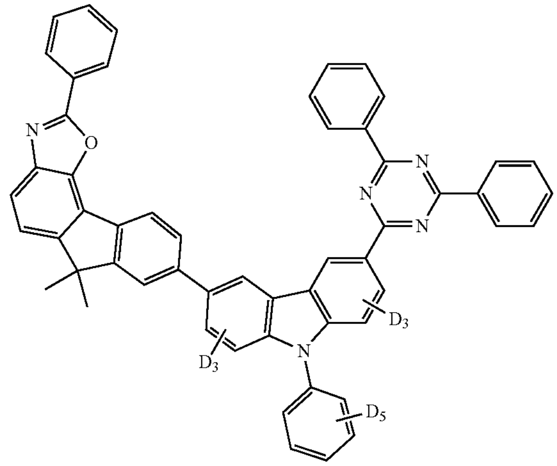

-continued
H15-D3
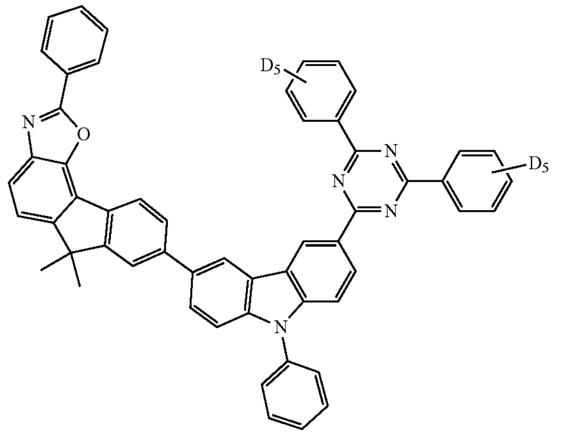
H15-D4
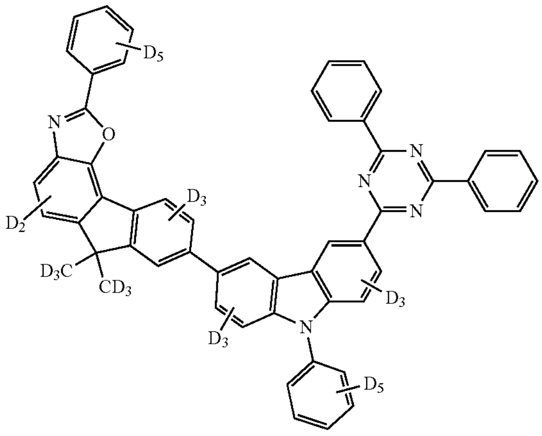
H15-D5
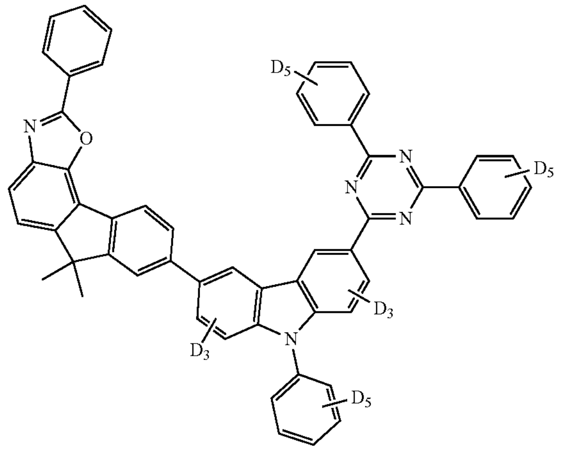
H15-D6
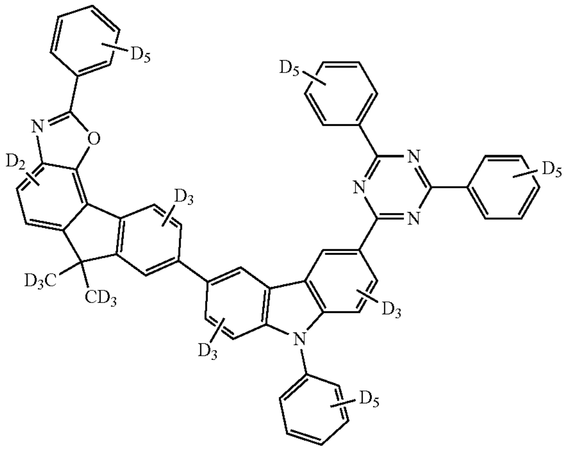
H16-D1
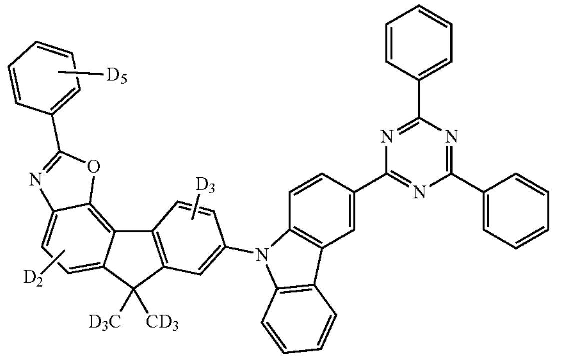
H16-D2
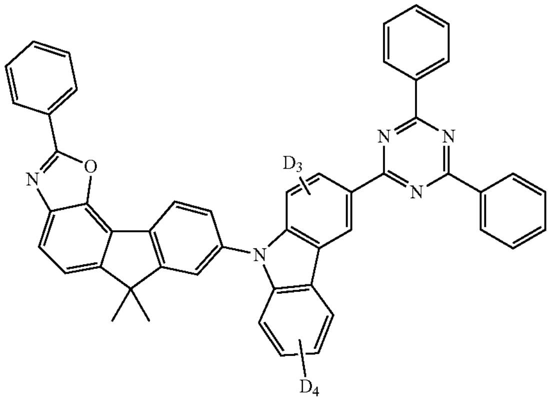

-continued
H16-D3
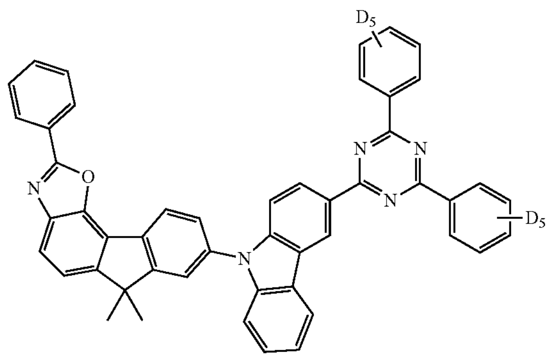
H16-D4
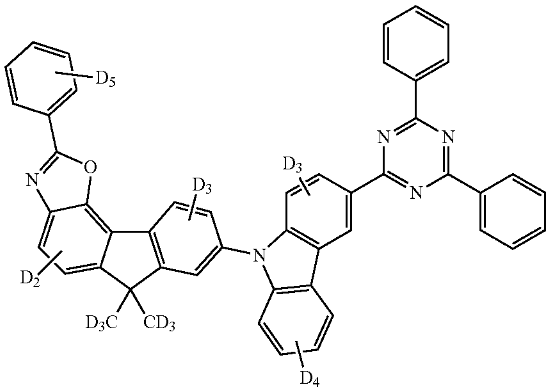
H16-D5
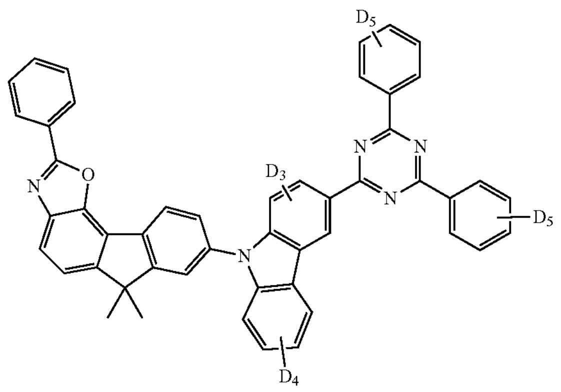
H16-D6
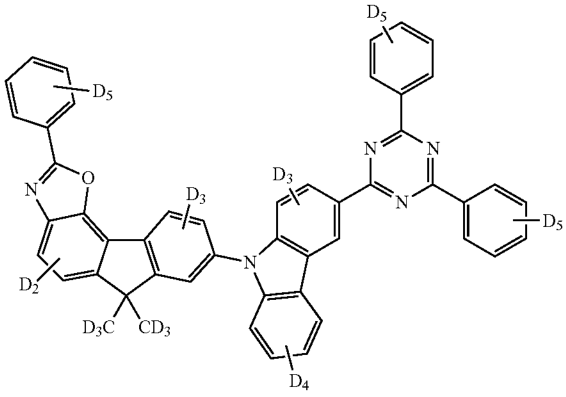
H17-D1
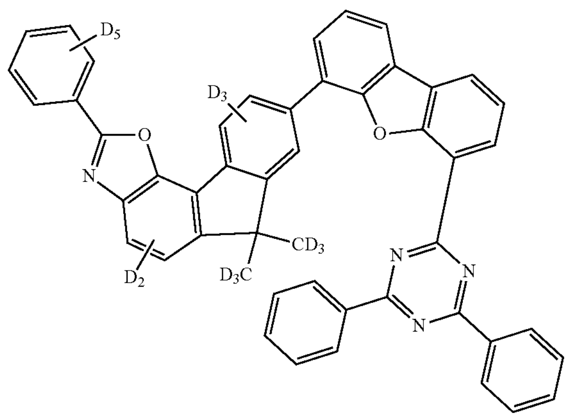
H17-D2
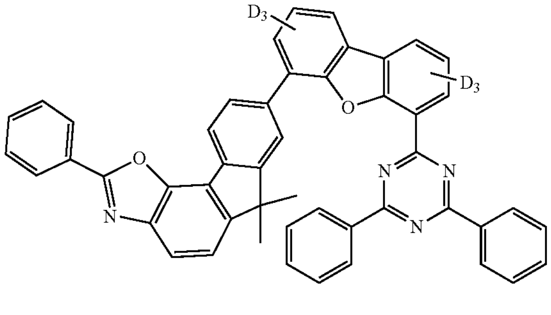

-continued
H17-D3
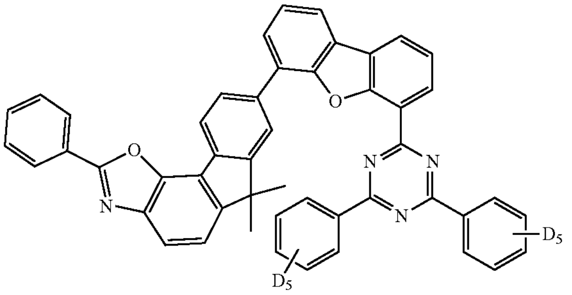
H17-D4
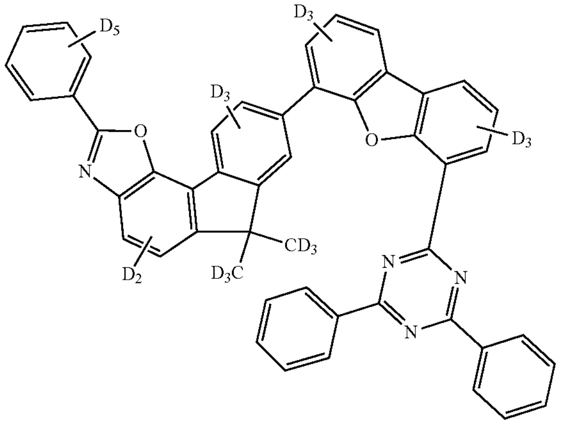
H17-D5
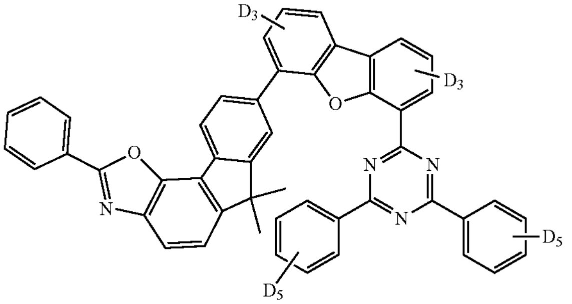
H17-D6
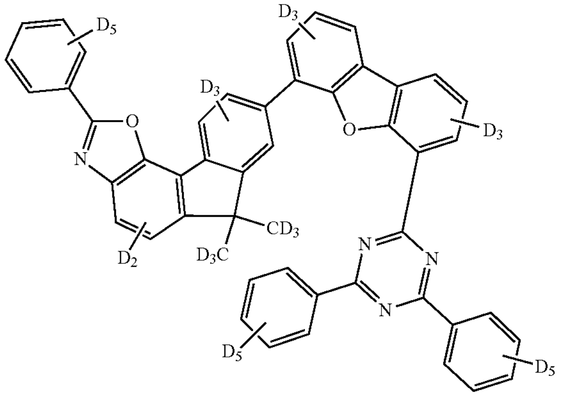
H18-D1
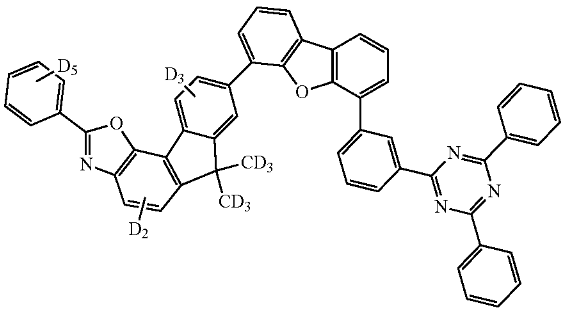
H18-D2
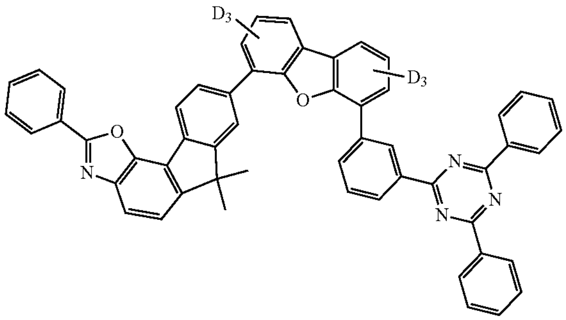
H18-D3
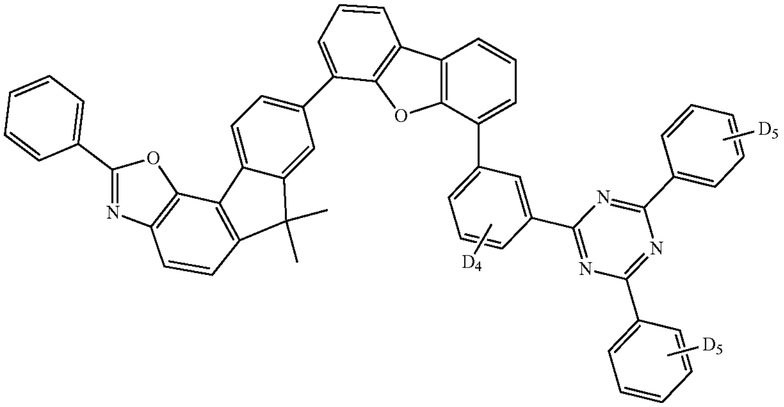

-continued
H15-D4
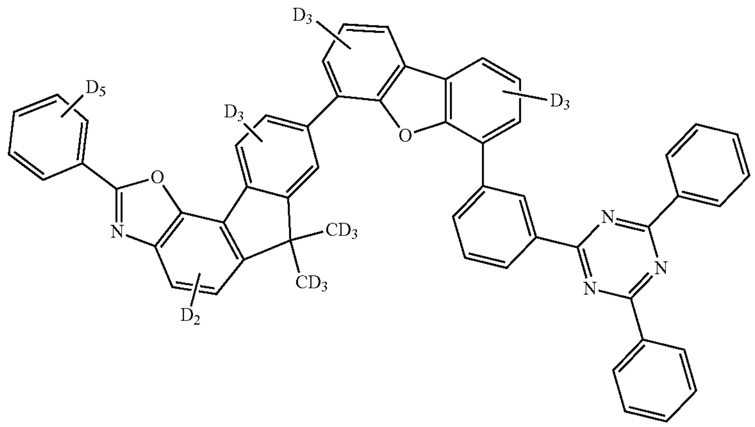
H18-D5
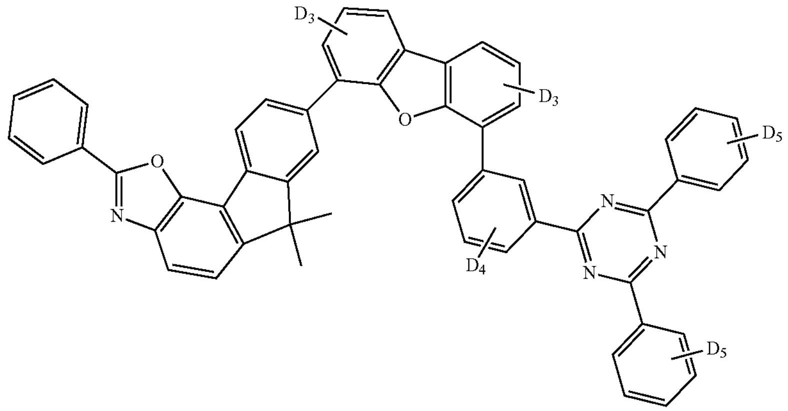
H18-D6
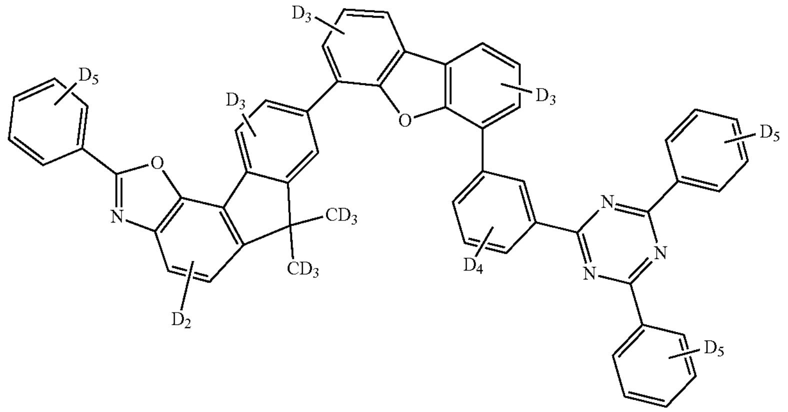
H19-D1
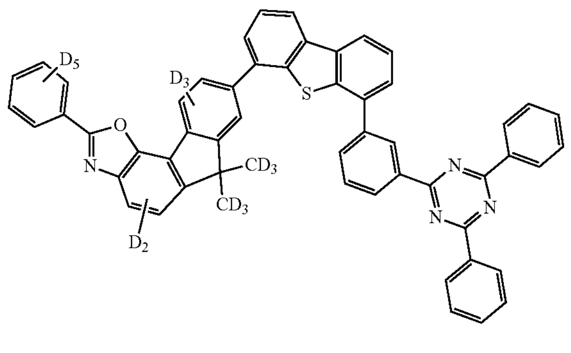
H19-D2
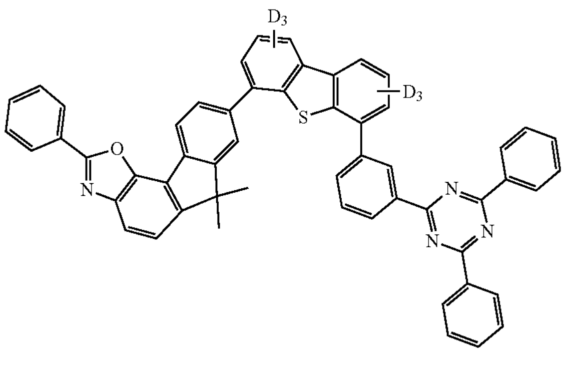

-continued
H19-D3
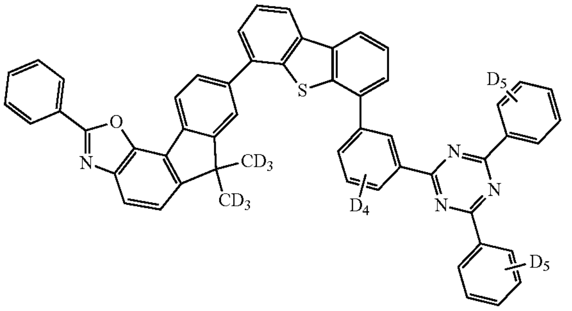
H19-D4
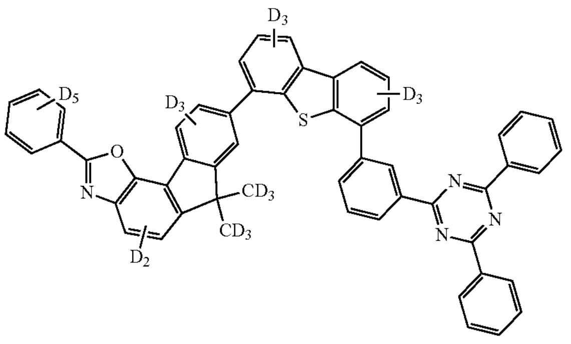
H19-D5
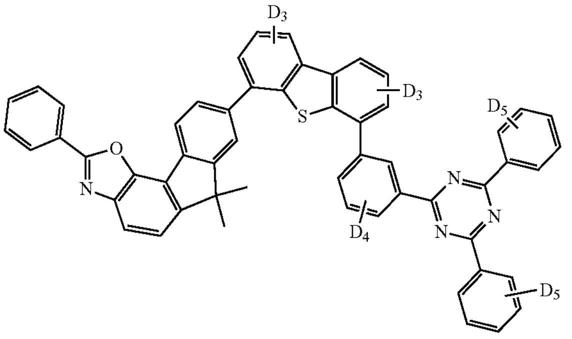
H19-D6
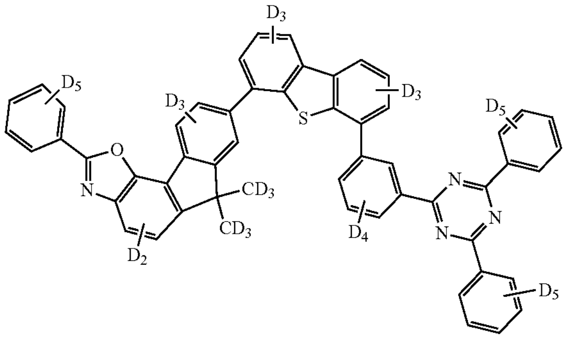
H20-D1
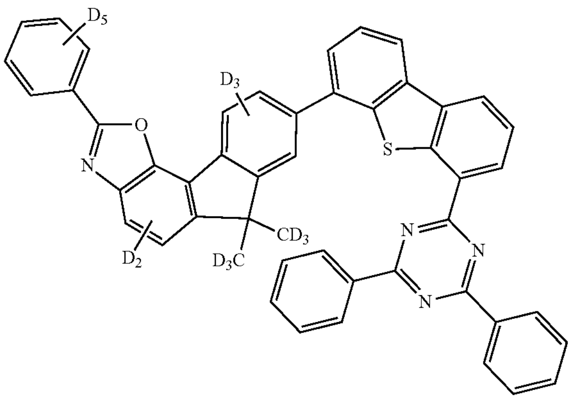
H20-D2
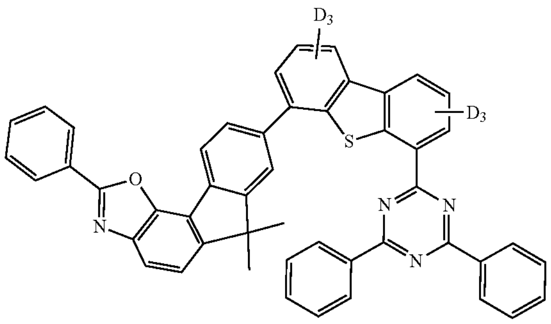
H20-D3
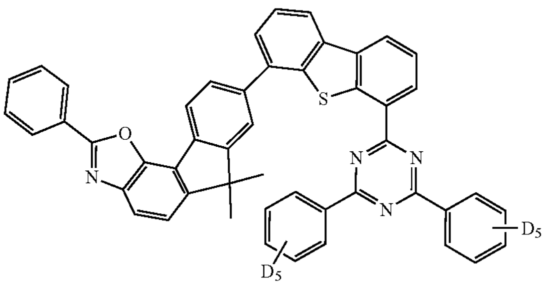
H20-D4
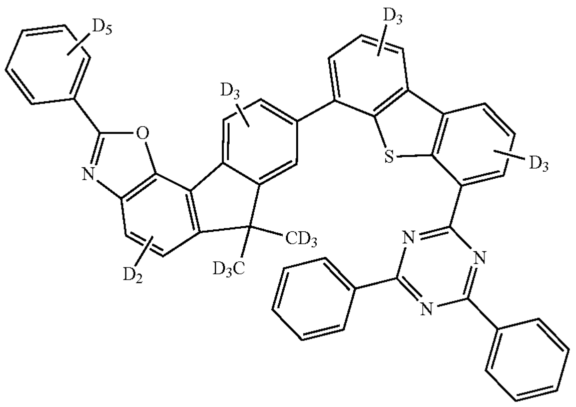

-continued
H20-D5
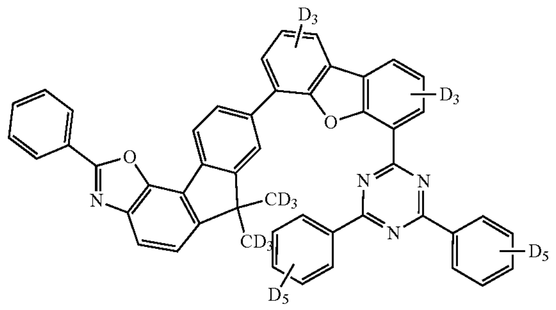
H20-D6
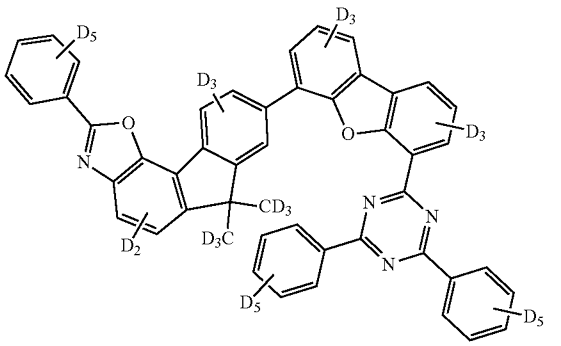
H21-D1
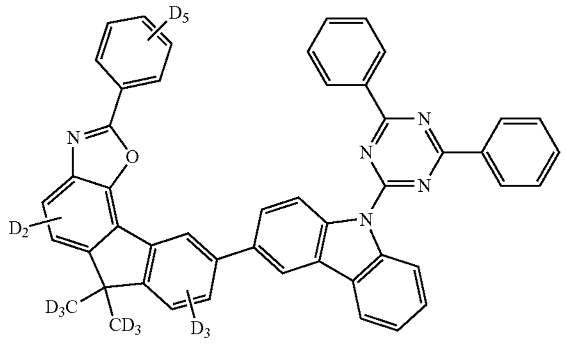
H21-D2
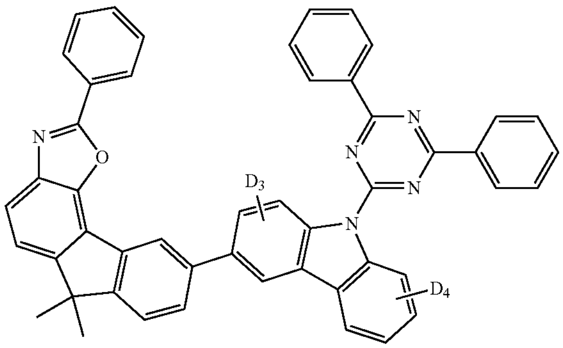
H21-D3
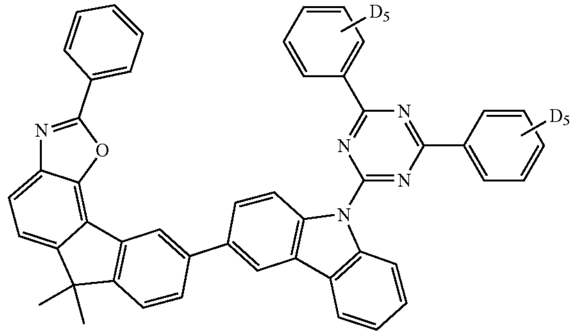
H21-D4
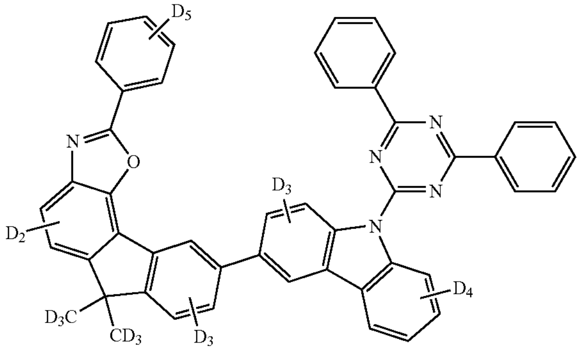
H21-D5
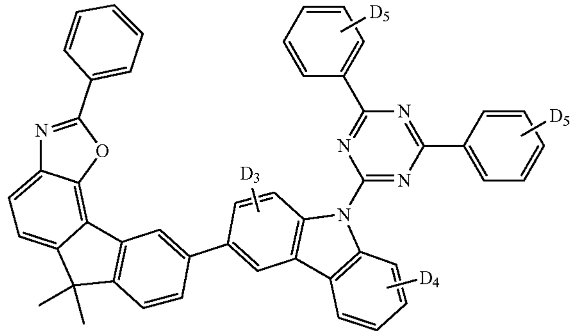
H21-D6
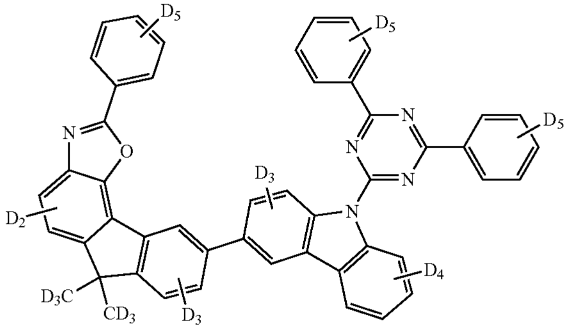

-continued
H22-D1
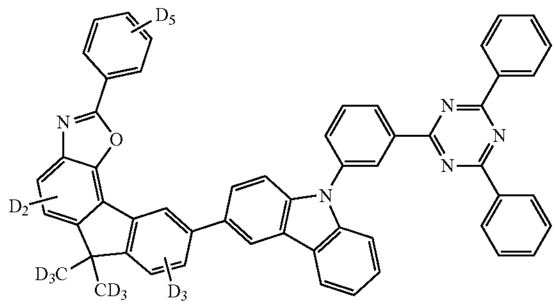
H22-D2
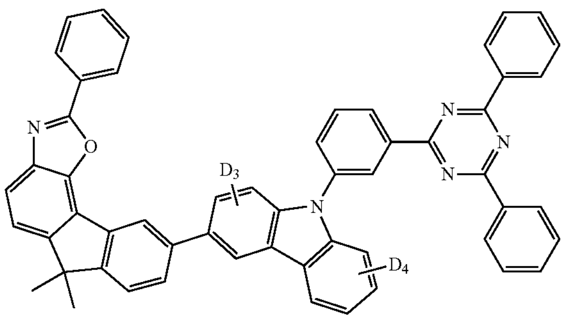
H22-D3
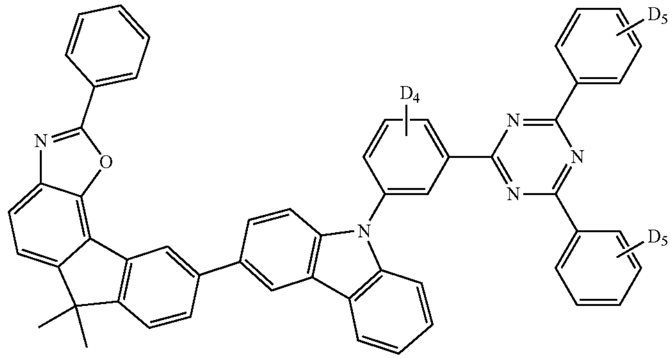
H22-D4
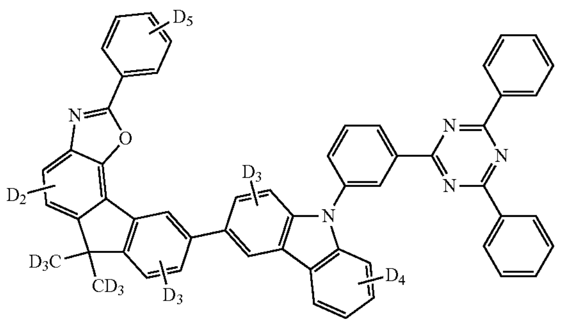
H22-D5
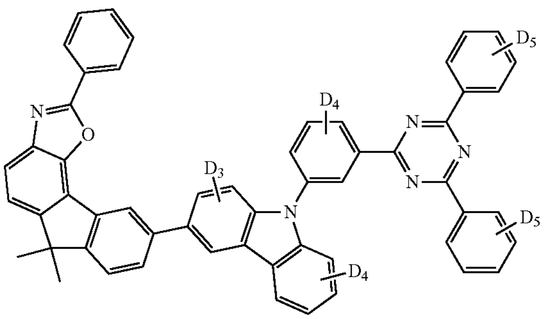
-continued
H22-D6
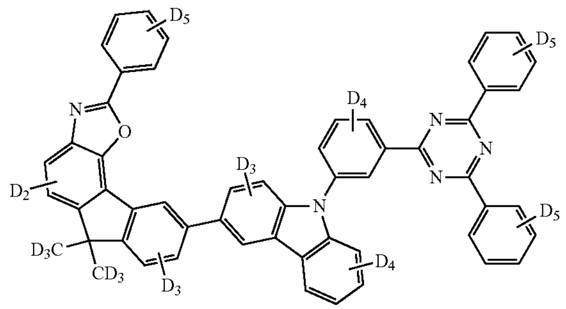
H23-D1
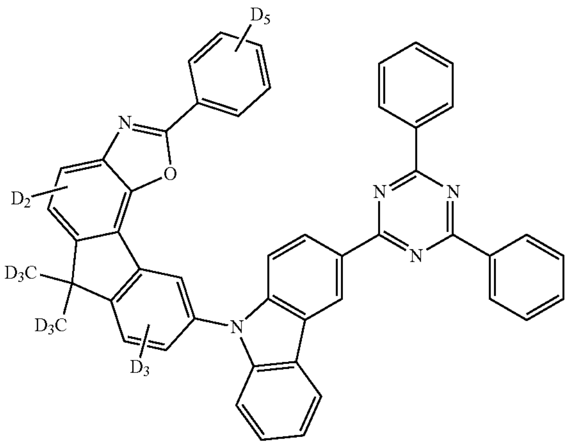

H23-D2
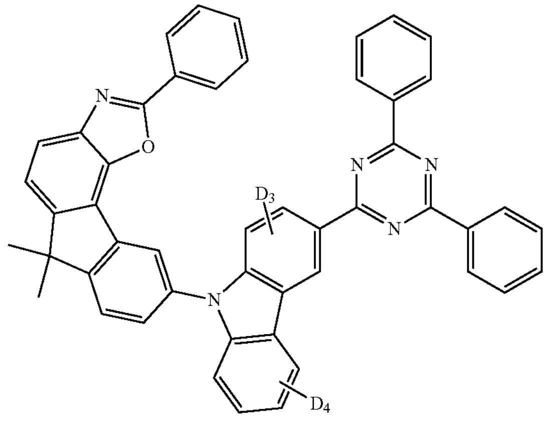
H23-D3
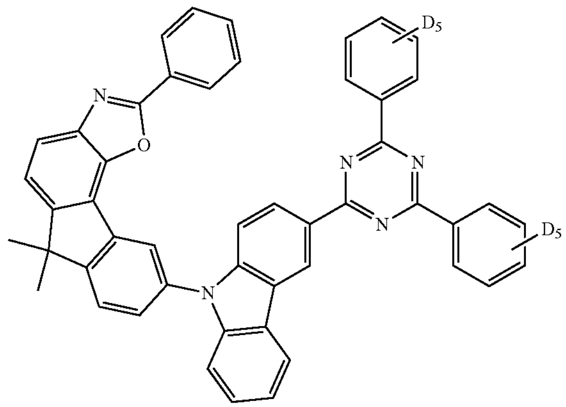
H23-D4
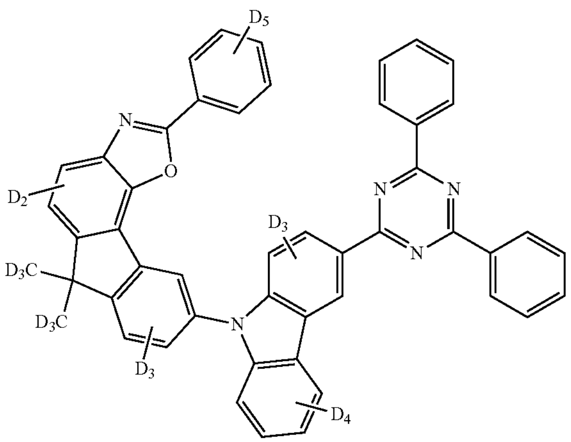
H23-D5
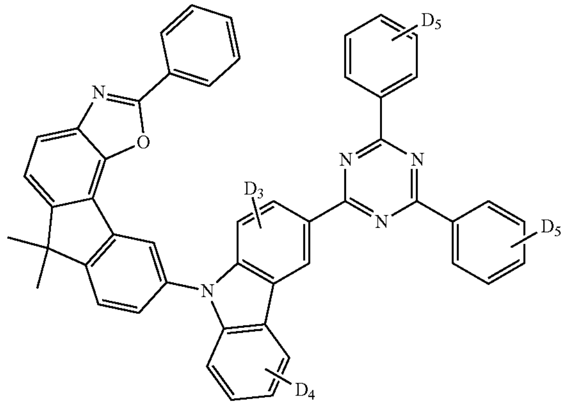
H23-D6
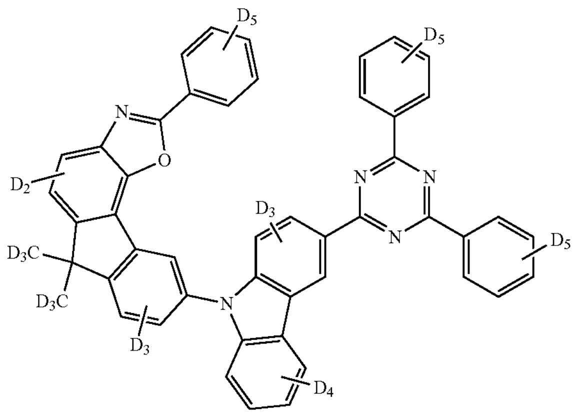
H24-D1
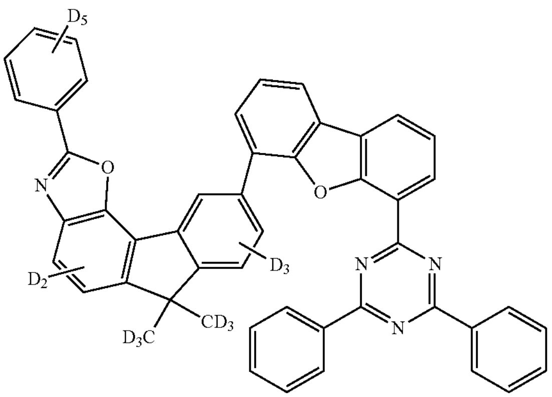

-continued
H24-D2
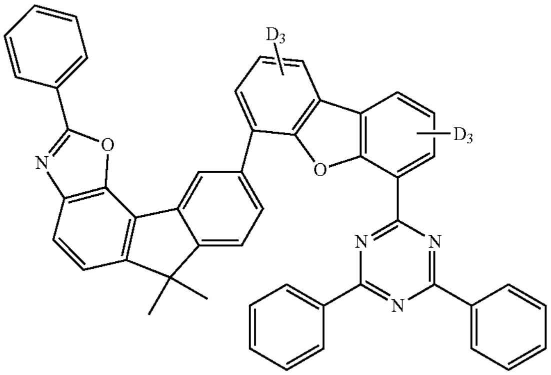
H24-D3
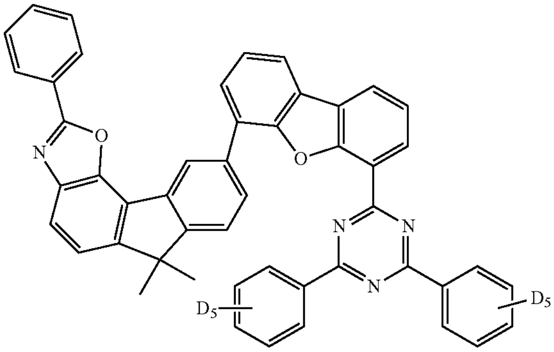
H24-D4
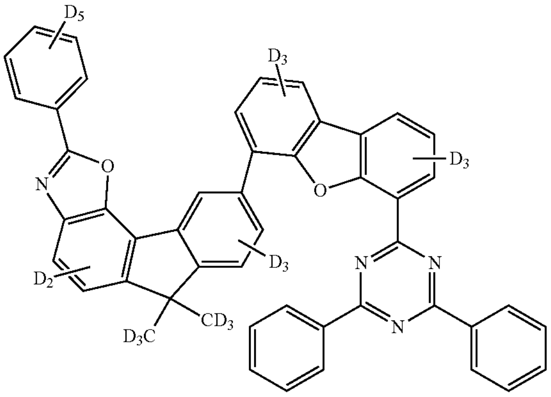
H24-D5
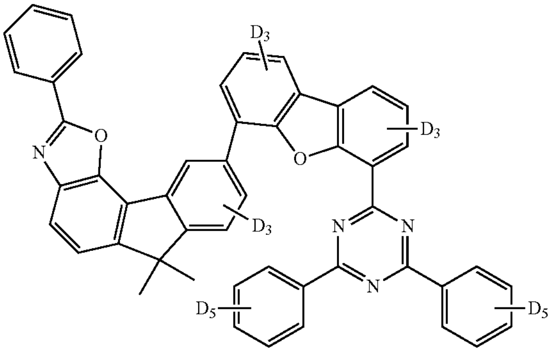
-continued
H24-D6
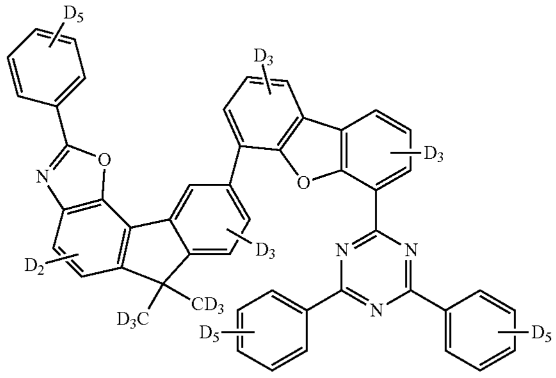
H25-D1
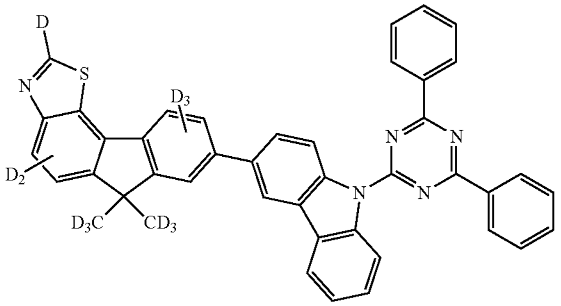
H25-D2
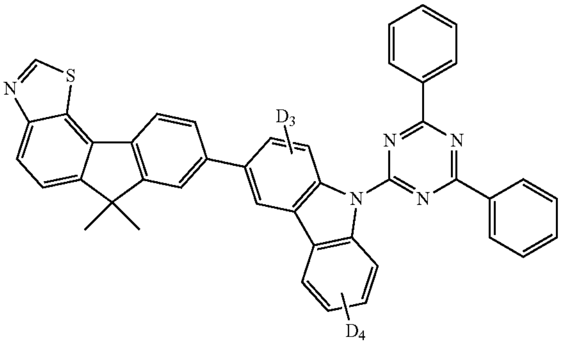
H25-D3
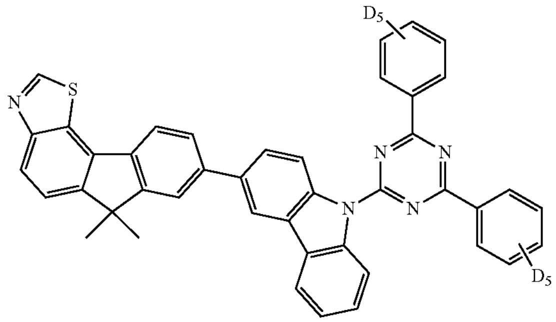

-continued
H25-D4
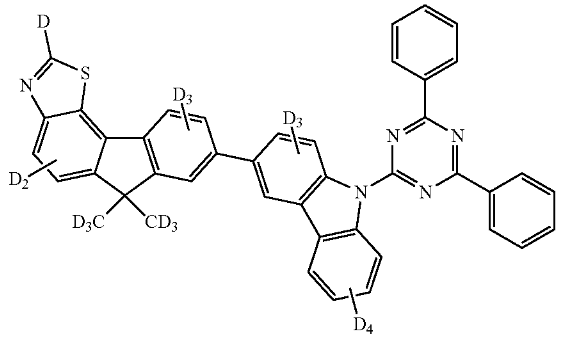
H25-D5
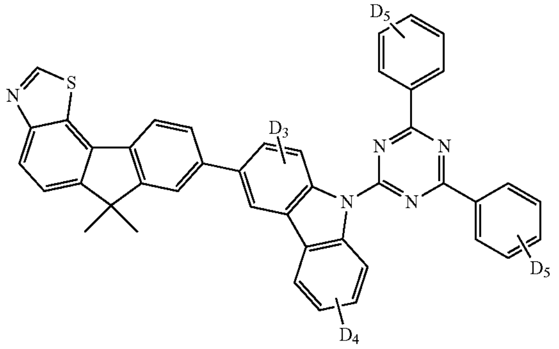
H25-D6
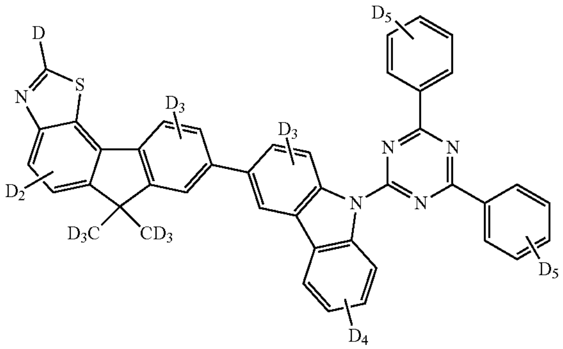
H26-D1
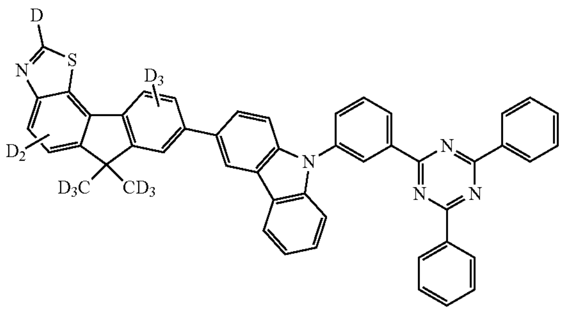
-continued
H26-D2
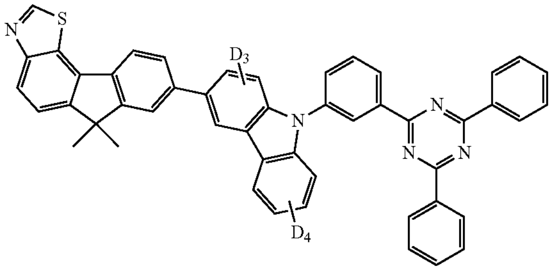
H26-D3
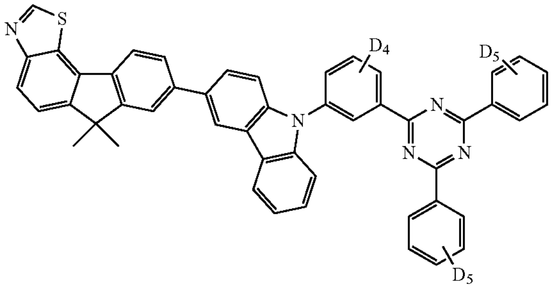
H26-D4
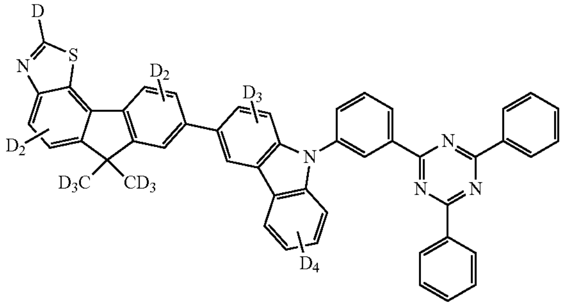
H26-D5
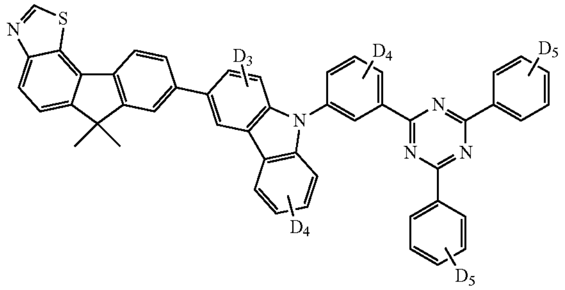
H26-D6
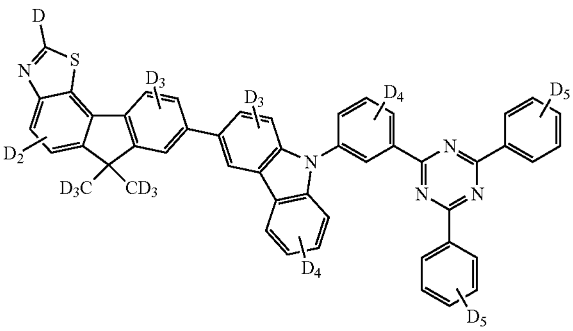

-continued
H27-D1
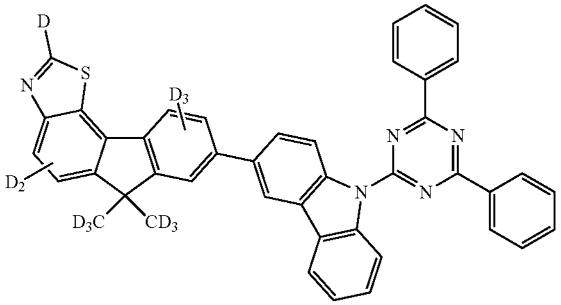
H27-D2
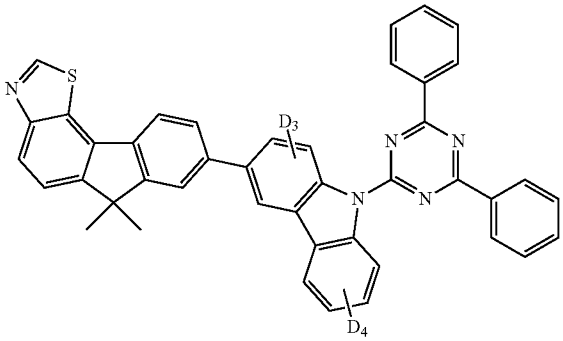
H27-D3
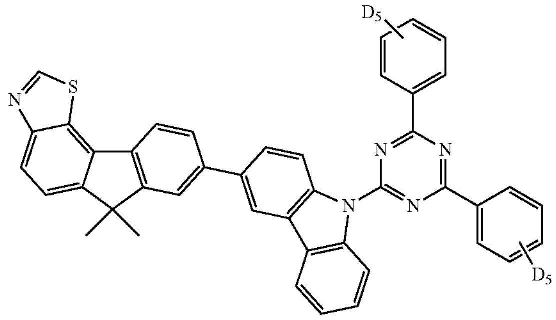
H27-D4
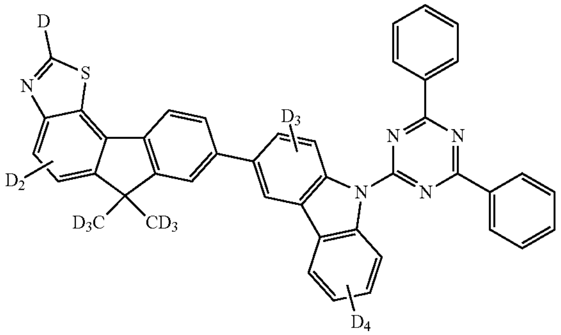
-continued
H27-D5
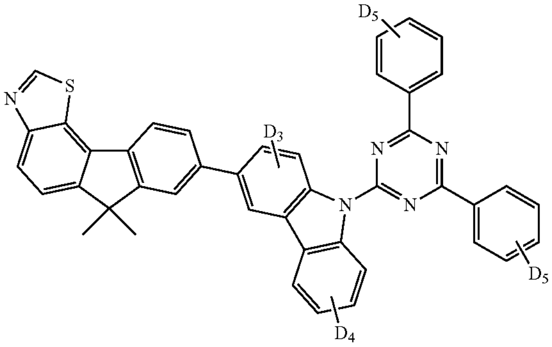
H27-D6
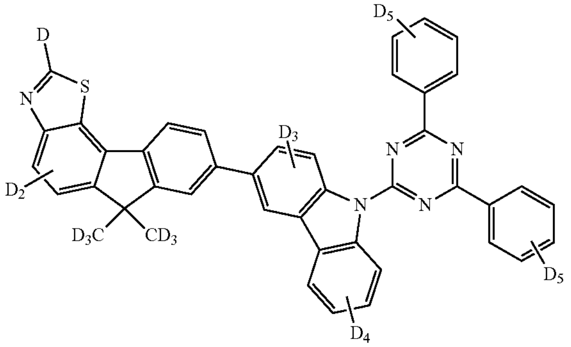
H28-D1
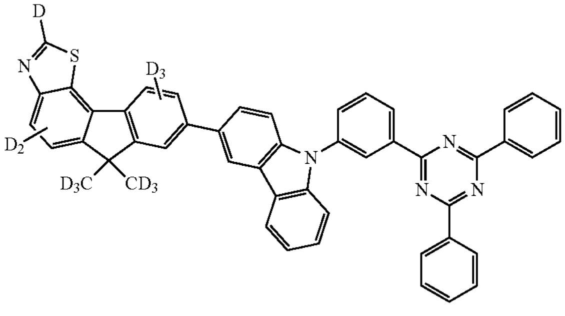
H28-D2
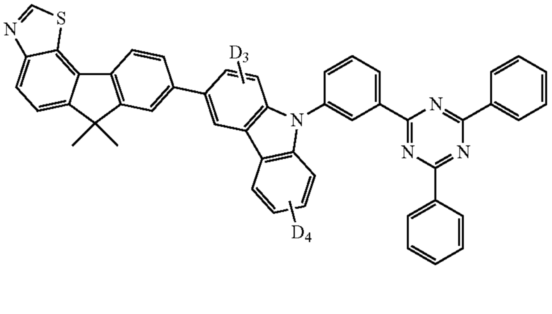

H28-D3
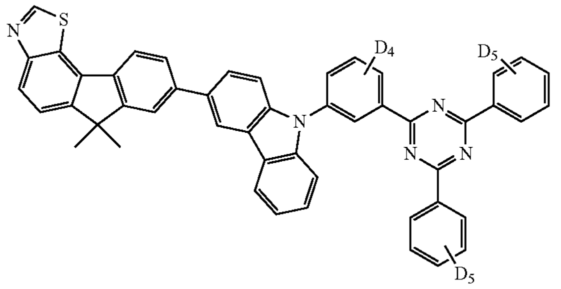
H28-D4
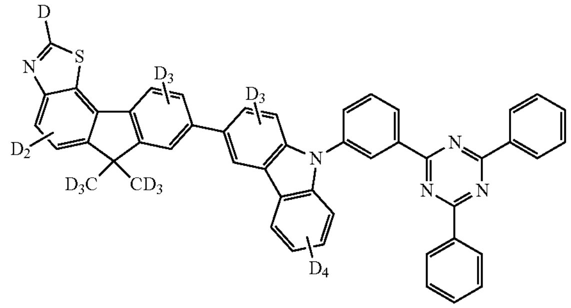
H28-D5
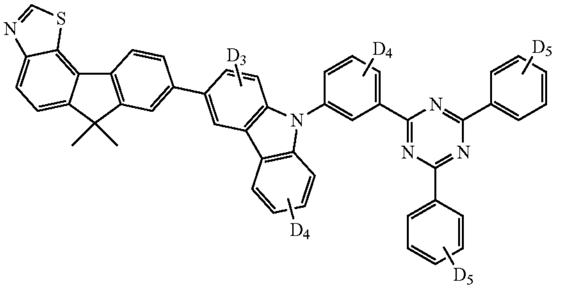
H28-D6
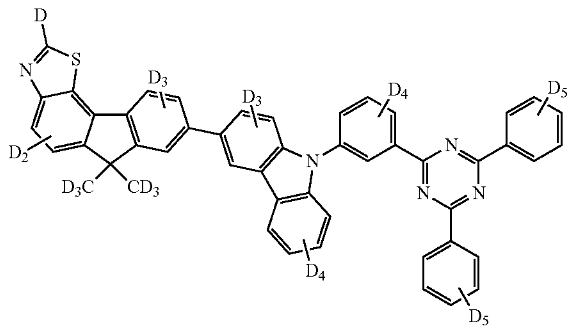
H29-D1
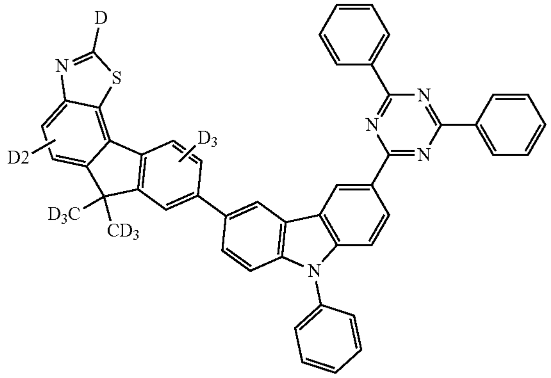
H29-D2
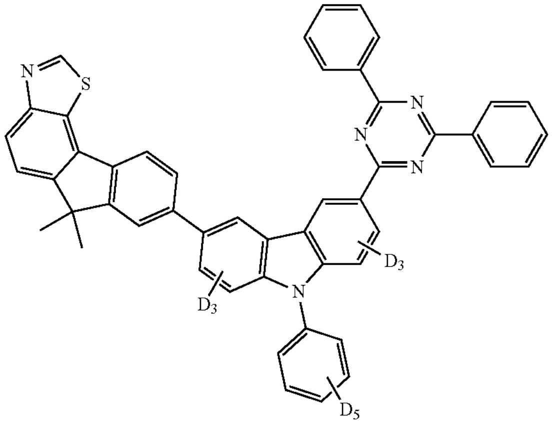
H29-D3
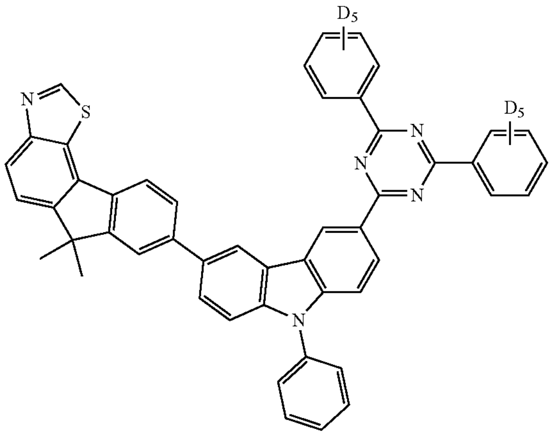

-continued
H29-D4
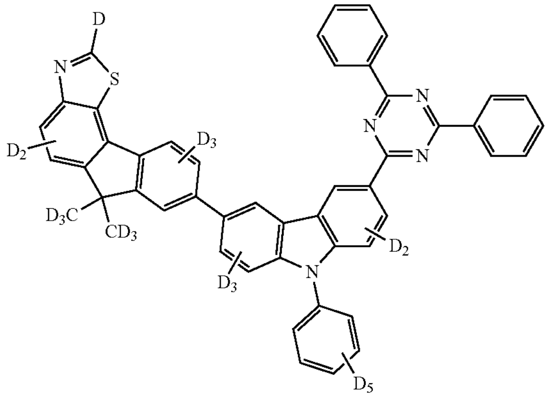
H29-D5
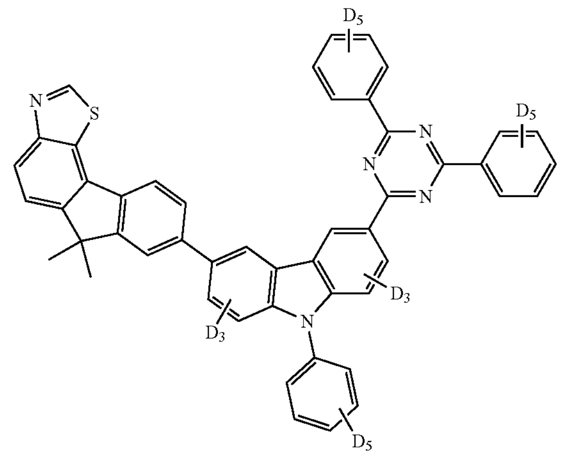
H29-D6
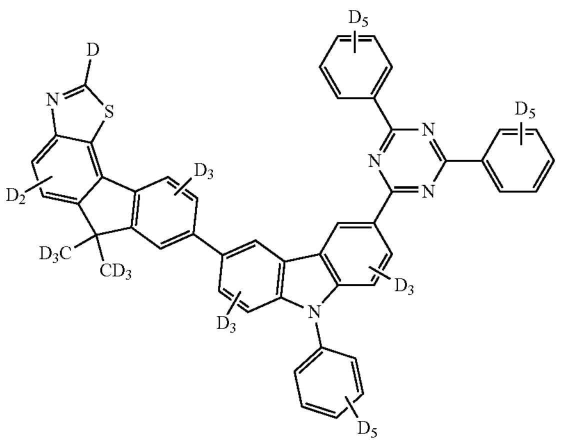
H30-D1
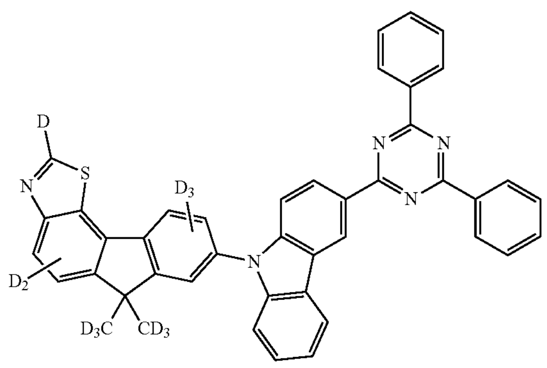
H30-D2
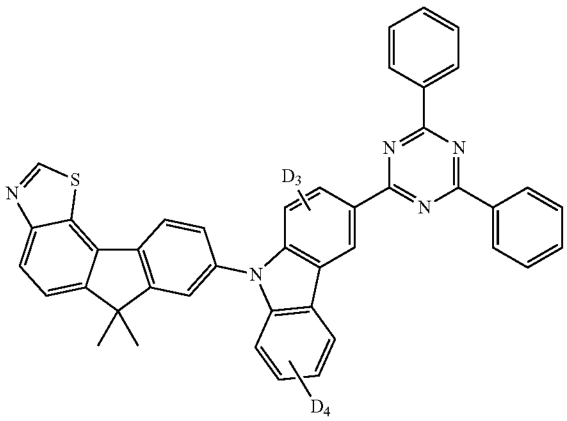
H30-D3
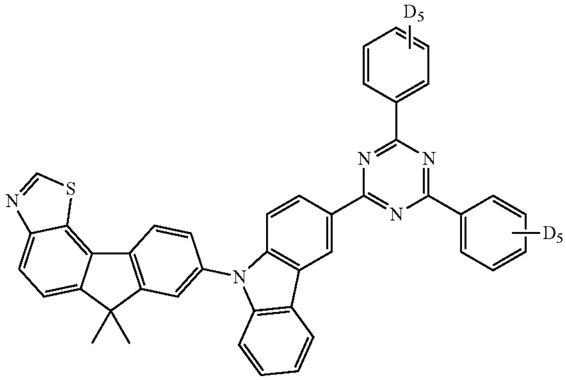
H30-D4
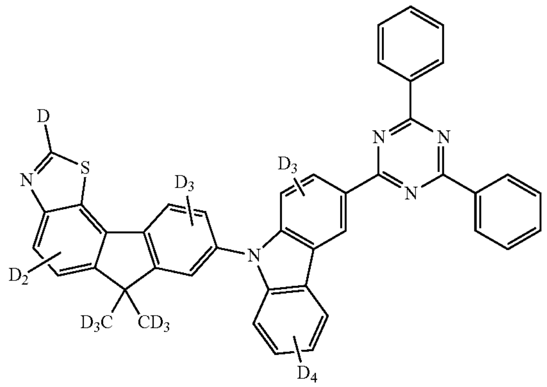

-continued
H30-D5
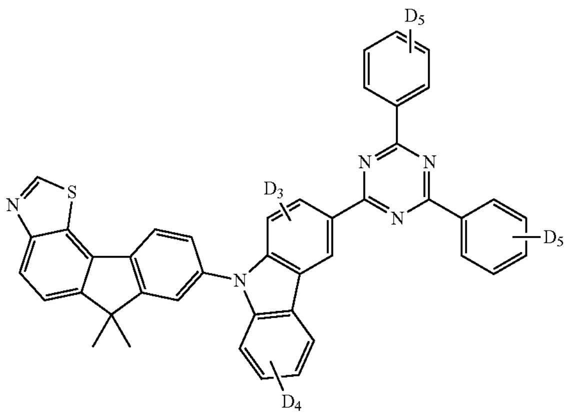
H30-D6
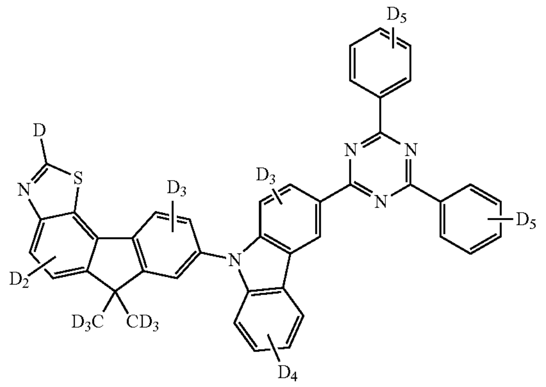
H31-D1
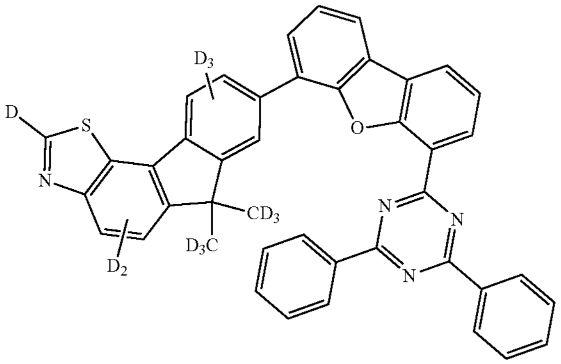
H31-D2
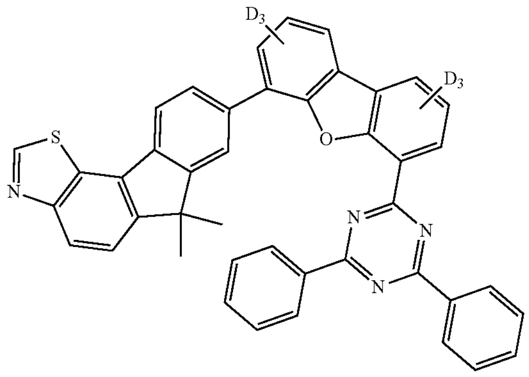
-continued
H31-D3
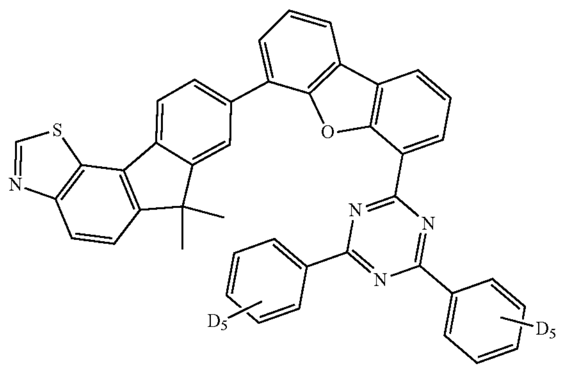
H31-D4
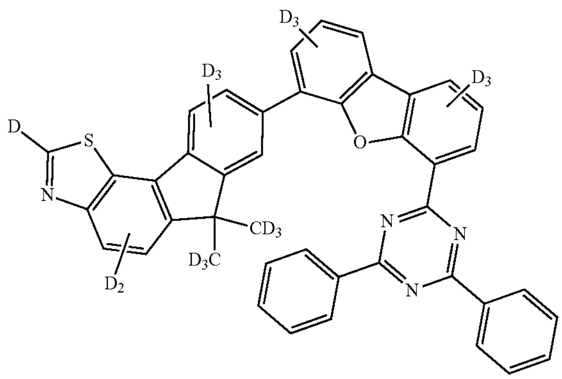
H31-D5
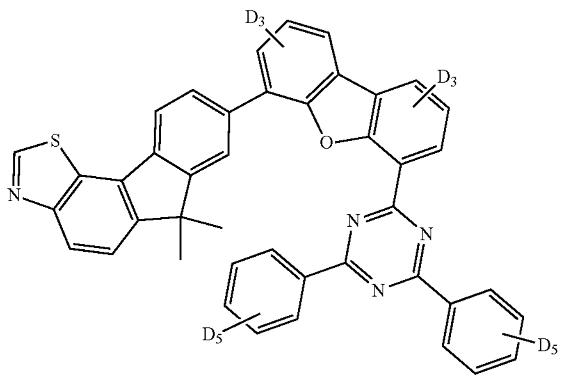
H31-D6
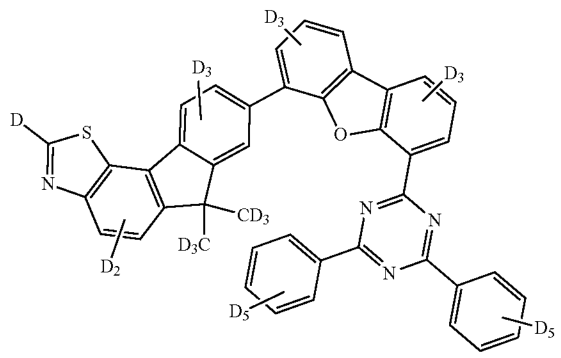

-continued
H32-D1
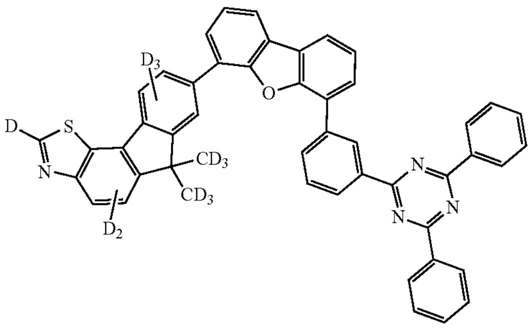
H32-D2
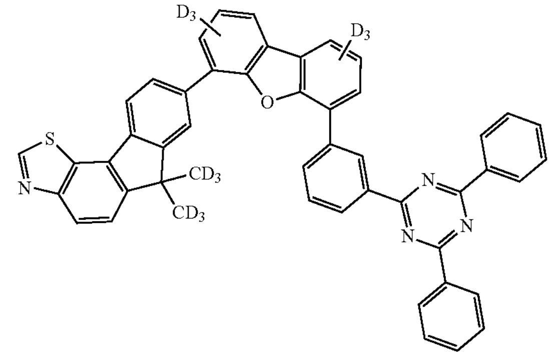
H32-D3
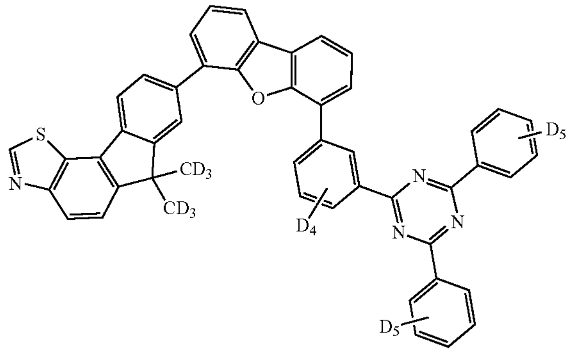
H32-D4
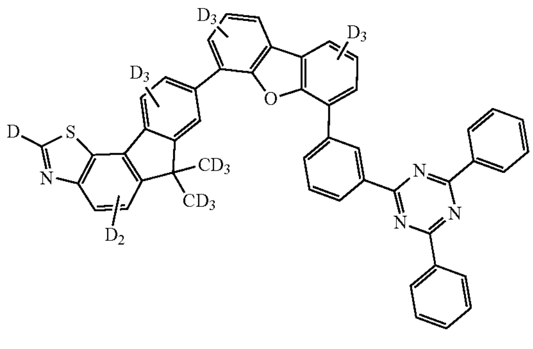
-continued
H32-D5
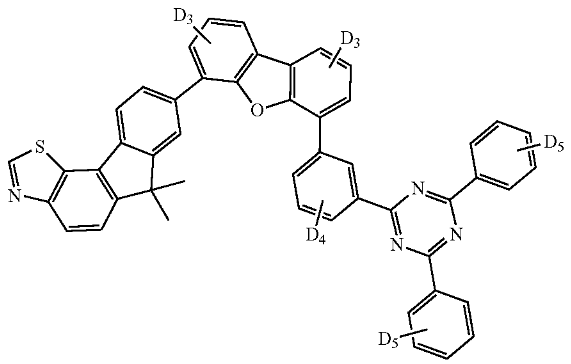
H32-D6
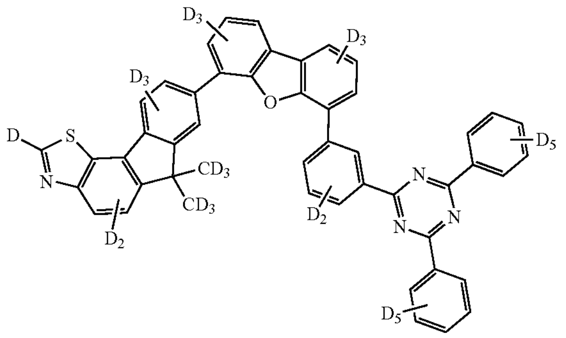
H33-D1
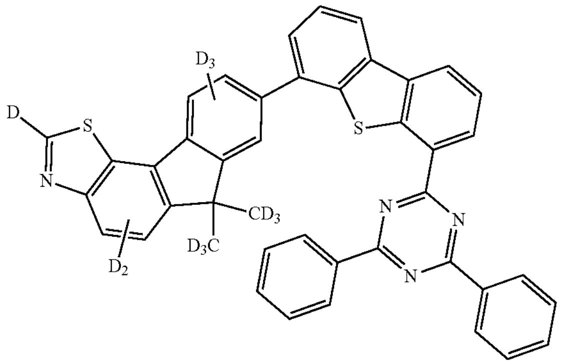
H33-D2
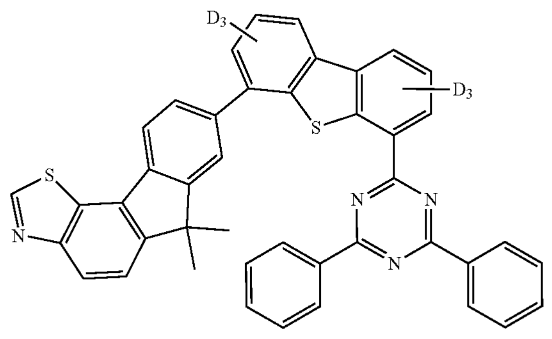

-continued
H33-D3
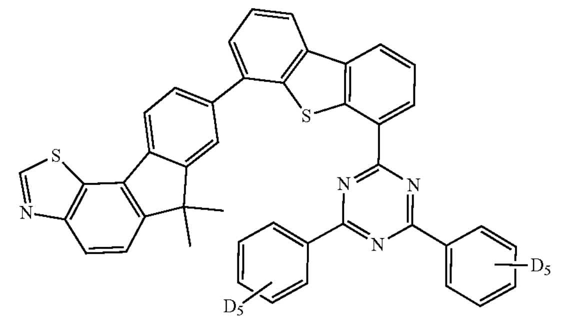
H33-D4
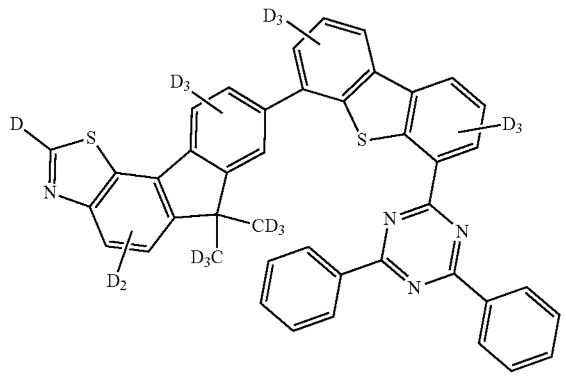
H33-D5
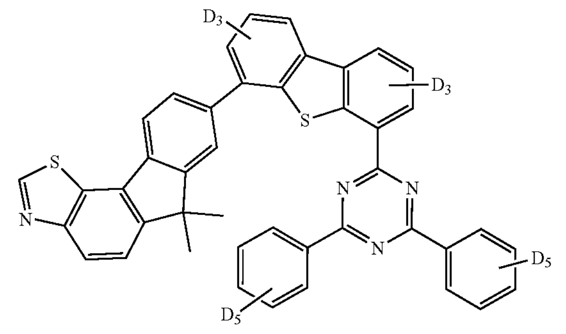
H33-D6
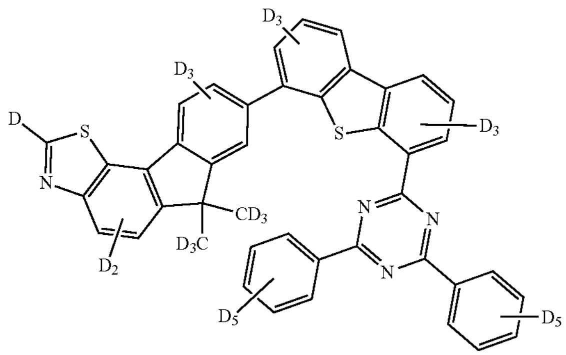
-continued
H34-D1
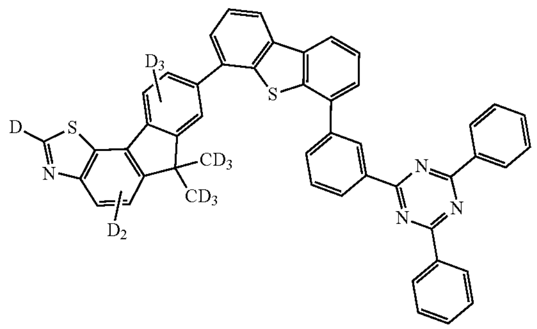
H34-D2
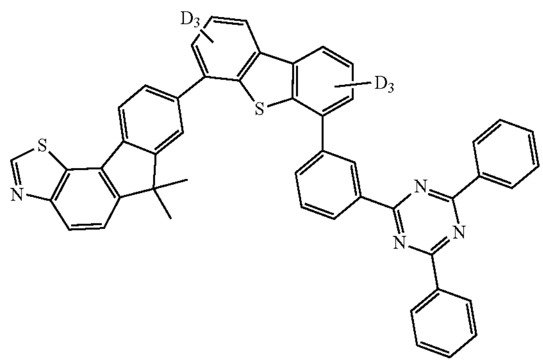
H34-D3
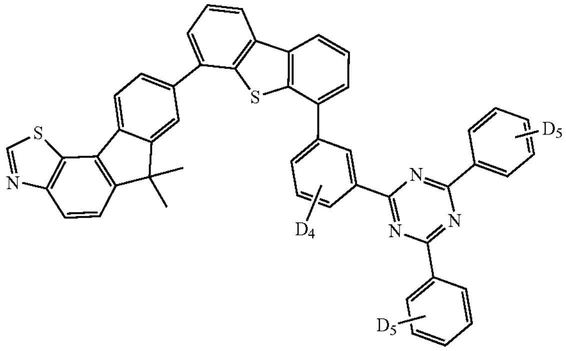
H34-D4
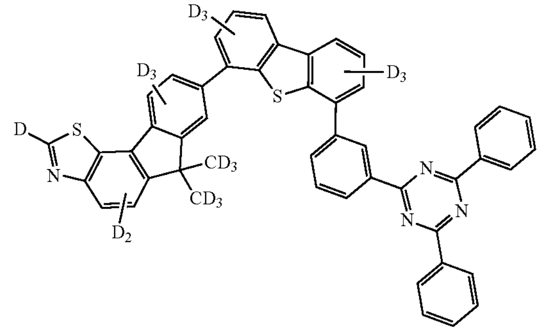

-continued
H34-D5
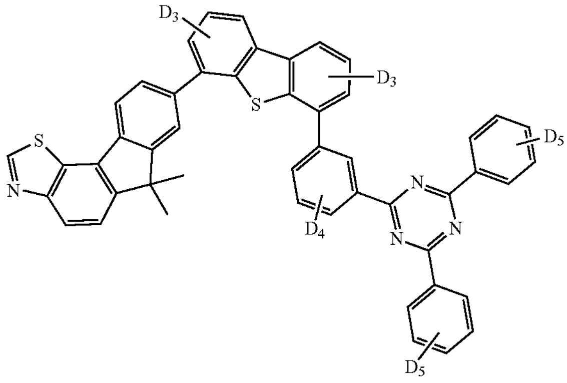
H34-D6
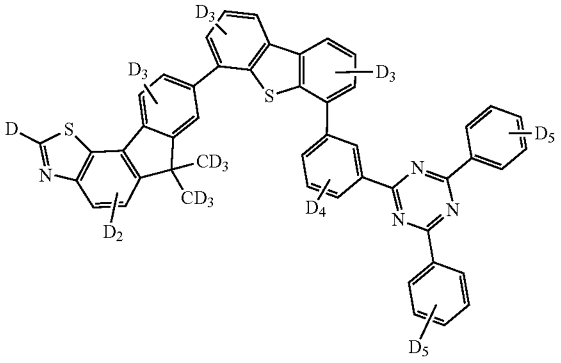
H35-D1
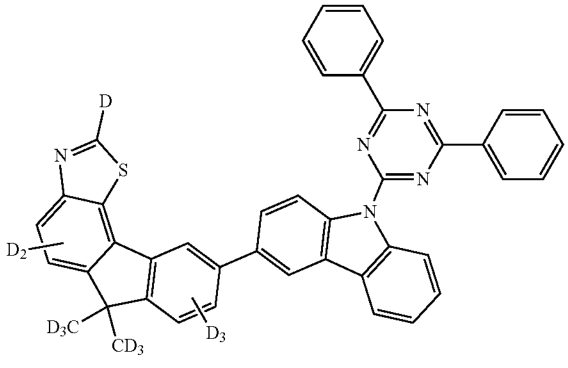
H35-D2
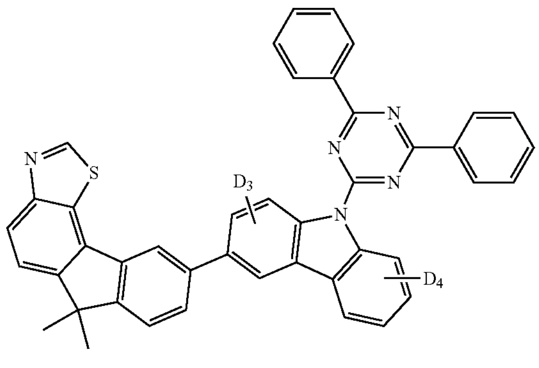
-continued
H35-D3
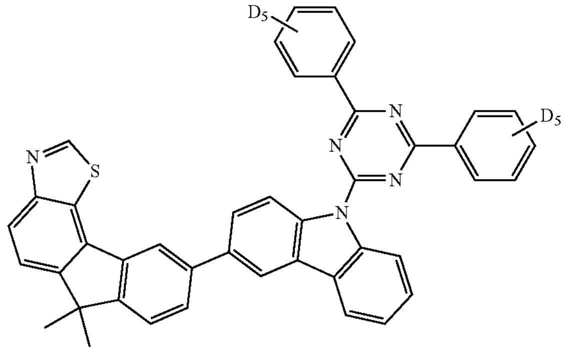
H35-D4
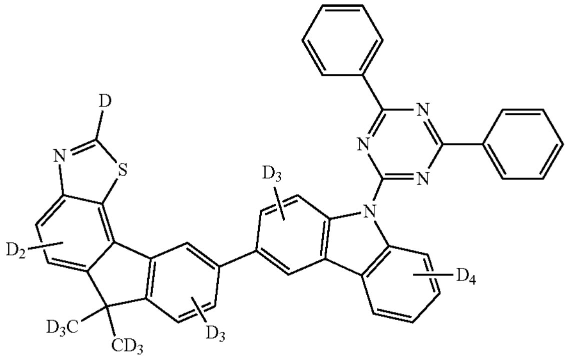
H35-D5
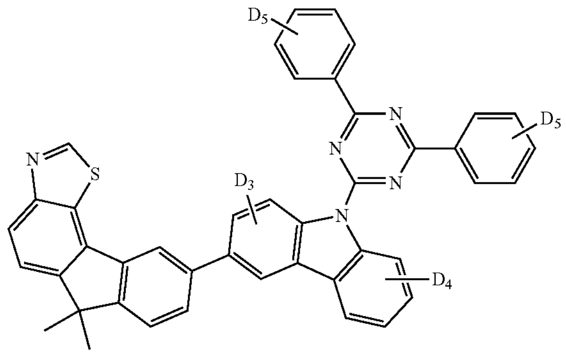
H35-D6
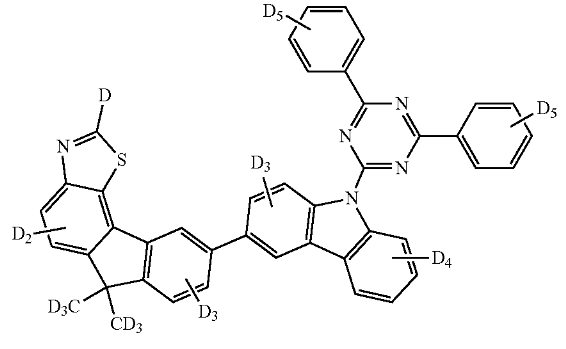

H36-D1
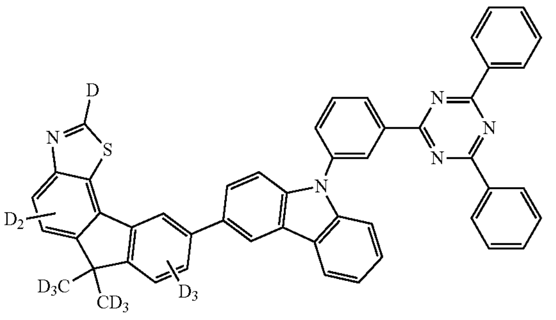
H36-D2
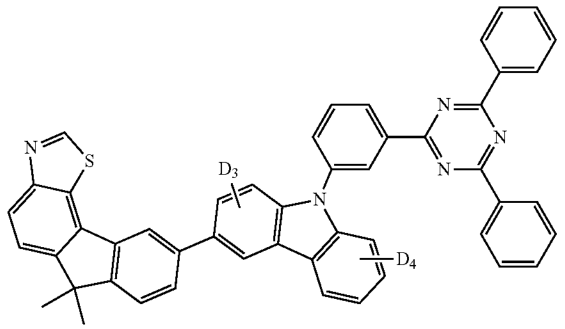
H36-D3
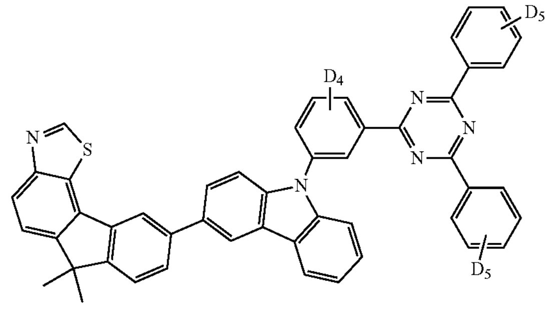
H36-D4
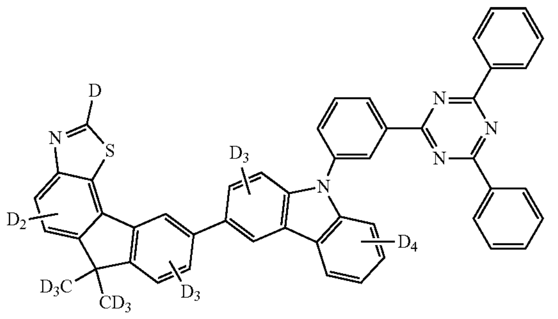
H36-D5
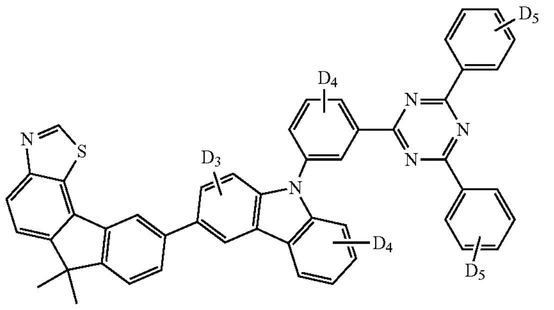
H36-D6
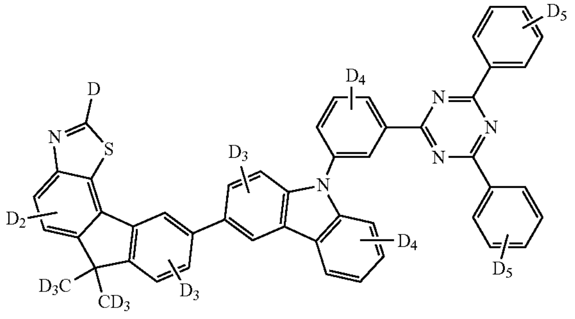
H37-D1
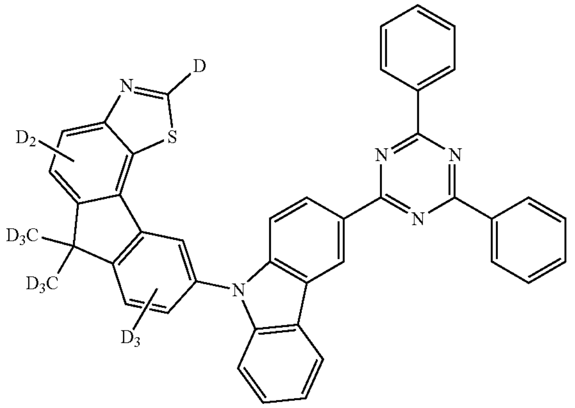
H37-D2
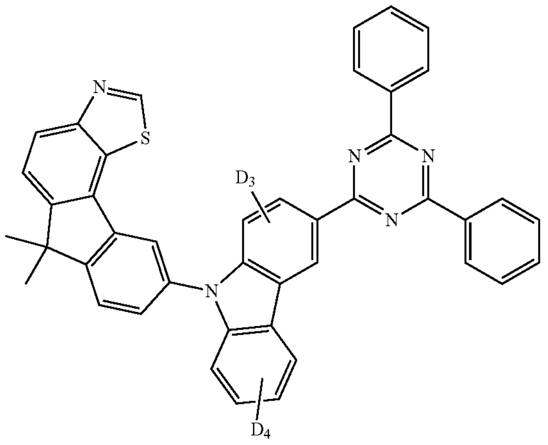

-continued
H37-D3
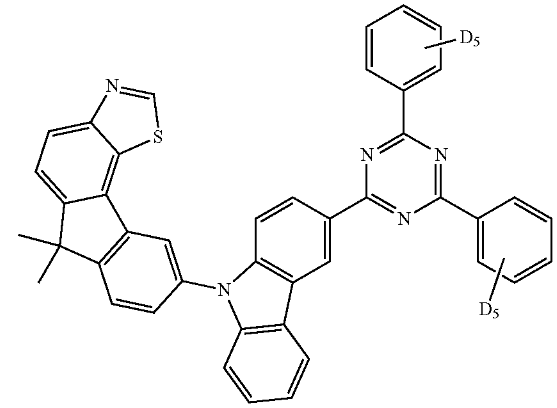
H37-D4
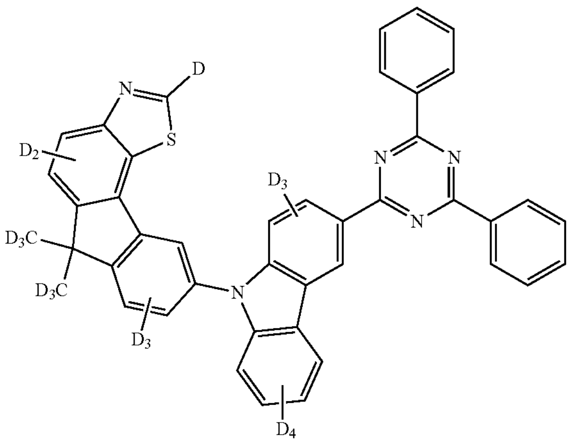
H37-D5
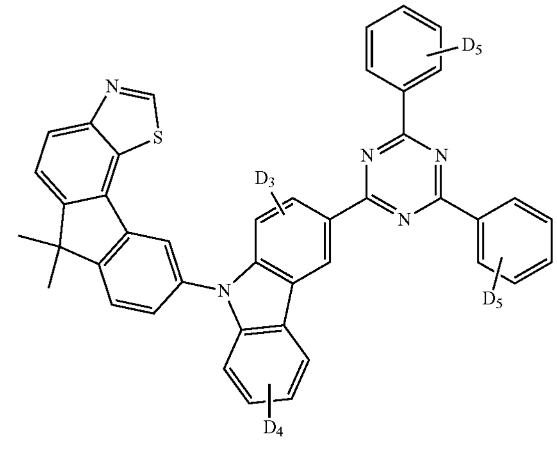
-continued
H37-D6
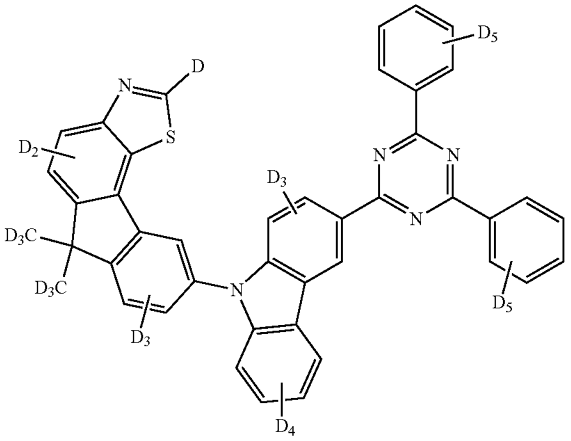
H38-D1
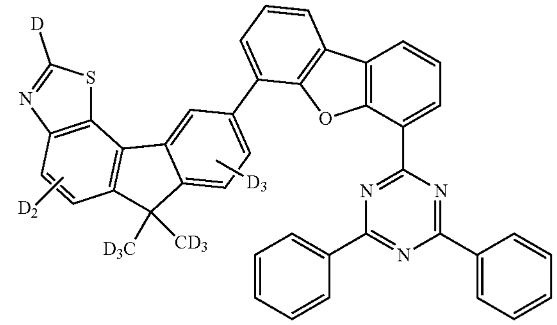
H38-D2
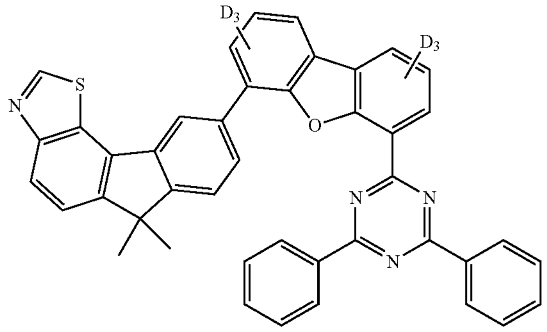
H38-D3
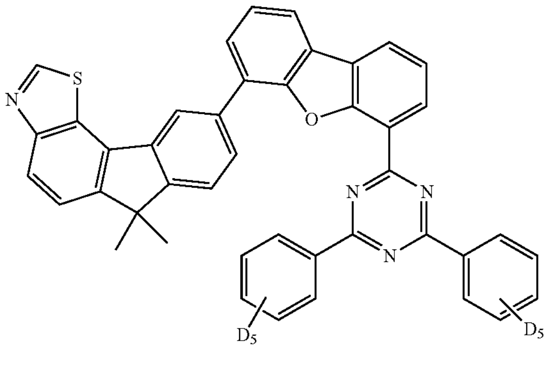

H38-D4
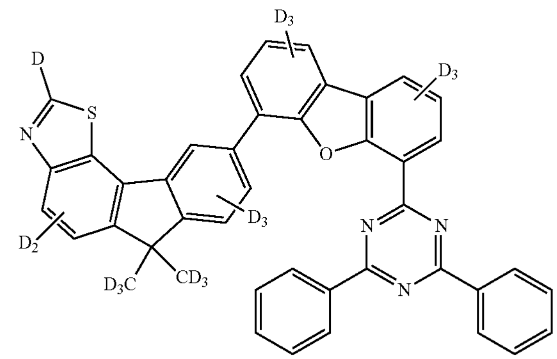
H38-D5
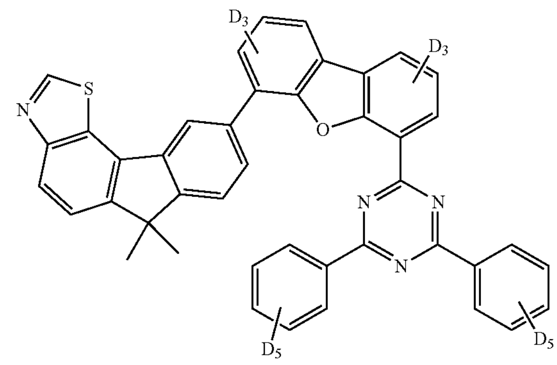
H38-D6
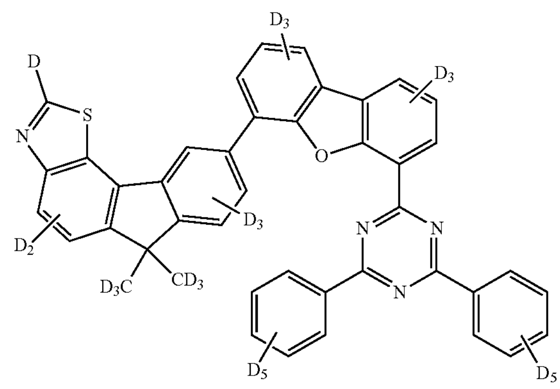
H39-D1
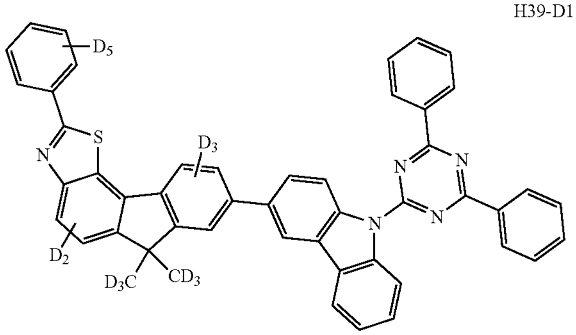
H39-D2
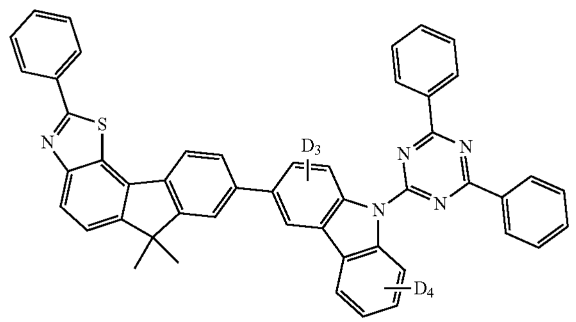
H39-D3
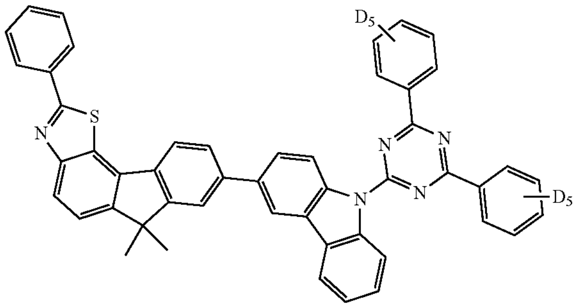
H39-D4
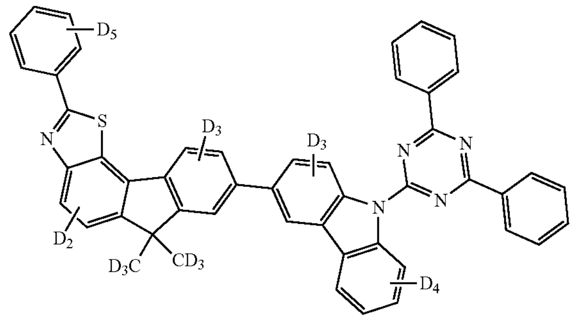
H39-D5
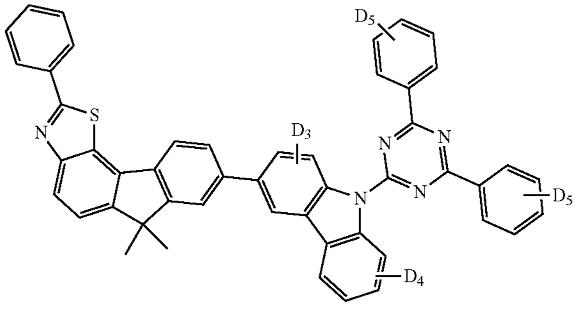

-continued
H39-D6
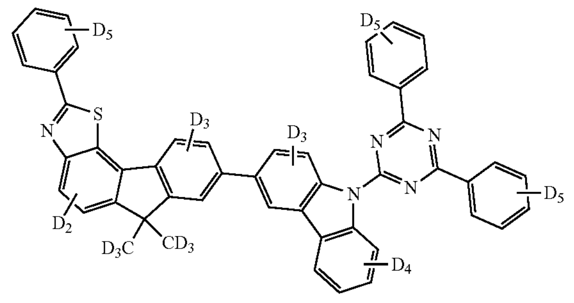
H40-D1
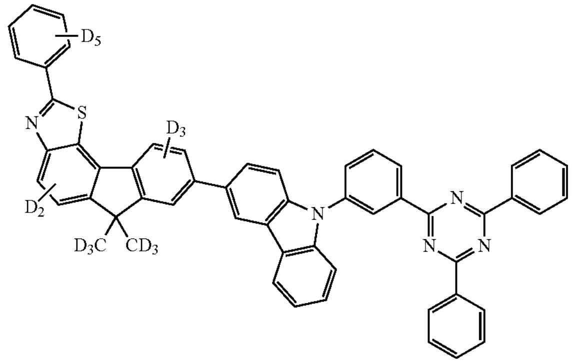
H40-D2
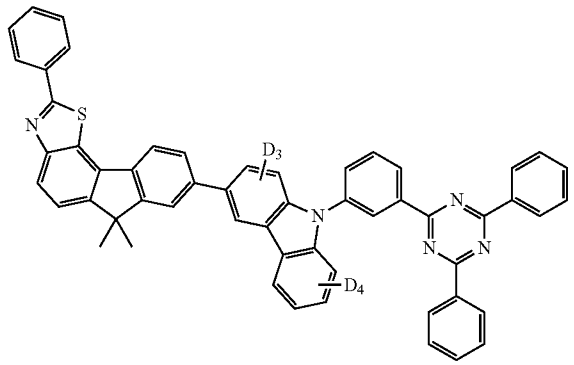
H40-D3
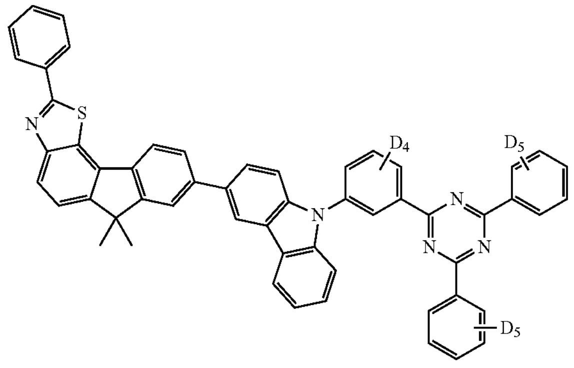
-continued
H40-D4
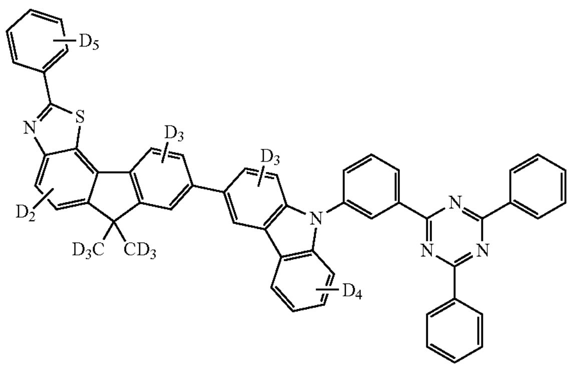
H40-D5
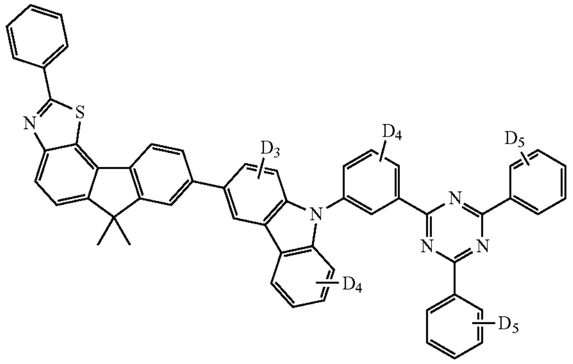
H40-D6
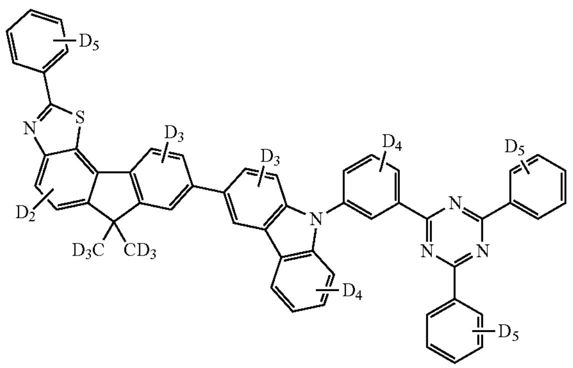
H41-D1
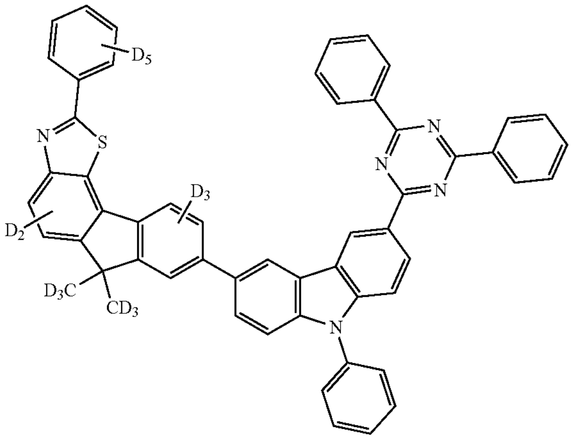

-continued
H41-D2
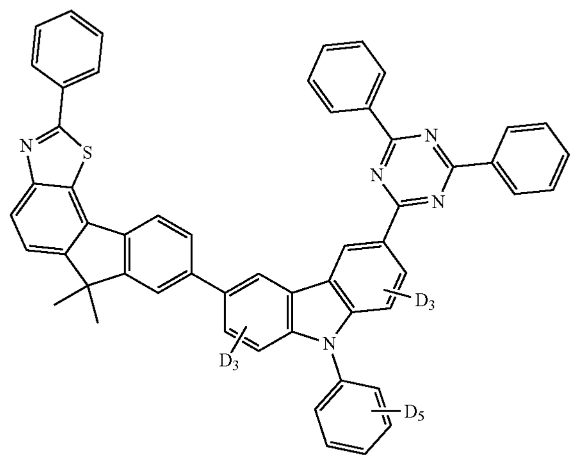
H41-D3
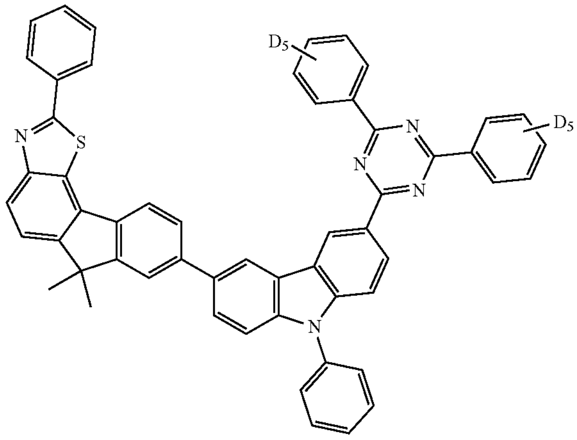
H41-D4
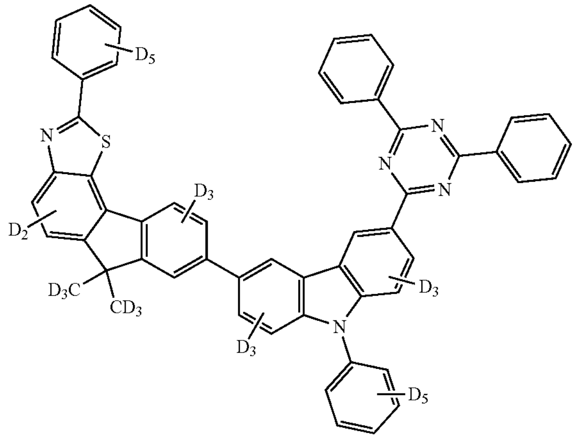
-continued
H41-D5
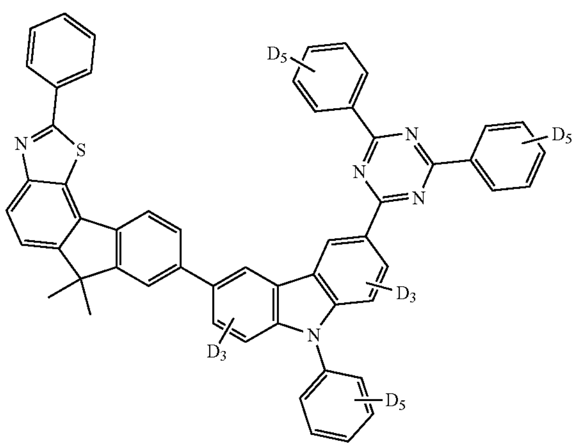
H41-D6
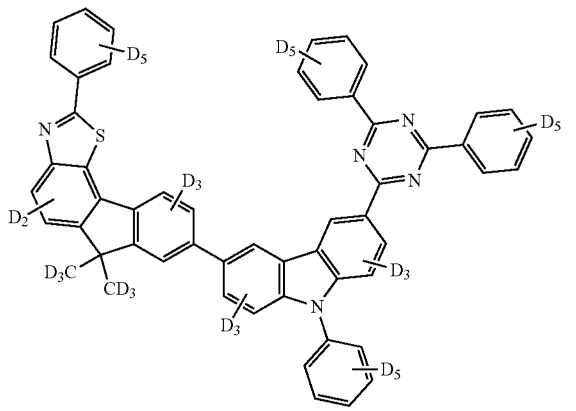
H42-D1
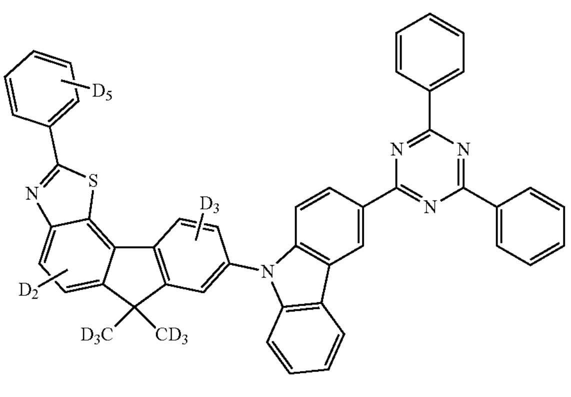

H42-D2
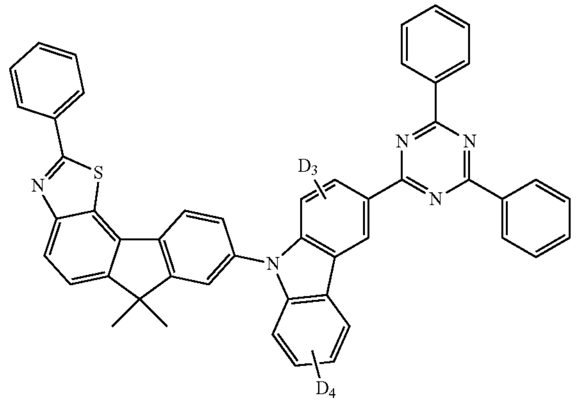
H42-D3
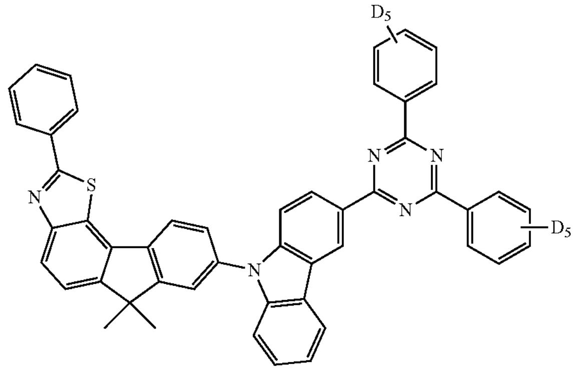
H42-D4
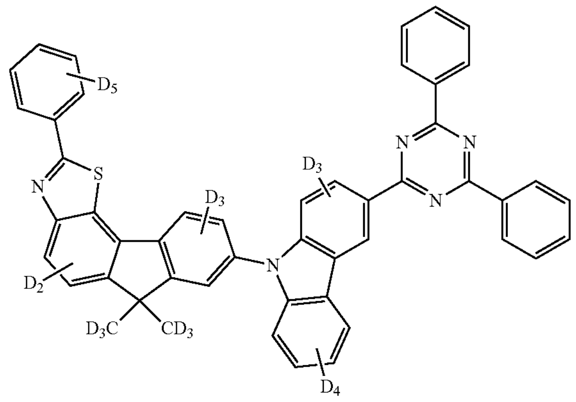
H42-D5
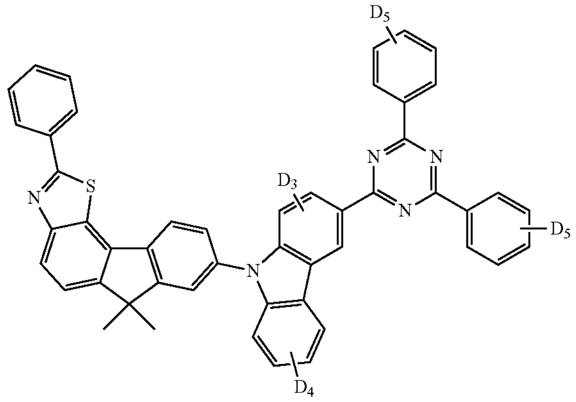
H42-D6
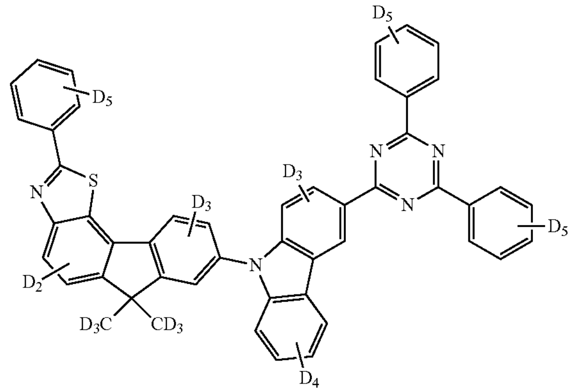
H45-D1
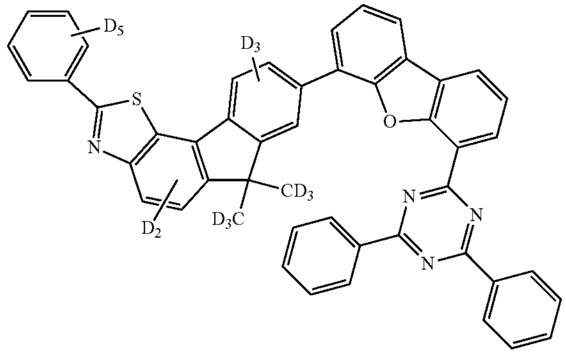
H45-D2
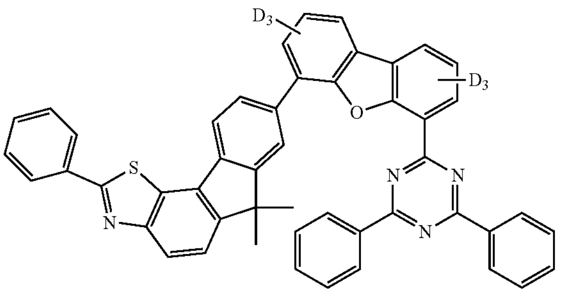

-continued
H45-D3
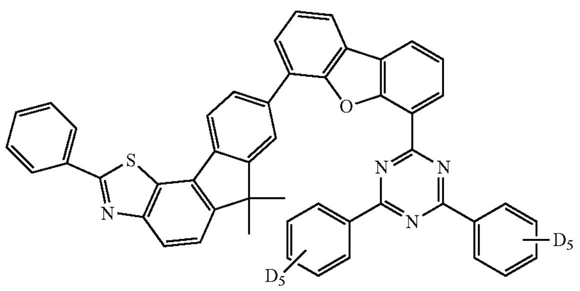
H45-D4
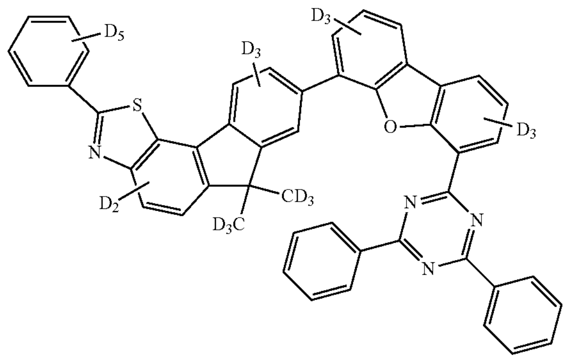
-continued
H45-D5
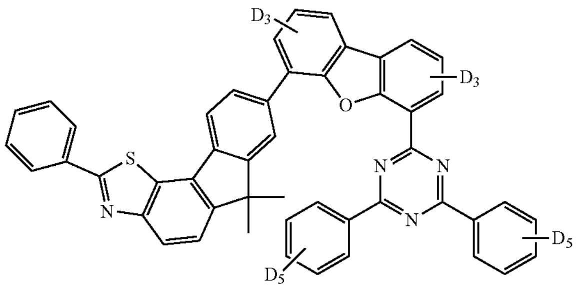
H45-D6
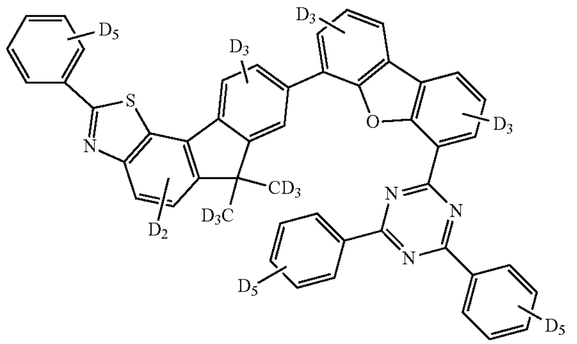
H46-D1
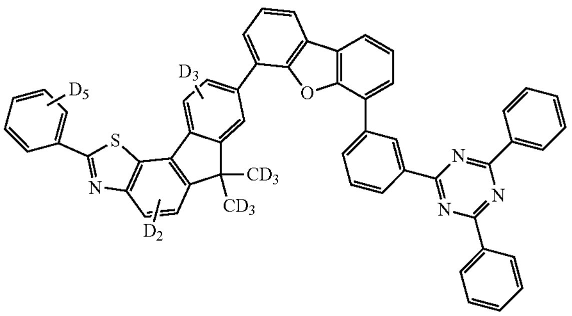
H46-D2
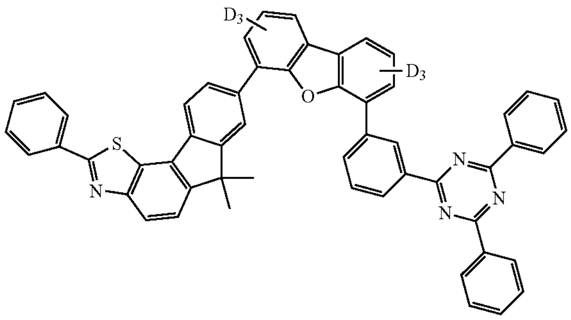
H46-D3
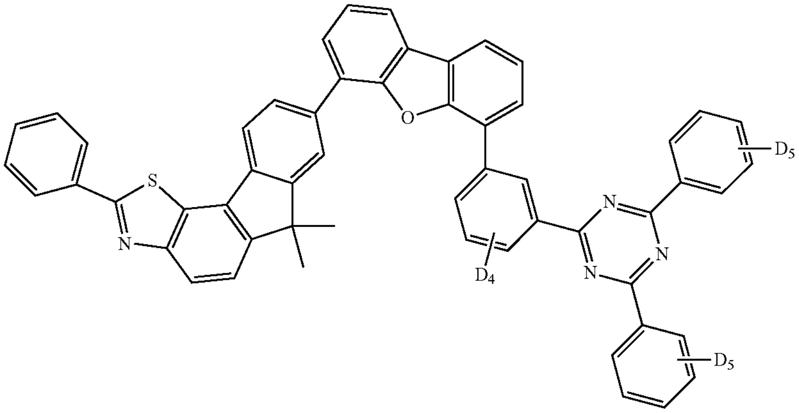

-continued
H46-D4
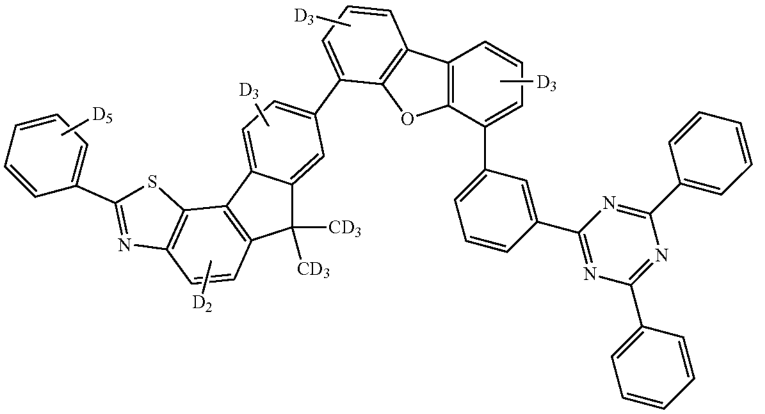
H46-D5
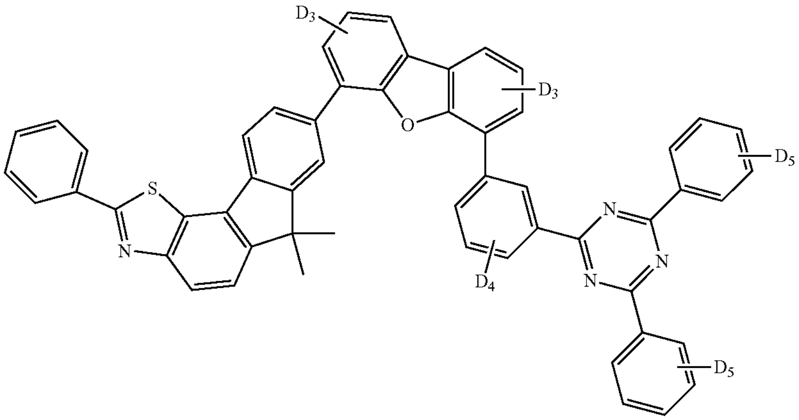
H46-D6
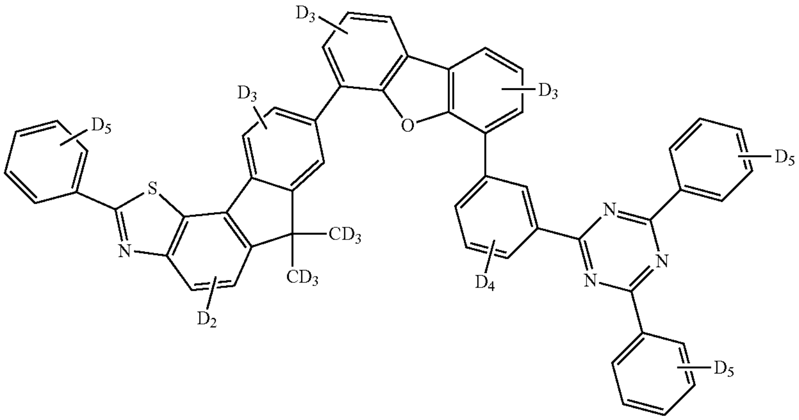
H47-D1
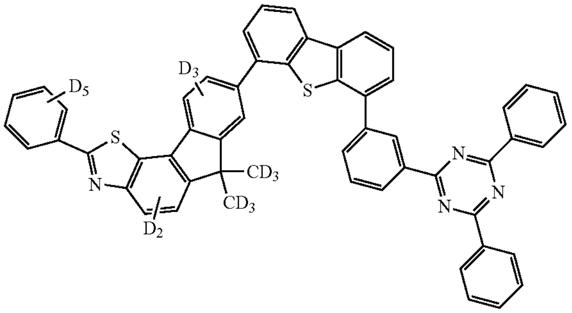
H47-D2
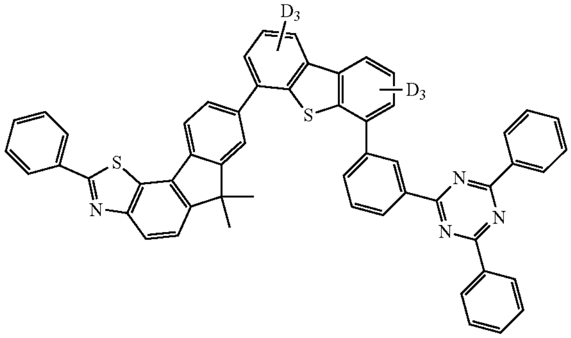

-continued
H47-D3
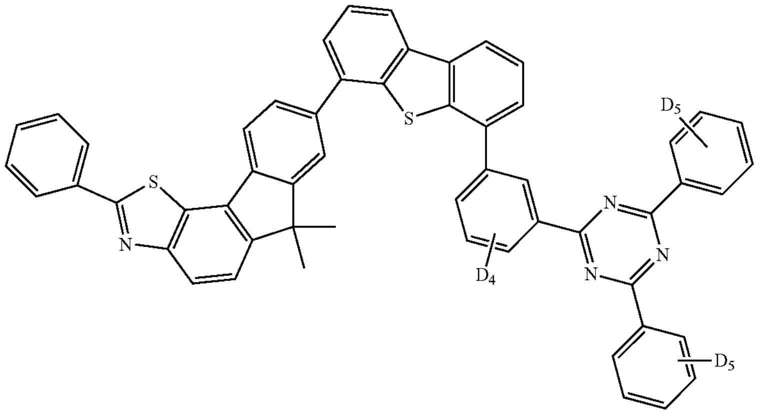
H47-D4
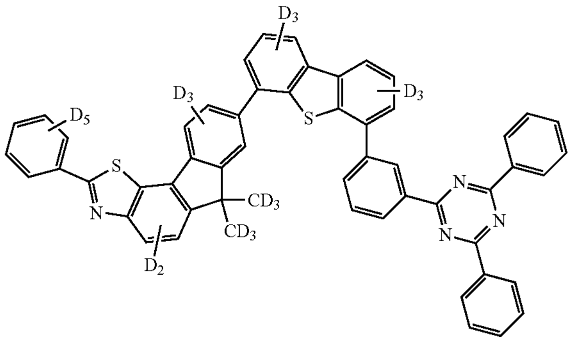
H47-D5
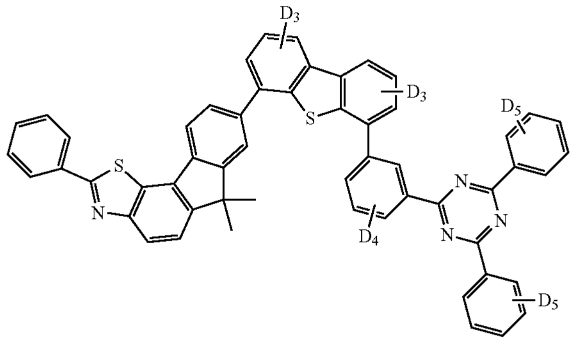
H47-D6
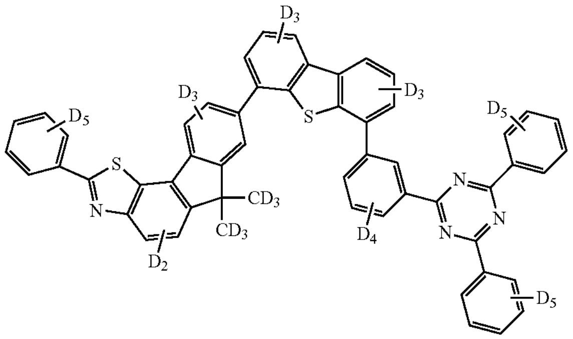
H48-D1
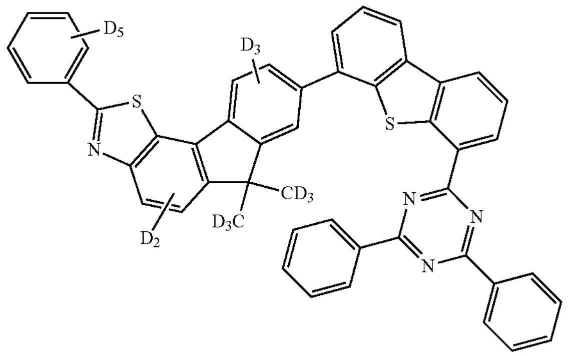
H48-D2
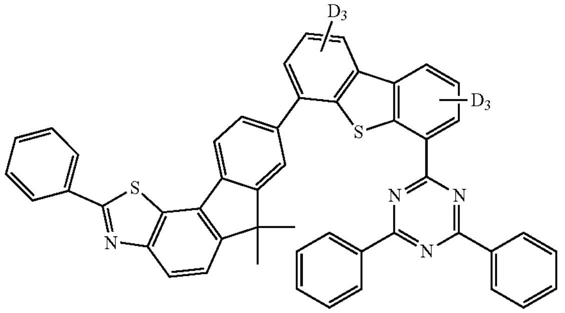
H48-D3
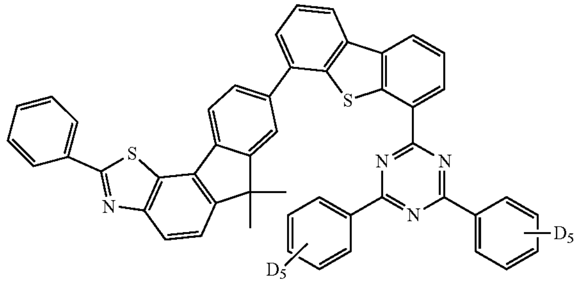

-continued
H48-D4
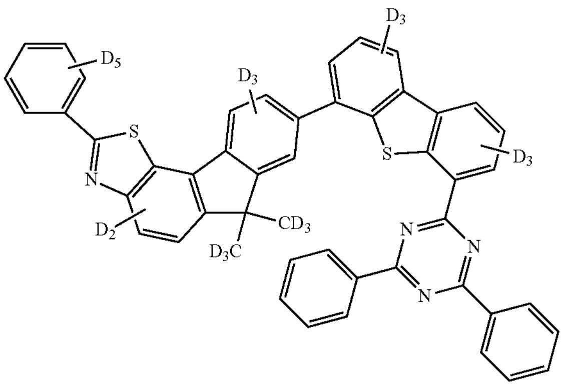
H48-D5
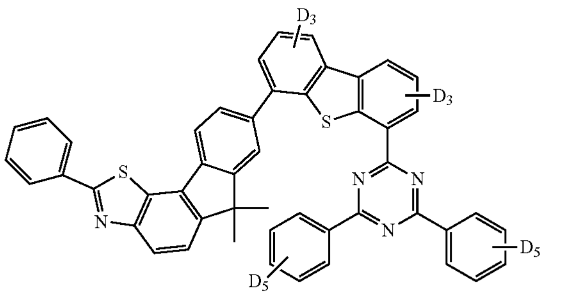
H48-D6
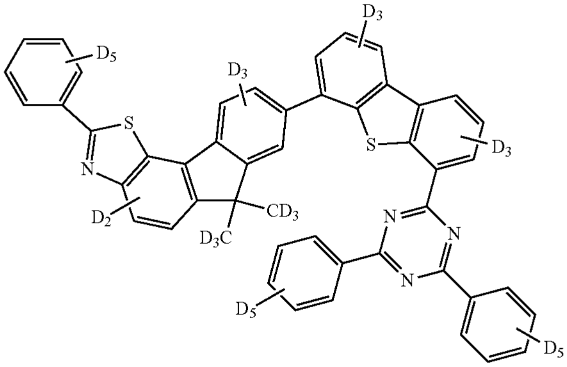
H48-D6
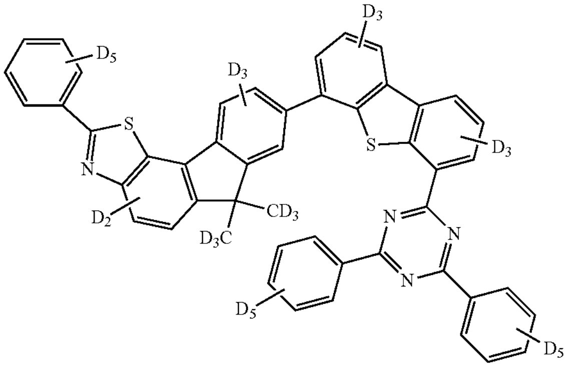
H49-D1
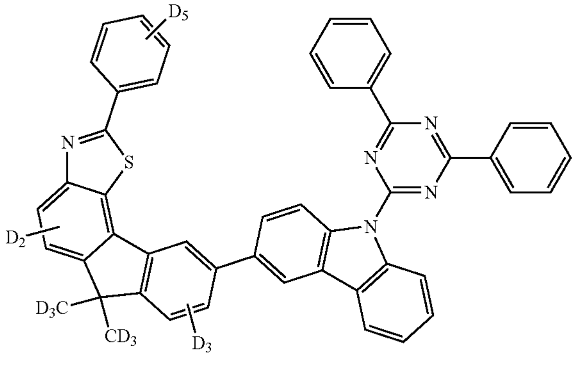
H49-D2
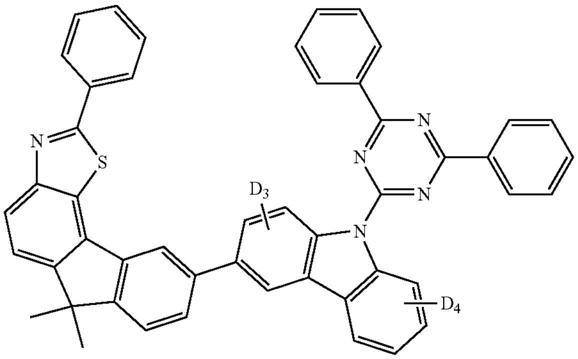
H49-D3
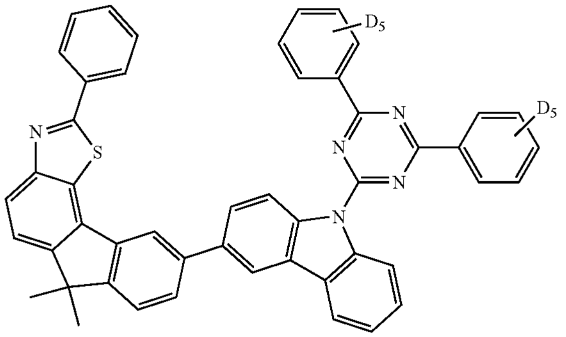

-continued
H49-D4
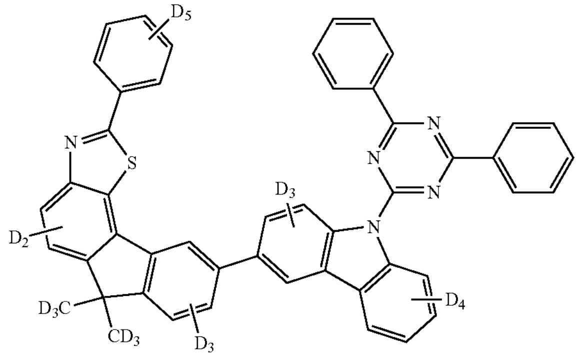
H49-D5
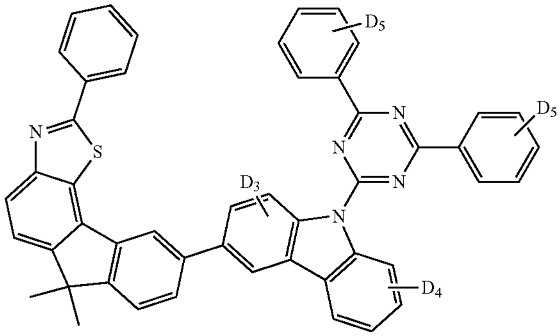
H49-D6
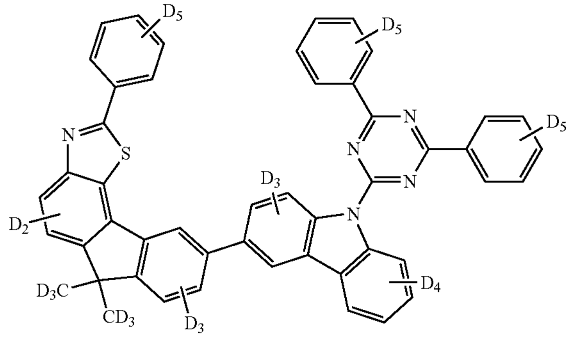
H50-D1
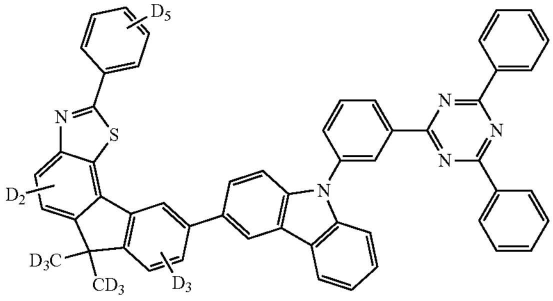
H50-D2
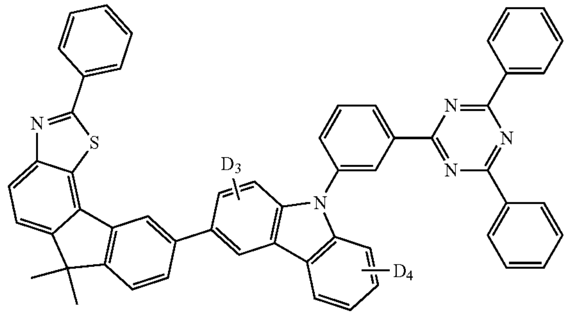
H50-D3
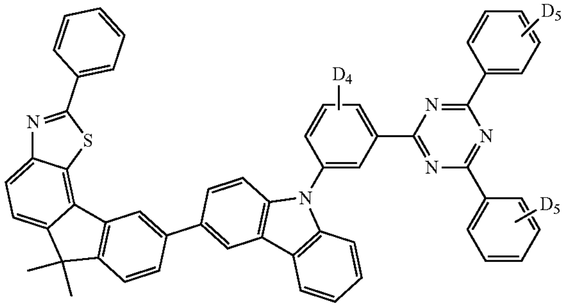
H50-D4
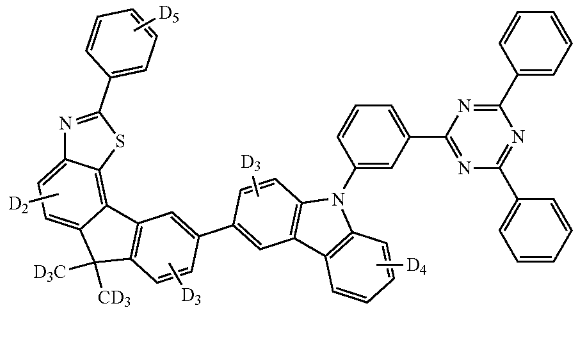
H50-D5
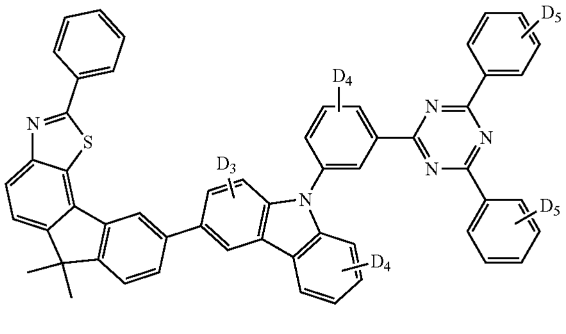

-continued
H50-D6
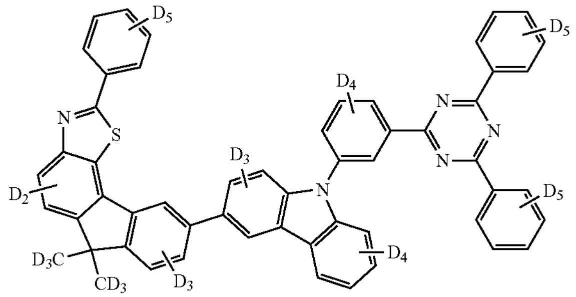
H51-D1
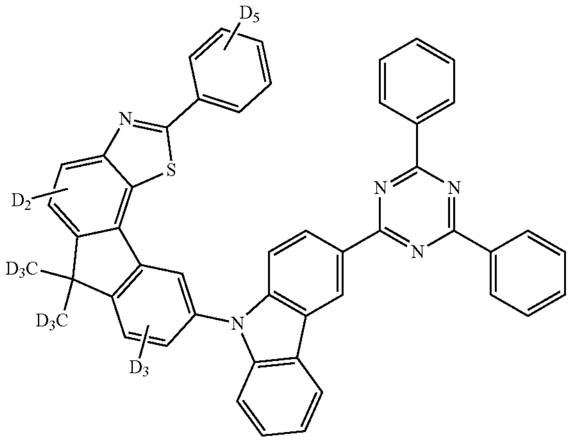
H51-D2
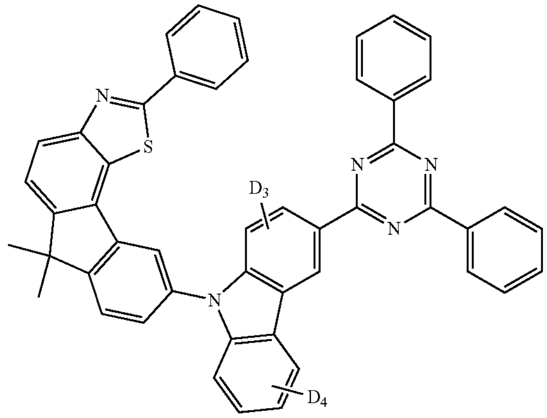
H51-D3
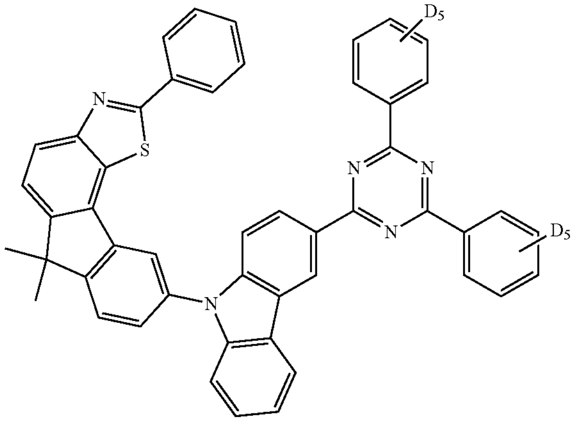
H51-D4
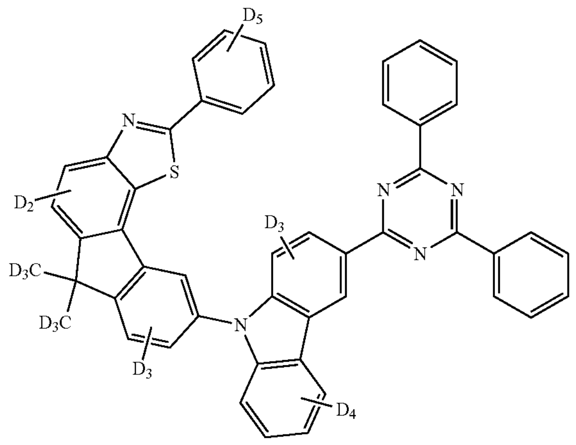
H51-D5
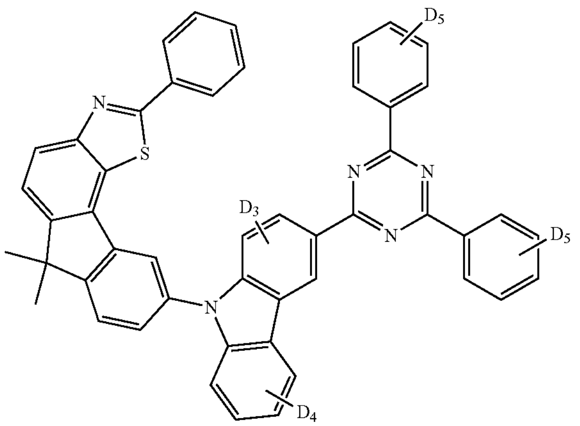

-continued
H51-D6
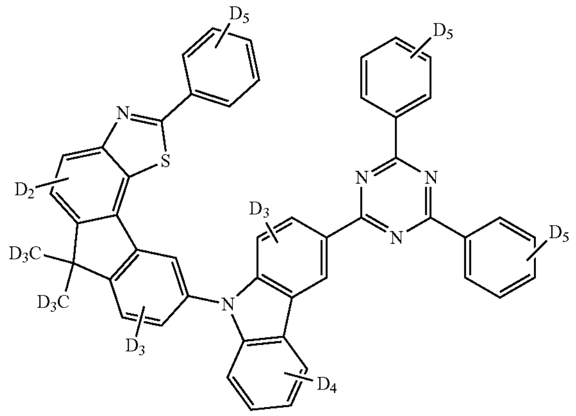
H52-D1
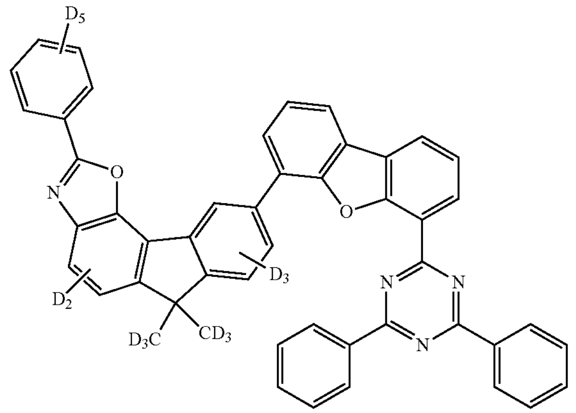
H52-D2
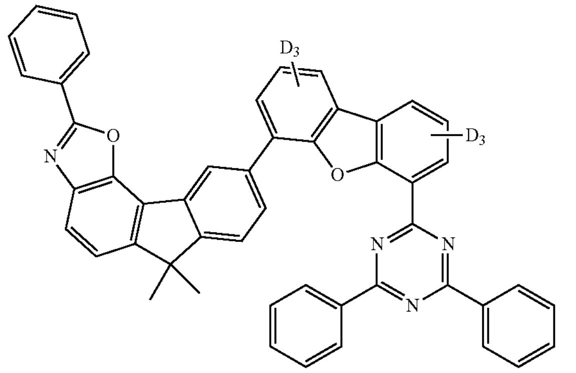
H52-D3
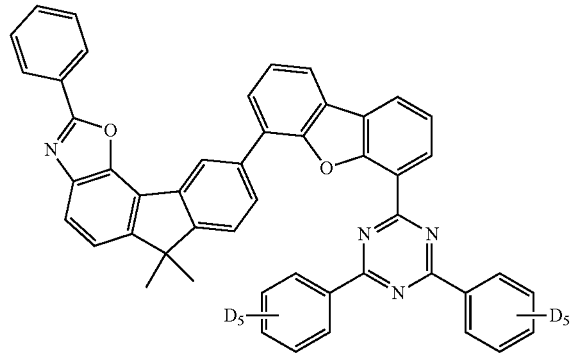
H52-D4
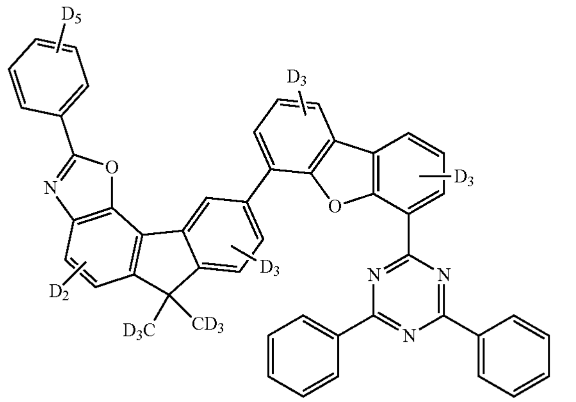
H52-D5
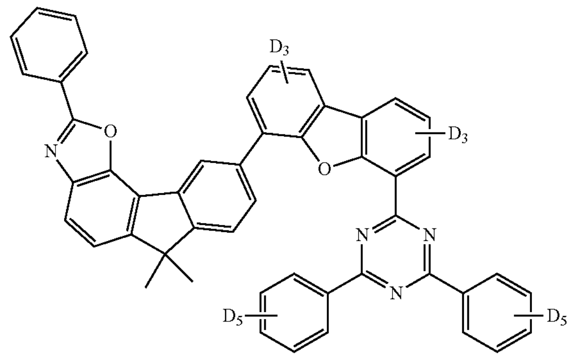

-continued

H52-D6

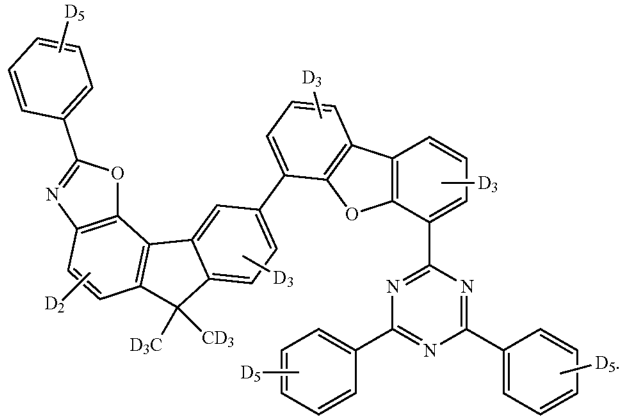

7. An organic light emitting device, comprising:
a substrate; and
an organic light emitting diode positioned on the substrate and including a first electrode;
a second electrode facing the first electrode; and a first emitting part between the first and second electrodes, the first emitting part including a first green emitting material layer,
wherein the first green emitting material layer includes a first compound that is an organic compound represented by Formula 1:

[Formula 1]

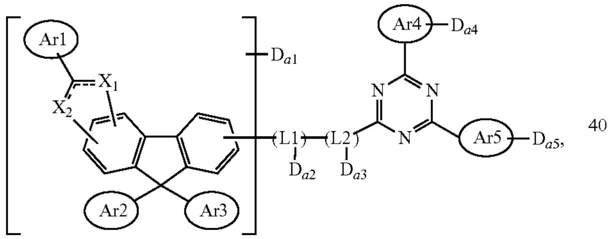

wherein L1 is a substituted or unsubstituted C5 to C30 heteroarylene group, and L2 is selected from the group consisting of a single bond, and a substituted or unsubstituted C6 to C30 arylene group,
wherein one of X1 and X2 is a nitrogen atom, and the other one of X1 and X2 is O or S,
wherein each of Ar1, Ar2, and Ar3 is independently selected from the group consisting of hydrogen, deuterium, a substituted or unsubstituted C1 to C10 alkyl group, a substituted or unsubstituted C6 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group,
wherein each of Ar4 and Ar5 is independently selected from the group consisting of a substituted or unsubstituted C6 to C30 aryl group, and a substituted or unsubstituted C3 to C30 heteroaryl group, and
wherein, a1 is an integer of 0 to 95, each of a2, a3, a4, and a5 is independently an integer of 0 to 30, and at least one of a1 to a5 is a positive integer.

8. The organic light emitting device according to claim 7, wherein the first green emitting material layer further includes a second compound represented by Formula 3:

[Formula 3]

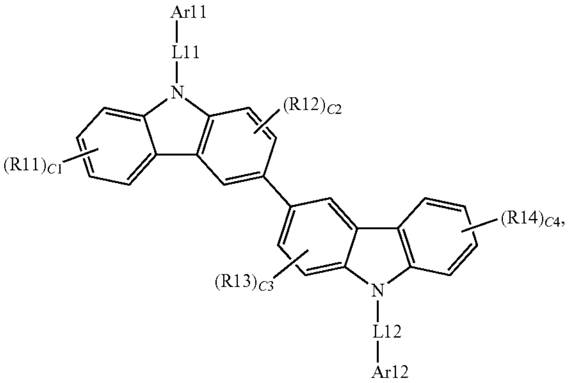

wherein each of R11, R12, R13, and R14 is independently selected from the group consisting of deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group,
wherein each of c1 and c4 is independently an integer of 0 to 4, and each of c2 and c3 is independently an integer of 0 to 3,
wherein each of L11 and L12 is independently selected from the group consisting of a single bond, a substituted or unsubstituted C6 to C30 arylene group, and a substituted or unsubstituted C3 to C30 heteroarylene group, and wherein each of Ar11 and Ar12 is independently selected from the group consisting of a single bond, a substituted or unsubstituted C6 to C30 aryl group, and a substituted or unsubstituted C3 to C30 heteroaryl group.
9. The organic light emitting device according to claim 8, wherein the second compound is one of the compounds in Formula 4:
[Formula 4]
BCz-1
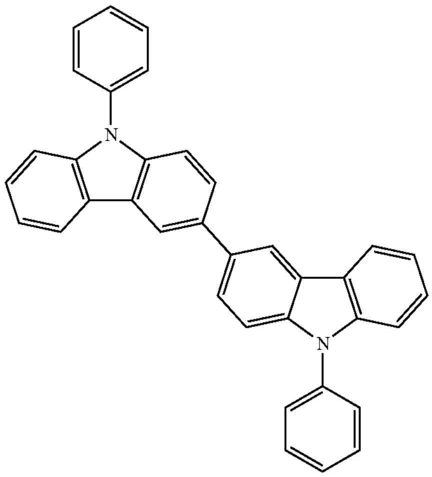
BCz-2
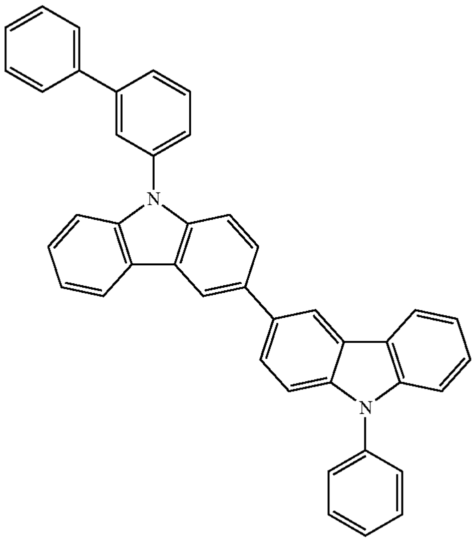
-continued
BCz-3
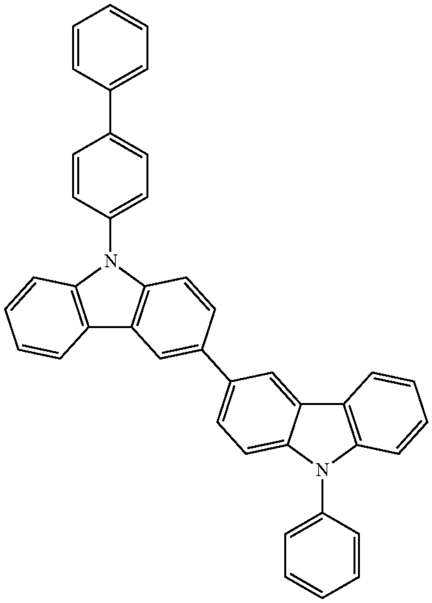
BCz-4
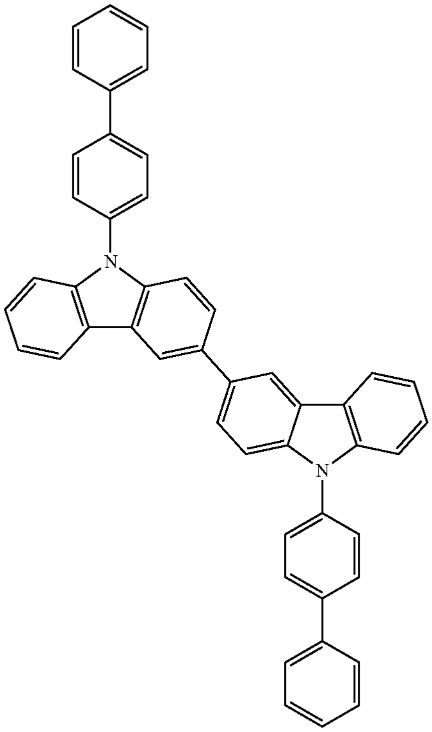

-continued
BCz-5
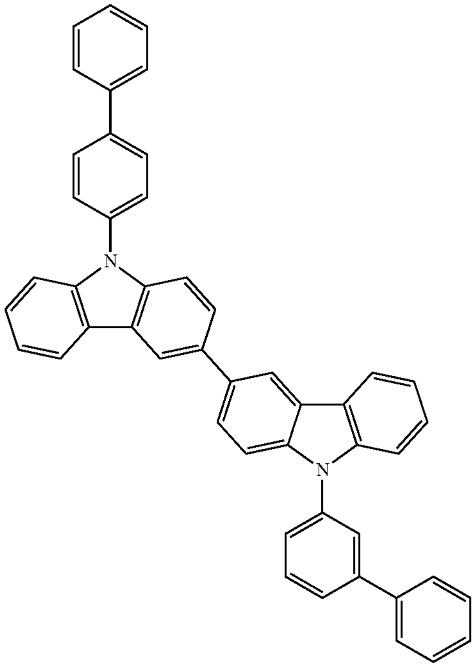
BCz-6
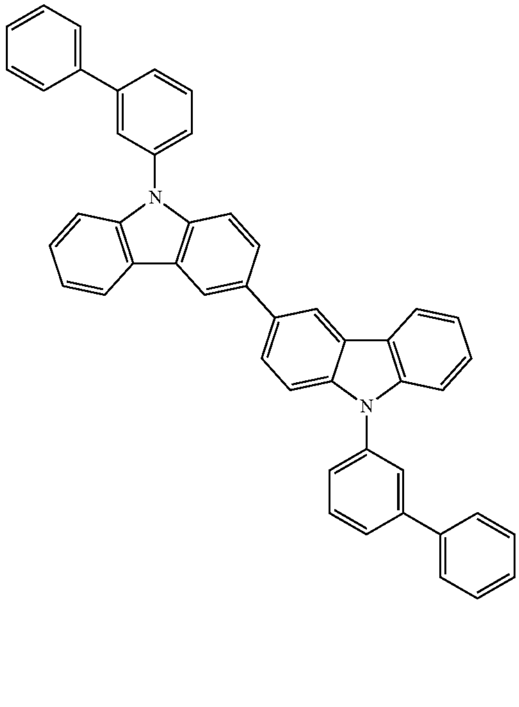
-continued
BCz-7
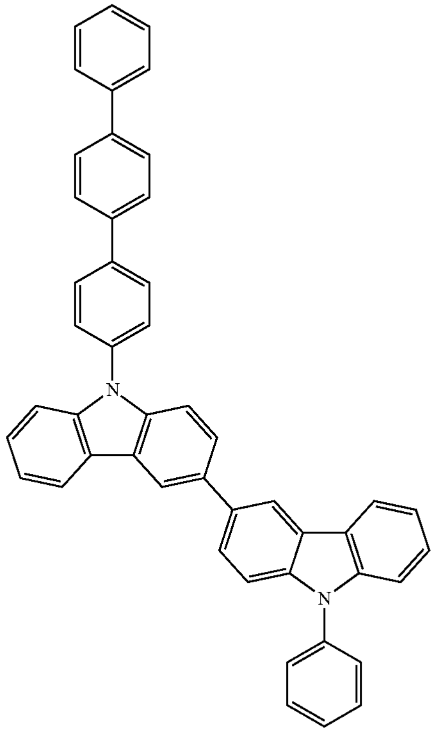
BCz-8
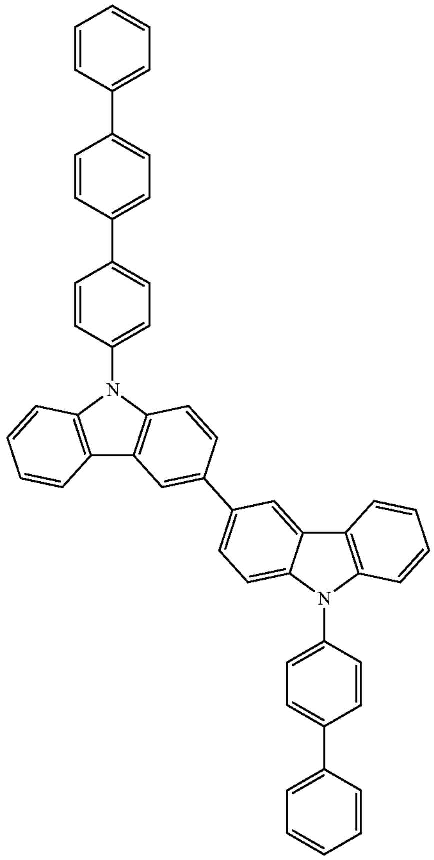

-continued
BCz-9
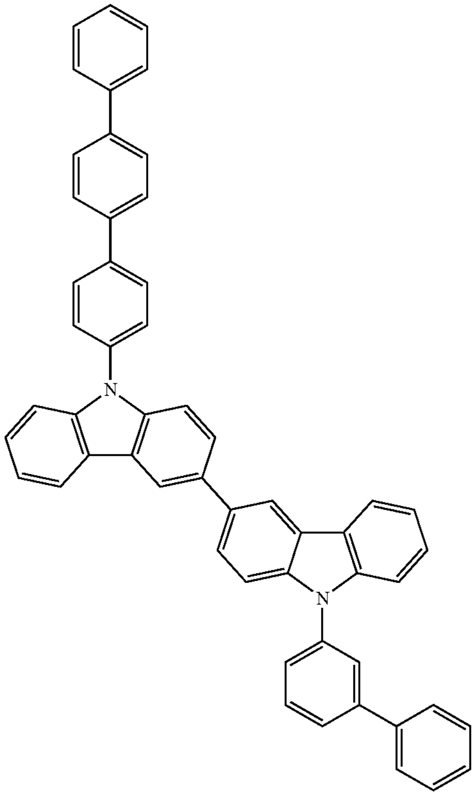
BCz-10
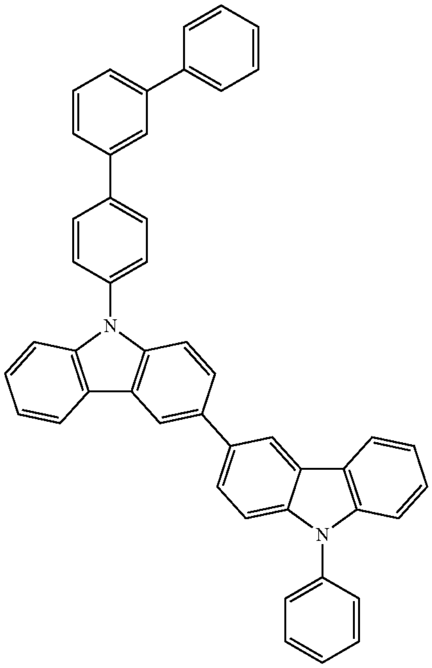
-continued
BCz-11
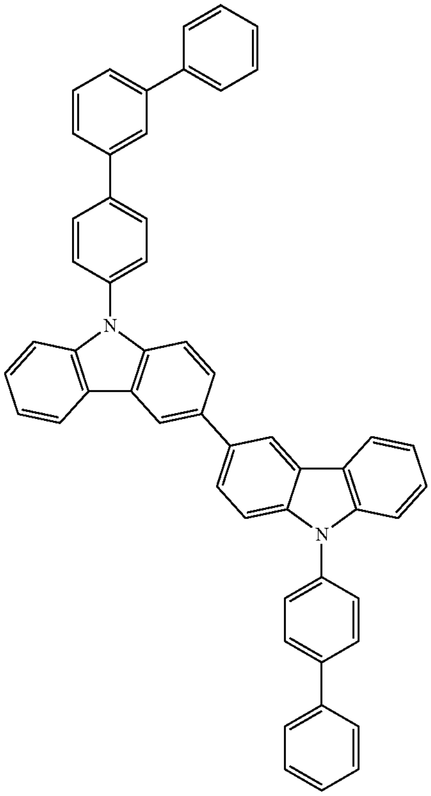
BCz-12
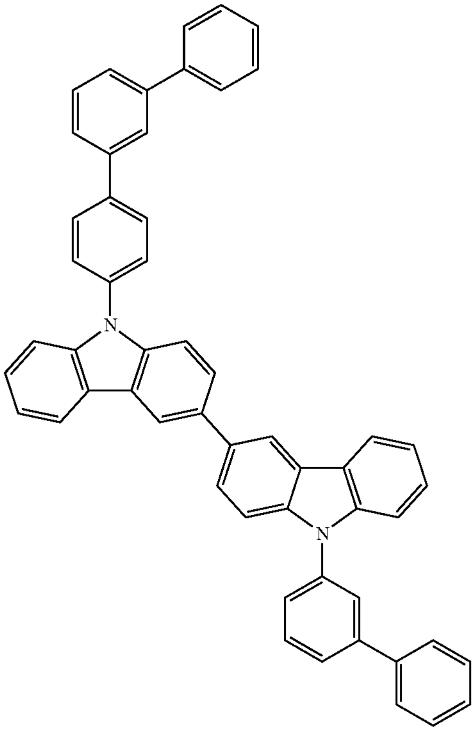

-continued
BCz-13
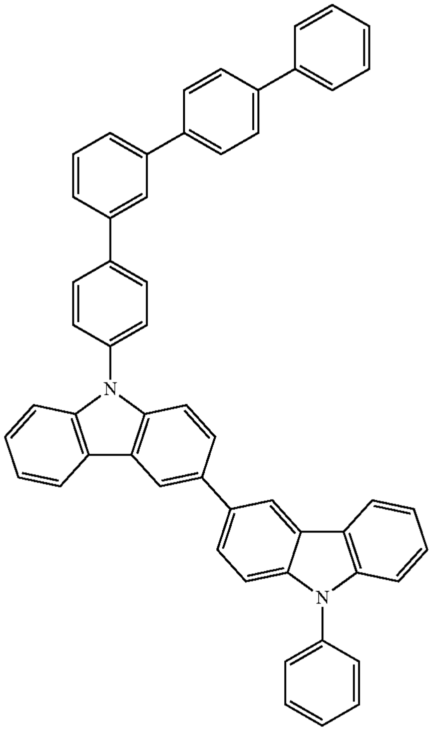
BCz-14
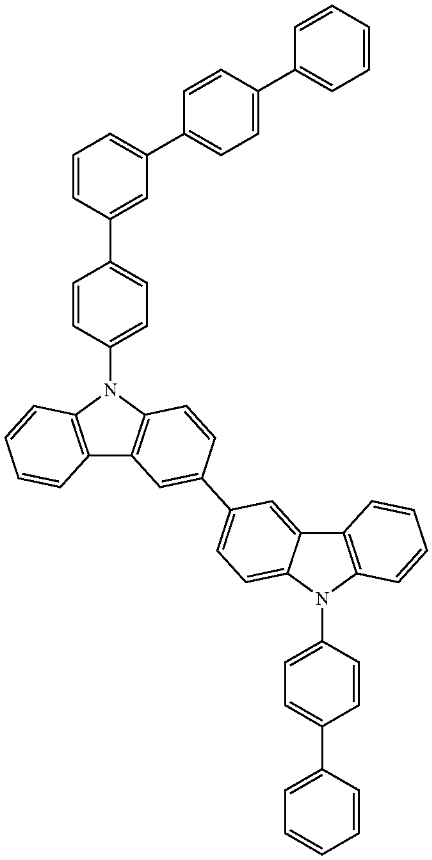
-continued
BCz-15
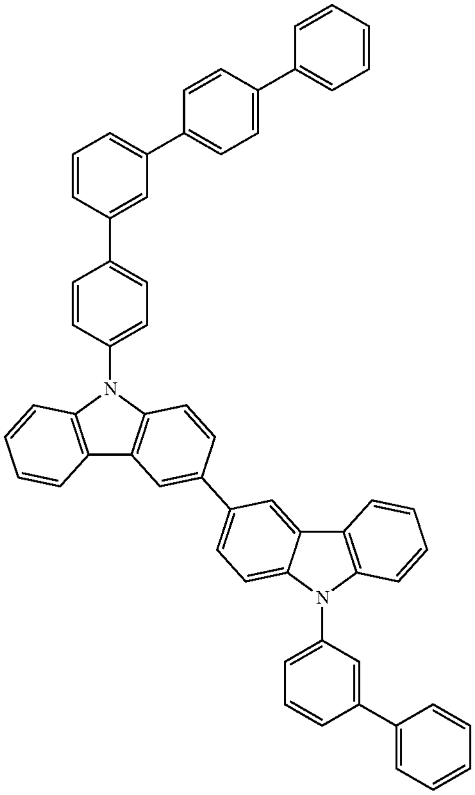
BCz-16
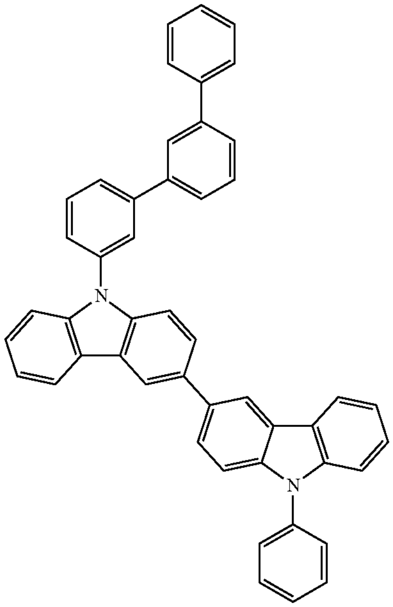

-continued
BCz-17
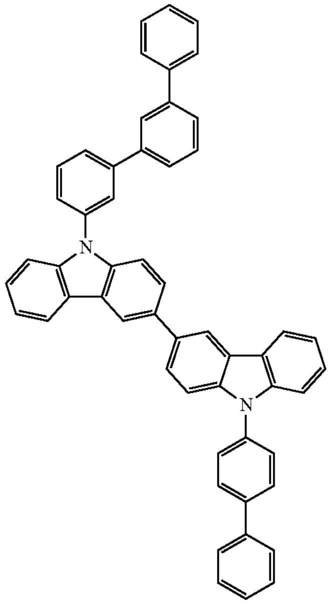
BCz-18
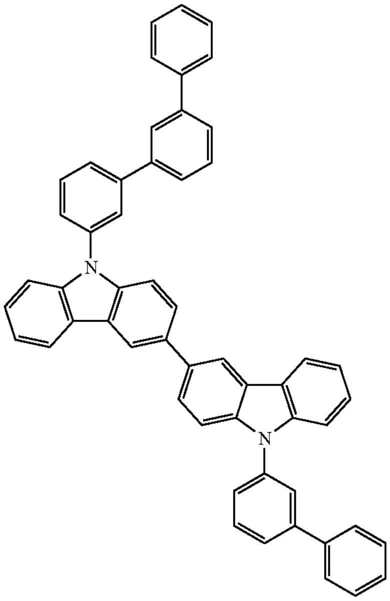
-continued
BCz-19
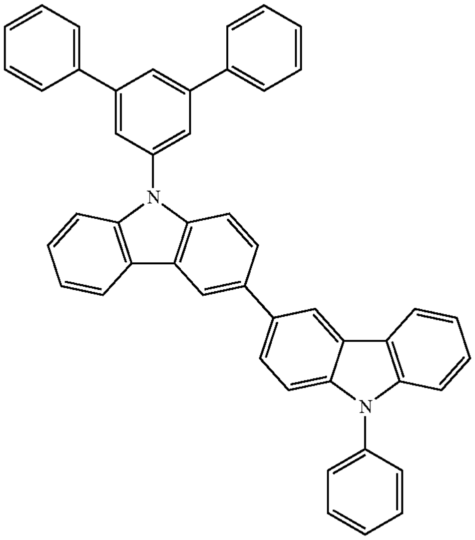
BCz-20
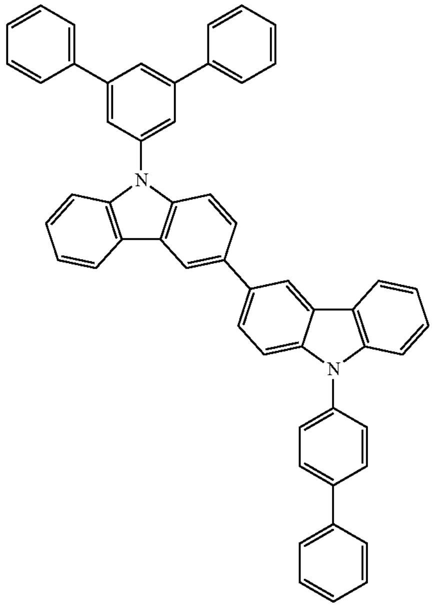

-continued
BCz-21
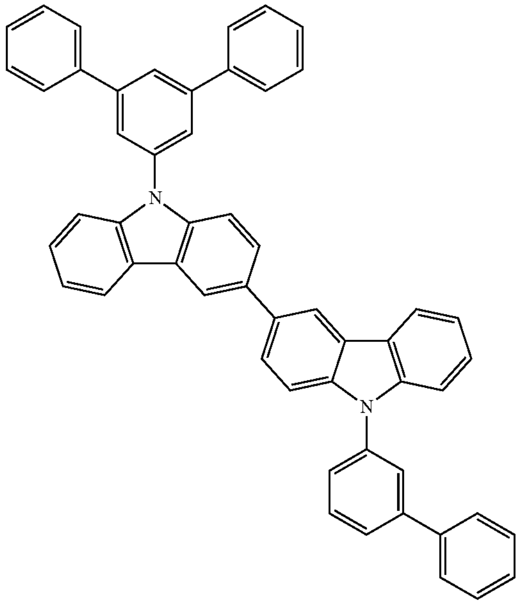
BCz-22
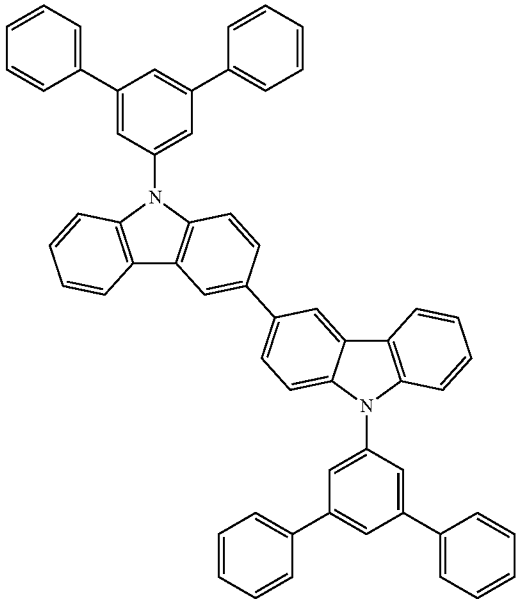
-continued
BCz-23
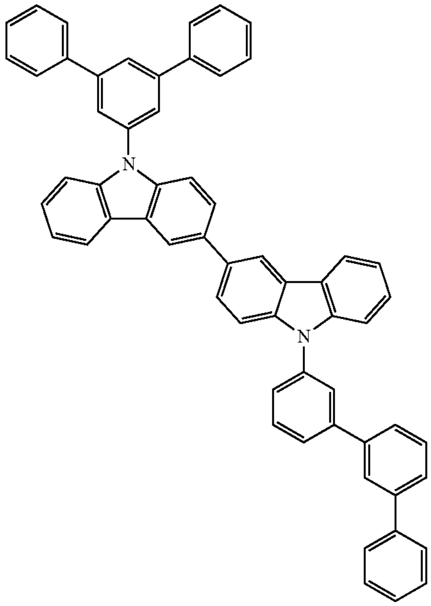
BCz-24
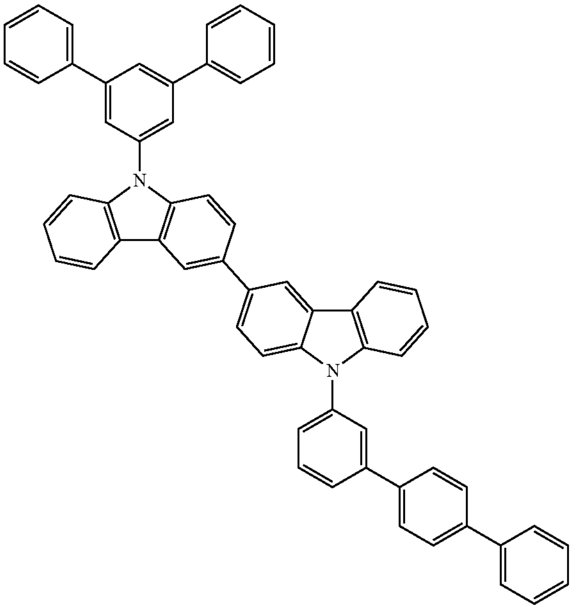

-continued

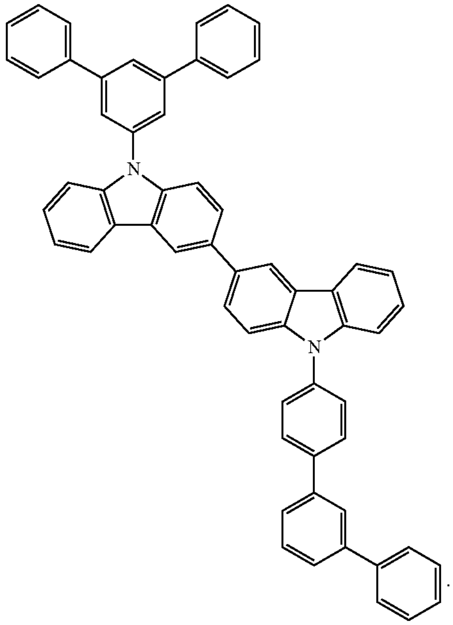

BCz-25

10. The organic light emitting device according to claim 7, wherein the first green emitting material layer further includes a third compound represented by Formula 5:

[Formula 5]

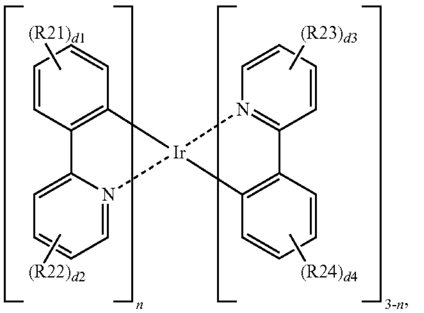

wherein each of R21, R22, R23, and R24 is independently selected from the group consisting of a substituted or unsubstituted C1 to C10 alkyl group, a substituted or unsubstituted C6 to C30 aryl group, and a substituted or unsubstituted C3 to C30 heteroaryl group, and wherein each of d1, d2, d3, and d4 is independently an integer of 0 to 4, and n is an integer of 1 to 3.

11. The organic light emitting device according to claim 10, wherein the third compound is one of the compounds in Formula 6:

[Formula 6]

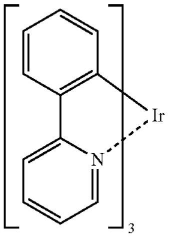

GD1

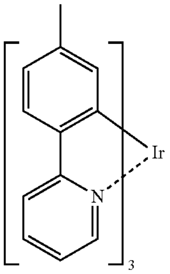

GD2

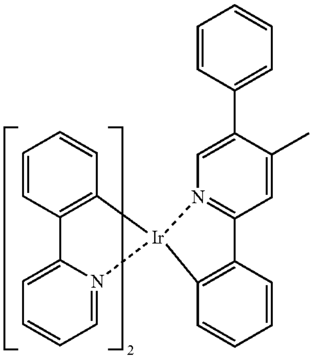

GD3

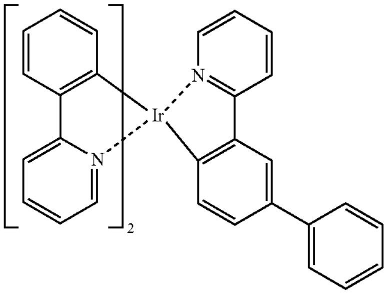

GD4

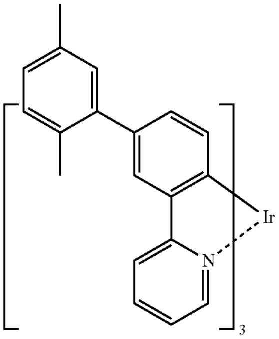

GD5

-continued

GD6

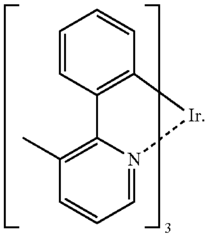

12. The organic light emitting device according to claim 7, wherein the first emitting part further includes a first electron transporting layer between the first green emitting material layer and the second electrode, wherein the first electron transporting layer includes an electron transporting material represented by Formula 7:

[Formula 7]

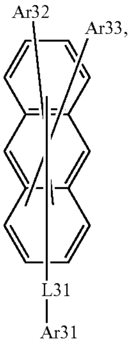

wherein L31 is selected from the group consisting of a single bond, a substituted or unsubstituted C6 to C30 arylene group, and a substituted or unsubstituted C3 to C30 heteroarylene group, wherein Ar31 is represented by Formula 7a or Formula 7b:

[Formula 7a]

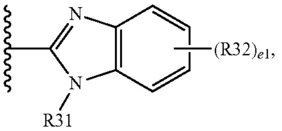

and

[Formula 7b]

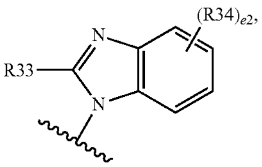

wherein each of Ar32 and Ar33 is independently selected from the group consisting of hydrogen, deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, wherein in the Formula 7a, R31 is selected from the group consisting of hydrogen, deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, R32 is selected from the group consisting of deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, and e1 is an integer of 0 to 4, wherein in the Formula 7b, R33 is selected from the group consisting of hydrogen, deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, R34 is selected from the group consisting of deuterium, a substituted or unsubstituted C1 to C10 alkyl group, a substituted or unsubstituted C3 to C30 cycloalkyl group, a substituted or unsubstituted C1 to C10 alkoxy group, a substituted or unsubstituted C6 to C30 aryloxy group, a substituted or unsubstituted C1 to C10 alkylthioxy group, a substituted or unsubstituted C6 to C30 arylthioxy group, a substituted or unsubstituted C1 to C10 alkylsulfoxy group, a substituted or unsubstituted C6 to C30 arylsulfoxy group, a substituted or unsubstituted C6 to C30 aryl group, and a substituted or unsubstituted C3 to C30 heteroaryl group, and e2 is an integer of 0 to 4.

13. The organic light emitting device according to claim 12, wherein the electron transporting material is one of the compounds in Formula 8:

[Formula 8]
ET1
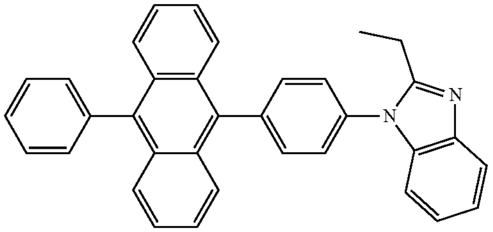
ET2
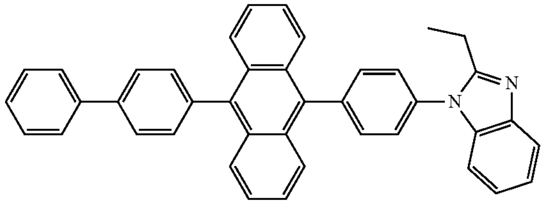
ET3
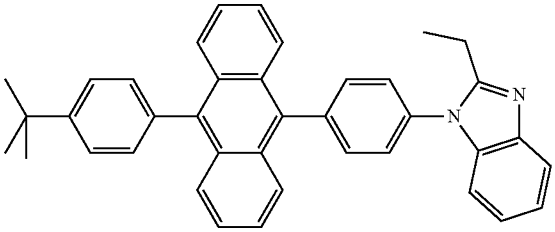
ET4
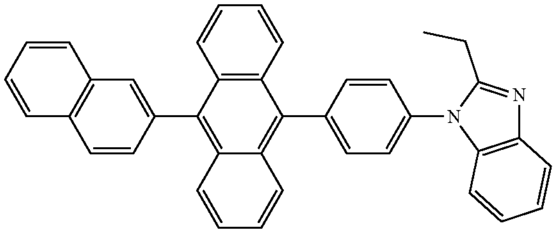
ET5
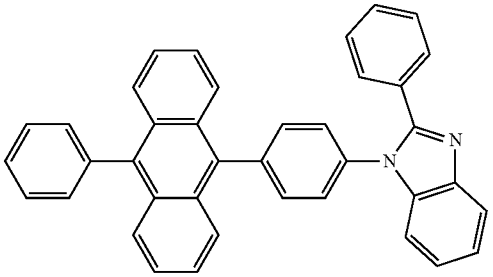
ET6
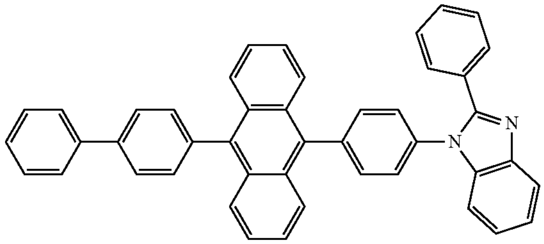
-continued
ET7
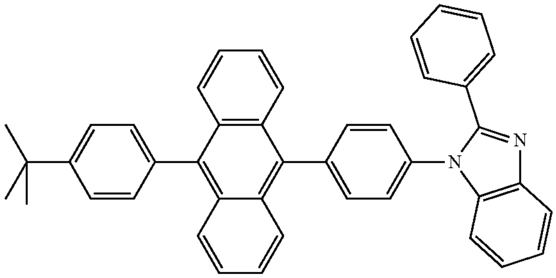
ET8
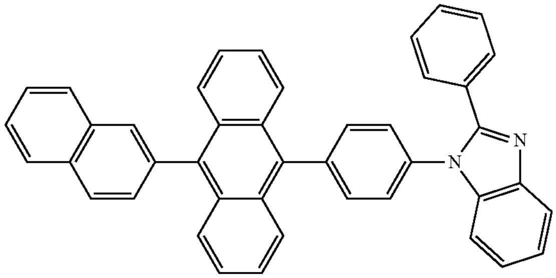
ET9
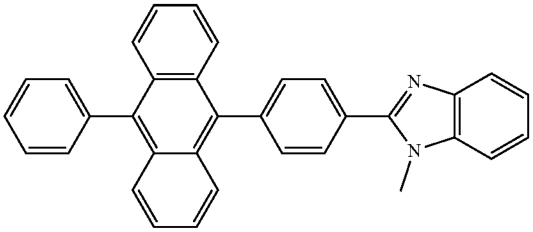
ET10
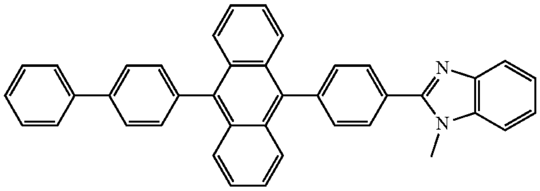
ET11
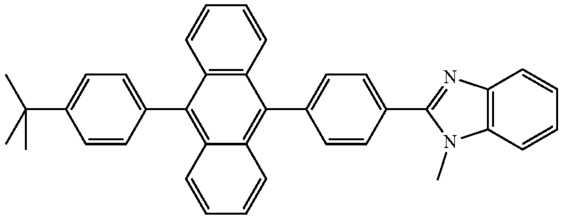
ET12
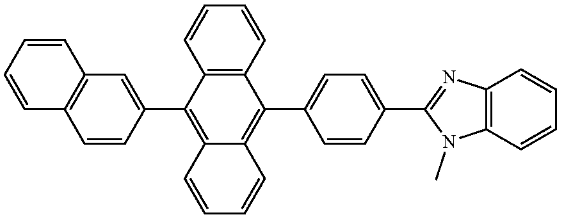

-continued
ET13
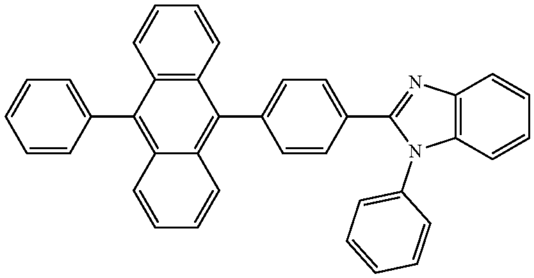
ET14
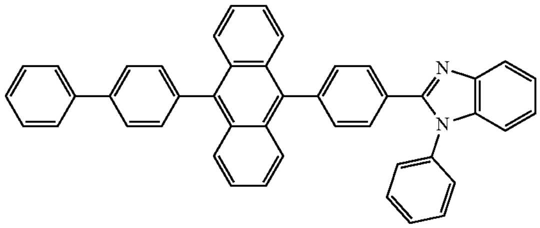
ET15
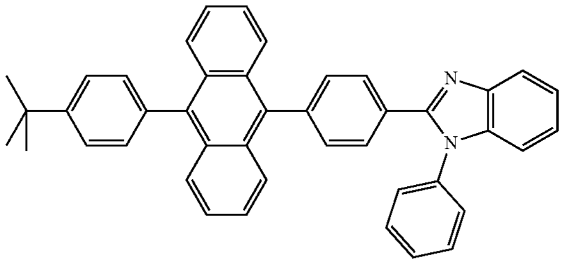
ET16
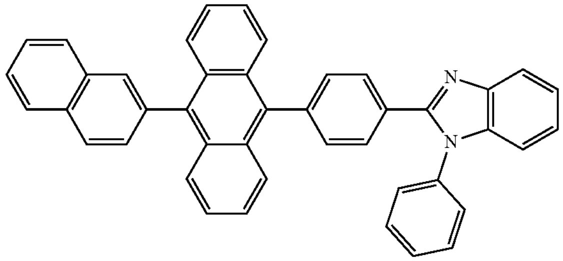
ZADN1
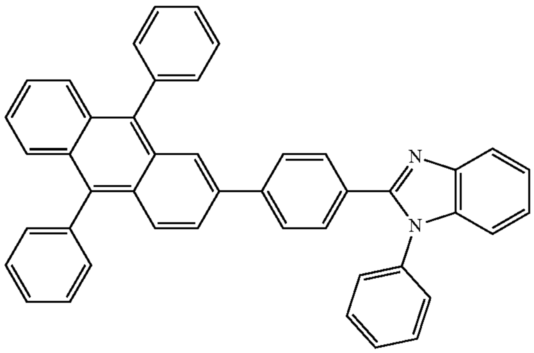
-continued
ZADN2
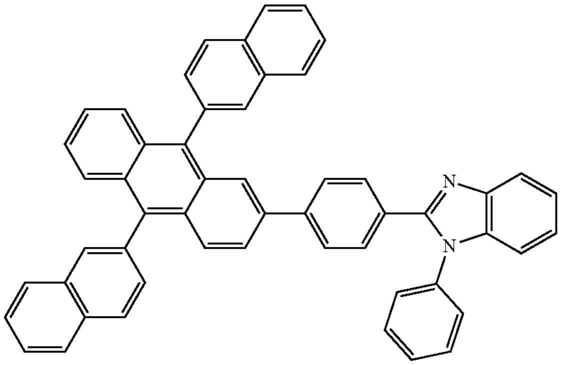
ZADN3
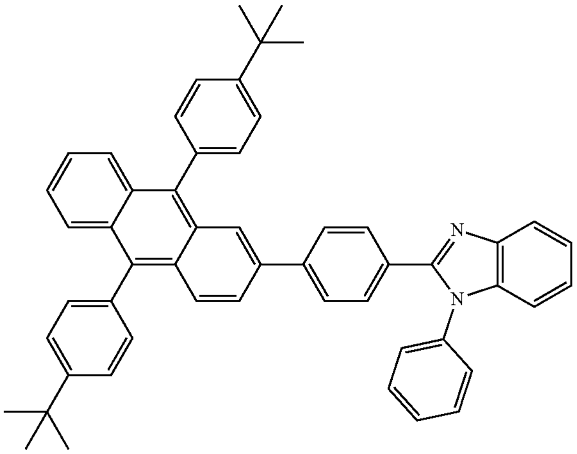
ZADN4
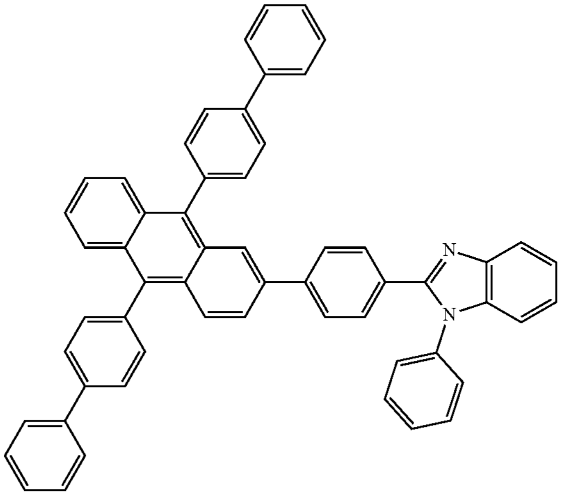

-continued
ZADN5
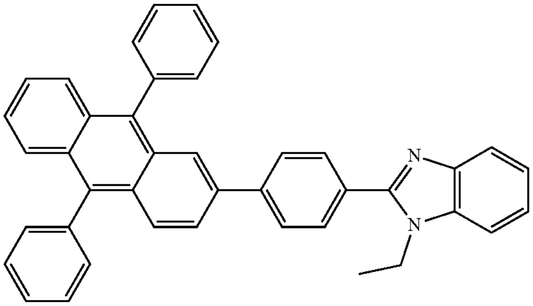
ZADN6
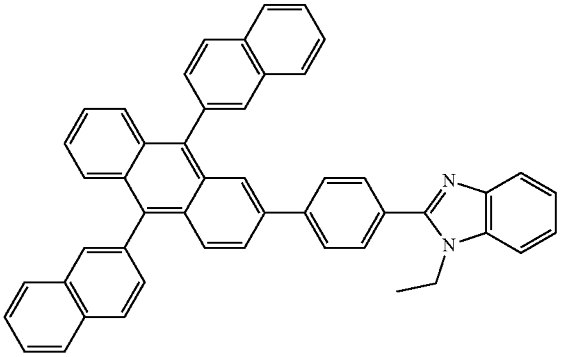
ZADN7
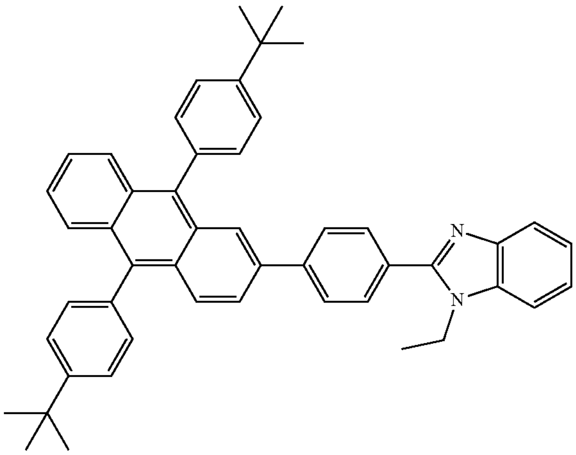
-continued
ZADN8
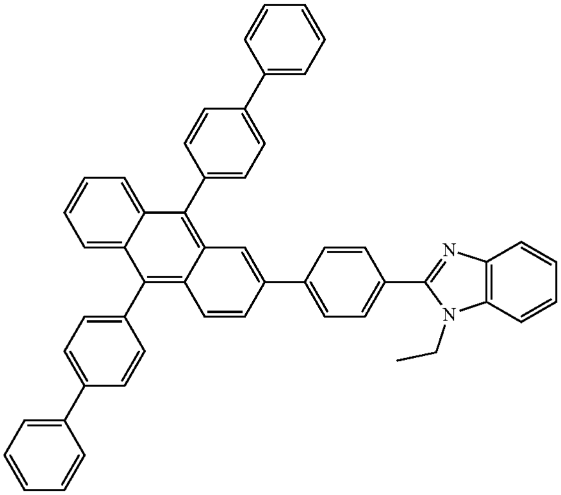
ZADN9
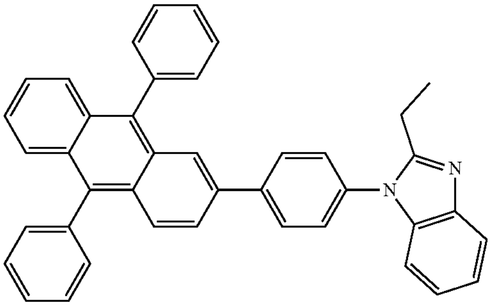
ZADN10
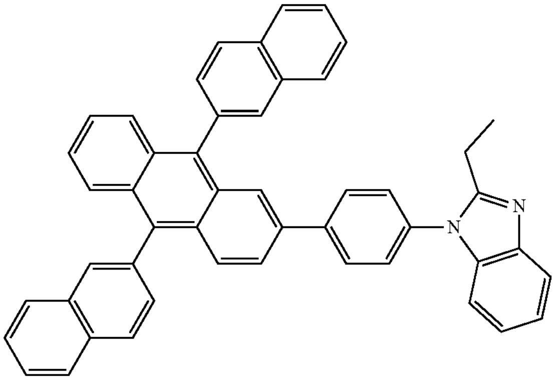

-continued

ZADN11

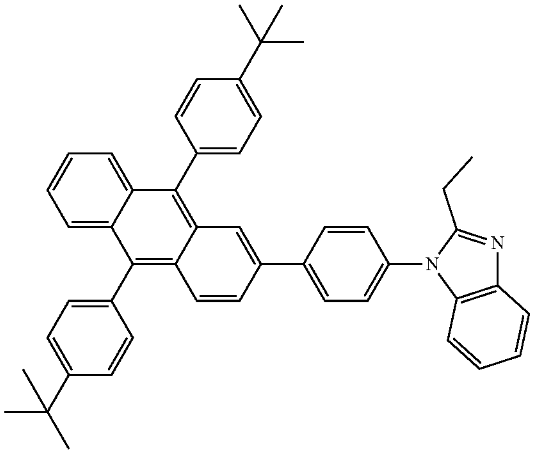

ZADN12

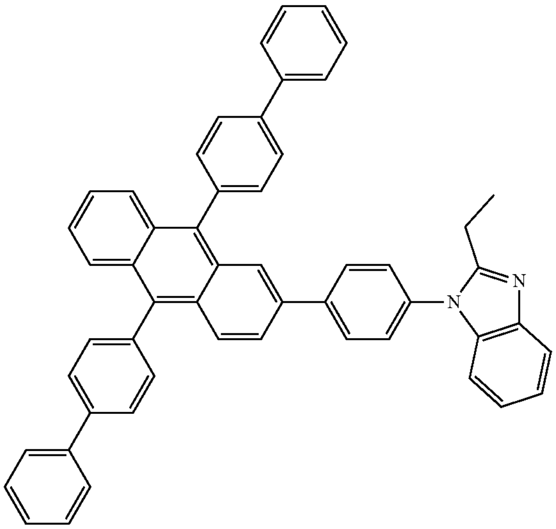

ZAD13

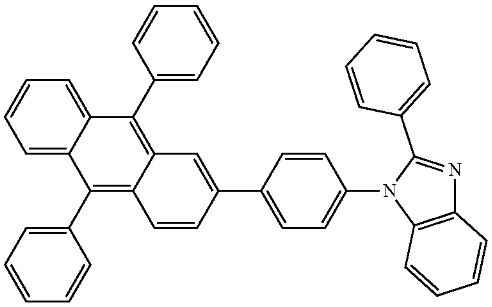

-continued

ZADN14

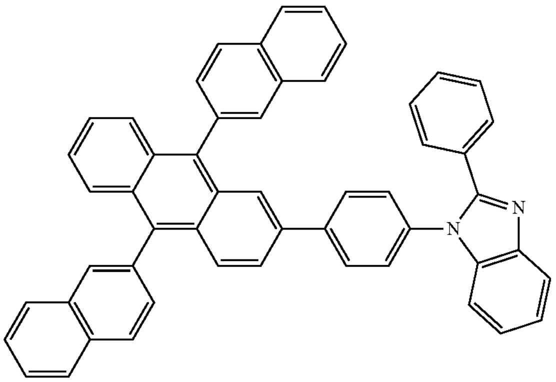

ZADN15

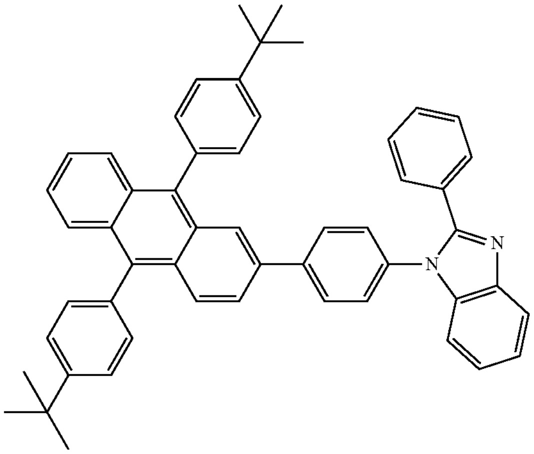

ZADN16

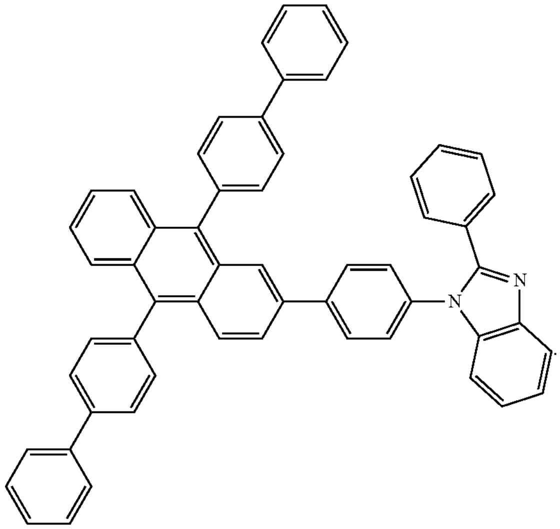

14. The organic light emitting device according to claim 7, further comprising:

a second emitting part including a second green emitting material layer and positioned between the first emitting part and the second electrode, wherein the second green emitting material layer includes the first compound.

15. The organic light emitting device according to claim 7, further comprising:

a second emitting part including a first blue emitting material layer and positioned between the first electrode and the first emitting part; and a third emitting part including a second blue emitting material layer and positioned between the first emitting part and the second electrode.

16. The organic light emitting device according to claim 15, wherein the first emitting part further includes a red emitting material layer between the second emitting part and the first green emitting material layer.

17. The organic light emitting device according to claim 16, wherein the first emitting part further includes a yellow-green emitting material layer between the first green emitting material layer and the red emitting material layer.

18. The organic light emitting device according to claim 7, wherein in the Formula 1, a1 is a positive integer, and each of a2, a3, a4, and a5 is 0.

19. The organic light emitting device according to claim 7, wherein in the Formula 1, each of a1 and a2 is a positive integer, and each of a3, a4, and a5 is 0.

20. The organic light emitting device according to claim 7, wherein the organic compound is one of the compounds in Formula 2:

[Formula 2]

H1-D1

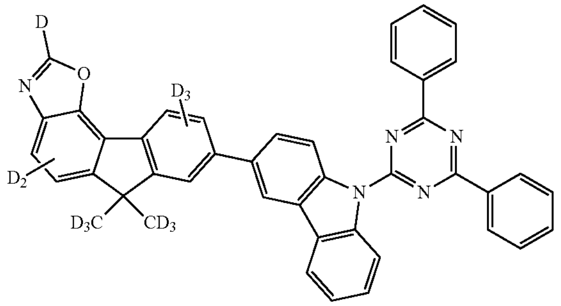

H1-D2

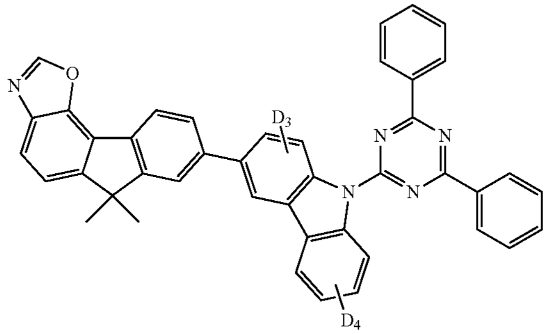

H1-D3

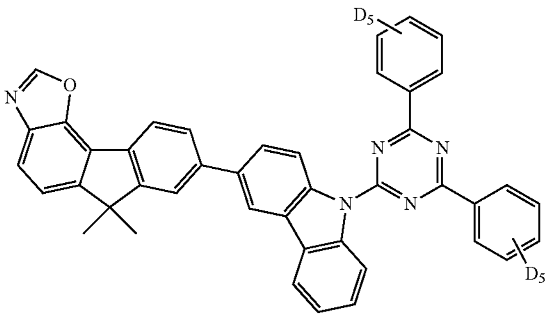

-continued

H1-D4

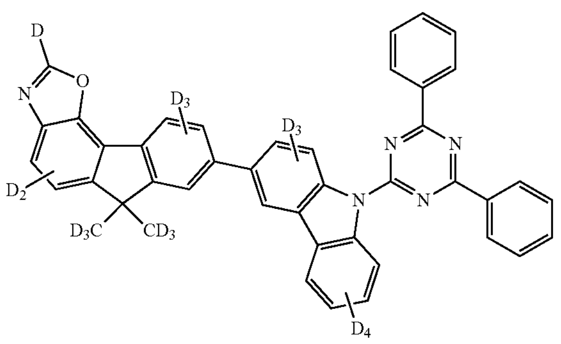

H1-D5

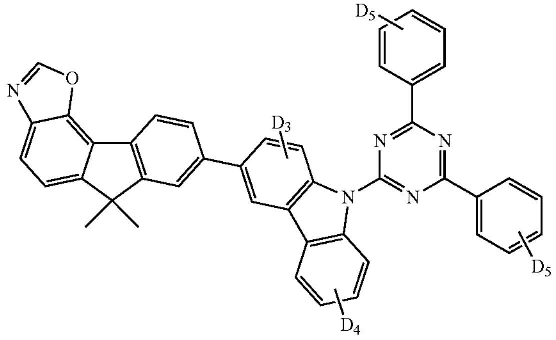

H1-D6

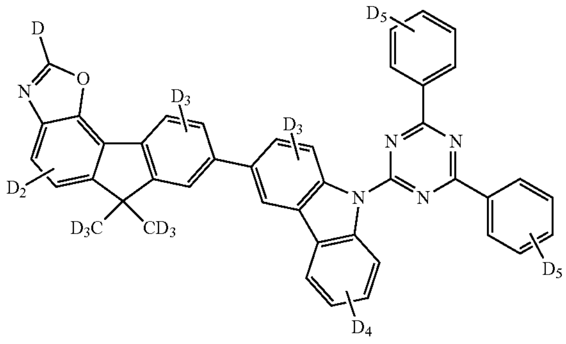

H2-D1

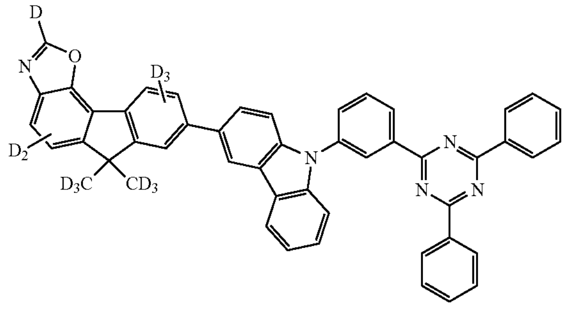

-continued
H2-D2
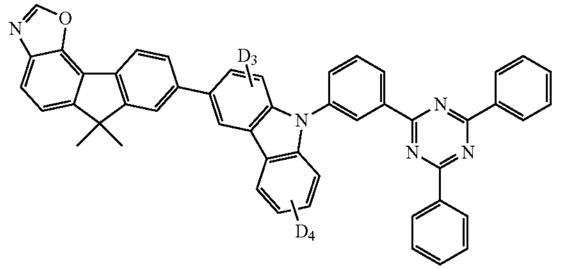
H2-D3
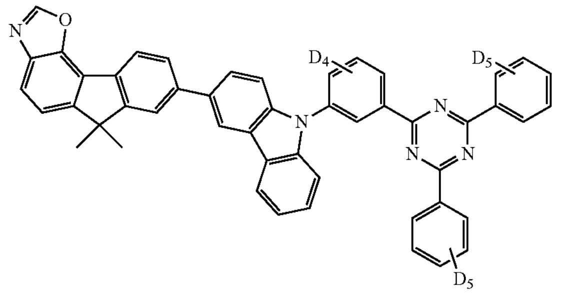
H2-D4
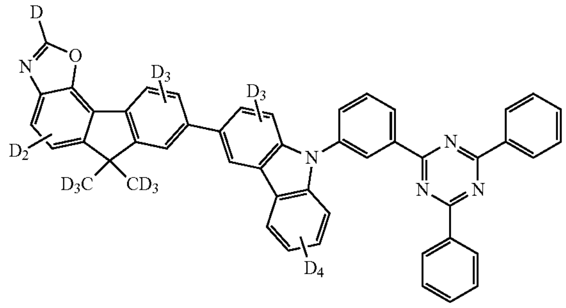
H2-D5
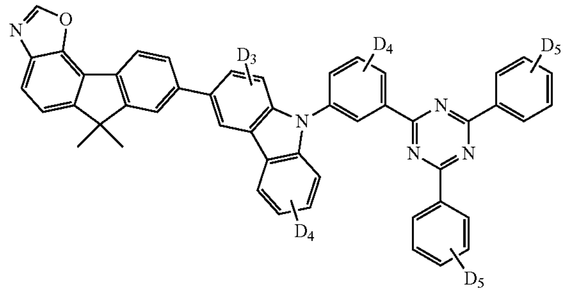
H2-D6
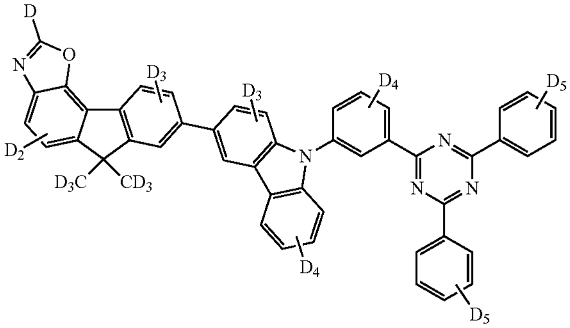
-continued
H3-D1
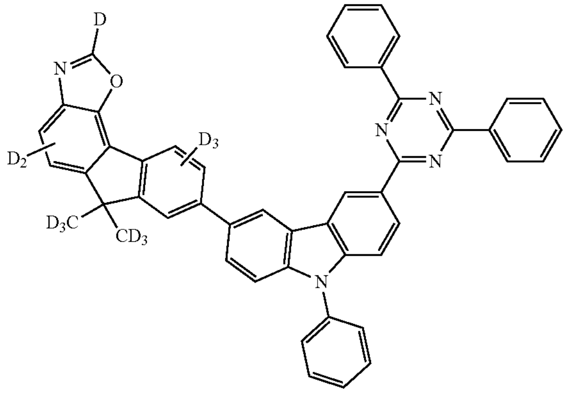
H3-D2
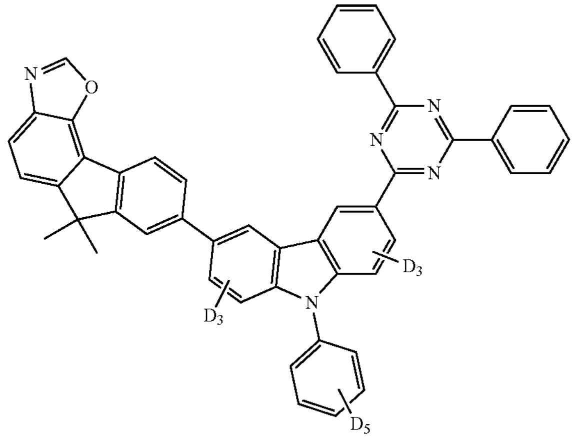
H3-D3
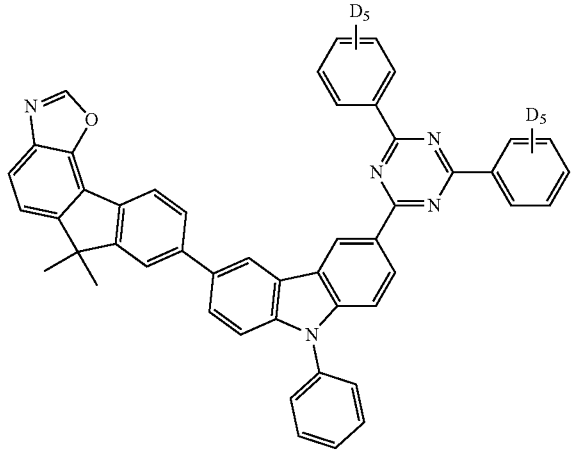

-continued
H3-D4
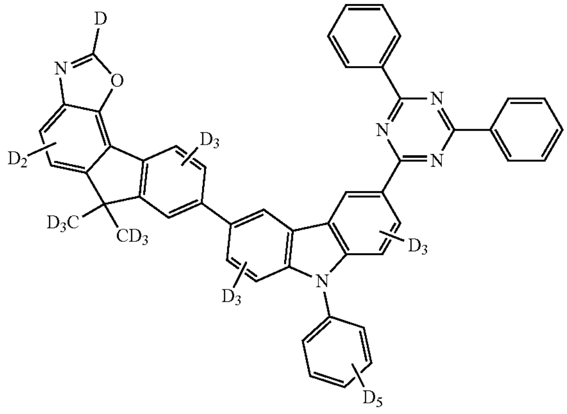
H3-D5
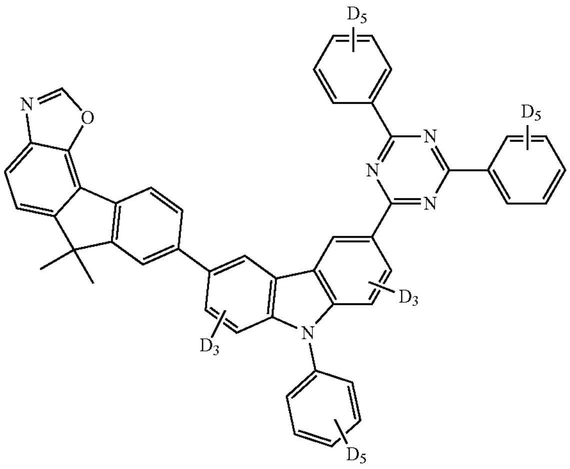
H3-D6
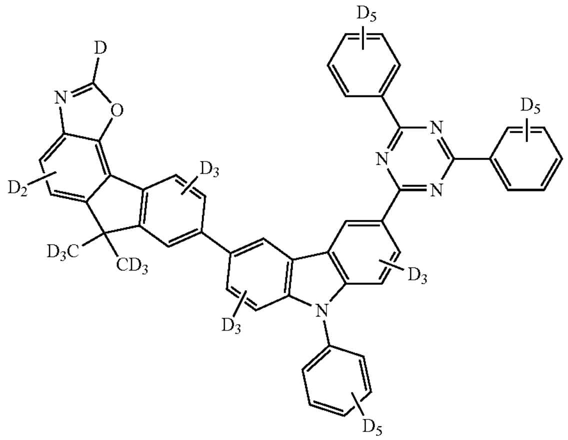
-continued
H4-D1
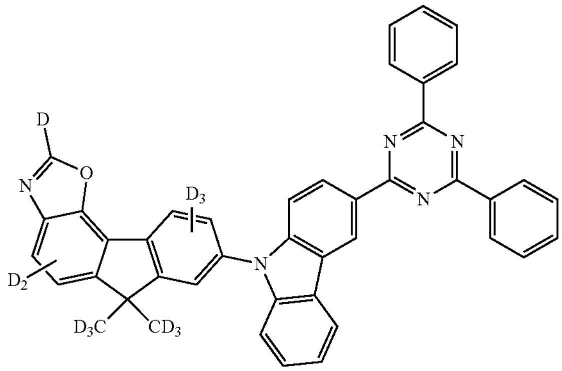
H4-D2
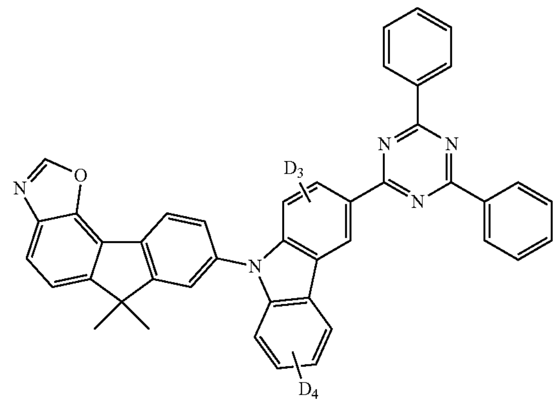
H4-D3
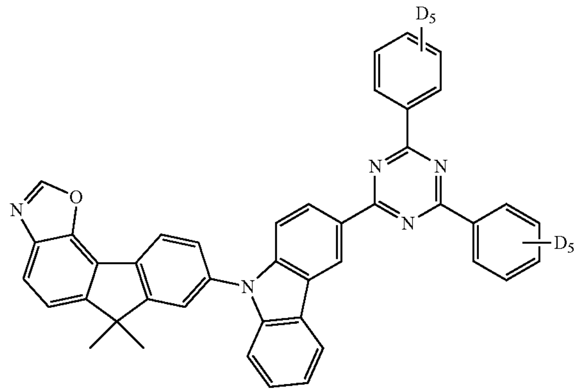
H4-D4
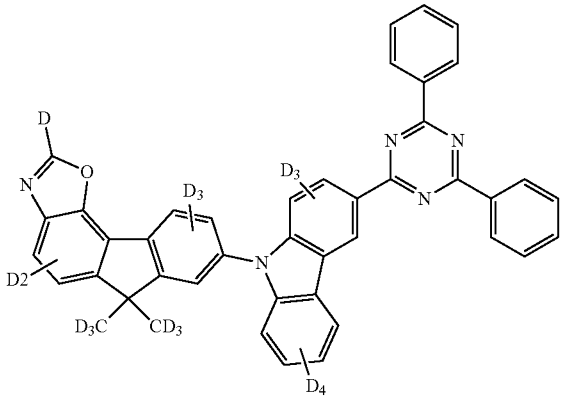

-continued
H4-D5
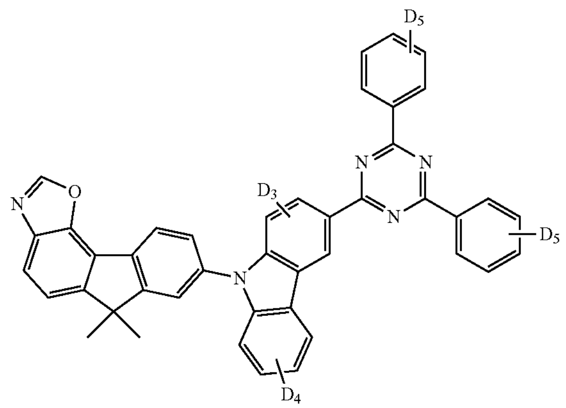
H4-D6
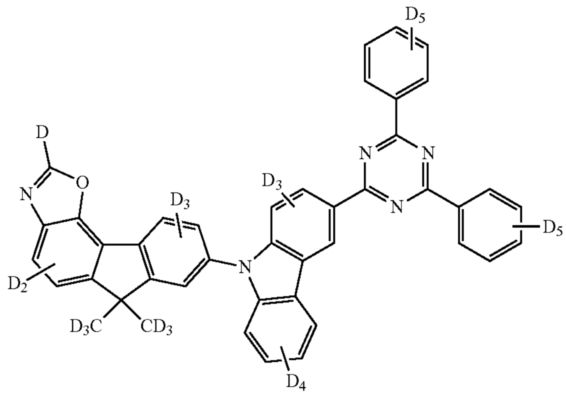
H5-D1
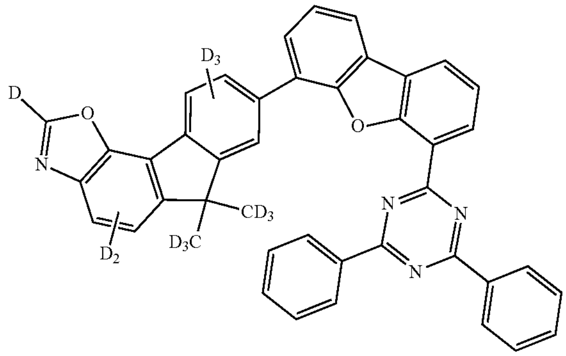
H5-D2
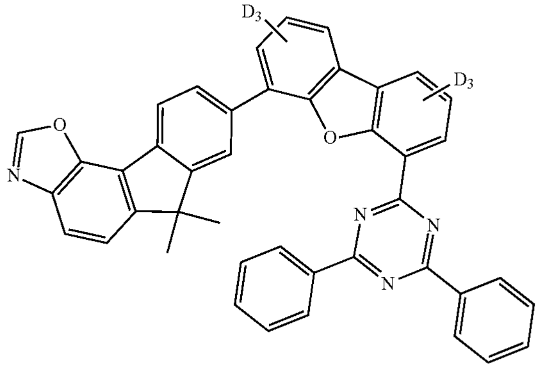
-continued
H5-D3
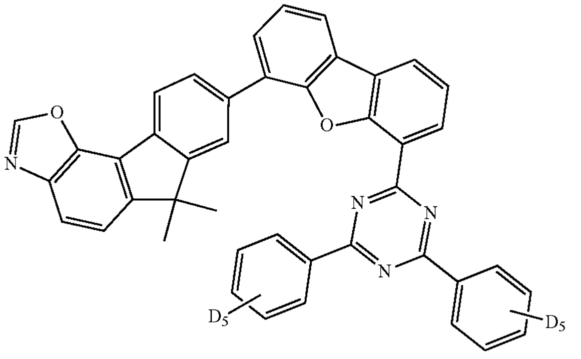
H5-D4
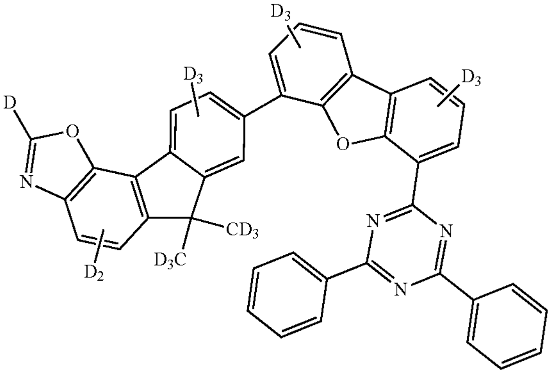
H5-D5
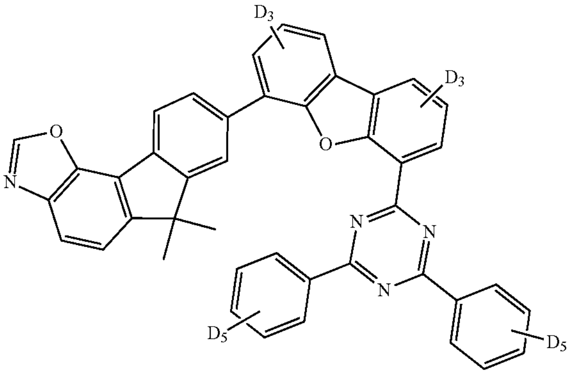
H5-D6
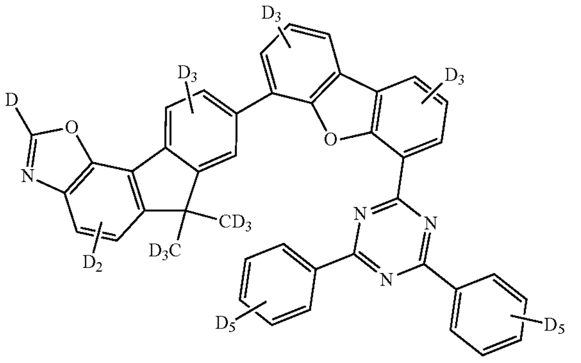

-continued
H6-D1
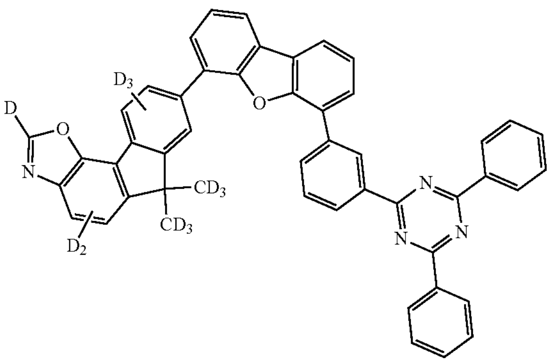
H6-D2
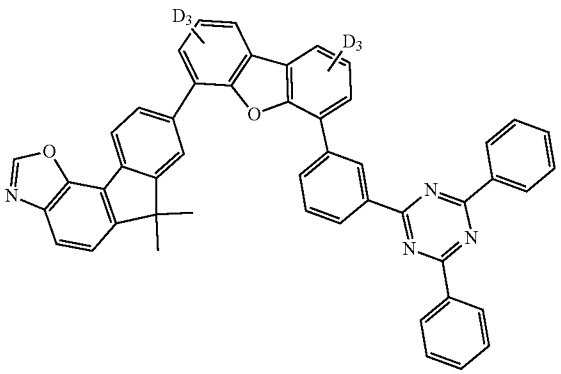
H6-D3
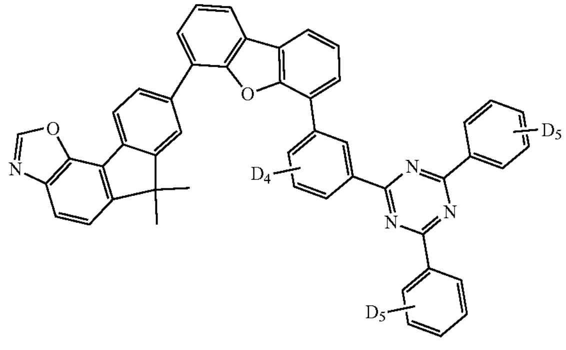
-continued
H6-D4
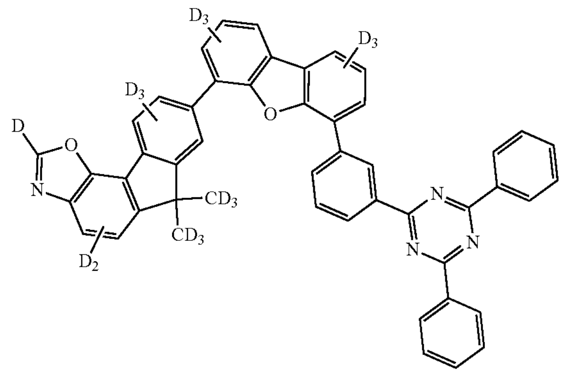
H6-D5
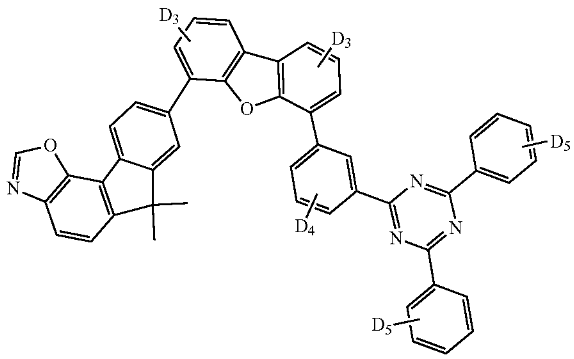
H6-D6
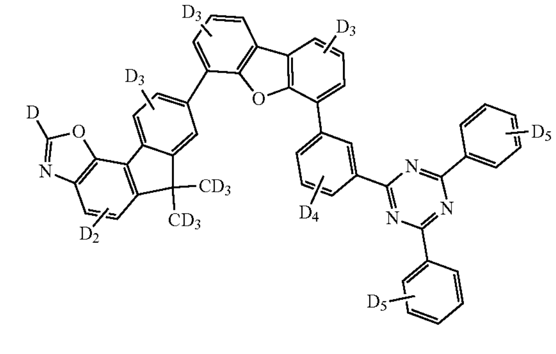
H7-D1
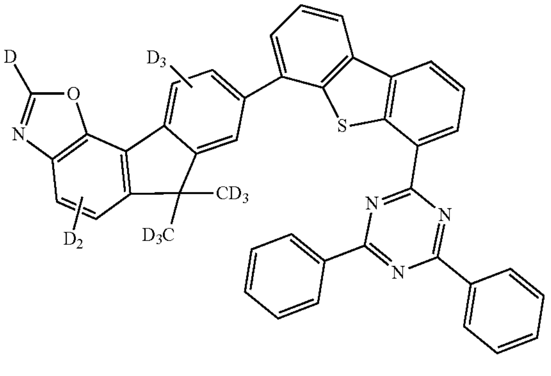
H7-D2
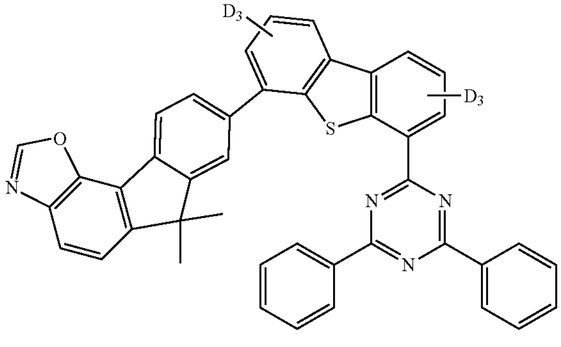

-continued
H7-D3
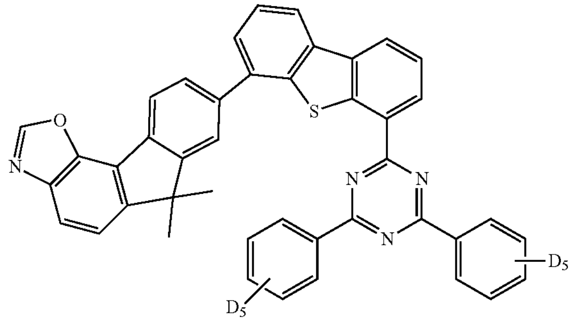
H7-D4
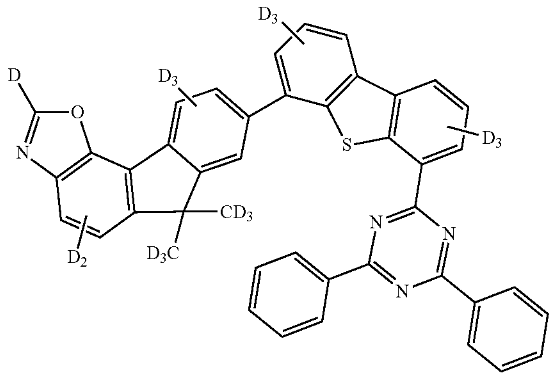
H7-D5
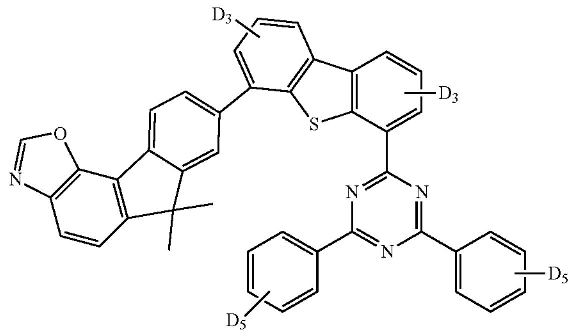
H7-D6
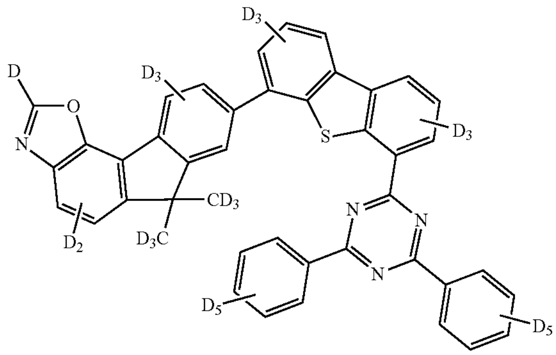
H8-D1
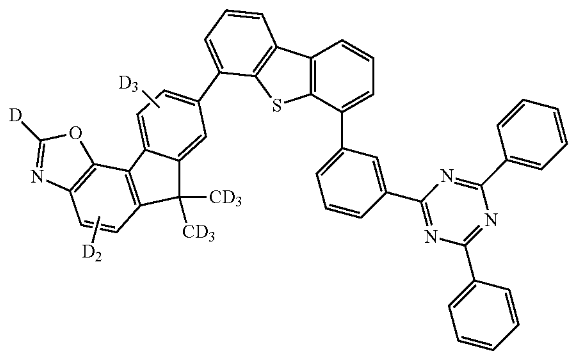
H8-D2
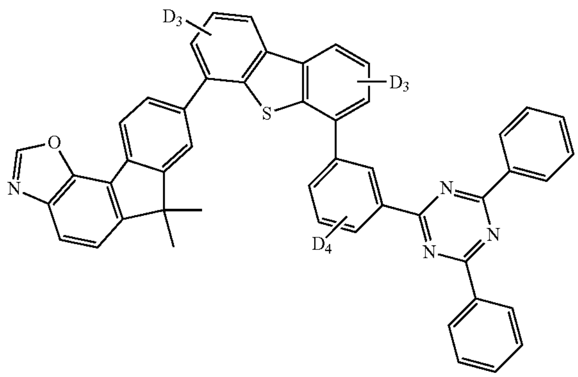
H8-D3
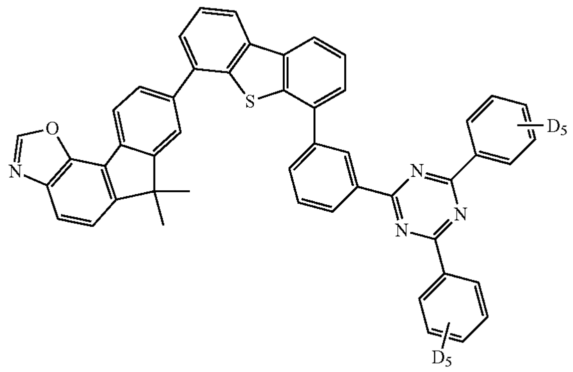
H8-D4
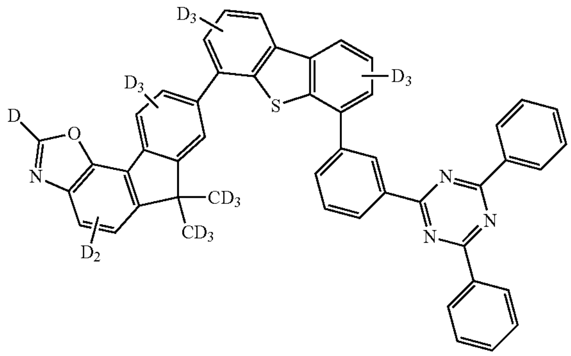

-continued
H8-D5
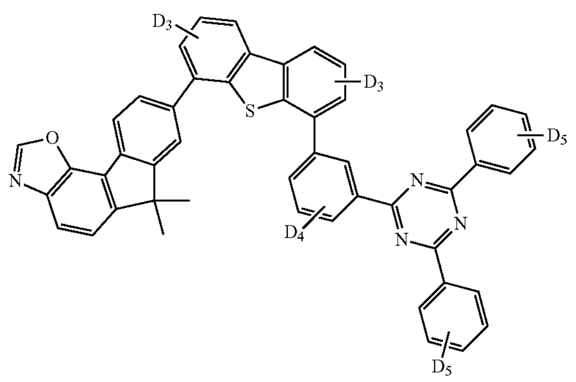
H8-D6
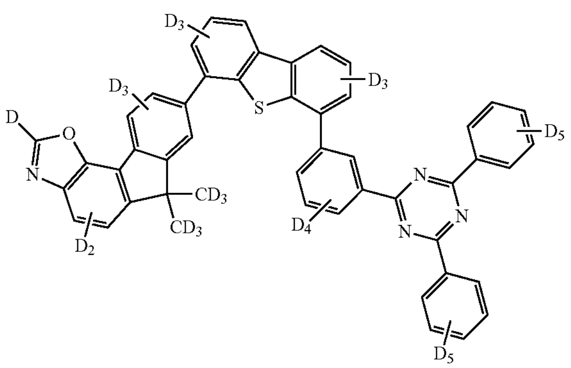
H9-D1
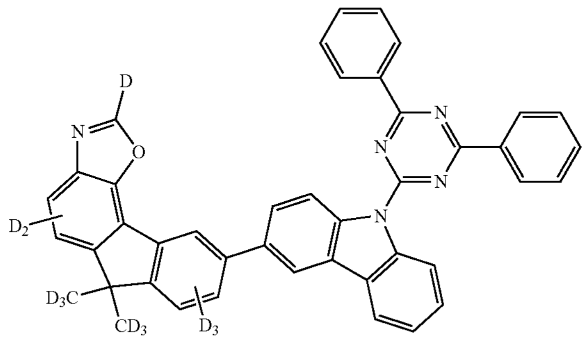
H9-D2
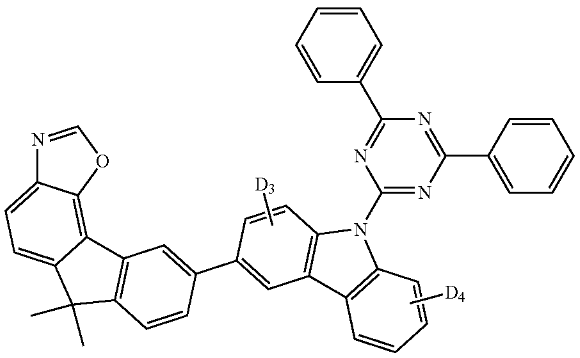
H9-D3
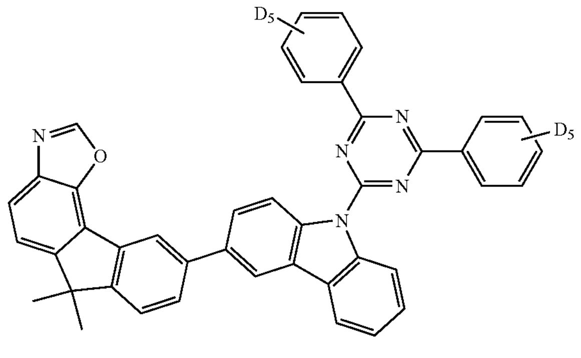
H9-D4
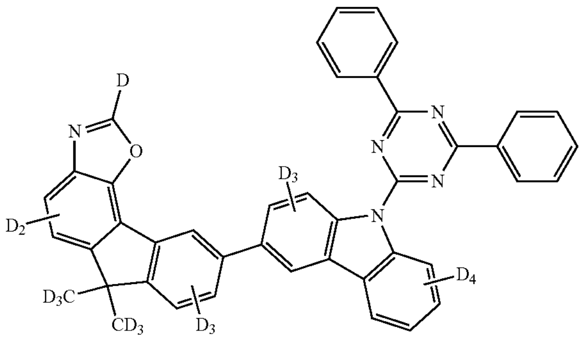
H9-D5
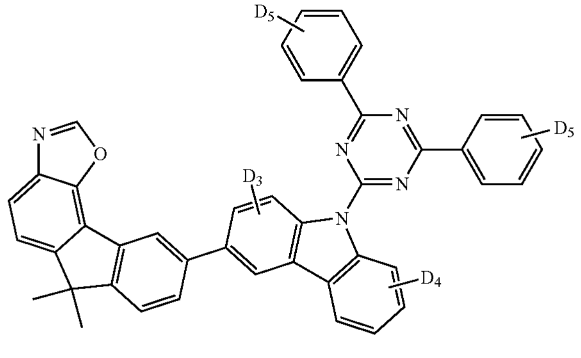
H9-D6
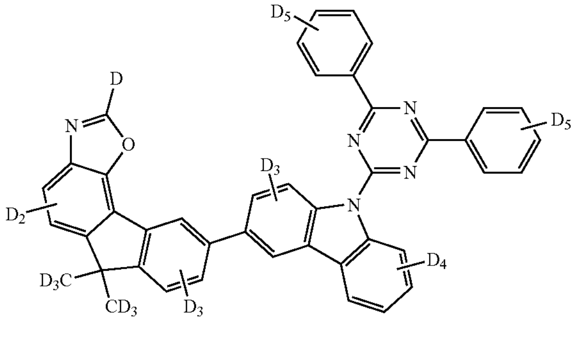

-continued
H10-D1
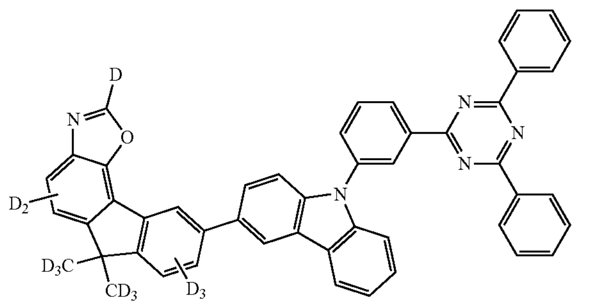
H10-D2
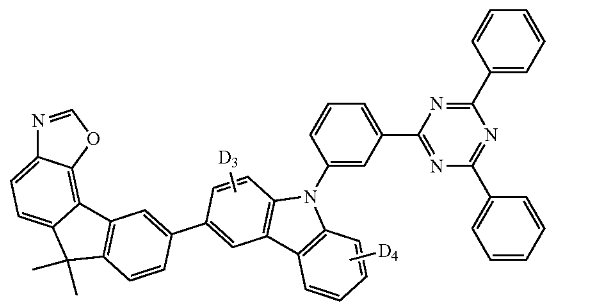
H10-D3
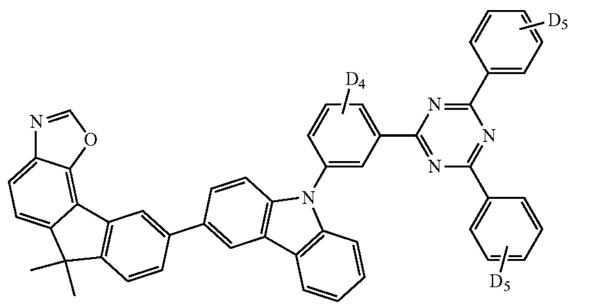
H10-D4
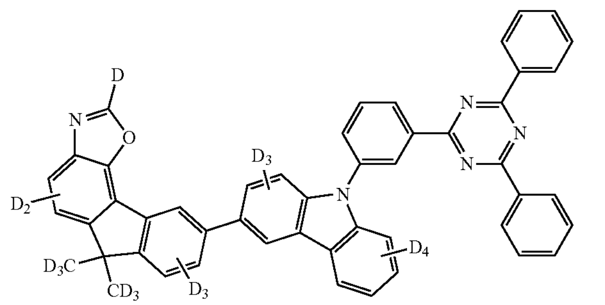
H10-D5
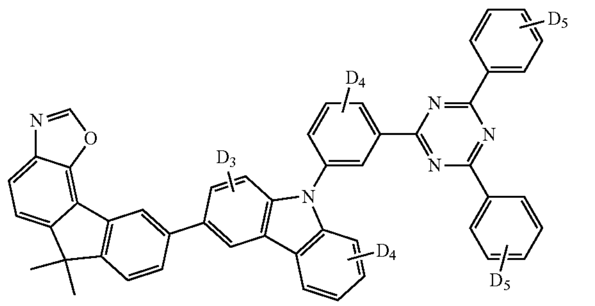
H10-D6
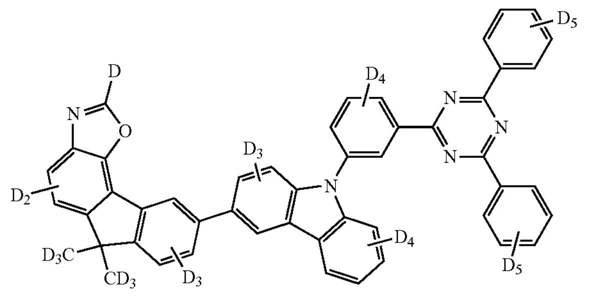
H11-D1
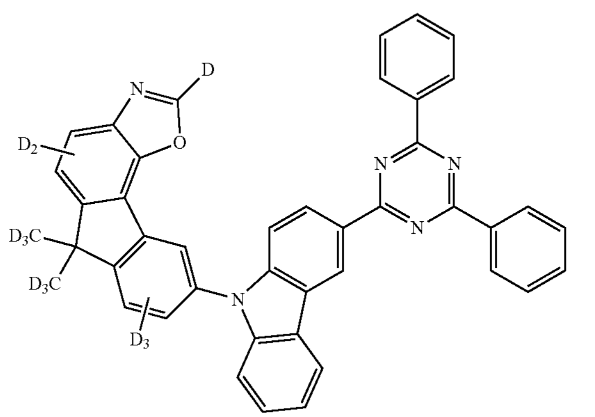
H11-D2
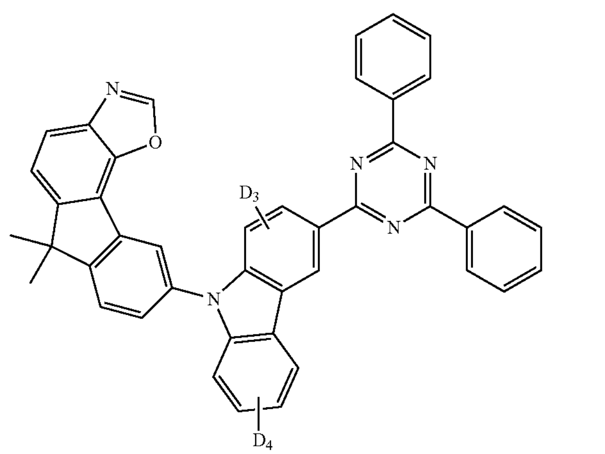

-continued
H11-D3
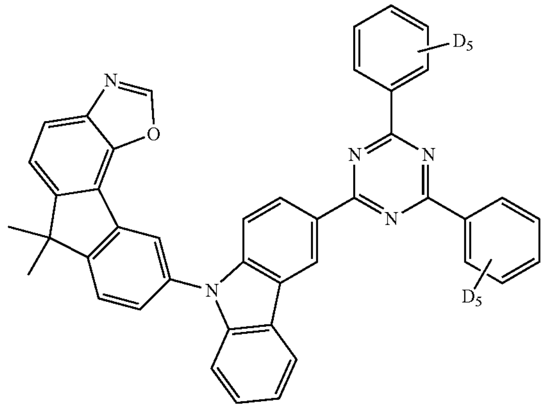
H11-D4
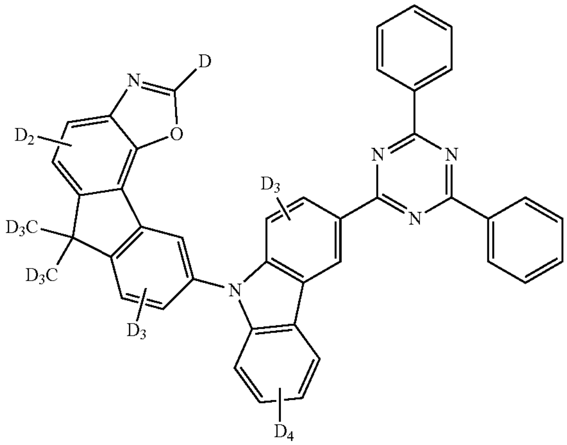
H11-D5
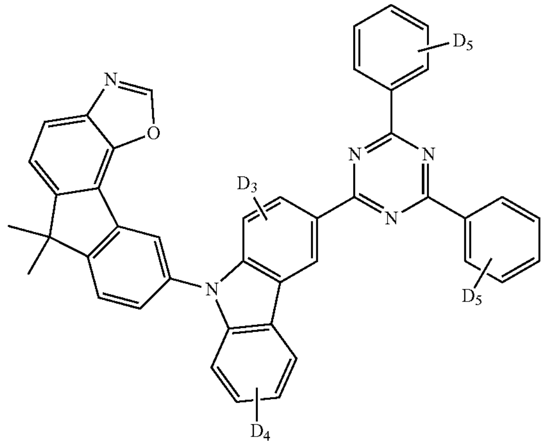
H11-D6
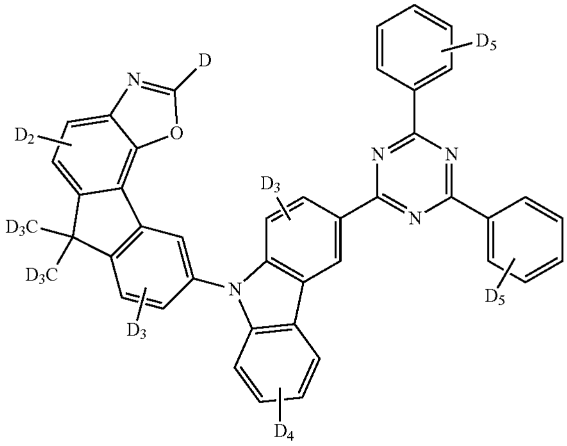
H12-D1
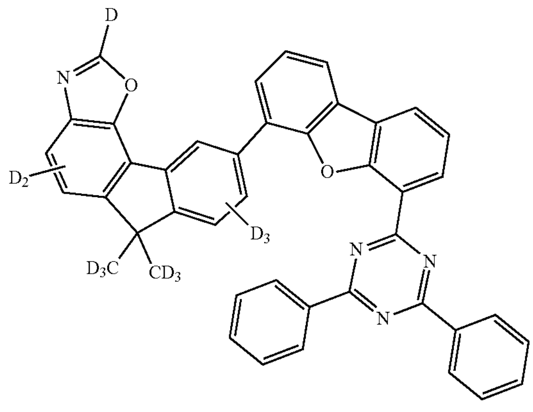
H12-D2
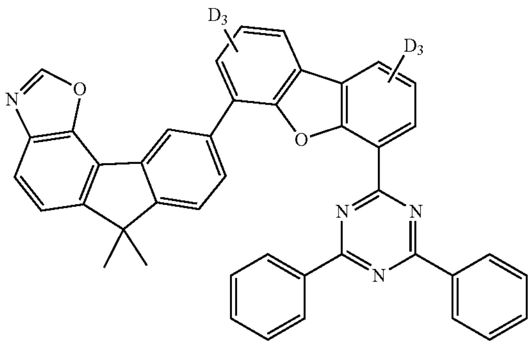

-continued
H12-D3
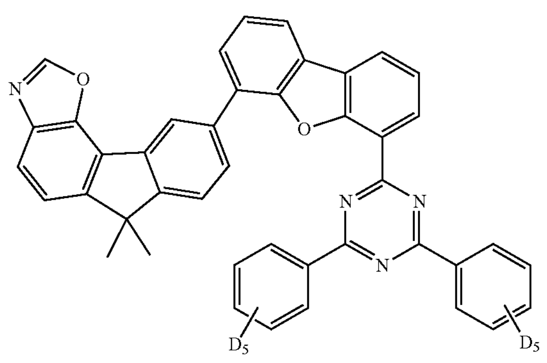
H12-D4
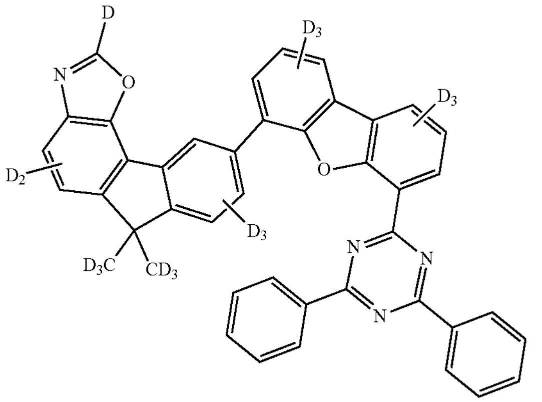
H12-D5
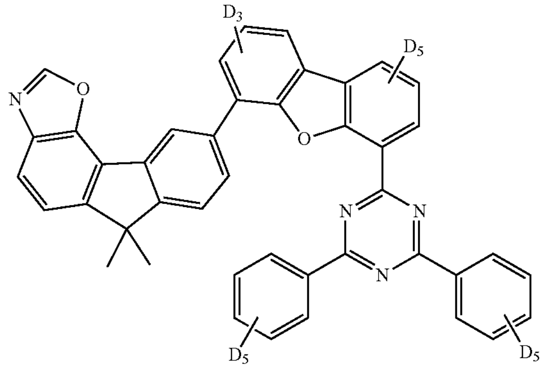
H12-D6
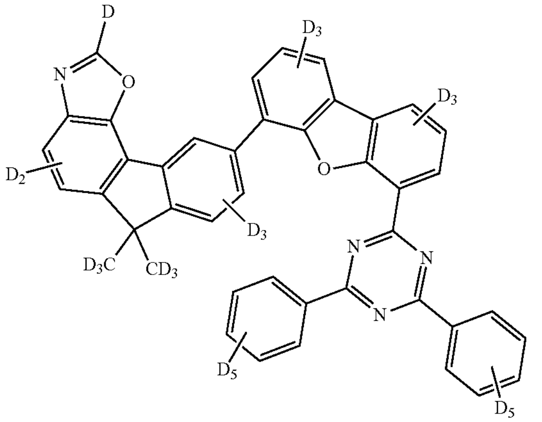
H13-D1
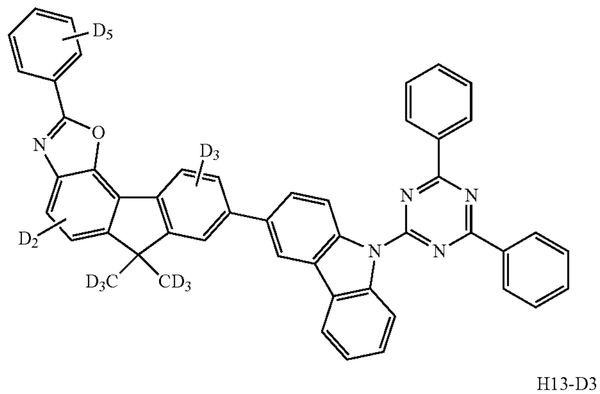
H13-D2
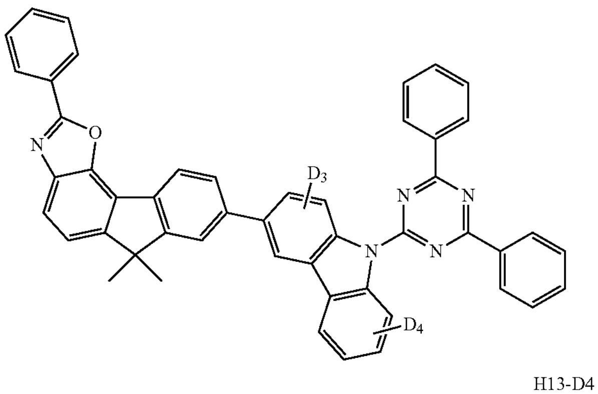
H13-D3
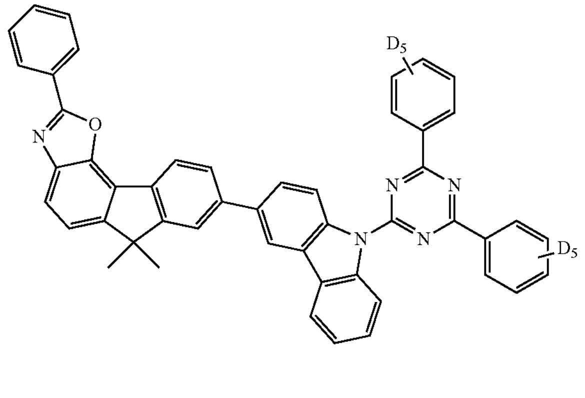
H13-D4
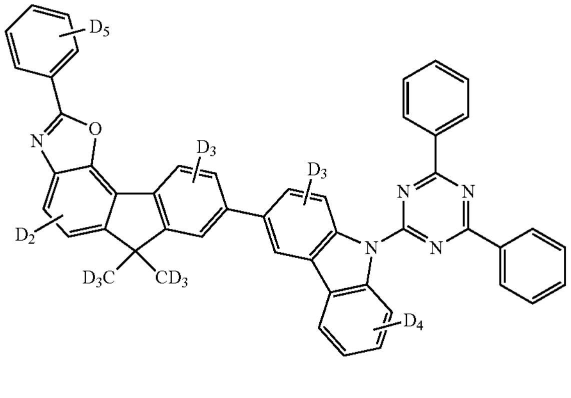

-continued
H13-D5
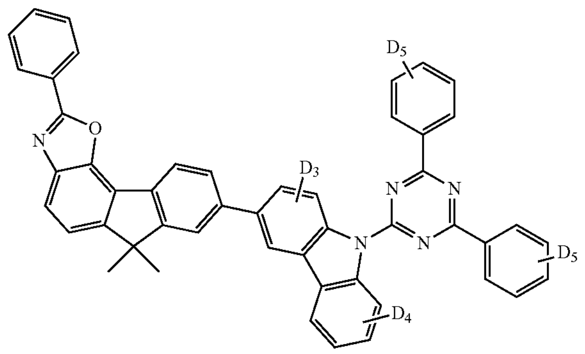
H13-D6
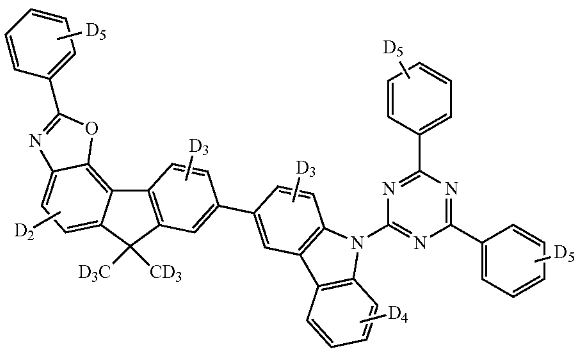
H14-D1
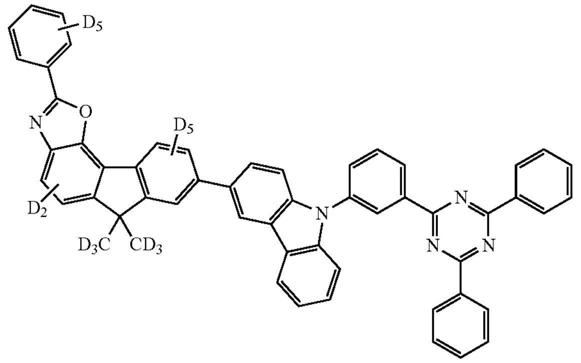
H14-D2
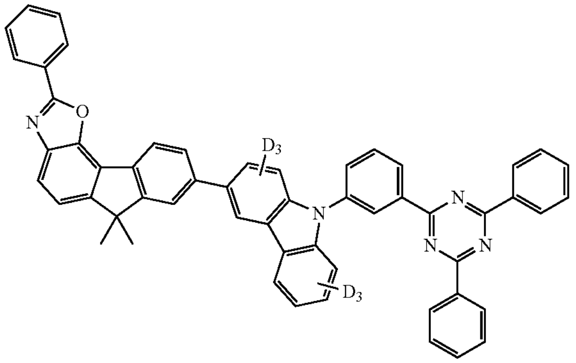
H14-D3
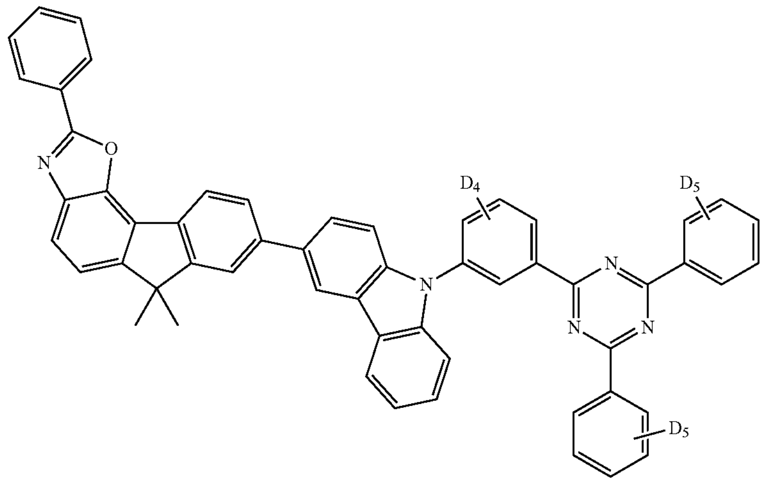

H14-D4
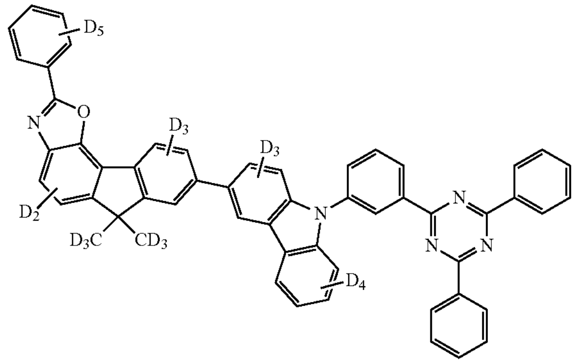
H14-D5
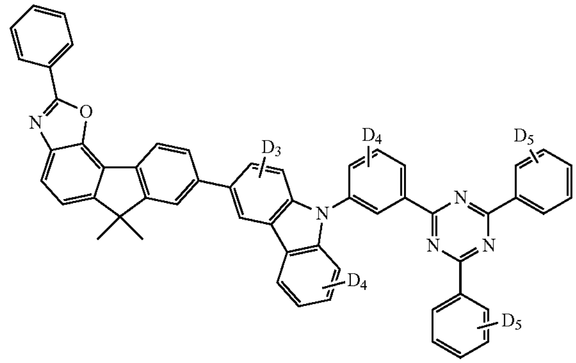
H14-D6
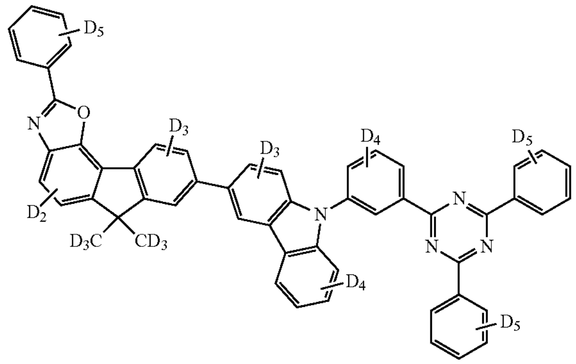
H15-D1
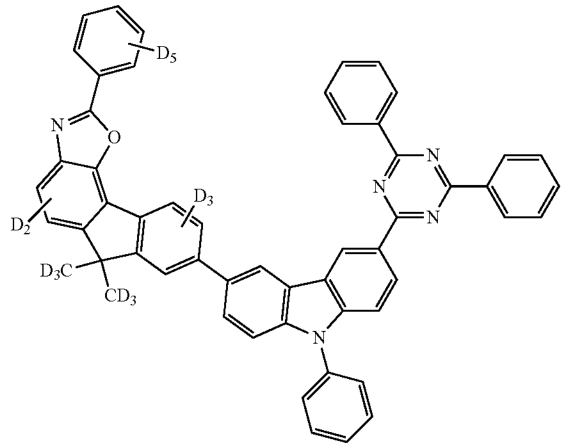
H15-D2
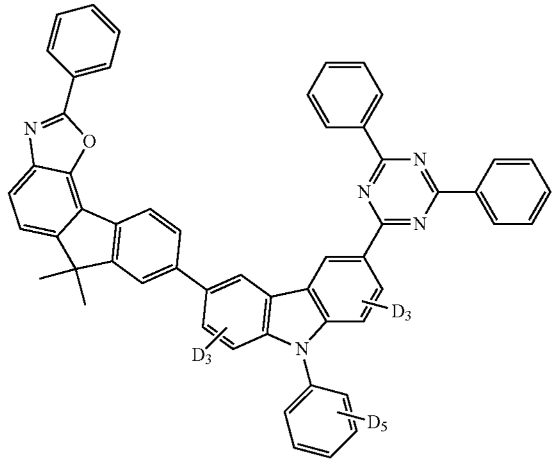
H15-D3
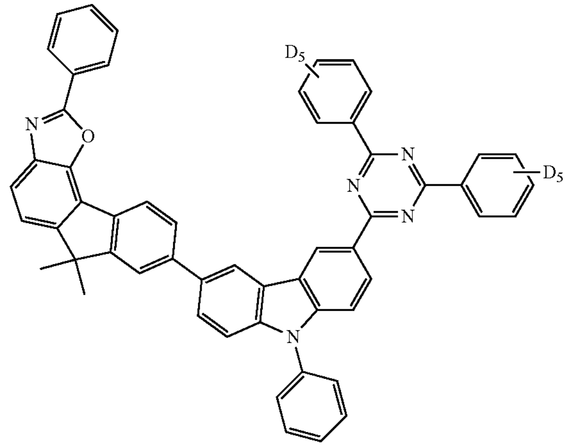

-continued
H15-D4
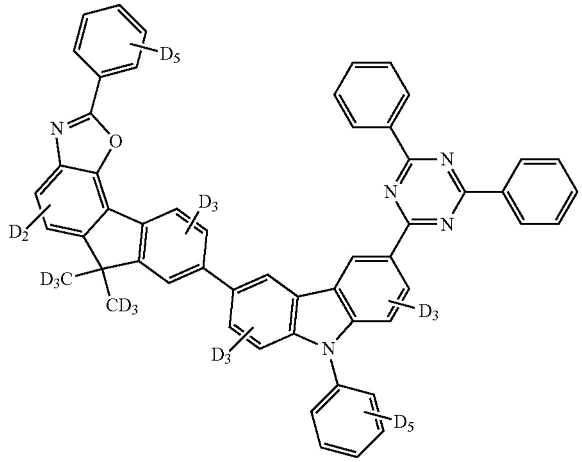
H15-D5
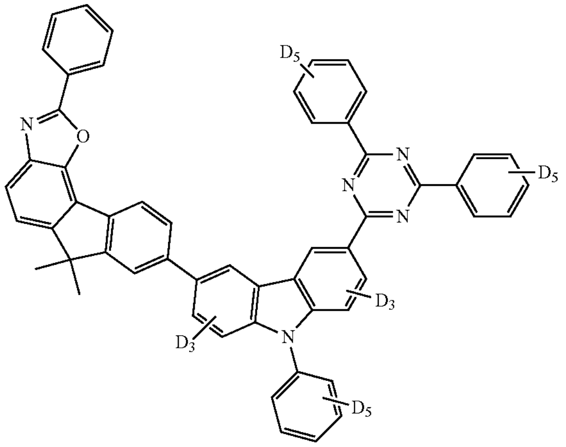
H15-D6
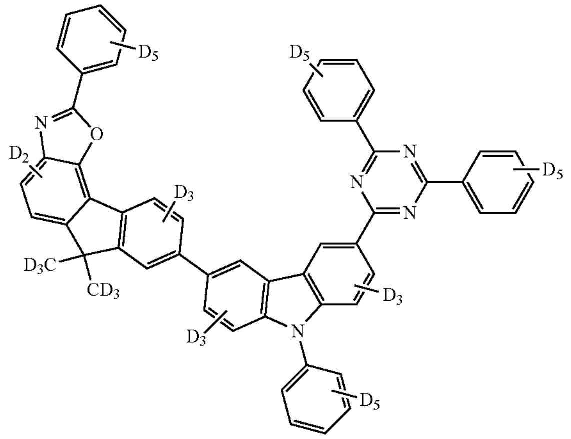
H16-D1
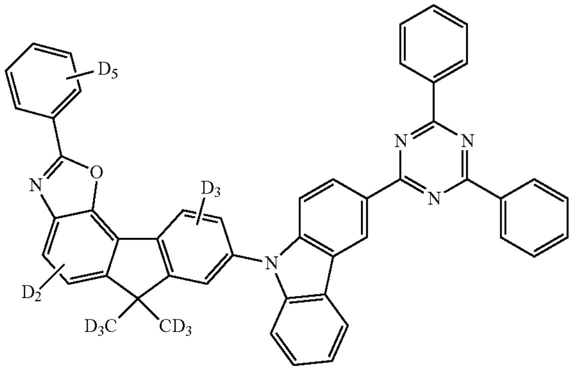
H16-D2
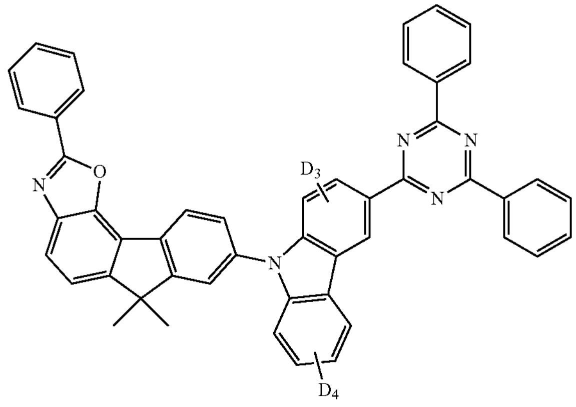
H16-D3
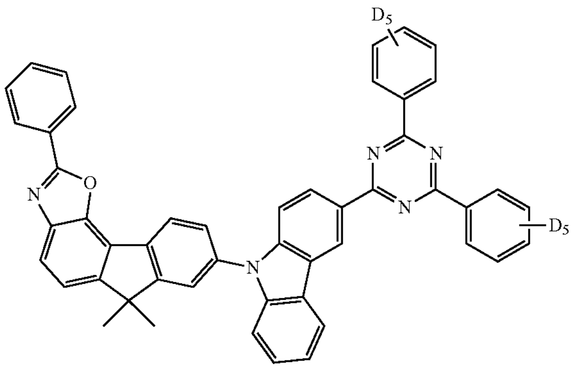

-continued
H16-D4
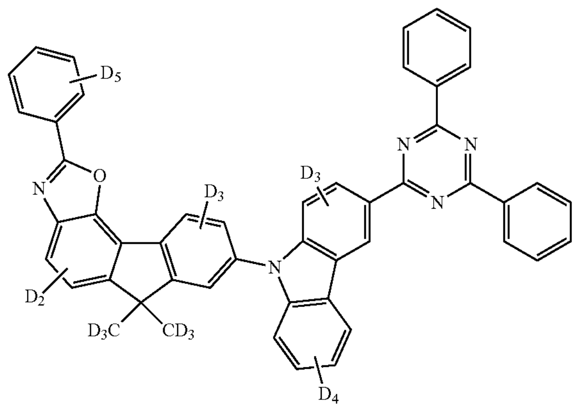
H16-D5
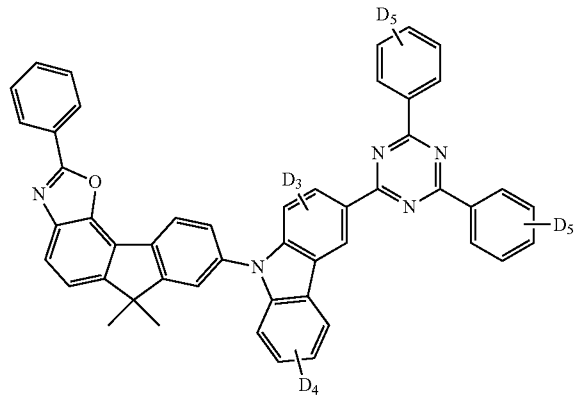
H16-D6
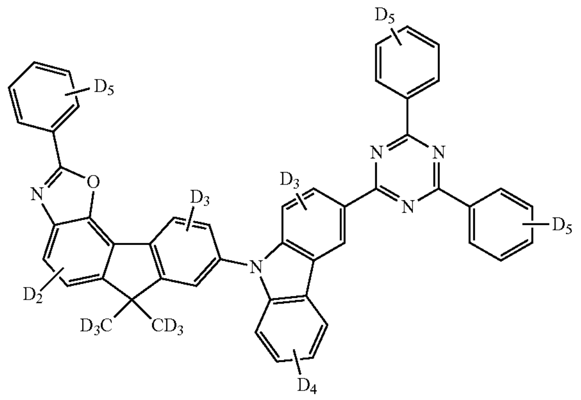
H17-D1
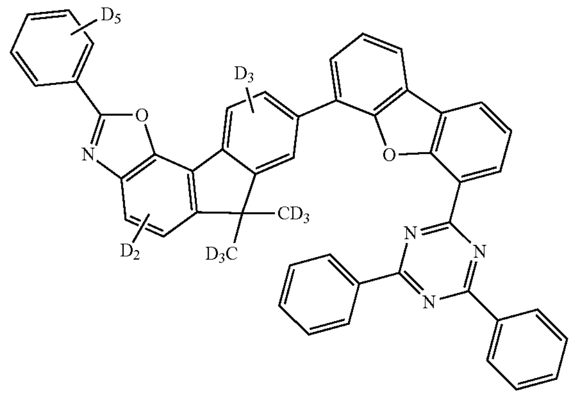
H17-D2
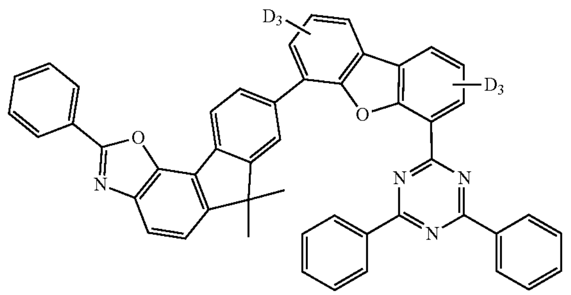
H17-D3
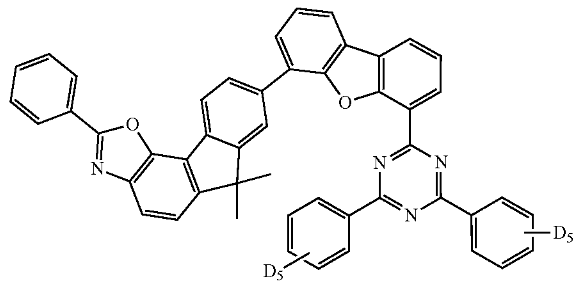
H17-D4
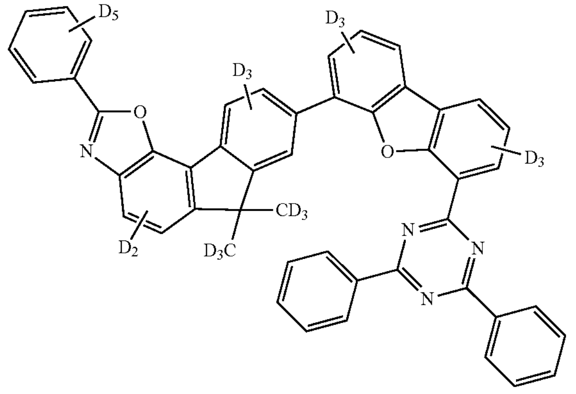
H17-D5
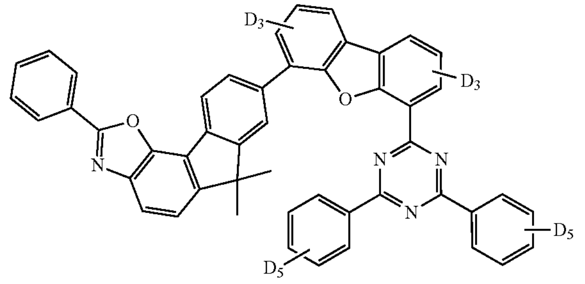

-continued
H17-D6
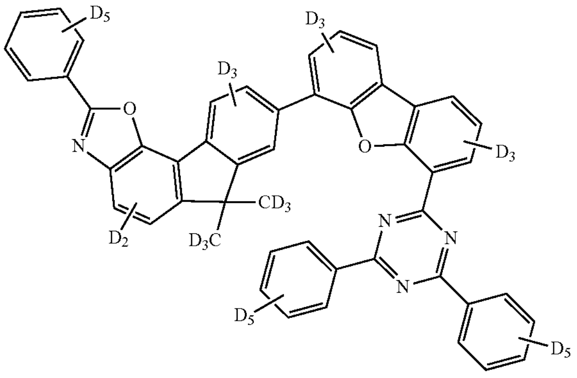
H18-D1
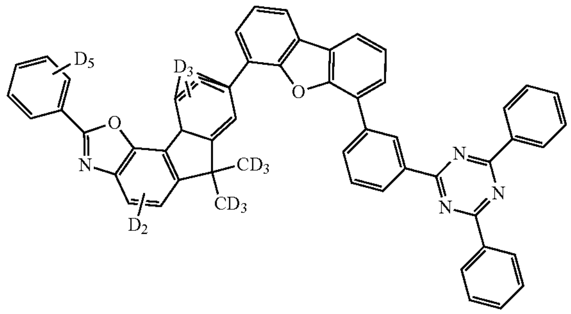
H18-D2
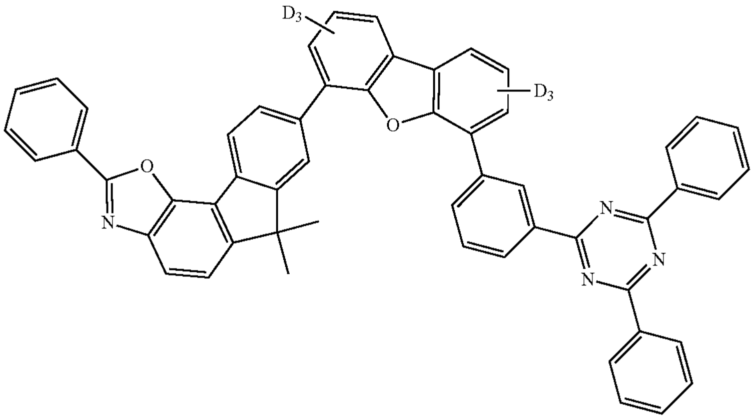
H18-D3
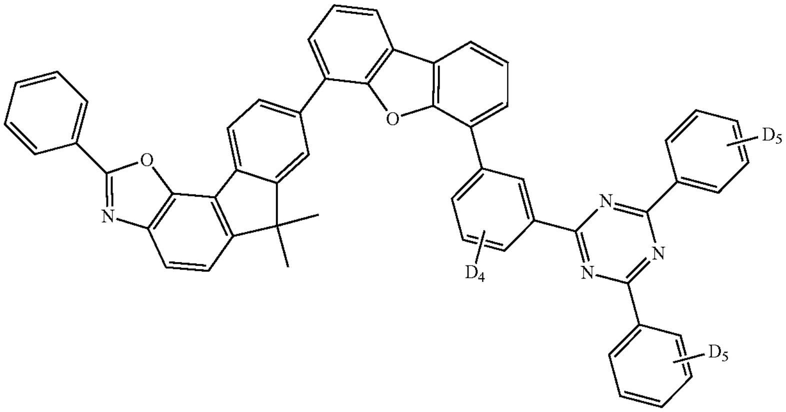
H18-D4
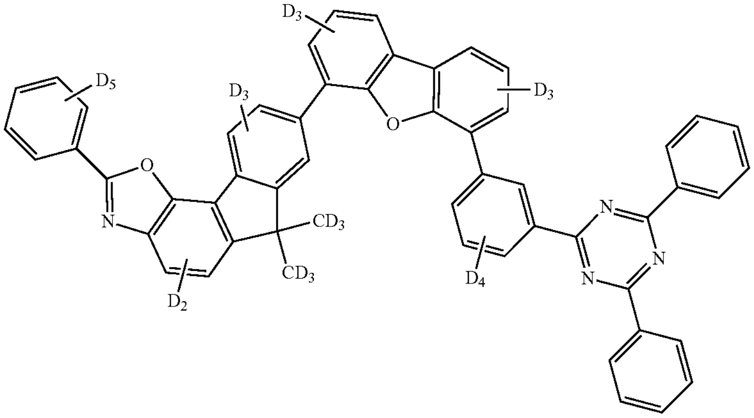

-continued
H18-D5
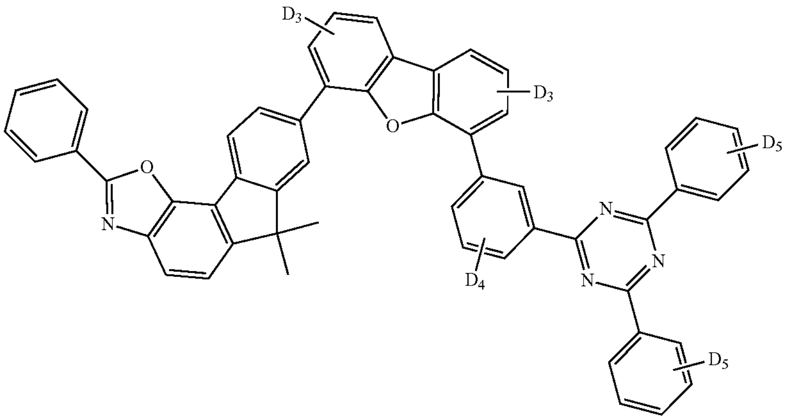
H18-D6
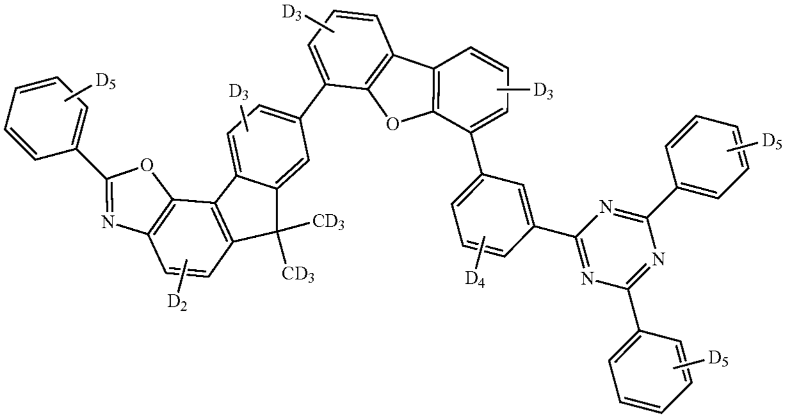
H19-D1
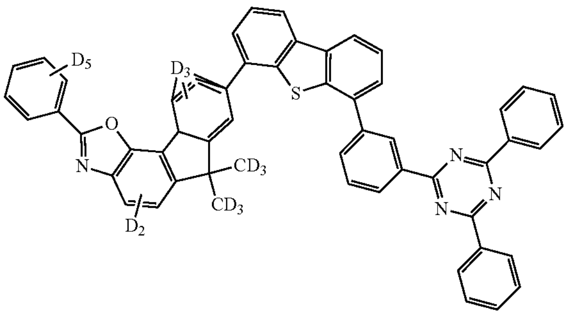
H19-D2
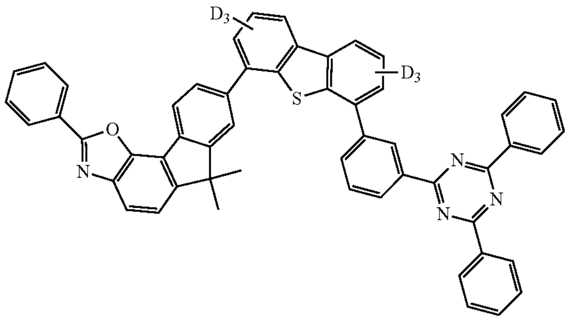
H19-D3
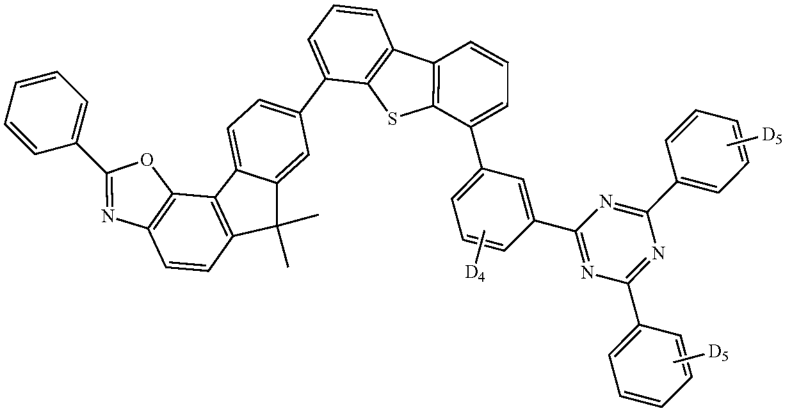

-continued
H19-D4
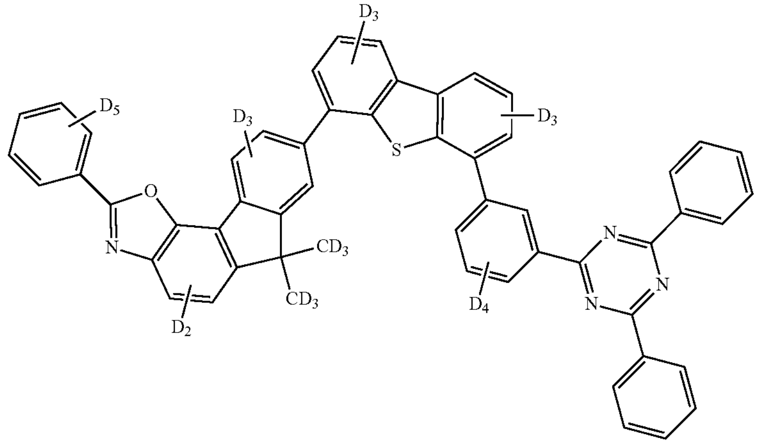
H19-D5
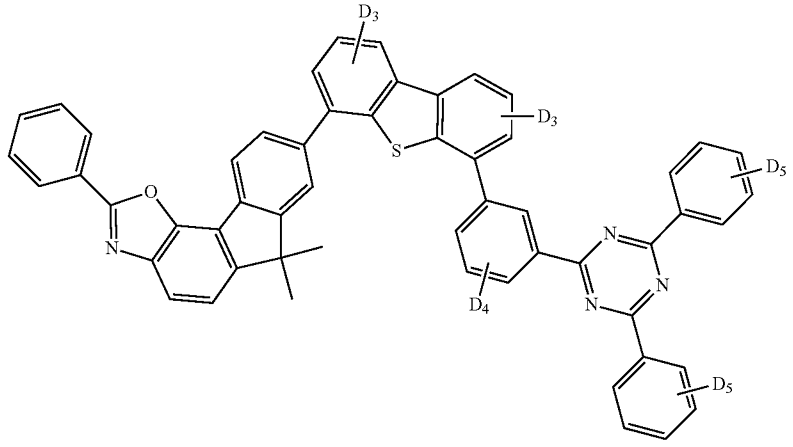
H19-D6
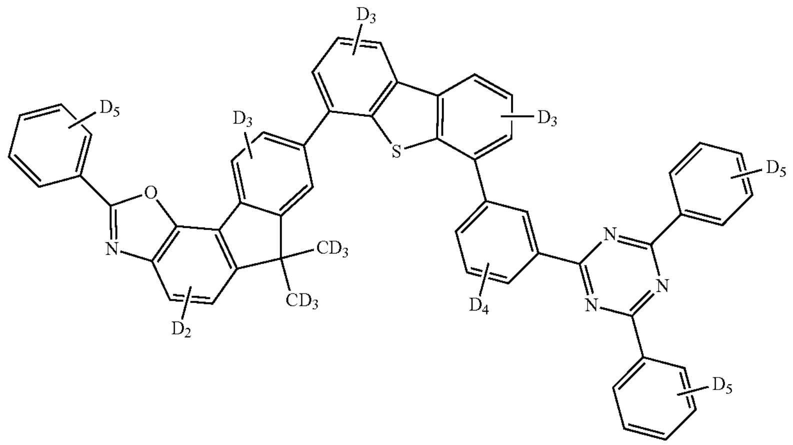

-continued
H20-D1
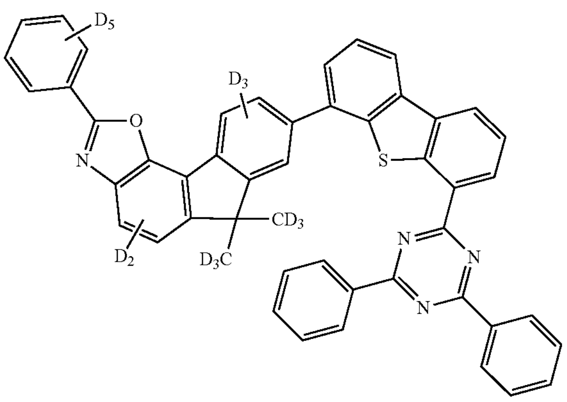
H20-D2
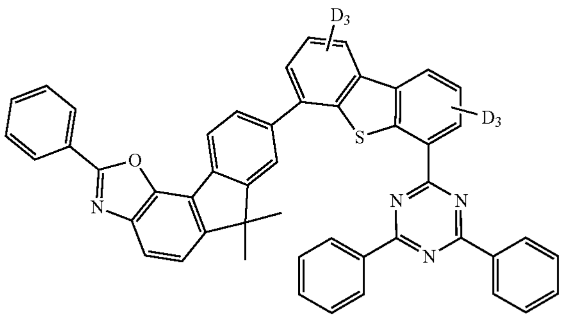
H20-D3
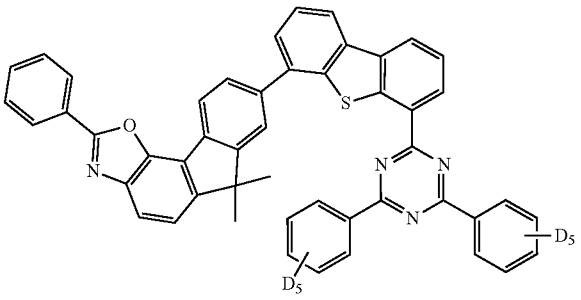
H20-D4
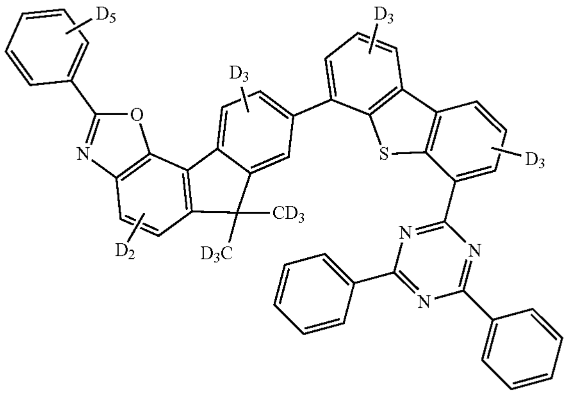
H20-D5
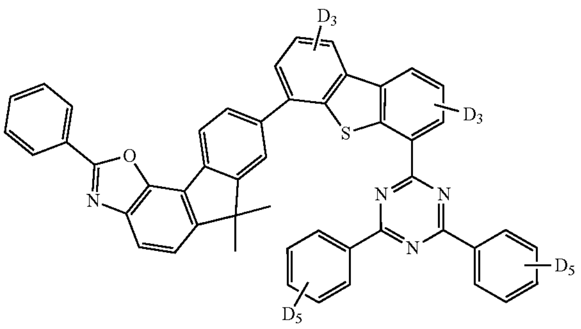
H20-D6
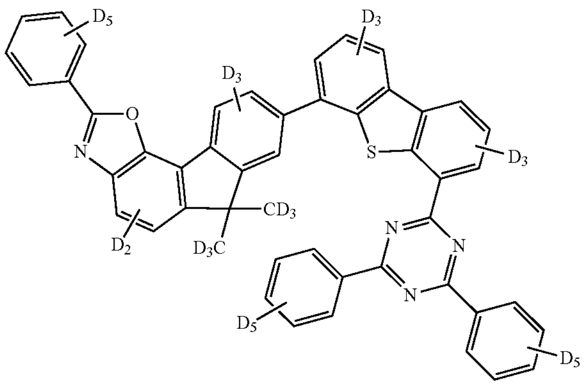
H21-D1
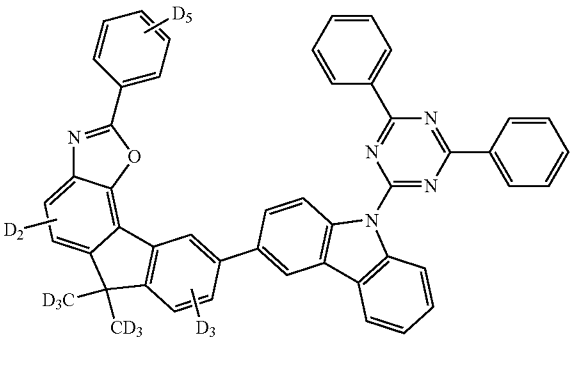
H21-D2
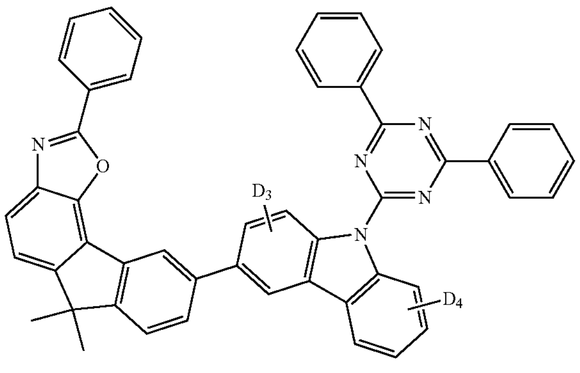

-continued
H21-D3
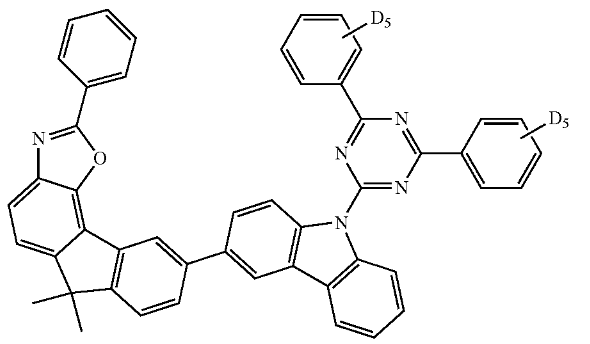
H21-D4
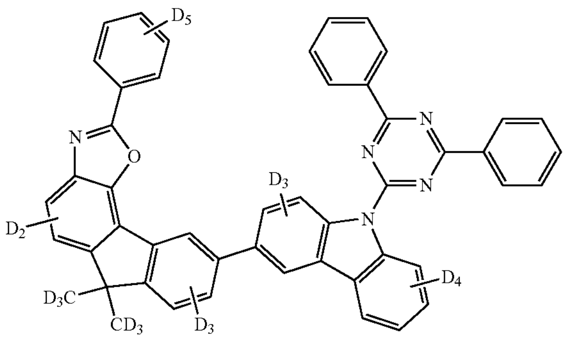
H21-D5
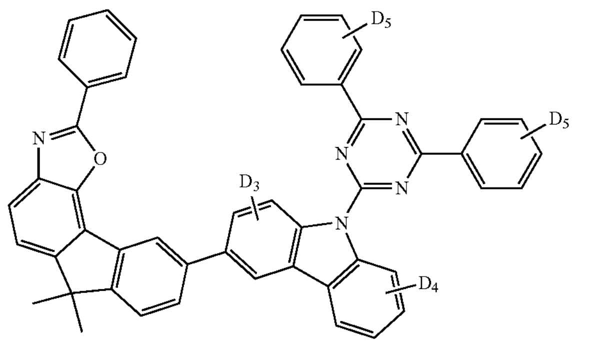
H21-D6
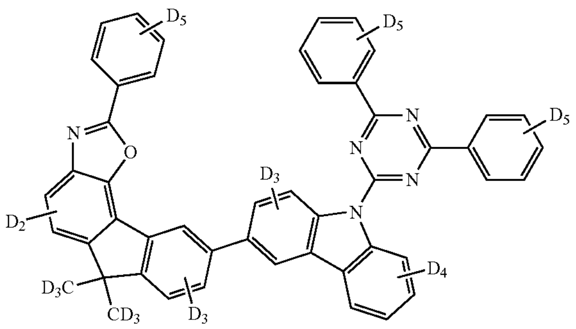
H22-D1
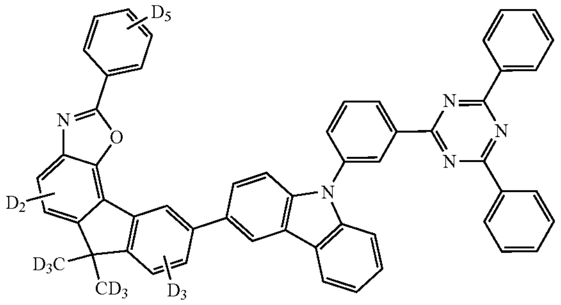
-continued
H22-D3
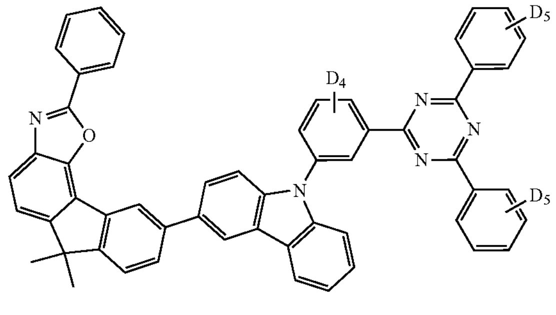
H22-D2
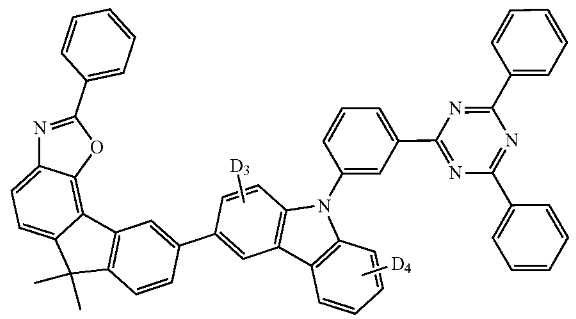
H22-D4
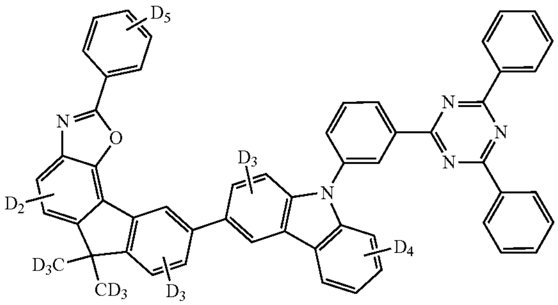

-continued
H22-D5
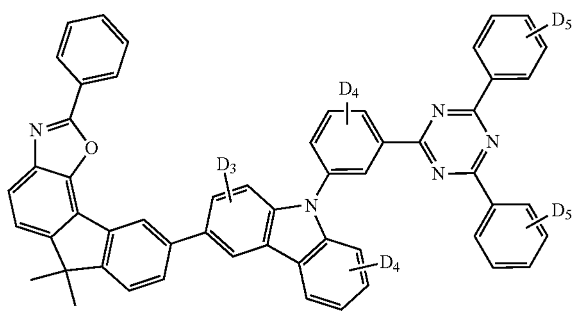
H22-D6
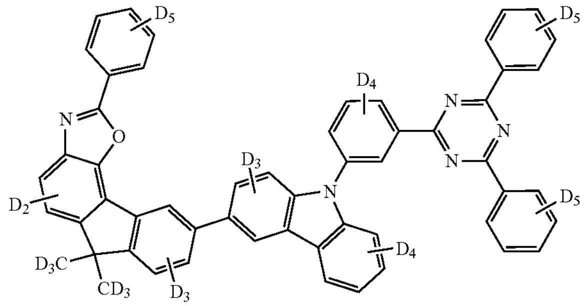
H23-D1
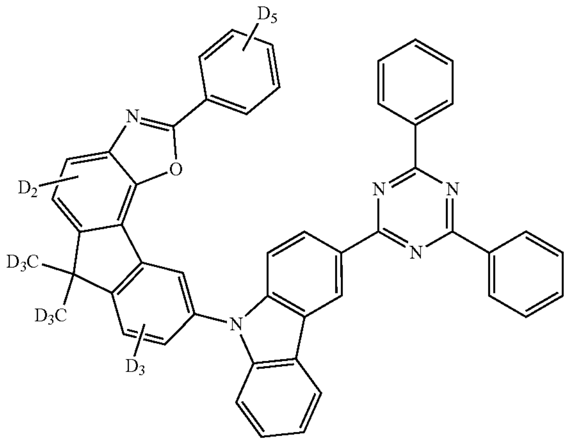
H23-D2
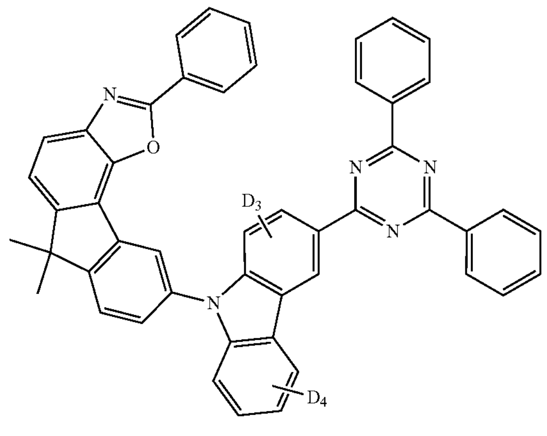
-continued
H23-D3
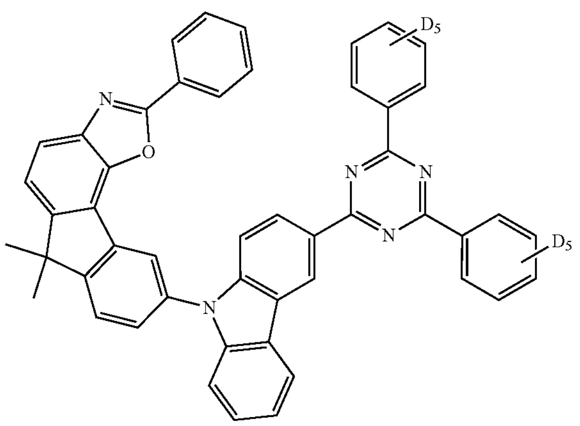
H23-D4
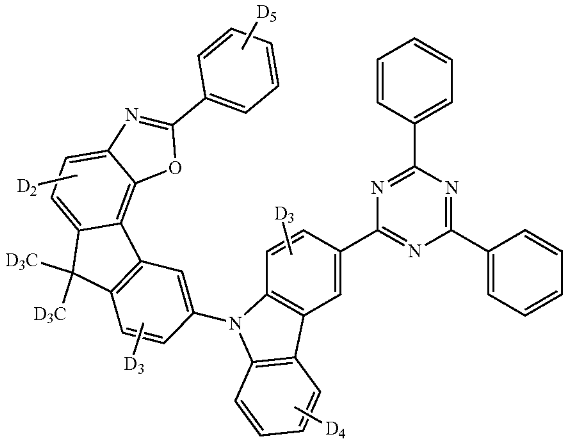
H23-D5
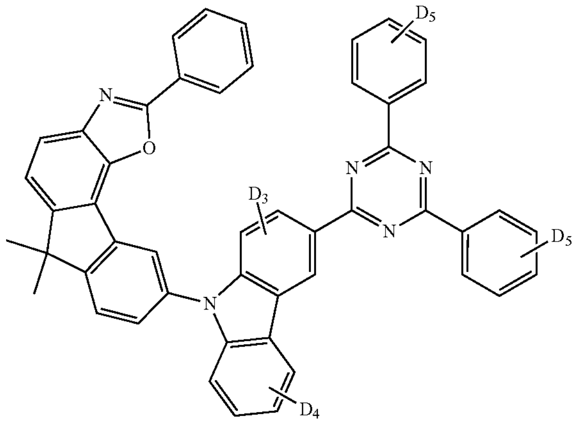

H23-D6
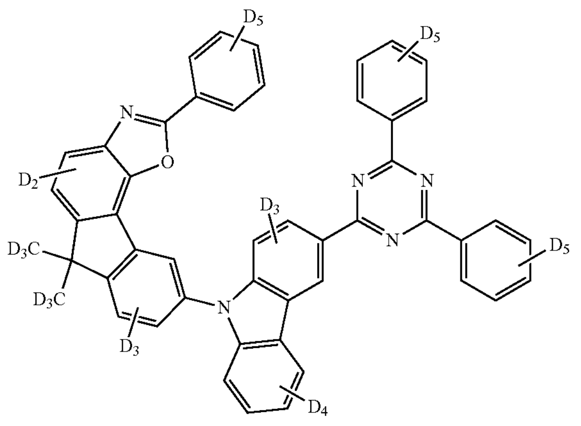
H24-D1
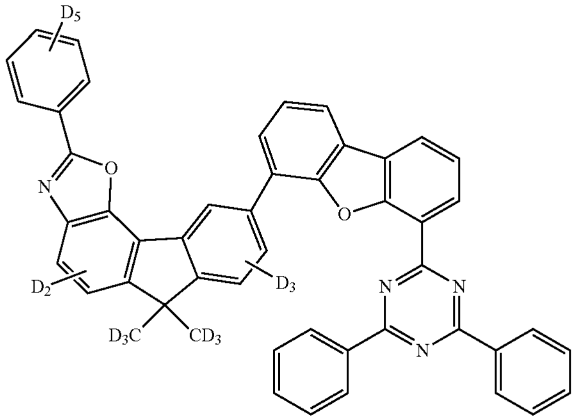
H24-D2
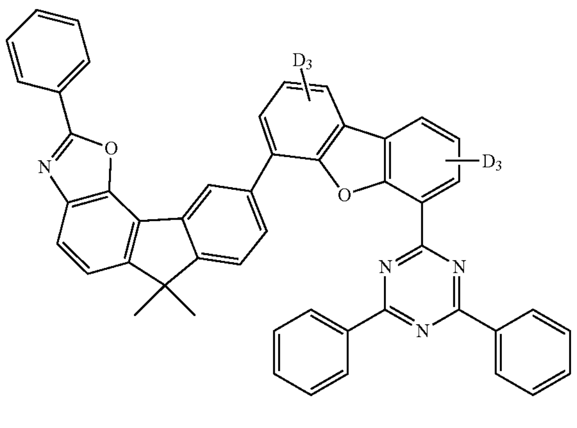
H24-D3
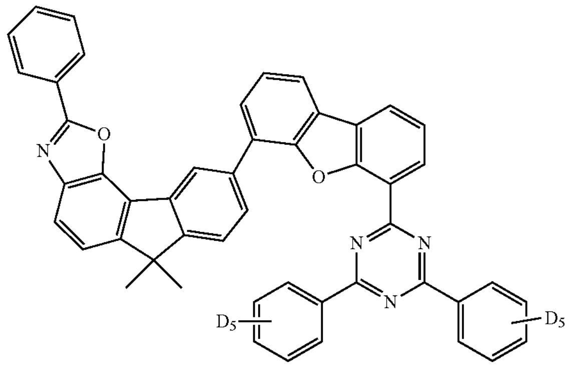
H24-D4
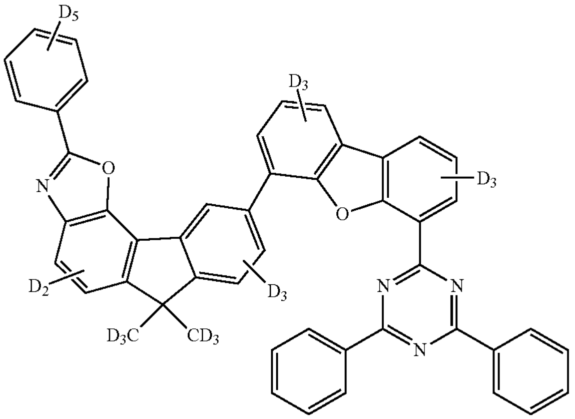
H24-D5
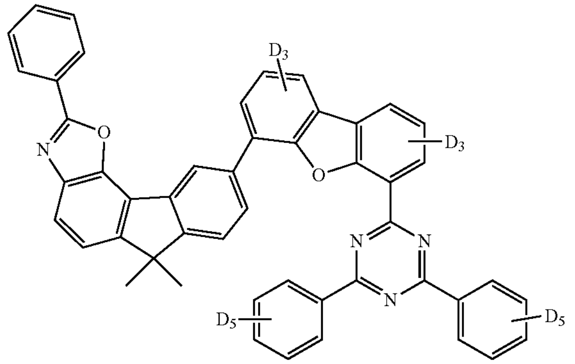
H24-D6
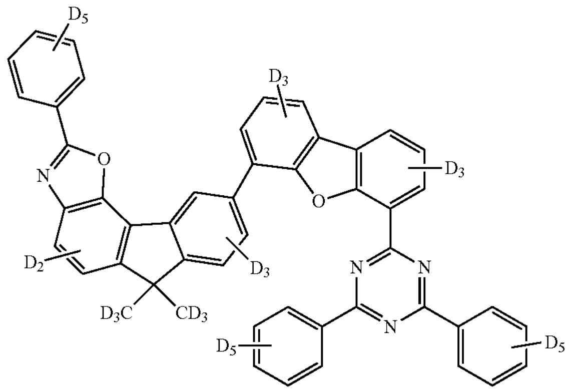

-continued
H25-D1
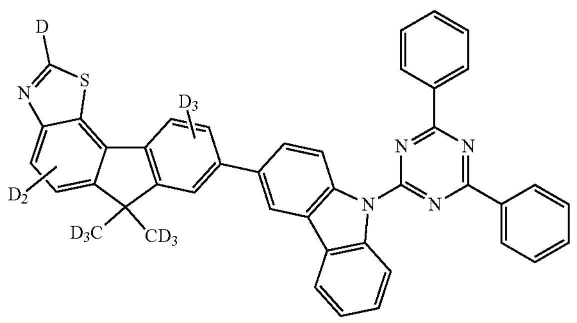
H25-D2
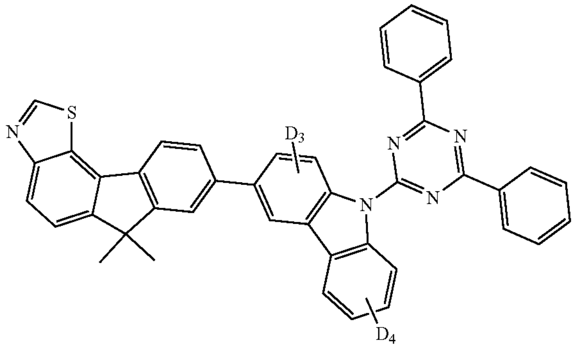
H25-D3
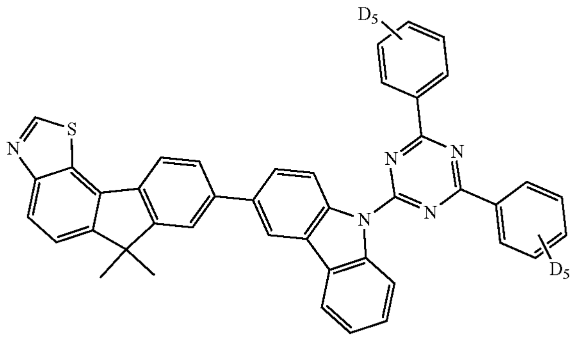
H25-D4
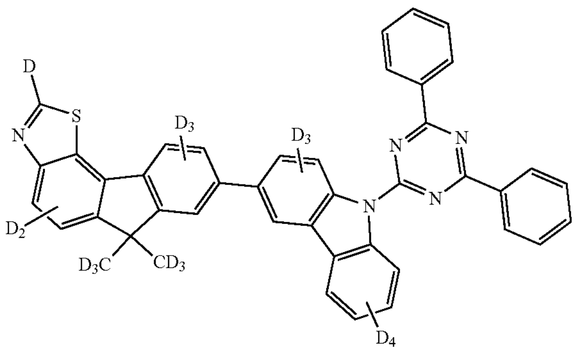
-continued
H25-D5
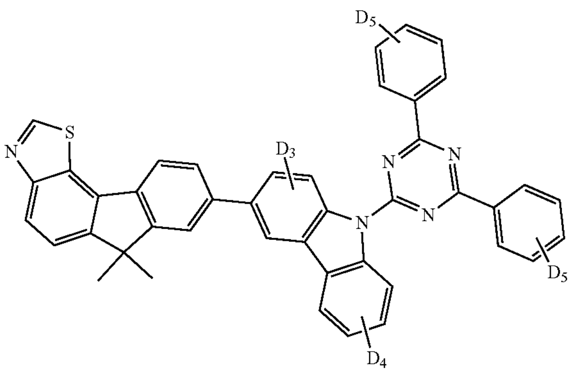
H25-D6
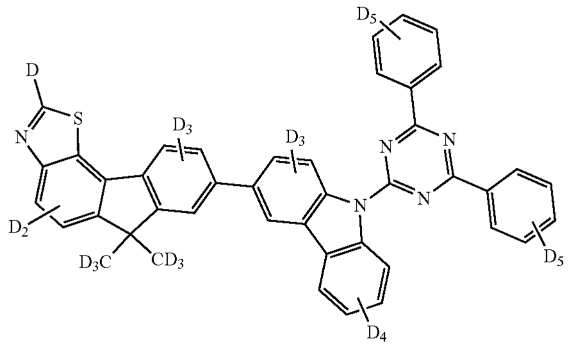
H26-D1
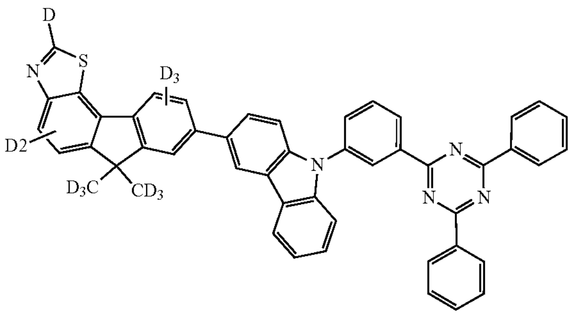
H26-D2
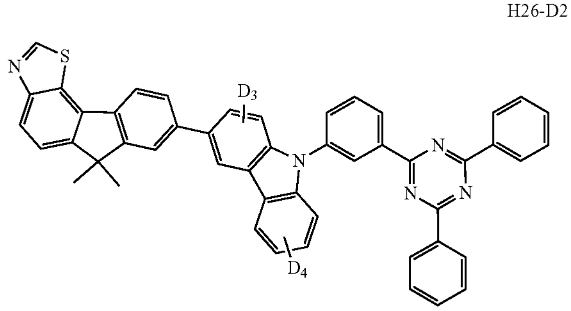

-continued
H26-D3
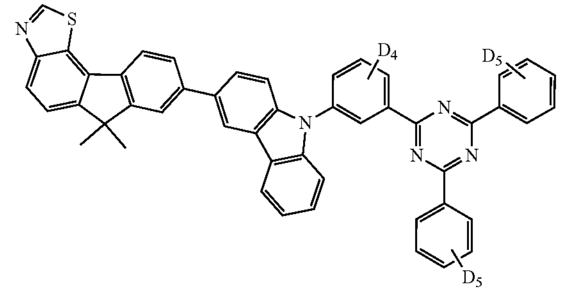
H26-D4
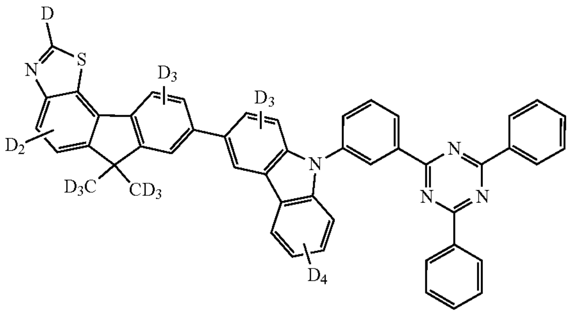
H26-D5
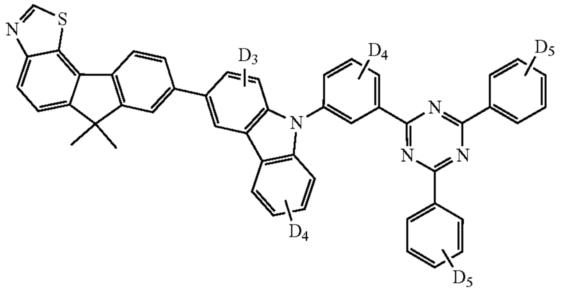
H26-D6
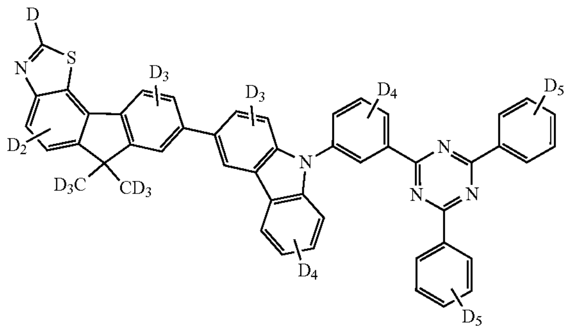
-continued
H27-D1
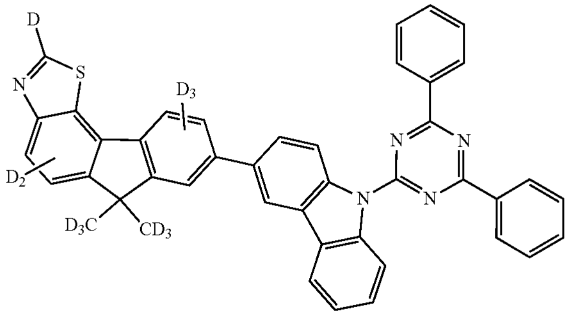
H27-D2
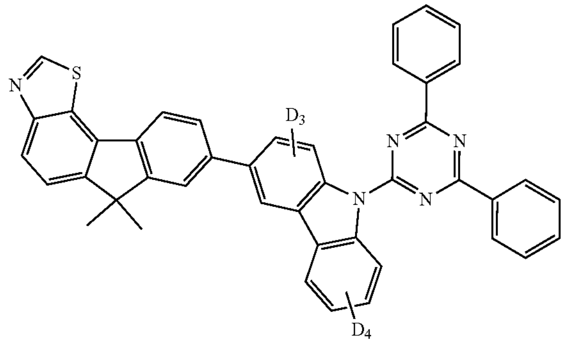
H27-D3
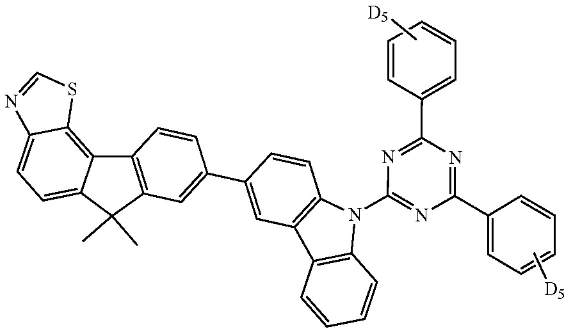
H27-D4
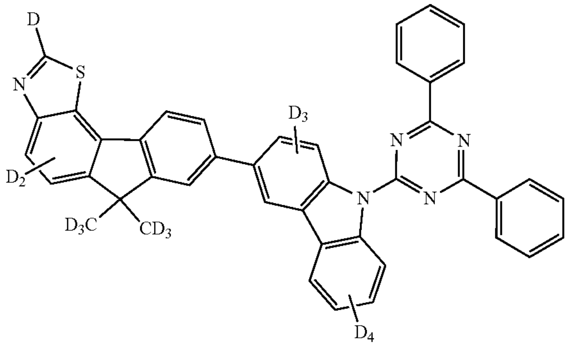

H27-D5
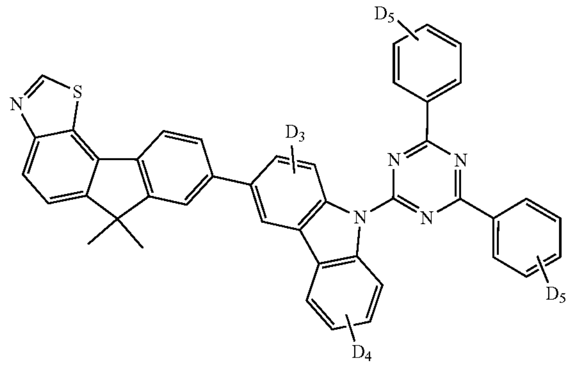
H27-D6
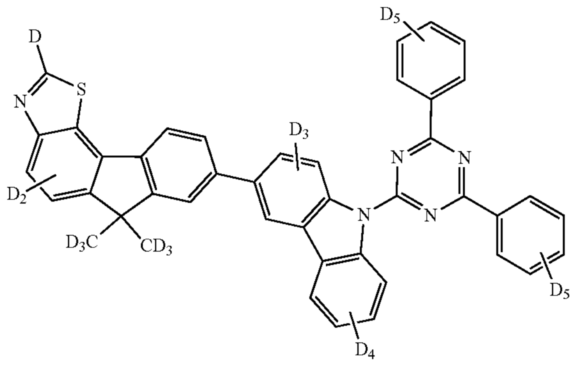
H28-D1
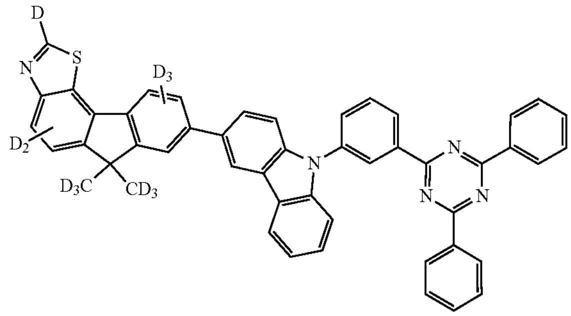
H28-D2
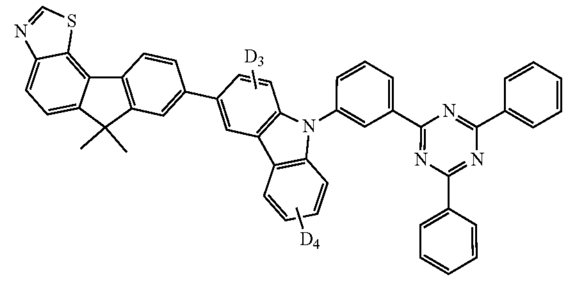
H28-D3
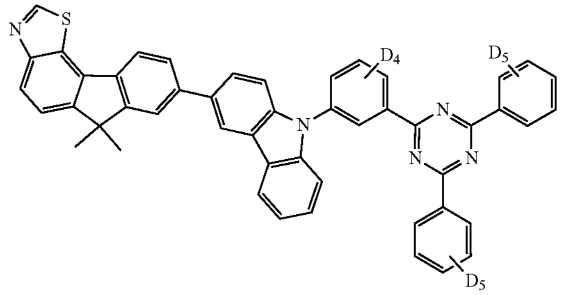
H28-D4
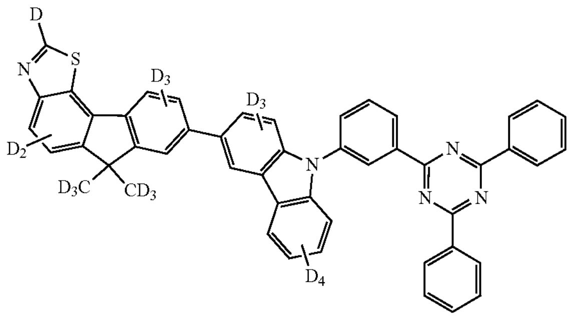
H28-D5
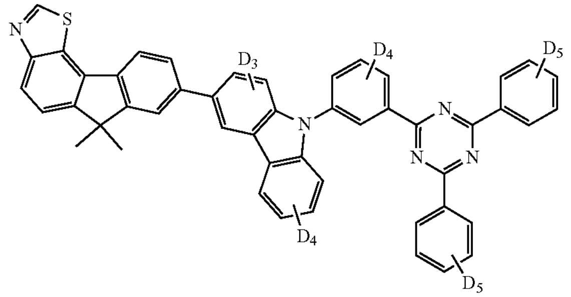
H28-D6
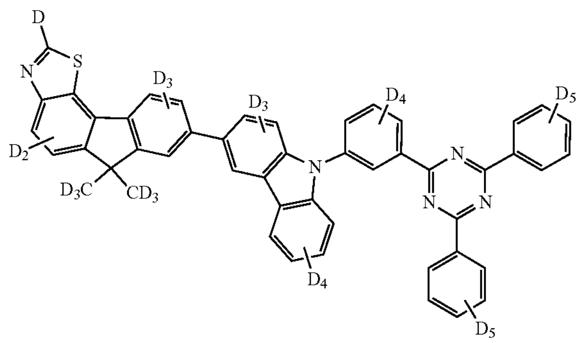

-continued
H29-D1
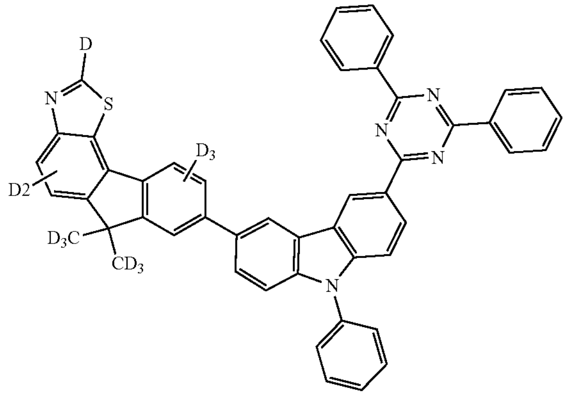
H29-D2
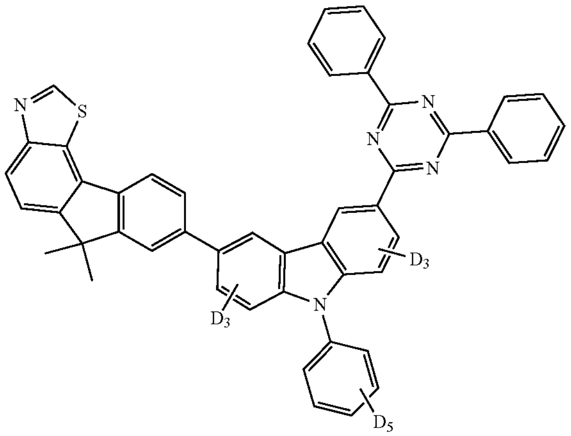
H29-D3
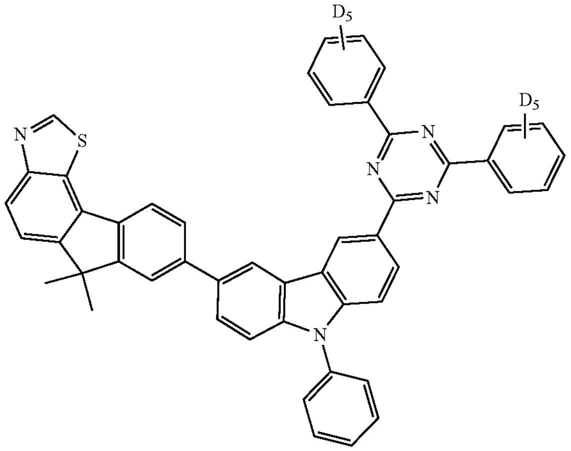
H29-D4
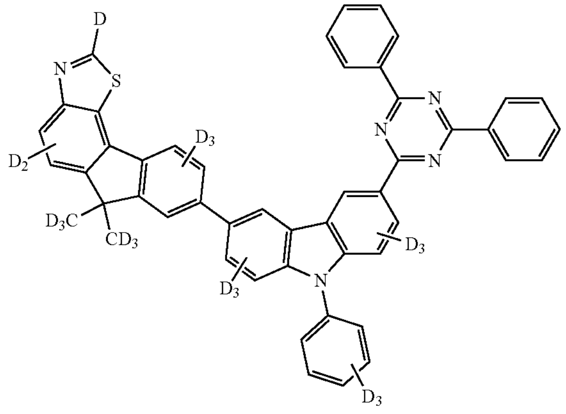
H29-D5
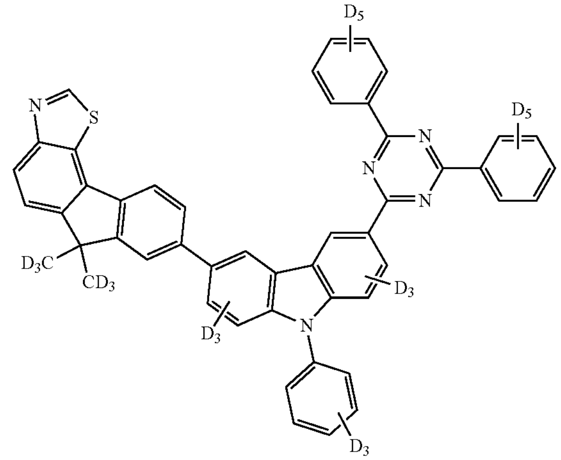
H29-D6
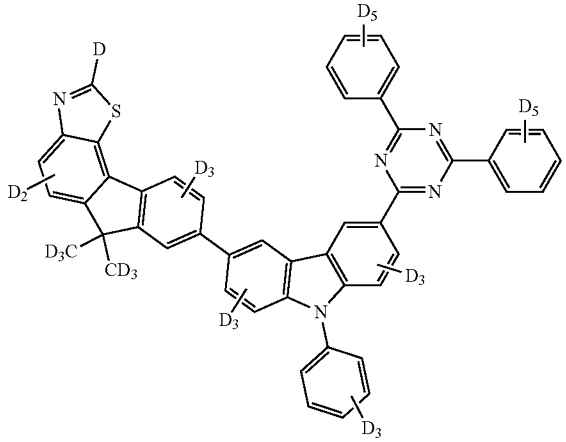

-continued
H30-D1
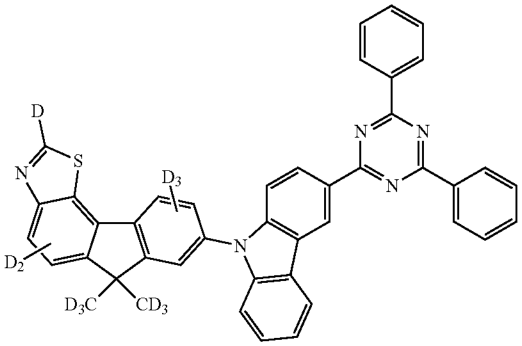
H30-D2
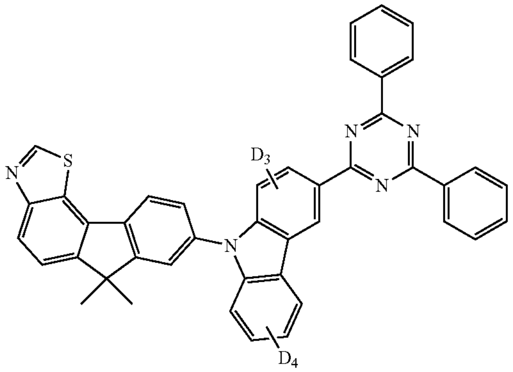
H30-D3
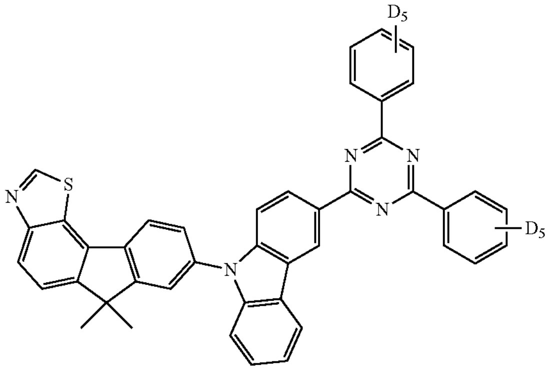
H30-D4
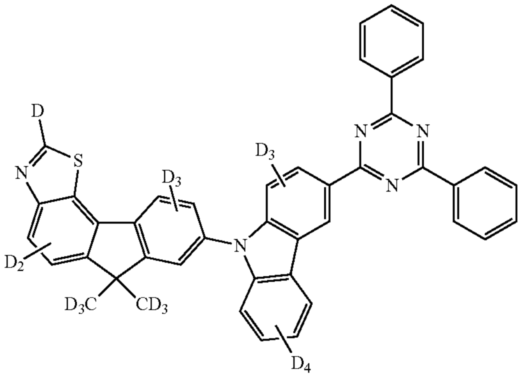
-continued
H30-D5
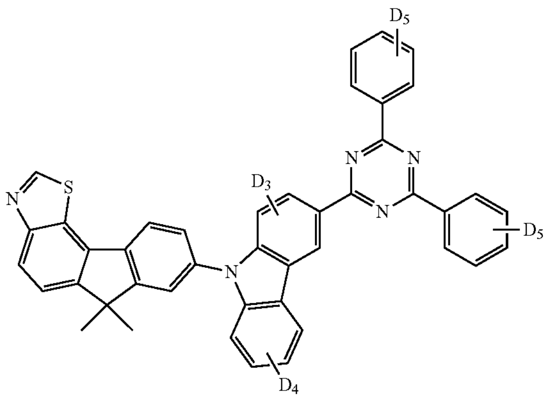
H30-D6
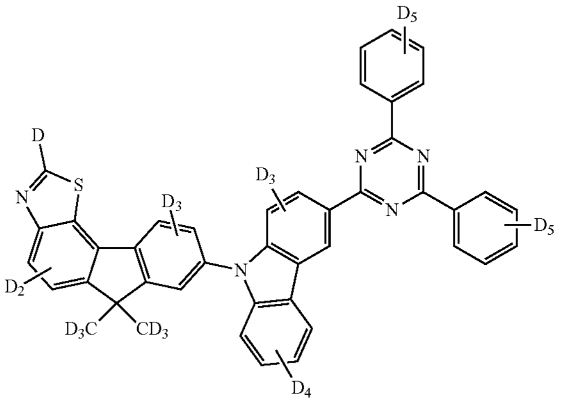
H31-D1
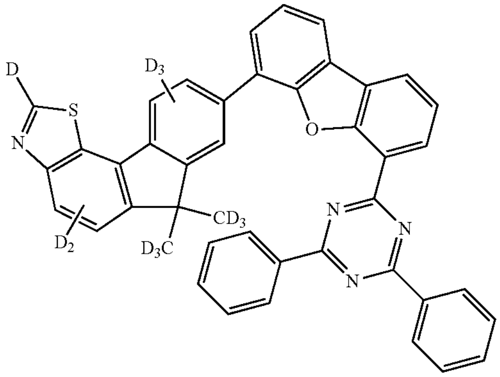
H31-D2
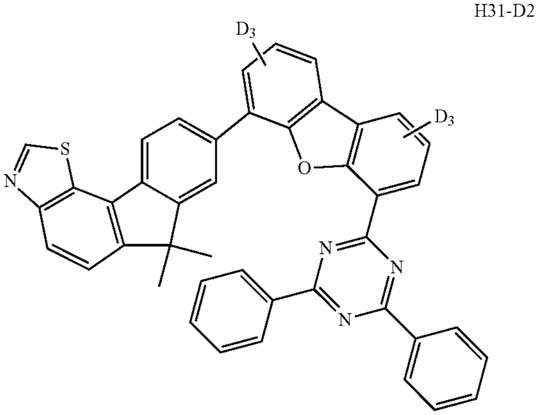

-continued
H31-D3
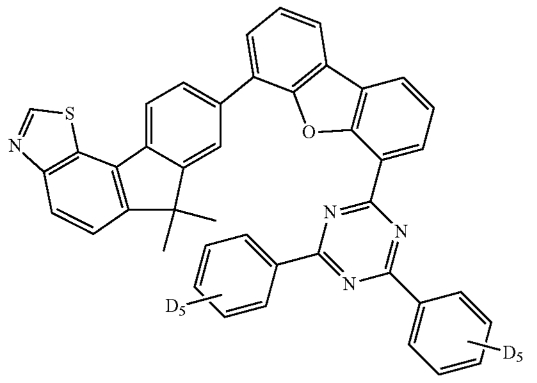
H31-D4
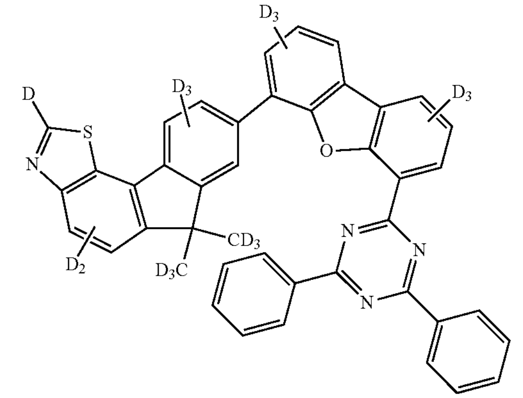
H31-D5
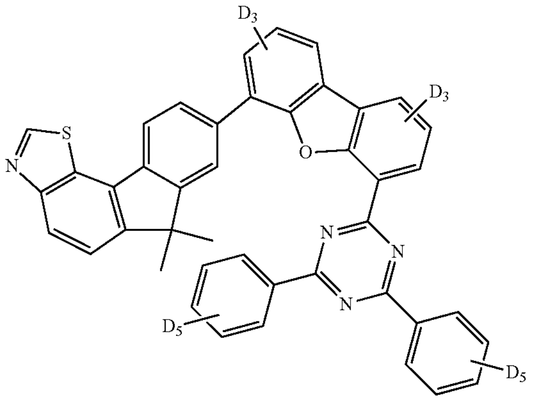
H31-D6
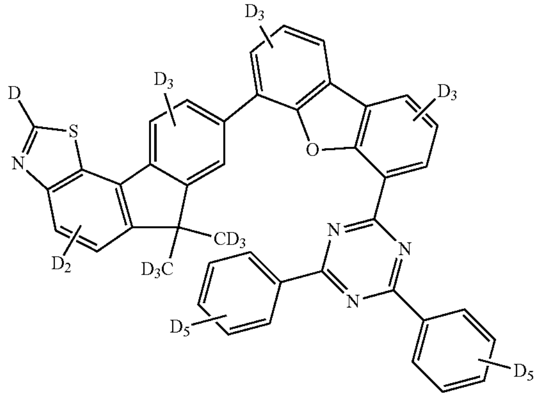
-continued
H32-D1
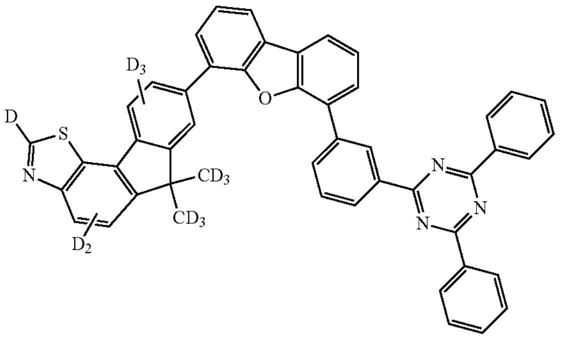
H32-D2
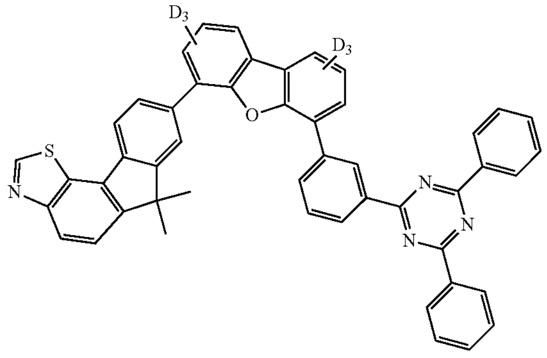
H32-D3
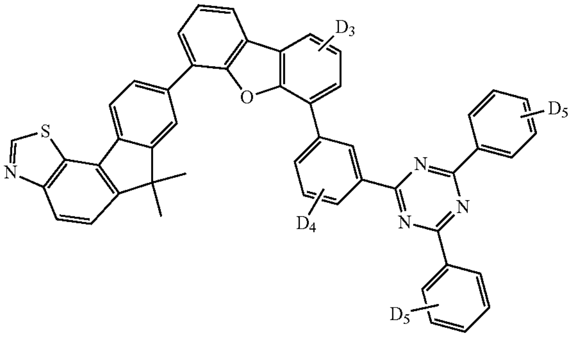
H32-D4
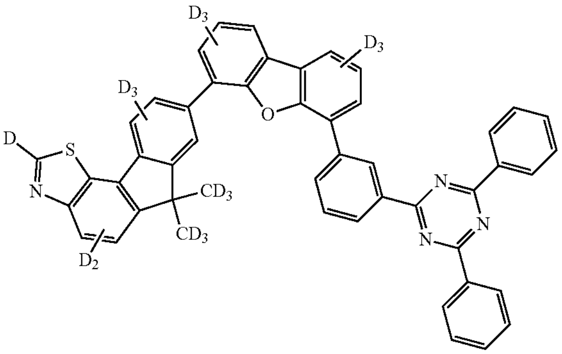

-continued
H32-D5
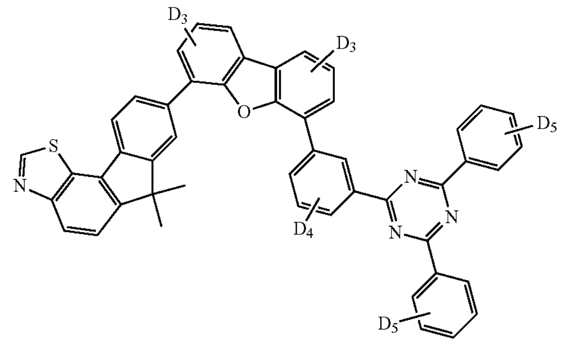
H32-D6
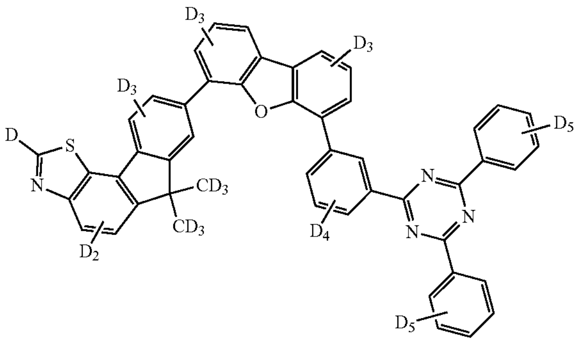
H33-D1
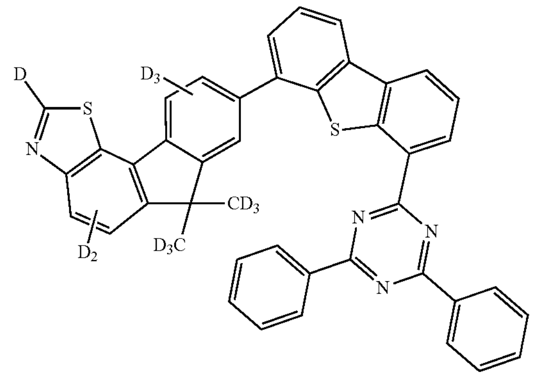
H33-D2
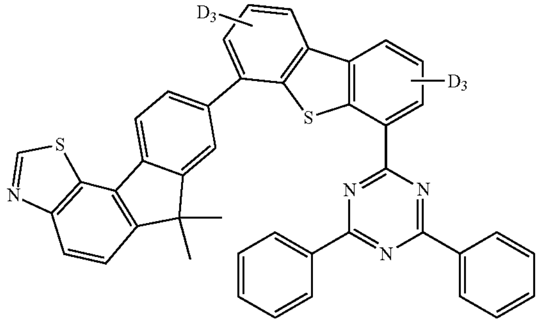
-continued
H33-D3
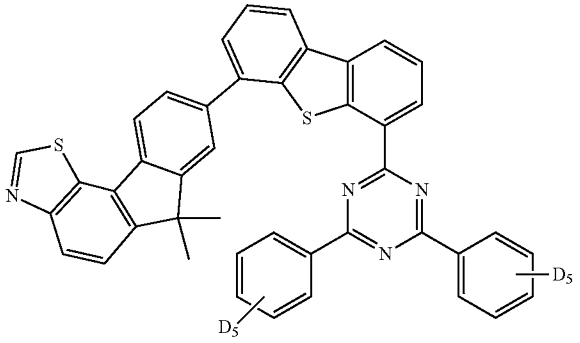
H33-D4
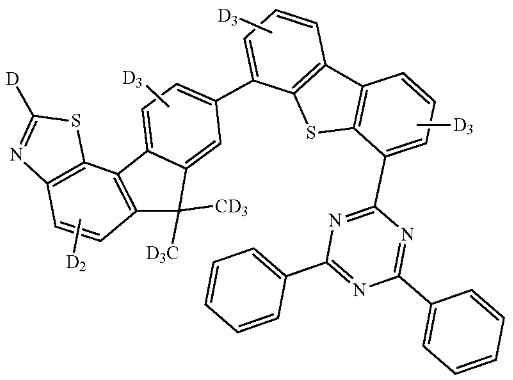
H33-D5
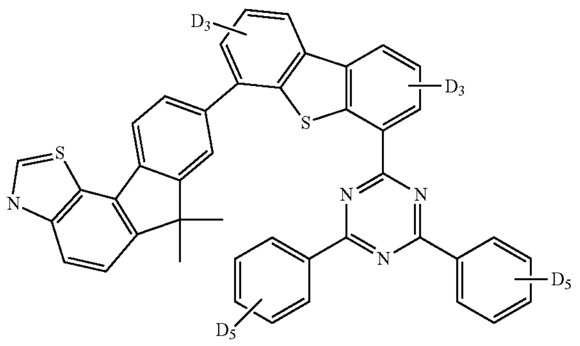
H33-D6
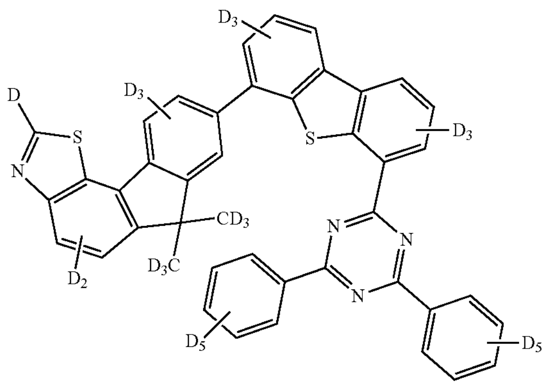

-continued
H34-D1
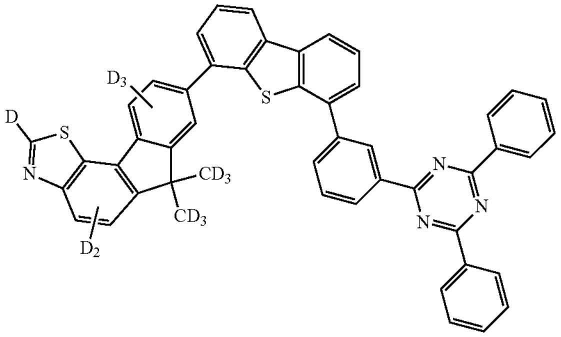
H34-D2
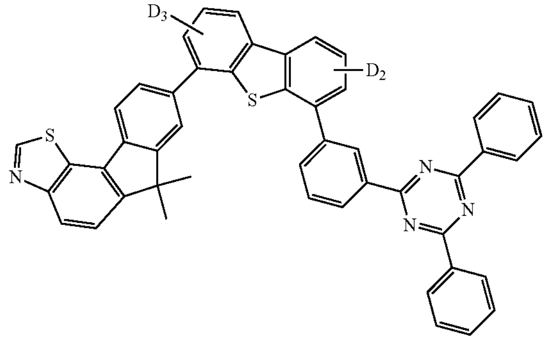
H34-D3
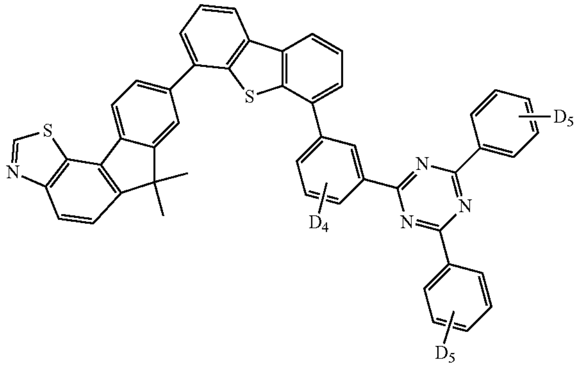
H34-D4
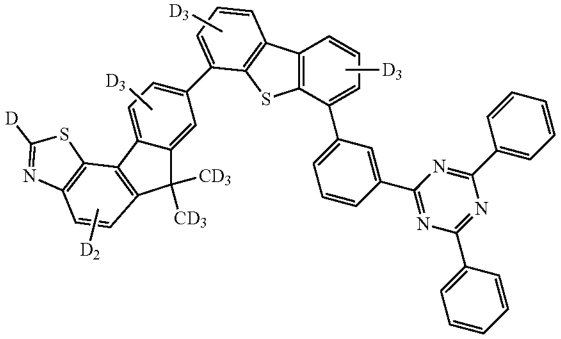
H34-D5
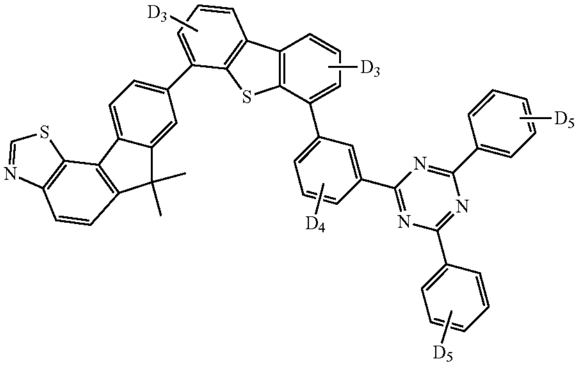
H34-D6
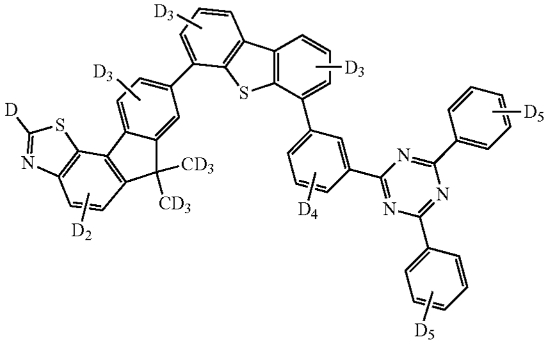
H35-D1
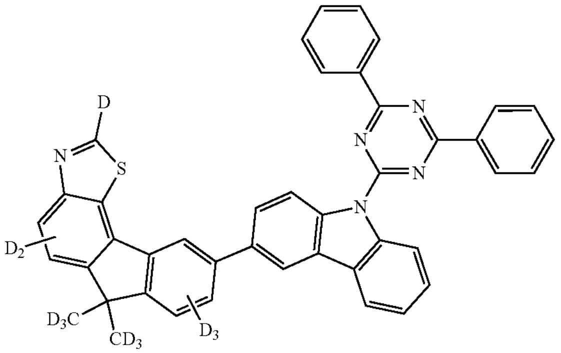
H35-D2
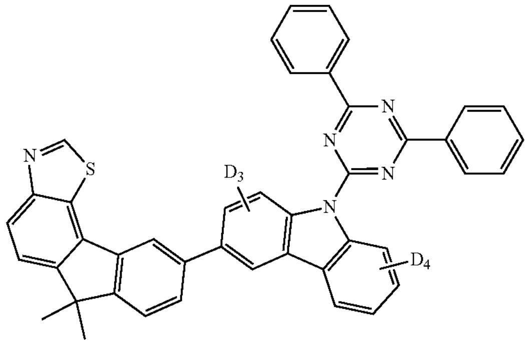

-continued
H35-D3
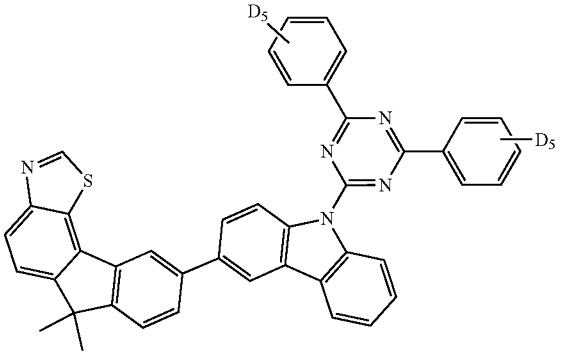
H35-D4
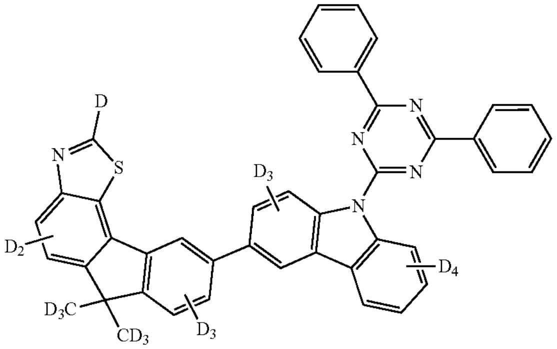
H35-D5
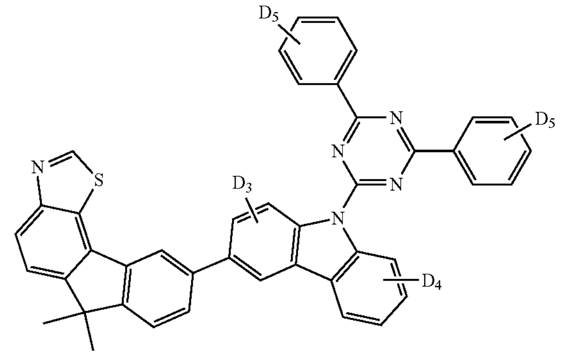
H35-D6
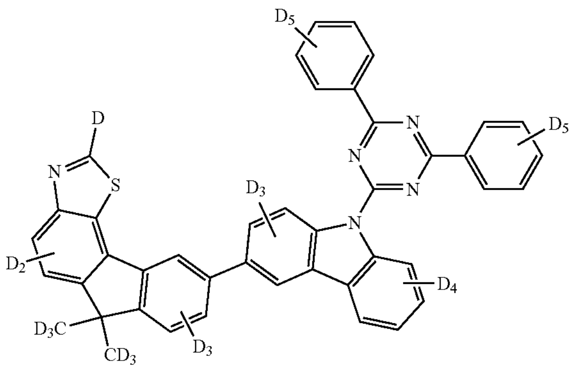
-continued
H36-D1
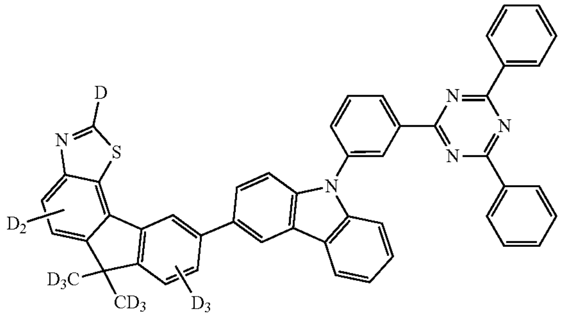
H36-D2
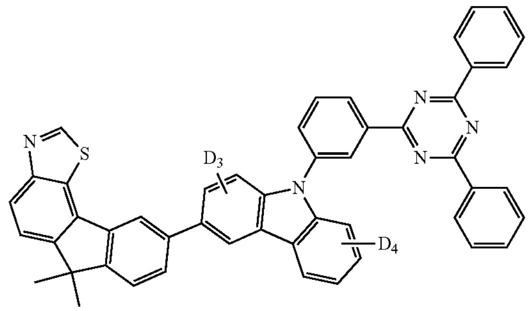
H36-D3
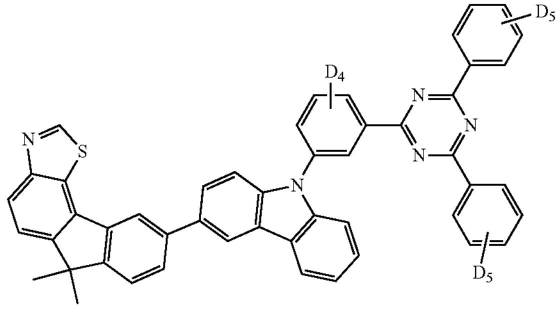
H36-D4
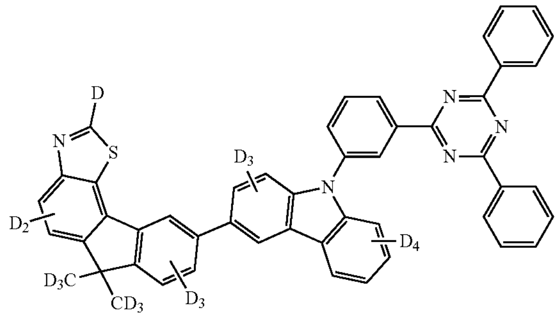

-continued
H36-D5
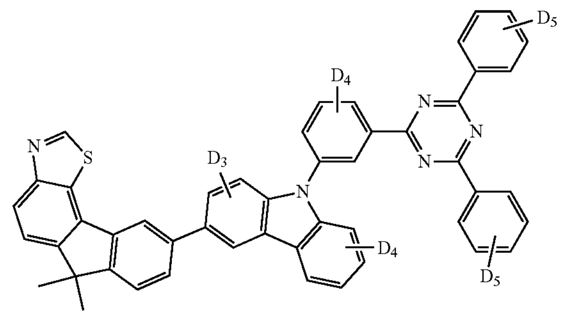
-continued
H36-D6
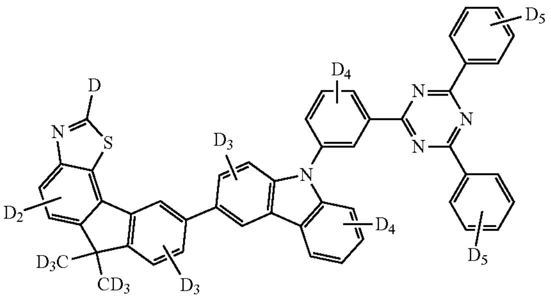
H37-D1
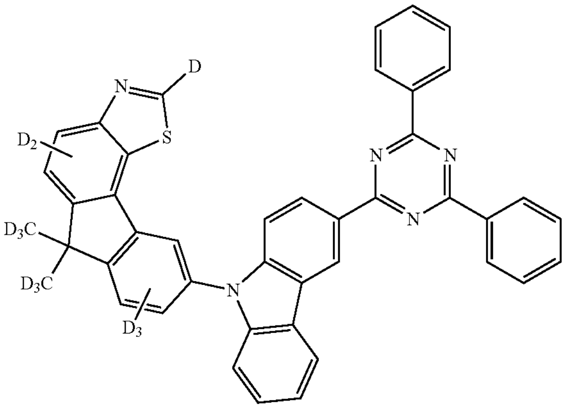
H37-D2
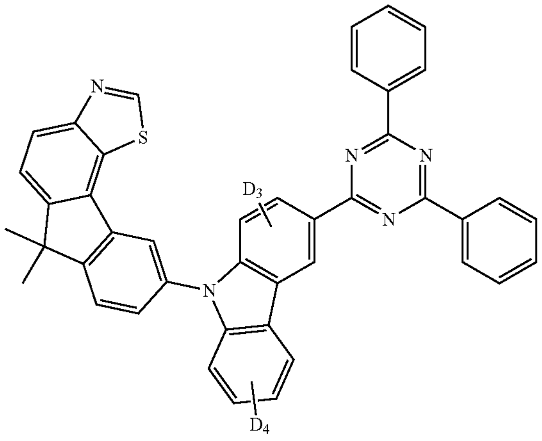
H37-D3
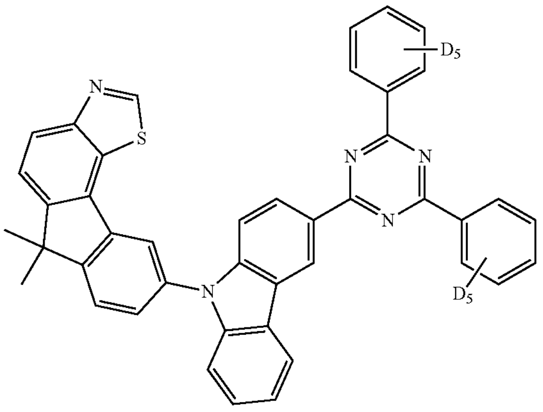
H37-D4
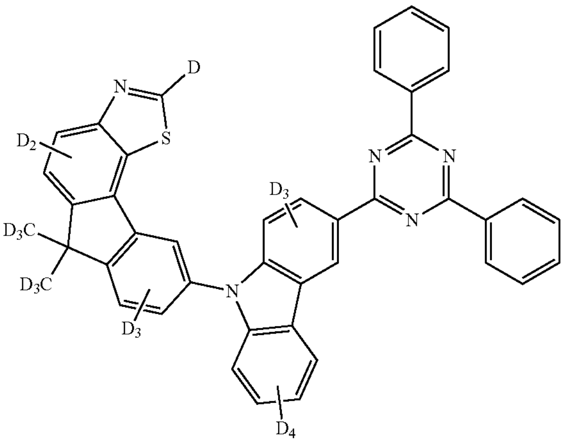

-continued
H37-D5
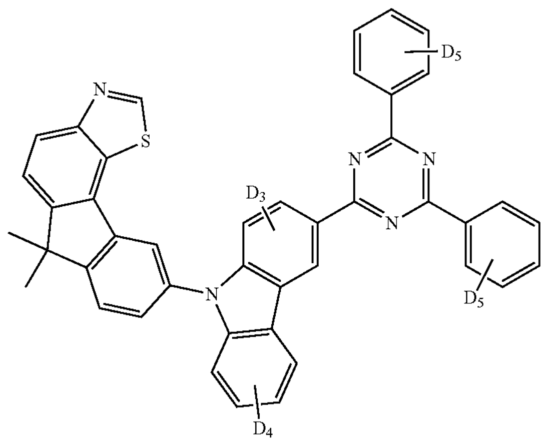
H37-D6
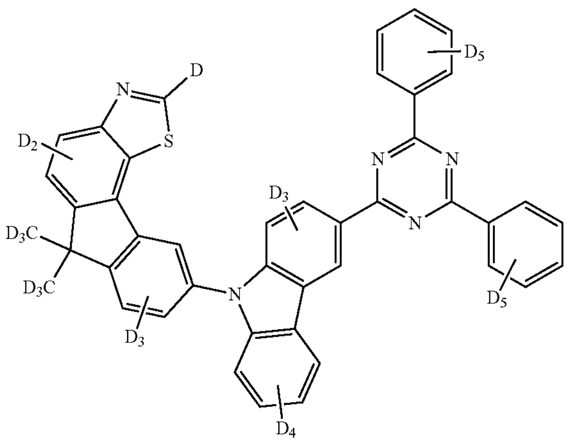
H38-D1
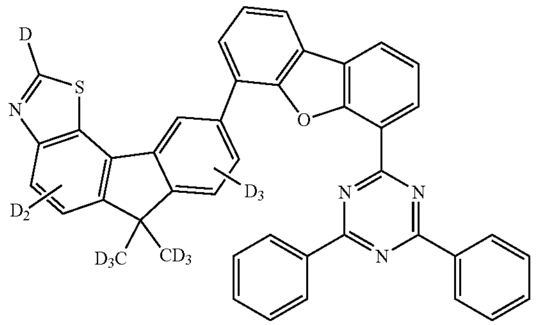
H38-D2
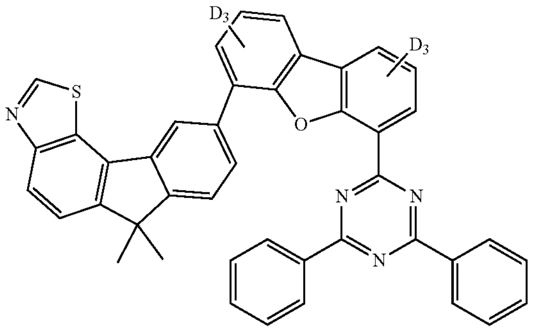
H38-D3
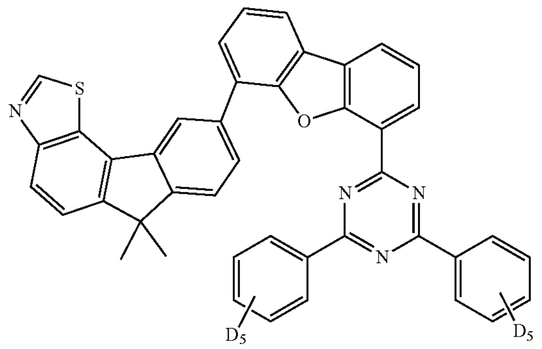
H38-D4
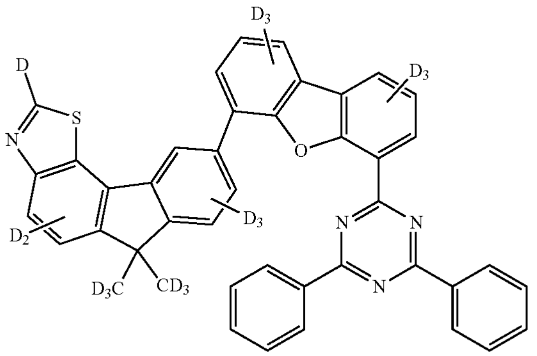
H38-D5
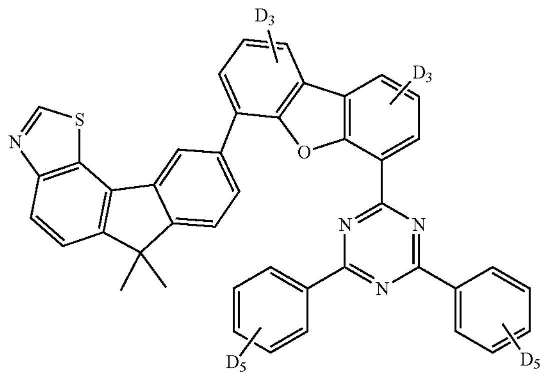
H38-D6
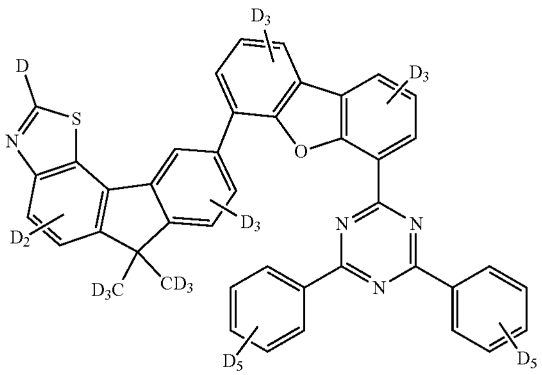

-continued
H39-D1
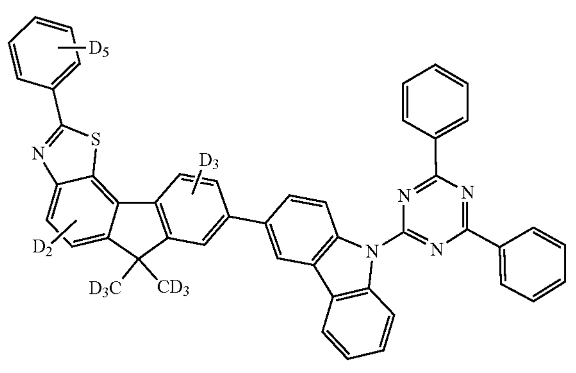
H39-D2
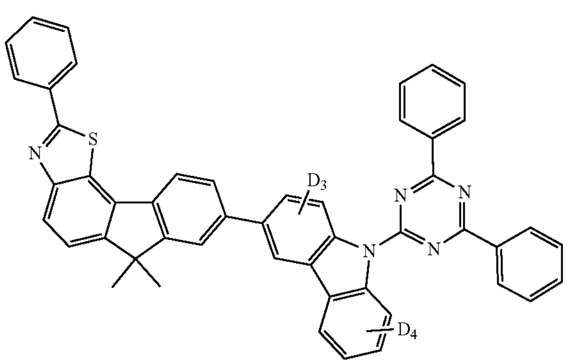
H39-D3
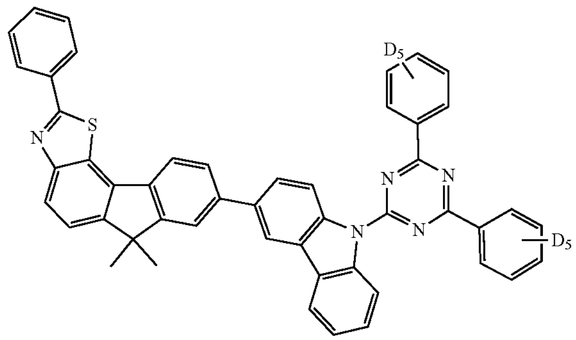
H39-D4
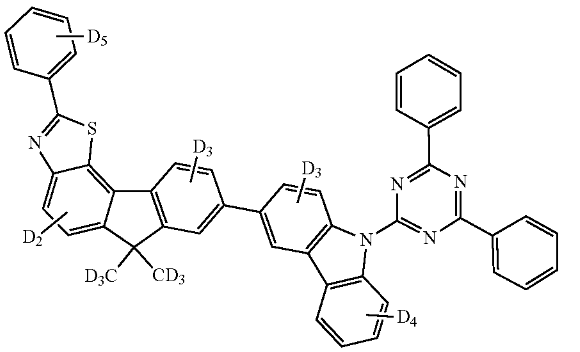
H39-D5
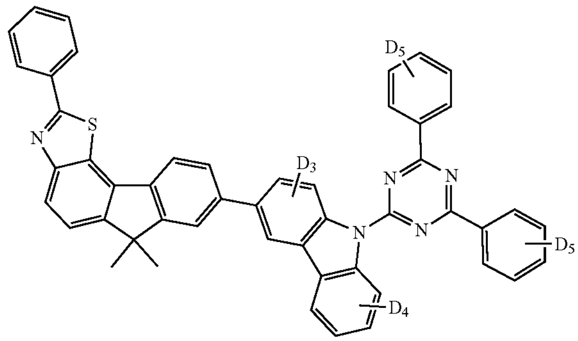
H39-D6
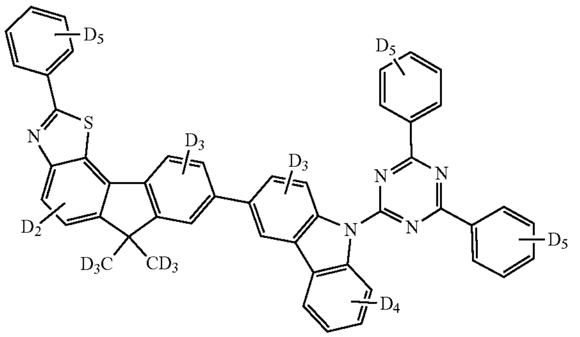
H40-D1
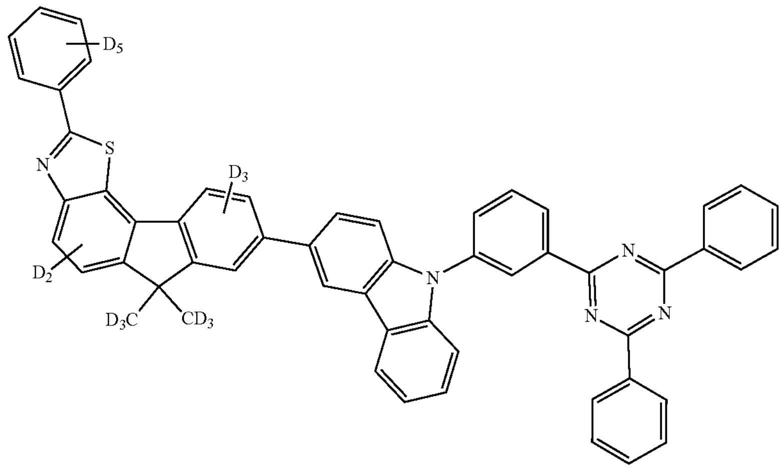

-continued
H40-D2
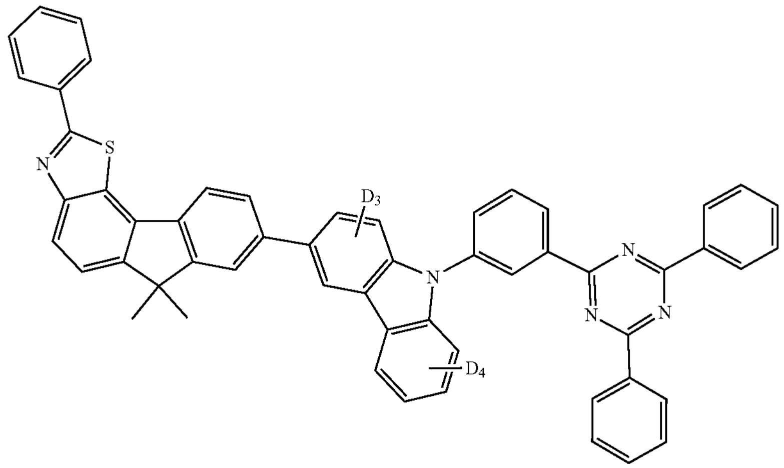
H40-D3
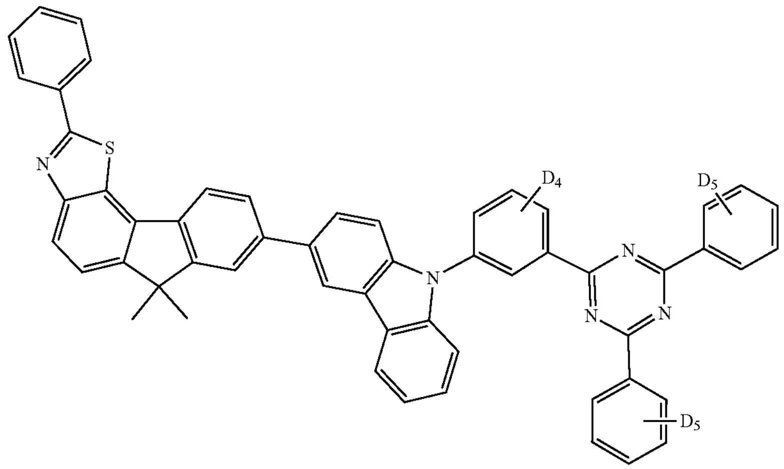
H40-D4
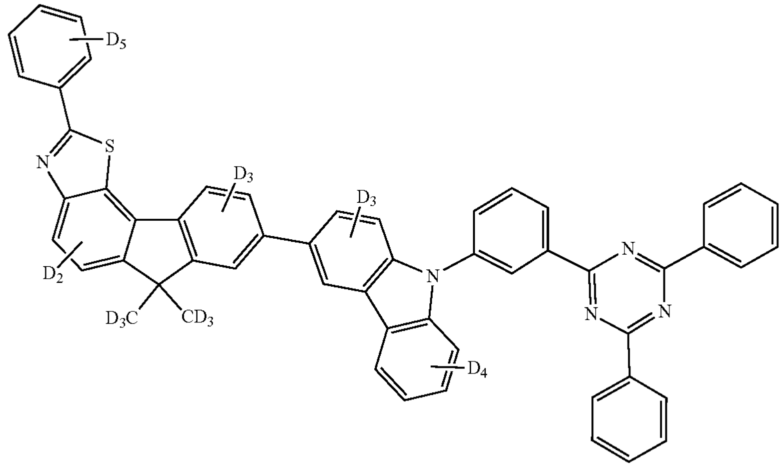

-continued
H40-D5
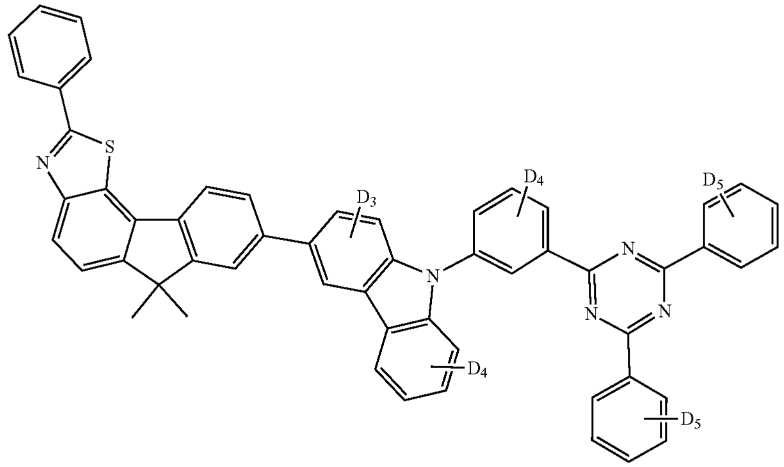
H40-D6
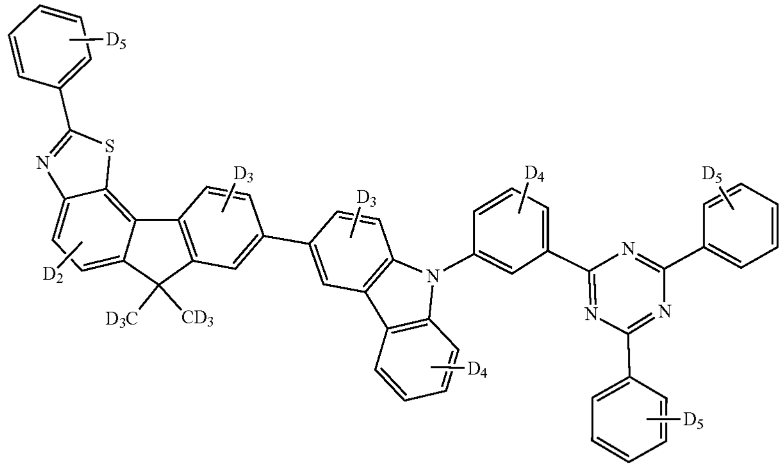
H41-D1
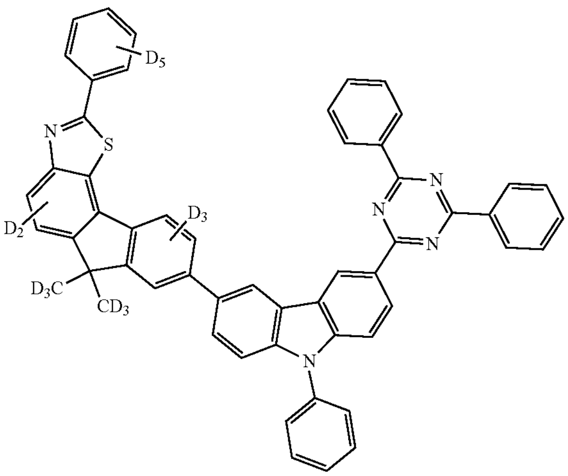
H41-D2
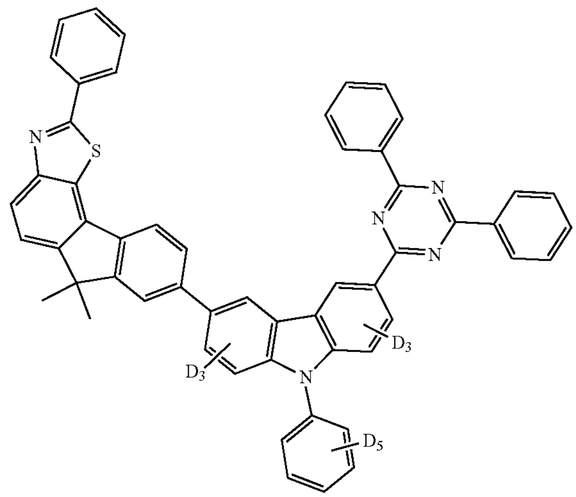

-continued
H41-D3
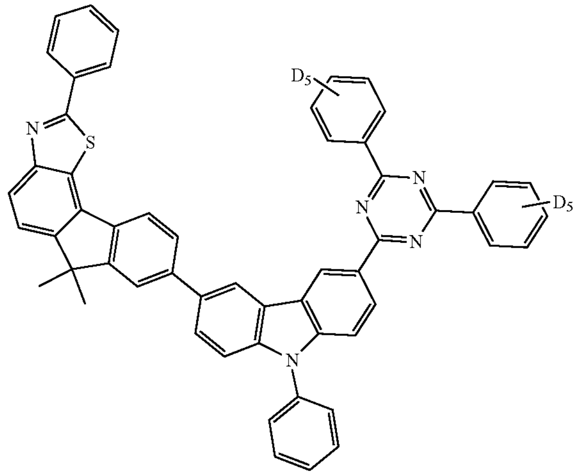
H41-D4
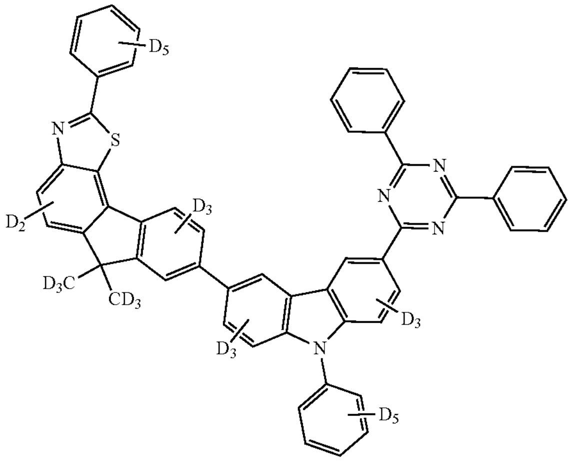
H41-D5
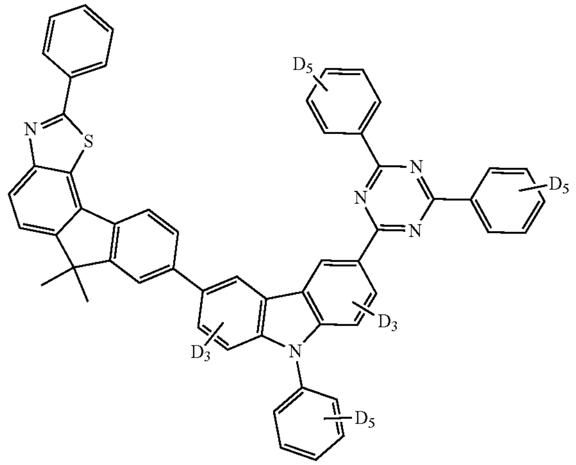
H41-D6
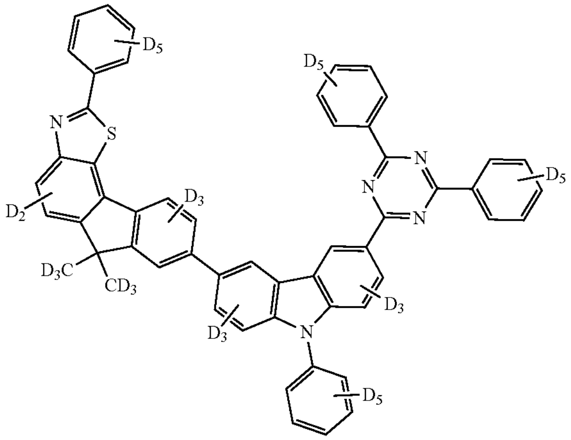
H42-D1
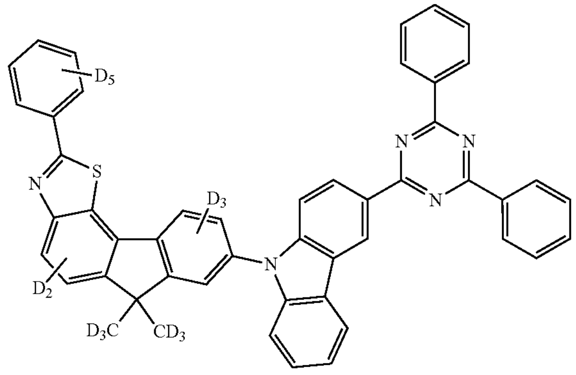
H42-D2
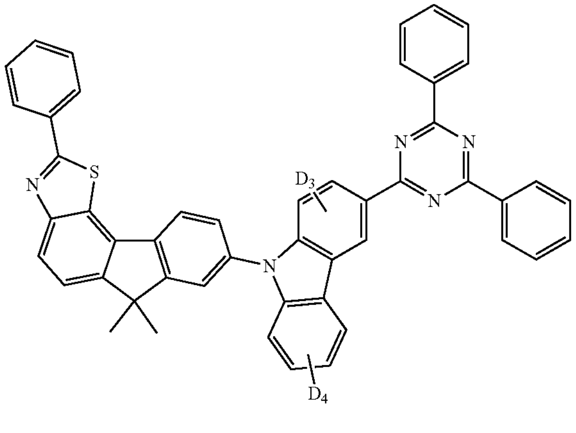

-continued
H42-D3
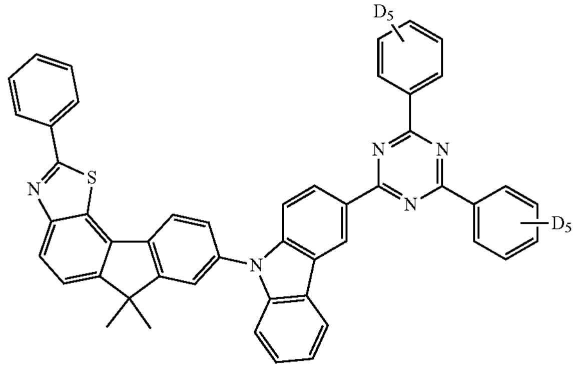
H42-D4
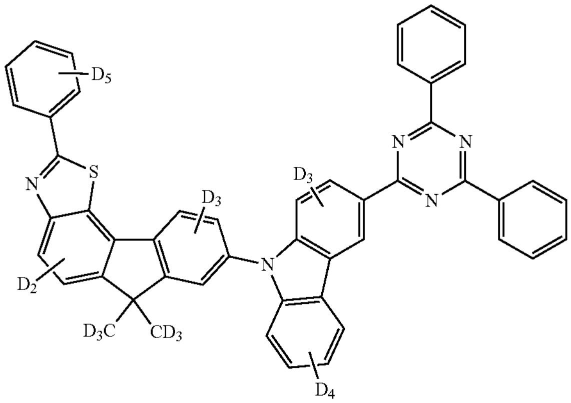
H42-D5
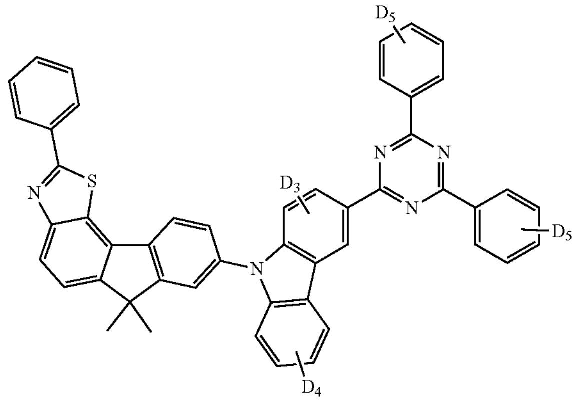
H42-D6
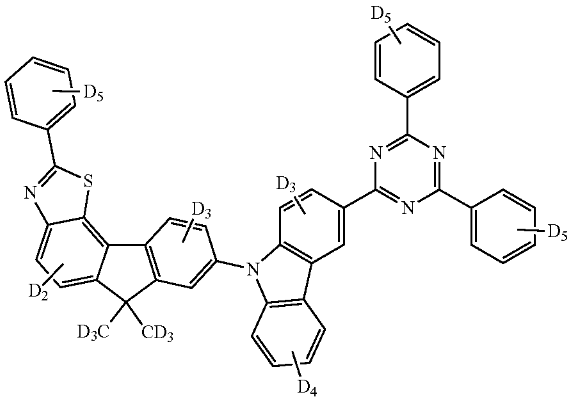
H45-D1
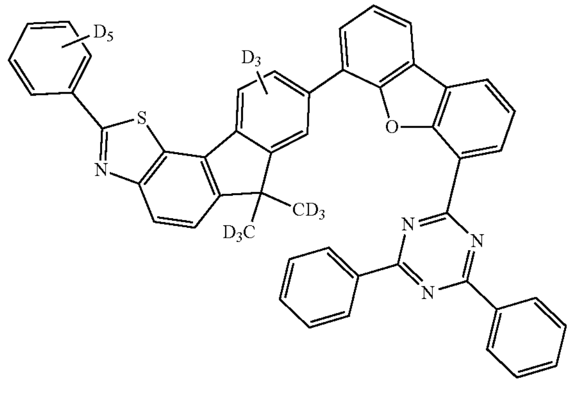
H45-D2
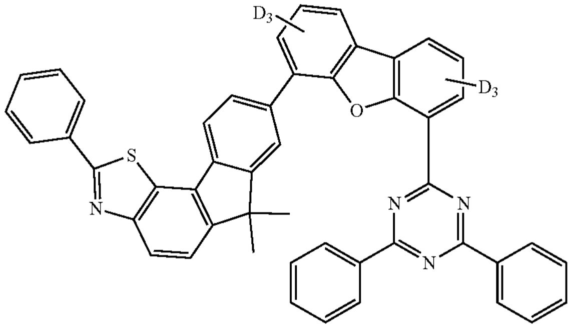
H45-D3
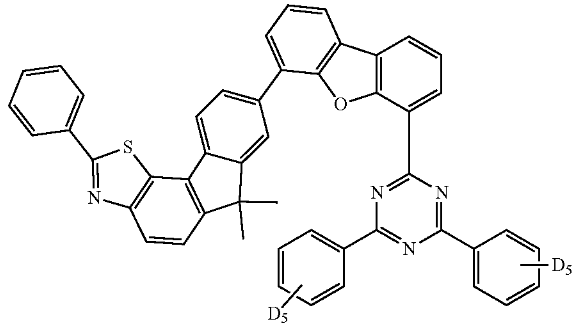

H45-D4
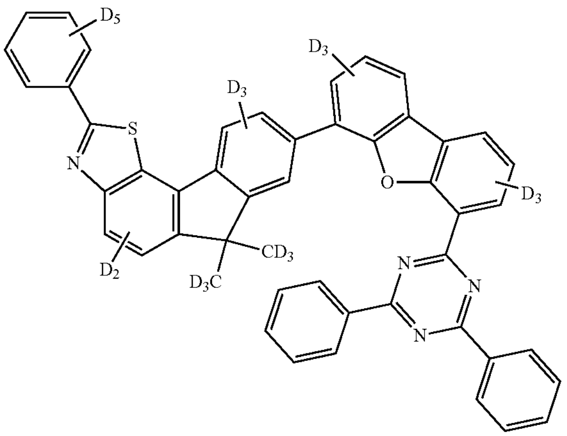
H45-D6
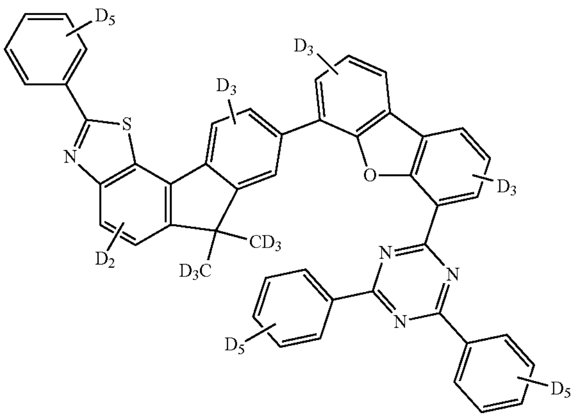
H46-D2
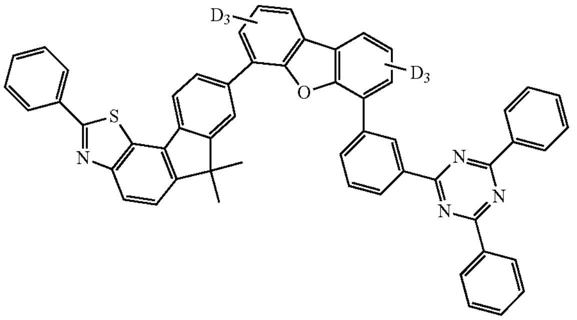
H46-D4
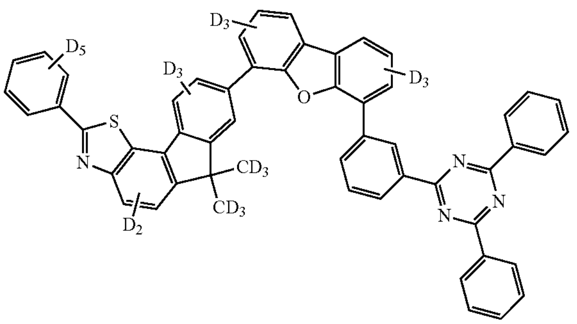
H45-D5
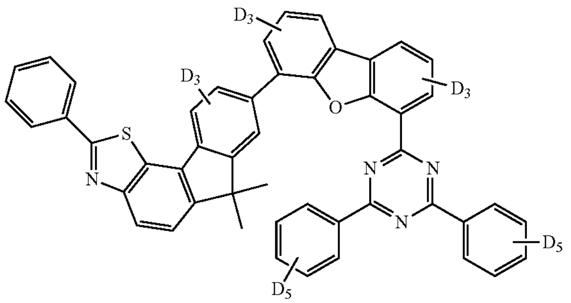
H46-D1
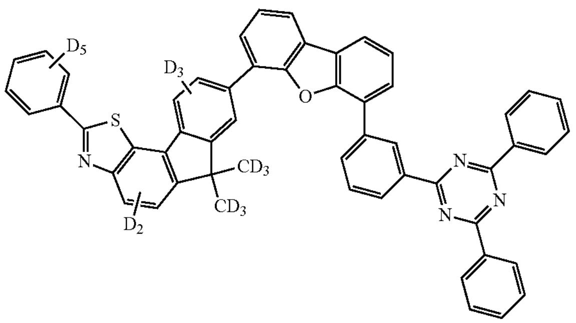
H46-D3
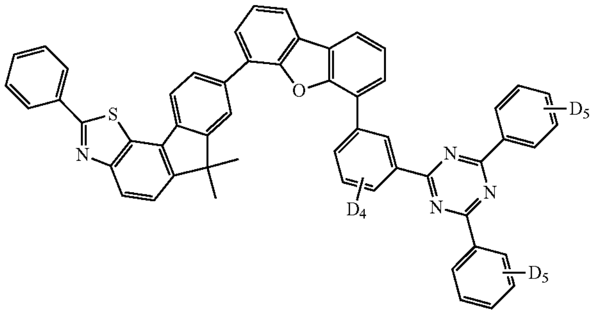
H46-D5
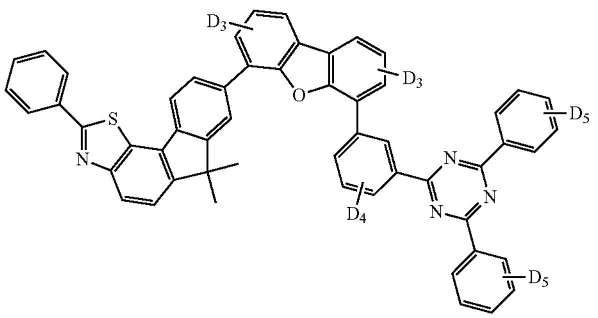

-continued
H46-D6
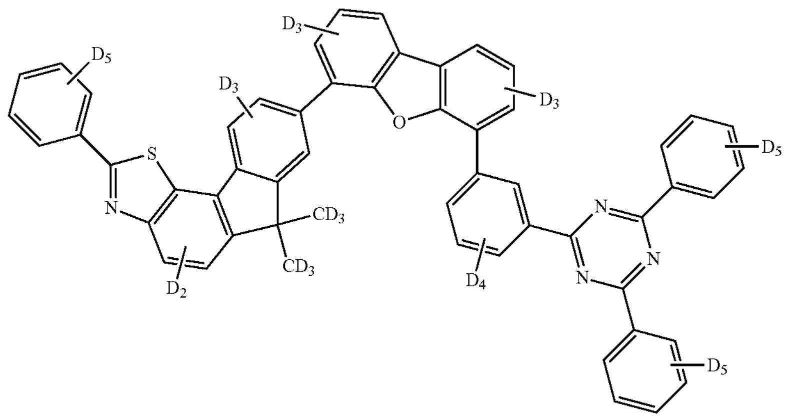
H47-D1
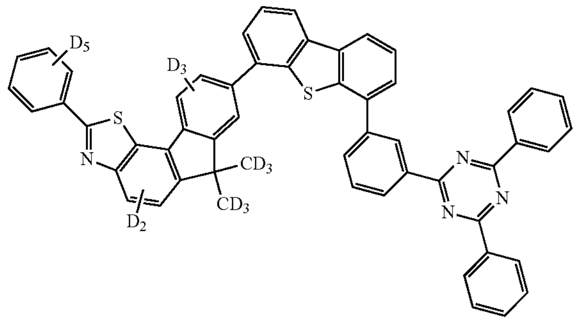
H47-D2
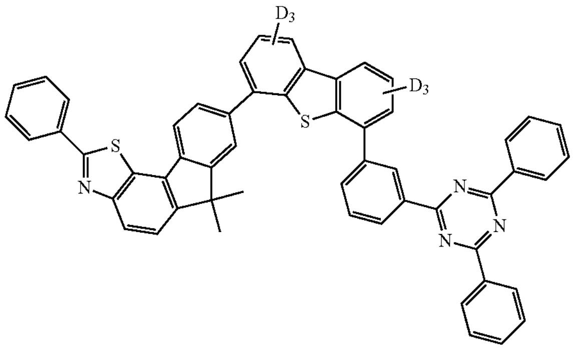
H47-D3
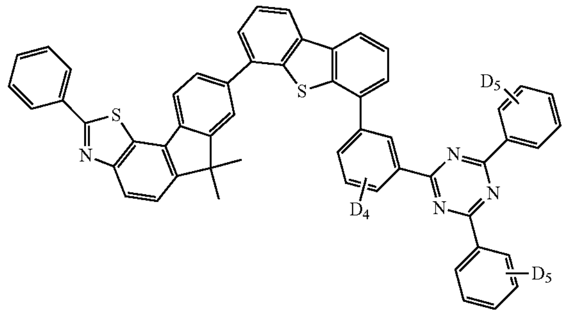
H47-D4
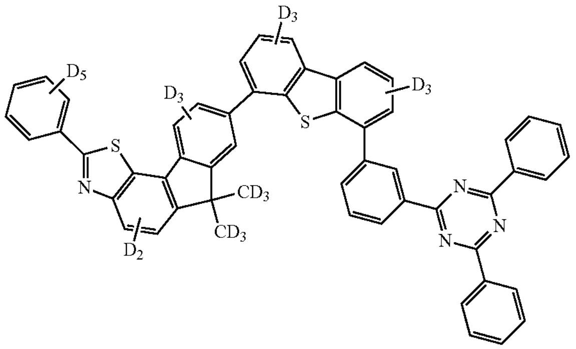
H47-D5
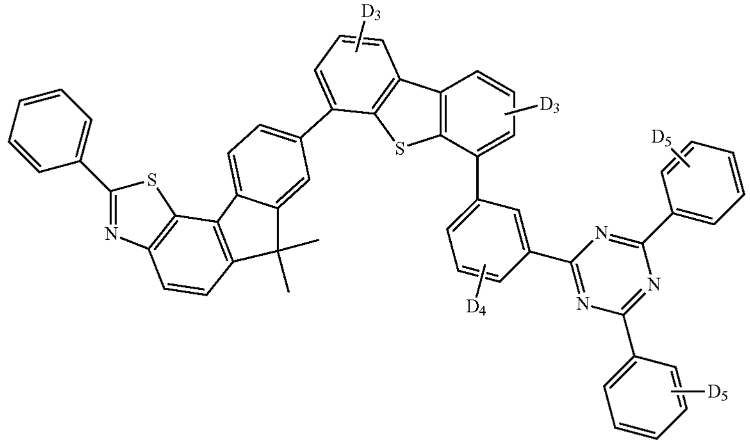

-continued
H47-D6
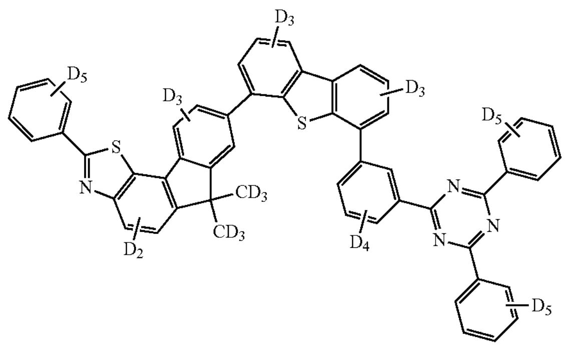
H48-D1
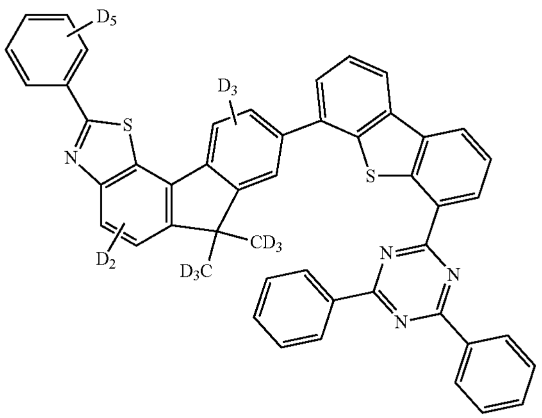
H48-D3
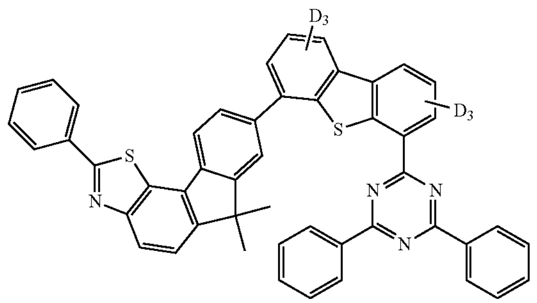
H48-D4
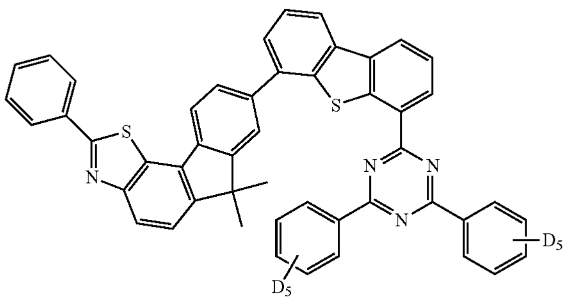
H48-D5
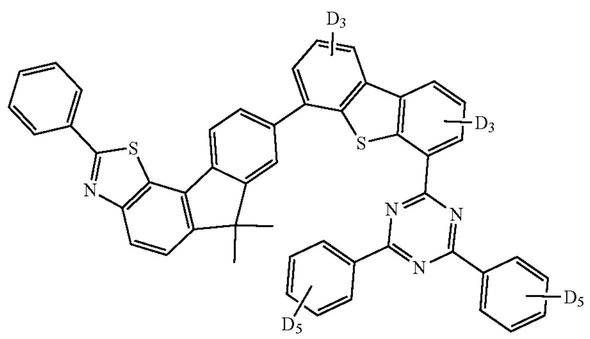
H48-D6
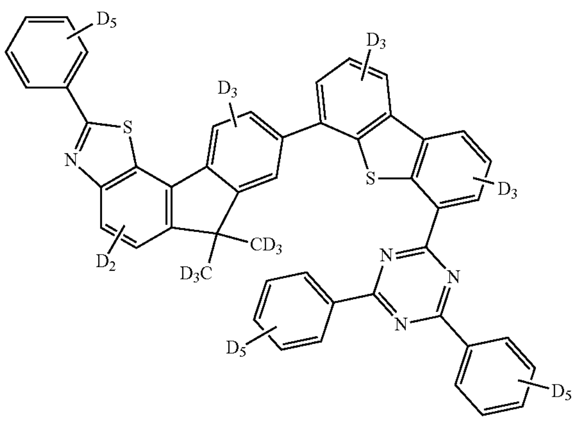
H49-D1
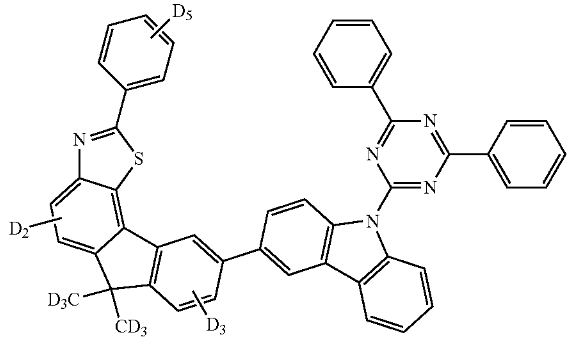
H49-D2
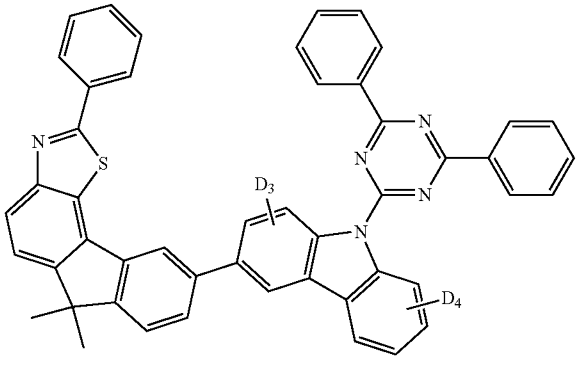

-continued
H49-D3
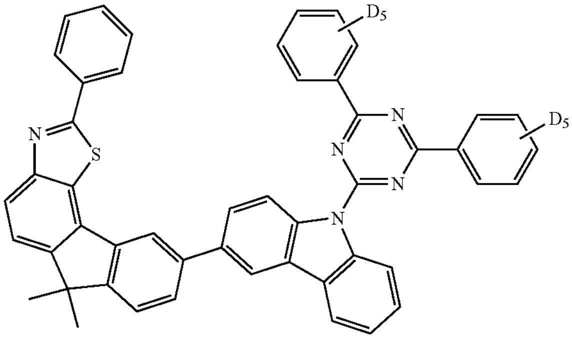
H49-D4
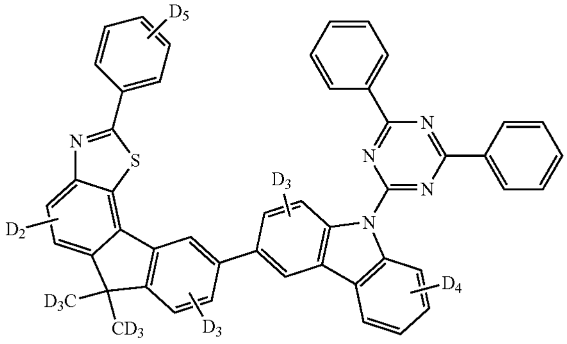
H49-D5
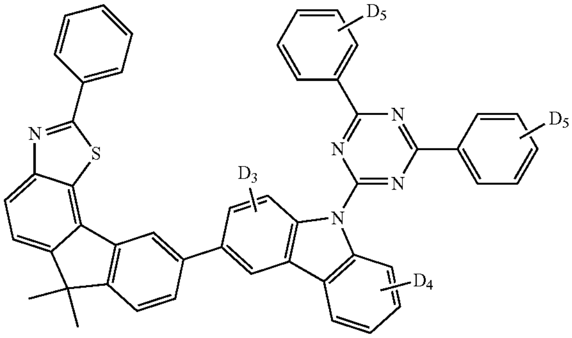
H49-D6
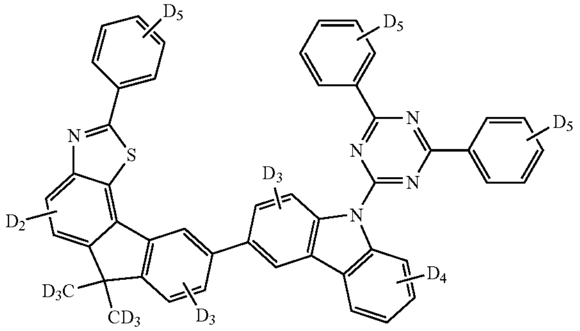
H50-D1
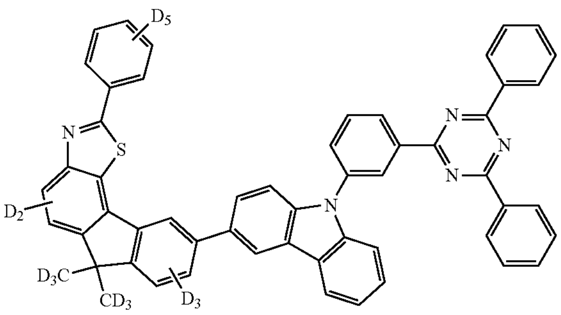
H50-D2
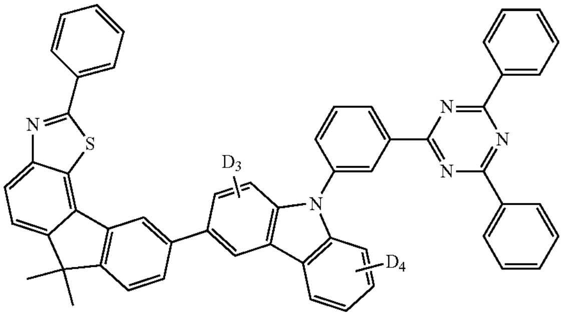
H50-D4
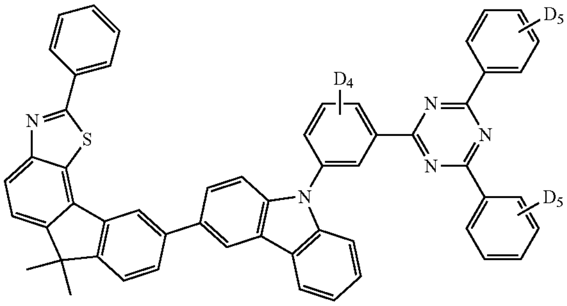
H50-D3
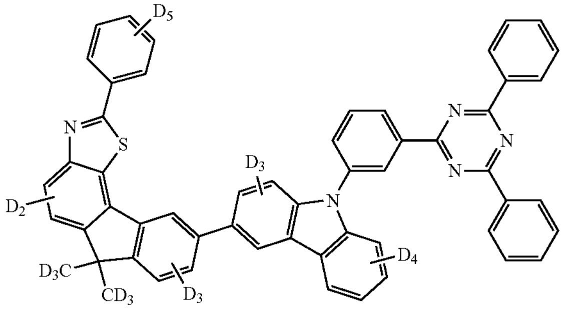

-continued
H50-D5
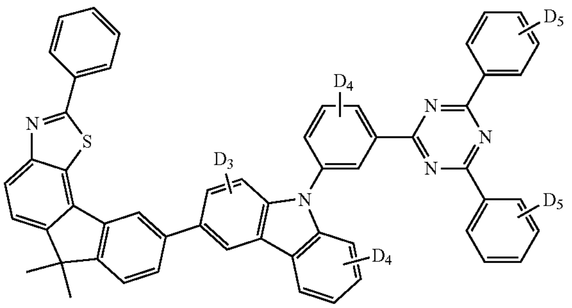
H50-D6
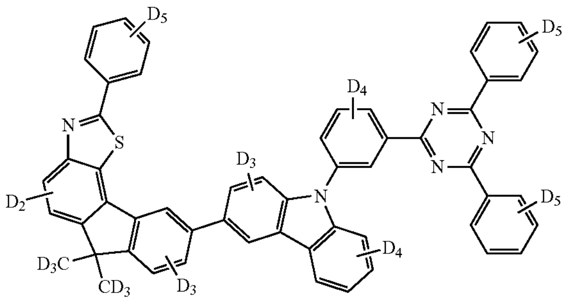
H51-D1
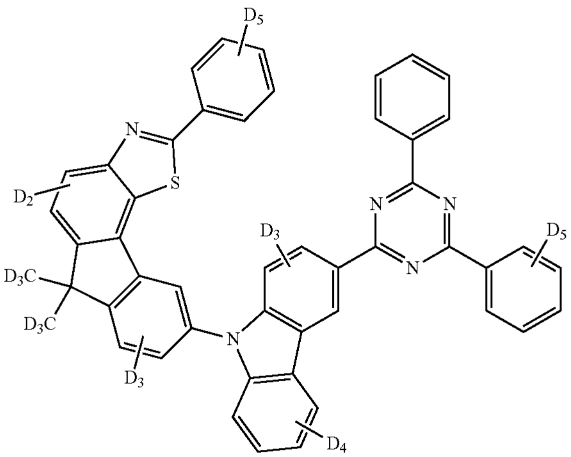
H51-D2
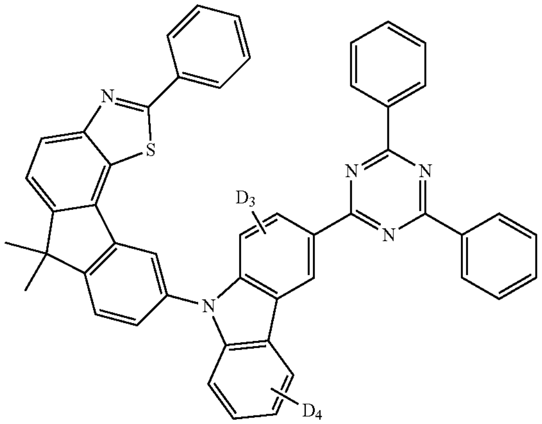
H51-D3
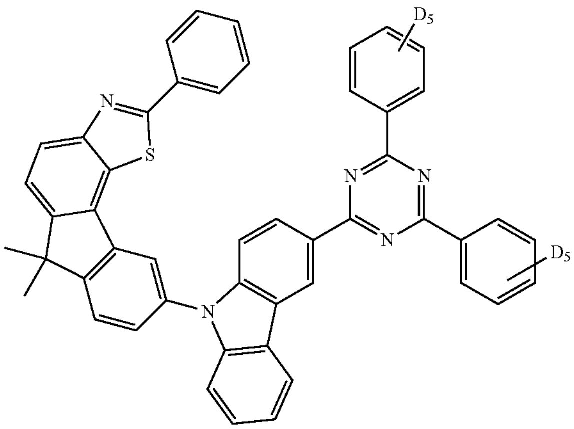
H51-D4
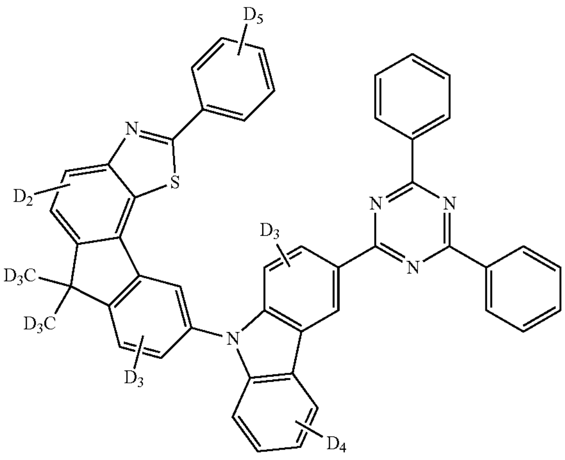

-continued
H51-D5
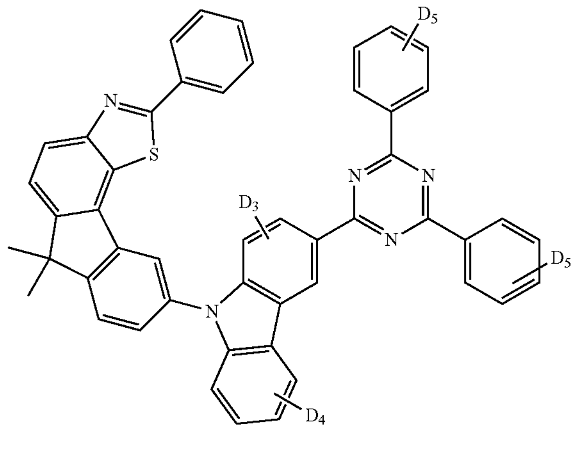
H51-D6
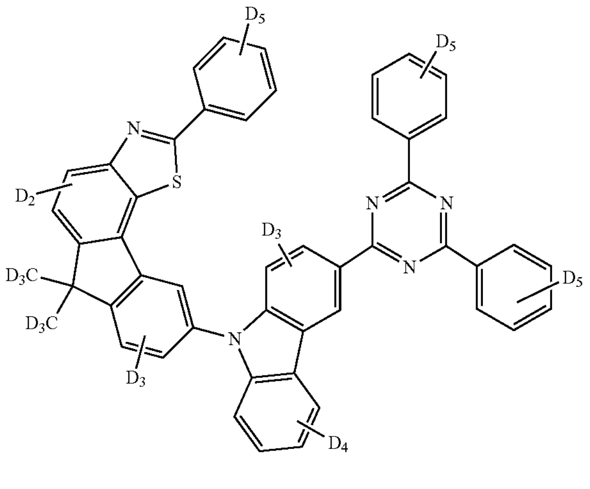
H52-D1
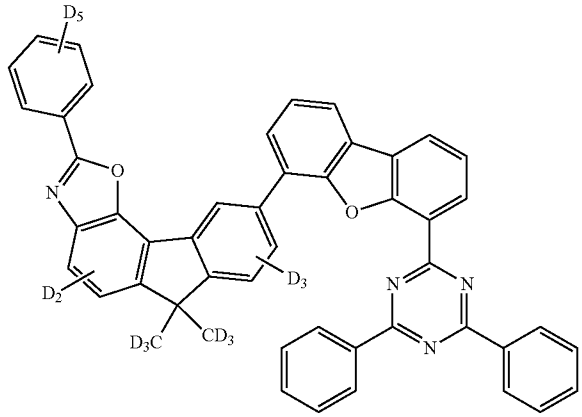
H52-D2
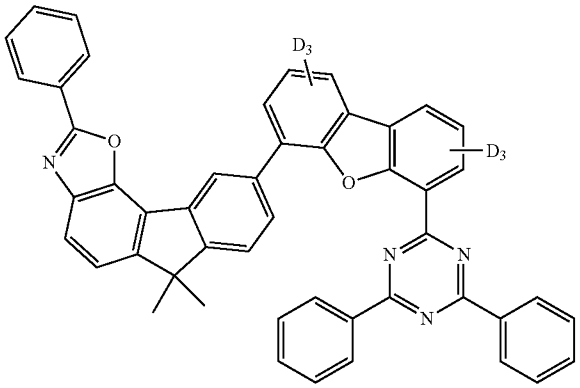
H52-D3
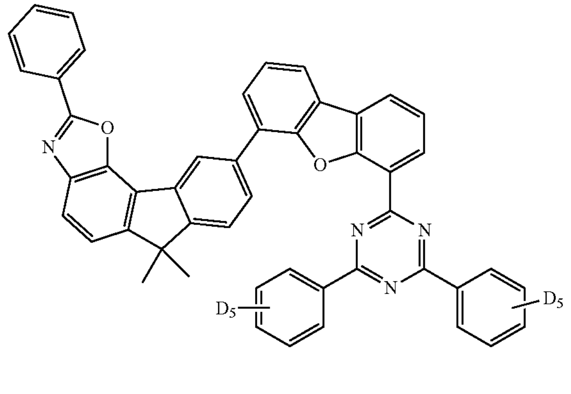
H52-D4
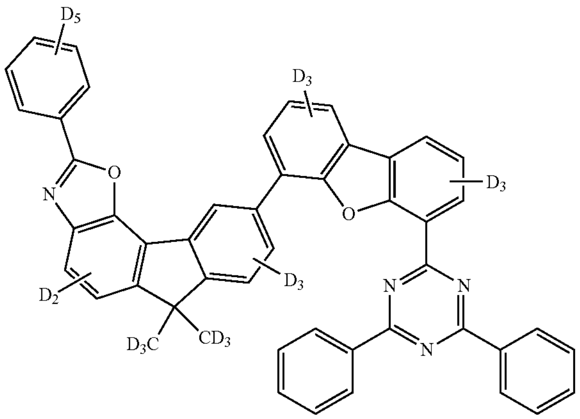

-continued
H52-D5
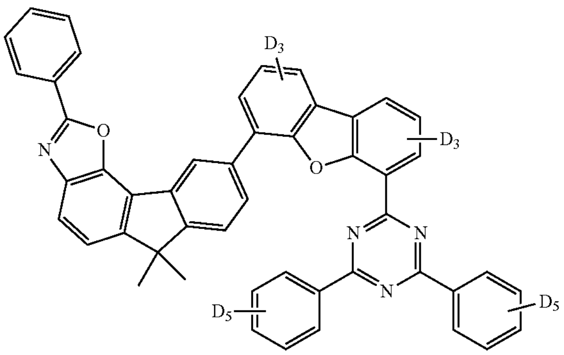
H52-D6
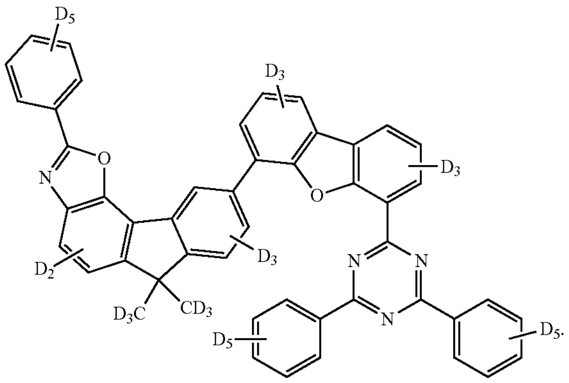
* * * * *